(12) United States Patent
Bolea

(10) Patent No.: US 9,186,511 B2
(45) Date of Patent: Nov. 17, 2015

(54) OBSTRUCTIVE SLEEP APNEA TREATMENT DEVICES, SYSTEMS AND METHODS

(71) Applicant: CYBERONICS, INC., Houston, TX (US)

(72) Inventor: Stephen L. Bolea, Watertown, MN (US)

(73) Assignee: CYBERONICS, INC., Houston, TX (US)

(*) Notice: Subject to any disclaimer, the term of this patent is extended or adjusted under 35 U.S.C. 154(b) by 0 days.

(21) Appl. No.: 14/178,104

(22) Filed: Feb. 11, 2014

(65) Prior Publication Data

US 2014/0228905 A1  Aug. 14, 2014

Related U.S. Application Data

(63) Continuation-in-part of application No. 13/106,460, filed on May 12, 2011, which is a continuation-in-part of application No. 12/835,984, filed on Jul. 14, 2010, which is a continuation of application No. 11/907,532, (Continued)

(51) Int. Cl.
*A61N 1/00* (2006.01)
*A61N 1/36* (2006.01)
(Continued)

(52) U.S. Cl.
CPC ............. *A61N 1/36139* (2013.01); *A61F 5/56* (2013.01); *A61N 1/0556* (2013.01); *A61N 1/3601* (2013.01); *A61N 1/3611* (2013.01); *A61N 1/3615* (2013.01); *A61B 5/08* (2013.01); *A61B 5/0809* (2013.01); *A61B 5/0826* (2013.01); *A61B 5/4818* (2013.01); *A61B 2017/248* (2013.01); *A61F 5/566* (2013.01); *A61N 1/3758* (2013.01);

(Continued)

(58) Field of Classification Search
CPC ............. A61N 1/00; A61N 1/08; A61N 1/34; A61N 1/3605; A61N 2001/083; A61B 5/04; A61B 5/08; A61B 5/085
See application file for complete search history.

(56) References Cited

U.S. PATENT DOCUMENTS

| 758,030 A | 4/1904 | Carence |
| 1,520,930 A | 12/1924 | Calhoun |

(Continued)

FOREIGN PATENT DOCUMENTS

| EP | 0 892 926 B1 | 6/2002 |
| EP | 0 900 102 B1 | 7/2004 |

(Continued)

OTHER PUBLICATIONS

Spence et al., "High-flow nasal cannula as a device to provide continuous positive airway pressure in infants," *Journal of Perinatology*, Dec. 2007, pp. 772-775, vol. 27 (12), Nature Publishing Group.

(Continued)

*Primary Examiner* — Christopher D Koharski
*Assistant Examiner* — Elizabeth K So
(74) *Attorney, Agent, or Firm* — Bookoff McAndrews

(57) ABSTRACT

A method of treating a patient, comprising: sensing a biological parameter indicative of respiration; analyzing the biological parameter to identify a respiratory cycle; identifying an inspiratory phase of the respiratory cycle; and delivering stimulation to a hypoglossal nerve of the patient, wherein stimulation is delivered if a duration of the inspiratory phase of the respiratory cycle is greater than a predetermined portion of a duration of the entire respiratory cycle.

19 Claims, 156 Drawing Sheets

Related U.S. Application Data filed on Oct. 12, 2007, now Pat. No. 7,809,442, application No. 14/178,104, which is a continuation-in-part of application No. 12/650,045, filed on Dec. 30, 2009, application No. 14/178,104, which is a continuation-in-part of application No. 13/205,315, filed on Aug. 8, 2011, now Pat. No. 8,855,771, which is a continuation of application No. 13/113,524, filed on May 23, 2011, now abandoned, application No. 14/178,104, which is a continuation-in-part of application No. 13/633,670, filed on Oct. 2, 2012.

(60) Provisional application No. 61/437,573, filed on Jan. 28, 2011, provisional application No. 60/851,386, filed on Oct. 13, 2006, provisional application No. 60/918,257, filed on Mar. 14, 2007, provisional application No. 61/204,008, filed on Dec. 31, 2008, provisional application No. 61/467,758, filed on Mar. 25, 2011, provisional application No. 61/437,573, filed on Jan. 28, 2011, provisional application No. 61/542,617, filed on Oct. 3, 2011.

(51) Int. Cl.
*A61N 1/05* (2006.01)
*A61B 5/08* (2006.01)
*A61B 5/00* (2006.01)
*A61N 1/372* (2006.01)
*A61N 1/375* (2006.01)
*A61F 5/56* (2006.01)
*A61B 17/24* (2006.01)

(52) U.S. Cl.
CPC ......... *A61N 1/37229* (2013.01); *A61N 1/37235* (2013.01)

(56) References Cited

U.S. PATENT DOCUMENTS

| | | |
|---|---|---|
| 1,701,277 A | 2/1929 | Shindel |
| 1,914,418 A | 6/1933 | Goyena |
| 2,046,664 A | 7/1936 | Weaver |
| 2,151,227 A | 3/1939 | Pawelek |
| 2,237,954 A | 4/1941 | Wilson |
| 2,243,360 A | 5/1941 | Slatis |
| 2,274,886 A | 3/1942 | Carroll |
| 2,526,586 A | 10/1950 | Shuff |
| 2,693,799 A | 11/1954 | Herman |
| 2,777,442 A | 1/1957 | Zelano |
| 2,928,388 A | 3/1960 | Jaroslaw |
| 3,457,917 A | 7/1969 | Mercurio |
| 3,513,839 A | 5/1970 | Vacante |
| 3,680,555 A | 8/1972 | Warncke |
| 3,722,509 A | 3/1973 | Nebel |
| 3,774,618 A | 11/1973 | Avery |
| 3,865,106 A | 2/1975 | Palush |
| 3,884,223 A | 5/1975 | Keindl |
| 3,906,936 A | 9/1975 | Habal |
| 4,220,150 A | 9/1980 | King |
| 4,221,217 A | 9/1980 | Amezcua |
| 4,267,831 A | 5/1981 | Aguilar |
| 4,374,527 A | 2/1983 | Iversen |
| 4,506,666 A | 3/1985 | Durkan |
| 4,567,892 A | 2/1986 | Plicchi et al. |
| 4,573,481 A | 3/1986 | Bullara |
| 4,777,963 A | 10/1988 | McKenna |
| 4,830,008 A | 5/1989 | Meer |
| 4,899,750 A | 2/1990 | Eckwall |
| 4,915,105 A | 4/1990 | Lee |
| 4,919,136 A | 4/1990 | Alt |
| 4,940,065 A | 7/1990 | Tanagho et al. |
| 4,960,133 A | 10/1990 | Hewson |
| 4,996,983 A | 3/1991 | AmRhein |
| 5,016,808 A | 5/1991 | Heil, Jr. et al. |
| 5,105,826 A | 4/1992 | Smits et al. |
| 5,121,754 A | 6/1992 | Mullett |
| 5,133,354 A | 7/1992 | Kallock |
| 5,146,918 A | 9/1992 | Kallok et al. |
| 5,158,080 A | 10/1992 | Kallock |
| 5,174,287 A | 12/1992 | Kallok et al. |
| 5,178,156 A | 1/1993 | Takishima et al. |
| 5,190,053 A | 3/1993 | Meer |
| 5,211,173 A | 5/1993 | Kallok et al. |
| 5,215,082 A | 6/1993 | Kallok et al. |
| 5,277,193 A | 1/1994 | Takishima et al. |
| 5,281,219 A | 1/1994 | Kallok et al. |
| 5,282,468 A | 2/1994 | Klepinski |
| 5,300,094 A | 4/1994 | Kallok et al. |
| 5,324,321 A | 6/1994 | Pohndorf et al. |
| 5,335,657 A | 8/1994 | Terry, Jr. et al. |
| 5,344,438 A | 9/1994 | Testerman et al. |
| 5,388,578 A | 2/1995 | Yomtov et al. |
| 5,392,773 A | 2/1995 | Bertrand |
| 5,417,205 A | 5/1995 | Wang |
| 5,425,359 A | 6/1995 | Liou |
| 5,458,629 A | 10/1995 | Baudino et al. |
| 5,483,969 A | 1/1996 | Testerman et al. |
| 5,485,836 A | 1/1996 | Lincoln |
| 5,485,851 A | 1/1996 | Erickson |
| 5,487,756 A | 1/1996 | Kallesoe et al. |
| 5,511,543 A | 4/1996 | Shirley |
| 5,522,382 A | 6/1996 | Sullivan et al. |
| 5,522,862 A | 6/1996 | Testerman et al. |
| 5,531,778 A | 7/1996 | Maschino et al. |
| 5,540,732 A * | 7/1996 | Testerman ............ 607/42 |
| 5,540,733 A | 7/1996 | Testerman et al. |
| 5,540,734 A | 7/1996 | Zabara |
| 5,546,938 A | 8/1996 | McKenzie |
| 5,549,655 A | 8/1996 | Erickson |
| 5,568,808 A | 10/1996 | Rimkus |
| 5,591,216 A | 1/1997 | Testerman et al. |
| 5,630,411 A | 5/1997 | Holscher |
| 5,682,881 A | 11/1997 | Winthrop et al. |
| 5,697,105 A | 12/1997 | White |
| 5,697,363 A | 12/1997 | Hart |
| 5,730,122 A | 3/1998 | Lurie |
| 5,740,798 A | 4/1998 | McKinney |
| 5,752,511 A | 5/1998 | Simmons et al. |
| 5,787,884 A | 8/1998 | Tovey |
| 5,826,579 A | 10/1998 | Remmers et al. |
| 5,848,589 A | 12/1998 | Welnetz |
| 5,855,552 A | 1/1999 | Houser et al. |
| 5,890,491 A | 4/1999 | Rimkus |
| 5,895,360 A | 4/1999 | Christopherson et al. |
| 5,919,220 A | 7/1999 | Stieglitz et al. |
| 5,922,014 A | 7/1999 | Warman et al. |
| 5,938,596 A | 8/1999 | Woloszko et al. |
| 5,944,680 A | 8/1999 | Christopherson et al. |
| 5,947,119 A | 9/1999 | Reznick |
| 6,010,459 A | 1/2000 | Silkoff et al. |
| 6,015,389 A | 1/2000 | Brown |
| 6,021,352 A | 2/2000 | Christopherson et al. |
| 6,021,354 A | 2/2000 | Warman et al. |
| 6,029,667 A | 2/2000 | Lurie |
| 6,041,780 A | 3/2000 | Richard |
| 6,066,165 A | 5/2000 | Racz |
| 6,098,624 A | 8/2000 | Utamaru |
| 6,109,262 A | 8/2000 | Tovey |
| 6,119,690 A | 9/2000 | Pantaleo |
| 6,126,611 A | 10/2000 | Bourgeois et al. |
| 6,132,384 A | 10/2000 | Christopherson et al. |
| 6,198,970 B1 | 3/2001 | Freed et al. |
| 6,201,994 B1 | 3/2001 | Warman et al. |
| 6,205,360 B1 | 3/2001 | Carter et al. |
| 6,217,527 B1 | 4/2001 | Selmon et al. |
| 6,221,049 B1 | 4/2001 | Selmon et al. |
| 6,231,546 B1 | 5/2001 | Milo et al. |
| 6,240,316 B1 | 5/2001 | Richmond et al. |
| 6,244,267 B1 | 6/2001 | Eifrig |
| 6,251,126 B1 | 6/2001 | Ottenhoff et al. |
| 6,269,269 B1 | 7/2001 | Ottenhoff et al. |
| 6,292,703 B1 | 9/2001 | Meier et al. |

(56) References Cited

U.S. PATENT DOCUMENTS

| | | |
|---|---|---|
| 6,345,202 B2 | 2/2002 | Richmond et al. |
| 6,366,815 B1 | 4/2002 | Haugland et al. |
| 6,460,539 B1 | 10/2002 | Japuntich et al. |
| 6,484,725 B1 | 11/2002 | Chi |
| 6,511,458 B2 | 1/2003 | Milo et al. |
| 6,514,217 B1 | 2/2003 | Selmon et al. |
| 6,542,776 B1 | 4/2003 | Gordon et al. |
| 6,561,188 B1 | 5/2003 | Ellis |
| 6,587,725 B1 | 7/2003 | Durand et al. |
| 6,600,956 B2 | 7/2003 | Maschino et al. |
| 6,606,521 B2 | 8/2003 | Paspa et al. |
| 6,626,179 B1 | 9/2003 | Pedley |
| 6,636,767 B1 | 10/2003 | Knudson et al. |
| 6,641,542 B2 | 11/2003 | Cho et al. |
| 6,647,289 B2 | 11/2003 | Prutchi |
| 6,651,652 B1 | 11/2003 | Ward |
| 6,718,982 B2 | 4/2004 | Smith et al. |
| 6,719,725 B2 | 4/2004 | Milo et al. |
| 6,721,603 B2 | 4/2004 | Zabara et al. |
| 6,772,015 B2 | 8/2004 | Dahl et al. |
| 6,776,162 B2 | 8/2004 | Wood |
| 6,799,575 B1 | 10/2004 | Carter |
| 6,819,958 B2 | 11/2004 | Weiner et al. |
| 6,829,503 B2 | 12/2004 | Alt |
| 6,829,508 B2 | 12/2004 | Schulman et al. |
| RE38,705 E | 2/2005 | Hill et al. |
| 6,876,885 B2 | 4/2005 | Swoyer et al. |
| 6,881,192 B1 | 4/2005 | Park |
| 6,883,518 B2 | 4/2005 | Mittelstadt et al. |
| 6,890,306 B2 | 5/2005 | Poezevera |
| 6,904,320 B2 | 6/2005 | Park et al. |
| 6,907,295 B2 | 6/2005 | Gross et al. |
| 6,928,324 B2 | 8/2005 | Park et al. |
| 6,978,171 B2 | 12/2005 | Goetz et al. |
| 6,997,177 B2 | 2/2006 | Wood |
| 7,027,869 B2 | 4/2006 | Danek et al. |
| 7,054,692 B1 | 5/2006 | Whitehurst et al. |
| 7,065,410 B2 | 6/2006 | Bardy et al. |
| 7,082,331 B1 | 7/2006 | Park et al. |
| 7,087,053 B2 | 8/2006 | Vanney |
| 7,089,932 B2 | 8/2006 | Dodds |
| 7,094,206 B2 | 8/2006 | Hoffman |
| 7,117,036 B2 | 10/2006 | Florio |
| 7,128,717 B1 | 10/2006 | Thatch et al. |
| 7,142,919 B2 | 11/2006 | Hine et al. |
| 7,149,573 B2 | 12/2006 | Wang |
| 7,152,604 B2 | 12/2006 | Hickle et al. |
| 7,155,278 B2 | 12/2006 | King et al. |
| 7,156,098 B2 | 1/2007 | Dolezal et al. |
| 7,160,252 B2 | 1/2007 | Cho |
| 7,160,255 B2 | 1/2007 | Saadat |
| 7,178,524 B2 | 2/2007 | Noble |
| 7,200,440 B2 | 4/2007 | Kim et al. |
| 7,225,034 B2 | 5/2007 | Ries et al. |
| 7,239,918 B2 | 7/2007 | Strother et al. |
| 7,239,920 B1 | 7/2007 | Thacker et al. |
| 7,242,987 B2 | 7/2007 | Holleman et al. |
| 7,277,749 B2 | 10/2007 | Gordon et al. |
| 7,283,867 B2 | 10/2007 | Strother et al. |
| 7,302,951 B2 | 12/2007 | Mittelstadt et al. |
| 7,313,442 B2 | 12/2007 | Velasco et al. |
| 7,346,398 B2 | 3/2008 | Gross et al. |
| 7,366,572 B2 | 4/2008 | Heruth et al. |
| 7,396,333 B2 | 7/2008 | Stahmann et al. |
| 7,438,686 B2 | 10/2008 | Cho et al. |
| 7,463,928 B2 | 12/2008 | Lee et al. |
| 7,473,227 B2 | 1/2009 | Hsu et al. |
| 7,515,968 B2 | 4/2009 | Metzler et al. |
| 7,524,292 B2 | 4/2009 | Cho et al. |
| 7,561,922 B2 | 7/2009 | Cohen et al. |
| 7,591,265 B2 | 9/2009 | Lee et al. |
| 7,596,413 B2 | 9/2009 | Libbus et al. |
| 7,596,414 B2 | 9/2009 | Whitehurst et al. |
| 7,627,375 B2 | 12/2009 | Bardy et al. |
| 7,630,771 B2 | 12/2009 | Cauller |
| 7,634,315 B2 | 12/2009 | Cholette |
| 7,636,602 B2 | 12/2009 | Baru Fassio et al. |
| 7,657,311 B2 | 2/2010 | Bardy et al. |
| 7,660,632 B2 | 2/2010 | Kirby et al. |
| 7,662,105 B2 | 2/2010 | Hatlestad |
| 7,672,728 B2 | 3/2010 | Libbus et al. |
| 7,672,729 B2 | 3/2010 | Koh et al. |
| 7,680,537 B2 | 3/2010 | Stahmann et al. |
| 7,680,538 B2 | 3/2010 | Durand et al. |
| 7,684,869 B2 | 3/2010 | Bradley et al. |
| 7,697,968 B2 | 4/2010 | Moore |
| 7,697,984 B2 | 4/2010 | Hill et al. |
| 7,697,990 B2 | 4/2010 | Ujhazy et al. |
| 7,717,848 B2 | 5/2010 | Heruth et al. |
| 7,720,534 B2 | 5/2010 | Bardy et al. |
| 7,725,195 B2 | 5/2010 | Lima et al. |
| 7,725,198 B2 | 5/2010 | Cross, Jr. et al. |
| 7,734,340 B2 | 6/2010 | De Ridder |
| 7,734,348 B2 | 6/2010 | Zhang et al. |
| 7,738,952 B2 | 6/2010 | Yun et al. |
| 7,747,323 B2 | 6/2010 | Libbus et al. |
| 7,751,880 B1 | 7/2010 | Cholette |
| 7,751,885 B2 | 7/2010 | Bardy et al. |
| 7,758,384 B2 | 7/2010 | Alexander et al. |
| 7,765,000 B2 | 7/2010 | Zhang et al. |
| 7,769,461 B2 | 8/2010 | Whitehurst et al. |
| 7,783,353 B2 | 8/2010 | Libbus et al. |
| 7,785,262 B2 | 8/2010 | Melker et al. |
| 7,787,959 B1 | 8/2010 | Morgan |
| 7,792,590 B1 | 9/2010 | Pianca et al. |
| 7,797,050 B2 | 9/2010 | Libbus et al. |
| 7,797,057 B2 | 9/2010 | Harris |
| 7,797,058 B2 | 9/2010 | Mrva et al. |
| 7,805,195 B2 | 9/2010 | Zealear |
| 7,809,442 B2 | 10/2010 | Bolea et al. |
| 7,813,797 B2 | 10/2010 | Bardy et al. |
| 7,813,802 B2 | 10/2010 | Tcheng et al. |
| 7,813,809 B2 | 10/2010 | Strother et al. |
| 7,818,063 B2 | 10/2010 | Wallace et al. |
| 7,822,486 B2 | 10/2010 | Foster et al. |
| 8,249,723 B2 | 8/2012 | McCreery |
| 8,311,645 B2 | 11/2012 | Bolea et al. |
| 8,386,046 B2 | 2/2013 | Tesfayesus et al. |
| 8,428,727 B2 | 4/2013 | Bolea et al. |
| 8,498,712 B2 | 7/2013 | Bolea et al. |
| 8,626,304 B2 | 1/2014 | Bolea et al. |
| 8,639,354 B2 | 1/2014 | Bolea et al. |
| 8,718,783 B2 | 5/2014 | Bolea et al. |
| 8,744,589 B2 | 6/2014 | Bolea et al. |
| 8,855,771 B2 | 10/2014 | Tesfayesus et al. |
| 2001/0010010 A1 | 7/2001 | Richmond et al. |
| 2001/0031929 A1 | 10/2001 | O'Toole |
| 2002/0010495 A1 | 1/2002 | Freed et al. |
| 2002/0049479 A1 | 4/2002 | Pitts |
| 2002/0092527 A1 | 7/2002 | Wood |
| 2002/0128700 A1 | 9/2002 | Cross |
| 2002/0166556 A1 | 11/2002 | Jacob |
| 2002/0195108 A1 | 12/2002 | Mittelstadt et al. |
| 2002/0195109 A1 | 12/2002 | Mittelstadt et al. |
| 2003/0034031 A1 | 2/2003 | Lev et al. |
| 2003/0078643 A1 | 4/2003 | Schulman et al. |
| 2003/0083696 A1 | 5/2003 | Avital |
| 2003/0093128 A1 | 5/2003 | Freed et al. |
| 2003/0106555 A1 | 6/2003 | Tovey |
| 2003/0106556 A1 | 6/2003 | Alperovich et al. |
| 2003/0114895 A1 | 6/2003 | Gordon et al. |
| 2003/0114905 A1 | 6/2003 | Kuzma |
| 2003/0153953 A1 | 8/2003 | Park et al. |
| 2003/0167018 A1 | 9/2003 | Wyckoff |
| 2003/0195571 A1 | 10/2003 | Burnes et al. |
| 2003/0209145 A1 | 11/2003 | Soper |
| 2003/0216789 A1 | 11/2003 | Deem et al. |
| 2004/0015204 A1 | 1/2004 | Whitehurst et al. |
| 2004/0020489 A1 | 2/2004 | Gillespie et al. |
| 2004/0049241 A1 | 3/2004 | Campos |
| 2004/0055603 A1 | 3/2004 | Bruce |
| 2004/0073272 A1 | 4/2004 | Knudson et al. |
| 2004/0089303 A1 | 5/2004 | Chien |
| 2004/0111139 A1 | 6/2004 | McCreery |

(56) References Cited

U.S. PATENT DOCUMENTS

| | | |
|---|---|---|
| 2004/0116819 A1 | 6/2004 | Alt |
| 2004/0116978 A1 | 6/2004 | Bradley |
| 2004/0138581 A1 | 7/2004 | Frei et al. |
| 2004/0153127 A1 | 8/2004 | Gordon et al. |
| 2004/0162499 A1 | 8/2004 | Nagai et al. |
| 2004/0194784 A1 | 10/2004 | Bertrand |
| 2004/0215288 A1 | 10/2004 | Lee et al. |
| 2004/0230278 A1 | 11/2004 | Dahl et al. |
| 2004/0233058 A1 | 11/2004 | Dodds |
| 2004/0260310 A1 | 12/2004 | Harris |
| 2004/0261791 A1 | 12/2004 | Horian |
| 2005/0004610 A1 | 1/2005 | Kim et al. |
| 2005/0010265 A1 | 1/2005 | Fassio et al. |
| 2005/0038490 A1 | 2/2005 | Gross et al. |
| 2005/0039757 A1 | 2/2005 | Wood |
| 2005/0043644 A1 | 2/2005 | Stahmann et al. |
| 2005/0043772 A1 | 2/2005 | Stahmann et al. |
| 2005/0076908 A1 | 4/2005 | Lee et al. |
| 2005/0085865 A1 | 4/2005 | Tehrani |
| 2005/0085866 A1 | 4/2005 | Tehrani |
| 2005/0085868 A1 | 4/2005 | Tehrani et al. |
| 2005/0085869 A1 | 4/2005 | Tehrani et al. |
| 2005/0085874 A1 | 4/2005 | Davis et al. |
| 2005/0098176 A1 | 5/2005 | Hoffrichter |
| 2005/0101833 A1 | 5/2005 | Hsu et al. |
| 2005/0119711 A1 | 6/2005 | Cho et al. |
| 2005/0139216 A1 | 6/2005 | Mittelstadt et al. |
| 2005/0165457 A1 | 7/2005 | Benser et al. |
| 2005/0209513 A1 | 9/2005 | Heruth et al. |
| 2005/0209643 A1 | 9/2005 | Heruth et al. |
| 2005/0234523 A1 | 10/2005 | Levin et al. |
| 2005/0235992 A1 | 10/2005 | Djupesland |
| 2005/0240241 A1 | 10/2005 | Yun et al. |
| 2005/0251216 A1 | 11/2005 | Hill et al. |
| 2005/0261747 A1 | 11/2005 | Schuler et al. |
| 2005/0267380 A1 | 12/2005 | Poezevara |
| 2005/0267547 A1 | 12/2005 | Knudson et al. |
| 2005/0277844 A1 | 12/2005 | Strother et al. |
| 2005/0277999 A1 | 12/2005 | Strother et al. |
| 2005/0278000 A1 | 12/2005 | Strother et al. |
| 2006/0004429 A1 | 1/2006 | Mrva et al. |
| 2006/0005842 A1 | 1/2006 | Rashad et al. |
| 2006/0025828 A1 | 2/2006 | Armstrong et al. |
| 2006/0030919 A1 | 2/2006 | Mrva et al. |
| 2006/0032497 A1 | 2/2006 | Doshi |
| 2006/0041295 A1 | 2/2006 | Osypka |
| 2006/0052836 A1 | 3/2006 | Kim et al. |
| 2006/0058588 A1 | 3/2006 | Zdeblick |
| 2006/0058852 A1 | 3/2006 | Koh et al. |
| 2006/0064029 A1 | 3/2006 | Arad |
| 2006/0064138 A1 | 3/2006 | Velasco et al. |
| 2006/0079802 A1 | 4/2006 | Jensen et al. |
| 2006/0095088 A1 | 5/2006 | De Ridder |
| 2006/0111755 A1 | 5/2006 | Stone et al. |
| 2006/0116739 A1 | 6/2006 | Betser et al. |
| 2006/0129189 A1 | 6/2006 | George et al. |
| 2006/0135886 A1 | 6/2006 | Lippert et al. |
| 2006/0136024 A1 | 6/2006 | Cohen et al. |
| 2006/0142815 A1 | 6/2006 | Tehrani et al. |
| 2006/0144398 A1 | 7/2006 | Doshi et al. |
| 2006/0149345 A1 | 7/2006 | Boggs et al. |
| 2006/0150978 A1 | 7/2006 | Doshi et al. |
| 2006/0150979 A1 | 7/2006 | Doshi et al. |
| 2006/0150980 A1 | 7/2006 | Kim |
| 2006/0167497 A1 | 7/2006 | Armstrong et al. |
| 2006/0184204 A1 | 8/2006 | He |
| 2006/0195170 A1 | 8/2006 | Cohen et al. |
| 2006/0211951 A1 | 9/2006 | Milajasevic et al. |
| 2006/0224209 A1 | 10/2006 | Meyer |
| 2006/0224211 A1 | 10/2006 | Durand |
| 2006/0241506 A1 | 10/2006 | Melker et al. |
| 2006/0241708 A1 | 10/2006 | Boute |
| 2006/0247729 A1 | 11/2006 | Tehrani et al. |
| 2006/0259079 A1 | 11/2006 | King |
| 2006/0264777 A1 | 11/2006 | Drew |
| 2006/0266369 A1 | 11/2006 | Atkinson et al. |
| 2006/0271118 A1 | 11/2006 | Libbus et al. |
| 2006/0271137 A1 | 11/2006 | Stanton-Hicks |
| 2006/0282127 A1 | 12/2006 | Zealear |
| 2006/0293720 A1 | 12/2006 | DiLorenzo |
| 2006/0293723 A1 | 12/2006 | Whitehurst et al. |
| 2007/0021785 A1 | 1/2007 | Inman et al. |
| 2007/0027482 A1 | 2/2007 | Parnis et al. |
| 2007/0038265 A1 | 2/2007 | Tcheng et al. |
| 2007/0043411 A1 | 2/2007 | Foster et al. |
| 2007/0095347 A1 | 5/2007 | Lampotang et al. |
| 2007/0125379 A1 | 6/2007 | Pierro et al. |
| 2007/0175478 A1 | 8/2007 | Brunst |
| 2007/0227542 A1 | 10/2007 | Kashmakov et al. |
| 2007/0239243 A1 | 10/2007 | Moffitt et al. |
| 2007/0277832 A1 | 12/2007 | Doshi et al. |
| 2007/0282410 A1 | 12/2007 | Cross et al. |
| 2007/0283692 A1 | 12/2007 | Tetsuka et al. |
| 2007/0283962 A1 | 12/2007 | Doshi et al. |
| 2007/0295338 A1 | 12/2007 | Loomas et al. |
| 2008/0023007 A1 | 1/2008 | Dolezal et al. |
| 2008/0027480 A1 | 1/2008 | van der Burg et al. |
| 2008/0027502 A1 | 1/2008 | Ransom |
| 2008/0041373 A1 | 2/2008 | Doshi et al. |
| 2008/0099029 A1 | 5/2008 | Lamberg |
| 2008/0103407 A1 | 5/2008 | Bolea et al. |
| 2008/0103545 A1 | 5/2008 | Bolea et al. |
| 2008/0163875 A1 | 7/2008 | Aarestad et al. |
| 2008/0183254 A1 | 7/2008 | Bly et al. |
| 2009/0044814 A1 | 2/2009 | Iancea et al. |
| 2009/0270707 A1 | 10/2009 | Alfoqaha et al. |
| 2009/0276024 A1 | 11/2009 | Bonde et al. |
| 2009/0308395 A1 | 12/2009 | Lee et al. |
| 2009/0318986 A1 | 12/2009 | Alo et al. |
| 2009/0326408 A1 | 12/2009 | Moon et al. |
| 2010/0016749 A1 | 1/2010 | Atsma et al. |
| 2010/0036285 A1 | 2/2010 | Govari et al. |
| 2010/0047376 A1 | 2/2010 | Imbeau et al. |
| 2010/0076536 A1 | 3/2010 | Merz et al. |
| 2010/0094379 A1 | 4/2010 | Meadows et al. |
| 2010/0100150 A1 | 4/2010 | Kirby et al. |
| 2010/0125310 A1 | 5/2010 | Wilson et al. |
| 2010/0131029 A1 | 5/2010 | Durand et al. |
| 2010/0137931 A1 | 6/2010 | Hopper et al. |
| 2010/0137949 A1 | 6/2010 | Mazgalev et al. |
| 2010/0137956 A1 | 6/2010 | Osypka et al. |
| 2010/0152553 A1 | 6/2010 | Ujhazy et al. |
| 2010/0174341 A1 | 7/2010 | Bolea et al. |
| 2010/0228133 A1 | 9/2010 | Averina et al. |
| 2010/0228317 A1 | 9/2010 | Libbus et al. |
| 2010/0241207 A1 | 9/2010 | Bluger |
| 2010/0257729 A1 | 10/2010 | Alexander et al. |
| 2010/0262209 A1 | 10/2010 | King et al. |
| 2011/0071591 A1 | 3/2011 | Bolea et al. |
| 2012/0017920 A1 | 1/2012 | Sanders |
| 2012/0022389 A1 | 1/2012 | Sanders |
| 2012/0192874 A1 | 8/2012 | Bolea et al. |
| 2013/0085546 A1 | 4/2013 | Bolea et al. |

FOREIGN PATENT DOCUMENTS

| | | |
|---|---|---|
| EP | 1 404 221 B1 | 2/2007 |
| EP | 1 854 494 A1 | 11/2007 |
| EP | 1 322 384 B1 | 12/2007 |
| JP | 53118893 | 10/1978 |
| JP | 9-294819 | 11/1997 |
| JP | 2000-506601 | 5/2000 |
| JP | 2000-508562 | 7/2000 |
| JP | 2003-305135 | 10/2003 |
| JP | 2004-508908 | 3/2004 |
| JP | 2004-532707 | 10/2004 |
| JP | 3688301 | 6/2005 |
| JP | 2005-521485 | 7/2005 |
| JP | 2007-21156 | 2/2007 |
| WO | WO 98/20938 | 5/1998 |
| WO | WO 02/24279 | 3/2002 |
| WO | WO 03/000133 | 1/2003 |
| WO | WO 03/000347 A1 | 1/2003 |
| WO | WO 03/082393 A1 | 10/2003 |

(56) References Cited

FOREIGN PATENT DOCUMENTS

| WO | WO 2005/004993 A1 | 1/2005 |
|---|---|---|
| WO | WO 2006/045251 A1 | 5/2006 |
| WO | WO 2006/063339 A2 | 6/2006 |
| WO | WO 2007/134458 A1 | 11/2007 |
| WO | WO 2008/046190 | 4/2008 |

OTHER PUBLICATIONS

Kirkness et al., "Nasal airflow dynamics: mechanisms and responses associated with an external nasal dilator strip," University of Western Sydney, T.C. Amis School of Science, Department of Respiratory Medicine, Westmead Hospital and University of Sydney, Westmead, Australia, 2000.

De Almeida et al., "Nasal pressure recordings to detect obstructive sleep apnea," *Sleep and Breathing*, Feb. 25, 2006, pp. 62-69, vol. 10 (2), Springer Heidelberg.

Saslow et al., "Work of breathing using high-flow nasal cannula in preterm infants," *Journal of Perinatology*, May 11, 2006, pp. 476-480, vol. 26 (8), Nature Publishing Group.

Campbell et al., "Nasal Continuous positive airway pressure from high flow cannula versus Infant Flow for preterm infants," *Journal of Perinatology*, Jul. 2006, pp. 546-549, vol. 26 (9), Nature Publishing Group.

Trevisanuto et al., "A new device for administration of continuous positive airway pressure in preterm infants: comparison with a standard nasal CPAP continuous positive airway pressure system," *Intensive Care Medicine*, Apr. 2005, pp. 859-864, vol. 31 (6), Springer-Verlag.

Verse et al., "New developments in the therapy of obstructive sleep apnea," *European Archives of Oto-Rhino-Laryngology*, Jan. 2001, pp. 31-37, vol. 258 (1), Springer-Verlag.

Paquereau et al., "Positive pressure titration in the treatment of obstructive sleep apnea syndrome using continuous airway positive pressure," *Revue Des Maladies Respiratoires*, Apr. 2000, pp. 459-465, vol. 17 (2), Masson Editeur.

Mahadevia et al., "Effects of expiratory positive airway pressure on sleep-induced respiratory abnormalities in patients with hypersomnia-sleep apnea syndrome," *Am. Rev. Respir. Dis.*, Feb. 1983, vol. 128, pp. 708-711.

Tiran et al., "An Improved Device for Posterior Rhinomanometry to Measure Nasal Resistance," *Journal of Biomechnical Engineering*, Nov. 2005, vol. 127, pp. 994-997.

Noseda et al., "Compliance with nasal continuous positive airway pressure assessed with a pressure monitor: pattern of use and influence of sleep habits," Chest Clinics and Sleep Laboratories, Hôpitaux Erasme et Brugmann, Université Libre de Bruxelles, Brussels, Belgium, 2000, vol. 94, pp. 76-81.

Goding Jr. et al., "Relief of Upper Airway Obstruction With Hypoglossal Nerve Stimulation in the Canine," *The Laryngoscope*, Feb. 1998, pp. 162-169, vol. 108, Lippincott-Raven Publishers, U.S.A.

Sahin et al., "Chronic recordings of hypoglossal nerve activity in a dog model of upper airway obstruction," *Journal of Applied Physiology* 87(6), 1999, The American Physiological Society, pp. 2197-2206.

Ferguson et al., "Effect of Mandibular and Tongue Protrusion on Upper Airway Size During Wakefulness," *American Journal of Respiratory and Critical Care Medicine*, 1997, pp. 1748-1754, vol. 1553.

Isono et al., "Interaction of cross-sectional area, driving pressure, and airflow of passive velopharynx," *American Physiological Society*, 1997, pp. 851-859, vol. 83.

Oliven et al., "Effect of genioglossus contraction on pharyngeal lumen and airflow in sleep apnoea patients," *European Respiratory Journal*, 2007, pp. 748-758, vol. 30, No. 4.

Huang et al. "Dilation of the oropharynx via selective stimulation of the hypoglossal nerve." J. Neural Eng. 2005; 2:73-80.

Statement of Grounds filed in Opposition of EP Pat. No. 2 116 274 dated Jul. 25, 2012 (32 pages).

Response to the Notice of Opposition for Opposition against patent EP 2 116 274 (Application No. 09 161 958.5) dated Dec. 2, 2013 (30 pages).

\* cited by examiner

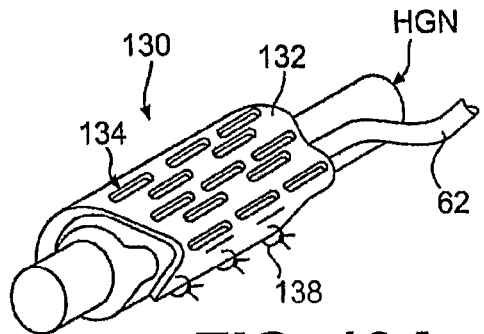 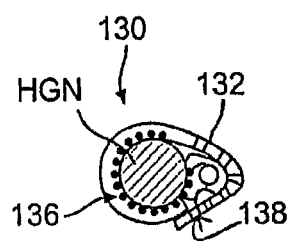
FIG. 13A  FIG. 13B
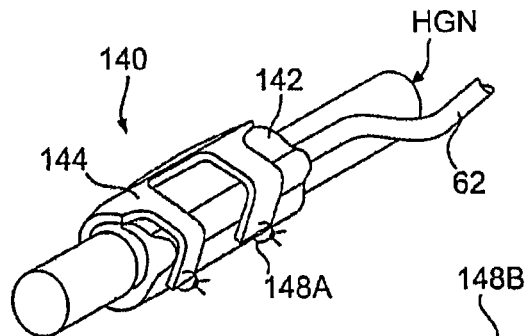 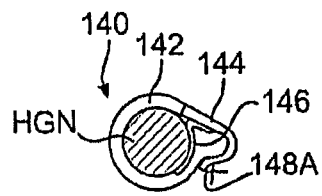
FIG. 14A  FIG. 14B
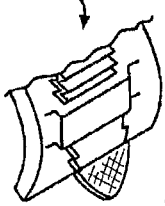
FIG. 14C
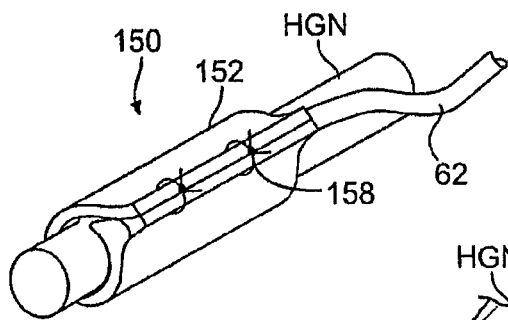 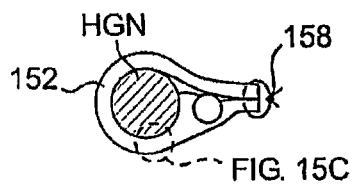
FIG. 15A  FIG. 15B
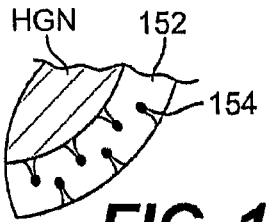
FIG. 15C

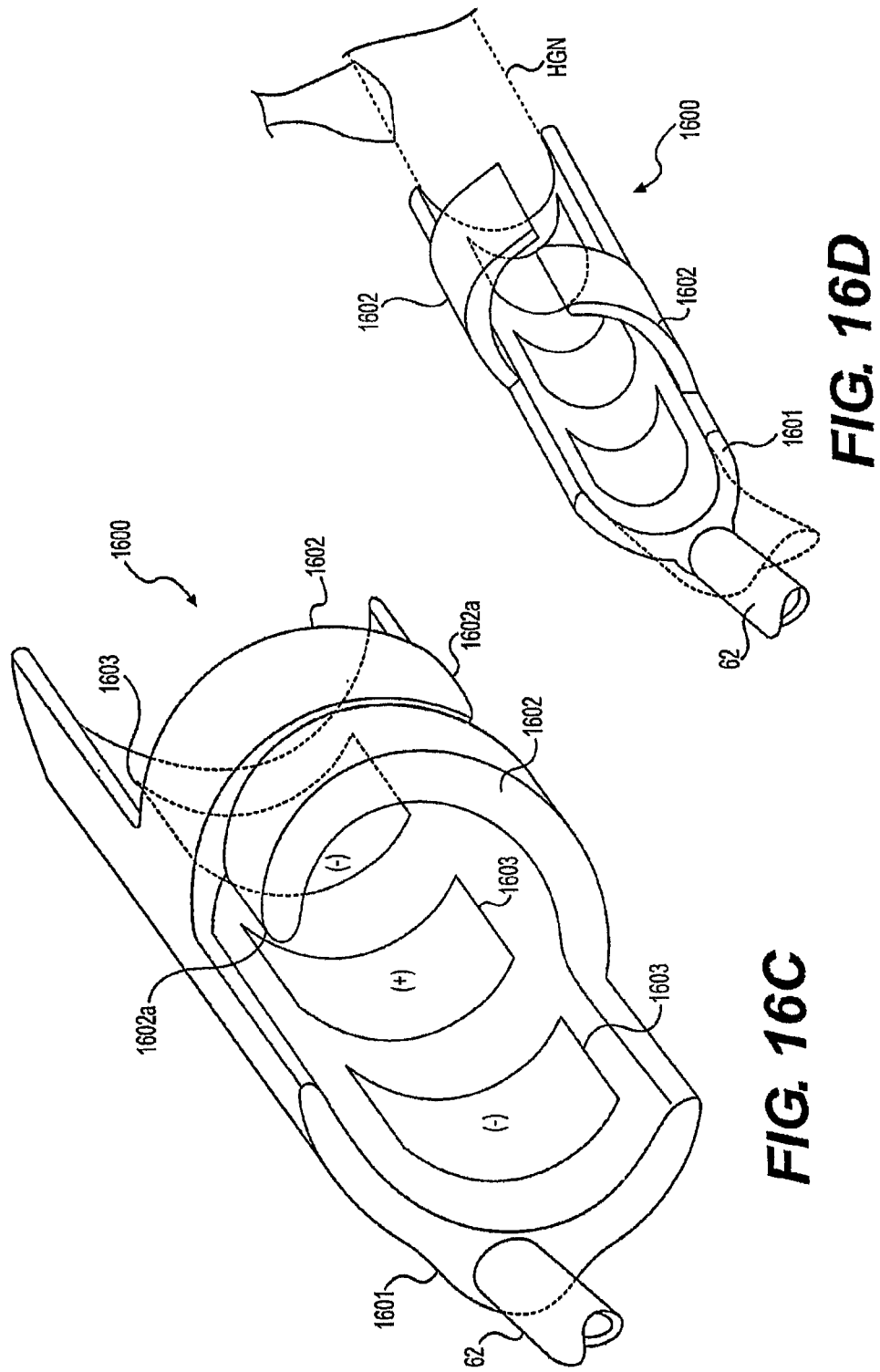

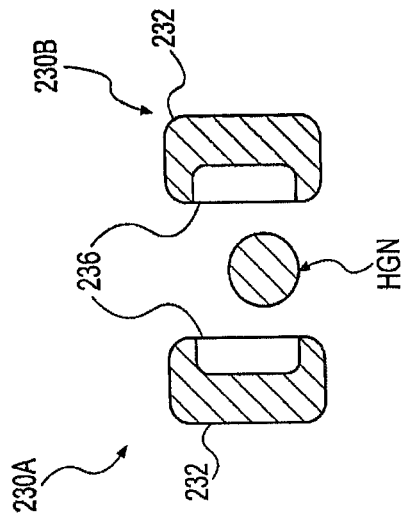
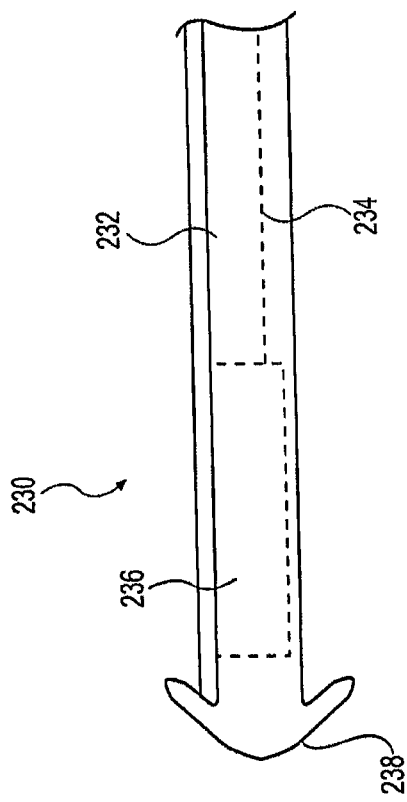

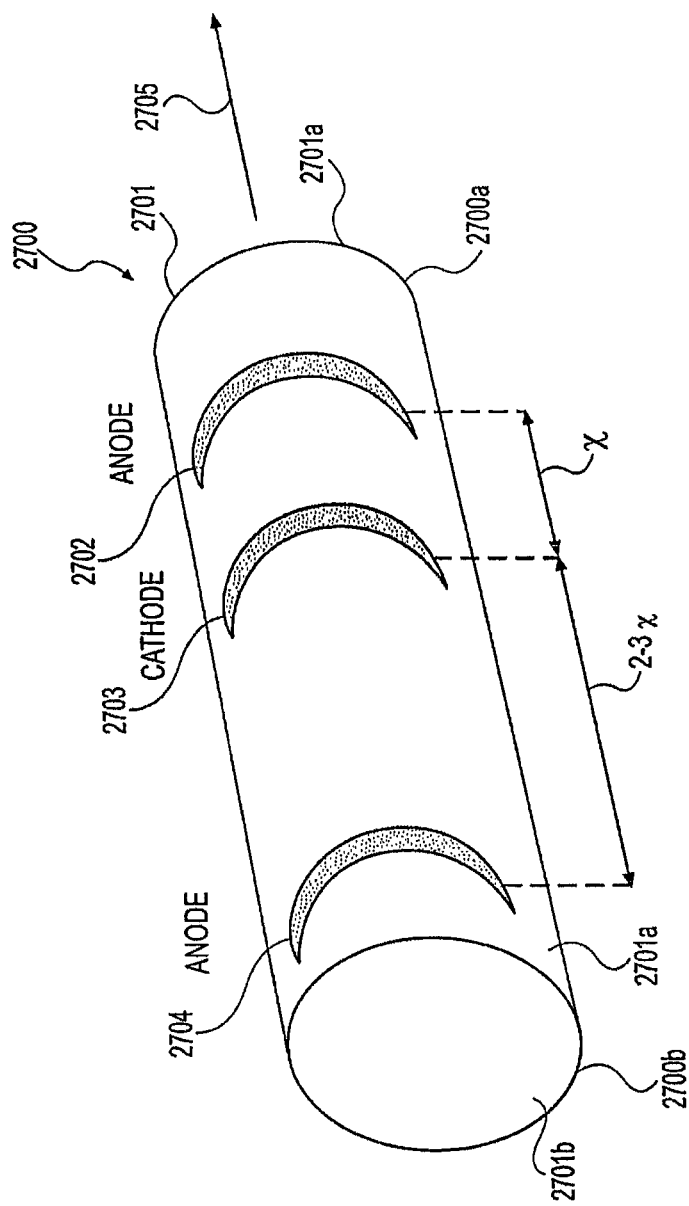

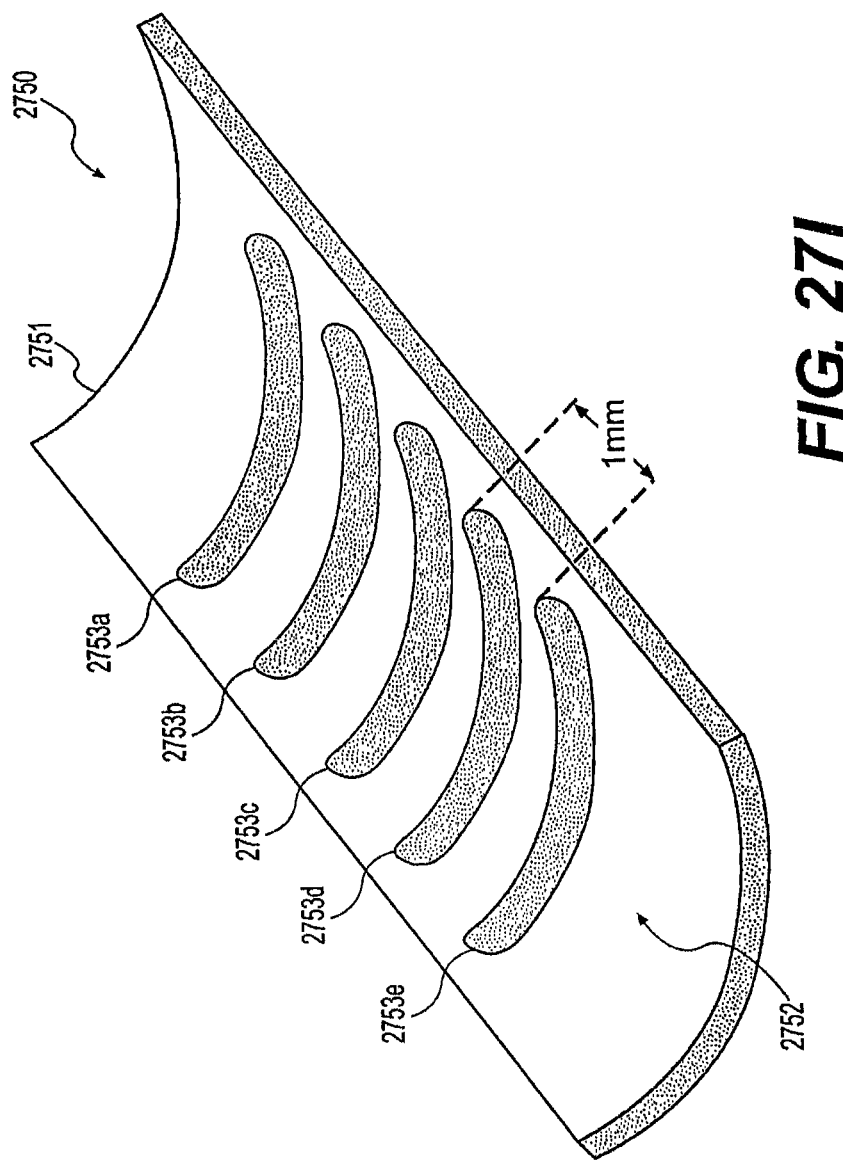

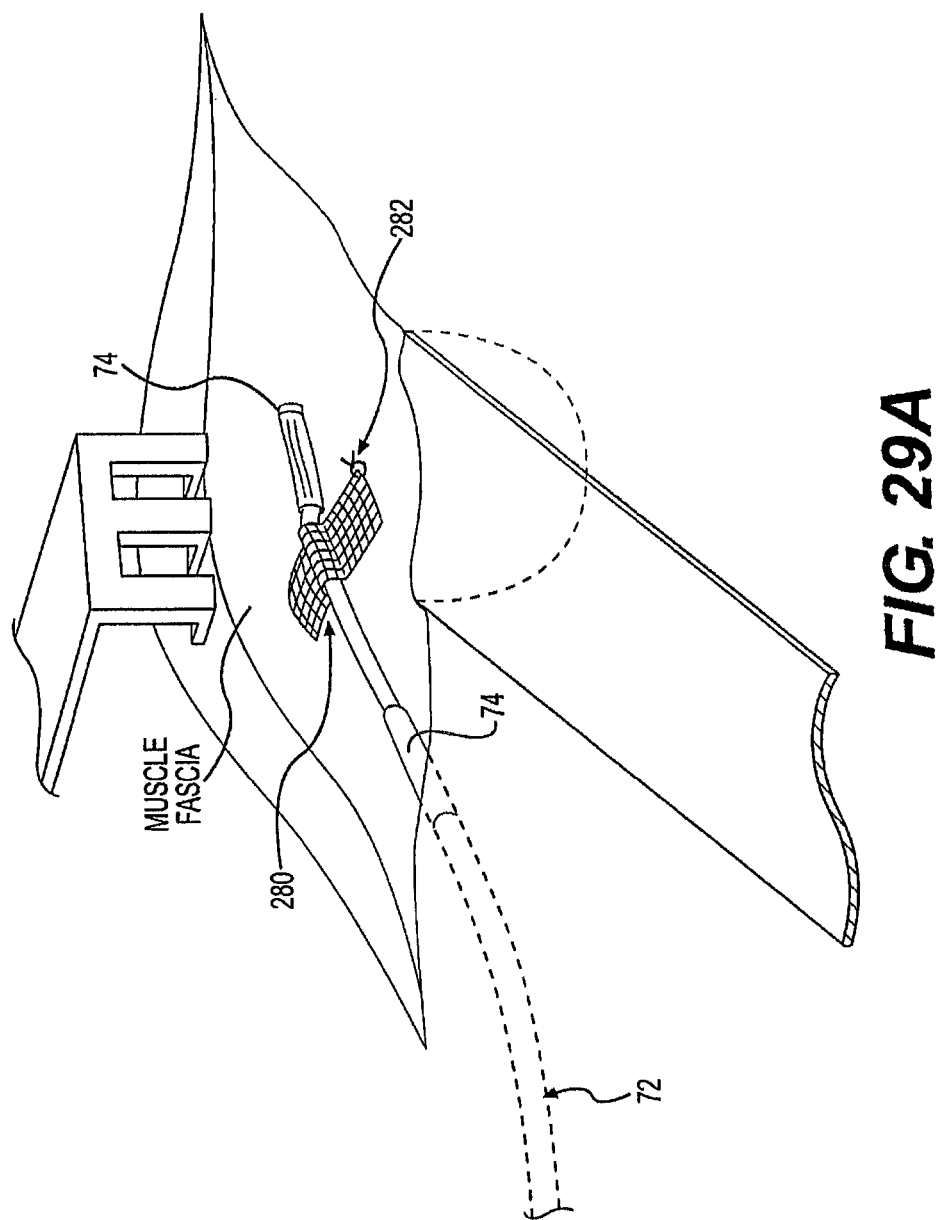

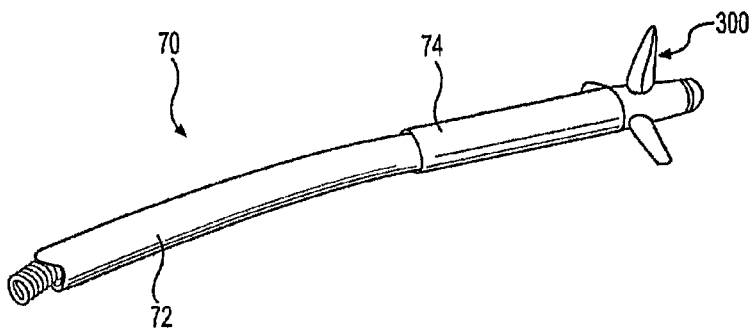
FIG. 31A
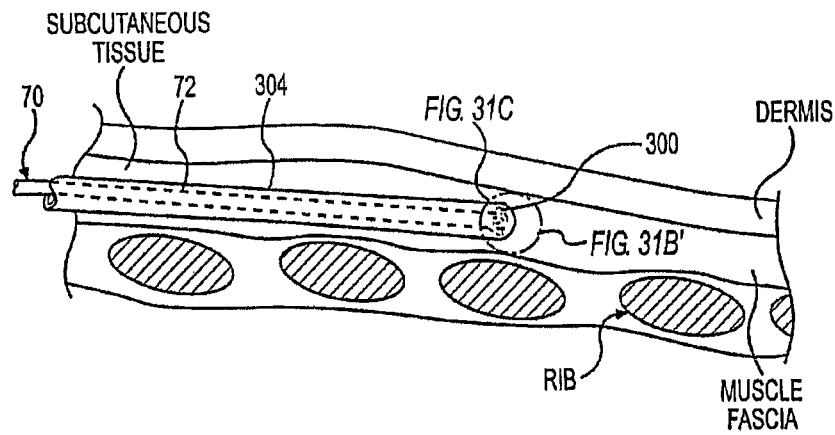
FIG. 31B
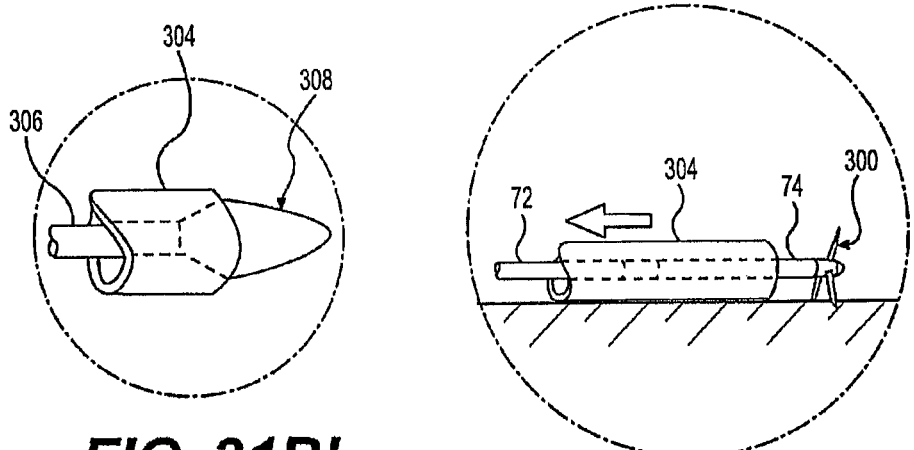
FIG. 31B'
FIG. 31C

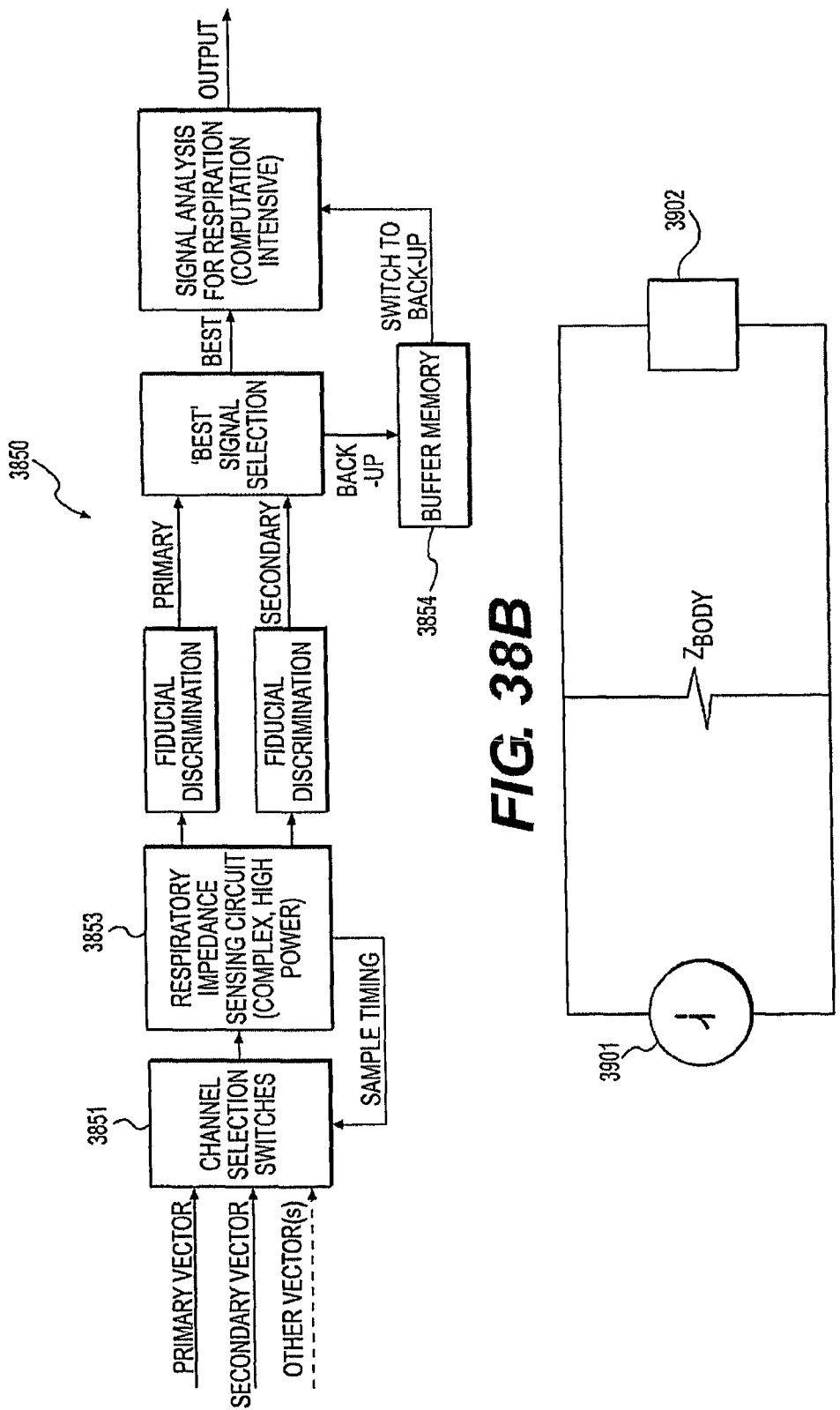

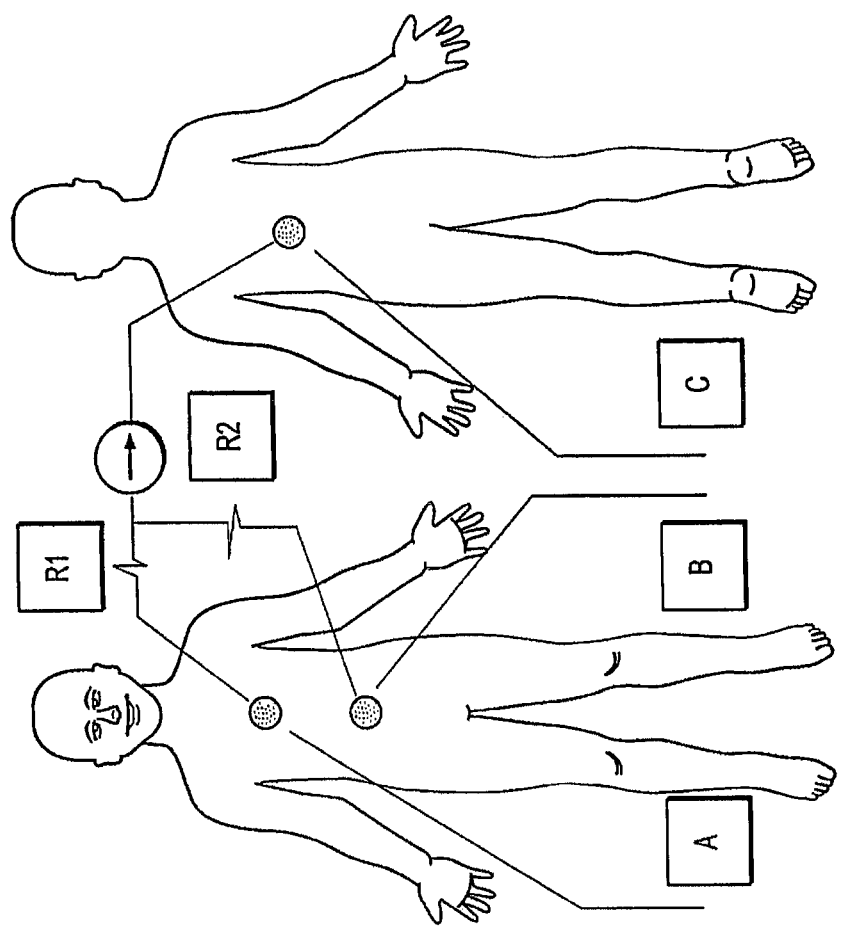

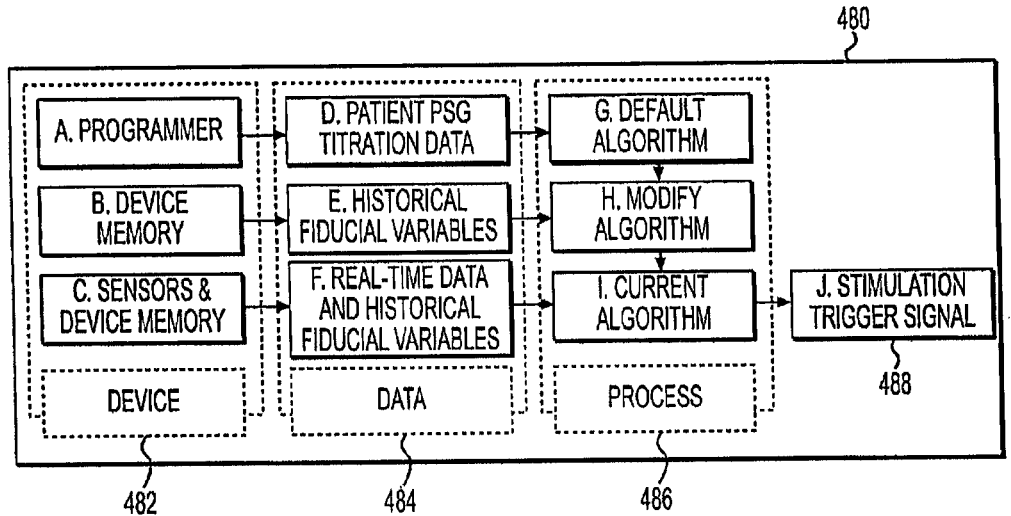

FIG. 48

| REFERENCE MARKER ON GRAPH | VARIABLE NAME | VALUE & TIME OF EVENT |
|---|---|---|
| T | T | TIME OF ONSET OF INSPIRATION AS INDICATED BY PRESSURE SENSOR IN-LINE WITH AIRFLOW. |
|  | T.est | ESTIMATED ONSET AS CALCULATED FROM HISTORICAL FIDUCIAL VARIABLES. |
|  | T.pred | PREDICTED ONSET AS CALCULATED FROM REAL-TIME DATA AND HISTORICAL FIDUCIAL VARIABLES. |
| A | Vmax t.Vmax | POSITIVE PEAK OF PRIMARY SIGNAL |
| B | Vmin t.Vmin | MINIMUM OF PRIMARY SIGNAL BETWEEN SUCCESSIVE POSITIVE PEAKS |
| C | dV.in t.dV.in | MOST POSITIVE 1ST DERIVATIVE DURING EXPIRATION |
| D | dV.ex t.dV.ex | MOST NEGATIVE 1ST DERIVATIVE DURING EXPIRATION |
| E | D2V.in t.d2V.in | MOST POSITIVE 2ND DERIVATIVE DURING INSPIRATION. THIS TYPICALLY OCCURS SOON AFTER ONSET OF INSPIRATION. |
| F | d2V.pk t.d2V.pk | MOST NEGATIVE 2ND DERIVATIVE SLOPE. THIS OCCURS AT OR NEAR THE POSITIVE PEAK OF PRIMARY SIGNAL. |
| G | d2V.ex t.d2V.ex | MOST POSITIVE 2ND DERIVATIVE FOLLOWING INSPIRATION. THIS TYPICALLY OCCURS NEAR THE OFFSET OF EXPIRATION. |
| C2 | V.in50 t.V.in50 | THE POINT AT WHICH THE PRIMARY SIGNAL'S MAGNITUDE IS 50% BETWEEN POSITIVE PEAK AND PRECEEDING MINIMUM. |
| D2 | V.ex50 t.V.ex50 | THE POINT AT WHICH THE PRIMARY SIGNAL'S MAGNITUDE IS 50% BETWEEEN POSITIVE PEAK AND FOLLOWING MINIMUM. |

FIG. 49

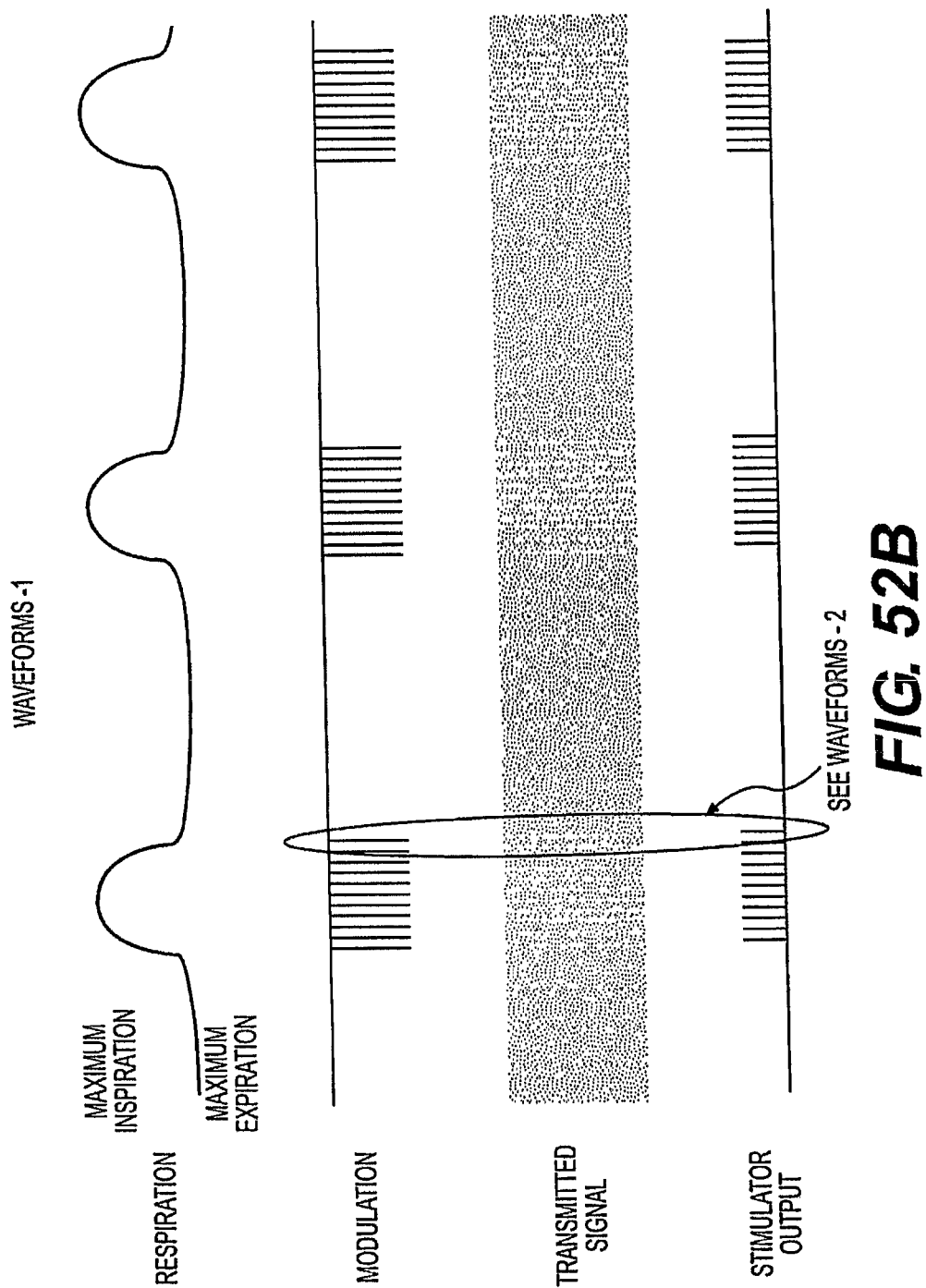

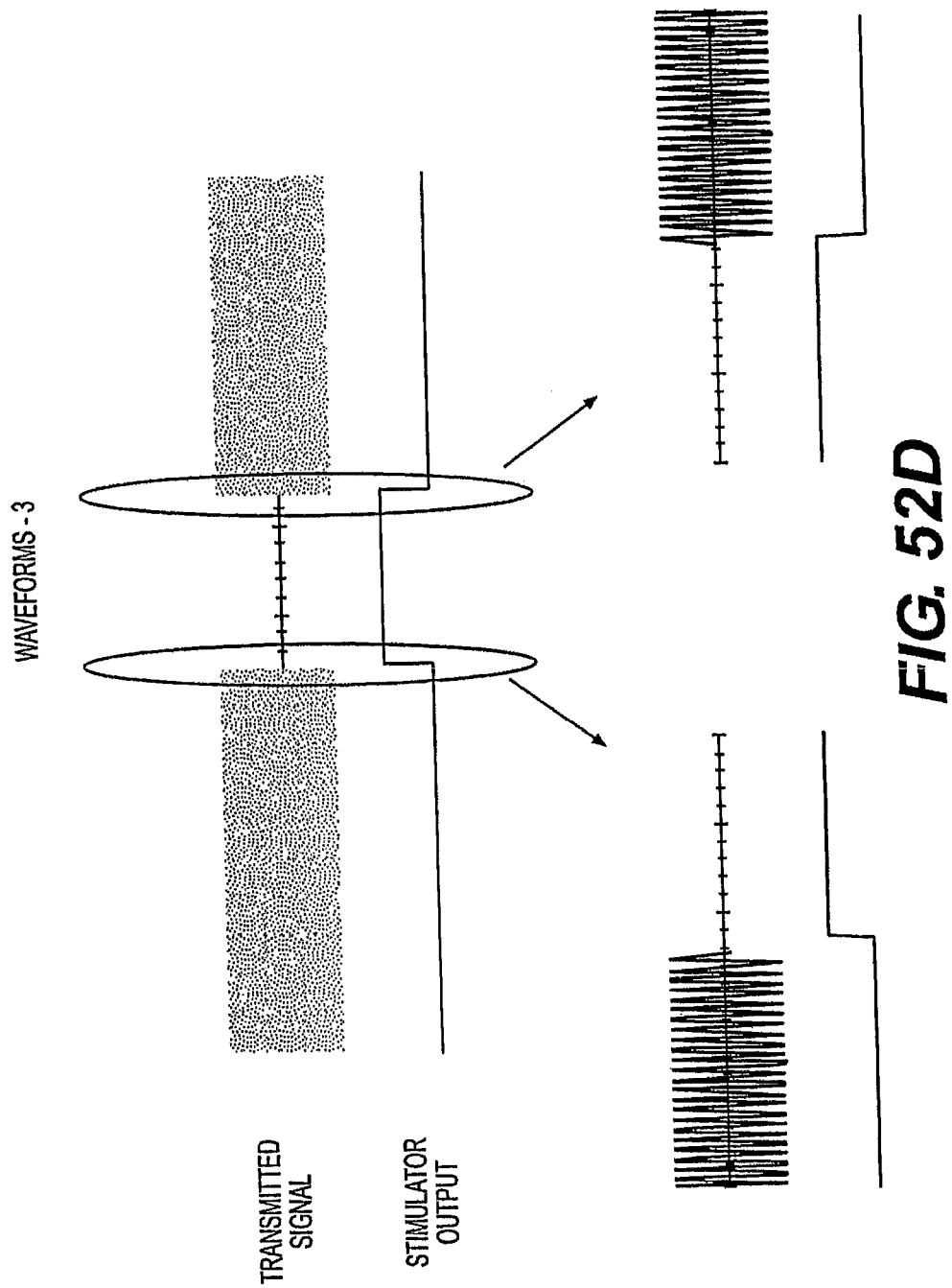

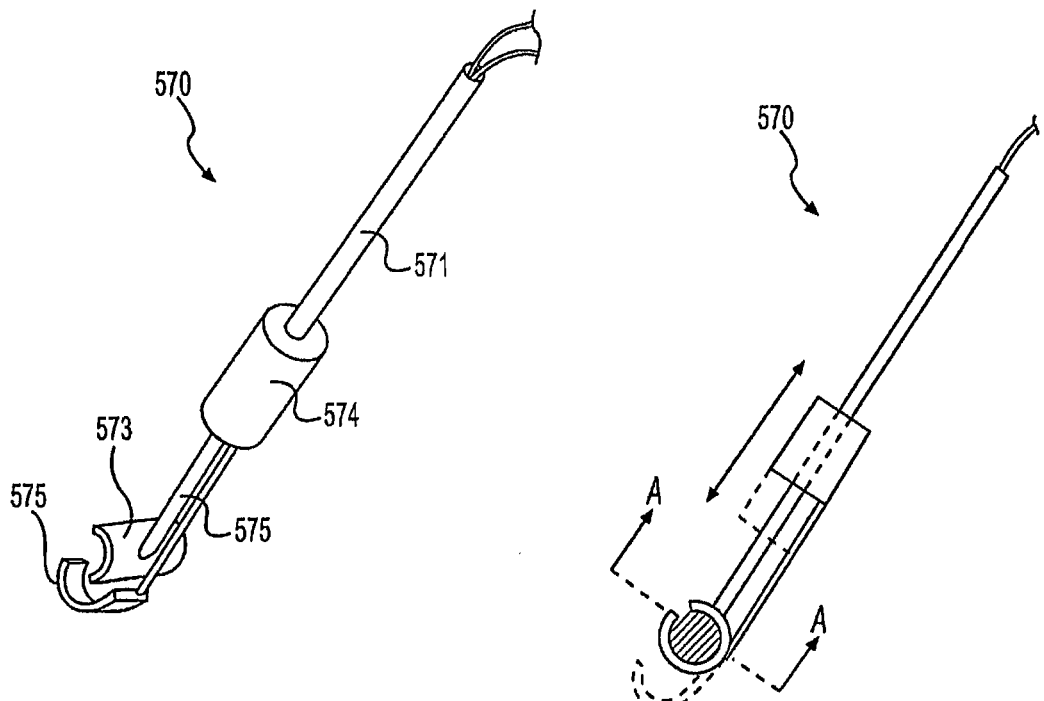
FIG. 57A
FIG. 57B
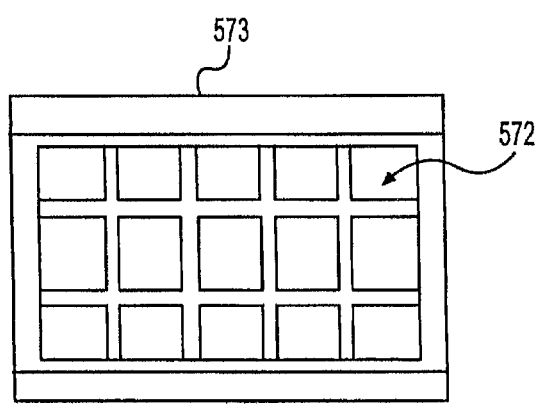
FIG. 57C

| | |
|---|---|
| P | Mask Pressure |
| P=hold | Pressure is set to eliminate flow restriction |
| ↓P1 | Decrease Mask Pressure 1 cmH2O |
| S(A) | Stimulation Intensity set to A mA |
| S(B) | Stimulation Intensity set to B mA |
| dS | Smallest available increment of stimulation intensity. Either 0.1mA or 0.25 mA. |
| S(B)=S(A)+dS | Stim Intensity for "B" set to "A" plus smallest available increment |
| ΔS | Stim Intensity Contrast. Largest allowed difference between A and B stimulation intensities. |
| S(B)=S(A)+ΔS? | Is Stim Intensity "B" equal to "a" plus largest allowed stim intensity contrast. |
| ↑S(A) | Increment channel A stim intensity by smallest available increment |
| ↑S(B) | Increment channel B stim intensity by smallest available increment |
| F(0) | Flow during non-stimulated breath. |
| F(A) | Flow during S(A) |
| F(B) | Flow during S(B) |
| F(0) = Restricted? | Is flow restricted during non-stimulated breath? |
| F(A) = Restricted? | Is flow restricted during S(A)? |
| F(A)>F(0)? | Is flow during S(A) greater than flow during non-stimulated breath? |
| F(B)>F(A)? | Is flow during S(B) greater than flow during S(A)? |
| S=OFF | Stimulation turned off. |
| S=0A | S(A) is delivered on every other breath. |
| S=0A0B | Out of a 4 breath series, the 1st and 3rd breaths are not stimmed, the S(A) is delivered on the 2nd breath and S(B) is delivered on the 4th breath |

FIG. 76B

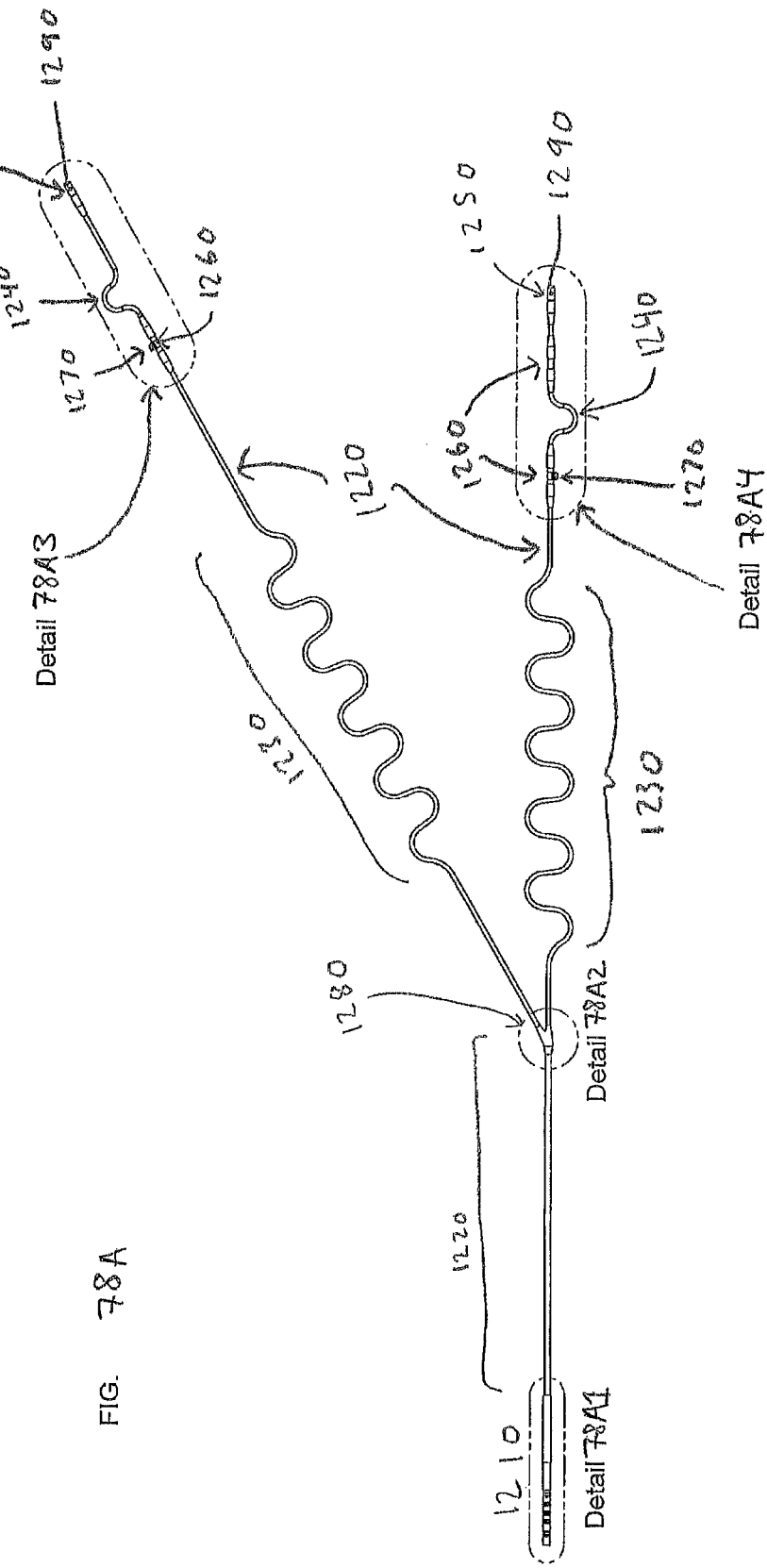

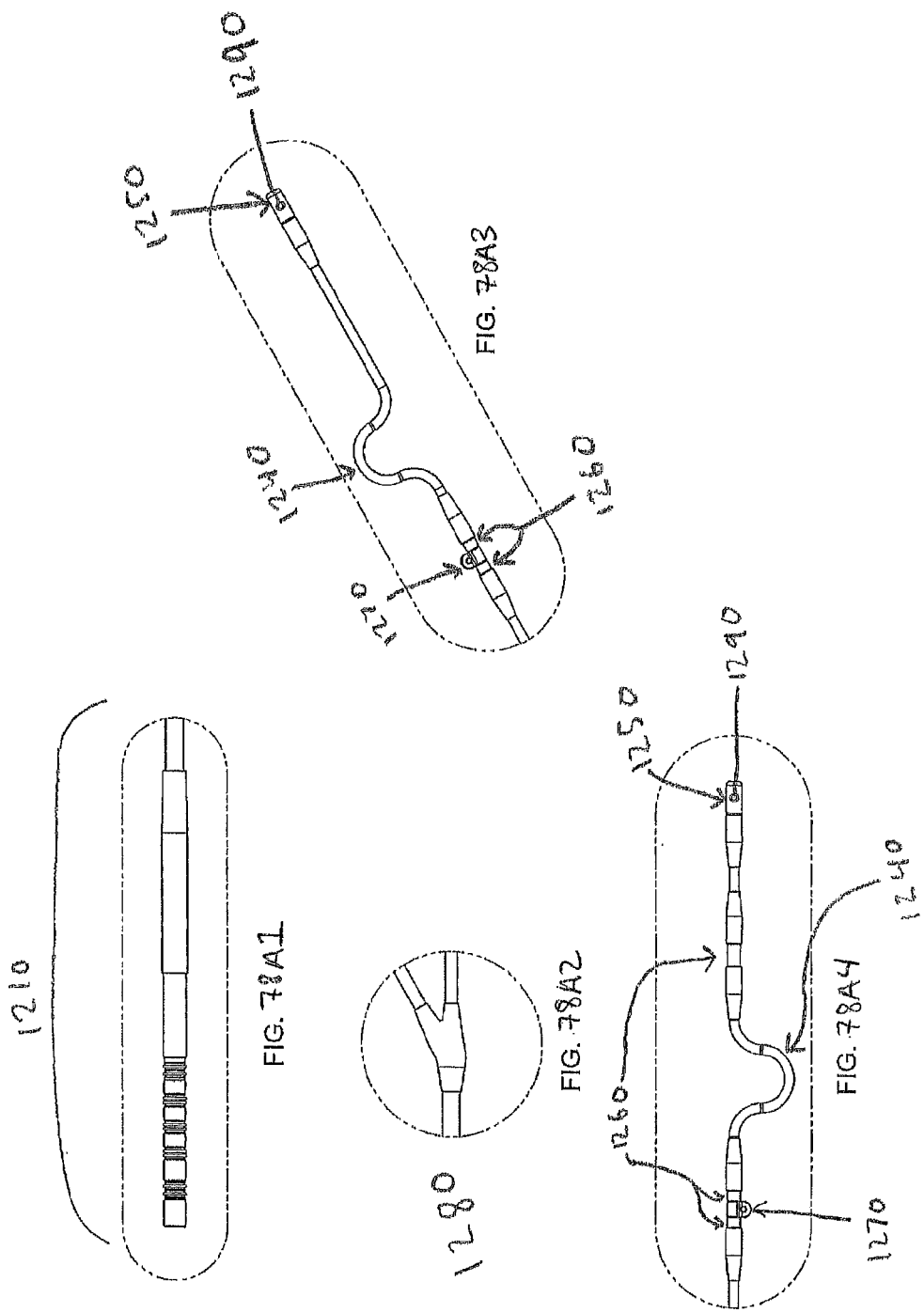

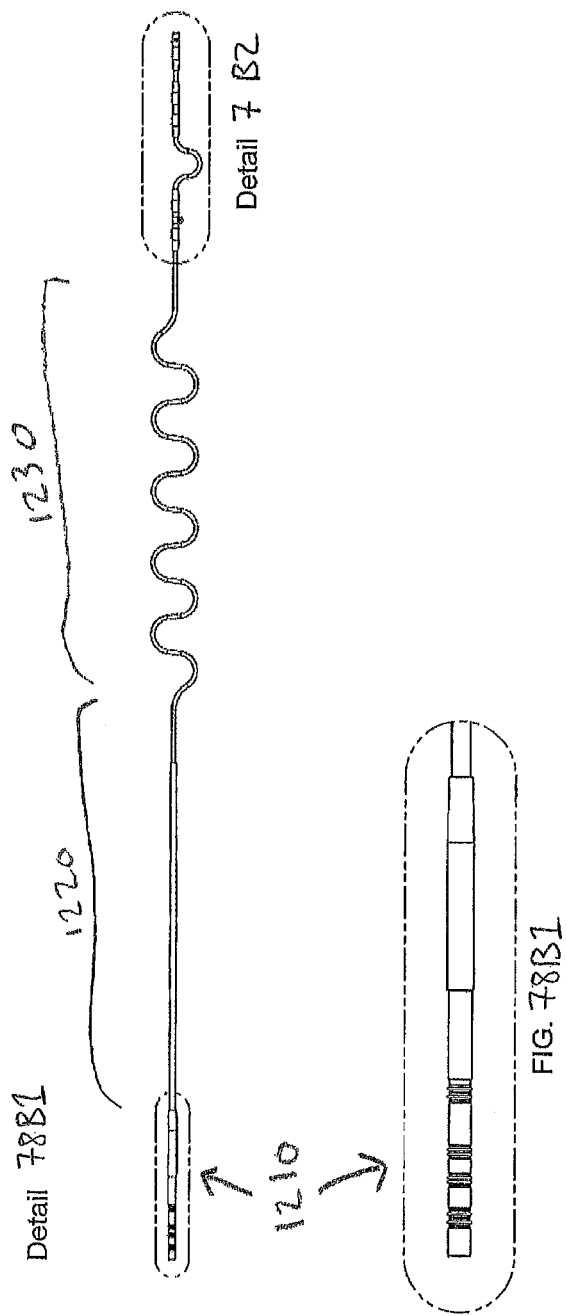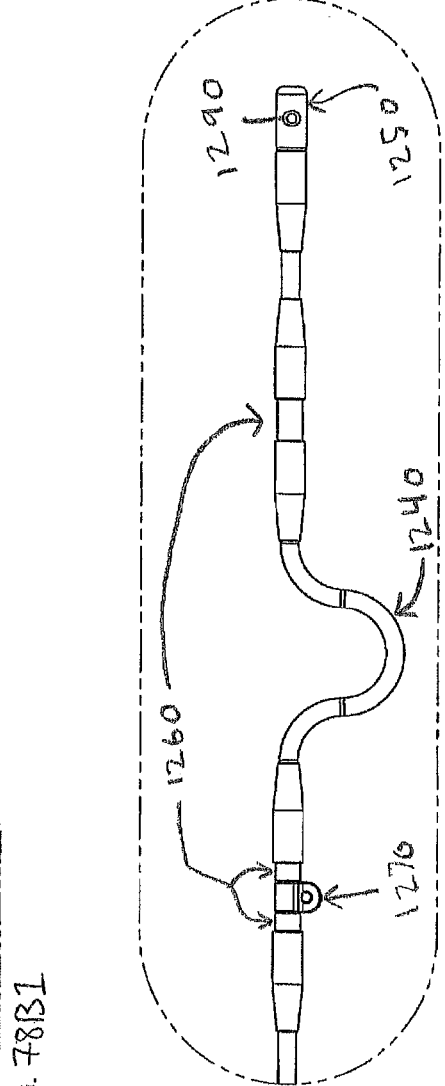

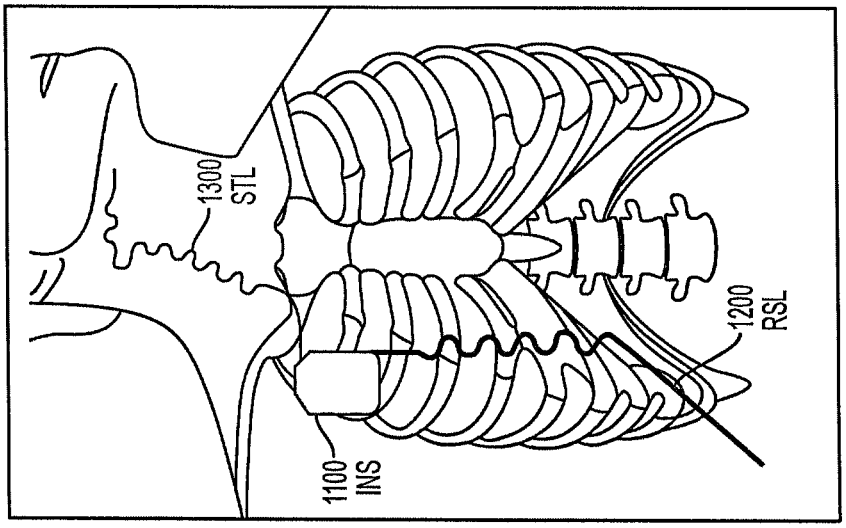
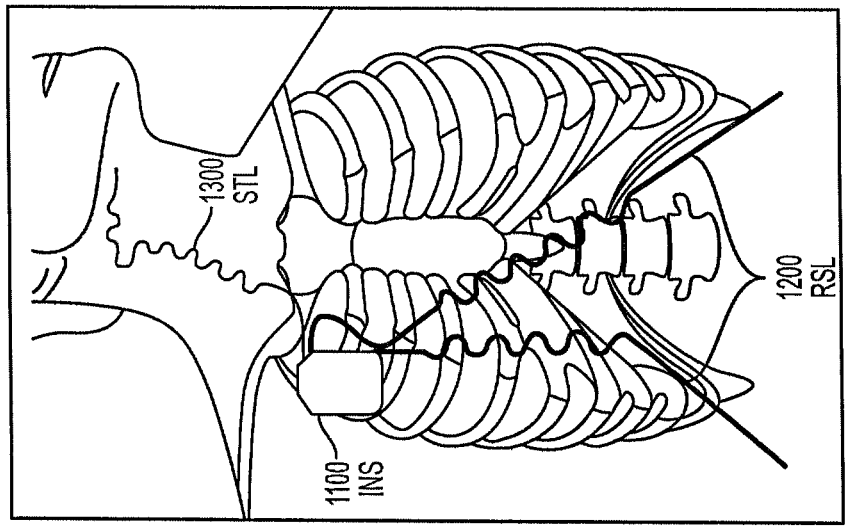

Default Stimulation

Basic Retention Intensity

Retention Intensity

Soft Start

Nested Stimulation

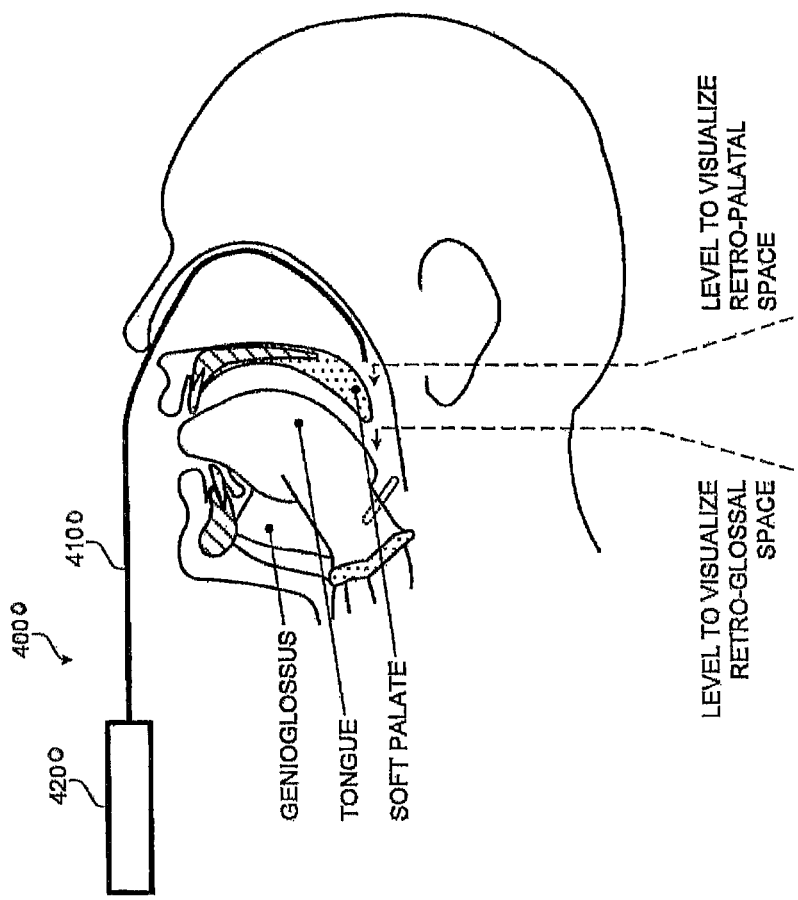
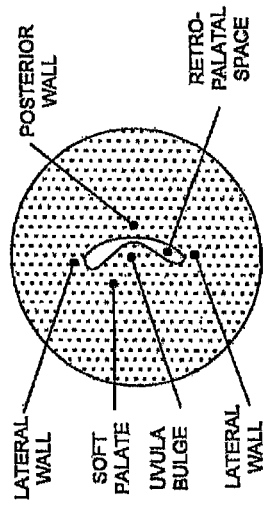
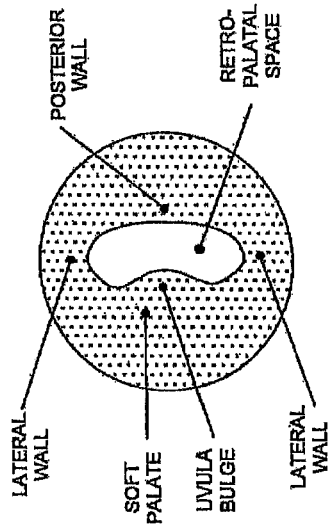
FIG. 88A
FIG. 88B
FIG. 88C

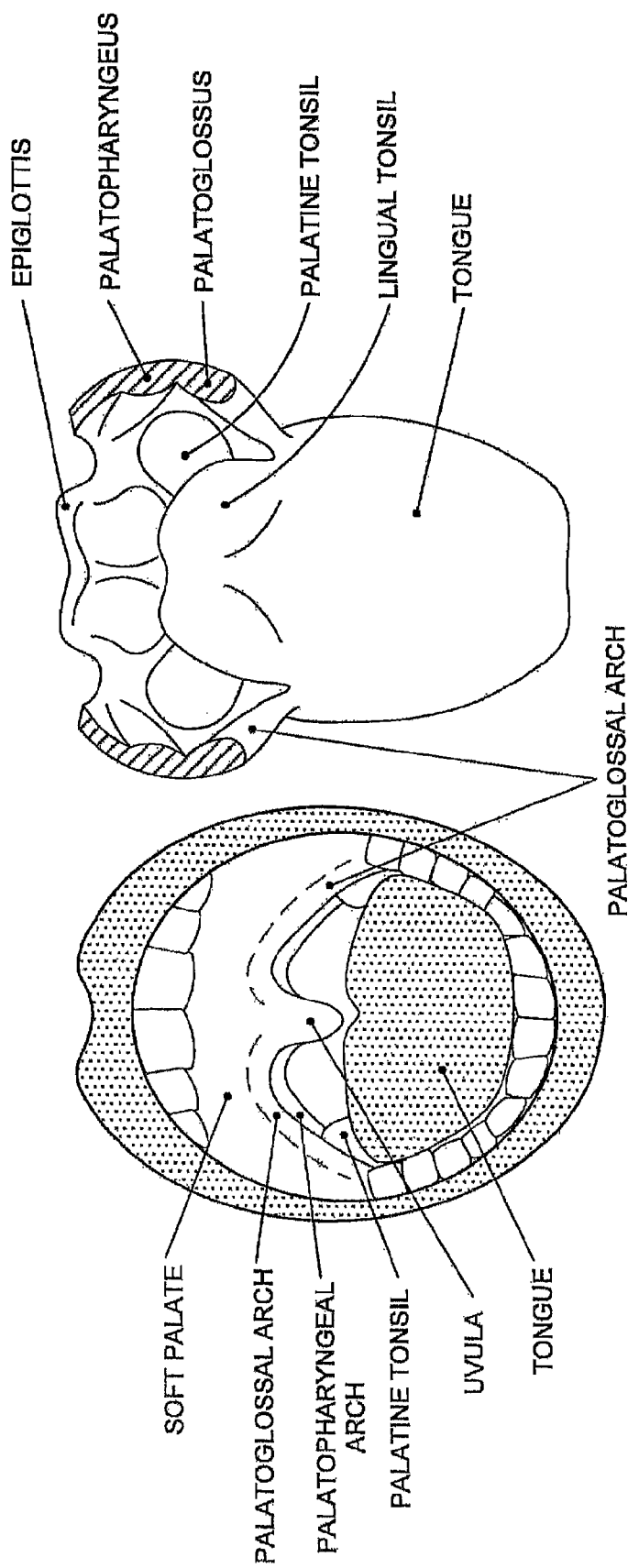

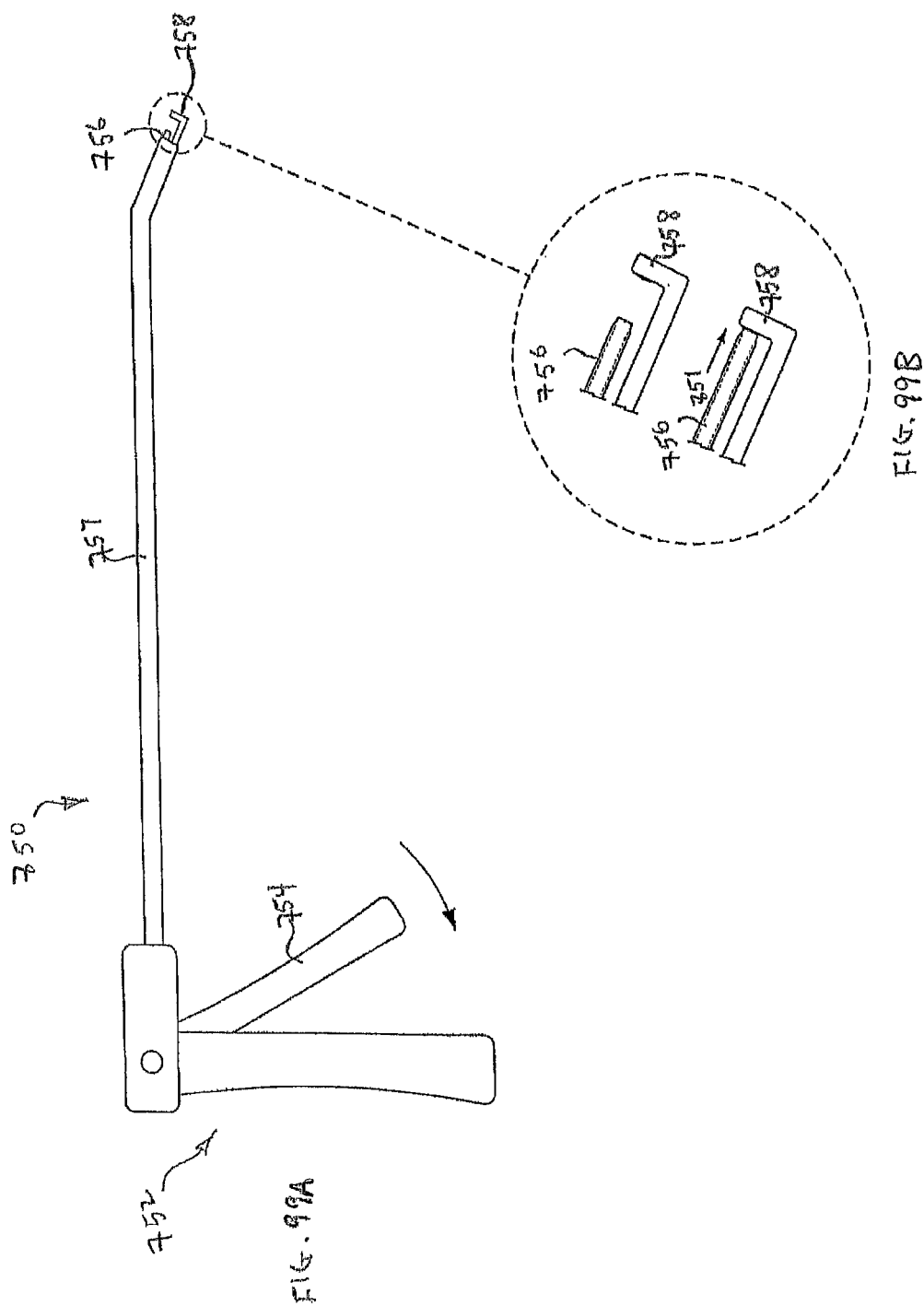

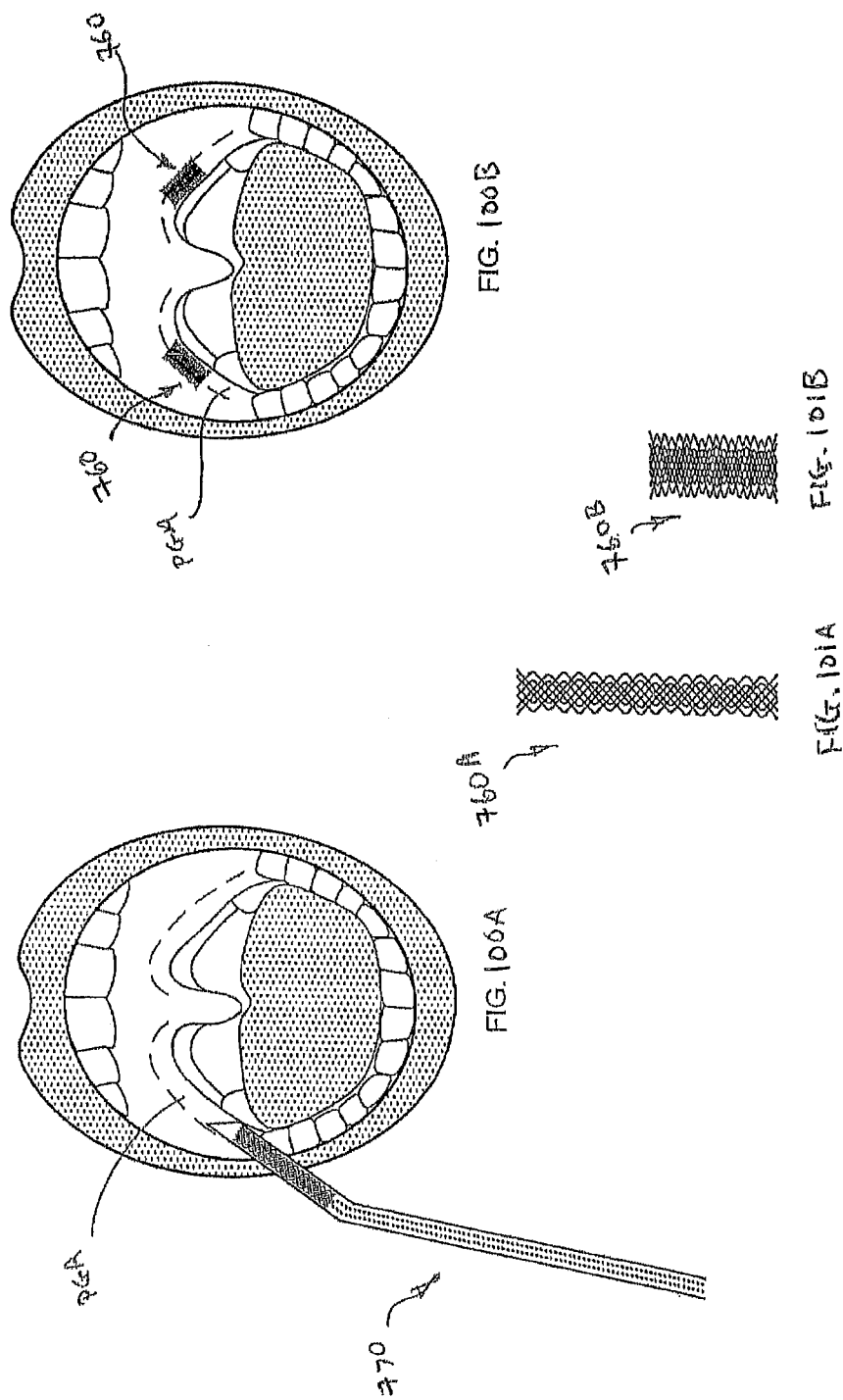

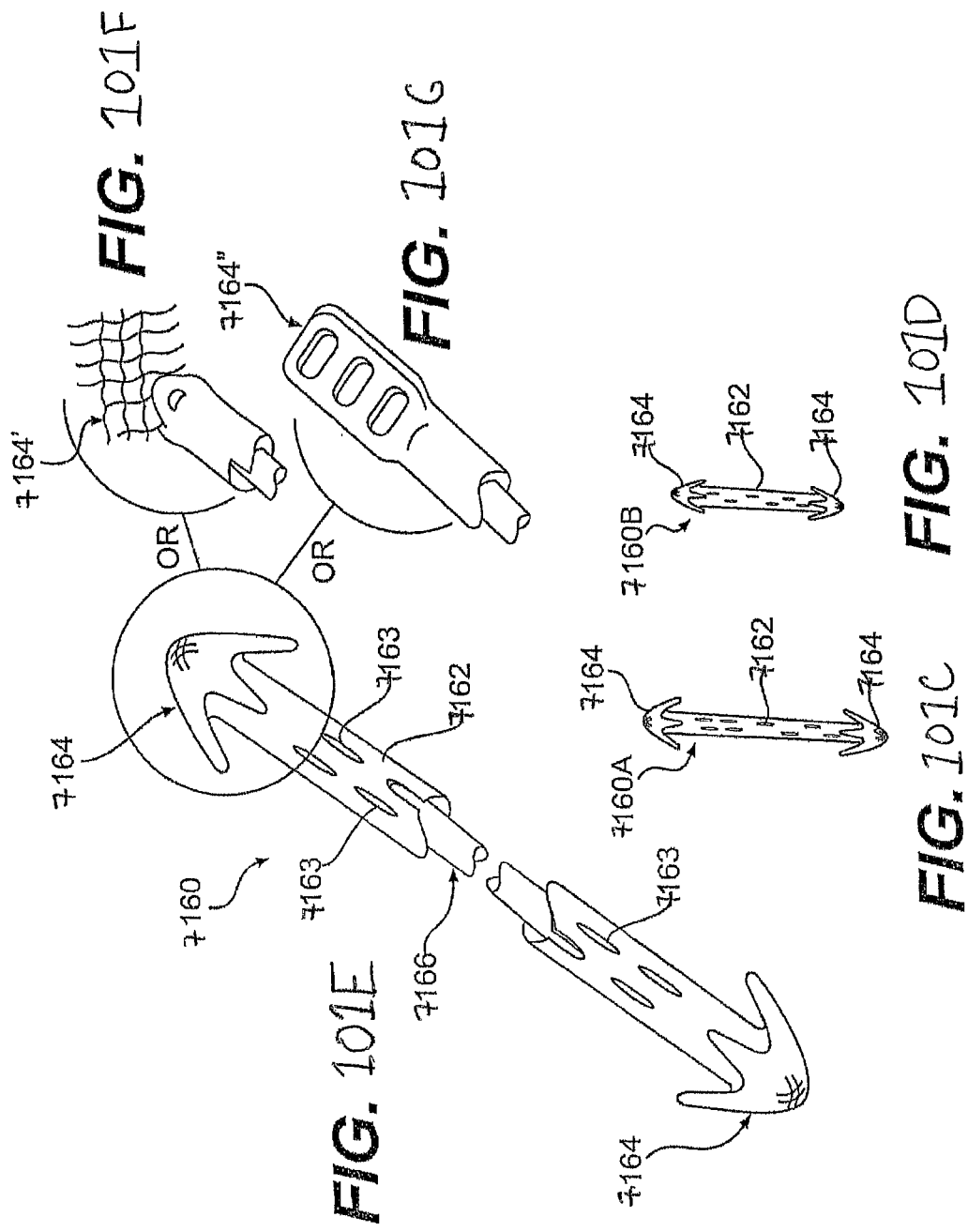

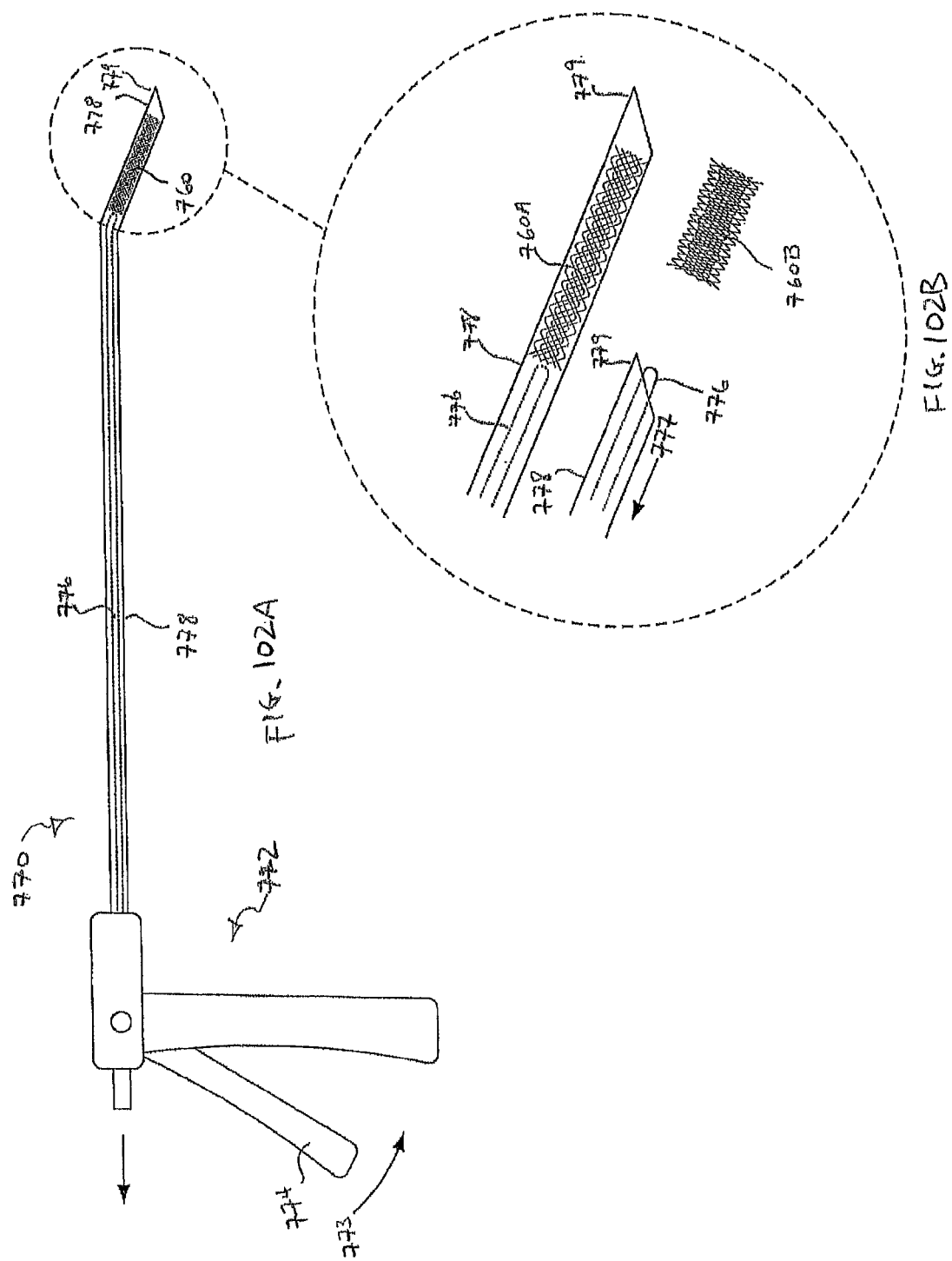

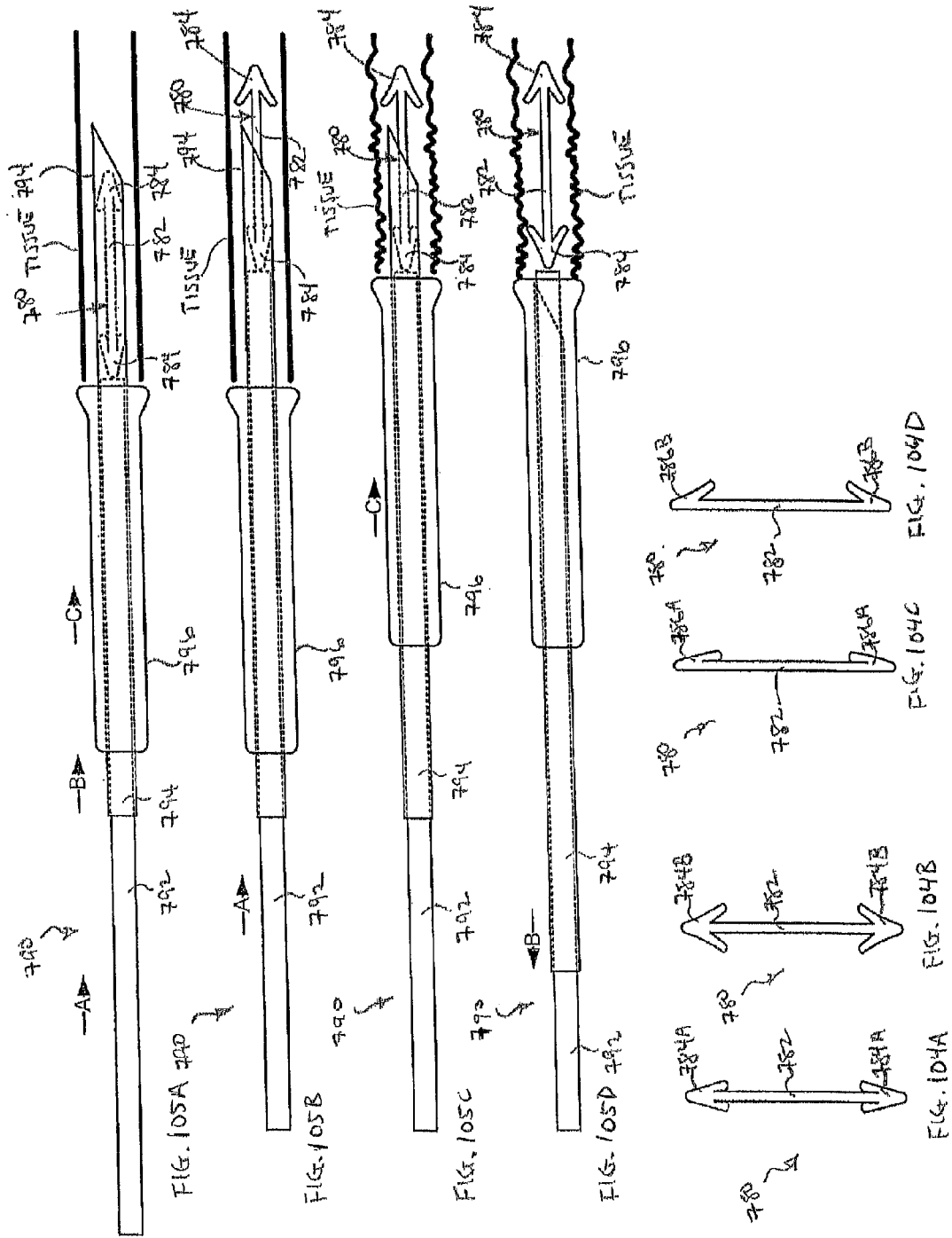

OBSTRUCTIVE SLEEP APNEA TREATMENT DEVICES, SYSTEMS AND METHODS

CROSS-REFERENCE TO RELATED APPLICATIONS

This application is a continuation-in-part application of U.S. application Ser. No. 12/835,984, filed Jul. 14, 2010, which is a continuation of U.S. application Ser. No. 11/907,532, filed Oct. 12, 2007, now U.S. Pat. No. 7,809,442, which claims the benefits of priority to U.S. Provisional Patent Application Nos. 60/851,386, filed Oct. 13, 2006, and 60/918,257, filed Mar. 14, 2007. This application is also a continuation-in-part application of U.S. application Ser. No. 12/650,045, filed Dec. 30, 3009, which claims the benefits of priority to U.S. Provisional Patent Application No. 61/204,008, filed Dec. 31, 2008. This application is also a continuation-in-part of U.S. application Ser. No. 13/106,460, filed May 12, 2011, which claims the benefits of priority to U.S. Provisional Patent Application No. 61/437,573, filed Jan. 28, 2011. This application is also a continuation-in-part of U.S. application Ser. No. 13/205,315, filed Aug. 8, 2011, which is a continuation of U.S. application Ser. No. 13/113,524, filed May 23, 2011, now abandoned, which claims the benefits of priority to U.S. Provisional Patent Application Nos. 61/467,758, filed Mar. 25, 2011, and 61/437,573, filed Jan. 28, 2011. This application is also a continuation-in-part of U.S. application Ser. No. 13/633,670, filed Oct. 8, 2013, which claims the benefits of priority to U.S. Provisional Patent Application No. 61/542,617, filed Oct. 3, 2011. This application is also related U.S. application Ser. No. 11/907,533, filed Oct. 12, 2007, now U.S. Pat. No. 8,417,343, which claims the benefits of priority to U.S. Provisional Patent Application Nos. 60/851,386, filed Oct. 13, 2006, and 60/918,257, filed Mar. 14, 2007. Each of the aforementioned applications is incorporated by reference herein in its entirety.

FIELD OF THE INVENTION

The embodiments described herein relate to devices, systems and associated methods for treating sleeping disorders. More particularly, the embodiments described herein relate to devices, systems and methods for treating obstructive sleep apnea.

The embodiments described herein relate to devices, systems and associated methods for treating sleep disordered breathing. More particularly, the embodiments described herein relate to devices, systems and methods for treating obstructive sleep apnea.

The embodiments described herein relate, for example, to devices and methods for modifying tissue of the upper airway for the treat of obstructive sleep apnea and snoring.

BACKGROUND OF THE INVENTION

Obstructive sleep apnea (OSA) is highly prevalent, affecting one in five adults in the United States. One in fifteen adults has moderate to severe OSA requiring treatment. Untreated OSA results in reduced quality of life measures and increased risk of disease including hypertension, stroke, heart disease, etc.

Continuous positive airway pressure (CPAP) is a standard treatment for OSA. While CPAP is non-invasive and highly effective, it is not well tolerated by patients. Patient compliance for CPAP is often reported to be between 40% and 60%.

Surgical treatment options for OSA are available too. However, they tend to be highly invasive (result in structural changes), irreversible, and have poor and/or inconsistent efficacy. Even the more effective surgical procedures are undesirable because they usually require multiple invasive and irreversible operations, they may alter a patient's appearance (e.g., maxillo-mandibular advancement), and/or they may be socially stigmatic (e.g., tracheostomy).

U.S. Pat. No. 4,830,008 to Meer proposes hypoglossal nerve stimulation as an alternative treatment for OSA. An example of an implanted hypoglossal nerve stimulator for OSA treatment is the Inspire™ technology developed by Medtronic, Inc. (Fridley, Minn.). The Inspire device is not FDA approved and is not for commercial sale. The Inspire device includes an implanted neurostimulator, an implanted nerve cuff electrode connected to the neurostimulator by a lead, and an implanted intra-thoracic pressure sensor for respiratory feedback, stimulus trigger, and/or timing of stimulus delivery. The Inspire device was shown to be efficacious (approximately 75% response rate as defined by a 50% or more reduction in RDI (Respiratory Disturbance Index) and a post RDI of .ltoreq.20) in an eight patient human clinical study, the results of which were published by Schwartz et al. and Eisele et al. However, both authors reported that only three of eight patients remained free from device malfunction, thus demonstrating the need for improvements.

Hypoglossal nerve stimulation has been proposed for the treatment of obstructive sleep apnea. An example of an implantable hypoglossal nerve stimulation system is described in U.S. Pat. No. 7,809,442 to Bolea et al. Published data suggest that response to hypoglossal nerve stimulation varies across subjects. Before undergoing a surgical procedure to implant a hypoglossal nerve stimulation system, it would be desirable to understand the likelihood of therapeutic success, and make clinical judgments accordingly. It would also be desirable to consider adjunct therapies to hypoglossal nerve stimulation to improve outcomes thereof.

SUMMARY OF THE INVENTION

To address this and other unmet needs, the present disclosure provides, in exemplary non-limiting embodiments, devices, systems and methods for nerve stimulation for OSA therapy as described in the following detailed description.

In addition, to address this and other unmet needs, the present disclosure offers, in one example embodiment, a method for treating obstructive sleep apnea by first performing an assessment of the patient that involves observing the patient's upper airway during a tongue protrusion maneuver. The assessment may, for example, be done using endoscopy to observe the upper airway while the patient is awake in the supine position. The tongue protrusion maneuver may, for example, involve the patient volitionally protruding the tongue to its maximal extent with the mouth open or the lips loosely touching the tongue. The tongue protrusion maneuver mimics the effect of genioglossus activation by hypoglossal nerve stimulation (HGNS). Thus, an adequate increase in airway size during the tongue protrusion maneuver would be indicative of likely therapeutic success with HGNS. If the assessment shows an adequate increase in airway size during the maneuver, a HGNS device may be implanted in the patient with a higher confidence in a successful outcome. The principles of the present disclosure may be applied to other therapeutic interventions for OSA involving the upper airway.

Furthermore, to address this and other unmet needs, the present disclosure provides, by way of example, not limitation, embodiments of devices and methods for treating OSA and snoring by modifying pharyngeal tissue of the upper airway such as, e.g., the palatoglossus, palatopharyngeus, pharyngeoepiglottis, and/or lateral walls. The methods described herein may be performed as an adjunct therapy or as a stand-alone procedure. For example, the methods disclosed herein may be combined with interventions targeting the tongue such as, e.g., hypoglossal nerve stimulation, genioglossus-advancement surgery, implantable devices that advance the tongue, mandibular advancement surgery, mandibular advancement oral appliances, etc.

Embodiments of the present disclosure improve the mechanical coupling between the tongue, the soft palate and the lateral walls and/or improve the mechanical properties of the connective structures. This may be accomplished, for example, by shortening or stiffening the palatoglossal arch, palatopharyngeal arch, pharyngoepiglottic fold, and/or lateral walls while retaining the integrity and function of the structures.

BRIEF DESCRIPTION OF THE DRAWINGS

It is to be understood that both the foregoing summary and the following detailed description are exemplary. Together with the following detailed description, the drawings illustrate exemplary embodiments and serve to explain certain principles. In the drawings:

FIGS. 13A, 13B, 14A-14C, 15A-15C, 16A-16F, 17, 18, 19A, 19B, 20, 21A, 21B, 22, and 22A-22D are schematic illustrations of various stimulation lead body and electrode designs for use in a neurostimulator system;

FIGS. 23A, 23B, 23C, 24A, 24B, and 24C schematically illustrate alternative implant procedures and associated tools for the stimulation lead;

FIGS. 27A-27H schematically illustrate field steering embodiments;

FIGS. 27I-27Q schematically illustrate alternative embodiments of nerve cuff electrodes with selective fiber stimulation mechanisms;

FIGS. 28, 29A-29C, 30, 31A-31C, 32A, 32B, 33A, and 33B schematically illustrate alternative fixation techniques for the respiration sensing lead;

FIGS. 38B, 38C, 39, 39A-39D, and 40-46 schematically illustrate alternative respiration signal processing techniques;

FIG. 47 schematically illustrates an alternative respiration detection technique;

FIGS. 48-50 schematically illustrate alternative stimulation trigger algorithms;

FIGS. 57A-57C, 58A, and 58B schematically illustrate alternative intra-operative tools.

FIGS. 73A, 73B, 73C, 74A, 74B, 75, 76A and 76B are charts illustrating various therapy titration methodologies.

FIG. 78A is a perspective view of a bifurcated respiration sensing lead which may be used in the system shown in FIG. 77;

FIG. 78A1 is a detailed perspective view of the proximal connector assembly of the respiration sensing lead shown in FIG. 77;

FIG. 78A2 is a detailed perspective view of the bifurcation section of the respiration sensing lead shown in FIG. 77;

FIG. 78A3 is a detailed perspective view of the contra-lateral distal body portion of the respiration sensing lead shown in FIG. 77;

FIG. 78A4 is a detailed perspective view of the ipsi-lateral distal body portion in the respiration sensing lead shown in FIG. 77;

FIG. 78B is a detailed perspective view of an alternative embodiment of the respiration sensing lead which may be used in the system shown in FIG. 77;

FIG. 78B1 is a detailed perspective view of the proximal connector assembly of the respiration sensing lead shown in FIG. 78B;

FIG. 78B2 is a detailed perspective view of the distal body portion of the respiration sensing lead shown in FIG. 78B;

FIG. 78C illustrates the implanted system shown in FIG. 77 with the respiration lead shown in FIG. 78A;

FIG. 78D illustrates the implanted system shown in FIG. 77 with the respiration lead shown in FIG. 78B;

FIG. 80J shows a stimulation regimen called core hours for the implantable neurostimulator shown in FIG. 77, as may be used as a therapy mode;

FIG. 88A is a schematic illustration showing an endoscope inserted into the airway FIGS. 88B and 88C are views of the upper airway from the endoscope shown in FIG. 88A while the tongue is in a resting awake state (FIG. 88B) and during a tongue protrusion maneuver (FIG. 88C);

FIG. 90 is a schematic illustration showing the structures of the upper airway from the oral cavity;

FIG. 91 is a schematic illustration showing isolated structures of the upper airway in a transverse section;

FIGS. 99A-99B are schematic illustrations of a tool for use in the method shown in FIGS. 98A-98B;

FIGS. 100A-100B are schematic illustrations of a method for shortening pharyngeal tissue using an implant device;

FIGS. 101A-101G are schematic illustrations of implant devices for use in the method shown in FIGS. 100A-100B;

FIGS. 102A-102B are schematic illustrations of a tool for use in the method shown in FIGS. 100A-100B;

FIGS. 104A-104D are schematic illustrations of implant devices for use in the method shown in FIGS. 103A-103B;

FIGS. 105A-105D are schematic illustrations of a tool for use in the method shown in FIGS. 103A-103B;

DETAILED DESCRIPTION OF EXEMPLARY EMBODIMENTS

The following detailed description should be read with reference to the drawings in which similar elements in different drawings are numbered the same. The drawings, which are not necessarily to scale, depict illustrative embodiments and are not intended to limit the scope of the invention.

Description of Fully Implanted Neurostimulator System

Figure 1:
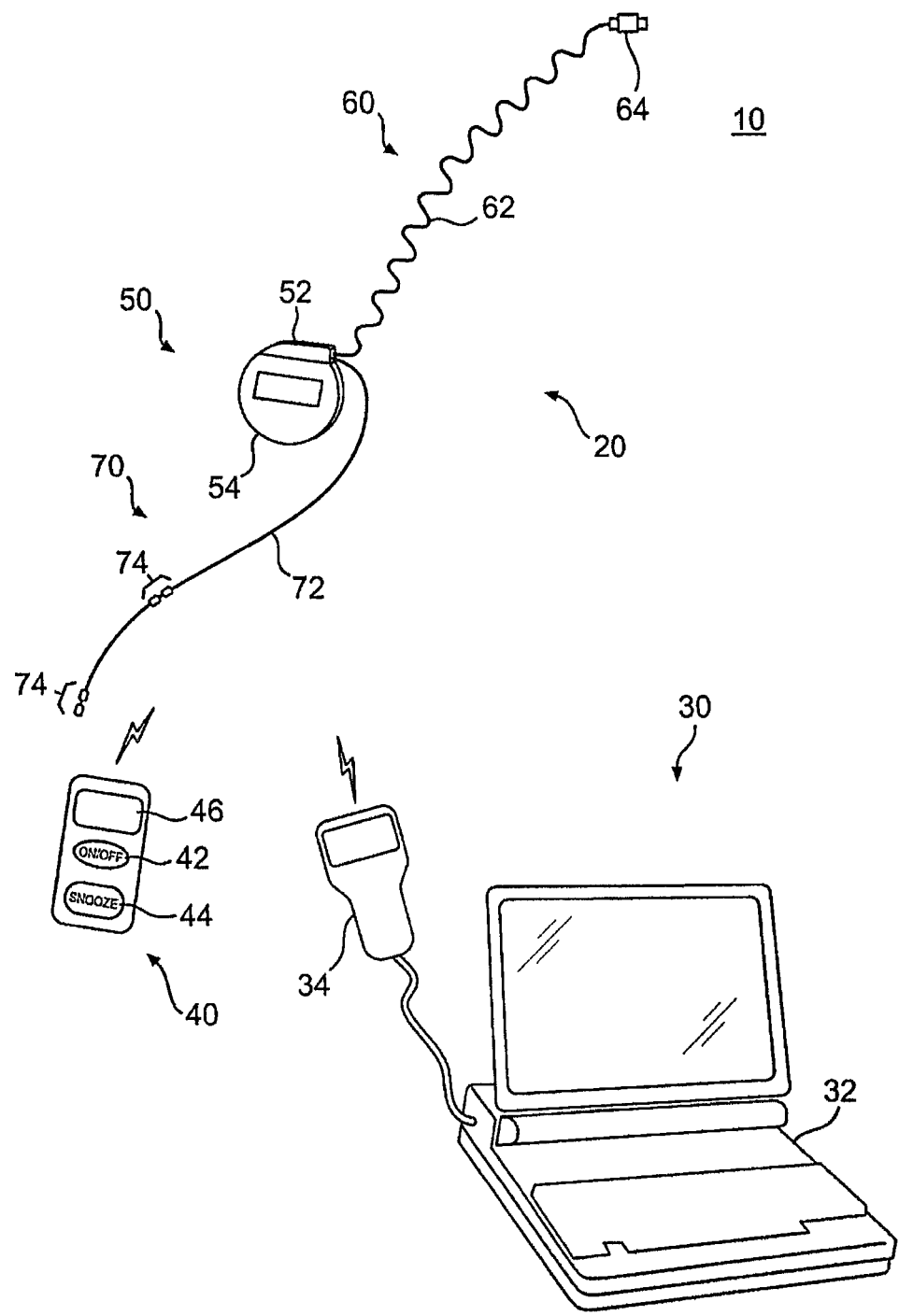
FIG. 1 is a schematic diagram showing a fully implanted neurostimulator system with associated physician programmer and patient controller for treating obstructive sleep apnea.

With reference to FIG. 1, a neurostimulator system 10 including implanted components 20, physician programmer 30 and patient controller 40 is shown schematically. The implanted components of the system 10 may generally include an implanted neurostimulator (INS) 50 (a.k.a., implanted pulse generator (IPG)), an implanted stimulation lead (or leads) 60, and an implanted respiration sensing lead (or leads) 70. The INS 50 generally includes a header 52 for connection of the leads 60/70, and a hermetically sealed housing 54 for the associated electronics and long-life or rechargeable battery (not visible). The stimulation lead 60 generally includes a lead body 62 with a proximal connector and a distal nerve electrode cuff 64. The respiration sensing lead 70 generally includes a lead body 72 with a proximal connector and one or more sensors 74 disposed on or along a distal portion thereof. Suitable designs of the INS 50, stimulation lead 60 and respiration sensing lead 70 are described in more detail hereinafter.

Figure 2:
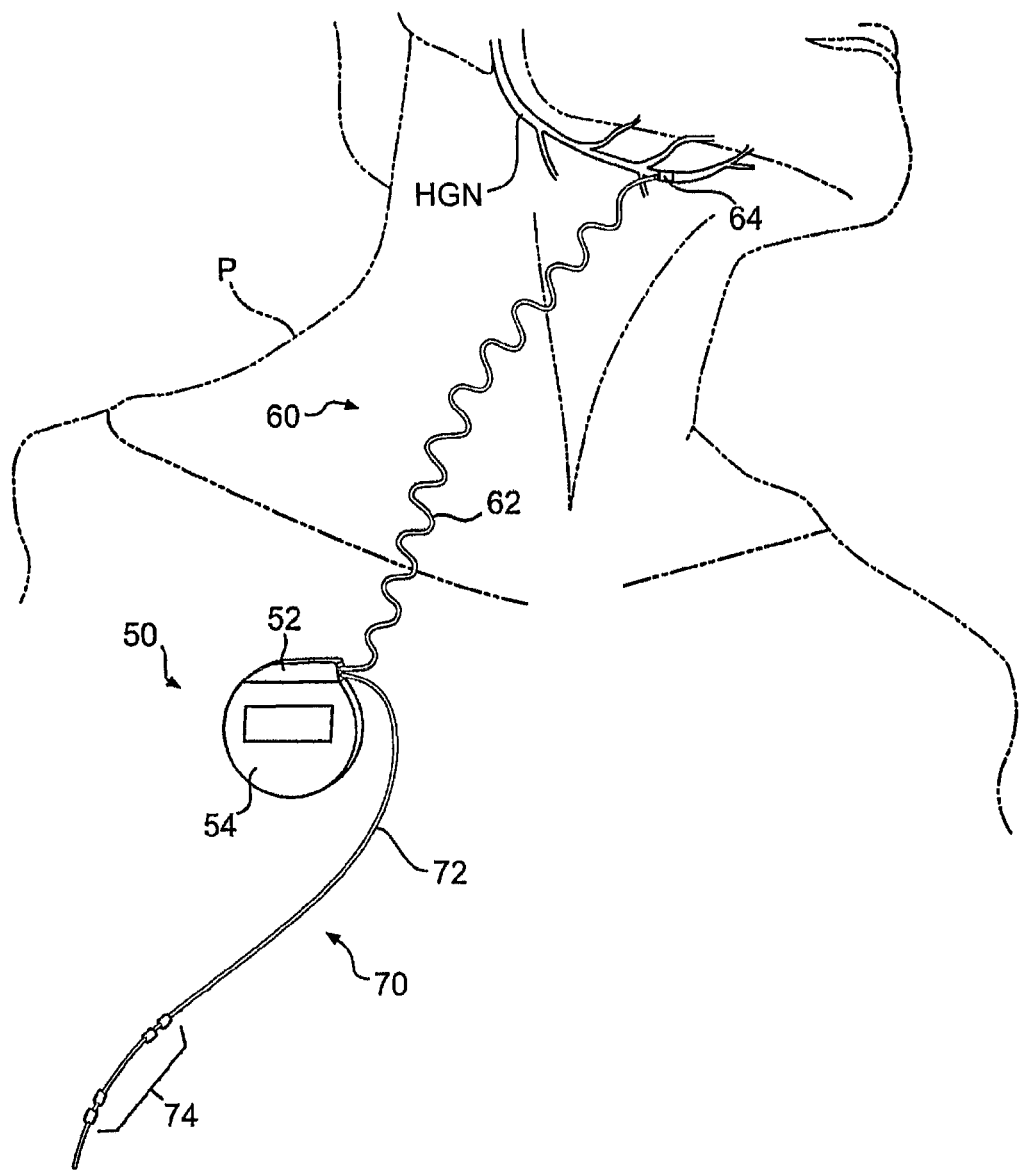
FIG. 2 is a schematic diagram showing the implantable components of FIG. 1 implanted in a patient.

As shown in FIG. 2, and by way of example, not limitation, the implanted components 20 (shown faded) of the neurostimulator system 10 are implanted in a patient P with the INS 50 disposed in a subcutaneous pocket, the stimulation lead body 62 disposed in a subcutaneous tunnel, the nerve cuff electrode 64 disposed on a nerve (e.g., hypoglossal nerve (HGN)) innervating a muscle (e.g., genioglossus muscle, not shown) controlling the upper airway, the respiration sensing lead body 72 disposed in a subcutaneous tunnel, and the respiration sensors 74 disposed adjacent lung tissue and/or intercostal muscles outside the pleural space.

Generally, electrical stimulus is delivered by the INS 50 via the stimulation lead 60 to a nerve innervating a muscle controlling upper airway patency to mitigate obstruction thereof. To reduce nerve and muscle fatigue, the stimulus may be delivered for only a portion of the respiratory cycle, such as during inspiration which corresponds to negative pressure in the upper airway. Stimulation may be thus triggered as a function of respiration as detected by respiration sensing lead 70 in a closed-loop feedback system. By way of example, the stimulus may be triggered to turn on at the end of expiration (or at the beginning of inspiration), and triggered to turn off at the beginning of expiration (or at the end of inspiration). Triggering the stimulus as a function of expiration improves capture of the entire inspiratory phase, including a brief pre-inspiratory phase of about 300 milliseconds, thus more closely mimicking normal activation of upper airway dilator muscles. Over-stimulation may cause nerve and/or muscle fatigue, but a 40% to 50% duty cycle may be safely tolerated, thus enabling limited over-stimulation. As an alternative, stimulus may be delivered independent of actual respiration wherein the stimulus duty cycle is set for an average inspiratory duration at a frequency approximately equal to an average respiratory cycle.

Stimulus may be delivered to one or more of a variety of nerve sites to activate one muscle or muscle groups controlling patency of the upper airway. For example, stimulation of the genioglossus muscle via the hypoglossal nerve moves or otherwise stiffens the anterior portion of the upper airway, thereby decreasing the critical pressure at which the upper airway collapses during inspiration and reducing the likelihood of an apnea or hypopnea event occurring during sleep. Because the systems described herein work at the level of the tongue, it may be desirable to combine this therapy with a therapy (e.g., UPPP or palatal implant) that work at the level of the soft palate, thus increasing efficacy for a broader range of patients.

With reference back to FIG. 1, the physician programmer 30 may comprise a computer 32 configured to control and program the INS 50 via a wireless link to a programming wand 34. The physician programmer 30 may be resident in a sleep lab where the patient undergoes a polysomnographic (PSG) study during which the patient sleeps while the INS 50 is programmed to optimize therapy.

The patient controller 40 may comprise control circuitry and associated user interface to allow the patient to control the system via a wireless telemetry link while at home, for example. The patient controller 40 may include a power switch 42 to turn the system on and slowly ramp up when the patient goes to sleep at night, and turn it off when the patient wakes in the morning. A snooze switch 44 may be used to temporarily put the INS 50 in standby mode during which electrical stimulus is paused for a preprogrammed period of time to allow the patient to temporarily wake, after which the INS 50 turns back on and ramps up to the desired stimulus level. A display 46 may be provided to indicate the status of the INS 50 (e.g., on, off or standby), to indicate satisfactory wireless telemetry link to the INS 50, to indicate remaining battery life of the INS 50, to indicate normal operation of the INS 50, and/or to indicate the need for patient action etc. Display 46 may be configured to be a dash-board-like display, and may be any suitable display available to those of ordinary skill in the art, such as, for example, an LED or LCD display. Furthermore, information may be communicated to the patient controller 40 for display purposes by any suitable means known to those of ordinary skill in the art. For example, communication of information may be achieved through inductively coupled or radio frequency telemetry. The patient controller 40 may also have programmability to adjust stimulus parameters (e.g., amplitude) within a pre-set range determined by the physician in order to improve efficacy and/or to reduce sensory perception, for example. Optionally, the patient controller 40 may be configured to function as the programming wand 34 of the physician programmer 30.

Furthermore, the patient controller 40 may be provided with one or more mechanisms for improving patient compliance. For example, patient controller 40 may be provided with a time-keeping mechanism having the capabilities of a conventional alarm clock. In certain embodiments, controller 40 may be programmed by the user and/or the physician to alert the user when action, such as, for example, turning the system 10 on or off, is required by the user. Controller 40 may be configured to alert the user by any suitable means known in the art. For example, controller 40 may emit an audible alarm at programmed time intervals. In other embodiments, the patient controller 40 may be used to monitor a patient. For example, the patient controller 40 may be programmed to periodically send reports of patient actions, patient compliance, system status, etc., to a clinician or caregiver via a telephone or computer network.

Figure 3:
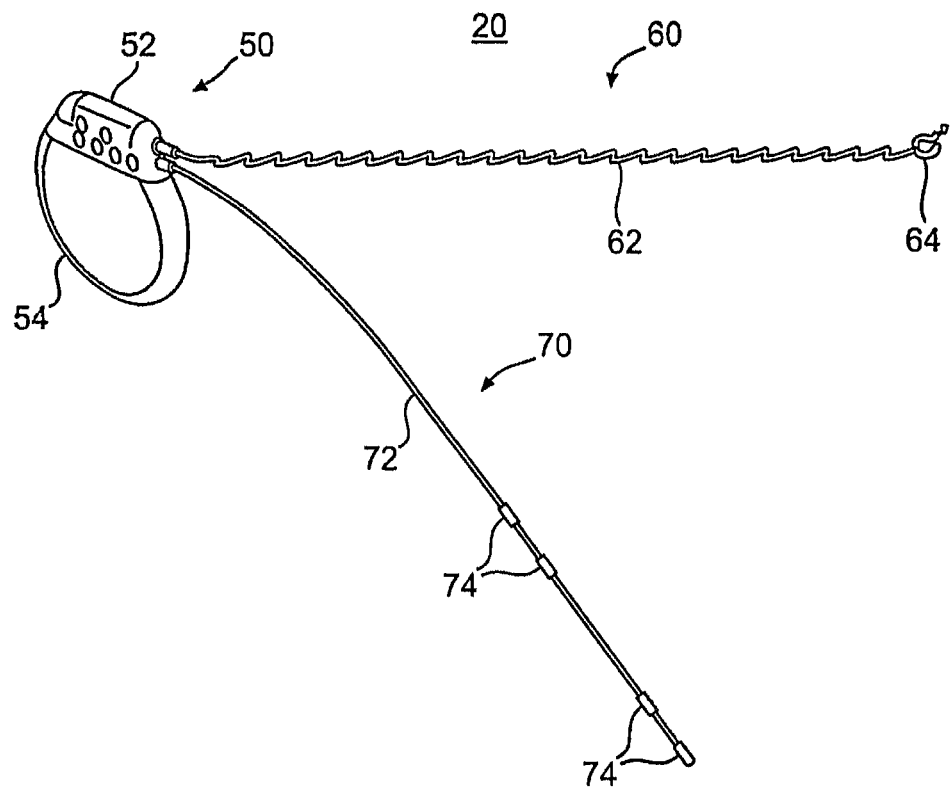
FIG. 3 is a perspective view of the implantable components shown in FIG. 1.

With reference to FIG. 3, the implanted components 20 are shown schematically with more detail. The implanted components include INS 50, stimulation lead 60, and respiration sensing lead 70. The INS 50 includes header 52 and housing 54. The stimulation lead 60 includes lead body 62 and nerve cuff electrode 64. The respiration sensing lead 70 includes lead body 72 and respiration sensors 74 (e.g., impedance sensing electrodes).

Figure 4:
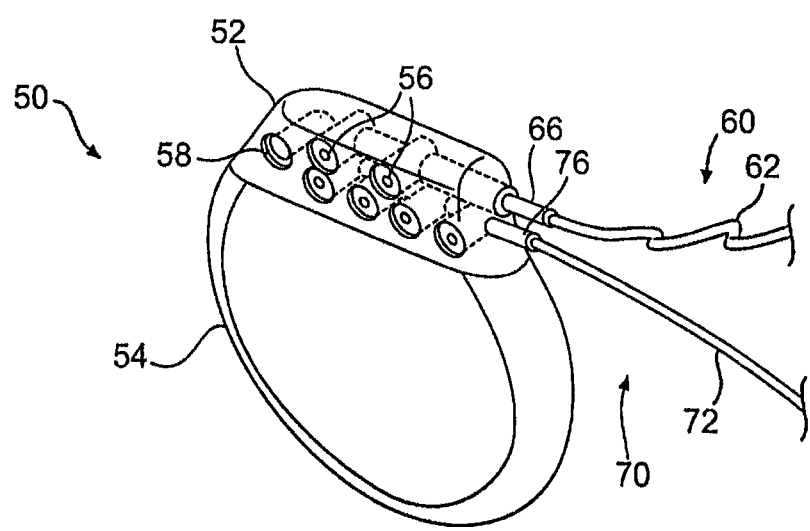
FIG. 4 is a detailed perspective view of the implantable neurostimulator (INS) shown in FIG. 3.

With reference to FIG. 4, the INS 50 is shown schematically in more detail. The INS 50 includes header 52 that may be formed using conventional molding or casting techniques and may comprise conventional materials such as epoxy or polyurethane (e.g., Tecothane brand polyurethane). The housing 54 may be formed using conventional stamping or forming techniques and may comprise conventional materials such as titanium or ceramic. The housing 54 may include one or more isolated electrodes, and/or if a conductive material is used for the housing 54, the housing 54 may comprise an electrode, which may be used for respiratory sensing, for example. The housing 54 may be hermetically sealed to the header 52 using conventional techniques. The header 52 may include two or more receptacles for receiving the proximal connectors 66/76 of the stimulation lead body 62 and respiration sensing lead body 72. The connectors 66/76 may comprise a conventional design such as IS 1 or other in-line designs. The header 52 may also include set screw seals and blocks 56 for receiving set screws (not shown) that establish electrical contact between the INS 50 and the conductors of the leads 60/70 via connectors 66/76, and that establish mechanical fixation thereto. Some electrical contact may be achieved through spring type or cam-locked mechanisms. As shown, two set screw arrangements 56 are shown for the stimulation lead 60 and four set screw arrangements 56 are shown for the respiration sensing lead 70, but the number may be adjusted for the number of conductors in each lead. A hole 58 may be provided in the header 52 for securing the INS 50 to subcutaneous tissue using a suture at the time of implantation.

The INS 50 may comprise a conventional implanted neurostimulator design used in neurostimulation applications, such as those available from Texcel (US), CCC (Uruguay) and NeuroTECH (Belgium), but modified for the present clinical application in terms of stimulation signal parameters, respiratory signal processing, trigger algorithm, patient control, physician programming, etc. The INS may contain a microprocessor and memory for storing and processing data and algorithms. Algorithms may be in the form of software and/or firmware, for example. One of several different embodiments of the neurostimulator may be implemented. For example, the neurostimulator may be an internal/implanted neurostimulator (INS) powered by a long-life primary battery or rechargeable battery, or an external neurostimulator (ENS) wirelessly linked (e.g., inductive) to an implanted receiver unit connected to the leads. The INS (or the receiver, unit of the ENS) may be implanted and optionally anchored in a number of different locations including a subcutaneous pocket in the pectoral region, the dorsal neck region, or cranial region behind the ear, for example.

The INS 50 may include any suitable circuitry and programming in accordance with the principles of the present disclosure. In one embodiment, INS 50 may include an activity sensor (not shown) for sensing the activity of a patient, including the amount of activity of the patient. The activity sensor may detect motion of a patient by any suitable means available to those of ordinary skill in the art. For example, a patient's motion may be detected by, for example, using an internal accelerometer and/or measuring the impedance of the patient's torso with, for example, the built-in respiration sensor discussed below, and/or measuring a tissue pressure on the surface of the implanted INS 50.

The data corresponding to a patient's detected motion may be stored, evaluated, and utilized in any of a number of various ways. In one embodiment, data corresponding to a patient's motion may be used to determine whether a patient is sleeping or awake. For example, when a patient's activity level falls below a predetermined threshold, it may be assumed that the patient is sleeping. Conversely, when the patient's activity level rises above the predetermined threshold, it may be assumed that the patient is awake. The activity sensor therefore may be used to facilitate selectively applying treatment when the patient is detected to be sleeping and/or inhibiting treatment when the patient is detected to be awake. Alternatively, data corresponding to a patient's motion may be evaluated over a long period of time, such as, for example, the first few months of treatment, for indications of improvement in a patient's quality of life. It is contemplated that increases in a patient's average level of daily activity will correspond to successful treatment of OSA. This, in turn, may correspond to improvements in the patient's quality of life.

Moreover, the INS 50 may include a long-life battery (not shown) which requires periodic replacement after years of service. Alternatively, the INS may include a rechargeable power source such as a rechargeable battery or super capacitor that is used instead of the long-life battery. To facilitate recharging, the INS may include a receiver coil inductively linked to a transmitter coil that is connected to a recharging unit powered by a larger battery or line power. Because the patient is stationary while sleeping, recharging may be scheduled to occur sometime during sleep to eliminate the need to carry the recharging unit during daily activities. The transmitter coil and the receiver coil may be arranged coaxially in parallel planes to maximize energy transfer efficiency, and may be held in proximity to each other by a patch, garment, or other means as described with reference to the external neurostimulator embodiments. Other examples of neurostimulator designs will be described in more detail hereinafter.

Figure 5:
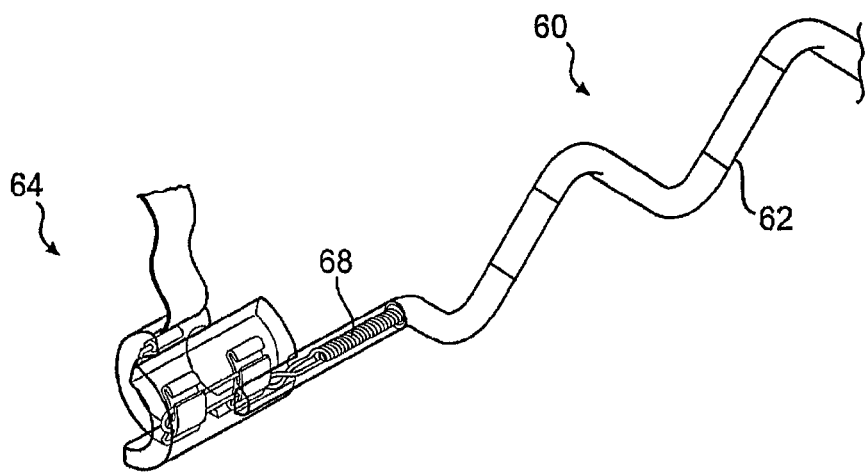
FIG. 5 is a detailed perspective view of the nerve cuff electrode and lead body shown in FIG. 3.

With reference to FIG. 5, the stimulation lead 60 may comprise a variety of different design embodiments and may be positioned at different anatomical sites. For example, a nerve cuff electrode(s) 64 may be attached to a nerve(s) innervating musculature affecting patency of the upper airway. As an alternative or in addition, the nerve cuff electrode 64 may be replaced with an intramuscular electrode and placed directly in the musculature affecting patency of the upper airway. The nerve electrode 64 may be attached to a specific branch of a nerve innervating the desired muscle(s), or may be attached to a proximal trunk of the nerve in which a specific fascicle innervating the desired muscle(s) is targeted by steering the stimulus with multiple electrodes. One or more electrodes may be used for attachment to one or more portions of nerves on one side (unilateral) of the body, or one or more electrodes may be used for attachment to one or more portions of nerves on both sides (bilateral) of the body. Variations in lead body 62 and electrode 64 design as well as variations in the target stimulation site or sites will be described in more detail hereinafter.

With continued reference to FIG. 5, the lead body 62 may be sigmoid shaped, for example, to reduce strain applied to the cuff electrode 64 when the lead body 62 is subject to movement. The sigmoid shape, which may alternatively comprise a variety of other waveform shapes, may have a wavelength of approximately 1.0 to 1.5 cm, and an amplitude of approximately 0.75 to 1.5 cm, for example. The lead body 62 may comprise a tubular jacket with electrical conductors 68 extending therein. The tubular jacket may comprise extruded silicone having an outside diameter of approximately 0.047 inches and an inside diameter of approximately 0.023 inches, for example. The tubular jacket may optionally have a covering of co-extruded polyurethane, for example, to improve durability. The conductors 68, shown in a transparent window in the jacket for purposes of illustration only, may comprise a bifilar coil of insulated (e.g., ETFE) braided stranded wire (BSW) of MP35NLT material. The number of conductors 68 is shown as two, but may be adjusted depending on the desired number of independent electrodes used.

The various embodiments of stimulation leads, for example, stimulation lead 60, disclosed herein may be fabricated by any suitable means known to those having ordinary skill in the art, and may be made from any suitable material. For example, the discussed sigmoid shape of the tubular jacket of lead body 62 may be formed by first extruding silicone in a semi-cured or semi cross-linked state. Next, the semi cross-linked extruded tubular jacket may be placed in a sigmoid mold and then allowed to become fully cross-linked. In particular, the semi cross-linked extruded tubular jacket may be placed in an oven and heated to convert the semi cross-linked silicone of the extruded tubular jacket to fully cross-linked silicone. Additionally, a lumen within the tubular jacket may be created along a longitudinal axis of the tubular jacket by any suitable means.

Furthermore, in accordance with the principles of the present disclosure, it is contemplated that one or more of the various embodiments of stimulation leads disclosed herein may be implanted in or near highly mobile portions of the body. For example, embodiments of the disclosed stimulation leads may be implanted in the ventral neck, for example, along a path between the clavicle and mandible of a patient. Additionally, although mastication, deglutition, and speech may result in mechanical loading on an implanted stimulation lead, it has been found that gross movement of the head and neck may create high mechanical stresses in the conductors of the lead body, lead jacket, and the junction between the conductor wires and the anchor points, such as, for example, the electrodes. Accordingly, it may be desirable to configure the various embodiments of stimulation leads to withstand certain predetermined amounts of fatigue and/or stresses, which may result from mechanical loading on a lead body due to gross movements of a patient's neck and head.

In particular, research has revealed that approximately 98% of the population may experience a 38.5% elongation or less in the distance between the clavicle and angle of the mandible (e.g., adjacent a contemplated area of implantation for a stimulation lead in accordance with the principles of this disclosure). It has also been found that the angular range of motion of the cervical spine between adjacent vertebrae may be approximately 12 degrees, thereby flexing the lead through this angle with a bend radius assumed to be approximately 1.0 centimeter. See Augustus A. White III et al., Clinical Biomechanics of the Spine, pp. 84, 356, and 373 (1978). Furthermore, the frequency of gross head movement through the range of motion in the contemplated area of implantation has been estimated to be approximately 300,000 cycles per year, or on the average approximately 50 times per waking hour.

Figure 5A:
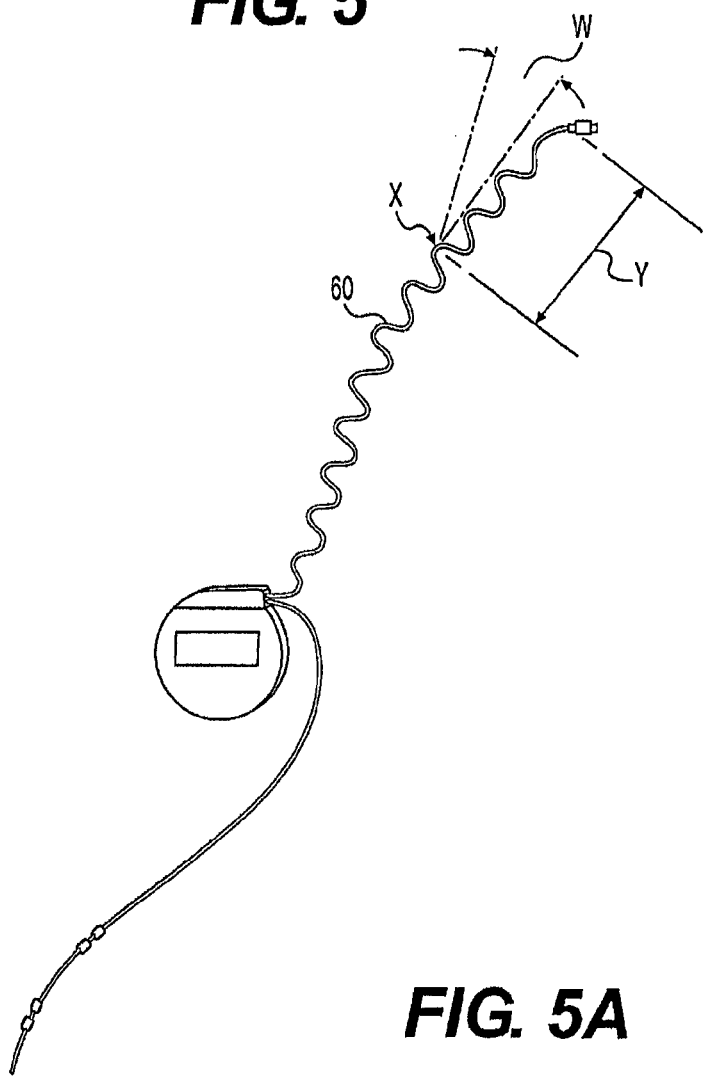
FIG. 5A is an illustration of exemplary movements a lead body may be configured to withstand.

Thus, it may be desirable to design a lead body that is capable of withstanding, among other things, the stresses imparted by the above-noted head and neck movements for an extended amount of time, such as, for example, ten years. In particular, in order to design a lead body that may remain functional for the exemplary ten year implanted life, it may be desirable to configure the lead bodies disclosed herein to withstand at least the above noted elongation and ranges of motion. For example, since implanted lead bodies are likely to be elongated by at least 38.5%, it may be desirable to design lead bodies to withstand being elongated by a predetermined distance Y, such as, for example, approximately 40% (+/−2%) from an initial unstressed state, for a minimum of 3.0 million cycles without failure, as depicted in FIG. 5A. In addition, since it is likely that an implanted lead body may experience an angular range of motion of at least 12 degrees, with a bend radius of approximately 1.0 centimeter, it may be desirable to configure the lead bodies to withstand being flexed around a predetermined radius X, such as, for example, 1.0 centimeter (+/−0.05 centimeters), for a predetermined amount of rotation W, such as, for example, from approximately 0 degrees to approximately 15 degrees (+/−3 degrees), such that the 15 degree maximum deflection occurs coincidentally with the maximum elongation of the lead body.

Figure 6:
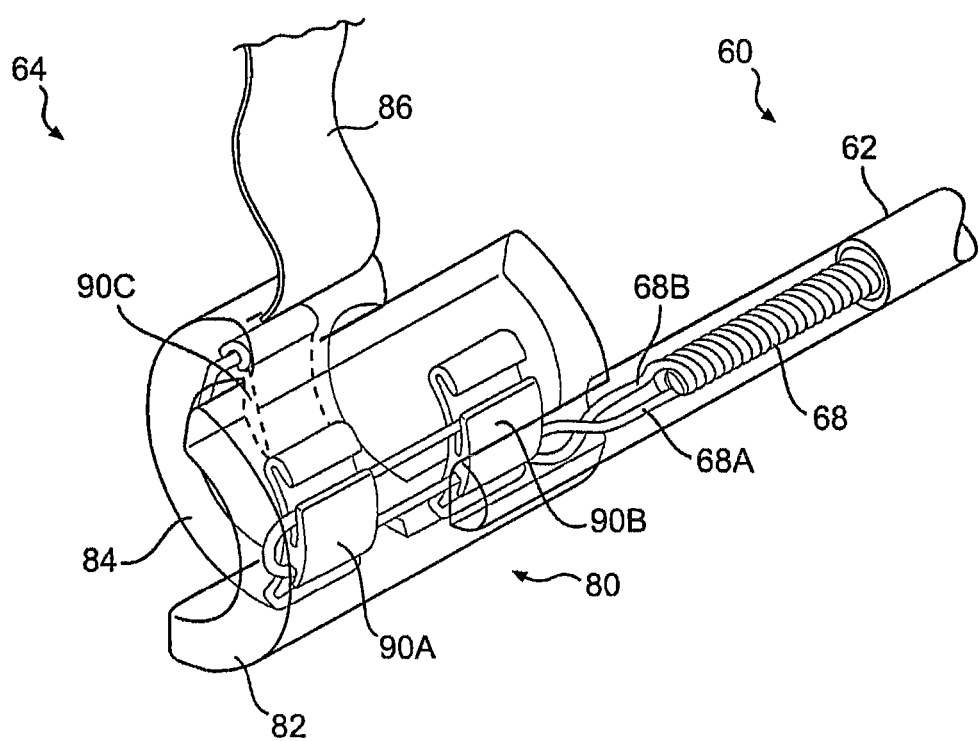
FIG. 6 is a close-up detailed perspective view of the nerve cuff electrode shown in FIG. 3.

With reference to FIG. 6, the nerve cuff electrode 64 may comprise a cuff body 80 having a lateral (or superficial) side 82 and a medial (or contralateral, or deep) side 84. The medial side 84 is narrower or shorter in length than the lateral side 82 to facilitate insertion of the medial side 84 around a nerve such that the medial side is on the deep side of the nerve and the lateral side is on the superficial side of the nerve. This configuration reduces the dissection of nerve branches and vascular supply required to get the cuff around a nerve. For the nerve cuff implant sites discussed herein, the medial side 84 may have a length of less than 6 mm, and preferably in the range of approximately 3 to 5 mm, for example. The lateral side 82 may have a length of more than 6 mm, and preferably in the range of approximately 7 to 8 mm, for example. The cuff body 80 may be compliant and may be available in different sizes with an inside diameter of approximately 2.5 to 3.0 mm or 3.0 to 3.5 mm, for example. The cuff size may also be adjusted depending on the nominal diameter of the nerve at the site of implantation. The cuff body 80 may have a wall thickness of approximately 1.0 mm and may be formed of molded silicone, for example, and may be reinforced with imbedded fibers or fabrics. An integral tow strap 86 may be used to facilitate wrapping the cuff around a nerve by first inserting the strap 86 under and around the deep side of the nerve and subsequently pulling the strap to bring the medial side 84 in position on the deep side of the nerve and the lateral side 82 on the superficial side of the nerve.

With continued reference to FIG. 6, the nerve cuff electrode 64 includes electrode contacts 90A, 90B, and 90C imbedded in the body 80 of the cuff, with their inside surface facing exposed to establish electrical contact with a nerve disposed therein. A transverse guarded tri-polar electrode arrangement is shown by way of example, not limitation, wherein electrode contacts 90A and 90B comprise anodes transversely guarding electrode contact 90C which comprises a cathode.

With this arrangement, the anode electrodes 90A and 90B are connected to a common conductor 68A imbedded in the body 80, and the cathode electrode 90C is connected to an independent conductor 68B extending from the lateral side 82 to the medial side 84 and imbedded in the body 80. By using the conductors 68 to make connections within the body 80 of the cuff 64, fatigue stresses are imposed on the conductors rather than the electrode contacts 90A, 90B and 90C.

Figure 7:
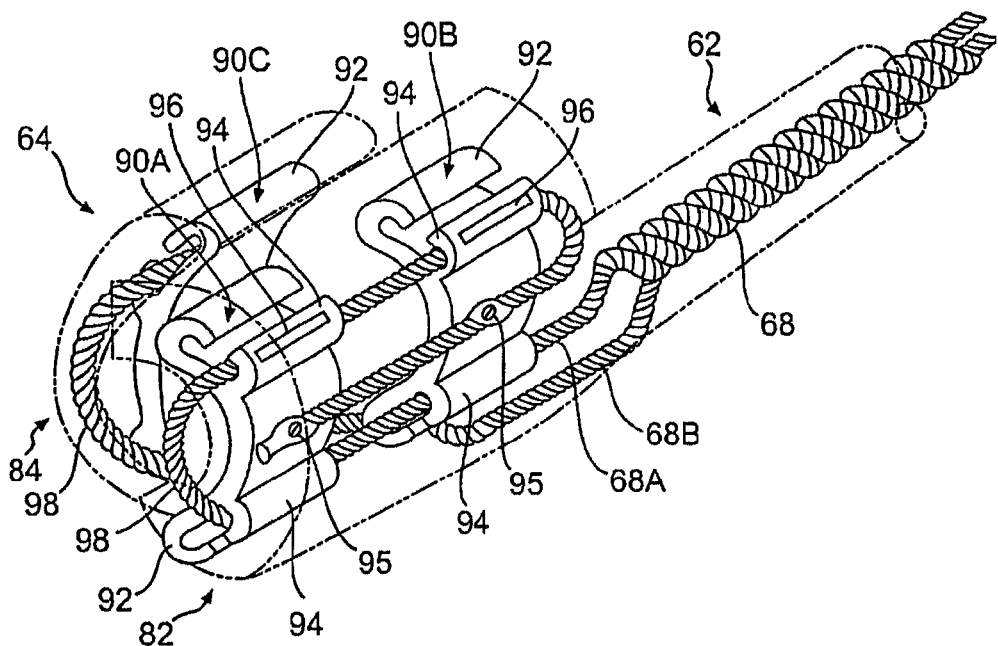
FIG. 7 is a detailed perspective view of the internal components of the nerve cuff electrode shown in FIG. 6.
Figure 8:
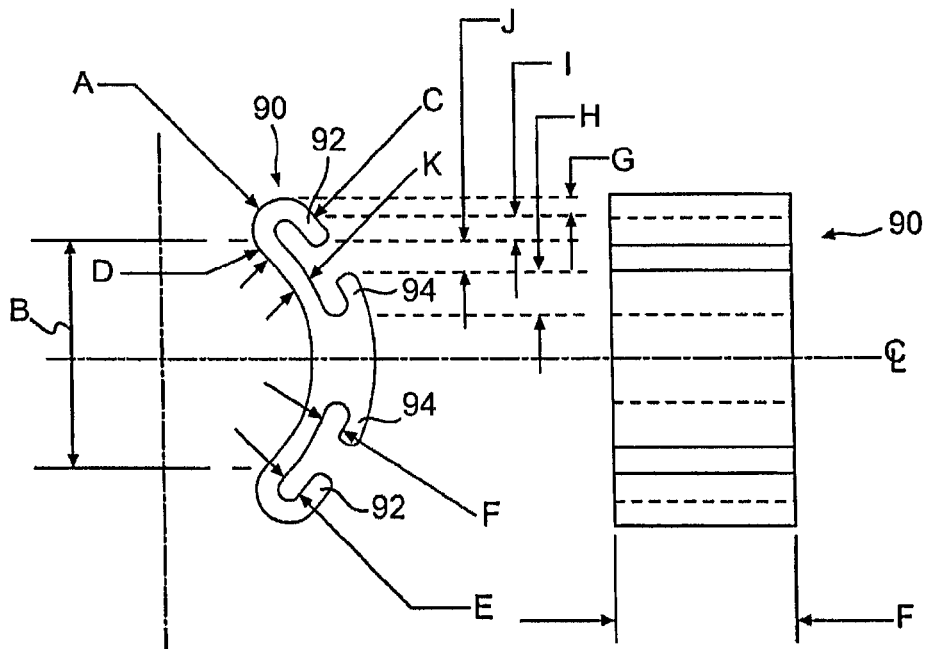
FIG. 8 shows side and end views of an electrode contact of the nerve cuff electrode shown in FIG. 7.

With additional reference to FIGS. 7 and 8, the electrode contacts 90A, 90B and 90C may thus be semi-circular shaped having an arc length of less than 180 degrees, and preferably an arc length of approximately 120 degrees, for example. Each electrode 90 may have two reverse bends (e.g., hooked or curled) portions 92 to provide mechanical fixation to the body 80 when imbedded therein. Each electrode 90 may also have two crimp tabs 94 defining grooves thereunder for crimping to the conductors 68 or for providing a passthrough. As shown in FIG. 7, conductor 68A passes through the grooves under the lower crimp tabs 94 of electrodes 90B and 90A, loops 98 around through the grooves under the upper crimp tabs 94 of electrodes 90A and 90B, is crimped 96 by the upper tabs 94 of electrodes 90A and 90B to provide mechanical and electrical connection, is looped again back between the crimp tabs 94 on the outside of the electrode contact 90, and is resistance spot welded 95 to provide redundancy in mechanical and electrical connection. Also as shown in FIG. 7, conductor 68B passes through the groove under the lower crimp tab 94 of electrode 90C, loops around through the groove under the upper crimp tab 94 of electrode 90C, and is crimped by the upper tab 94 of electrode 90C to provide mechanical and electrical connection. This arrangement avoids off-axis tensile loading at the crimp sites 96 which may otherwise fail due to stress concentration, and the looped portion 98 provides additional strain relief.

FIG. 8 provides example dimensions (inches) of an electrode contact 90 for a 2.5 mm inside diameter cuff, wherein the electrode is formed of 90/10 or 80/20 platinum iridium alloy formed by wire EDM, for example. As illustrated, and as exemplary and approximate dimensions, electrode contact 90 may include a surface A having a full radius, a dimension B of 0.079 inches from tangent to tangent, a dimension C of 0.020 inches (3.times.), a radius of curvature D of 0.049 R with a 16 micro-inch RMS, a dimension E of 0.008 inches (2.times.), a dimension F of 0.0065 inches (+/−0.001 inches) (2.times.), a dimension G of 0.006 inches (+0.002 inches, −0.001 inches) (2.times.), a dimension H of 0.014 inches (2.times.), a dimension I of 0.010 inches (2.times.), a dimension J of 0.010 inches (2.times.), and a dimension K of 0.006 inches (+/− 0.001 inches).

Figure 9B:
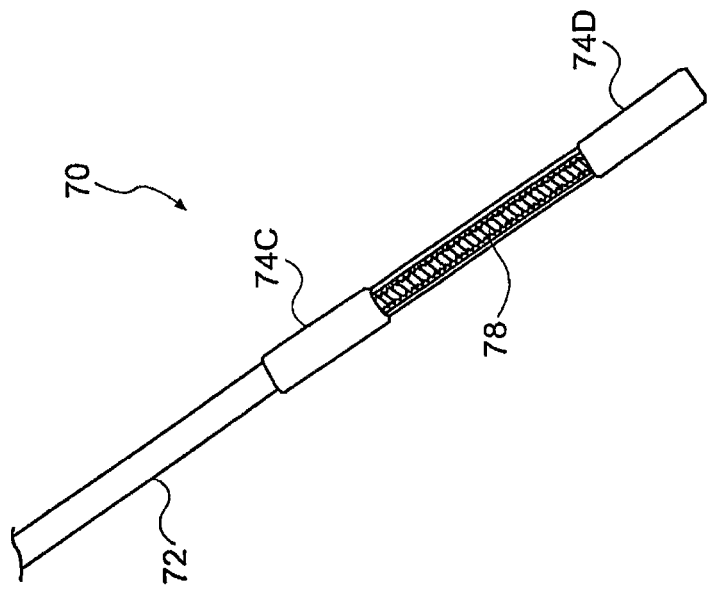
FIGS. 9A and 9B are perspective views of the respiration sensing lead shown in FIG. 3.
Figure 9A:
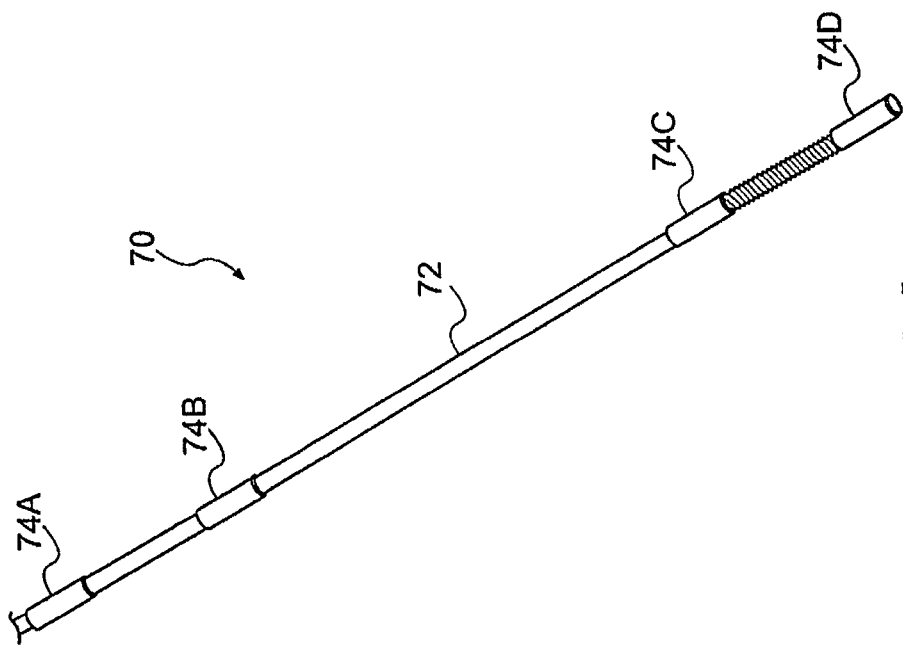

With reference to FIGS. 9A and 9B, a distal portion of the respiration sensing lead 70 and a distal detail of the sensing lead 70, respectively, are shown schematically. In the illustrated embodiment, the respiration sensing lead 70 and associated sensors 74 are implanted as shown in FIG. 2. However, the respiration sensor(s) may comprise a variety of different design embodiments, both implanted and external, and may be positioned at different anatomical sites. Generally, the respiratory sensor(s) may be internal/implanted or external, and may be connected to the neurostimulator via a wired or wireless link. The respiratory sensor(s) may detect respiration directly or a surrogate thereof. The respiratory sensor(s) may measure, for example, respiratory airflow, respiratory effort (e.g., diaphragmatic or thoracic movement), intra-pleural pressure, lung impedance, respiratory drive, upper airway EMG, changes in tissue impedance in and around the lung(s) including the lungs, diaphragm and/or liver, acoustic airflow or any of a number other parameters indicative of respiration. Detailed examples of suitable respiration sensing leads and sensors will be described in more detail hereinafter.

With continued reference to FIGS. 9A and 9B, the respiration sensing lead 70 includes a lead body 72 and a plurality of respiration sensors 74A-74D comprising ring electrodes for sensing bio-impedance. The lead body 72 of the respiration sensing lead 70 may include a jacket cover comprising an extruded silicone tube optionally including a polyurethane cover (80A durometer), or may comprise an extruded polyurethane tube (55D durometer). The ring electrodes 74A-74D may comprise 90/10 or 80/20 platinum iridium alloy tubes having an outside diameter of 0.050 inches and a length of 5 mm, and secured to the jacket cover by laser welding and/or adhesive bonding, for example. The lead body 72 may include a plurality of conductors 78 as seen in the transparent window in the jacket cover, which is shown for purposes of illustration only. The conductors 78 may comprise insulated and coiled BSW or solid wire (optionally DFT silver core wire) disposed in the tubular jacket, with one conductor provided for each ring electrode 74A-74D requiring independent control. Generally, the impedance electrodes 74A-74D may comprise current emitting electrodes and voltage sensing electrodes for detecting respiration by changes in bio-impedance. The number, spacing, anatomical location and function of the impedance electrodes will be described in more detail hereinafter.

System 10 may also include a plurality of diagnostic mechanisms (e.g., circuitry and/or programming) for monitoring and/or determining the functionality of certain components, such as, for example, stimulation lead 60. In particular, system 10 may include one or more switching circuits (not shown) that facilitate connection of the respiratory/trans-thoracic impedance sensing circuits of the present disclosure (discussed in greater detail below) to stimulation lead 60 for measuring the impedance of lead 60. In some embodiments, the impedance sensing circuit may be connected to each electrode pair. In other embodiments, the impedance sensing circuit may be connected between the case of the implanted INS 50 and each conductor 68 within the lead 60. While those having ordinary skill in the art will readily recognize that any suitable impedance sensing method may be utilized to monitor and/or determine the functionality of lead 60, the respiratory/trans-thoracic impedance sensing circuit of the present disclosure may be preferred, since this circuit may be capable of identifying small changes in impedance rather than the large changes detectable by standard methods.

As alluded to above, sensing the impedance of lead 60 may provide for monitoring and/or determining the functionality of lead 60. Specifically, sensing the impedance of lead 60 may facilitate diagnosing and distinguishing between differing types of failures of lead 60. In particular, research has revealed that changes in the impedance of lead 60 may be indicative of certain types of failures, including, but not limited to, corrosion, high contact resistance, breakage, and/or shorting. For example, a broken wire inside the lead could be identified by an excessively high lead impedance value. Corrosion of an electrode with its resultant decrease in effective electrode surface area could be identified by a smaller increase in impedance of that electrode. Similarly, an abnormally low value could correspond with a short between conductors in the lead, or an abrasion of the lead body that exposed a conductor to the tissue. Measuring from the case of the INS to each electrode allows independent identification of the integrity of each wire/electrode in the lead. In addition, sensing the impedance of lead 60 may facilitate periodic, automated adjustment of stimulation pulse amplitude so as to maintain constant current, energy, and/or charge delivery using a simpler voltage mode delivery circuit. Such automated adjustment may facilitate ensuring safety and effectiveness by consistently delivering the prescribed current, energy, or charge in the presence of tissue/electrode impedance variations. By consistently controlling the delivery of only the minimally required energy necessary for stimulation of the nerve, the stimulation amplitude may be programmed closer to the actual stimulation threshold rather than programming a wide margin to ensure continued effectiveness. This enhances safety and reduces power consumption. Moreover, sensing the impedance of lead 60 may allow monitoring of certain system dynamics, such as, for example, doses actually delivered to a patient.

Description of Implant Procedure

Figure 10:
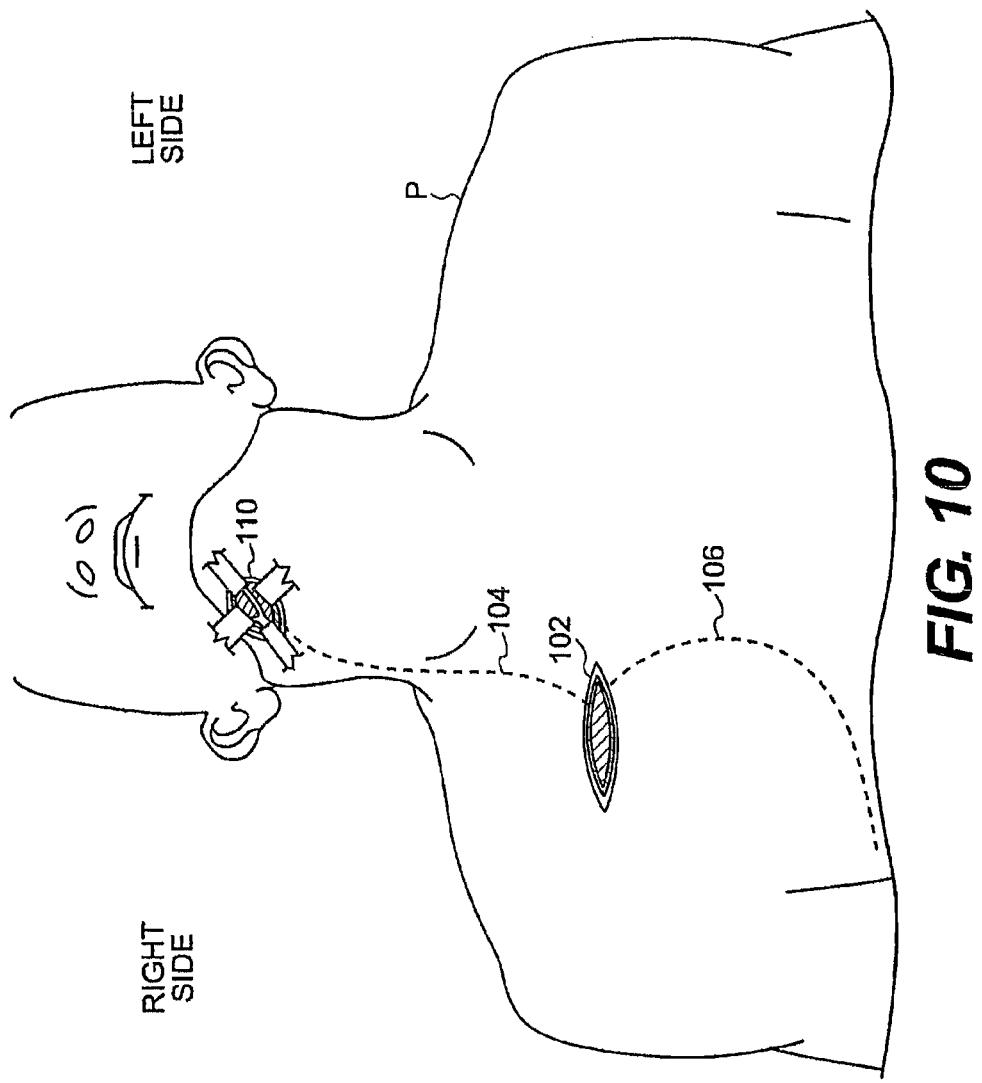
FIG. 10 schematically illustrates surgical access and tunneling sites for implanting the system illustrated in FIG. 2.

With reference to FIG. 10, surgical access sites are schematically shown for implanting the internal neurostimulator components 20 shown in FIG. 1. The internal neurostimulator components 20 may be surgically implanted in a patient on the right or left side. The right side may be preferred because it leaves the left side available for implantation of a pacemaker, defibrillator, etc., which are traditionally implanted on the left side. The right side may also be preferred because it lends itself to a clean respiratory signal less susceptible to cardiac artifact and also offers placement of respiratory sensors across the interface between the lung, diaphragm and liver for better detection of impedance changes during respiration.

With continued reference to FIG. 10, the INS (not shown) may be implanted in a subcutaneous pocket 102 in the pectoral region, for example. The stimulation lead (not shown) may be implanted in a subcutaneous tunnel 104 along (e.g., over or under) the platysma muscle in the neck region. The respiration sensing lead (not shown) may be implanted in a subcutaneous tunnel 106 extending adjacent the ribcage to an area adjacent lung tissue and/or intercostal muscles outside the pleural space. The nerve cuff electrode (not shown) may be attached to a nerve by surgical dissection at a surgical access site 110 proximate the targeted stimulation site. In the illustrated example, the target nerve is the right hypoglossal nerve and the surgical access site is in the submandibular region.

Figure 11A:
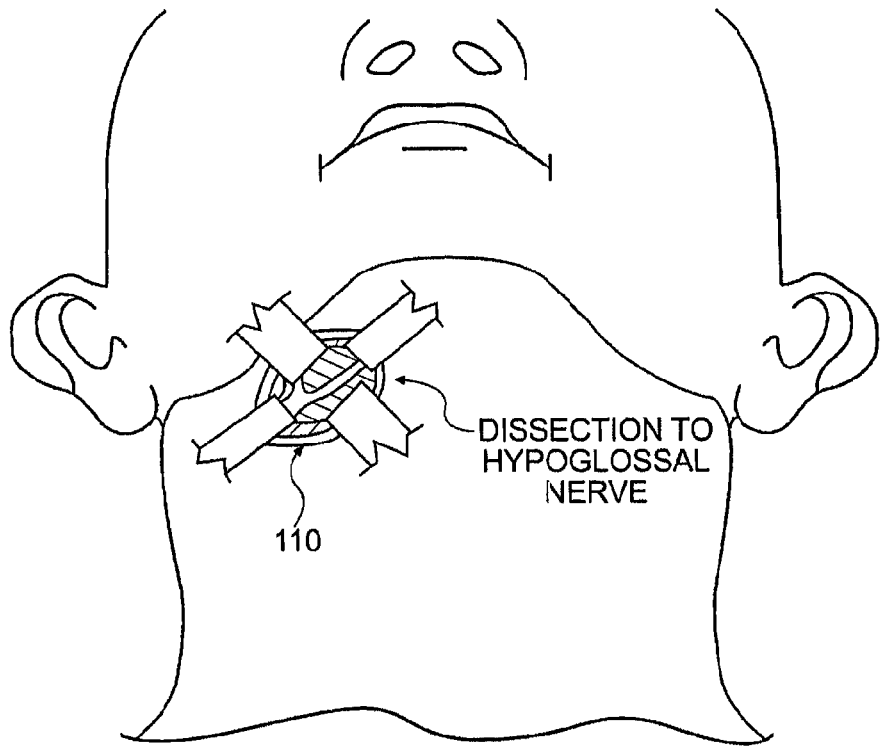
FIGS. 11A and 11B schematically illustrate dissection to a hypoglossal nerve.
Figure 11B:
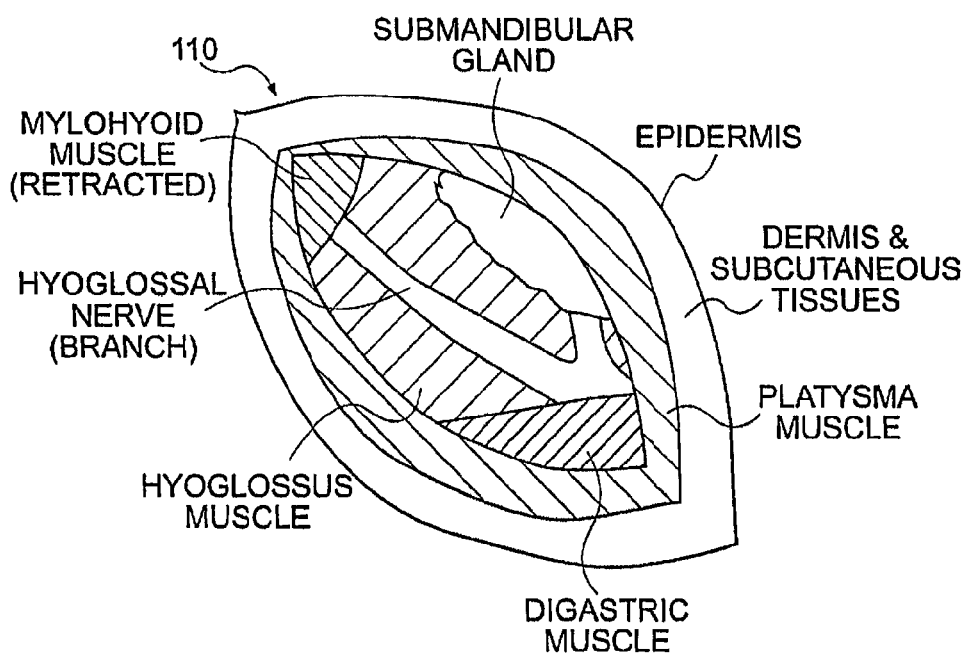

With reference to FIGS. 11A and 11B, a surgical dissection 110 to the hypoglossal nerve is shown schematically. A unilateral dissection is shown, but a bilateral approach for bilateral stimulation may also be employed. Conventional surgical dissection techniques may be employed. The branch of the hypoglossal nerve (usually a medial or distal branch) leading to the genioglossus muscle may be identified by stimulating the hypoglossal nerve at different locations and observing the tongue for protrusion. Because elongation and/or flexion may be mistaken for protrusion, it may be desirable to observe the upper airway using a flexible fiber optic scope (e.g., nasopharyngoscope) inserted into the patient's nose, through the nasal passages, past the nasopharynx and velopharynx to view of the oropharynx and hypopharynx and visually confirm an increase in airway caliber by anterior displacement (protrusion) of the tongue base when the nerve branch is stimulated.

The implant procedure may be performed with the patient under general anesthesia in a hospital setting on an out-patient basis. Alternatively, local anesthesia (at the surgical access sites and along the subcutaneous tunnels) may be used together with a sedative in a surgical center or physician office setting. As a further alternative, a facial nerve block may be employed. After a post-surgical healing period of about several weeks, the patient may return for a polysomnographic (PSG) test or sleep study at a sleep center for programming the system and titrating the therapy. A trialing period may be employed prior to full implantation wherein the hypoglossal nerve or the genioglossus muscle is stimulated with fine wire electrodes in a sleep study and the efficacy of delivering stimulus to the hypoglossal nerve or directly to the genioglossus muscle is observed and measured by reduction in apnea hypopnea index, for example.

Other nerve target sites are described elsewhere herein and may be accessed by similar surgical access techniques. As an alternative to surgical dissection, less invasive approaches such as percutaneous or laparoscopic access techniques may be utilized, making use of associated tools such as tubular sheaths, trocars, etc.

Description of Alternative Stimulation Target Sites

Figure 12:
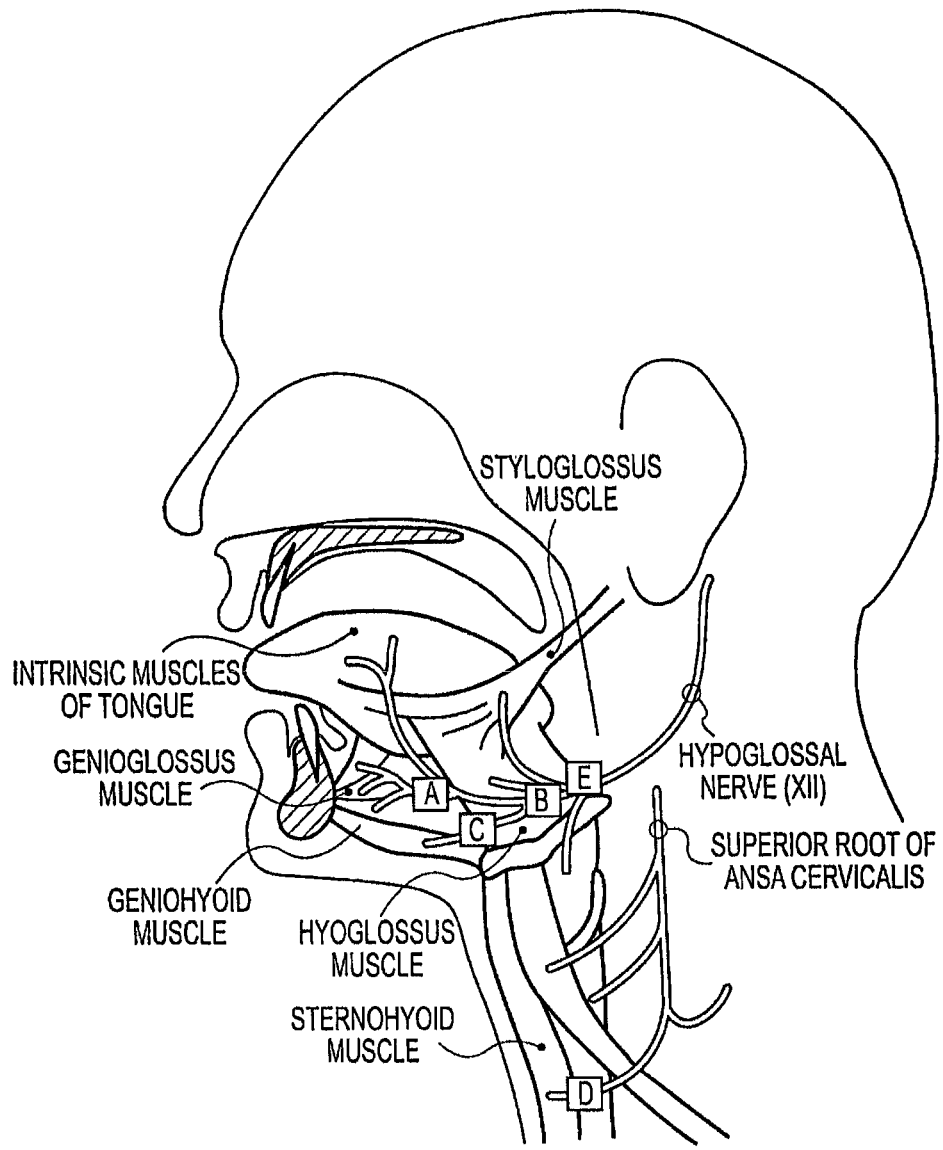
FIGS. 12 and 12A-12D schematically illustrate various possible nerve stimulation sites for activating muscles controlling the upper airway.
Figure 12A:
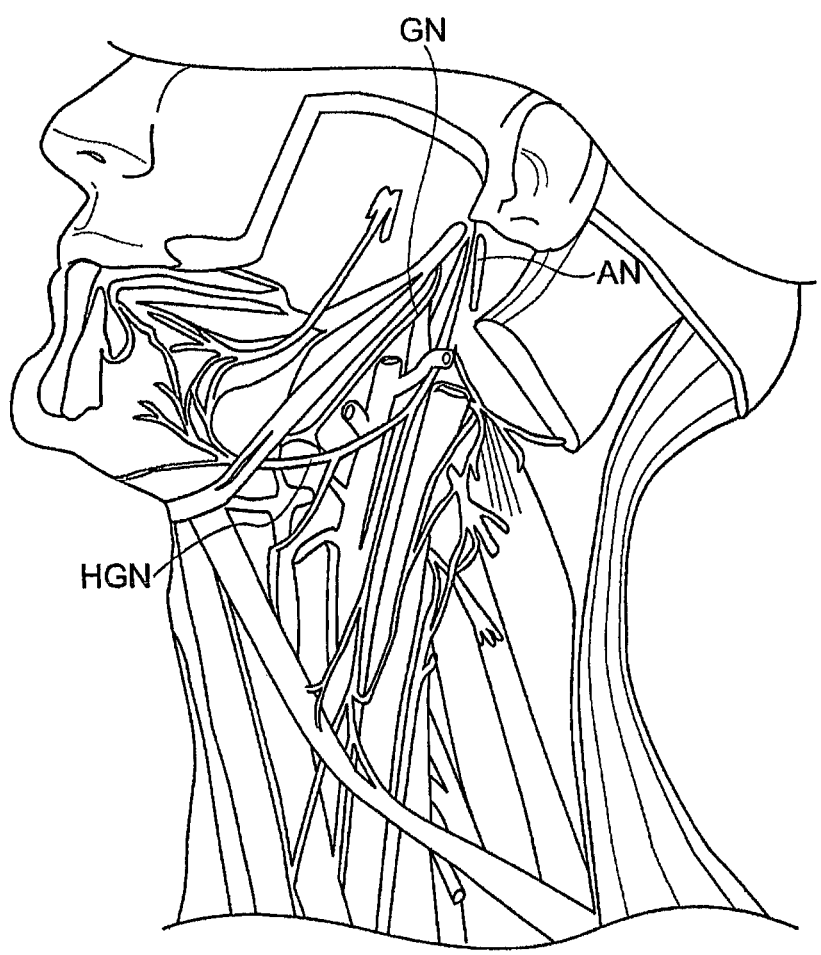
Figure 12B:
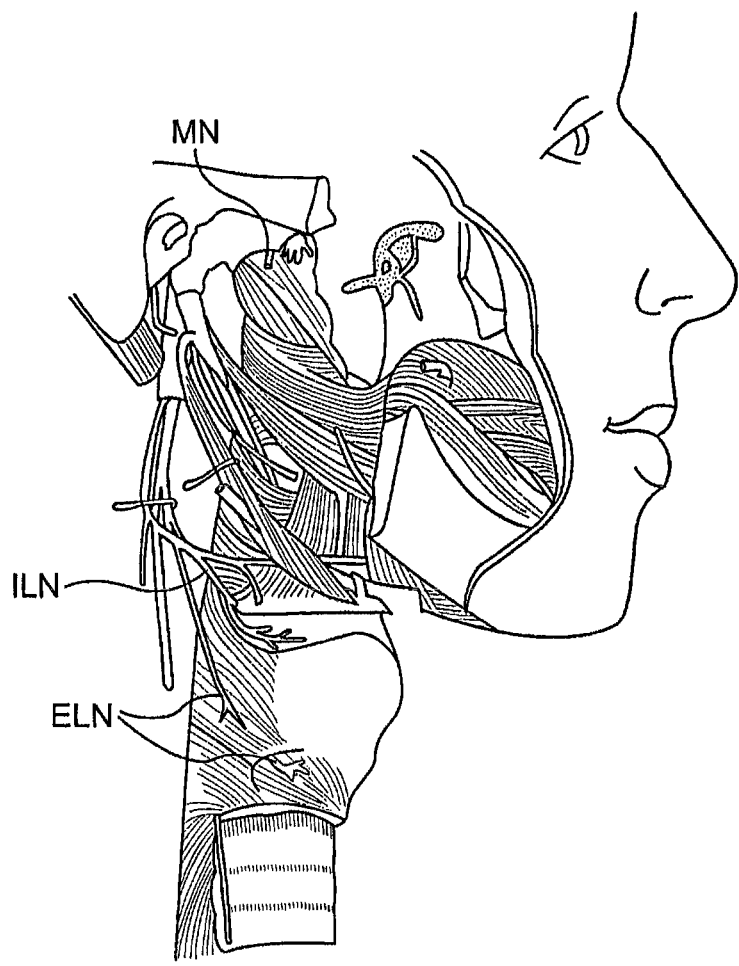
Figure 12C:
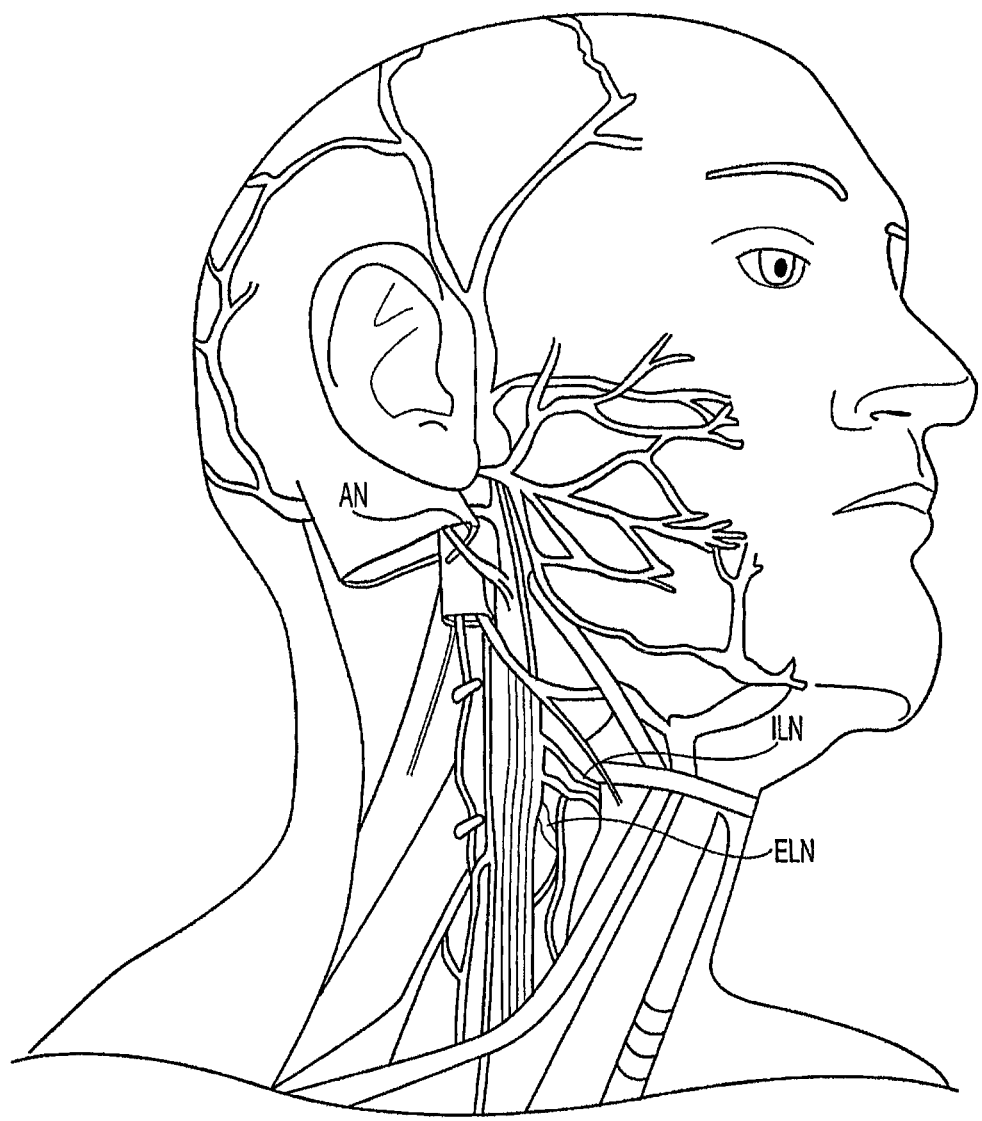
Figure 12D:
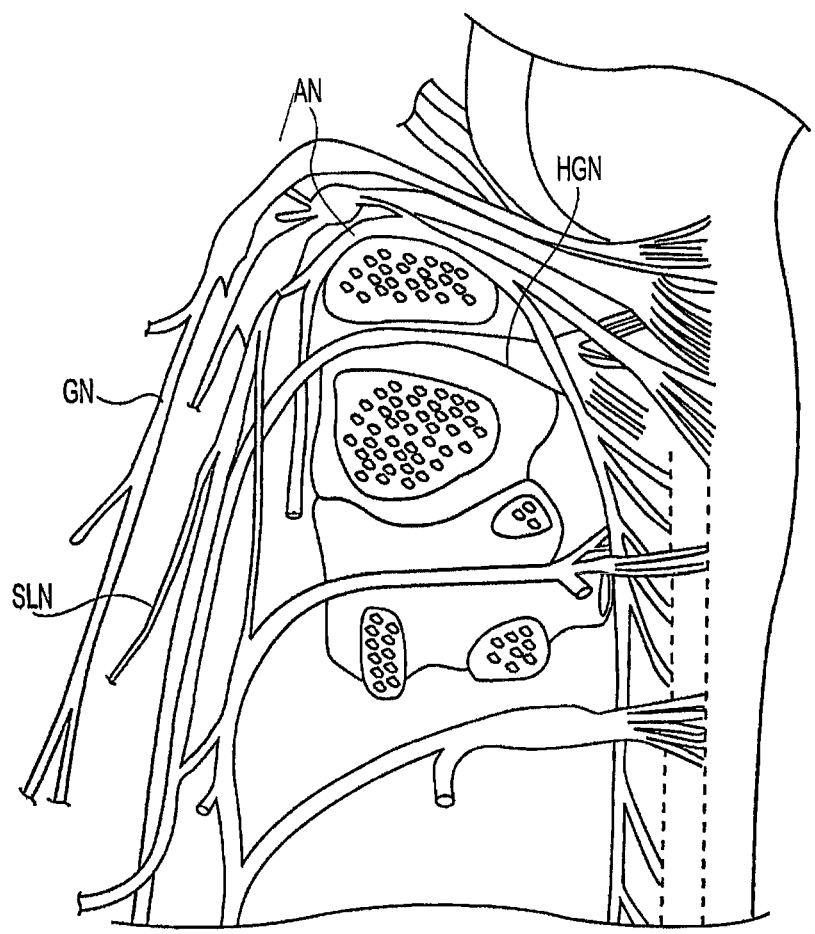

With reference to FIG. 12, various possible nerve and/or direct muscle stimulation sites are shown for stimulating muscles controlling patency of the upper airway. In addition to the upper airway which generally includes the pharyngeal space, other nerves and dilator muscles of the nasal passage and nasopharyngeal space may be selectively targeted for stimulation. A general description of the muscles and nerves suitable for stimulation follows, of which the pharyngeal nerves and muscles are shown in detail in FIG. 12.

Airway dilator muscles and associated nerves suitable for activation include are described in the following text and associated drawings. The dilator naris muscle functions to widen the anterior nasal aperture (i.e., flares nostrils) and is innervated by the buccal branch of the facial nerve (cranial nerve VII). The tensor veli palatine muscle functions to stiffen the soft palate and is innervated by the medial (or internal) pterygoid branch of the mandibular nerve MN. The genioglossus muscle is an extrinsic pharyngeal muscle connecting the base of the tongue to the chin and functions to protrude the tongue. The genioglossus muscle is typically innervated by a distal or medial branch (or branches) of the right and left hypoglossal nerve. The geniohyoid muscle connects the hyoid bone to the chin and the sternohyoid muscle attaches the hyoid bone to the sternum. The geniohyoid muscle functions to pull the hyoid bone anterosuperiorly, the sternohyoid muscle functions to pull hyoid bone inferiorly, and collectively (i.e., co-activation) they function to pull the hyoid bone anteriorly. The geniohyoid muscle is innervated by the hypoglossal nerve, and the sternohyoid muscle is innervated by the ansa cervicalis nerve.

By way of example, a nerve electrode may be attached to a specific branch of the hypoglossal nerve innervating the genioglossus muscle (tongue protruder), or may be attached to a more proximal portion (e.g., trunk) of the hypoglossal nerve in which a specific fascicle innervating the genioglossus muscle is targeted by steering the stimulus using an electrode array. Activating the genioglossus muscle causes the tongue to protrude thus increasing the size of anterior aspect of the upper airway or otherwise resisting collapse during inspiration.

As an alternative to activation of any or a combination of the airway dilator muscles, co-activation of airway dilator and airway restrictor or retruder muscles may be used to stiffen the airway and maintain patency. By way of example, a nerve electrode may be attached to specific branches of the hypoglossal nerve innervating the genioglossus muscle (tongue protruder), in addition to the hyoglossus and styloglossus muscles (tongue retruders), or may be attached to a more proximal portion (e.g., trunk) of the hypoglossal nerve in which specific fascicles innervating the genioglossus, hyoglossus and styloglossus muscles are targeted by steering the stimulus using an electrode array. Activating the hyoglossus and styloglossus muscles causes the tongue to retract, and when co-activated with the genioglossus, causes the tongue to stiffen thus supporting the anterior aspect of the upper airway and resisting collapse during inspiration. Because the tongue retruder muscles may overbear the tongue protruder muscle under equal co-activation, unbalanced co-activation may be desired. Thus, a greater stimulus (e.g., longer stimulation period, larger stimulation amplitude, higher stimulation frequency, etc.) or an earlier initiated stimulus may be delivered to the portion(s) of the hypoglossal nerve innervating the genioglossus muscle than to the portion(s) of the hypoglossal nerve innervating the hyoglossus and styloglossus muscles.

With continued reference to FIG. 12, examples of suitable nerve stimulation sites include B; A+C; A+C+D; B+D; C+D; and E. Sites B and E may benefit from selective activation by field steering using an electrode array. As mentioned before, nerve electrodes may be placed at these target nerve(s) and/or intramuscular electrodes may be placed directly in the muscle(s) innervated by the target nerve(s).

Site A is a distal or medial branch of the hypoglossal nerve proximal of a branch innervating the genioglossus muscle and distal of a branch innervating the geniohyoid muscle. Site B is a more proximal portion of the hypoglossal nerve proximal of the branches innervating the genioglossus muscle and the geniohyoid muscle, and distal of the branches innervating the hyoglossus muscle and the styloglossus muscle. Site C is a medial branch of the hypoglossal nerve proximal of a branch innervating the geniohyoid muscle and distal of branches innervating the hyoglossus muscle and the styloglossus muscle. Site D is a branch of the ansa cervicalis nerve distal of the nerve root and innervating the sternohyoid. Site E is a very proximal portion (trunk) of the hypoglossal nerve proximal of the branches innervating the genioglossus, hyoglossus and styloglossus muscles.

Activating site B involves implanting an electrode on a hypoglossal nerve proximal of the branches innervating the genioglossus muscle and the geniohyoid muscle, and distal of the branches innervating the hyoglossus muscle and the styloglossus muscle.

Co-activating sites A+C involves implanting a first electrode on a hypoglossal nerve proximal of a branch innervating the genioglossus muscle and distal of a branch innervating the geniohyoid muscle, and implanting a second electrode on the hypoglossal nerve proximal of a branch innervating the geniohyoid muscle and distal of branches innervating the hyoglossus muscle and the styloglossus muscle.

Co-activating sites A+C+D involves implanting a first electrode on a hypoglossal nerve proximal of a branch innervating the genioglossus muscle and distal of a branch innervating the geniohyoid muscle; implanting a second electrode on the hypoglossal nerve proximal of a branch innervating the geniohyoid muscle and distal of branches innervating the hyoglossus muscle and the styloglossus muscle; and implanting a third electrode on a branch of an ansa cervicalis nerve distal of the nerve root and innervating the sternohyoid.

Co-activating sites B+D involves implanting a first electrode on a hypoglossal nerve proximal of branches innervating the genioglossus muscle and the geniohyoid muscle, and distal of branches innervating the hyoglossus muscle and the styloglossus muscle; and implanting a second electrode on a branch of an ansa cervicalis nerve distal of the nerve root and innervating the sternohyoid.

Co-activating sites C+D involves implanting a first electrode on a hypoglossal nerve proximal of a branch innervating the geniohyoid muscle, and distal of branches innervating the hyoglossus muscle and the styloglossus muscle and implanting a second electrode on a branch of an ansa cervicalis nerve distal of the nerve root and innervating the sternohyoid.

Activating site E involves implanting an electrode on a hypoglossal nerve proximal of the branches innervating the genioglossus, hyoglossus and styloglossus muscles; and selectively activating (e.g., by field steering) the genioglossus muscle before or more than the hyoglossus and styloglossus muscles.

With reference now to FIGS. 12A-12D, additional possible nerve stimulation sites are shown for effecting muscles controlling patency of the upper airway. For example, the cranial root of the accessory nerve AN (cranial nerve XI) innervates the levator veli palatini muscle of the soft palate, which elevates the soft palate. The cranial root of the accessory nerve AN also innervates the palatoglossus muscle, which functions to pull the soft palate inferiorly when the genioglossus is co-activated via the hypoglossal nerve (HGN). Moreover, because the cranial root of the accessory nerve AN also innervates various other muscles including, but not limited to, the palatopharyngeus, specific fibers in the accessory nerve AN may be selectively stimulated with one or more of the fiber selective stimulation means described in greater detail below, in order to only activate desired fibers of the nerve. The glossopharyngeal nerve GN. (cranial nerve IX) innervates the stylopharyngeus, which functions to dilate the lateral walls of the pharynx. However, since the glossopharyngeal nerve GN is a multi-function nerve with both afferent and efferent fibers, one or more of the fiber selective stimulation means described in greater detail below may be used to facilitate targeting the fibers that innervate only the stylopharyngeus. The cranial root of the accessory nerve AN and the glossopharyngeal nerve GN may be singularly activated, or these nerves may be co-activated with other nerve sites, such as, for example, the hypoglossal nerve, for increased efficacy.

Another possible nerve stimulation site may include the superior laryngeal nerve SLN. The superior laryngeal nerve SLN descends posterior and medial from the internal carotid artery and divides into the internal laryngeal nerve ILN and external laryngeal nerve ELN. While the external laryngeal nerve ELN descends behind the sternohyoid with the superior thyroid artery, the internal laryngeal nerve ILN descends near the superior laryngeal artery. The internal laryngeal nerve ILN contains sensory (afferent) fibers that are connected to receptors in the larynx. Some of these receptors include, but are not limited to, mechanoreceptors which detect pressure changes in a patient's upper airway associated with its collapse and institute a physiological response to re-open the patient's upper airway. Therefore, stimulation of specific afferent fibers inside the ILN nerve may result in triggering a reflex response that causes upper airway dilation by activating several muscles groups.

As discussed below, the superior laryngeal nerve SLN, in addition to being a sensory nerve, is also a motor nerve.

Therefore, it is contemplated that one or more of the fiber selective stimulation means described in greater detail below may be utilized to facilitate only stimulating the sensory or afferent fibers of the nerve.

Description of Alternative Nerve Electrodes

Any of the alternative nerve electrode designs described hereinafter may be employed in the systems described herein, with modifications to position, orientation, arrangement, integration, etc. made as dictated by the particular embodiment employed. Examples of other nerve electrode designs are described in U.S. Pat. No. 5,531,778, to Maschino et al., U.S. Pat. No. 4,979,511 to Terry, Jr., and U.S. Pat. No. 4,573,481 to Bullara, the entire disclosures of which are incorporated herein by reference.

With reference to the following figures, various alternative electrode designs for use in the systems described above are schematically illustrated. In each of the embodiments, by way of example, not limitation, the lead body and electrode cuff may comprise the same or similar materials formed in the same or similar manner as described previously. For example, the lead body may comprise a polymeric jacket formed of silicone, polyurethane, or a co-extrusion thereof. The jacket may contain insulated wire conductors made from BSW or solid wire comprising MP35N, MP35N with Ag core, stainless steel or Tantalum, among others. The lead body may be sigmoid shaped to accommodate neck and mandibular movement. Also, a guarded cathode tri-polar electrode arrangement (e.g., anode-cathode-anode) may be used, with the electrodes made of 90/10 or 80/20 PtIr alloy with silicone or polyurethane backing.

With specific reference to FIGS. 13A and 13B, a self-sizing and expandable design is shown to accommodate nerve swelling and/or over-tightening. FIG. 13A shows a perspective view of a nerve electrode cuff 130 on a nerve such as a hypoglossal nerve, and FIG. 13B shows a cross-sectional view of the nerve cuff electrode 130 on the nerve. In this embodiment, the implantable nerve cuff electrode 130 comprises a compliant sheet wrap 132 configured to be wrapped about a nerve and secured thereto by connecting opposite portions of the sheet by sutures 138, for example. The sheet 132 includes a plurality of radially and longitudinally distributed fenestrations 134 to allow expansion of the sheet 132 to accommodate nerve swelling and/or over tightening. Electrode contacts 136 comprising a coil, foil strip, conductive elastomer or individual solid conductors may be carried by the sheet 132 with an exposed inside surface to establish electrical contact with the nerve.

With specific reference to FIGS. 14A-14C, another self-sizing and expandable design is shown to accommodate nerve swelling and/or over-tightening FIG. 14A shows a perspective view of a nerve electrode cuff 140 on a nerve such as a hypoglossal nerve, and FIG. 14B shows a cross-sectional view of the nerve cuff electrode 140 on the nerve. In this embodiment, the implantable nerve cuff electrode 140 comprises a compliant sheet wrap 142 configured to be wrapped about a nerve and secured thereto by connecting opposite portions of the sheet by sutures 148A, or by a buckle 148B as shown in FIG. 14C, for example. The opposite portions of the sheet 142 comprise one or more narrow strips 144 integral with the sheet 142 to allow expansion and to accommodate nerve swelling and/or over tightening. Electrode contacts 146 comprising a coil, foil strip, conductive elastomer or individual solid conductors may be carried by the sheet 142 with an exposed inside surface to establish electrical contact with the nerve.

With specific reference to FIGS. 15A-15C, another self-sizing and expandable design is shown to accommodate nerve swelling and/or over-tightening. FIG. 15A shows a perspective view of a nerve electrode cuff 150 on a nerve such as a hypoglossal nerve, and FIG. 15B shows a cross-sectional view of the nerve cuff electrode 150 on the nerve. In this embodiment, the implantable nerve cuff electrode 150 comprises a compliant sheet wrap 152 configured to be wrapped about a nerve and secured thereto by connecting opposite portions of the sheet 152 by sutures 158, for example. The opposite portions of the sheet 152 are offset from the nerve and a thickened portion of the sheet 152 fills the offset space. The offset distance reduces the amount of compressive force that the electrode cuff can exert on the nerve. To further reduce the pressure on the nerve, the sheet 152 includes a plurality of radially distributed slits 154 extending partly through the thickness of the sheet 152 to allow expansion and to accommodate nerve swelling and/or over tightening.

Figure 16A:
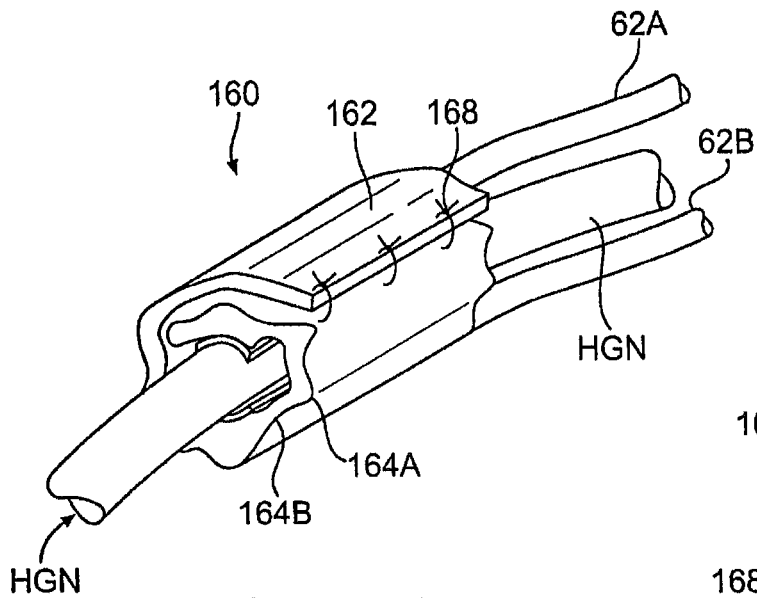
Figure 16B:
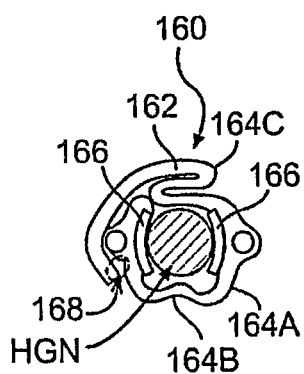

With specific reference to FIGS. 16A and 16B, another self-sizing and expandable design is shown to accommodate nerve swelling and/or over-tightening. FIG. 16A shows a perspective view of a nerve electrode cuff 160 on a nerve such as a hypoglossal nerve, and FIG. 16B shows a cross-sectional view of the nerve cuff electrode 160 on the nerve. In this embodiment, the implantable nerve cuff electrode 160 comprises a compliant sheet wrap 162 configured to be wrapped about a nerve and secured thereto by connecting opposite portions of the sheet 162 by sutures 168, for example. The sheet 162 includes a plurality of radially distributed and longitudinally extending convolutions 164 that may comprise alternative thick 164A and thin 164B portions in the sheet 162 and/or overlapping portions 164C of the sheet 162 to allow expansion and to accommodate nerve swelling and/or over tightening. Electrode contacts 166 comprising a coil, foil strip, conductive elastomer or individual solid conductors may be carried by the sheet 162 with an exposed inside surface to establish electrical contact with the nerve. Nerve cuff electrode 160 may accommodate one or two lead bodies 62A, 62B for connection to the electrode contacts 166 on the same or opposite sides of the nerve.

Turning now to FIGS. 16C-16D, additional self-sizing and expandable designs are shown to accommodate nerve swelling and/or over-tightening. With specific reference to FIG. 16C, there is depicted a nerve cuff electrode 1600 having a cuff body with a relatively wide semi-cylindrical lateral side 1601 and a plurality of opposing arms 1602 extending thereform for placement on the deep (contralateral) side of the nerve. Although the embodiment depicted in FIG. 16C includes two such opposing arms 1602, nerve cuff electrode 1600 may include any suitable number of opposing arms 1602. Lateral side 1601 may include an array of electrode contacts 1603. For example, in the depicted embodiment, lateral side may include three electrode contacts 1603. The three electrode contacts 1603 may include one cathode electrode contact 1603 disposed between two anode electrode contacts 1603, as shown.

Arms 1602 may be secured around a nerve (not shown) by any suitable means. For example, it is contemplated that arms 1602 may be elastic in nature, so as to gently grasp the nerve on its deep (contralateral) side. Alternatively, arms 1602 may be actively secured about a nerve by, for example, suturing an end portion of arms 1602 to, e.g., a portion of lateral side 1601. In embodiments where arms 1602 may be actively secured about a nerve, arms 1602 may be provided with a safety mechanism (not shown) that permits nerve cuff electrode 1600 to become disengaged from a nerve it is secured about upon the application of a predetermined amount of force. This predetermined force will be established at a level that is below that which can cause damage to the nerve.

As shown in FIG. 16D, opposing arms 1602 may be configured to expand and/or deform as necessary, in order to accommodate nerve swelling caused by, for example, localized trauma inflicted upon the nerve during cuff implantation. For example, each of opposing arms 1602 may have an unattached terminal end 1602a. In order to facilitate expansion, opposing arms 1602 may be also made from any suitable material known to those having ordinary skill in the art. For example, arms 1602 may be made from an elastomer, such as, for example, silicone or polyurethane. Additionally, one or both of arms 1602 may be provided with one or more limiting mechanisms (not shown) to limit the amount of expansion arms 1602 may undergo as a result of, for example, nerve swelling. Such limiting mechanisms may include any suitable mechanism, including, but not limited to, flanges, barbs, and/or sutures.

Figure 16E:
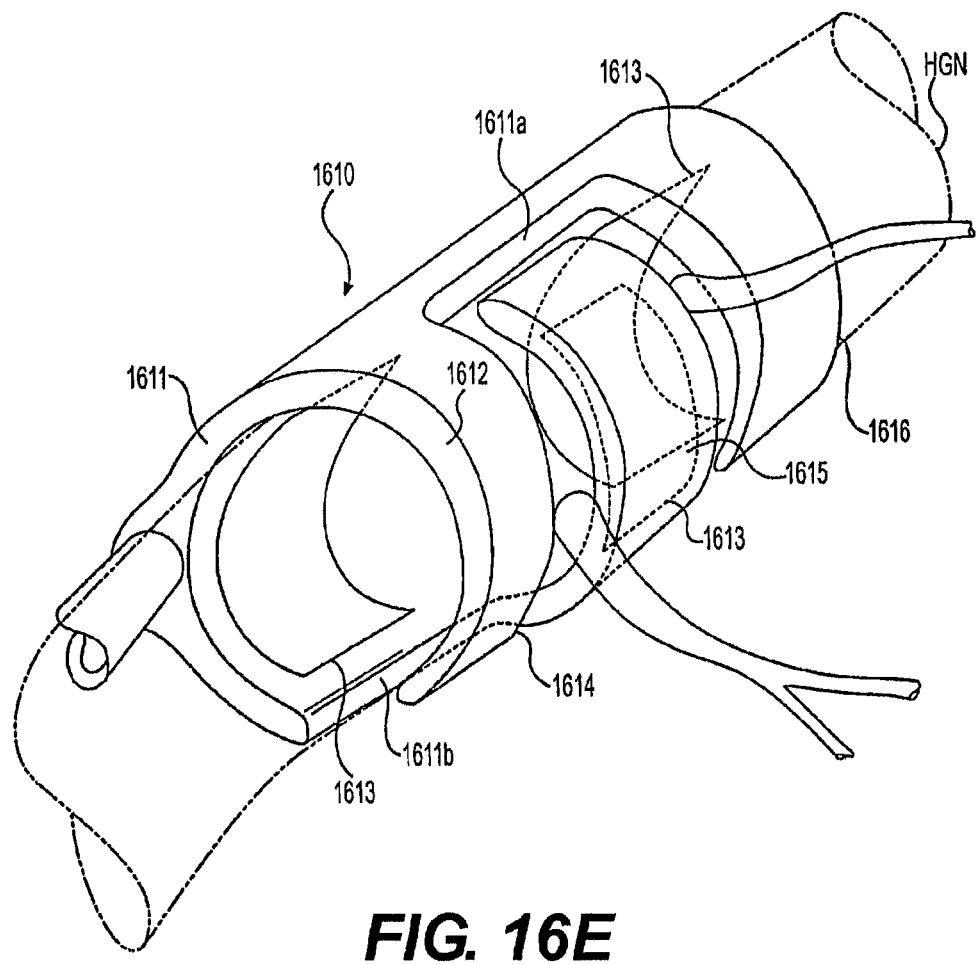

With reference to FIG. 16E, there is depicted another design of a self-sizing and expandable nerve cuff electrode 1610. For the purposes of this disclosure, nerve cuff electrode 1610 may be substantially similar to nerve cuff electrode 1600 depicted in FIGS. 16C-16D. Nerve cuff electrode 1610, however, may differ from nerve cuff electrode 1600 in at least two significant ways. First, for example, lateral side 1611 of nerve cuff electrode 1610 may carry two anode electrode contacts 1613 and the medial side 1612 may carry one cathode electrode contact 1613 in an arrangement that may be referred to as transverse guarded tri-polar. Second, for example, nerve cuff electrode 1610 may include three arms 1614-1616 extending from lateral side 1611. In the depicted embodiment, arms 1614 and 1616 may be configured to extend substantially in the same direction from the same edge 1611a of lateral side 1611, while arm 1615 may be configured to extend in substantially the opposing direction from an opposing edge 1611b of lateral side 1611. In the depicted embodiment, arm 1615 may be disposed between arms 1614 and 1616, and may be configured to carry the cathode electrode contact 1613, as mentioned above. However, any suitable arrangement of arms 1614-1616 and/or electrode contacts 1613 may be utilized within the principles of this disclosure.

Figure 16F:
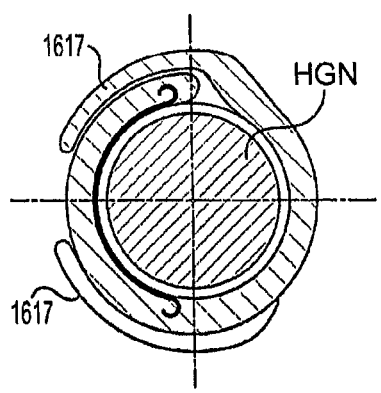

As shown in FIG. 16F, certain embodiments of nerve curve electrode 1600 and/or nerve cuff electrode 1610 may include one or more elongated arms 1617. Arms 1617 may include any suitable length, so as to allow arms 1617 to wrap around a body portion of the cuff electrode one or more times in a spiral-like fashion, when the cuff electrode is mounted about an un-swollen nerve. However, arms 1617 may allow the cuff electrode to remain mounted on the nerve as it accommodates large amounts of nerve swelling by unraveling and/or unwrapping as the nerve swells. For example, each of the arms 1617 may overlap lateral side 1601 or 1611 to accommodate larger amounts of nerve swelling without allowing the cuff to become detached from the nerve. The elongated arms 1617 may extend around the body of the cuff electrode to form a spiral when the nerve is in a substantially un-swollen state, as shown.

Figure 17:
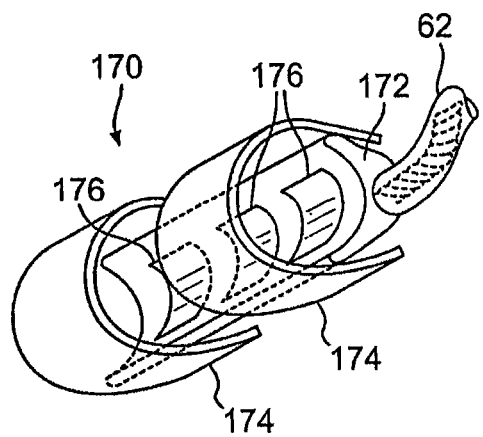
Figure 18:
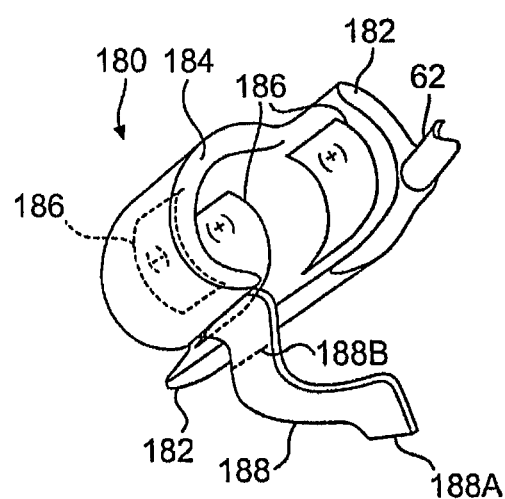

With reference to FIG. 17, a modular nerve electrode cuff 170 is shown that includes a semi-cylindrical body portion 172 with an array of electrode contacts 176 with separate insulative strips 174 for placement on the deep (contralateral side) of the nerve, which typically has more nerve branches and connecting blood vessels. In this embodiment, independent placement of the electrode body 172 on the superficial (lateral) side of the nerve and placement of the insulative strips 174 on the deep (contralateral) side of the nerve minimizes dissection. The strips 174 may be connected to the electrode body 172 by sutures or buckles as described previously. This embodiment is also self-sizing to accommodate nerve swelling and/or over-tightening. With reference to FIG. 18, a nerve cuff electrode 180 is shown that has a cuff body with a relatively wide semi-cylindrical lateral side 182 and a relatively narrow semi-cylindrical medial side 184 that may extend through a small fenestration around the deep (contralateral) side of a nerve to securely and gently grasp the nerve while minimizing dissection. In the illustrated example, the lateral side 182 carries two anode electrode contacts 186 and the medial side 184 carries one cathode electrode contact 186 in an arrangement that may be referred to as transverse guarded tri-polar. A tow strap 188 is provided for inserting the medial side 184 around the deep side of the nerve. The tow strap 188 may be integrally formed with the medial side 184 of the cuff body, and may include a reinforced tip 188A with a serrated or marked cut line 188B.

Figure 19A:
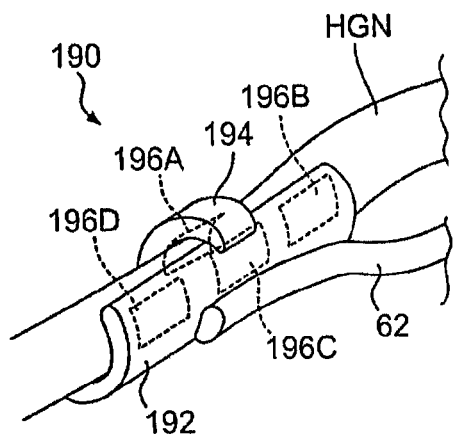
Figure 19B:
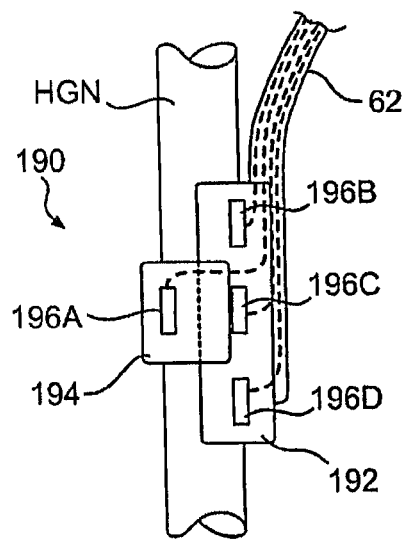

With reference to FIGS. 19A and 19B, a nerve cuff electrode 190 is shown that has a cuff body with a relatively wide semi-cylindrical lateral side 192 and a relatively narrow semi-cylindrical medial side 194 that may extend through a small fenestration around the deep (contralateral) side of a nerve to securely and gently grasp the nerve while minimizing dissection. In the illustrated example, the lateral side 192 carries one cathode electrode contact 196C and two guarding anode electrode contacts 196B and 196D, and the medial side 194 carries one anode electrode contact 196A in an arrangement that may be referred to as transverse and longitudinal guarded quad-polar. The provision of guarding electrode contacts 196B and 196C reduces extrinsic stimulation due to the lack of insulative material on the medial side 194. The embodiments of FIGS. 18, 19A and 19B illustrate two different electrode contact arrangements, but the number and arrangement may be modified to suit the particular application.

Figure 20:
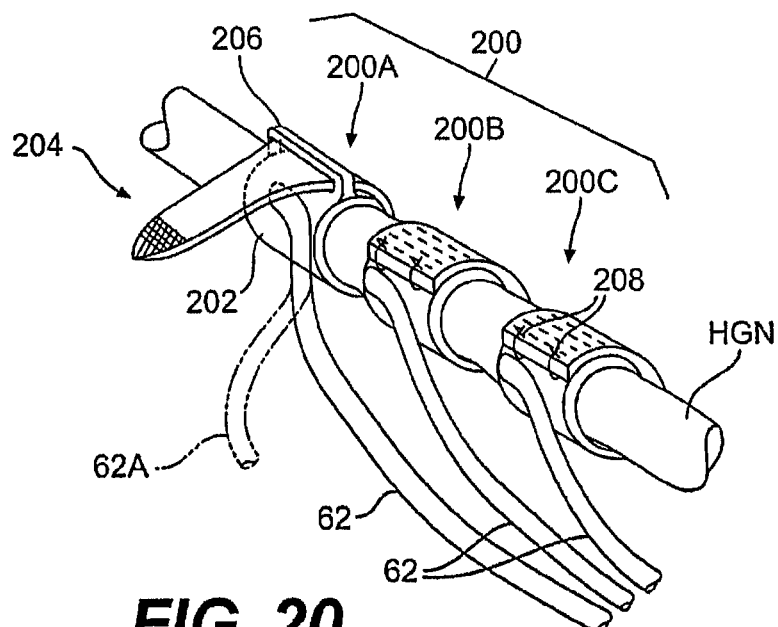

With reference to FIG. 20, a nerve cuff electrode array 200 is shown that utilizes a series of relatively narrow independent cuffs 200A, 200B and 200C with corresponding independent lead bodies 62. Providing a series of relatively narrow independent cuffs 200A, 200B and 200C minimizes the required dissection around the nerve for implantation thereof. Also, the series of independent cuffs 200A, 200B and 200C allows more selectivity in electrode placement to adjust for anatomical variation or multiple target stimulation sites, for example. Providing multiple independent lead bodies 62 allows for more options in routing and placement of the individual lead bodies 62 (e.g., alternate placement of lead body 62A) and also prevents tissue encapsulation around the lead bodies 62 from collectively affecting encapsulation of the nerve cuffs 200. Each of the cuffs 200A, 200B and 200C may include a cuff body 202 with one or more imbedded electrode contacts (not shown) and a tow strap 204 as described before. Also, each of the cuffs 200A, 200B and 200C may include suture 208 or a buckle 206 to lock onto the tow strap 204 for connecting opposite ends of the body 202 around the nerve.

Figure 21A:
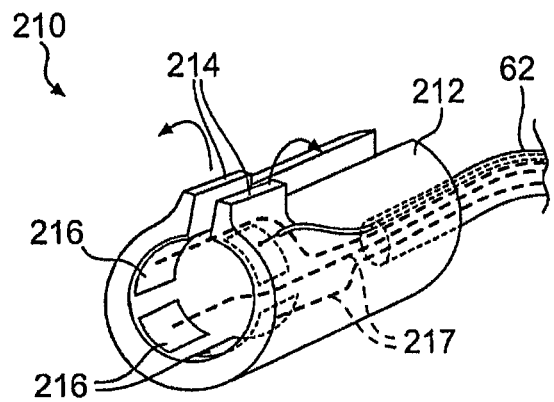
Figure 21B:
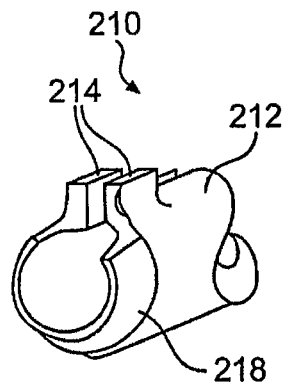

With reference to FIGS. 21A and 21B, a nerve cuff electrode 210 is shown with multiple electrode contacts 216 radially spaced around the inside surface of a compliant split cuff body 212 to establish multiple electrical contact points around the circumference of the nerve. Each of the electrode contacts 216 may be connected to independent conductors in the lead body 62 via axially extending wires 217. This arrangement allows for field steering as discussed herein. The compliant split cuff body 212 together with axially extending wires 217 allows for self-sizing to accommodate nerve swelling and/or over-tightening. One or more pairs of tabs 214 extending from opposite end portions of the cuff body 212 may be connected by a suture (not shown) as described herein. As shown in FIG. 21B, the proximal and distal ends of the cuff body 212 may have tapered thickness extensions 218 to provide strain relief and reduce mechanical irritation of the nerve due to contact with the edge of the cuff.

Figure 22:
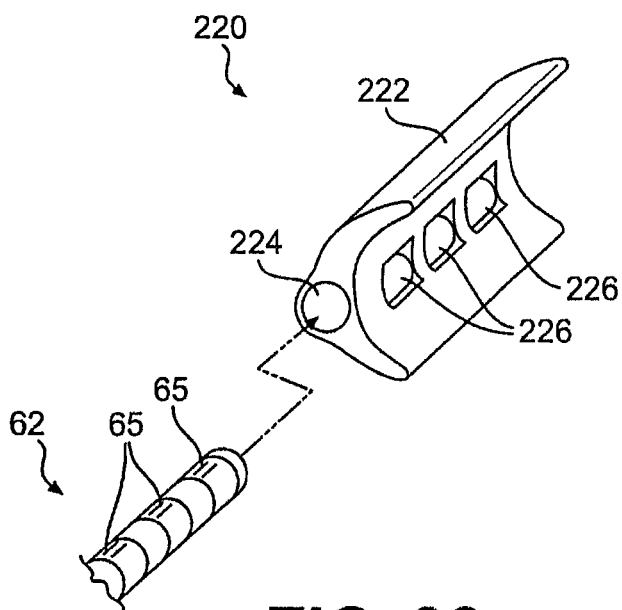

With reference to FIG. 22, a nerve cuff electrode 220 is shown with a separable lead 62 in what may be referred to as a modular design. In this embodiment, the nerve cuff electrode 220 includes a semi-circular flexible cuff body (or housing) 222 with a receptacle 224 configured to accommodate a distal end of a lead body 62 therein. The receptacle 224 may provide a releasable mechanical lock to the lead body 52 as by a press fit, mating detents, etc. The distal end of the lead body 62 carries an array of ring electrodes 65, with windows 226 provided in the cuff body 222 configured to align with the ring electrodes 65 and permit exposure of the ring electrodes 65 to the nerve to establish electrical connection therebetween. The cuff body 222 may be attached to the nerve or simply placed adjacent the nerve. Any of the cuff designs described herein may be provided with a receptacle to accommodate a removable lead body. This embodiment allows postoperative removal of the lead body 62 without removal of the cuff 220, which may be beneficial in revision operations, for example.

Figure 22A:
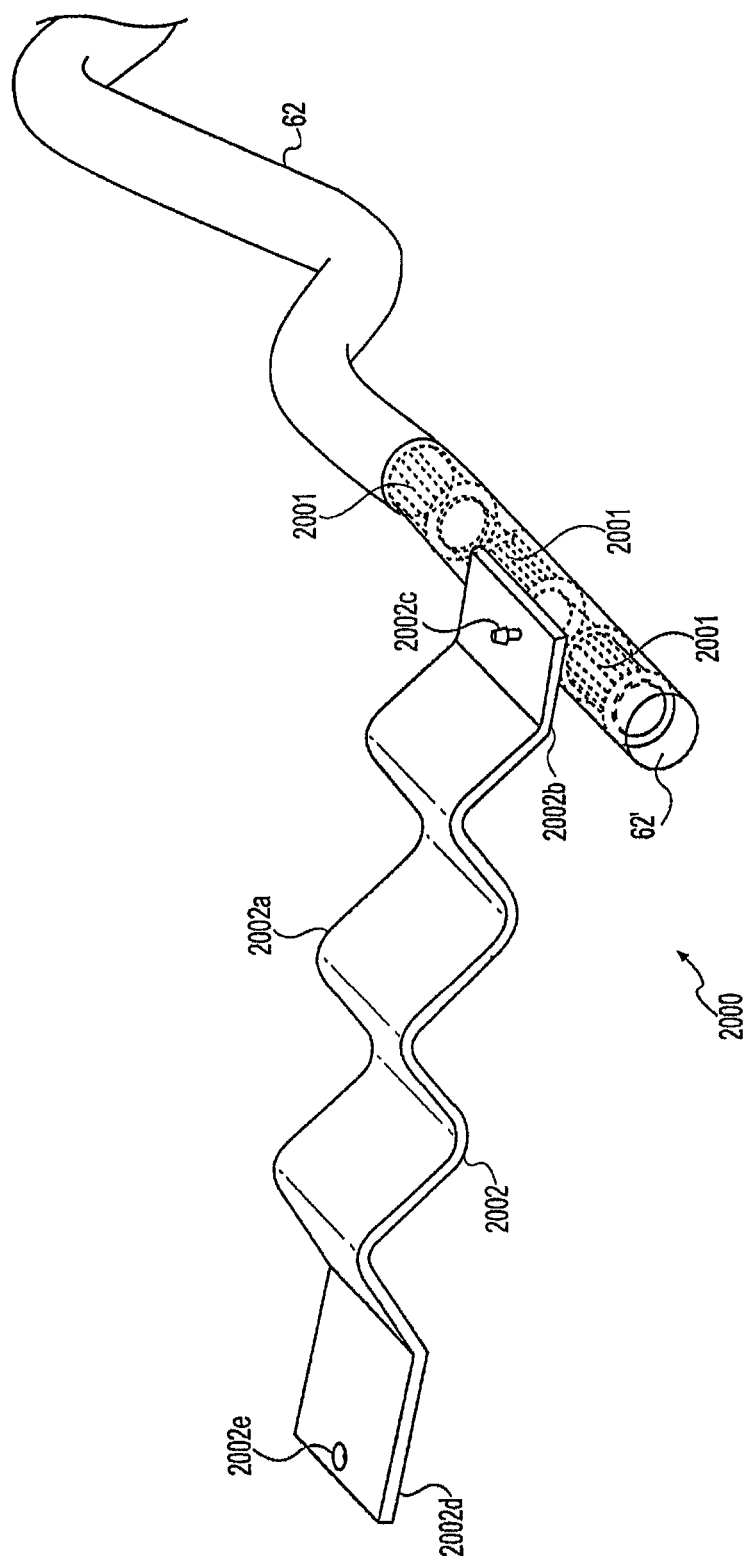

Turning now to FIG. 22A, there is depicted another design for a nerve cuff electrode 2000 where a substantially cylindrical distal portion 62' of lead body 62 carries an array of electrodes 2001. Electrodes 2001 may include ring electrodes that extend completely around the circumference of lead body 62, or, alternatively, may include generally semi-circular electrodes that extend partially around the circumference of lead body 62. The electrode may be selectively insulated on any portion of its surface to allow directional stimulation. Nerve cuff electrode 2000 may further include a nerve securing mechanism for securing lead body 62 to a nerve, such as, for example, a hypoglossal nerve. The nerve securing mechanism may include, for example, a compliant sheet wrap 2002 that is attached on one end to a distal portion of lead body 62, and unattached on the other opposing end. Compliant sheet wrap 2002 may be attached to lead body 62 by any suitable means.

Figure 22B:
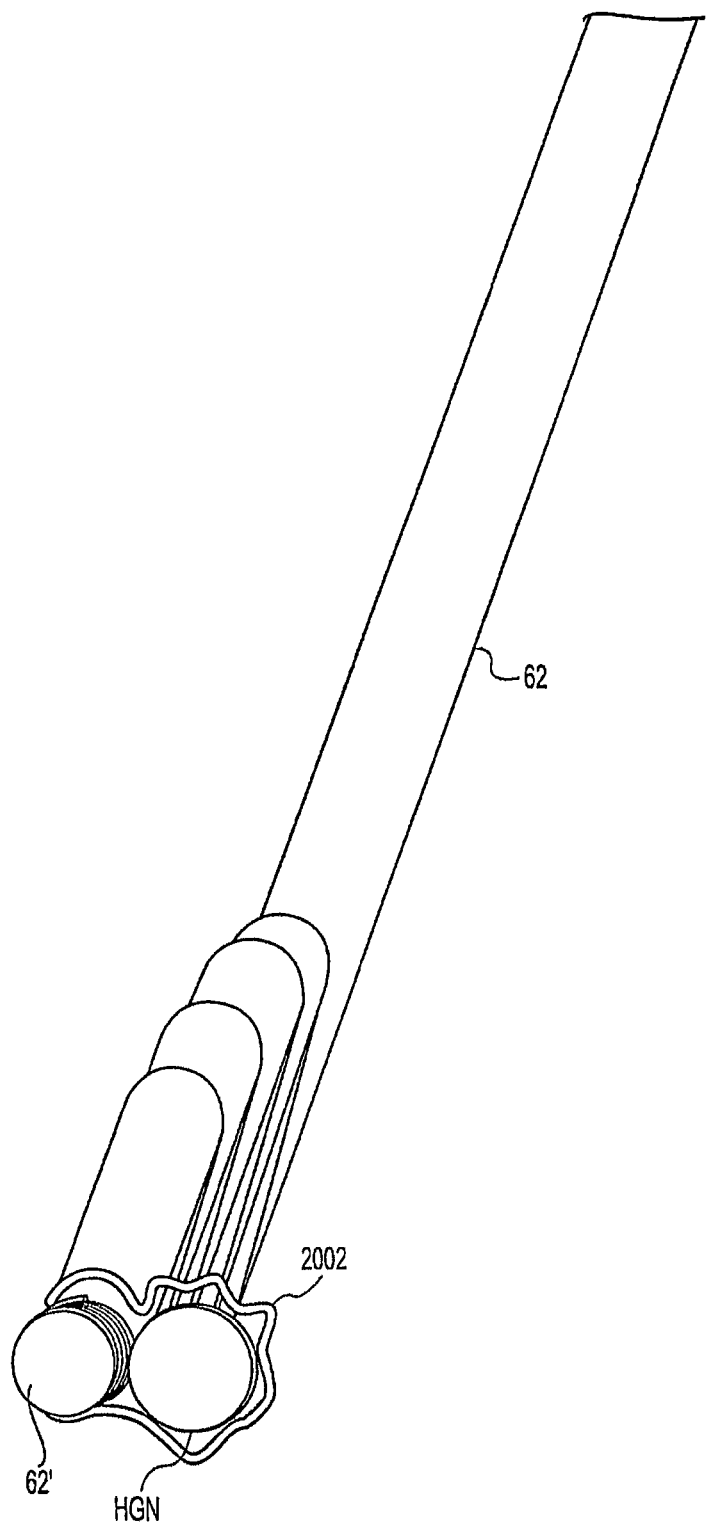
Figure 22C:
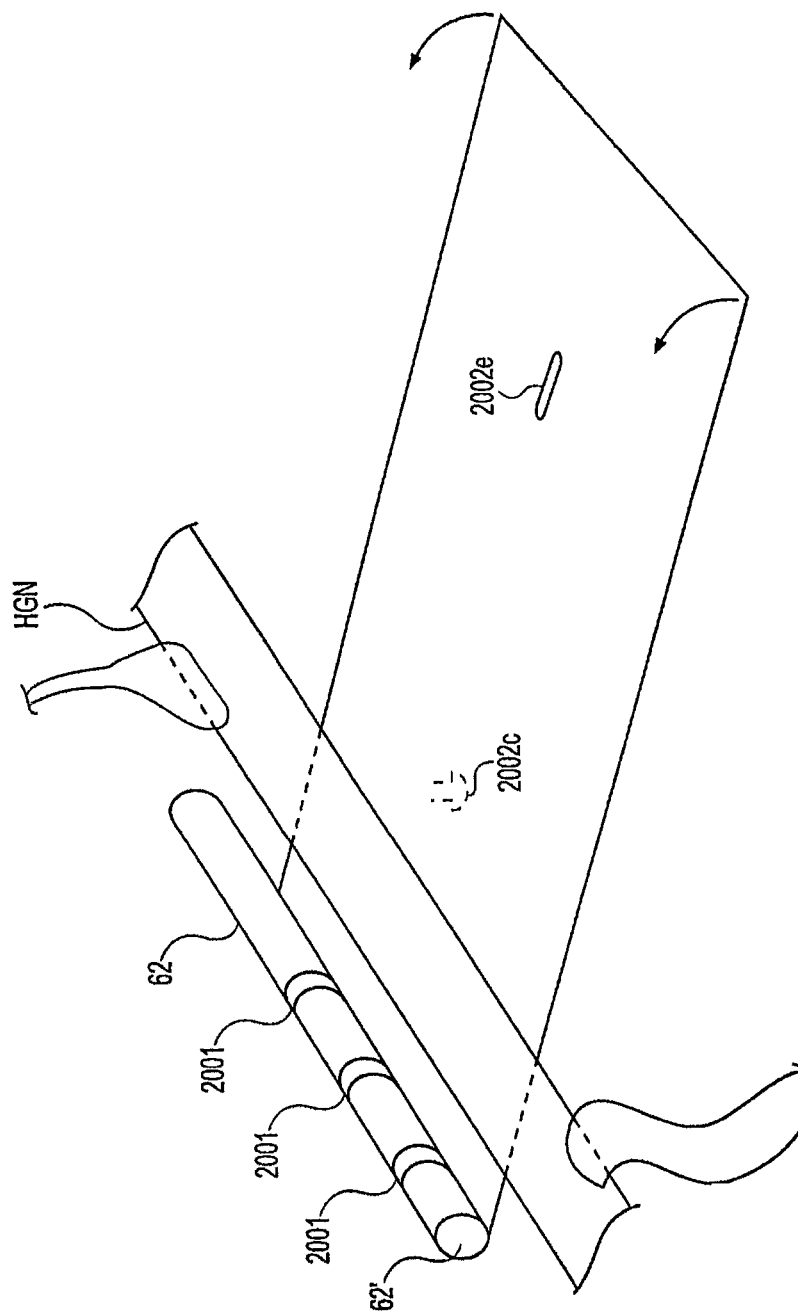

As shown in FIG. 22B, compliant sheet wrap 2002 may be configured to be wrapped around a nerve and secured thereto by, for example, connecting opposite portions of the sheet wrap 2002 together. Sheet wrap 2002 may be provided with one or more features to facilitate such connections. For example, it is contemplated that a portion 2002b of sheet wrap 2002 that is closest to lead body 62 may be provided with a projection 2002c that is configured for insertion into a corresponding opening 2002e provided on a portion 2002d of sheet wrap 2002 that is opposite portion 2002b. Opening 2002e may be configured to retain projection 2002c despite the forces exerted on sheet wrap 2002 during normal nerve swelling. However, opening 2002e may be configured to release projection 2002c when forces greater than a predetermined threshold are exerted on sheet wrap 2002, so as to prevent injury to the nerve. As shown in FIG. 22C, in some embodiments, opening 2002e may be provided as a slot, which, in addition to securing projection 2002c, may allow projection 2002c to slide within the opening 2002e, thereby allowing expansion of the sheet wrap 2002 to accommodate nerve swelling and/or over tightening of the sheet wrap 2002. Additionally, both portions 2002b and 2002d may be provided with suitable openings to facilitate the insertion of sutures (not shown) or other suitable fastening mechanisms. Sheet wrap 2002 may have any desired width. For example, sheet wrap 2002 may have a substantially tapered width, in order to securely wrap the nerve while minimizing dissection.

Compliant sheet wrap 2002 may be provided with any of a number of means that allow sheet wrap 2002 to expand, in order to accommodate nerve swelling and/or over tightening. For example, in one embodiment, sheet wrap 2002 may be provided with a plurality of radially and/or longitudinally distributed fenestrations (not shown). In other embodiments, sheet wrap 2002 may be provided with a plurality of undulations 2002a, such as, for example, sigmoid undulations, which may allow for expansion of sheet wrap 2002.

Figure 22D:
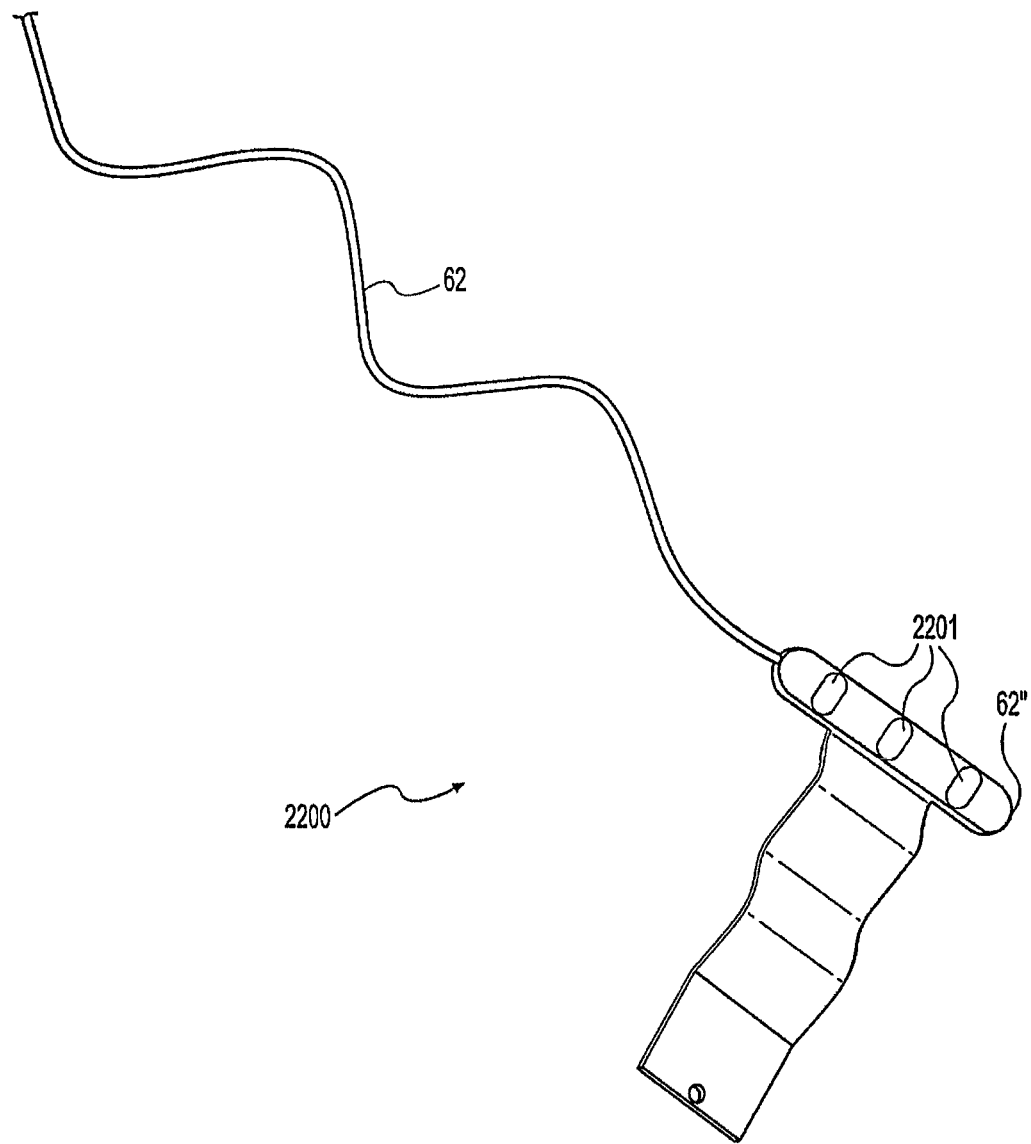

With reference now to FIG. 22D, there is depicted another design for a nerve cuff electrode 2200 where a distal portion 62" of lead body 62 carries an array of electrodes 2201. For the purposes of this disclosure, nerve cuff electrode 2200 may include substantially the same features as nerve cuff electrode 2000 depicted in FIGS. 22A-22C. Nerve cuff electrode 2200, however, may differ from nerve cuff electrode 2000 in that distal portion 62" may be substantially flat or paddle-shaped. Furthermore, electrode contacts 2201, rather than being circular or semi-circular in configuration, may be substantially, flat in configuration. In certain procedures, it is contemplated that the paddle-shaped distal portion 62", along with the substantially flat electrode contacts 2201, may promote greater contact between electrode contacts 2201 and the nerve they are mounted upon.

Description of Alternative Implant Procedure for the Stimulation Lead

Figure 23C:
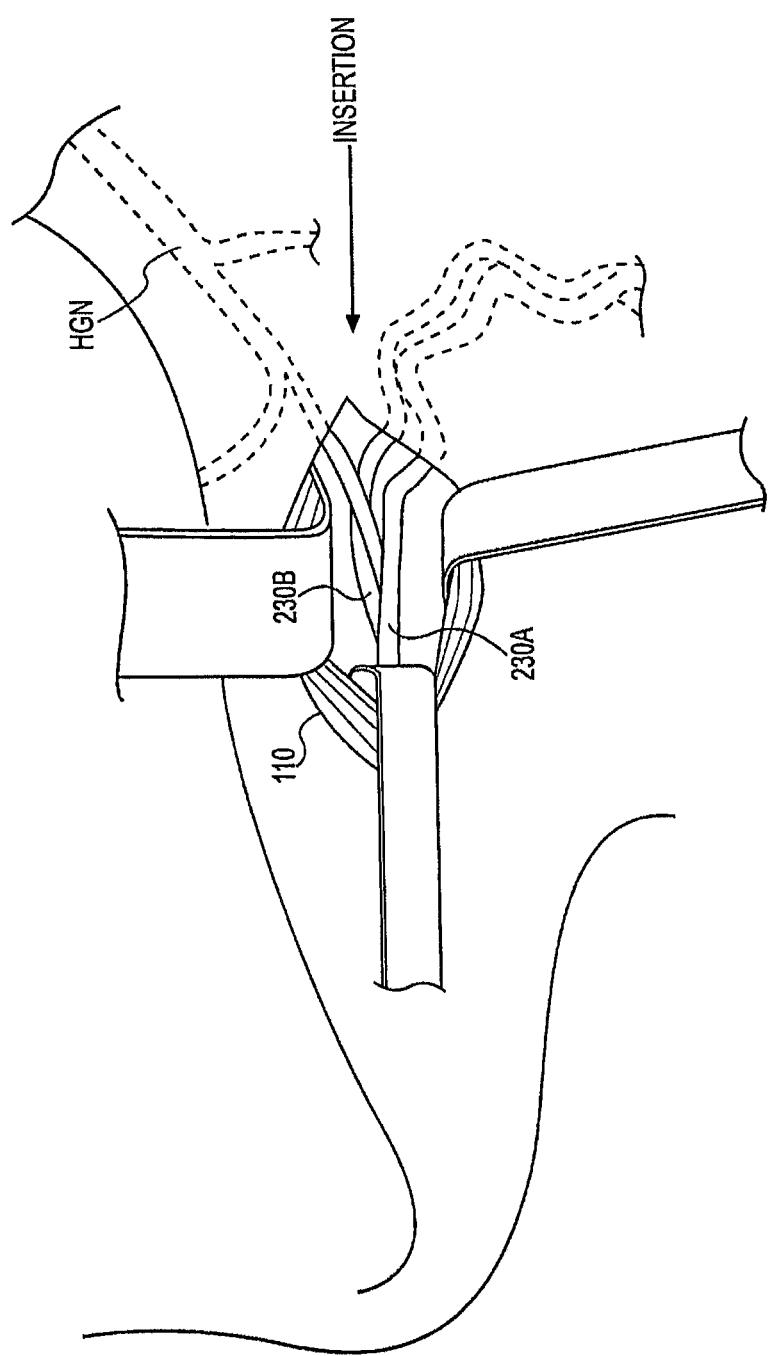

With reference to FIGS. 23A-23C, an insertable paddle-shaped lead 230 design is shown. The insertable lead 230 may have a paddle-shape (rectangular) cross-section with a tubular jacket 232 and one or more conductors 234 extending therethrough to one or more distally placed electrode contact(s) 236. The electrode contact(s) 236 may be imbedded in a molded distal end of the jacket 232 such that the electrode contact 236 has an exposed surface to face the nerve when implanted as shown in FIG. 23B. The space between the nerve and electrode is shown for purposes of illustration only, as the electrodes may be placed in direct contact with the nerve. Soft tines 238 may be integrally formed at the distal end of the tubular jacket 232 for purposes of mild fixation to tissue when implanted. The insertable lead 230 is configured to be placed adjacent to the nerve (thereby negating the need for a cuff) by inserting the lead 230 at the surgical access site 110 and following the nerve distally until the electrode contacts 236 are placed adjacent the target stimulation site. The insertable lead 232 may be used alone or in conjunction with another lead as shown in FIGS. 23B and 23C. In the illustrated example, a first lead 230A is inserted along a superficial side of the nerve and a second lead 230B is inserted along a deep side of the nerve.

A method of implanting lead 230 may generally comprise accessing a proximal extent of the nerve by minimal surgical dissection and retraction of the mylohyoid muscle as shown in FIG. 23C. Special tools may alternatively be employed for percutaneous or laparoscopic access as shown and described with reference to FIGS. 24A-24C. Subsequently, two paddle-shaped leads 230 with distal electrode contacts 236 may be inserted into the surgical access site and advanced beyond the access site along a distal aspect of the nerve to the desired stimulation site on either side of the nerve. These techniques minimize trauma and facilitate rapid recovery.

Figure 24A:
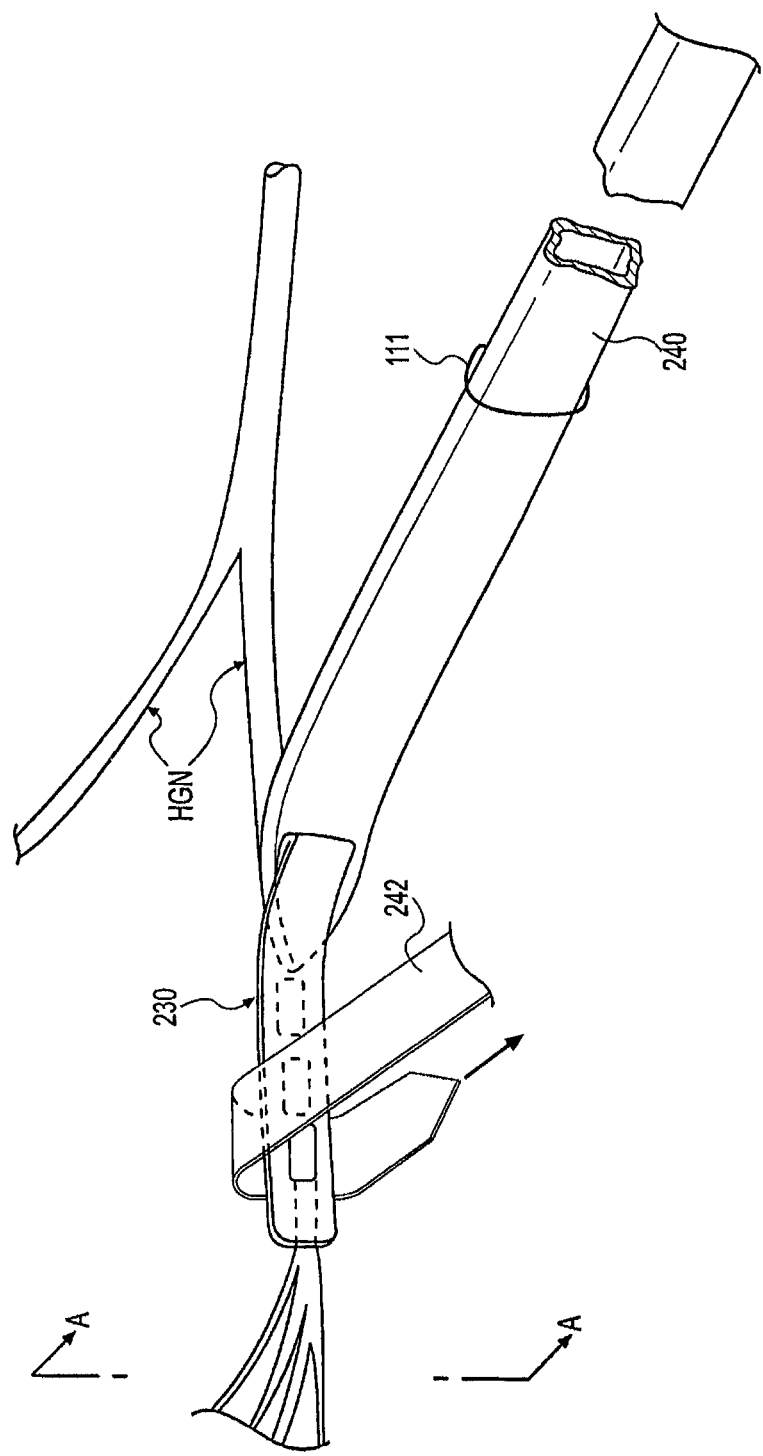
Figure 24C:
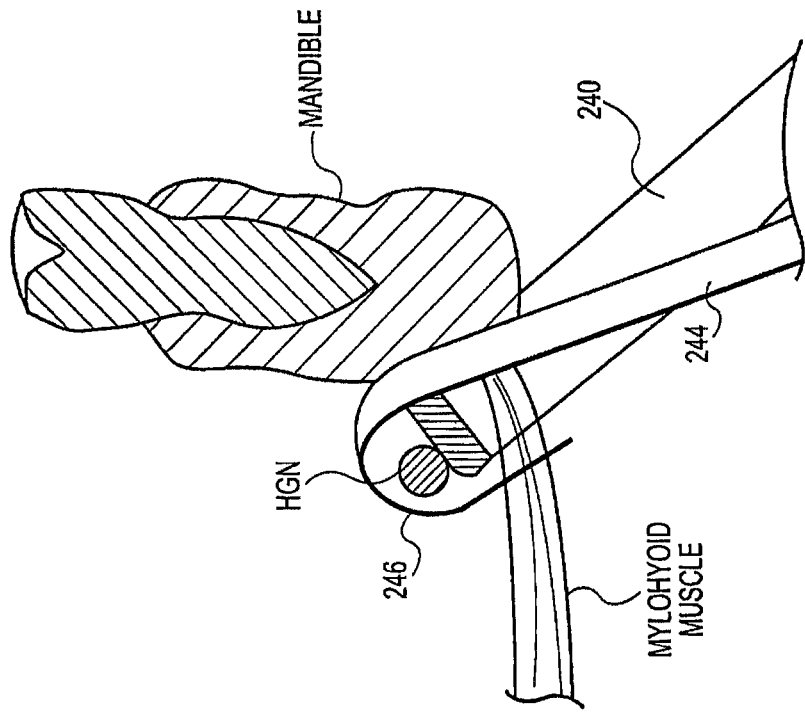
Figure 24B:
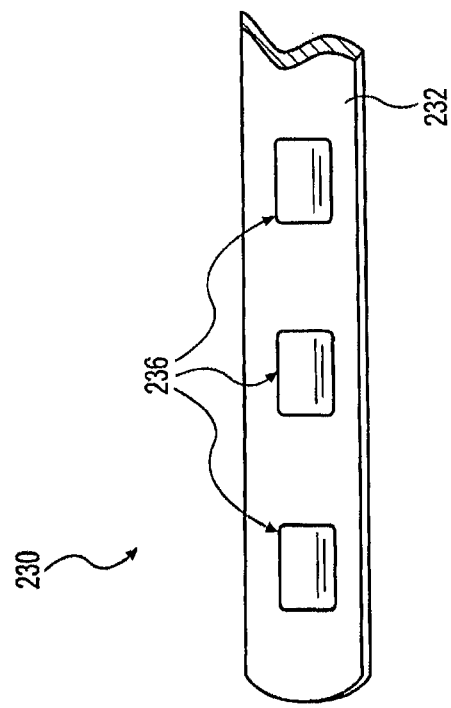

A less invasive method of implanting a paddle-shaped lead 230 is shown in FIGS. 24A-24C. In this embodiment, a rectangular tubular trocar 240 with a sharpened curved tip is placed through a percutaneous access site 111 until a distal end thereof is adjacent the superficial side of the nerve. A paddle-shaped lead 230 is inserted through the lumen of the trocar 240 and advanced distally beyond the distal end of the trocar 240 along the nerve, until the electrode contacts 236 are positioned at the target stimulation site. As shown in FIG.

24B, which is a view taken along line A-A in FIG. 24A, the insertable lead 230 includes multiple electrode contacts 236 in an anode-cathode-anode arrangement, for example, on one side thereof to face the nerve when implanted. In this embodiment, tines are omitted to facilitate smooth passage of the lead 230 through the trocar. To establish fixation around the nerve and to provide electrical insulation, a backer strap 242 of insulative material may be placed around the deep side of the nerve. To facilitate percutaneous insertion of the backer 242, a curved tip needle 244 may be inserted through a percutaneous access site until the tip is adjacent the nerve near the target stimulation site. A guide wire 246 with a J-shaped tip may then be inserted through the needle 244 and around the nerve. The backer 242 may then be towed around using the guide wire 246 as a leader, and secured in place by a buckle (not shown), for example.

Figure 25:
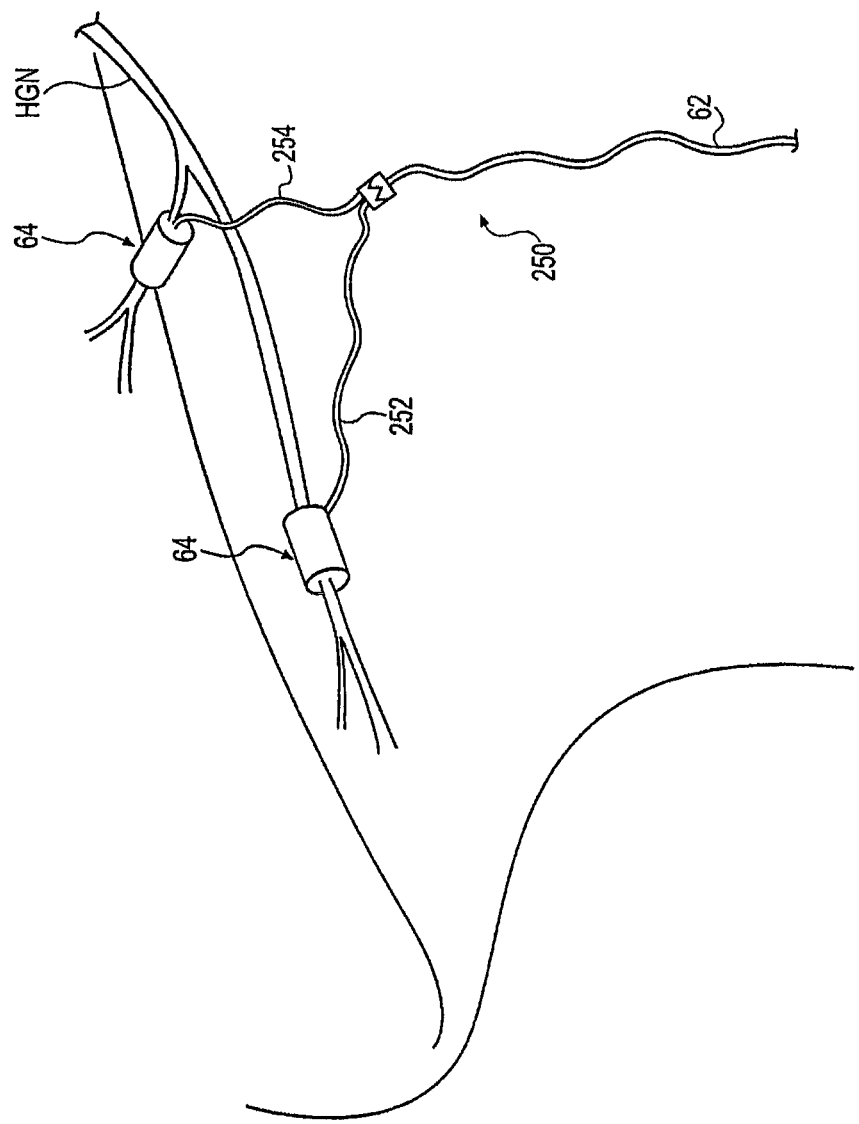
FIG. 25 schematically illustrates an alternative bifurcated lead body design.

With reference to FIG. 25, a bifurcated lead 250 is shown to facilitate separate attachment of electrode cuffs 64 to different branches of the same nerve or different nerves for purposes described previously. Any of the nerve cuff electrode or intramuscular electrode designs described herein may be used with the bifurcated lead 250 as shown. In the illustrated example, a first lead furcation 252 and a second lead furcation 254 are shown merging into a common lead body 62. Each furcation 252 and 254 may be the same or similar construction as the lead body 62, with modification in the number of conductors. More than two electrode cuffs 64 may be utilized with corresponding number of lead furcations.

Description of Stimulation Lead Anchoring Alternatives

Figure 26A:
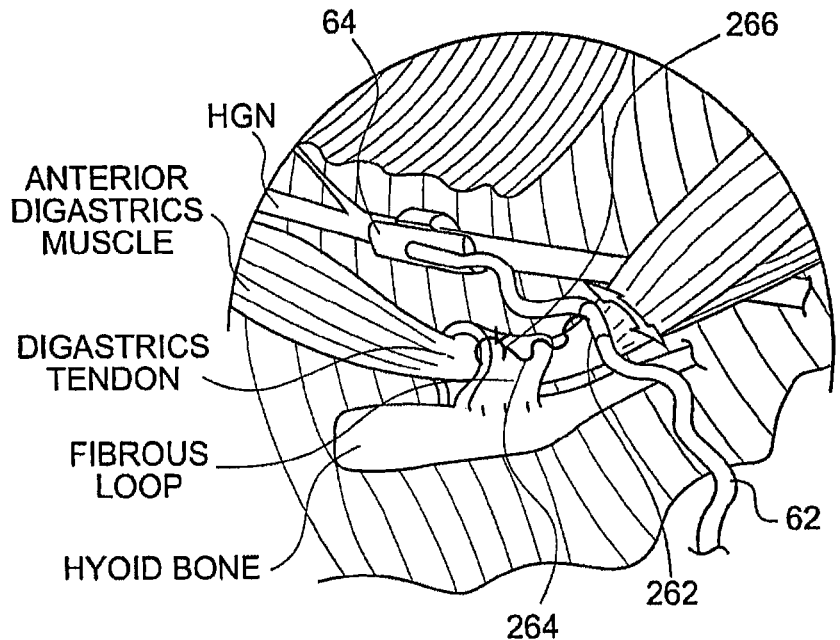
FIGS. 26A-26B schematically illustrate alternative fixation techniques for the stimulation lead and electrode cuff.
Figure 26B:
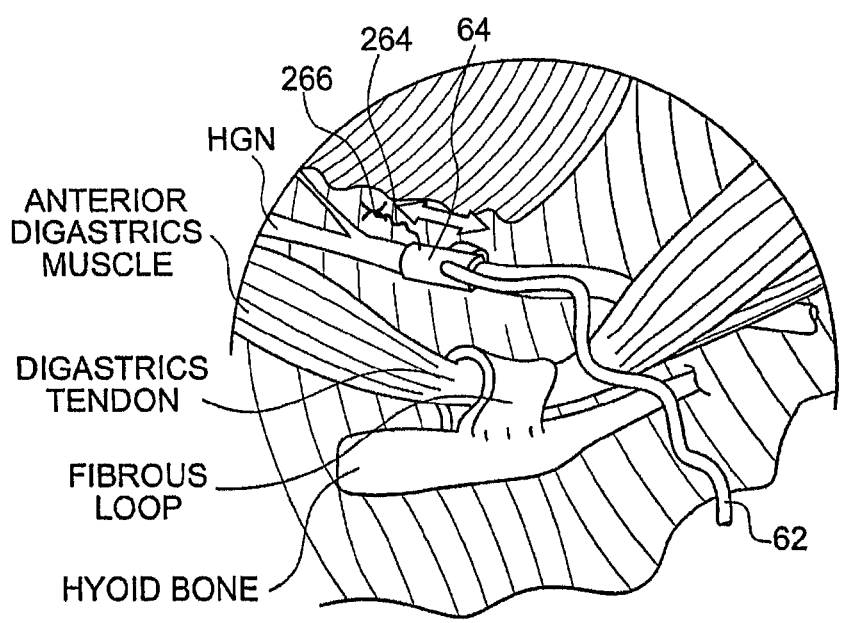

With reference to FIGS. 26A and 26B, an elastic tether 264 with a limited length is utilized to prevent high levels of traction on the electrode cuff 64 around the hypoglossal nerve (or other nerve in the area) resulting from gross head movement. In other words, tether 264 relieves stress applied to the electrode cuff 64 by the lead body 62. FIGS. 26A and 26B are detailed views of the area around the dissection to the hypoglossal nerve, showing alternative embodiments of attachment of the tether 264. The proximal end of the tether 264 may be attached to the lead body 62 as shown in FIG. 26A or attached to the electrode cuff 64 as shown in FIG. 26B. The distal end of the tether 264 may be attached to the fibrous loop carrying the digastrics tendon as shown in FIG. 26A or attached to adjacent musculature as shown in FIG. 26B.

By way of example, not limitation, and as shown in FIG. 26A, a tubular collar 262 is disposed on the lead body 62 to provide connection of the tether 264 to the lead body 62 such that the lead body 62 is effectively attached via suture 266 and tether 264 to the fibrous loop surrounding the digastrics tendon. The tether 264 allows movement of the attachment point to the lead body 62 (i.e., at collar 262) until the tether 264 is straight. At this point, any significant tensile load in the caudal direction will be borne on the fibrous loop and not on the electrode cuff 64 or nerve. This is especially advantageous during healing before a fibrous sheath has formed around the lead body 62 and electrode cuff 64, thus ensuring that the cuff 64 will not be pulled off of the nerve. It should be noted that the length of the tether 262 may be less than the length of the lead body 62 between the attachment point (i.e., at collar 262) and the cuff 64 when the tensile load builds significantly due to elongation of this section of lead body 62.

The tether 264 may be formed from a sigmoid length of braided permanent suture coated with an elastomer (such as silicone or polyurethane) to maintain the sigmoid shape when in the unloaded state. The tether 264 may also be made from a monofilament suture thermoformed or molded into a sigmoid shape. The distal end of the tether 264 may be attached to the fibrous loop using a suture 266 or staple or other secure means. Note that the tether 264 may be made from a biodegradable suture that will remain in place only during healing.

Also by way of example, not limitation, an alternative is shown in FIG. 26B wherein the tether 264 is attached to the electrode cuff 64. The distal end of the tether 264 may be attached to the adjacent musculature by suture 266 such the musculature innervated by branches of the hypoglossal nerve or other musculature in the area where the electrode cuff 64 is attached to the nerve. The tether 264 ensures that the electrode cuff 64 and the hypoglossal nerve are free to move relative to the adjacent musculature (e.g., hyoglossal). As significant tensile load is applied to the lead body 62 due to gross head movement, the tether 264 will straighten, transmitting load to the muscle rather then to the nerve or electrode cuff 64.

Figure 26C:
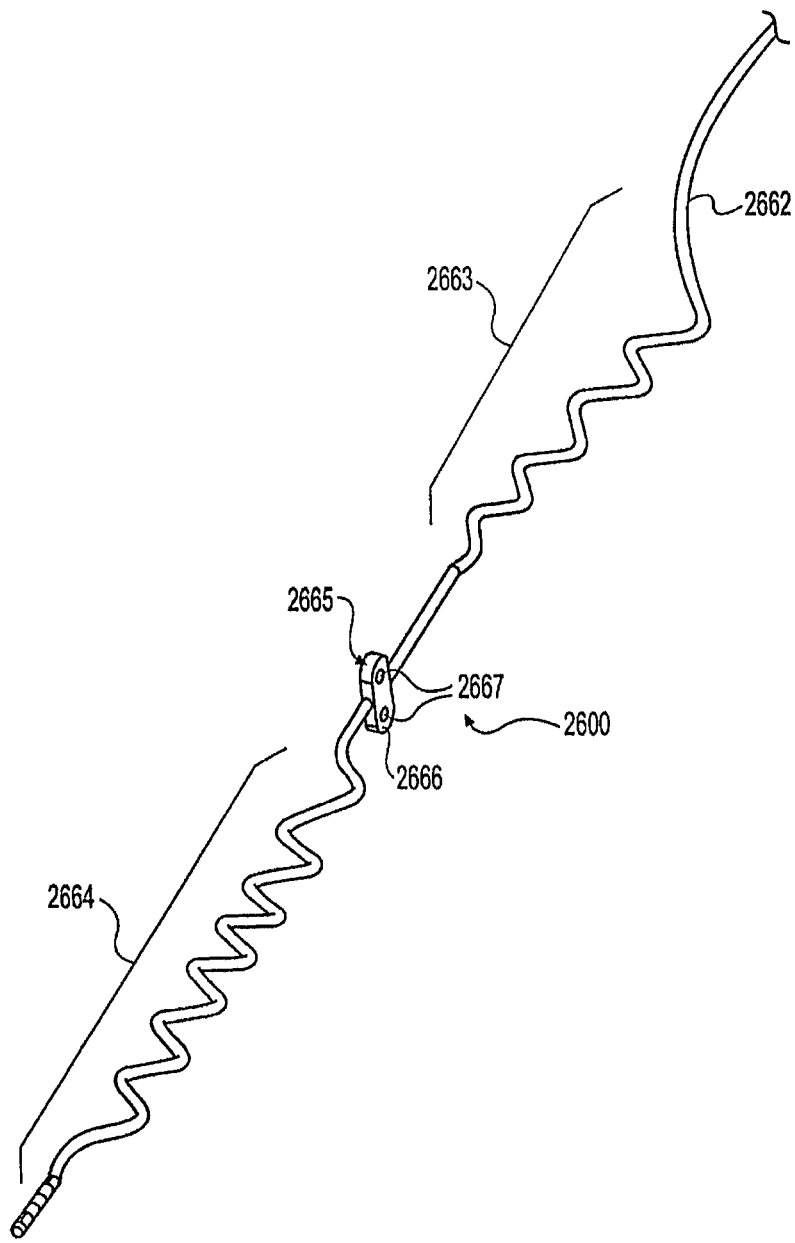
FIG. 26C schematically illustrates an alternative embodiment of a stimulation lead having a fixation mechanism.

As alluded to above, stimulation lead 60 may comprise a number of differing design embodiments. One such embodiment has been discussed above with respect to FIG. 5. Another such embodiment is depicted in FIG. 26C, which illustrates a stimulation lead 2600. Stimulation lead 2600 may be substantially similar to and/or may include one or more of the features described in connection with stimulation lead 60. As shown in FIG. 26C, stimulation lead 2600 may include a lead body 2662 having a first, proximal lead body portion 2663. First lead body portion 2663 may be substantially similar to lead body 62. For example, first lead body portion 2663 may include a similar flexibility as lead body 62. Lead body 2662 may further include a second, distal lead body portion 2664 leading to the distal end of lead body 2662 at the nerve cuff electrode. Second lead body portion 2664 may include a material property that is different than lead body portion 2663, such as, for example, a greater flexibility, in order to accommodate stresses imparted upon lead body 2662 by a nerve cuff electrode and movement of the patient's head, neck, and other neighboring body portions. The highly flexible distal portion 2664 reduces the stress (torque and tension) imparted by lead body 2662 on the electrode cuff, thereby reducing the likelihood that the cuff will be detached from the nerve or damage the nerve.

Lead body portion 2664 may be made more flexible than lead body portion 2663 by any of a variety of ways. For example, lead body portion 2664 may be made from a material having differing flexibility. Alternatively, the diameters of the braided stranded wires (BSW) and/or wire insulation that make up the lead body portion 2664 may be reduced when possible.

With continuing reference to FIG. 26C, stimulation lead 2600 may further include an anchor 2665 operably connected to lead body 2662. Although anchor 2665 in the illustrated embodiment is depicted as being disposed in between lead body portions 2663 and 2664, anchor 2665 may be disposed at any suitable location along the length of lead body 2662. Furthermore, anchor 2665 may be fixedly or movably connected to lead body 2662.

Anchor 2665 may include any suitable configuration known in the art. For example, anchor 2665 may include a substantially flat body portion 2666. Body portion 2666 may be configured to be secured to tissue, such as, for example, tissue proximate a treatment site, by any suitable means available in the art. For example, body portion 2666 may be provided with openings 2667 to facilitate, for example, suturing anchor 2665 to nearby tissue. Anchor 2665 can thereby isolate stress (tension) to one portion of lead body 2662, and particularly portion 2663, caused by gross head and neck movement.

Description of Field Steering Alternatives

With reference to FIGS. 27A-27G, a field steering nerve cuff electrode 64 is shown schematically. As seen in FIG.

27A, the nerve cuff electrode 64 may include four electrode contacts 90A-90D to enable field steering, and various arrangements of the electrode contacts 90A-90D are shown in FIGS. 27B-27G. Each of FIGS. 27B-27G includes a top view of the cuff 64 to schematically illustrate the electrical field (activating function) and an end view of the cuff 64 to schematically illustrate the area of the nerve effectively stimulated. With this approach, electrical field steering may be used to stimulate a select area or fascicle(s) within a nerve or nerve bundle to activate select muscle groups as described herein.

Figure 27A:
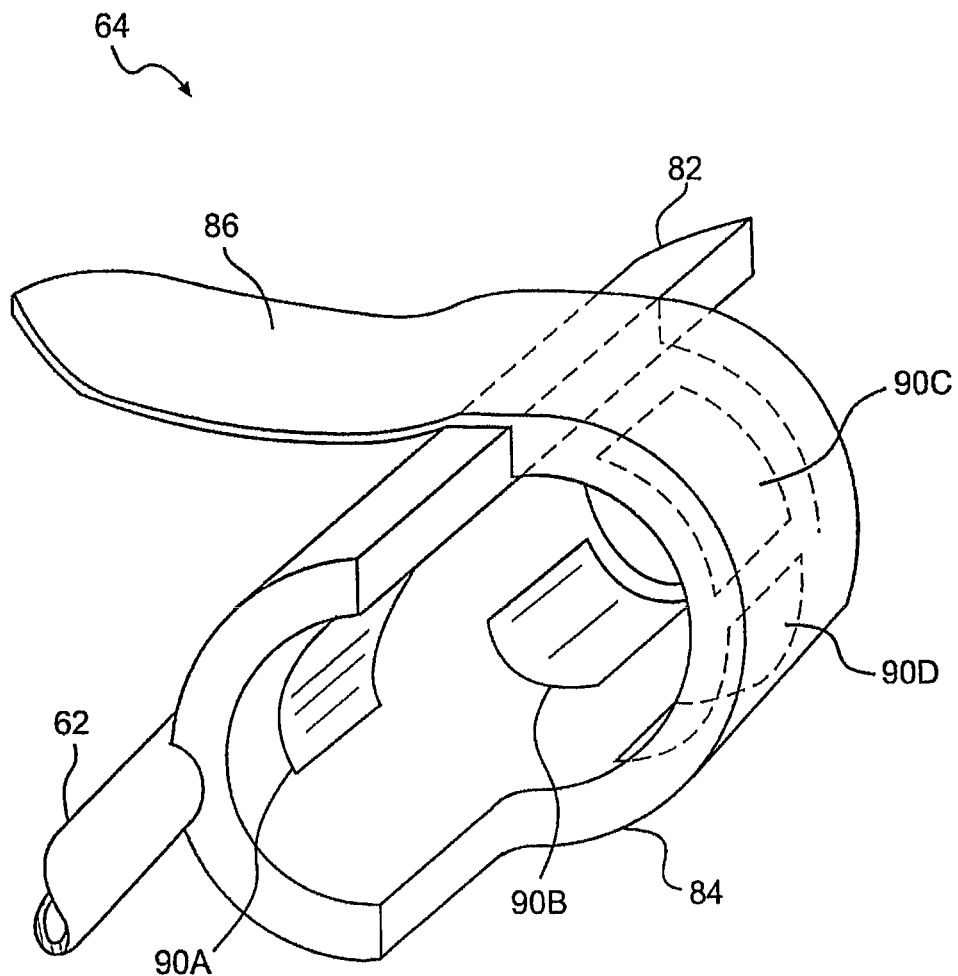

With specific reference to FIG. 27A, the nerve cuff electrode 64 may comprise a cuff body having a lateral (or superficial) side 82 and a medial (or contralateral, or deep) side 84. The medial side 84 is narrower or shorter in length than the lateral side 82 to facilitate insertion of the medial side 84 around a nerve such that the medial side is on the deep side of the nerve and the lateral side is on the superficial side of the nerve. An integral tow strap 86 may be used to facilitate wrapping the cuff around a nerve. The nerve cuff electrode 64 includes electrode contacts 90A, 90B, 90C and 90D imbedded in the body of the cuff, with their inside surface facing exposed to establish electrical contact with a nerve disposed therein. Electrode contacts 90A and 90B are longitudinally and radially spaced from each other. Electrode contacts 90C and 90D are radially spaced from each other and positioned longitudinally between electrode contacts 90A and 90B. Each of the four electrode contacts may be operated independently via four separate conductors (four filar) in the lead body 62.

With specific reference to FIGS. 27B-27G, each includes a top view (left side) to schematically illustrate the electrical field or activating function (labeled E), and an end view (right side) to schematically illustrate the area of the nerve effectively stimulated (labeled S) and the area of the nerve effectively not stimulated (labeled NS). Electrodes 90A-90D are labeled A-D for sake of simplicity only. The polarity of the electrodes is also indicated, with each of the cathodes designated with a negative sign (−) and each of the anodes designated with a positive sign (+).

Figure 27B:
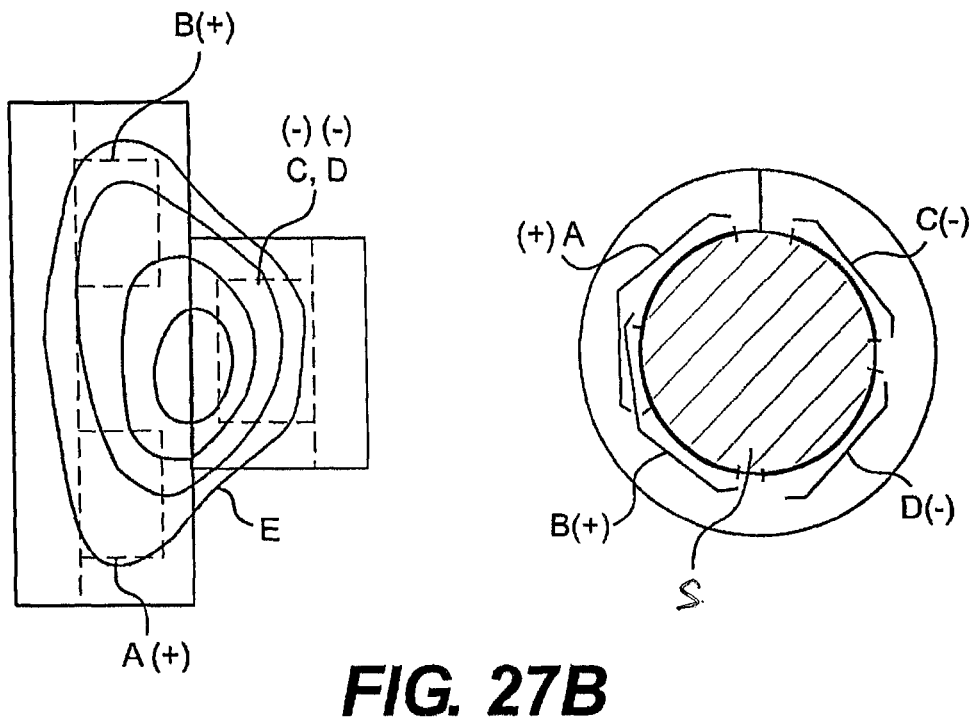

With reference to FIG. 27B, a tripolar transverse guarded cathode arrangement is shown with electrodes C and D comprising cathodes and electrodes A and B comprising anodes, thus stimulating the entire cross-section of the nerve.

Figure 27C:
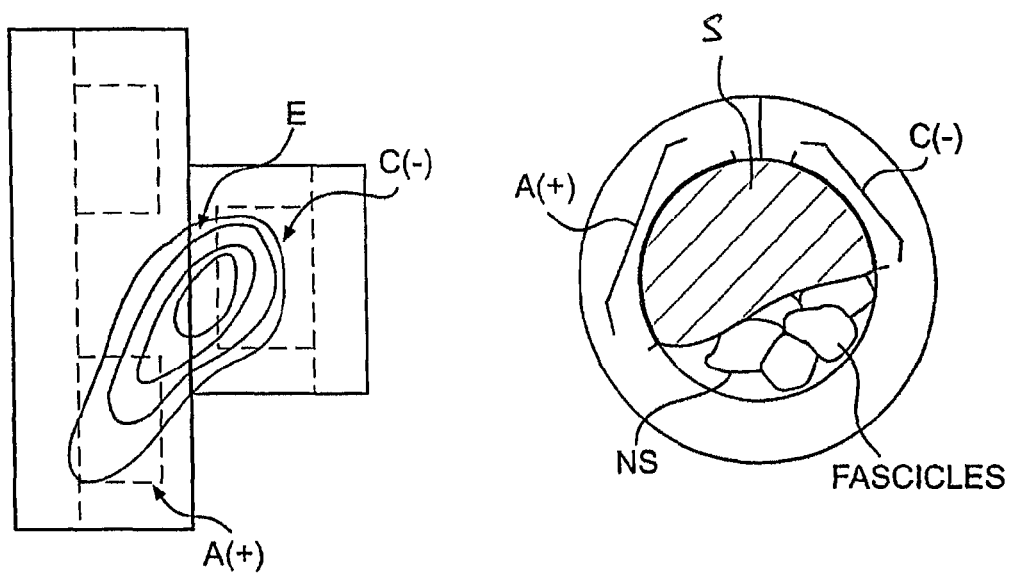
Figure 27D:
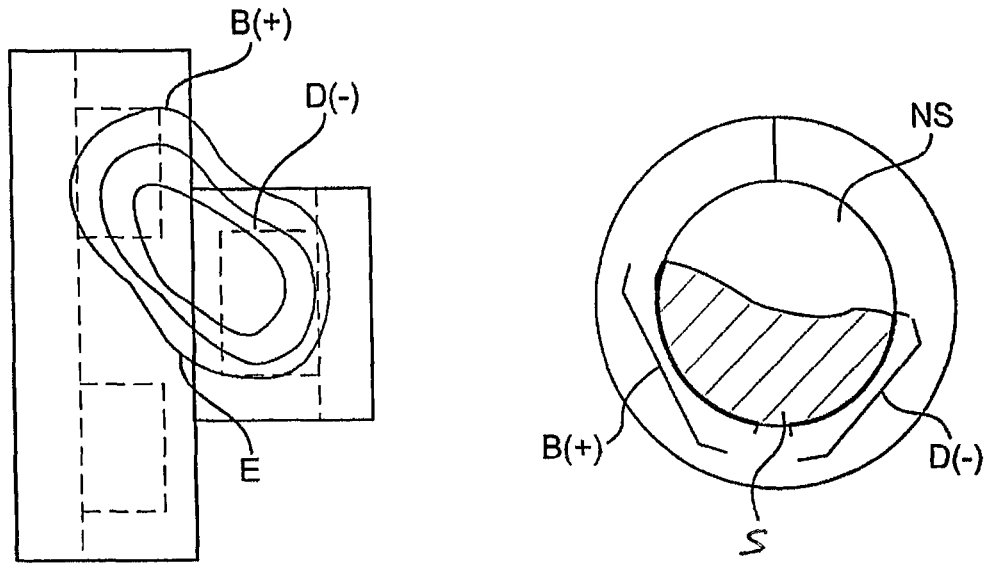

With reference to FIG. 27C, a bipolar diagonal arrangement is shown with electrode C comprising a cathode and electrode A comprising an anode, wherein the fascicles that are stimulated may comprise superior fascicles of the hypoglossal nerve, and the fascicles that are not stimulated may comprise inferior fascicles of the hypoglossal nerve (e.g., fascicles that innervate the intrinsic muscles of the tongue With reference to FIG. 27D, another bipolar diagonal arrangement is shown with electrode D comprising a cathode and electrode B comprising an anode, wherein the fascicles that are stimulated may comprise inferior fascicles of the hypoglossal nerve.

Figure 27E:
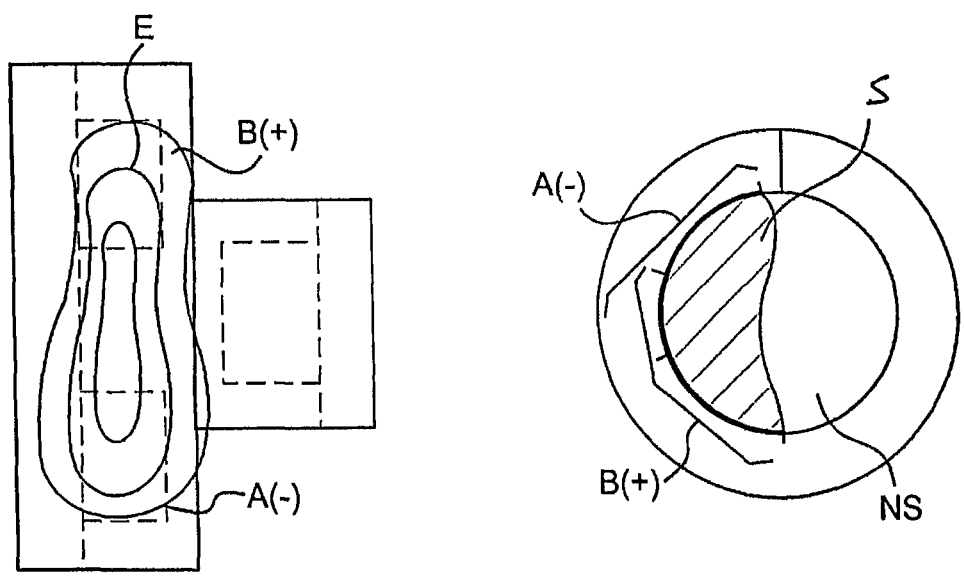

With reference to FIG. 27E, a bipolar axial arrangement is shown with electrode A comprising a cathode and electrode B comprising an anode, wherein the fascicles that are stimulated may comprise lateral fascicles of the hypoglossal nerve.

Figure 27F:
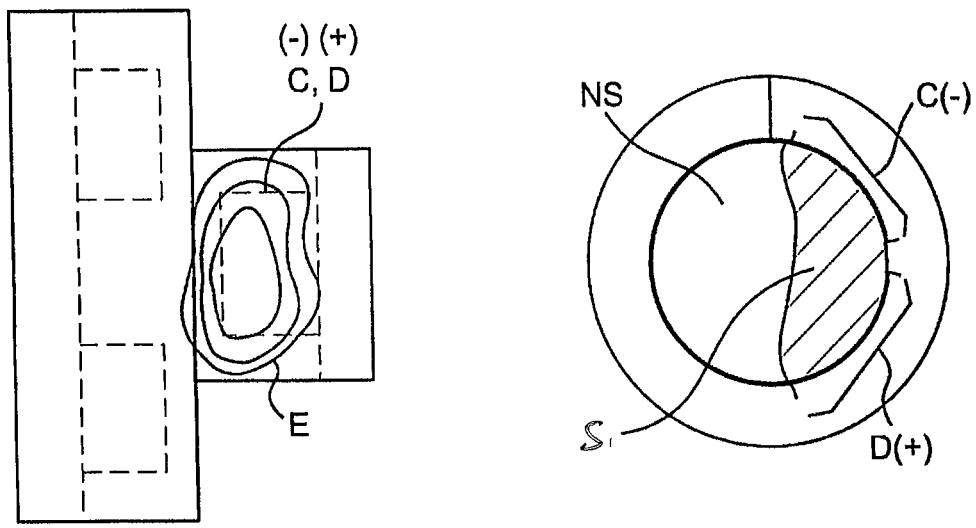

With reference to FIG. 27F, a bipolar transverse arrangement is shown with electrode C comprising a cathode and electrode D comprising an anode, wherein the fascicles that are stimulated may comprise medial fascicles of the hypoglossal nerve.

Figure 27G:
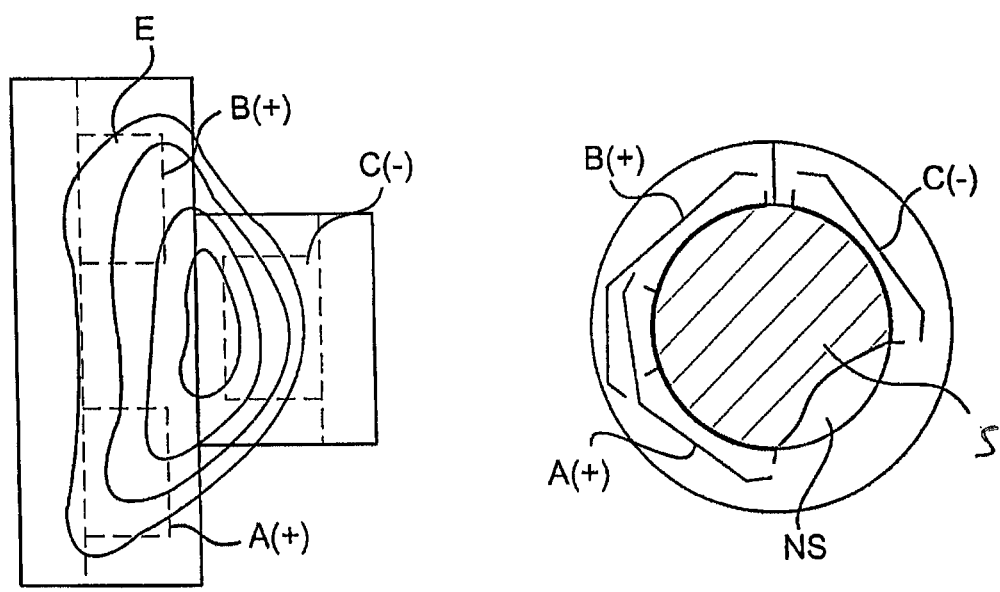

With reference to FIG. 27G, a modified tripolar transverse guarded cathode arrangement is shown with electrode C comprising a cathode and electrodes A and B comprising anodes, thus stimulating the entire cross-section of the nerve with the exception of the inferior medial fascicles.

Nerves like the hypoglossal nerve or superior laryngeal nerve typically include a plurality of fibers having relatively larger diameters and a plurality of fibers having relatively smaller diameters. In the case of single function nerves, such as, for example, the hypoglossal nerve HGN, all of the nerve fibers may either be sensory or motor in function. However, in the case of multi-function nerves, such as, for example, the superior laryngeal nerve SLN, the fibers having relatively larger diameters are typically motor (efferent) fibers, and the fibers having relatively smaller diameters are typically sensory (afferent) fibers. Accordingly, there may be a need to selectively stimulate the differing diameter fibers in a nerve.

Turning now to FIG. 27H, there is depicted an embodiment of a uni-directional stimulation electrode 2700 having a distal end 2700a and a proximal end 2700b. Electrode 2700 may include a substantially cylindrical nerve cuff 2701 in accordance with the principles of the present disclosure. As illustrated, nerve cuff 2701 may include an outer surface 2701a and an inner surface 2701b. Electrode 2700 may further include a plurality of electrode contacts 2702-2704. Electrode contacts 2702-2704 may be used as any suitable electrode contact known to those of ordinary skill in the art. For example, electrode contact 2702 may be used as an anode, electrode contact 2703 may be used as a cathode, and electrode contact 2704 may be used as a second anode. Electrode contacts 2702-2704 may also include any suitable shape and/or configuration known in the art. For example, electrode contacts 2702-2704 may include a substantially semi-circular configuration.

Electrode contacts 2702-2704 may be disposed on nerve cuff 2701 in any suitable configuration to achieve the desired effect. For example, electrode contacts 2702-2704 may be disposed on inner surface 2701b. As depicted in FIG. 27H, cathode electrode contact 2703 may be disposed approximately equidistant from distal end 2700a and proximal end 2700b, and anode electrode contacts 2702 may be differentially spaced around cathode electrode contact 2703, so as to control the direction of stimulation of electrode 2700. For example, anode electrode contact 2702 may be spaced from cathode electrode contact 2703 by any suitable distance .chi., while second anode electrode contact 2704 may be spaced from cathode electrode contact 2703 by a distance that is approximately two or three times greater than distance .chi. In this exemplary configuration, the direction of stimulation may be in the direction of arrow 2705.

In use, electrode 2700 may be implanted upon a nerve in accordance with the principles of this disclosure. Electrode 2700 may be oriented on the nerve it is implanted on in any suitable manner, such as, for example, according to the direction of intended stimulation. Thus, in circumstances where it may be desired to stimulate efferent (motor) fibers of a nerve, such as, for example, the superior laryngeal nerve SLN, while avoiding stimulation to afferent (sensory) fibers of the nerve, the electrode 2700 may be oriented on the nerve in a manner such that anode electrode contact 2702 is located distally of cathode electrode contact 2703, with distal and proximal designations based on the relative location of the electrode contact on the nerve. Alternatively, in circumstances where it may be desired to stimulate afferent fibers of a nerve while avoiding stimulation of efferent fibers of the nerve, the electrode 2700 may be oriented on the nerve in a manner such that anode electrode contact 2702 is located proximally of cathode electrode contact 2703.

With reference now to FIG. 27I, there is depicted an embodiment of a stimulation electrode 2750 for, among other things, selectively stimulating differing diameter fibers of a nerve, such as, for example, the hypoglossal nerve or superior laryngeal nerve. Electrode 2750 may include a body 2751, and may include any suitable configuration in accordance with the principles of the present disclosure. Additionally, electrode 2750 may include an array 2752 of suitable electrode contacts known to those skilled in the art. Although the depicted embodiment of electrode 2750 includes five electrode contacts 2753a-2753e, array 2752 may include a greater or lesser number of electrode contacts. Electrode contacts 2753a-2753e may be disposed on body 2751 in any suitable configuration to produce the desired effect. For example, as depicted in FIG. 27I, electrode contacts 2753a-2753e may be disposed serially, with approximately a one (1) millimeter spacing in between each electrode contact 2753a-2753e. Electrode contacts 2753a-2753e may be configured to function as either anode electrode contacts or cathode electrode contacts, as desired.

Electrode contacts 2753 may be connected to an implanted neurostimulator (INS), such as, for example, INS 50, in accordance with the present disclosure. The INS may be programmed to select any of electrode contacts 2753a-2753e for nerve stimulation. For example, in circumstances where it may be desired to stimulate the smaller diameter fibers of a nerve, it is contemplated that all electrode contacts 2753a-2753e may be selected for nerve stimulation, since closely spaced electrode contacts typically affect smaller diameter fibers (e.g., afferent or sensory fibers). In these circumstances, electrode contacts 2753a, 2753c, and 2753e may function as anode electrode contacts and electrode contacts 2'753b and 2753d may function as cathode electrode contacts. In circumstances where it may be desired to stimulate the larger diameter fibers of a nerve, it is contemplated that only electrode contacts 2753a, 2753c, and 2753e may be selected for nerve stimulation, since loosely spaced electrode contacts typically affect larger diameter fibers (e.g., efferent or motor fibers). In these circumstances, electrode contacts 2753a and 2753e may function as anode electrode contacts, and 2753c may function as a cathode electrode contact.

Alternatively, electrode 2750 may be utilized to reduce muscle fatigue when implanted on single function nerves, such as, for example, the hypoglossal nerve. In such circumstances, muscle fatigue may be reduced by alternatively switching between using loosely spaced electrode contacts 2753a, 2753c, and 2753e, to stimulate large diameter fibers, and closely spaced electrode contacts 2753a-2753e, to stimulate small diameter fibers.

Figure 27K:
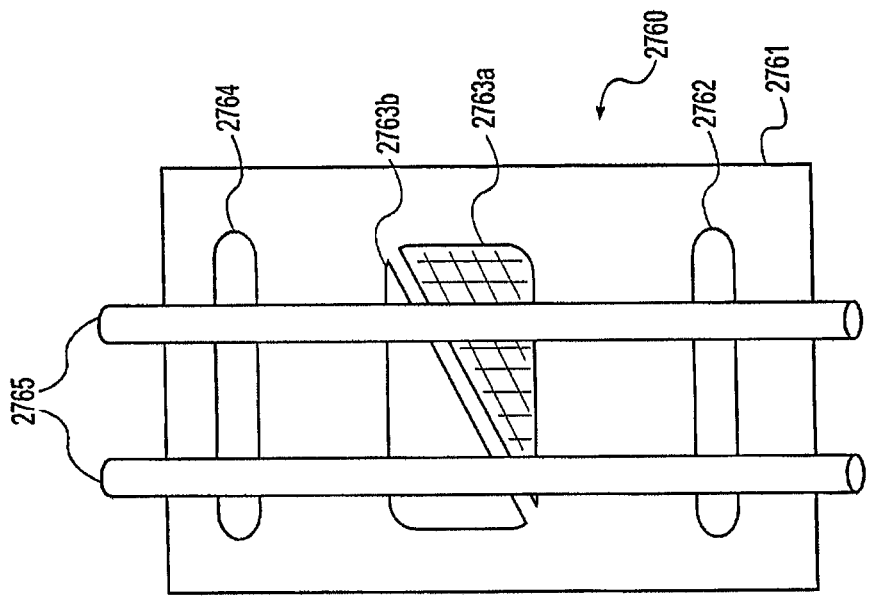
Figure 27J:
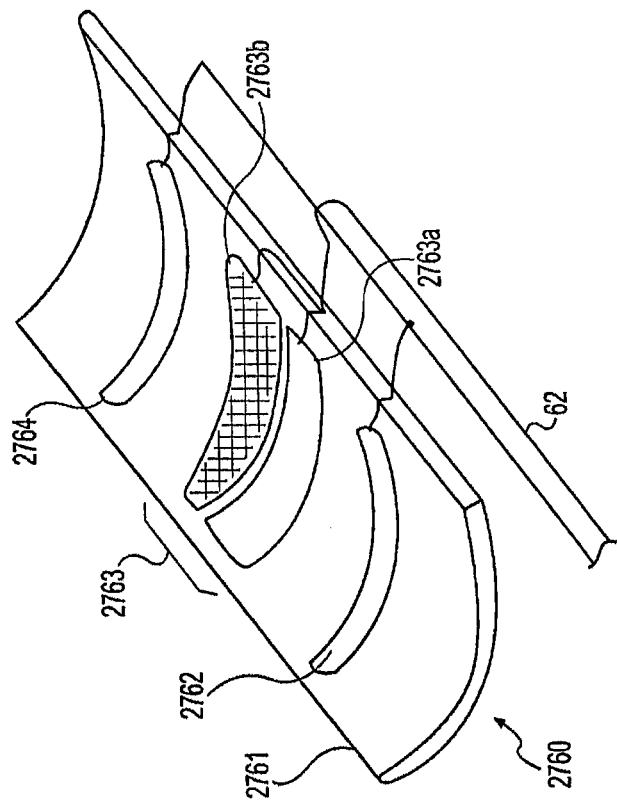

Turning to FIGS. 27J-27K, in accordance with the present disclosure, there is depicted another embodiment of a nerve cuff electrode 2760 for facilitating reduction in muscle fatigue. Nerve cuff electrode 2760 may include a body 2761 having a plurality of electrode contacts 2762, 2763, and 2764. Electrode contacts 2762-2764 may include any suitable electrode contacts in accordance with the present disclosure. Although the depicted embodiment of nerve cuff electrode 2760 includes three electrode contacts 2762-2764, nerve cuff electrode 2760 may include a greater or lesser number of electrode contacts. Furthermore, electrode contacts may be disposed on body 2761 in any suitable configuration to achieve the desired effect, such as, for example, serially, as depicted. In the depicted embodiment, electrode contacts 2762 and 2764 may function as anode electrode contacts, while electrode contact 2763 may function as a cathode electrode contact. Electrode contact 2763 may include two distinct, substantially triangularly shaped portions 2763a and 2763b. However, portions 2763a and 2763b may include any suitable shape. In addition, portions 2763a and 2763b may be configured to be of differing conductive properties, so that, for the same stimulation pulse (e.g., a slow rising, small amplitude pulse having a relatively long duration of approximately 0.2 to 0.35 milliseconds) applied to each of the portions 2763a and 2763b, the resultant charge densities at the surface of each of the portions 2763a and 2763b may be different. For example, portions 2763a and 2763b may be made of electrically differing materials. For discussion purposes only, it is assumed that portion 2763a is configured to deliver a charge density lower than that of portion 2763b. However, portion 2763a may be configured to deliver a charge density that is higher than the charge density of portion 2763b.

Since the small diameter fibers of a nerve are typically stimulated by low charge densities and large diameter fibers of the nerve are typically stimulated by high charge densities, portions 2763a and 2763b may be sequentially utilized to alternate between stimulating the small and large diameter fibers of a nerve. In other words, in use, a stimulation pulse may be first delivered to portion 2763a to stimulate the small diameter fibers of a nerve. A subsequent stimulation pulse may be then delivered to portion 2763b to stimulate the large diameter fibers of a nerve. It is contemplated that alternating between stimulating the small and large diameter fibers of a nerve may facilitate reducing muscle fatigue while also ensuring sufficient muscle mass is stimulated to maintain the necessary contraction and force generation to successfully treat OSA.

Figure 27L:
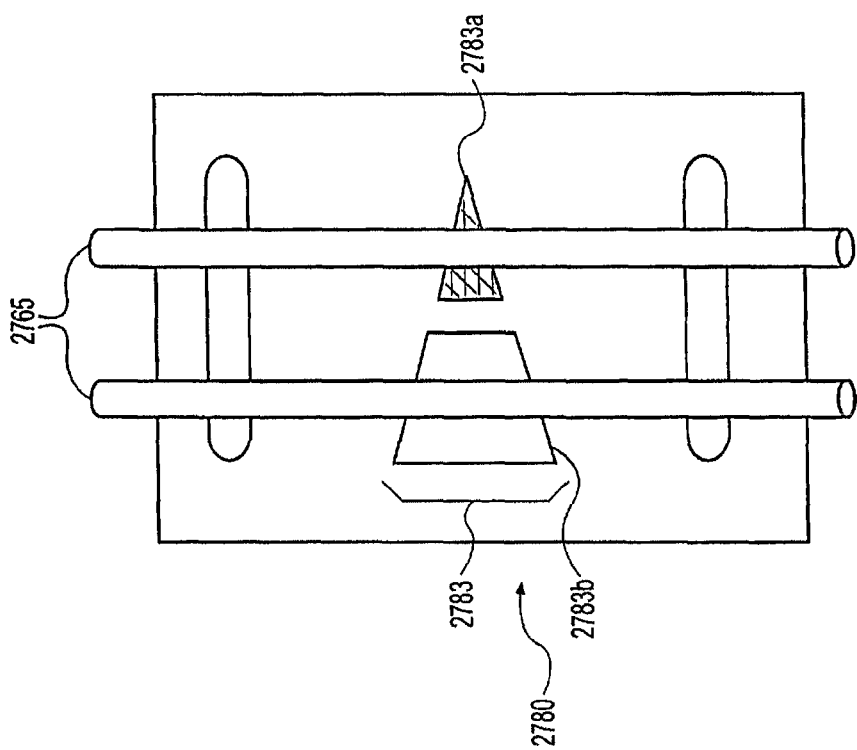
Figure 27M:
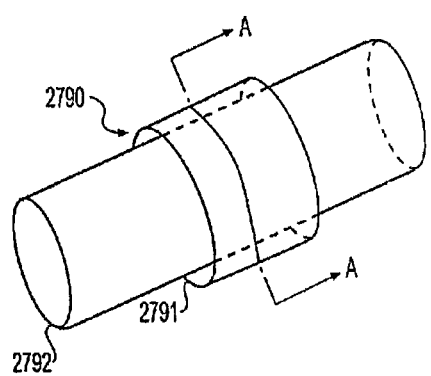
Figure 27N:
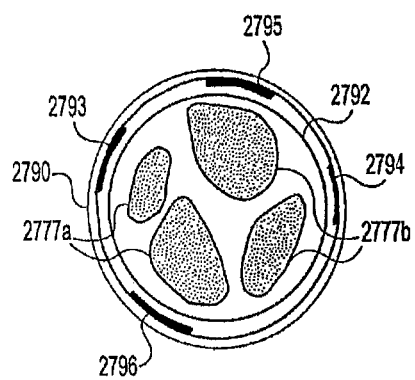
Figure 27O:
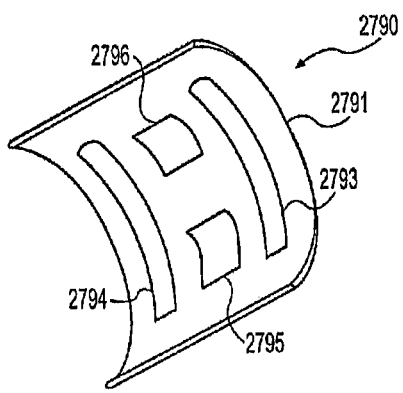

Turning now to FIG. 27L, there is illustrated yet another embodiment of a nerve cuff electrode 2780 for facilitating reduction in muscle fatigue. For the purposes of this disclosure, nerve cuff electrode 2780 may be substantially similar to nerve cuff electrode 2760. Nerve cuff electrode 2780, however, may differ from nerve cuff electrode 2760 in at least one significant way. For example, rather than having two substantially triangular portions, cathode electrode contact 2783 may comprise two substantially different portions 2783a and 2783b. Portions 2783a and 2783b may be spaced apart from one another and may include differing surface areas. For example, as illustrated, portion 2783a may include a smaller surface area than portion 2783b. Furthermore, portions 2783a and 2783b may include any suitable shape known in the art. Although portions 2783a and 2783b in the illustrated embodiment together define a substantially triangular shaped electrode contact 2783, portions 2783a and 2783b together may or may not define any suitable shape known in the art.

Each of portions 2783a and 2783b may be configured to be substantially similar in conductance despite their differing surface areas. For example, portion 2783a may be made of a first material having a relatively lower conductance, while portion 2783b may be made of a second material having a relatively higher conductance. Thus, when subjected to the same stimulation pulse (e.g., a slow rising, small amplitude pulse having a relatively long duration of approximately 0.2 to 0.35 milliseconds), portion 2783a may have a higher charge density than portion 2783b because of its relatively smaller surface area than portion 2783b. Similarly, when subjected to the same stimulation pulse, portion 2783b may have a lower charge density than portion 2783a because of its relatively larger surface area than portion 2783a. Accordingly, because of the differing charge densities, portion 2783a may be adapted to stimulate large diameter fibers of a nerve, and portion 2783b may be adapted to stimulate small diameter fibers of the nerve.

In use, a stimulation pulse may be first delivered to portion 2783a to stimulate the large diameter fibers of a nerve. A subsequent stimulation pulse may be then delivered to portion 2783*b* to stimulate the small diameter fibers of the nerve. It is contemplated that alternating between stimulating the small and large diameter fibers of a nerve may facilitate muscle fatigue while also ensuring that sufficient muscle mass is stimulated to maintain the necessary contraction and force generation to successfully treat OSA.

In certain embodiments, such as when nerve cuff electrodes 2760 and 2780 are implanted on a multi-function nerve (e.g., the superior laryngeal nerve SLN), it is contemplated that portions 2763*a*/2763*b* and portions 2783*a*/2783*b* may be utilized to selectively stimulate either the afferent or efferent fibers of the nerve.

With reference now to FIGS. 27M-27Q, there is depicted yet another embodiment of a nerve cuff electrode 2790 for minimizing muscle fatigue. Nerve cuff electrode 2790 may include a cuff body 2791 for mounting about a nerve 2792 in accordance with the present disclosure. Cuff body 2791 may include a plurality of electrode contacts 2793-2796 also in accordance with the present disclosure. Although the depicted embodiment of nerve cuff electrode 2790 includes four electrode contacts 2793-2796, nerve cuff electrode 2790 may include a greater or lesser number of electrode contacts.

Figure 27P:
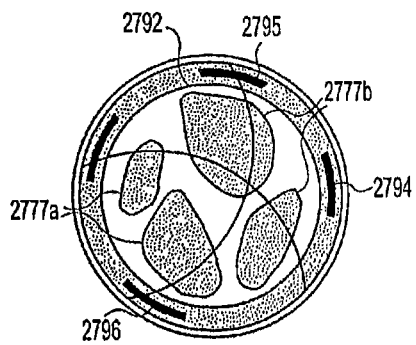
Figure 27Q:
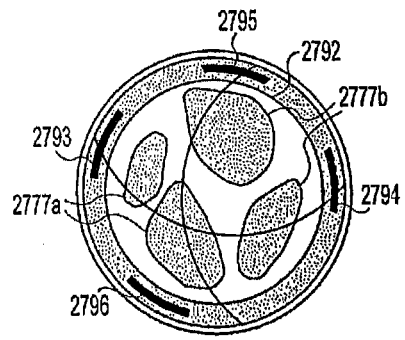
Figure 28:
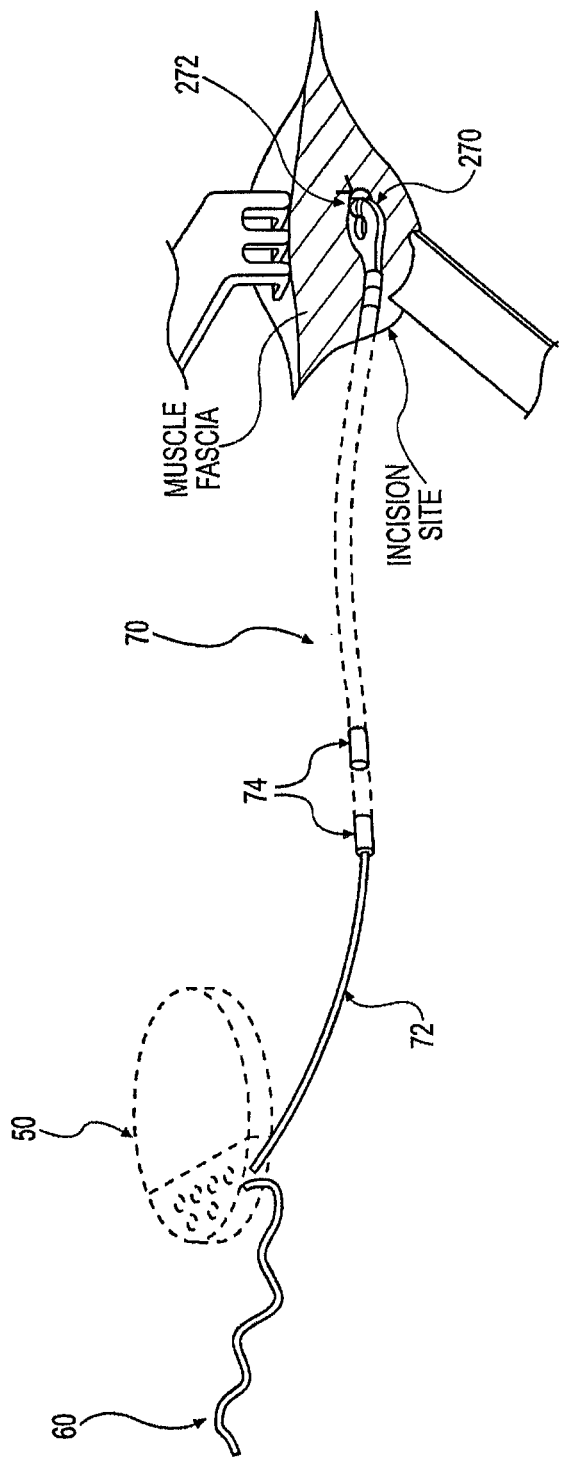

Nerve cuff electrode 2790 may be configured to selectively stimulate both small diameter fibers contained in fascicle 2777*a* and large diameter fibers contained in fascicle 2777*b* of nerve 2792. For example, as shown in FIG. 27P, by applying an exemplary slow rising, long pulse width waveform to electrode contacts 2796 and 2793, nerve cuff electrode 2790 may stimulate the small diameter fibers contained in fascicle 2777*a* of nerve 2792. Similarly, as shown in FIG. 27Q, by applying an exemplary fast rising, short pulse width waveform to electrode contacts 2794 and 2795, nerve cuff electrode 2790 may stimulate the large diameter fibers contained in fascicle 2777*b* of nerve 2792. Fascicles 2777*a* and 2777*b* may be stimulated simultaneously or separately. In embodiments, where it is desirable to stimulate fibers contained in fascicles 2777*a* and 2777*b*, the pulse generator (e.g., INS 50) may be provided with dual output ports.

Description of Respiration Sensing Lead Anchoring Alternatives

With reference to the following figures, various additional or alternative anchoring features for the respiration sensing lead 70 are schematically illustrated. Anchoring the respiration sensing lead 70 reduces motion artifact in the respiration signal and stabilizes the bio-impedance vector relative to the anatomy.

In each of the embodiments, by way of example, not limitation, the respiration sensing lead 70 includes a lead body 70 with a proximal connector and a plurality of distal respiration sensors 74 comprising ring electrodes for sensing bio-impedance. The lead body 72 of the respiration sensing lead 70 may include a jacket cover containing a plurality of conductors 78, one for each ring electrode 74 requiring independent control. Generally, the impedance electrodes 74 may comprise current emitting electrodes and voltage sensing electrodes for detecting respiration by changes in bio-impedance.

With reference to FIGS. 28-33, various fixation devices and methods are shown to acutely and/or chronically stabilize the respiratory sensing lead 70. With specific reference to FIG. 28, the INS 50 is shown in a subcutaneous pocket and the stimulation lead 60 is shown in a subcutaneous tunnel extending superiorly from the pocket. The respiration sensing lead 70 is shown in a subcutaneous tunnel superficial to muscle fascia around the rib cage. A suture tab or ring 270 may be formed with or otherwise connected to the distal end of the lead body 72. Near the distal end of the lead 70, a small surgical incision may be formed to provide access to the suture tab 270 and the muscle fascia under the lead 70. The suture tab 270 allows the distal end of the lead 70 to be secured to the underlying muscle fascia by suture or staple 272, for example, which may be dissolvable or permanent. Both dissolvable and permanent sutures/staples provide for acute stability and fixation until the lead body 72 is encapsulated. Permanent sutures/staples provide for chronic stability and fixation beyond what tissue encapsulation otherwise provides.

Figure 29B:
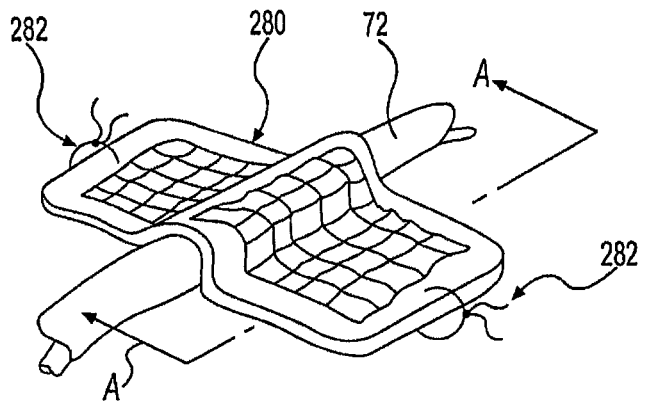
Figure 29C:
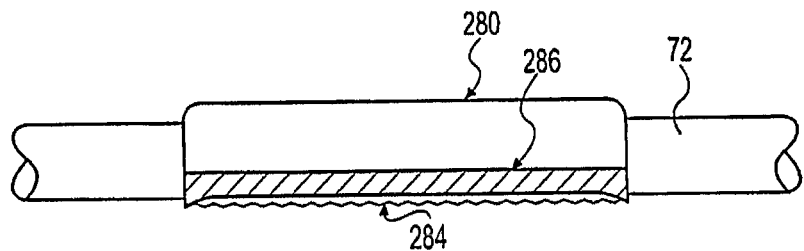

With reference to FIGS. 29A-29C, a fabric tab 280 may be used in place of or in addition to suture tab 270. As seen in FIG. 29A, the fabric tab 280 may be placed over a distal portion of the lead body 72, such as between two distal electrodes 74. A small surgical incision may be formed proximate the distal end of the lead 70 and the fabric tab 280 may be placed over the over the lead body 72 and secured to the underlying muscle fascia by suture or staple 282, for example, which may be dissolvable or permanent, to provide acute and/or chronic stability and fixation. With reference to FIGS. 29B and 29C (cross-sectional view taken along line A-A), the fabric tab 280 may comprise a fabric layer (e.g., polyester) 284 to promote chronic tissue ingrowth to the muscle fascia and a smooth flexible outer layer (silicone or polyurethane) 286 for acute connection by suture or staple 282.

Figure 30:
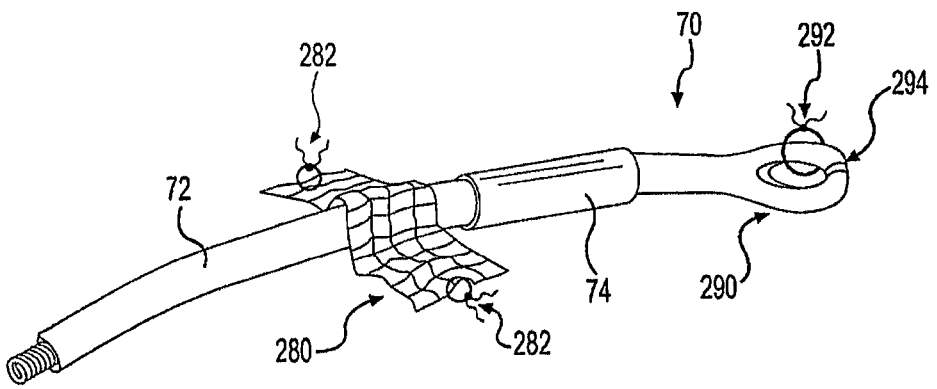

With reference to FIG. 30, lead 70 includes a split ring 290 that may be formed with or otherwise connected to the distal end of the lead body 72. The split ring 290 allows the distal end of the lead 70 to be secured to the underlying muscle fascia by suture or staple 292, for example, which may be dissolvable or permanent. The ring 290 may be formed of compliant material (e.g., silicone or polyurethane) and may include a slit 294 (normally closed) that allows the lead 70 to be explanted by pulling the lead 70 and allowing the suture 292 to slip through the slit 294, or if used without a suture, to allow the ring to deform and slide through the tissue encapsulation. To further facilitate explanation, a dissolvable fabric tab 282 may be used to acutely stabilize the lead 70 but allow chronic removal.

With reference to FIGS. 31A-31C, deployable anchor tines 300 may be used to facilitate fixation of the lead 70. As seen in FIG. 31A, the self-expanding tines 300 may be molded integrally with the lead body 72 or connected thereto by over-molding, for example. The tines 300 may comprise relatively resilient soft material such as silicone or polyurethane. The resilient tines 300 allow the lead 70 to be delivered via a tubular sheath or trocar 304 tunneled to the target sensing site, wherein the tines 300 assume a first collapsed delivery configuration and a second expanded deployed configuration. As seen in FIGS. 31B and 31B, the tubular sheath or trocar 304 may be initially tunneled to the target site using an obtruator 306 with a blunt dissection tip 308. After the distal end of the tubular sheath 304 has been tunneled into position by blunt dissection using the obtruator 306, the obtruator 306 may be removed proximally from the sheath 304 and the lead 70 with collapsible tines 300 may be inserted therein. As seen in FIG. 31C, when the distal end of the lead 70 is in the desired position, the sheath 304 may be proximally retracted to deploy the tines 300 to engage the muscle fascia and adjacent subcutaneous tissue, thus anchoring the lead 70 in place.

Figure 32A:
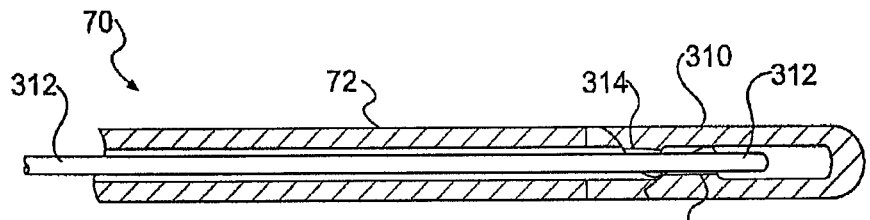
Figure 32B:
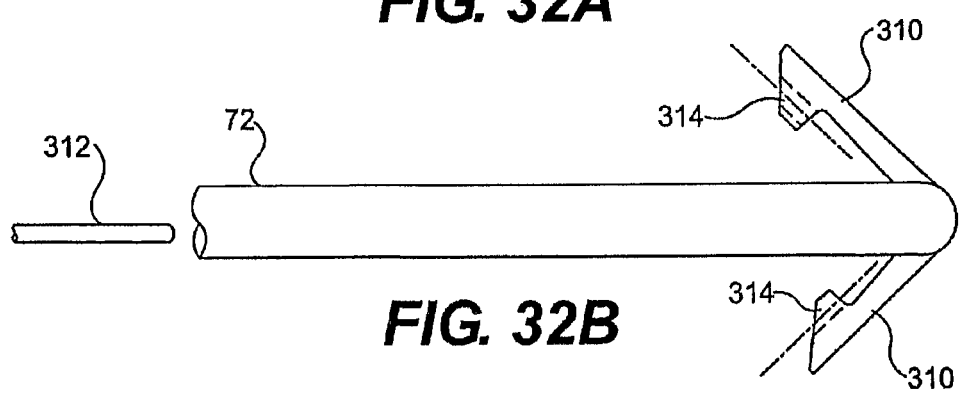

With reference to FIGS. 32A and 32B, an alternative deployable fixation embodiment is shown schematically. In this embodiment, self-expanding tines 310 are held in a collapsed configuration by retention wire 312 disposed in the lumen of the lead body 72 as shown in FIG. 32A. Each of the tines 310 includes a hole 314 through which the retention wire 312 passes to hold the tines 310 in a first collapsed delivery configuration as shown In FIG. 32A, and proximal withdrawal of the retention wire 314 releases the resilient tines 310 to a second expanded deployed configuration as shown in FIG. 32B. The lead 70 may be tunneled to the desired target site with the tines 310 in the collapsed configuration. Once in position, the wire 312 may be pulled proximally to release the tines 310 and secure the lead 70 to the underlying muscle fascia and adjacent subcutaneous tissue to establish fixation thereof.

Figure 33A:
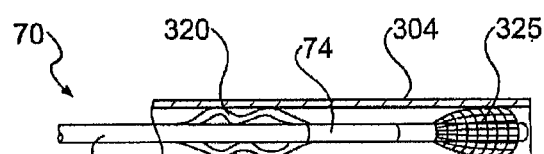
Figure 33B:
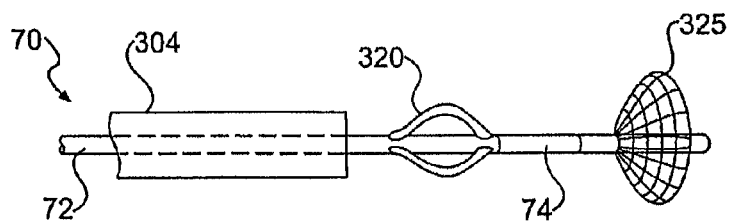

With reference to FIGS. 33A and 33B, another alternative deployable fixation embodiment is shown schematically. In this embodiment, self-expanding structures such as one or more resilient protrusions 320 and/or a resilient mesh 325 may be incorporated (either alone or in combination) into the distal end of the lead 70. By way of example, not limitation, resilient protrusions 320 may comprise silicone or polyurethane loops and resilient mesh 325 may comprise a polyester fabric connected to or formed integrally with the lead body 72. Both the resilient protrusions 320 and the resilient mesh 325 may be delivered in a collapsed delivery configuration inside tubular sheath 304 as shown in FIG. 33A, and deployed at the desired target site by proximal retraction of the sheath 304 to release the self-expanding structures 320/325 to an expanded deployed configuration as shown in FIG. 33B. Both the resilient protrusions 320 and the resilient mesh 325 engage the underlying muscle fascia through tissue encapsulation and adjacent subcutaneous tissues to provide fixation of the lead 70 thereto.

Other fixation embodiments may be used as well. For example, the fixation element may engage the muscle fascia and adjacent subcutaneous tissues or may be embedded therein. To this end, the electrodes may alternatively comprise intramuscular electrodes such as barbs or helical screws.

Description of Respiration Sensing Electrode Alternatives

A description of the various alternatives in number, spacing, anatomical location and function of the impedance electrodes follows. Generally, in each of the following embodiments, the respiration sensing lead includes a lead body and a plurality of respiration sensors comprising ring electrodes for sensing bio-impedance. The lead body may include a plurality of insulated conductors disposed therein, with one conductor provided for each ring electrode requiring independent connection and/or control. The impedance electrodes may comprise current emitting electrodes and voltage sensing electrodes for detecting respiration by changes in bio-impedance.

Figure 34:
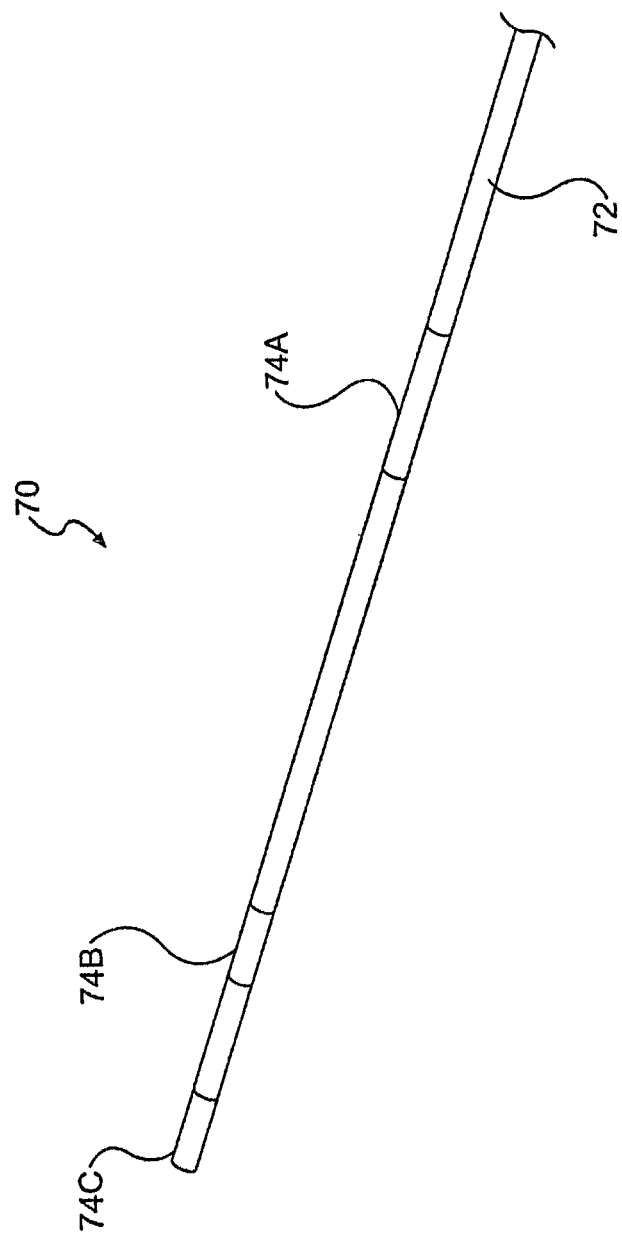
FIG. 34 schematically illustrates the distal portion of an exemplary respiration sensing lead FIGS. 35A-35E and 36 schematically illustrate alternative electrode arrangements on the respiration sensing lead.

With reference to FIG. 34, the distal portion of a respiration sensing lead 70 is shown by way of example, not limitation. The respiration sensing lead 70 includes a lead body 72 with a proximal connector and a plurality of distal impedance electrodes 74. In this example, the lead body 72 and electrodes 74 are cylindrical with a diameter of 0.050 inches. The distal current-carrying electrode 74A may be 5 mm long and may be separated from the voltage-sensing electrode 74B by 15 mm. The distal voltage sensing electrode may be 5 mm long and may be separated from the proximal combination current-carrying voltage-sensing electrode 74C by 100 mm. The proximal electrode 74C may be 10 mm long. The proximal portion of the lead 70 is not shown, but would be connected to the INS (not shown) as described previously. The lead body incorporates a plurality of insulated electrical conductors (not shown), each of which correspond to an electrode 74A-74C. The electrodes and conductors may be made of an alloy of platinum-iridium. The lead body 72 may comprise a tubular extrusion of polyurethane, silicone, or a co-extrusion of polyurethane over silicone. The conductors may be formed of multi-filar wire coiled to provide extensibility for comfort and durability under high-cycle fatigue.

Figure 35A:
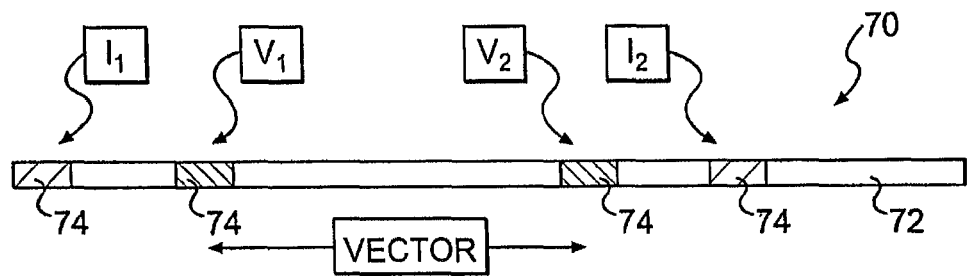
Figure 35B:
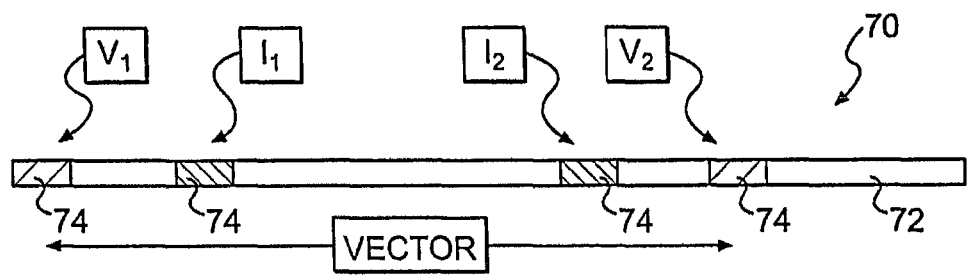
Figure 35C:
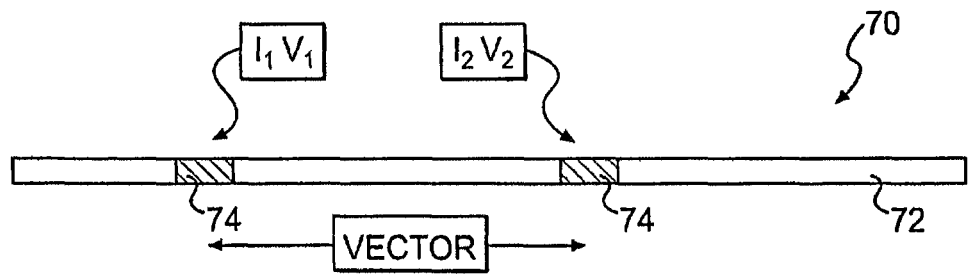
Figure 35D:
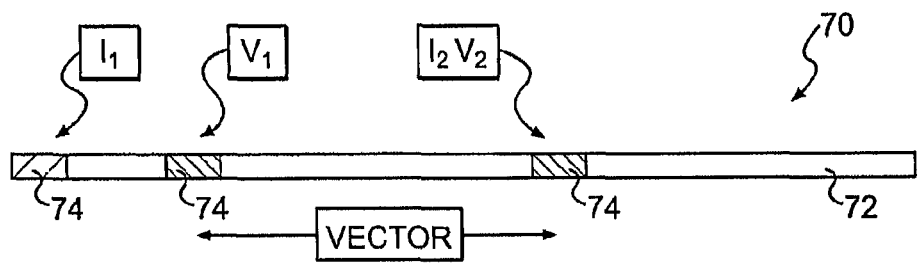
Figure 35E:
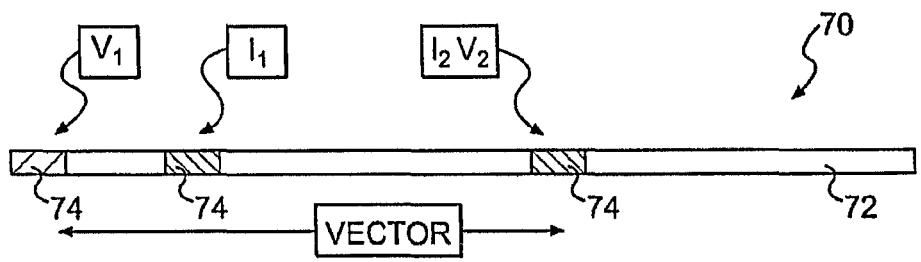

With reference to FIGS. 35A-35E, the position of the electrodes 74 may be characterized in terms of bio-impedance or bio-Z vectors. The bio-Z vector may be defined by the locations of the voltage-sensing electrodes (labeled $V_1$ & $V_2$). The voltage-sensing electrodes may be located on either side of the current-carrying electrodes (labeled $I_1$ & $I_2$). For example, it is possible to locate either one or both of the voltage-sensing electrodes between the current-carrying electrodes as shown in FIG. 35A (4-wire configuration ($I_1$-$V_1$-$V_2$-$I_2$)), and it is possible to locate either one or both of the current-carrying electrodes between the voltage-sensing electrodes as shown in FIG. 35B (inverted 4-wire configuration ($V_1$-$I_1$-$I_2$-$V_2$)). While at least two separate electrodes ($I_1$ & $I_2$) are required to carry current and at least two separate electrodes ($V_1$ & $V_2$) are required to measure voltage, it is possible to combine the current carrying and voltage sensing functions in a common electrode. Examples of combining voltage sensing and current carrying electrodes are shown in FIGS. 35C-35E. FIG. 35C (2-wire configuration ($I_1V_1$-$I_2V_2$)) shows combination electrode $I_1V_1$ and $I_2V_2$ where each of these electrodes is used to carry current and sense voltage. FIGS. 35D (3-wire configuration ($I_1$-$V_1$-$I_2V_2$)) and 35E (inverted 3-wire configuration ($V_1$-$I_1$-$I_2$-$V_2$)) show combination electrode $I_2V_2$ which is used to carry current and sense voltage.

Figure 36:
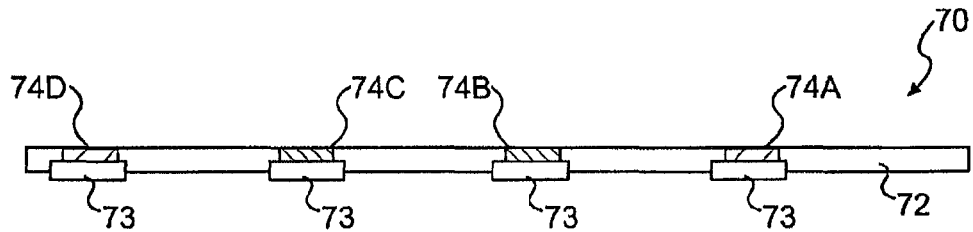

With reference to FIG. 36, insulative material such as strips 73 may cover one side of one or more electrodes 74A-74D to provide directional current-carrying and/or voltage-sensing. The insulative strips may comprise a polymeric coating (e.g., adhesive) and may be arranged to face outward (toward the dermis) such that the exposed conductive side of each electrode 74 faces inward (toward the muscle fascia and thoracic cavity). Other examples of directional electrodes would be substantially two-dimensional electrodes such as discs or paddles which are conductive on only one side. Another example of a directional electrode would be a substantially cylindrical electrode which is held in a particular orientation by sutures or sutured wings. Another example of a directional electrode would be an electrode on the face or header of the implanted pulse generator. It would likely be desirable for the pulse generator to have a non-conductive surface surrounding the location of the electrode.

In addition to the cylindrical electrodes shown, other electrode configurations are possible as well. For example, the electrodes may be bi-directional with one planar electrode surface separated from another planar electrode surface by insulative material. Alternatively or in combination, circular hoop electrodes may be placed concentrically on a planar insulative surface. To mitigate edge effects, each electrode may comprise a center primary electrode with two secondary side electrodes separated by resistive elements and arranged in series. An alternative is to have each primary current-carrying electrode connected by a resistive element to a single secondary side electrode. The conductive housing of the INS 50 may serve as an current-carrying electrode or voltage-sensing electrode. Alternatively or in addition, an electrode may be mounted to the housing of the INS 50.

Because bio-impedance has both a real and imaginary component, it is possible to measure the bio-Z phase as well as magnitude. It may be preferable to extract both magnitude and phase information from the bio-Z measurement because the movement of the lung-diaphragm-liver interface causes a significant change in the phase angle of the measured impedance. This may be valuable because motion artifacts of other tissue have less impact on the bio-Z phase angle than they do on the bio-Z magnitude. This means the bio-Z phase angle is a relatively robust measure of diaphragm movement even during motion artifacts.

An example of a bio-Z signal source is a modulated constant-current pulse train. The modulation may be such that it does not interfere with the stimulation signal. For example, if the stimulation signal is 30 Hz, the bio-Z signal source signal may be modulated at 30 Hz or a sub-multiple of 30 Hz such that bio-Z and stimulation do not occur simultaneously. The pulses in the pulse train may have a pulse width between 1 uS to 1 mS, such as 100 uS or 10 uS. The pulses may be separated by a period of time roughly equal to the pulse width (i.e., on-time of the pulses). The number of pulses in a train may be determined by a trade-off between signal-to-noise and power consumption. For example, no more than 100 pulses or no more than 10 pulses may be necessary in any given pulse train. The magnitude of current delivered during the pulse on-time may be between 10 uA and 500 uA, such as 50 uA.

Other wave forms of bio-Z source signal may be used, including, without limitation, pulse, pulse train, bi-phasic pulse, bi-phasic pulse train, sinusoidal, sinusoidal w/ramping, square wave, and square w/ramping. The bio-Z source signal may be constant current or non-constant current, such as a voltage source, for example. If a non-constant current source is used, the delivered current may be monitored to calculate the impedance value. The current-carrying electrodes may have a single current source, a split-current source (one current source split between two or more current-carrying electrodes), or a current mirror source (one current source that maintains set current levels to two or more current-carrying electrodes). Different characteristics of the sensed signal may be measured including, without limitation, magnitude, phase shift of sensed voltage relative to the current source signal, and multi-frequency magnitude and/or phase shift of the sensed signal. Multi-frequency information may be obtained by applying multiple signal sources at different frequencies or a single signal source which contains two or more frequency components. One example of a single multi-frequency source signal is a square wave current pulse. The resultant voltage waveform would contain the same frequency components as the square wave current pulse which would allow extraction of Bio-Z data for more than a single frequency.

Figure 37:
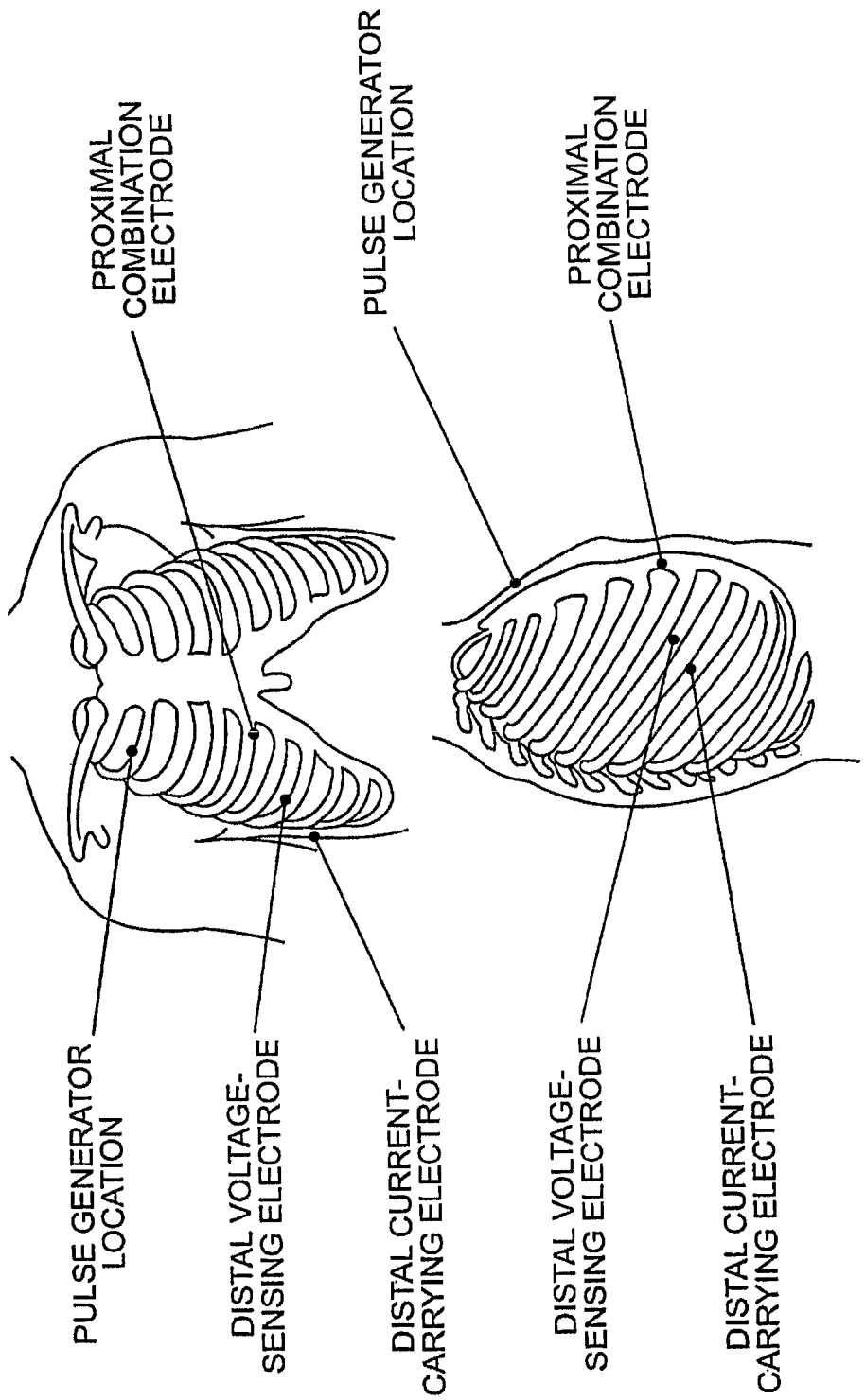
FIGS. 37, and 37A-37D schematically illustrate various anatomical positions or bio-Z vectors for the electrodes on the respiration sensing lead.

With reference to FIG. 37, the bio-Z vector may be oriented with regard to the anatomy in a number of different ways. For example, using the electrode arrangement illustrated in FIG. 34 and the anatomical illustration in FIG. 37, the bio-Z vector may be arranged such that the proximal combination electrode is located just to the right of and above the xiphoid below the pectoral muscle between the 5th and 6th ribs and the distal current-carrying electrode is located mid-lateral between the 7th and 8th ribs, with the distal voltage-sensing electrode positioned between the 6th and 7th ribs 10 mm proximal of the distal current-carrying electrode. This arrangement places the electrodes along the interface between the right lung, diaphragm and liver on the right side of the thoracic cavity. The lung-diaphragm-liver interface moves relative to the bio-Z vector with every respiratory cycle. Because the lung has relatively high impedance when inflated and the liver has relatively low impedance due to the conductivity of blood therein, this bio-Z vector arrangement across the lung-diaphragm-liver interface provides for a strong respiratory signal that is indicative of changes between inspiration and expiration. In addition, because the heart is situated more on the left side, positioning the bio-Z vector on the right side reduces cardiac artifact. The net result is a bio-Z vector that provides an excellent signal-to-noise ratio.

A variety of different bio-Z vector orientations relative to the anatomy may be employed. Generally, bio-Z vectors for monitoring respiration may be located on the thorax. However, bio-Z electrodes located in the head and neck may also be used to define respiratory bio-Z vectors. By way of example, not limitation, the bio-Z vector may be arranged transthoracically (e.g., bilaterally across the thorax), anteriorly on the thorax (e.g., bilaterally across the thoracic midline), across the lung-diaphragm-liver interface, perpendicular to intercostal muscles, between adjacent ribs, etc. A single bio-Z vector may be used, or multiple independent vectors may be used, potentially necessitating multiple sensing leads. One or more bio-Z sub-vectors within a given bio-Z vector may be used as well.

Figure 37A:
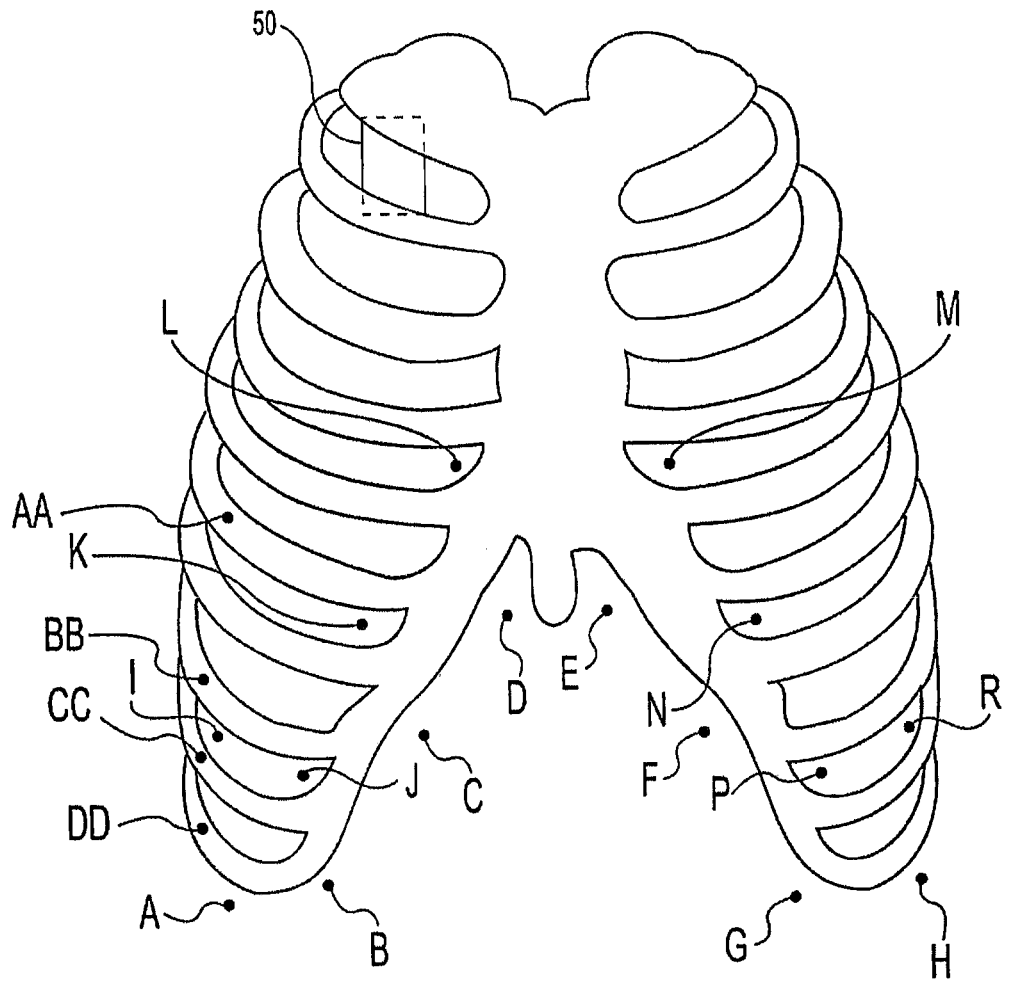
Figure 37B:
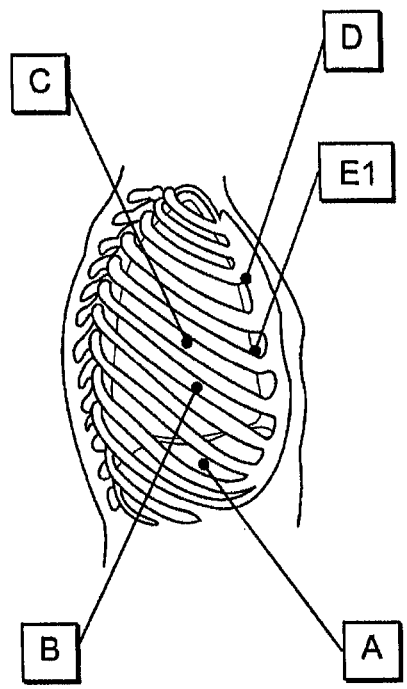
Figure 37C:
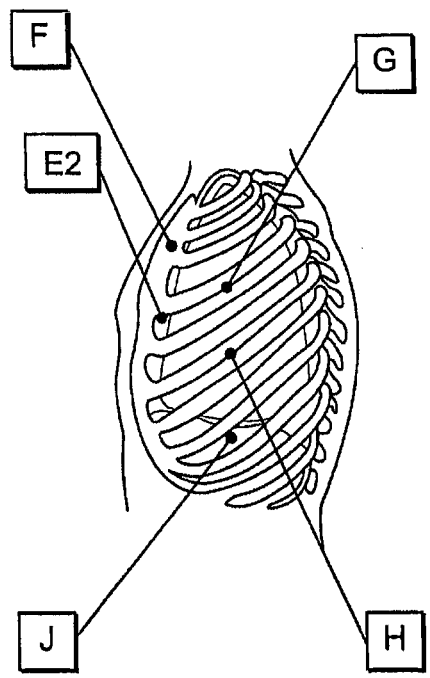
Figure 37D:
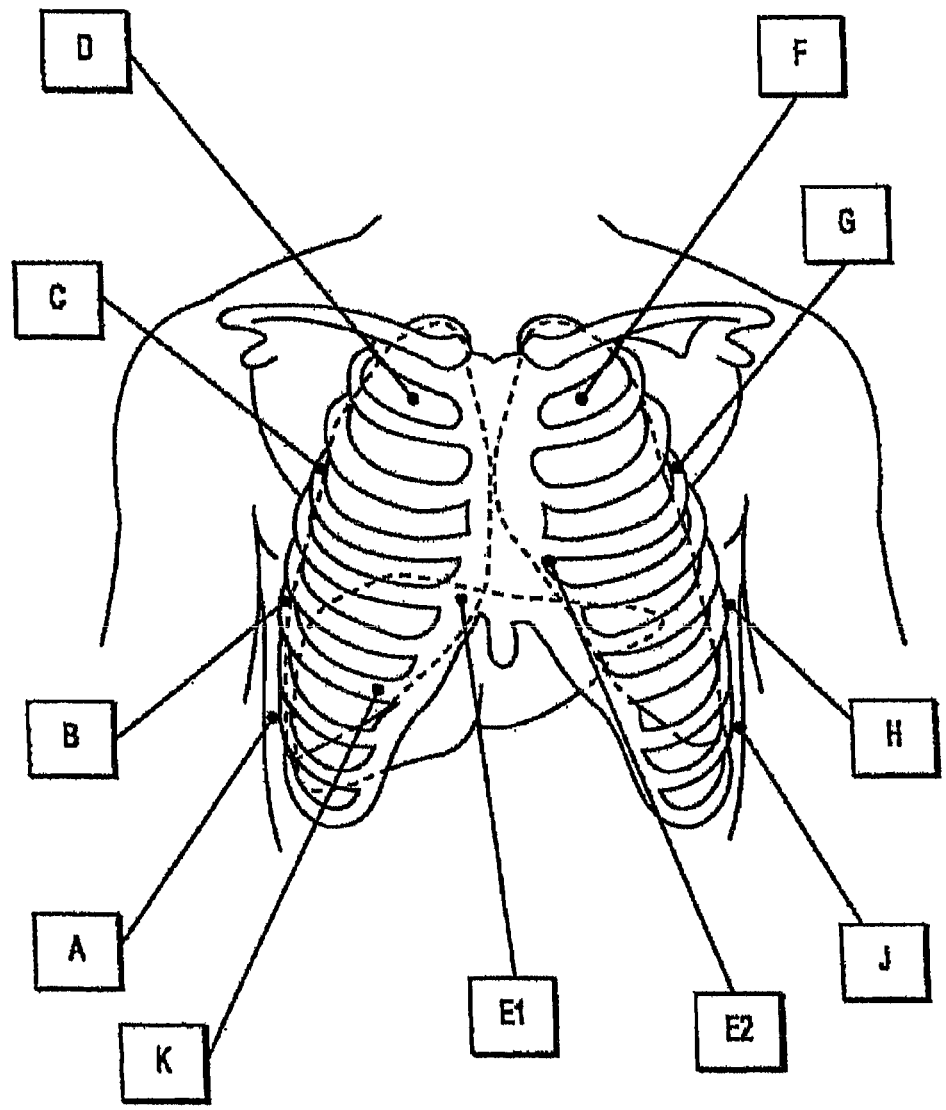

With reference to FIGS. 37A-37C, thoracic locations defining examples of bio-Z vectors are shown schematically. FIGS. 37A and 37D are frontal views of the thorax, FIG. 37B is a right-side view of the thorax, and FIG. 37C is a left-side view of the thorax; In each of FIGS. 37A-37D, the outline of the lungs and upper profile of the diaphragm are shown. As mentioned previously, a bio-Z vector may be defined by the locations of the voltage-sensing electrodes. Thus, FIGS. 37A-37D show locations for voltage sensing electrodes which would define the bio-Z vector.

There are several short bio-Z vectors which provide excellent signals correlated to diaphragmatic movement. In general, these vectors have at least one end at or near the lower edge of the ribcage. The short diaphragmatic bio-Z vectors have been successfully used in canines in vector lengths ranging from approximately less than ½ inch to a few inches in length. FIG. 37A shows a variety of locations which are representative of the locations which define such vectors. Locations shown just below the ribcage on the person's right side are designated as A, B, C, and D. Locations shown just below the ribcage on the person's left side are E, F, G, and H. Locations shown just above the lower edge of the ribcage on the person's right side are I, J, K, and L. Locations shown just above the lower edge of the ribcage on the person's left side are M, N, P, and Q. The locations just above the lower edge of the ribcage would fall within a few inches of the lower edge. Short diaphragmatic monitoring vectors would be comprised of location pairs which are relatively closely spaced. For example, vectors D-E, D-C, D-L, and D-K all provide good diaphragmatic signal. The possible vectors fall into three groups. Exemplary vectors which measure primarily diaphragmatic muscle contraction are A-B, B-C, C-D, D-E, E-F, F-G, and G-H. Exemplary vectors which measure a combination of diaphragmatic muscle contraction combined with movement of the lung into the pleural pocket as the diaphragm contracts are I-J, P-R, A-I, A-J, B-I, B-J, G-P, H-R, H-P, and G-R. Exemplary vectors which measure diaphragmatic muscle contraction combined with movement of the diaphragm away from the thoracic wall as that portion of the lung expands are J-K, K-L, M-N, and N-P. It is known that the signal from any given location may be affected by body position and free vs. obstructed respiration. The respiratory signal from short vectors at or near the lower edge of the ribcage may be more robust (e.g., may be not be substantially affected) to body position and obstructed respiration. A further means of obtaining a signal which may be also more robust to body position would be to measure the respiratory impedance from complimentary vectors and sum the resulting bio-Z measurements. Complimentary vectors would be mirror-images or nearly mirror images of one another. Examples of vectors and their mirror images may be C-D and E-F, B-C and G-F, C-K and F-N.

By way of example, not limitation, the following bio-Z vectors may be effective for monitoring respiration and/or for measuring artifacts for subsequent removal of the artifact from the respiration signal. Vector C-G is across the upper left and upper right lobes of the lungs, and provides a good signal of ribcage expansion with moderate cardiac artifact. Vector D-F is a short-path version of C-G that provides a good respiratory signature largely correlated with ribcage expansion, with less cardiac artifact than C-G, but may be sensitive to movement of arms due to location on pectoral muscles. Vector C-D is a short-path ipsilateral vector of the upper right lung that may be sensitive to arm movement but has less cardiac artifact. Vector B-H is a transverse vector of the thoracic cavity that captures the bulk of the lungs and diaphragm movement. Vector B-H, however, may be relatively less susceptible to changes in body position, and may still provide a generally good signal when the patient changes positions. In certain circumstances, the signal produced by vector B-H may have a less than desired signal to noise ratio. However, it is contemplated that generally available methods of signal processing in accordance with the present disclosure may be utilized the improve signal to noise ratio of the signal produced by Vector B-H. Vector A-E is an ipsilateral vector across the lung-diaphragm-liver interface. Because the liver is higher in conductivity and has a different impedance phase angle than the lung, vector A-E1 yields a good signal on both bio-Z magnitude and phase with limited cardiac artifact. Vector B-K is an ipsilateral vector across the lung-diaphragm-liver interface that is substantially between a common set of ribs with a current path that is mostly perpendicular to the intercostal muscles. Because resistivity of muscle is much higher perpendicular to the muscle direction than parallel, vector B-K reduces current-shunting through the muscle which otherwise detracts from the signal of the lung-diaphragm-liver interface. Vector A-K is an ipsilateral vector across the lung-diaphragm-liver interface similar to vector A-E 1 but is more sensitive to movement of the lung-diaphragm-liver interface than to changes in resistivity of the lung-diaphragm-liver interface due to inspired air volume and is thus a good indicator of diaphragm movement. Vector B-E1 is a vector across the middle and lower right lung and is good for detecting diaphragm movement with little cardiac artifact. Vector C-E1 is a vector across the upper and middle right lung and is also good for detecting diaphragm movement with little cardiac artifact. Vector D-E1 is a vector across the upper right lung with little cardiac artifact. Vector A-D is an ipsilateral across a substantial portion of the right lung and diaphragm with little cardiac artifact, but may be susceptible to motion artifact due to arm movement. Vector E1-E2 is a vector across the heart and provides a good cardiac signal that may be used for removing cardiac artifact from a respiratory signal. Vector E2-J is a vector across the lung-diaphragm-stomach interface that provides a good measure of diaphragm movement using bio-Z phase vs. magnitude because the stomach has almost no capacitive component and generally low conductivity. Vector L-M is a trans-diaphragm vector that is generally across the lung-diaphragm-liver interface with little cardiac artifact. Vector L-M may be relatively less susceptible to body position and movement and may yield a good signal even if the patient is laying on the side of the sensing lead. In embodiments where the signal produced by vector L-M has a less than desired signal to noise ratio, it is contemplated that generally available methods of signal processing may be utilized to improve the signal to noise ratio of the signal produced by vector L-M.

Electrodes placed at any of the above-noted locations may include, but are not limited to, combination electrodes, such as, for example, electrodes capable of both providing a current charge and sensing a voltage.

With reference to FIGS. 37A and 38D, an exemplary vector selection method 3800 for detecting and utilizing a signal from the vector that produces the most desirable signal of all vectors is discussed. The disclosed vector selection method 3800 may be performed continuously, periodically, singularly, and/or may be repeated as desired. For example, method 3800 may be performed once in a 24 hour period. In addition, one or more steps associated with method 3800 may be selectively omitted and/or the steps associated with method 3800 may be performed in any order. The steps associated with method 3800 are described in a particular sequence for exemplary purposes only.

With specific reference to FIG. 38D, method 3800 may include a plurality of steps 3801-3803 for detecting and utilizing the signal with the best characteristics of all signals produced by a plurality of vectors. Specifically, method 3800 may include sampling short distance vectors first to determine if any of these vectors are producing a desirable signal, step 3801. Method 3800 may also include sampling intermediate distance vectors if the short distance vectors are not producing a desirable signal, step 3802. Method 3800 may further include sampling long distance vectors if the intermediate distance vectors are not producing a desirable signal, step 3803.

Turning to FIG. 37A, there is depicted an exemplary embodiment of a neurostimulator in accordance with the principles of the present disclosure. The exemplary neurostimulator may include an implanted INS 50 and implanted electrode contacts AA-DD. While the depicted embodiment includes electrode contacts AA-DD disposed between a patient's 5th and lowest ribs, electrode contacts AA-DD may be disposed at any suitable location. Furthermore, electrode contacts AA-DD may include, but are not limited to, the combination electrodes discussed above. In the depicted embodiment, exemplary short distance vectors may include the vectors between, for example, adjacent electrode contacts AA, BB, CC, and DD; exemplary intermediate distance vectors may include the vectors AA-CC, AA-DD, and BB-DD, and exemplary long distance vectors may include the vectors between the INS 50 and each of electrode contacts AA-DD.

Figure 38A:
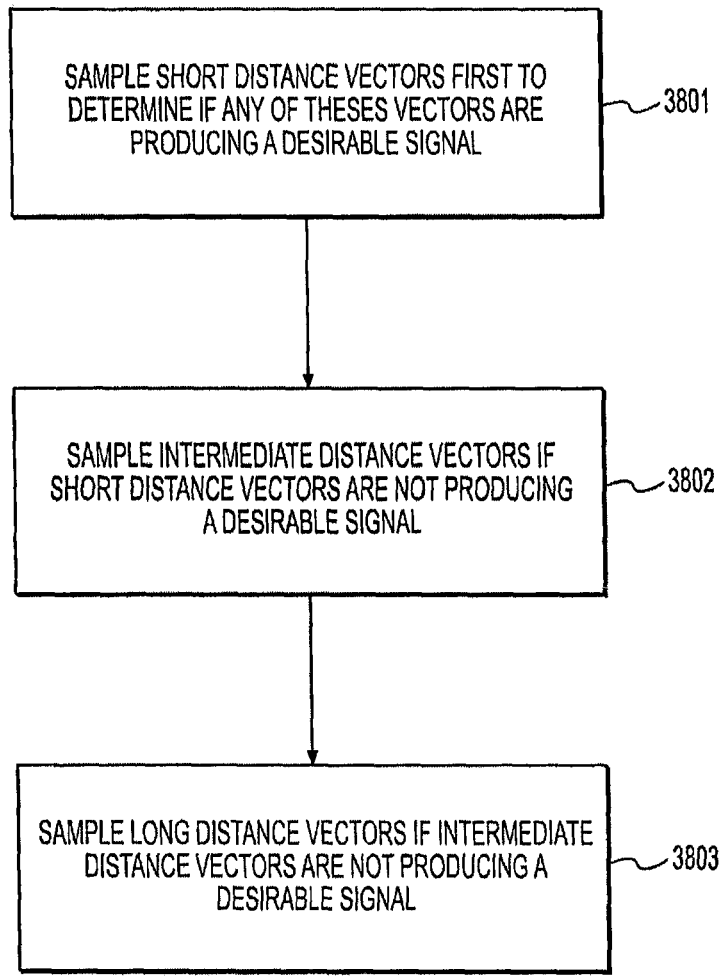
FIG. 38A illustrates an exemplary method of sampling a plurality of vector signals.

With reference to FIG. 37A and FIG. 38A, step 3801 may include, for example, sampling short distance vectors AA-BB, BB-CC, and CC-DD first to determine whether any of these vectors may be producing a sufficient signal in accordance with the principles of this disclosure, since these vectors generally produce signals with desirable signal to noise ratios. Next, step 3802 of method 3800 may include sampling the intermediate distance vectors AA-CC, AA-DD, and BB-DD if the short distance vectors are producing a less than desirable signal. Lastly, step 3803 of method 3800 may include sampling the long distance vectors INS-AA, INS-BB, INS-CC, and INS-DD if the intermediate distance vectors are producing a less than desirable signal.

In some embodiments, it is contemplated that several short, intermediate, and long distance vectors may be continually sampled, even if a desirable signal is being received from a short distance vector, in order to identify secondary vector signals that may be utilized if the currently utilized vector signal fails for any reason. However, fully processing the data from signals generated by all of the vectors may require complex sensing circuitry and processing of detection algorithms that may utilize undesirable amounts of battery power. Therefore, it may be desirable to only monitor selected characteristics of the secondary vector signals. With specific reference to FIG. 38B, there is depicted an embodiment of a method 3850 for utilizing multiple sensing channels to optimize respiratory sensing with minimal additional hardware and power consumption. It uses a single sensing circuit which is time multiplexed (interleaved) to sample each of the vectors. Since, as noted above, fully processing the data from all vector signals may require higher computational power, method 3850 may be used to identify the best vector signal for respiration detection, while simultaneously monitoring the remaining vectors signals for only relevant fiducial points. These fiducial points may include, but are not limited to, significant "landmarks" within a signal, such as, for example, peak amplitude and time, point of highest slew rate, and zero crossing. The detected fiducial points for the secondary vector signals may be then stored in a circular buffer memory 3854 for analysis if the primary signal fails for any reason, thereby, allowing immediate switching to an alternate vector signal and eliminating the need for a long signal acquisition period after a need to switch vector signals has been determined.

In particular, method 3850 may include feeding the signals from all available vectors into a plurality of channel selection switches 3851. The signals may be then analyzed for relevant fiducials by the respiratory impedance sensing circuit 3853. Once relevant fiducials have been discriminated, it may be possible to identify the best vector signal for respiration signal analysis. The fiducials of the remaining vectors may be then stored in circular buffer memory 3854 (as noted above) to facilitate switching to a secondary vector signal if the primary signal is no longer suitable for respiration detection.

The periodic monitoring (or interleaving) of secondary vector signals may facilitate faster switching to those vector signals when necessary. In particular, it is contemplated that when a decision to switch to a secondary vector signal is made (i.e., when the primary signals degrades to a point where it is no loner desirable for detecting respiration), the saved data (e.g., relevant fiducials) may be used to "seed" a signal analysis algorithm with recently collected data, so as to promote faster vector switching by eliminating the need to wait for collection of sufficient data for the secondary vector signal. In other words, because select information of a secondary signal is available before the signal is actually used for respiration detection, analysis of the secondary signal for, among other things, respiration detection may begin slightly faster than it would have if no data was available.

Furthermore, in certain embodiments, additional impedance sensors may be used as backup sensors to the sensor generating the primary vector signal. In these embodiments, data from the secondary sensors may be also analyzed to identify and save relevant fiducials in the memory. This stored information may be used to provide supplemental or alternate information to facilitate identifying appropriate respiratory timing, when switching vector signals becomes necessary as a result of primary signal degradation.

The respiratory bio-Z signal is partly due to the resistivity change which occurs when air infuses lung tissue, partly due to the relative movement of electrodes as the rib cage expands, and partly due to the displacement of other body fluids, tissue and organs as the lungs move along with the ribcage and diaphragm. As described above, each vector measures certain of these changes to different extents. It may be desirable, therefore, to combine vectors which have complementary information or even redundant information to improve the respiratory information of the bio-Z signal. To this end, multiple vectors may be used. For example, one vector may be used to sense changes in the lung-diaphragm-liver interface and a second vector may be used to detect changes (e.g., expansion, contraction) of the lung(s). Examples of the former include A-K, B-K, A-E1, B-E1, and A-B. Examples of the later include D-F, B-D, C-G, D-E1, and C-E1. Note that some vector combinations which share a common vector endpoint such as A-E1, D-E1 and B-E1, B-D may use a common electrode which would simplify the respiratory sensing lead or leads.

An advantage of using the lung-diaphragm-liver interface vector is that it provides a robust signal indicative of the movement of the diaphragm throughout the respiratory cycle. The liver is almost two times more electrically conductive than lung tissue so a relatively large bio-Z signal can be obtained by monitoring the movement of the lung-diaphragm-liver interface. Because the liver functions to filter all the blood in the body, the liver is nearly completely infused with blood. This helps to dampen out the cardiac artifact associated with the pulsatile flow of the circulatory system. Another advantage of this location is that vectors can be selected which avoid significant current path through the heart or major arteries which will help reduce cardiac artifact.

It is worth noting that diaphragm movement is not necessarily synchronous with inspiration or expiration. Diaphragm movement typically causes and therefore precedes inspiration and expiration. Respiratory mechanics do allow for paradoxical motion of the ribcage and diaphragm, so diaphragm movement is not necessarily coincident with inspiration. During REM sleep, the diaphragm is the dominant respiratory driver and paradoxical motion of the ribs and diaphragm can be problematic, especially if movement of the ribcage is being relied upon as an inspiratory indicator. Monitoring the diaphragm for pre-inspiratory movement becomes especially valuable under these circumstances. Bio-Z monitoring of the diaphragm can be used as a more sophisticated indicator of impending inspiration rather than the antiquated approach of desperately trying to identify and respond to inspiration in pseudo-real time based on sensors which are responding to characteristics of inspiration.

For purposes of monitoring respiration, it is desirable to minimize shunting of the electrical current through tissues which are not of interest. Shunting may result in at least two problems: reduced signal from the lungs; and increased chance of artifacts from the shunted current path. Skeletal muscle has non-isotropic conductivity. The muscle's transverse resistivity (1600 ohm-cm) is more than 5 times its longitudinal resistivity (300 ohm-cm). In order to minimize the adverse effect of shunting current, it is desirable to select bio-Z sensing vectors which are perpendicular to muscle structure if possible. One such example is to locate two or more electrodes of a bio-Z sensing array substantially aligned with the ribs because the intercostal muscles are substantially perpendicular to the ribs.

Description of Respiration Signal Processing

Figure 39:
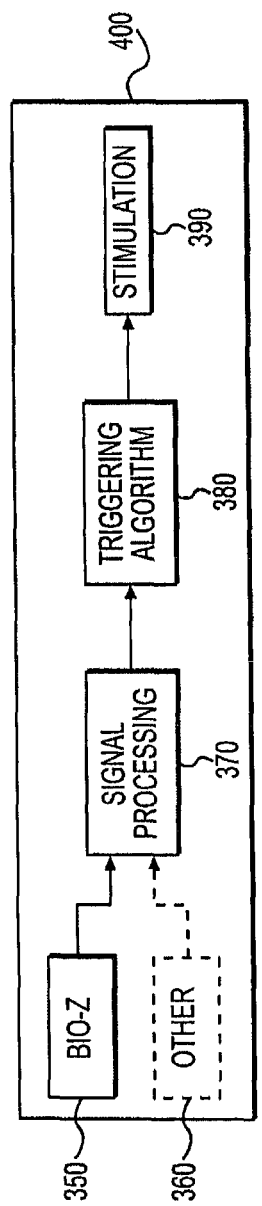

With reference to FIG. 39, the neurostimulation system described herein may operate in a closed-loop process 400 wherein stimulation of the targeted nerve may be delivered as a function of a sensed feedback parameter (e.g., respiration). For example, stimulation of the hypoglossal nerve may be triggered to occur during the inspiratory phase of respiration. Alternatively, the neurostimulation system described herein may operate in an open-loop process wherein stimulation is delivered as a function of preset conditions (e.g., historical average of sleeping respiratory rate).

With continued reference to FIG. 39, the closed-loop process 400 may involve a number of generalized steps to condition the sensed feedback parameter (e.g., bio-Z) into a useable trigger signal for stimulation. For example, the closed-loop process 400 may include the initial step of sensing respiration 350 using bio-Z, for example, and optionally sensing other parameters 360 indicative of respiration or other physiologic process. The sensed signal indicative of respiration (or other parameter) may be signal processed 370 to derive a usable signal and desired fiducials. A trigger algorithm 380, which will be discussed in greater detail below, may then be applied to the processed signal to control delivery of the stimulation signal 390.

As noted above, the present disclosure contemplates conditioning sensed bio-impedance into a useable trigger signal for stimulation. However, one exemplary limitation to using sensed bio-impedance may be the body's nominal impedance. In practice, a sensed bio-impedance signal may be obtained by applying a suitable, known current through one portion of a tissue of interest and measuring the voltage potential across the same tissue. This measurement technique is illustrated in FIG. 38C and may be referred to herein as the "direct measurement" technique. The applied current and measured voltage potentials may be used to calculate the impedance of the tissue. It is this measured impedance that may constitute the sensed bio-impedance signal. However, sense bio-impedance signals of the present disclosure have been found to typically include two components, a relatively large nominal body impedance component and a relatively small respiratory impedance component. Thus, since the body's impedance constitutes a large portion of the sensed signal, it may be difficult to detect that relatively small impedance changes associated with respiration on top of a body's nominal impedance. Therefore, in accordance with the principles of the present disclosure, it may be desirable to "filter" the sensed impedance signal in a manner so as to remove most or all of the body's nominal impedance, in order to improve resolution of the respiratory signal. In some embodiments, this may be achieved with the aid of a conventional Wheatstone bridge at or near the front-end of an impedance measuring circuit. In particular, the Wheatstone bridge may facilitate precise measurements of the relatively small impedance changes associated with respiration by removing most, if not all, of the body's nominal impedance.

Figure 39A:
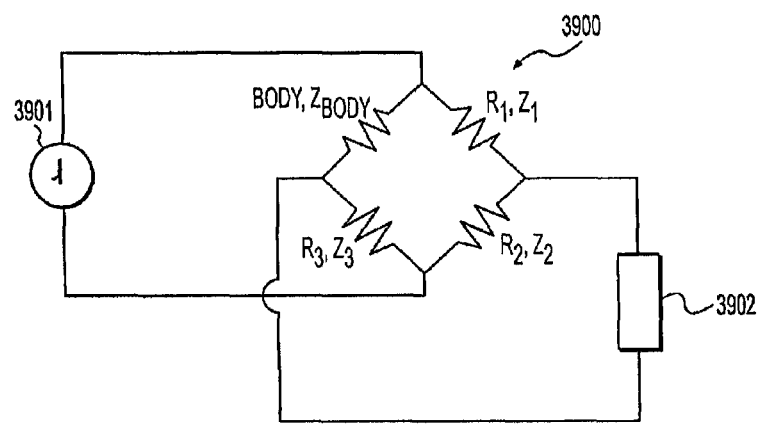

Turning now to FIG. 39A, there is depicted an exemplary Wheatstone bridge 3900. The Wheatstone bridge 3900 may include an electrical current source 3901. Wheatstone bridge 3900 may also include a first resistor $R_1$ having an impedance $Z_1$ connected in series to a second resistor $R_2$ having an impedance $Z_2$. Resistors $R_1$ and $R_2$ may be connected in parallel to resistor $R_3$ having an impedance $Z_3$, which may be connected serially to the patient's body having an impedance $Z_{body}$. As discussed below, impedances $Z_2$ and $Z_3$ may be substantially similar to each other. Wheatstone bridge 3900 may further include any suitable voltage measuring device, such as, for example, those used in conjunction the direct measurement technique described above.

In use, the impedance $Z_1$ of exemplary bridge 3900 may be closely matched to the expected impedance of a patient's body $Z_{body}$, the impedance $Z_2$ matched to impedance $Z_3$, and the voltage potential across voltage measuring device 3902 may be measured. It is contemplated that if impedances $Z_1$-$Z_3$ are closely matched to $Z_{body}$, the measured voltage potential across voltage measuring device 3902 will be predominantly due to respiratory impedance changes and the voltage signal due to the body's nominal impedance will be largely removed. Further, it is contemplated that the voltage changes measured at 3902 due to respiratory impedance changes will have an amplitude that is approximately ½ of the amplitude of the voltage changes, measured with the above-noted direct-measurement technique, assuming the same currently flow through the body. The removal of the voltage signal due to the body's nominal impedance while retaining ½ of the voltage signal amplitude due to changes in respiratory impedance, may facilitate detecting the small impedance changes associated with respiration by improving the resolution of those changes.

Figure 39B:
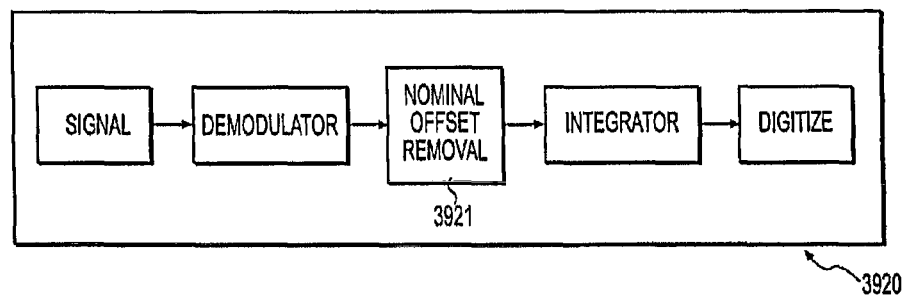

In other embodiments, the body's nominal impedance may be removed or reduced from a sensed signal by, for example, introducing a nominal offset removal module 3921 into an impedance measuring circuit 3920 of the present disclosure, as depicted in FIG. 39B. An exemplary impedance-measuring circuit may generally include feeding a sensed respiratory signal into a demodulator. The signal exiting the demodulator may be then fed into an integrator, and the integrated signal exiting the integrator may then be digitized for analysis. It is therefore contemplated that introducing nominal offset removal module 3921 to act upon the upon the signal exiting the demodulator may achieve the desired effect of removing or reducing the body's nominal impedance from a sensed impedance signal.

Figure 39C:
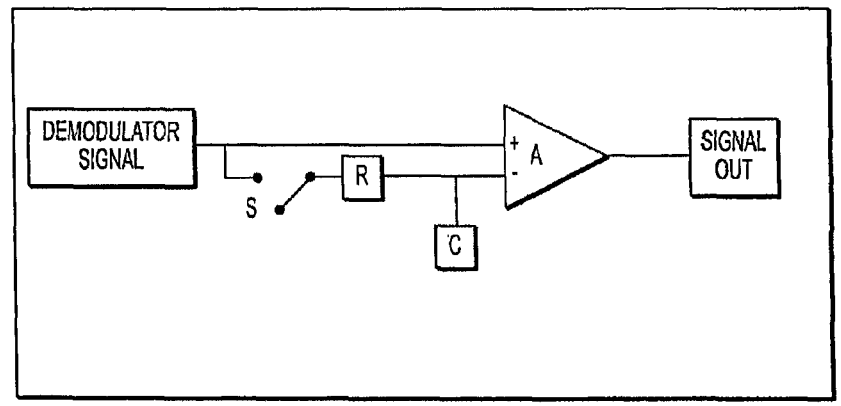

Turning now to FIG. 39C, module 3921 may include a switch S, a resistor R, a capacitor C, and a non-inverting amplifier A. The switch S, resistor R, and capacitor C create a sample and hold reference voltage to the difference amplifier A. The amplifier subtracts this reference voltage from the input signal. The result is to remove or reduce the nominal body impedance component of the signal leaving mainly the respiratory component of the measured impedance. The Resistor-Capacitor (R-C) combination is selected such that it will track with changes in nominal impedance levels but does not significantly distort the respiratory signal. Respiratory signal frequency components of interest are typically between 0.05 Hz and 3 Hz. There are several options for how the Nominal Offset Removal may be operated. An implanted bio-impedance circuit would typically use a modulated excitation signal for measuring impedance. In that case, the switch, S may be open when there is no signal present and may be closed whenever a signal is present. For example, if a Demodulator Signal is present for 1 ms every 100 ms, switch S would be closed during all or a part of the time that Signal In is present. Switch S may also be operated such that it does not close on every instance when Demodulator Signal is present. The switch S, may be closed on every $10^{th}$ or $100^{th}$ instance when Demodulator Signal is present. A third possibility is to close switch S only when Signal Out causes the Integrator to reach an unacceptable threshold. The integrator reaching an unacceptable threshold may be indicative that the reference voltage provided by the R-C combination is no longer providing a sufficiently good estimate of the nominal signal component and so needs to be updated with new information.

Figure 39D:
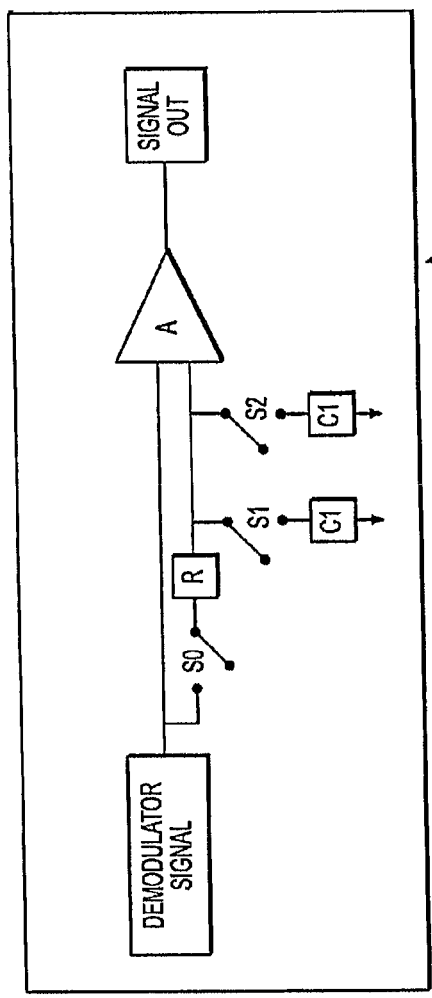

Turning now to FIG. 39D, there is depicted an alternative embodiment of nominal offset removal module. A further improvement on the Nominal Offset Removal module is shown in FIG. 39D. If it is desired, to measure two or more different impedance signals it will be necessary to have a different nominal offset reference voltage provided to amplifier A for each signal. It is also desirable to keep the component count as low as possible. In the diagram below, S0 snd S1 may be closed and S2 may be open to provide an offset reference for a first signal with the appropriate combination of R-C1. S0 and S2 may be closed and S1 may be open to provide an offset reference for a second signal with the appropriate combination of R-C2. This strategy allows rapid sequential measurement of two or more impedance signals.

Figure 40:
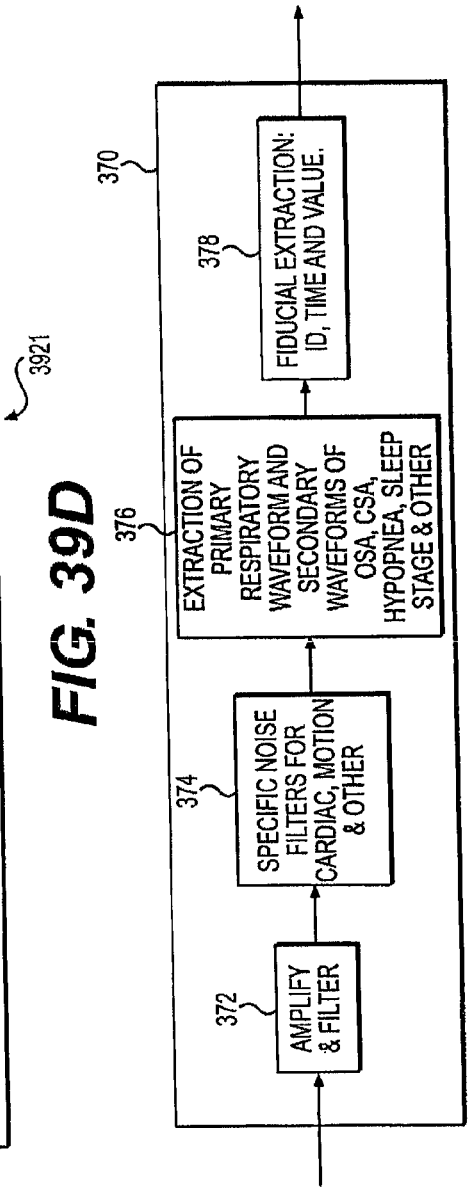

With reference to FIG. 40, the signal processing step 370 may include general signal amplification and noise filtering 372. The step of amplification and filtering 372 may include band pass filtering to remove DC offset, for example. The respiratory waveform may then be processed to remove specific noise artifacts 374 such as cardiac noise, motion noise, etc. A clean respiratory waveform may then be extracted 376 along with other waveforms indicative of specific events such as obstructive sleep apnea (OSA), central sleep apnea (CSA), hypopnea, sleep stage, etc. Specific fiducial points may then be extracted and identified (e.g., type, time, and value).

The step of removing specific noise artifacts 374 may be performed in a number of different ways. However, before signal processing 374, both cardiac and motion noise artifact may be mitigated. For example, both cardiac and motion noise artifact may be mitigated prior to signal processing 374 by selection of bio-Z vectors that are less susceptible to noise (motion and/or cardiac) as described previously. In addition, motion artifact may be mitigated before signal processing 374 by minimizing movement of the sensing lead and electrodes relative to the body using anchoring techniques described elsewhere herein. Furthermore, motion artifact may be mitigated prior to signal processing 374 by minimizing relative movement between the current-carrying electrodes and the voltage-sensing electrodes, such as by using combined current-carrying and voltage-sensing electrodes.

After cardiac and motion artifact has been mitigated using the pre-signal processing techniques described above, both cardiac and motion artifact may be removed by signal processing 374.

For example, the signal processing step 374 may involve the use of a low pass filter (e.g., less than 1 Hz) to remove cardiac frequency noise components which typically occur at 0.5 to 2.0 Hz, whereas resting respiration frequency typically occurs below 1.0 Hz.

Figure 41:
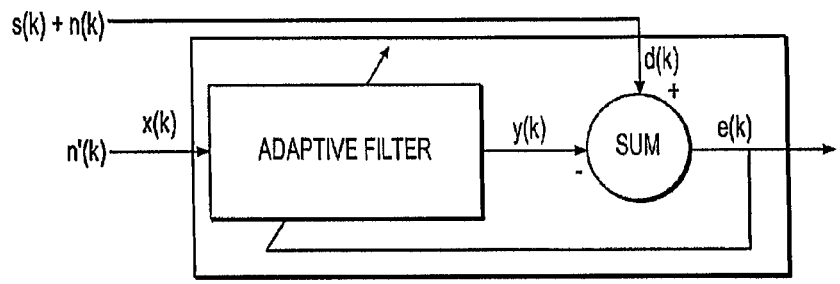

Alternatively, the signal processing step 374 may involve the use of a band pass or high pass filter (e.g., greater than 1 Hz) to obtain a cardiac sync signal to enable removal of the cardiac noise from the bio-Z signal in real time using an adaptive filter, for example. Adaptive filters enable removal of noise from a signal in real time, and an example of an adaptive filter is illustrated in FIG. 41. To remove cardiac artifact from the bio-Z signal which contains both cardiac noise n(k) and respiratory information s(k), a signal n'(k) that represents cardiac noise is input to the adaptive filter and the adaptive filter adjusts its coefficients to reduce the value of the difference between y(k) and d(k), removing the noise and resulting in a clean signal in e(k). Notice that in this application, the error signal actually converges to the input data signal, rather than converging to zero.

Another signal processing technique to remove cardiac noise is to combine signals from two or more bio-Z vectors wherein respiration is the predominate signal with some cardiac noise. This may also be used to reduce motion artifact and other asynchronous noise. Each of the two or more signals from different bio-Z vectors may be weighted prior to combining them into a resultant signal Vw(i). If it is assumed that (a) the respiratory bio-impedance is the largest component in each measured vector, (b) the non-respiratory signal components in one vector are substantially independent of the non-respiratory components in the other vector, and (c) the ratio of the non-respiratory component to the respiratory components in one vector is substantially equal to the same ratio in the other vector, then a simple weighting scheme may be used wherein each signal is divided by it's historic peak-to-peak magnitude and the results are added. For example, if $M_A$=historical average peak-to-peak magnitude of signal from vector A, $M_B$=historical average peak-to-peak magnitude of signal from vector B, $V_A(i)$=data point (i) from vector A, $V_B(i)$=data point (i) from vector B, then the resultant signal Vw(i) (i.e., weighted average of A & B for data point (i)) may be expressed as $V_W(i)=V_A(i)/M_A+V_B(i)/M_B$.

Yet another signal processing technique for removing cardiac noise is to subtract a first signal that is predominantly respiration from a second signal that is predominantly cardiac. For example, the first signal may be from a predominantly respiratory bio-Z vector (e.g., vector B-H) with some cardiac noise, and the second signal may be from a predominantly cardiac bio-Z vector (e.g., vector E1-E2) with some respiration signal. Each of the two signals from the different bio-Z vectors may be weighted prior to subtracting them. The appropriate weighting may be determined, for example, by calculating the power density spectra in the range of 2-4 Hz for a range of weighted differences across at least several respiratory cycles. A minimum will occur in the power density spectra for the weighted averages which are sufficiently optimal.

Motion artifact may be removed by signal processing 374 as well. Motion artifact may be identified and rejected using signal processing techniques such as monitoring voltage magnitude, testing the correlation of magnitude and phase, and/or testing correlation at two or more frequencies. Motion artifacts may cause a large change in measured bio-impedance. A typical feature of motion artifacts is that the voltage swings are much larger than respiration. Another feature is that the voltage changes are highly erratic. Using these characteristics, which will be described in more detail below, motion artifact may be removed from the respiration signal.

Figure 42:
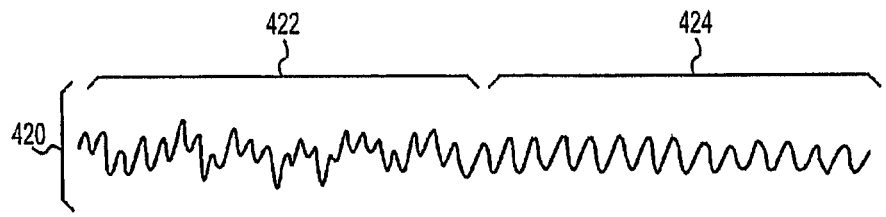
Figure 43:
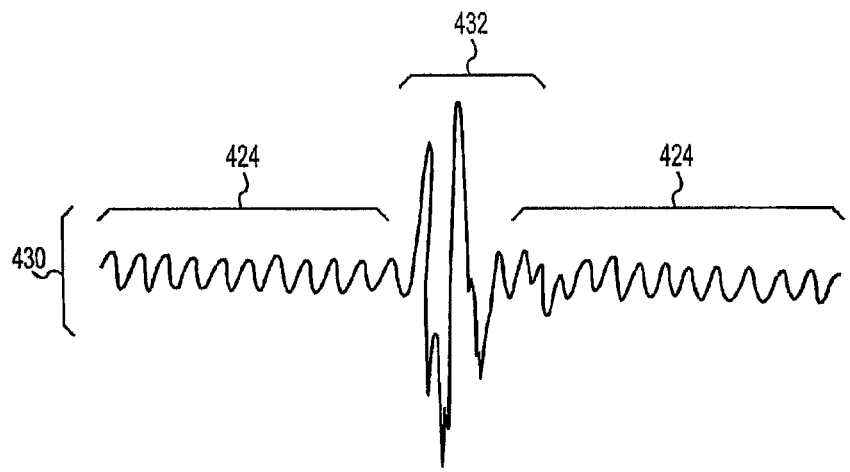
Figure 44:
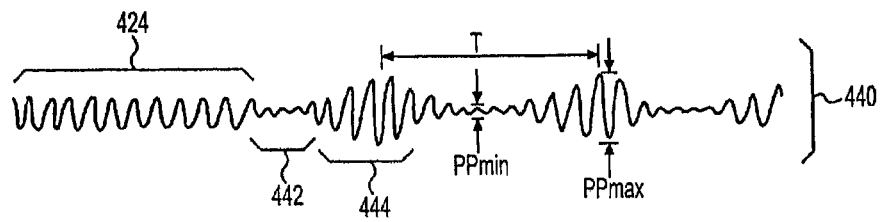
Figure 45:
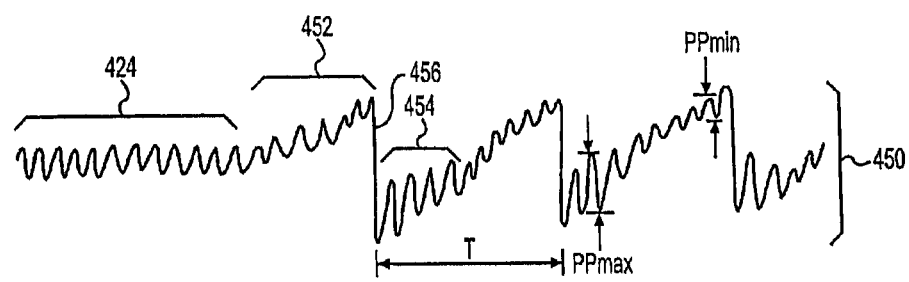
Figure 46:
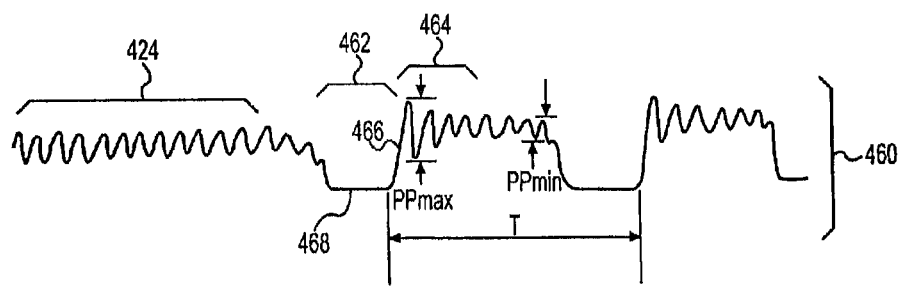

The step of extracting waveforms indicative of respiration and other events 374 may be better explained with reference to FIGS. 42-46 which schematically illustrate various representative unfiltered bio-Z signals. FIG. 42 schematically illustrates a bio-Z signal 420 with representative signatures indicative normal respiration (i.e., event free) during an awake period 422 and a sleeping period 424. FIG. 43 schematically illustrates a bio-Z signal 430 with representative signatures indicative of normal respiration during sleeping periods 424 interrupted by a period of motion 432 (i.e., motion artifact). FIG. 44 schematically illustrates a bio-Z signal 440 with representative signatures indicative of normal respiration during a sleeping period 424 followed by periods of hypopnea (HYP) 442 and recovery 444. FIG. 45 schematically illustrates a bio-Z signal 450 with representative signatures indicative of normal respiration during a sleeping period 424 followed by periods of obstructive sleep apnea (OSA) 452 and recovery 454 (which typically includes an initial gasp 456). FIG. 46 schematically illustrates a bio-Z signal 460 with representative signatures indicative of normal respiration during a sleeping period 424 followed by periods of central sleep apnea (CSA) 462 (which typically includes a cessation in breathing 468) and recovery 464.

The step of extracting 374 waveform data indicative of an awake period 422 vs. a sleep period 424 from a bio-Z signal 420 may be explained in more detail with reference to FIG. 42. In addition, the step of filtering 372 waveform data indicative of motion 432 from a bio-Z signal 430 may be explained in more detail with reference to FIG. 43. One way to determine if a person is awake or moving is to monitor the coefficient of variation (CV) of sequential peak-to-peak (PP) magnitudes over a given period of time. CV is calculated by taking the standard deviation (or a similar measure of variation) of the difference between sequential PP magnitudes and dividing it by the average (or a similar statistic) of the PP magnitudes. N is the number of respiratory cycles which occur in the selected period of time.

The CV may be calculated as follows:

$$CV = \frac{sd(dPP)}{\overline{PP}}$$

Where $$sd(dPP) = \sqrt{\frac{\sum_{i=1}^{N}(dPP_i - \overline{dPP})}{(N-1)}}$$

$$\overline{dPP} = \frac{\sum_{i=1}^{N}(dPP_i)}{(N)}$$

$$dPP_i = PP_{i+1} - PP_i$$

$$\overline{PP} = \frac{\sum_{i=1}^{N}(PP_i)}{(N)}$$

Generally, if the CV is greater than 0.20 over a one minute period then person is awake. Also generally, if the CV is less than 0.20 over a one-minute period then person is asleep. These events may be flagged for the step of fiducial extraction 378 wherein data (e.g., event duration, CV, PP range, PPmin, PPmax, etc.) may be time stamped and stored with an event identifier. If CV is greater than 1.00 over a 20 second period then body movement is affecting the bio-Z signal. By way of example, not limitation, if body movement is detected, then (a) stimulation may be delivered in an open loop fashion (e.g., based on historical respiratory data); (b) stimulation may be delivered constantly the same or lower level; or (c) stimulation may be turned off during the period of movement. The selected stimulation response to detected movement may be preset by the physician programmer or by the patient control device. Other stimulation responses may be employed as will be described hereinafter.

In each of FIGS. 44-46, maximum and minimum peak-to-peak magnitudes (PPmax and PPmin) may be compared to distinguish hypopnea (HYP), obstructive sleep apnea (OSA), and central sleep apnea (CSA) events. Generally, PP values may be compared within a window defined by the event (HYP, OSA, CSA) and the recovery period thereafter. Also generally, the window in which PP values are taken excludes transitional events (e.g., gasp 456, 466). As a general alternative, peak-to-peak phases may be used instead of peak-to-peak magnitude. The hypopnea and apnea events may be flagged for the step of fiducial extraction 378 wherein data (e.g., event duration, CV, PP range, PPmin, PPmax, etc.) may be time stamped and stored with an event identifier.

A typical indication of hypopnea (HYP) and apnea (OSA, CSA) events is a recurrent event followed by a recovery. The period (T) of each event (where PP oscillates between PPmax and PPmin and back to PPmax) may be about 15 to 120 seconds, depending on the individual. The largest PP values observed during hypopneas and apneas are usually between 2 and 5 times larger than those observed during regular breathing 424 during sleep. The ratio of the PPmax to PPmin during recurrent hypopnea and apnea events is about 2 or more. During the event and recovery periods (excluding transitional events), PP values of adjacent respiratory cycles do not typically change abruptly and it is rare for the change in PP amplitude to be more than 50% of PPmax. One exception to this observation is that some people gasp 456, 466 (i.e., transitional event) as they recover from a CSA or OSA event.

The ratio of successive PP magnitudes during normal (non-event) sleep 424 is mostly random. The ratio of successive PP magnitudes during apnea and hypopnea events will tend to be a non-random sequence due to the oscillatory pattern of the PP values. Recurrent apneas and hypopneas may be diagnosed by applying a statistical test to the sequence of successive PP ratios.

The step of extracting 374 waveform data indicative of an hypopnea event 442 from a bio-Z signal 440 may be explained in more detail with reference to FIG. 44. The ratio of PPmax to PPmin during recurrent hypopneas is typically between 2 and 5. This is in contrast to CSA's which have very small PPmin due to the complete cessation of breathing. This results in CSA's having PPmax to PPmin ratios larger than 5. Accordingly, hypopnea events may be detected, identified and flagged for the step of fiducial extraction 378 wherein data (e.g., event duration, CV, PP range, PPmin, PPmax, etc.) may be time stamped and stored with an event identifier.

The step of extracting 374 waveform data indicative of an OSA event 452 from a bio-Z signal 450 may be explained in more detail with reference to FIG. 45. The sharp change 456 in the bio-Z respiratory magnitude due to OSA is typically in the range of 1 to 4 times the magnitude of the peak-to-peak respiratory cycle magnitude. The sharp change 456 typically takes less than 5 seconds to occur. OSA tends to occur in a recurring sequence where the period (T) between sequential events is between 15 and 120 seconds. A one-minute period is commonly observed. According to these characteristics, OSA events may be detected, identified and flagged for the step of fiducial extraction 378 wherein data (e.g., event duration, CV, PP range, PPmin, PPmax, etc.) may be time stamped and stored with an event identifier.

The step of extracting 374 waveform data indicative of a CSA event 462 from a bio-Z signal 460 may be explained in more detail with reference to FIG. 46. The behavior of the Bio-Z signal throughout recurrent CSA events differ from other hypopnea and OSA in three ways. First, during CSA there is complete cessation of respiratory activity which results in a flat Bio-Z signal. This means the ratio of PPmax to PPmin is typically greater than 5 during recurrent CSA events. The duration of the estimated respiratory cycle may also be used to distinguish between CSA from OSA and hypopnea. The lack of respiratory activity during CSA results in an inflated estimate for the respiratory cycle period. The PP typically does not vary by more than 50% for successive cycles. The respiratory cycle duration during a CSA event is more than twice as long as the duration of the respiratory cycles preceding the CSA event. Second, during CSA the Bio-Z magnitude will drift outside the PP magnitude range observed during respiration. It has been observed that with the onset of central sleep apnea (CSA) the magnitude and phase of the Bio-Z signal settle to a steady-state value outside the peak-to-peak range observed during the normal respiratory cycle during sleep. Third, upon arousal from CSA a person will typically gasp. This gasp results in a large PP. The PP of the first respiratory cycle following the CSA event and the PP observed during the CSA (which is essentially noise) will exceed 50% of PPmax.

With continued reference to FIG. 46, the flat portions 468 of the data traces are periods of respiratory cessation. Upon arousal the subject gasps 466 and the raw bio-Z signal resumes cyclic oscillation above the static impedance level observed during CSA. According to these characteristics, CSA events may be detected, identified and flagged for the step of fiducial extraction 378 wherein data (e.g., event duration, CV, PP range, PPmin, PPmax, etc.) may be time stamped and stored with an event identifier.

The step of extracting 374 waveform data indicative of sleep stage (e.g., rapid eye movement (REM) sleep vs. no-rapid eye movement (NREM) sleep) may be performed by comparing the phase difference between a first vector and a second vector wherein the first bio-Z vector is along the lung-diaphragm-liver interface (e.g., vector A-K or vector B-K) and the second bio-Z vector is about the lung(s). Examples of the first bio-Z vector include A-K, B-K, A-E1, B-E1, and A-B. Examples of the second bio-Z vector include D-F, B-D, C-G, D-E1, and C-E1. Note that some vector combinations which share a common vector endpoint such as A-E1, D-E1 and B-E1, B-D may use a common electrode and to simplify the respiratory sensing lead or leads. Typically, during NREM sleep, the two vectors are substantially in phase. During REM sleep, the diaphragm is the primary respiratory driver and a common consequence is paradoxical motion of the ribcage and diaphragm (i.e., the two vectors are substantially out of phase). This characteristic would allow for an effective monitor of a person's ability to reach REM sleep. Accordingly, REM and NREM sleep stages may be detected, identified, and flagged for the step of fiducial extraction 378 wherein characteristic data (e.g., event duration, phase, etc.) may be time stamped and stored with an event identifier.

An alternative method of detecting an OSA event is to make use of a split current electrode arrangement as shown in FIG. 47 which shows the positions of three electrodes on the subject. Electrode A may be above the zyphoid, electrode B may be just above the belly button, and electrode C may be on the back a couple of inches below electrode A. Electrodes A and B are connected to a common constant current source through resistors R1 and R2. The voltage measured across the current source is a measure of the bio-impedance during normal respiration. The voltage across R1 is an indicator of the paradoxical motion associated with apnea. An unbalanced current split between R1 and R2 resulting in large bio-Z voltage swings is indicative of OSA. During normal respiration or even very deep breaths there is almost no effect on the apnea detection channel. Accordingly, OSA events may be detected, identified, and flagged for the step of fiducial extraction 378 wherein characteristic data (e.g., event duration, voltage swing magnitude, etc.) may be time stamped and stored with an event identifier.

Generally, the extracted 378 waveform and event data may be used for therapy tracking, for stimulus titration, and/or for closed loop therapy control. For example, data indicative of apneas and hypopneas (or other events) may be stored by the INS 50 and/or telemetered to the patient controlled 40. The data may be subsequently transmitted or downloaded to the physician programmer 30. The data may be used to determine therapeutic efficacy (e.g., apnea hypopnea index, amount of REM sleep, etc.) and/or to titrate stimulus parameters using the physician programmer 30. The data may also be used to control stimulus in a closed loop fashion by, for example, increasing stimulus intensity during periods of increased apnea and hypopnea occurrence or decreasing stimulus intensity during periods of decreased apnea and hypopnea occurrence (which may be observed if a muscle conditioning effect is seen with chronic use). Further, the data may be used to turn stimulus on (e.g., when apnea or hypopnea events start occurring or when motion artifact is absent) or to turn stimulus off (e.g., when no apnea or hypopnea events are occurring over a present time period or when motion artifact is predominant).
Description of Stimulus Trigger Algorithms As mentioned previously with reference to FIG. 39, the neurostimulation system described herein may operate in a closed-loop process wherein the step of delivering stimulation 390 to the targeted nerve may be a function of a sensed feedback parameter (e.g., respiration). For example, stimulation of the hypoglossal nerve may be triggered to occur during the inspiratory phase of respiration. In a health human subject, the hypoglossal nerve is triggered about 300 mS before inspiration. Accordingly, a predictive algorithm may be used to predict the inspiratory phase and deliver stimulation accordingly. FIG. 48 schematically illustrates a system 480 including devices, data and processes for implementing a self-adjusting predictive trigger algorithm.

The system components 482 involved in implementing the algorithm may include the physician programmer (or patient controller), INS and associated device memory, and the respiratory sensor(s). The sensors and device memory are the sources of real-time data and historical fiducial data which the current algorithm uses to generate a stimulation trigger signal. The data 484 utilized in implementing the algorithm may include patient specific data derived from a sleep study (i.e., PSG data), data from titrating the system post implantation, and historic and real-time respiratory data including respiratory and event fiducials. The processes 486 utilized in implementing the algorithm may include providing a default algorithm pre-programmed in the INS, patient controller or physician programmer, modifying the default algorithm, and deriving a current algorithm used to generate a trigger signal 488.

More specifically, the processes 486 utilized in implementing a predictive trigger algorithm may involve several sub-steps. First, a default algorithm may be provided to predict onset of inspiration from fiducial data. Selecting an appropriate default algorithm may depend on identifying the simplest and most robust fiducial data subsets which allow effective prediction of onset. It also may depend on a reliable means of modifying the algorithm for optimal performance. Second, modification of the default algorithm may require a reference datum. The reference datum may be the estimated onset for past respiratory cycles. It is therefore useful to precisely estimate inspiratory onset for previous respiratory cycles from historical fiducial data. This estimation of inspiratory onset for previous respiratory cycles may be specific to person, sensor location, sleep stage, sleep position, or a variety of other factors. Third, the current algorithm may be derived from real-time and historical data to yield a stimulation trigger signal 488.

Figure 47A:
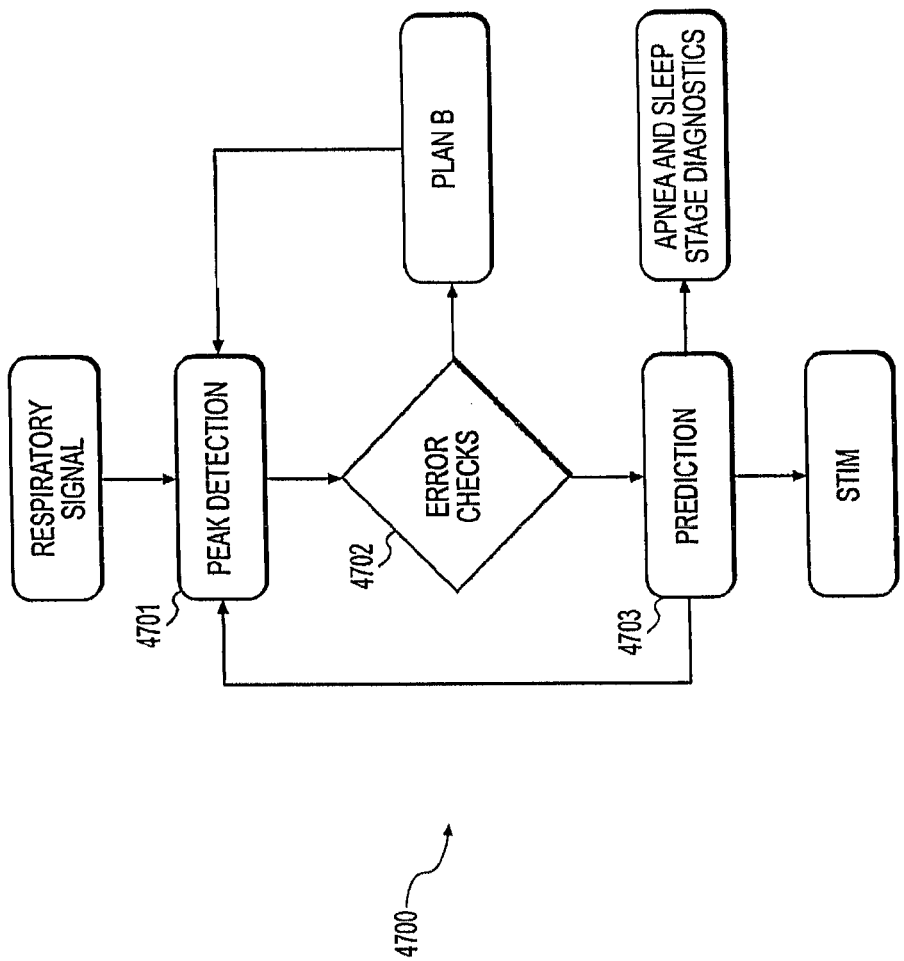
FIGS. 47A-47D illustrate an exemplary stimulation trigger algorithm.

As alluded to above, a trigger algorithm, such as, for example, trigger algorithm 4700 depicted in FIG. 47A, may be applied to a detected respiratory signal to begin and/or control delivery of the stimulation signal. As illustrated, trigger algorithm 4700 may include a plurality of sub-routines 4701-4703 for performing various analyses on a sensed respiratory signal. These sub-routines may include, but are not limited to, performing peak detection 4701, error checking 4702, and prediction 4703, on a detected respiratory signal.

Figure 47B:
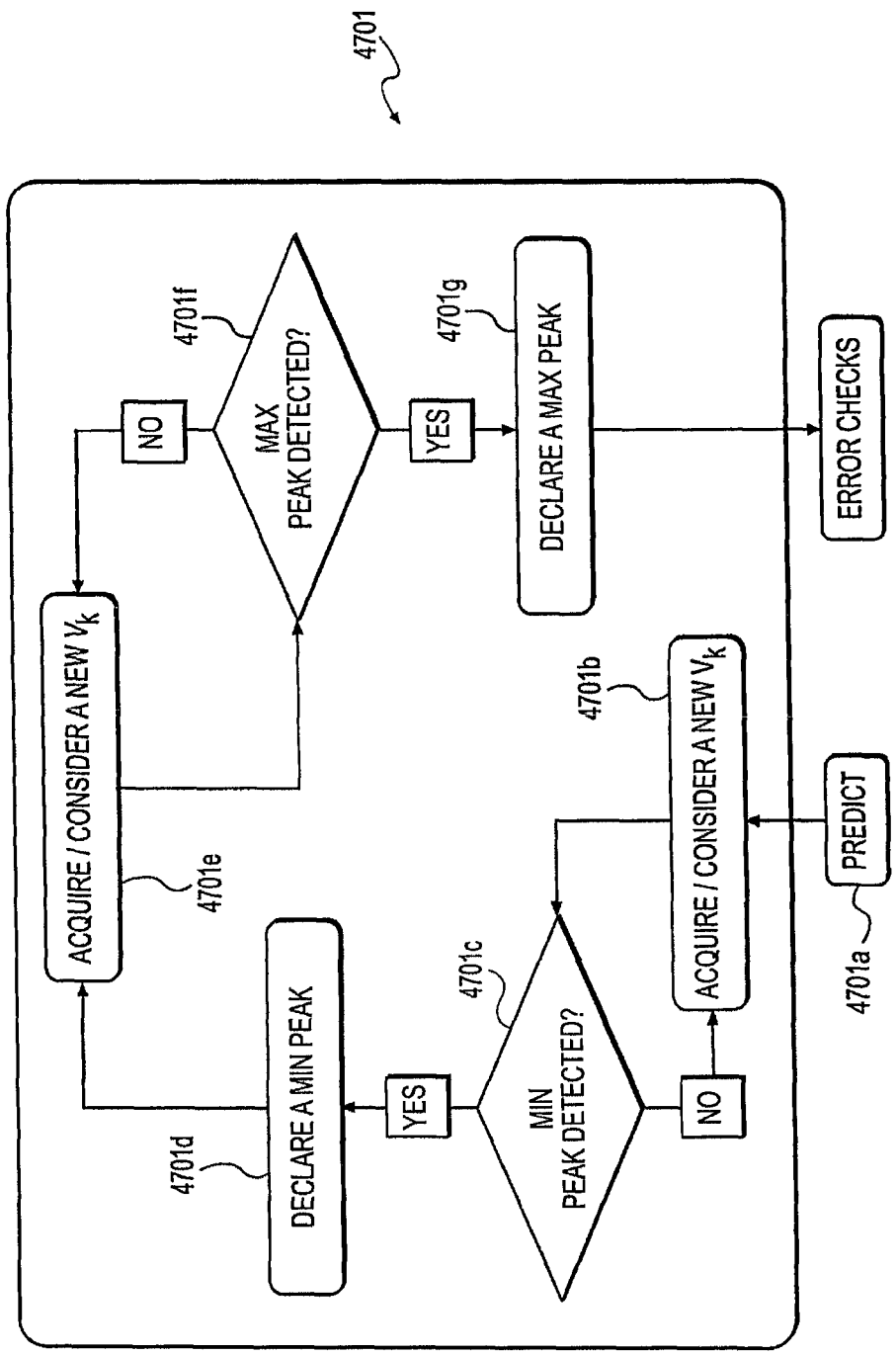
Figure 47C:
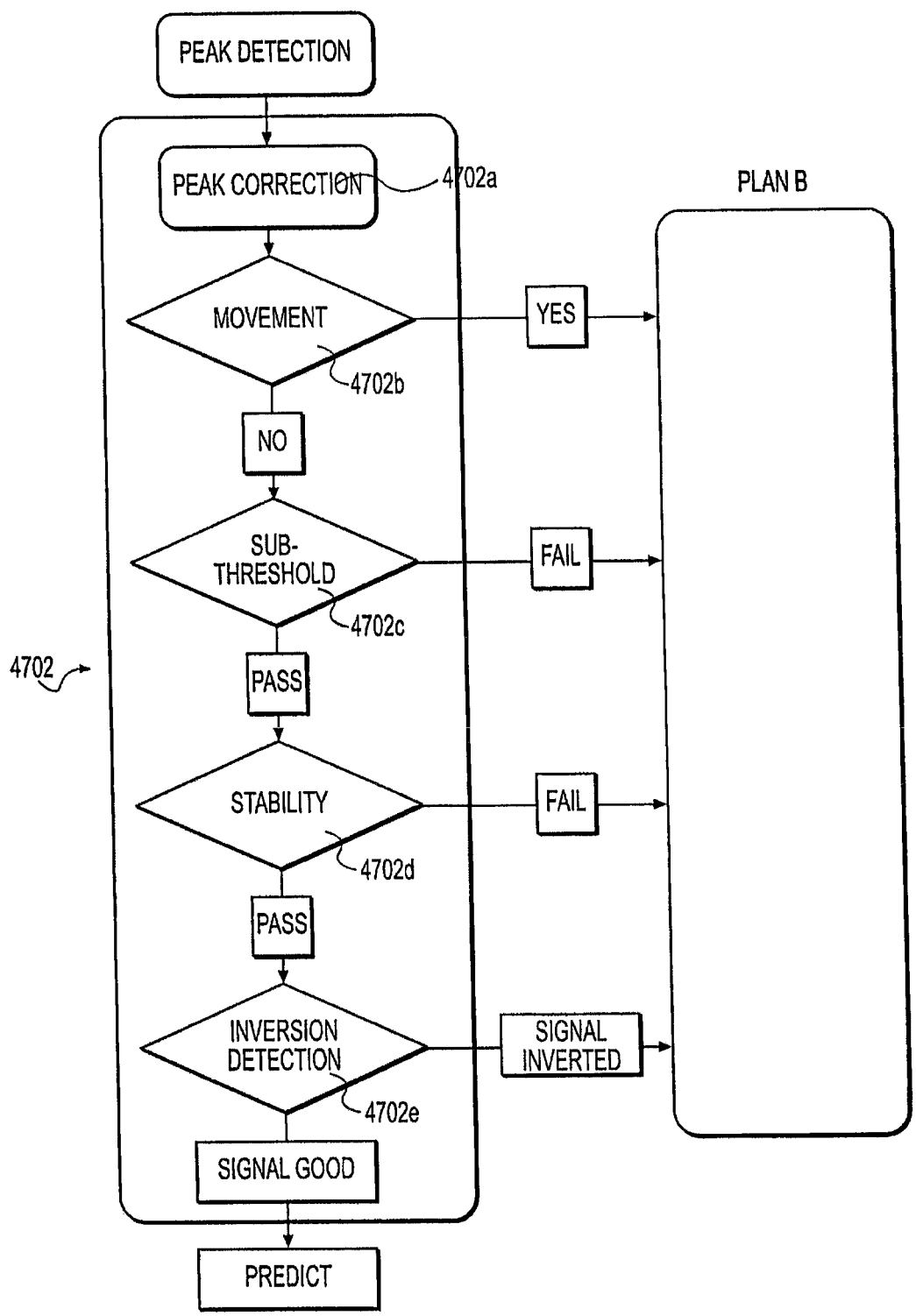
Figure 47D:
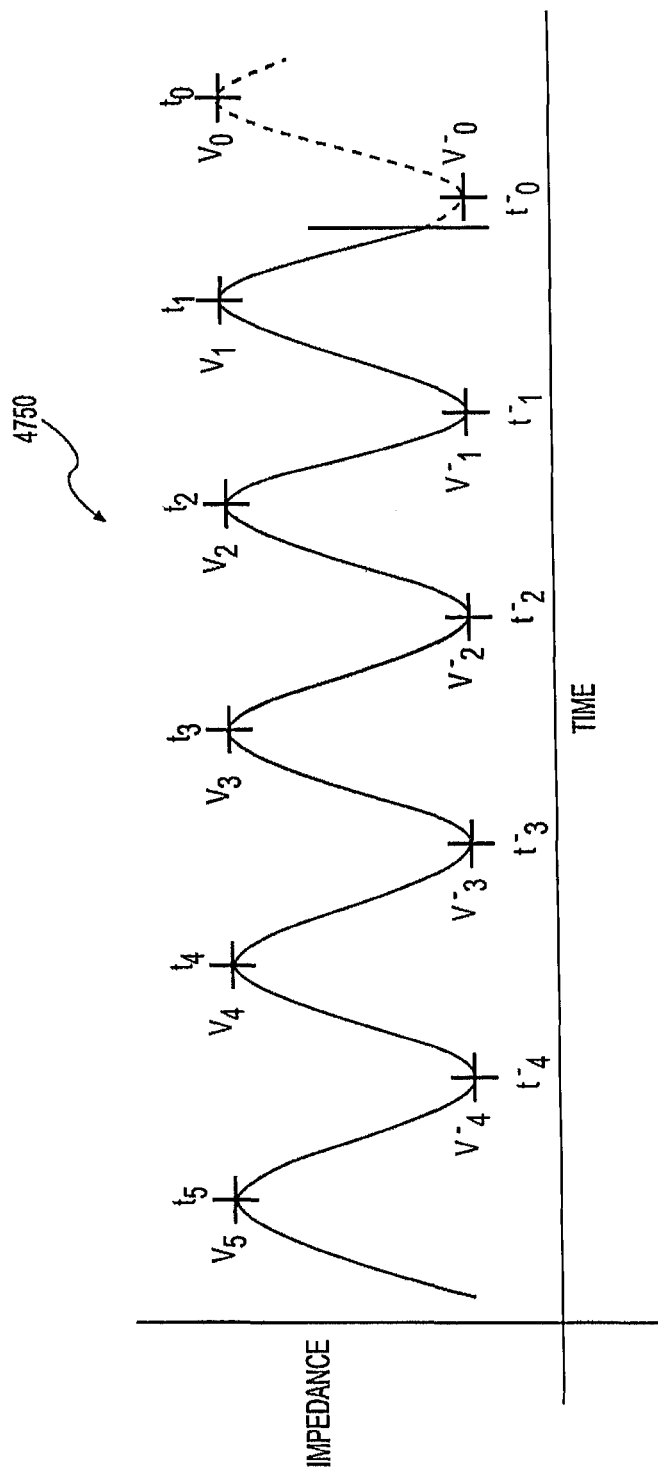

With reference now to FIG. 47D, there is depicted an exemplary sensed respiratory signal 4750. Respiratory signal 4750 may be displayed as a substantially sinusoidal waveform having a component that varies with time. As shown in FIG. 47D, respiratory signal 4750 may include a plurality of peaks, such as, for example, the peak located at $v_4 t_4$, and a plurality of valleys, such as, for example, the valley located $v^-_4 t^-_4$. Therefore, as will be discussed in greater detail below, peak detection sub-routine 4701 may be applied to sensed respiratory signal 4750 to detect the peaks of signal 4750. Error checking sub-routine 4702 may be applied to signal 4750 to, among other things, ensure signal 4750 is an accurate representation of a respiration and free from undesirable artifacts caused by for example, a patient's movement or cardiac activity. Prediction sub-routine 4703 may then be applied to signal 4750 to predict when future peaks will occur in accordance with the sensed signal 4750.

With reference to FIG. 47B, peak detection 4701 may include a plurality of steps 4701a-g. Step 4701a may include first detecting the peaks, such as, for example, the peak located at $v_4 t_4$, of signal 4750. The detected peaks may be an indication of when onset of expiration occurs during the monitored respiratory cycles. Next, step 4701b may include acquiring and/or considering a new voltage $V_k$, where $V_k$ may be the most recently acquired data point time $T_k$ under consideration, where a number of recently acquired data points may be under consideration. Step 4701c may determine whether the data points under consideration meet the criteria to indicate that a minimum (min) peak has been detected. One example of such a criteria to indicate a minimum peak has been detected is if the oldest data point under consideration, $V_{k+m}$ is less than more recent data points under consideration, $(V_{k+m-1} \ldots V_k)$, which can be expressed mathematically as $V_{k+m} \leq \min(V_{k+m-1} \ldots V_k)$. Another example of such a criteria to indicate a minimum peak has been detected is if the most recent data point under consideration, $V_k$, is greater than all other less-recently acquired data points under consideration, $(V_{k+m} \ldots V_{k+1})$, which can be expressed mathematically as $V_k \geq \max(V_{k+m-1} \ldots V_{k+1})$. If the criteria for detecting a minimum peak is not met, step 4701b may be repeated to acquire and/or consider a new voltage $V_k$. If the criteria has been met, step 4701d may declare a minimum peak reference. Next, step 4701e may again acquire and/or consider a new voltage $V_k$. Subsequently, step 4701f may determine whether the data points under consideration meet the criteria to indicate a maximum peak has been detected. One example of such a criteria to indicate a maximum peak has been detected is if the oldest data point under consideration, $V_{k+m}$, is greater than more recent data points under consideration $(V_{k+m-1} \ldots V_k)$, which can be expressed mathematically as $V_{k+m} \leq \max(V_{k+m-1} \ldots V_k)$. Another example of such a criteria to indicate a maximum peak has been detected is if the most recent data point under consideration, $V_k$, is less than all other less-recently acquired data points under consideration, $(V_{k+m} \ldots V_{k+1})$, which can be expressed mathematically as $V_k \leq \max(V_{k+m} \ldots V_{k+1})$. If the criteria for detecting a maximum peak is not met, step 4701e may be repeated to acquire and/or consider a new voltage $V_k$. If the criteria has been met, step 4701g may declare a maximum peak, and trigger algorithm 4700 may proceed to error-checking sub-routine 4702. The declared peak will depend on the criteria used for peak detection. For example, if the criteria for detecting a can was base on comparing $V_k$ to less recently acquired data points, $(V_{k+m} \ldots V_{k+1})$, then the peak magnitude and time would be declared to be $V_{k+m/2}$, $t_{k+m/2}$. As another example, if the criteria for detecting a peak was based on comparing the oldest considered data point, $V_{k+m}$, to more recently acquired data points $(V_{k+m} \ldots V_k)$, then the peak magnitude and time would be declared to be $V_{k+m}$, $t_{k+m}$.

With reference now to FIG. 47C, error-checking sub-routine 4702 may include a plurality of steps 4702a-e to determine whether a sensed respiratory signal may be adequate for respiration detection. For example, step 4702a, peak correction, may include receiving information relating to the peaks detected in step 4701 and corrections, as necessary. Next, steps 4702b-e may include analyzing the sensed respiratory signal to determine whether the signal includes "noise" caused by a patient's movement (4702b), whether the signal is sub-threshold (e.g., has a relatively low amplitude) (4702c), whether the signal is sufficiently stable (4702d), and whether the inversion detection is possible with the sensed signal (4702e). If the sensed signal passes all of error-checking steps 4702b-e, trigger algorithm 4700 may proceed to prediction sub-routine 4703. However, if the sensed signal fails any of steps 4702b-e, the trigger algorithm may terminate and the pulse generator (e.g., INS 50) may either cease stimulation, continue stimulation with continuous pulses of predetermined duration, and/or continue to stimulate at the same or a fraction (e.g., one quarter) of the stimulation rate for the most recently measured respiratory cycle, as discussed in greater detail below.

As described above, a peak is declared for a given set of data points under consideration when a peak detection criteria is met. The declared peak itself may be used in further algorithm calculations or a more precise estimate of peak time and voltage may be calculated. The more precise estimates of peak time and voltage are referred to as the peak correction. With regard to step 4702a, peak correction may be calculated as follows:

$$\Delta V_{pk,i} = V_{pk,i} - V_{pk,i-1} \text{ for } -n \leq i \leq n$$

$V_{pk,0}$ is defined to be the declared peak for which a correction is being calculated. The difference in voltage between successive data points is calculated for a given number of data points, n, to either side of the declared peak.

$$\Delta V_{pk,0th} = \frac{1}{2n} \sum (\Delta V_{pk,i})$$

The peak in signal ideally occurs when the rate of change of the signal is zero. Taking successive differences in measured voltage is an approximation to the rate of change of the signal. Linear regression is used on a range of successive differences to estimate the point in time when the rate of change is zero. Due to the fact that the data points are collected at equal increments of time, calculating the statistics $\Delta V_{pk,0th}$, $\Delta V_{pk,1st}$ and DEN allows a simple calculation based on linear regression to estimate the point in time at which the rate of change of the signal is zero.

$$\Delta V_{pk,1st} = \sum (i * \Delta V_{pk,i}) \text{ for } -n \leq i \leq n$$

$$DEN = \sum (i^2) \text{ for } -n \leq i \leq n$$

$$\text{Correction} = \Delta V_{pk,0th} \left( \frac{DEN}{\Delta V_{pk,1st}} \right)$$

Additionally, an estimated peak time after correction may be determined as follows:

$$t'_{pk,0} = t_{pk,0} + \text{Correction}$$

With regards to step 4702e, a peak curvature estimate for inversion detection can be obtained from one of the statistics, $\Delta V_{pk,1st}$, calculated for peak correction. Maximum peaks are sharper than minimum peaks and so typically have higher values of $\Delta V_{pk,1st}$. One means of determining if a signal is inverted would be to compare the values of $\Delta V_{pk,1st}$ for a series of maximum peaks to a series of minimum peaks.

With renewed reference to FIG. 47, prediction sub-routine 4703 may include predicting the time between sequentially identified peaks with either a parametric option or a non-parametric option. The parametric option makes a prediction of the duration of the next respiratory period based on the average duration of recent respiratory cycles and the rate of change of the duration of recent respiratory cycles. The parametric option also takes advantage of the fact that data points are collected at equal increments of time which simplifies the linear regression calculation. The parametric option may be defined as follows:

$$\Delta t_i = t_i - t_{i-1}$$

Zeroth order estimate of next peak.

$$\Delta t_{0,0th} = 1/n \cdot \Sigma(\Delta t_i), \text{ for } 1 \leq i \leq n$$

where n is the number of past respiration cycles used.
First Order Estimate $$\Delta t_{0,1st} = \sum \left(i - \left(\frac{n+1}{2}\right) * \Delta t_i\right), \text{ for } 1 \leq i \leq n$$

$$DEN1 = \sum \left(\left(i - \left(\frac{n+1}{2}\right)\right)^2\right), \text{ for } 1 \leq i \leq n$$

Predicted Interval Length for Current Respiration Cycle $$\Delta t_{0,pred} = \Delta t_{0,0th} + \left(\frac{\Delta t_{0,1st}}{DEN1}\right) \cdot \left(\frac{n+1}{2}\right)$$

Next Predicted Offset at $$t_{0,pred} = t_1 + \Delta t_{0,pred}$$

Begin therapy delivery at:
$t_{therapy} = t_1 + (1-DC) * \Delta t_{0,pred}$, where DC may be the allowable duty cycle for therapy delivery.

The non-parametric option is very similar to the parametric option in that it also estimates the duration of the next respiratory period based on the nominal duration of recent respiratory cycles and the rate of change of the duration of recent respiratory periods. The method is explained in more detail in "Nonparametric Statistic Method" by Hollander and Wolfe in sections related to the Theil statistic and the Hodges-Lehman, there disclose of which is incorporated herein by reference. The non-parametric prediction method may be defined as follows:

$$\Delta t_i = t_i - t_{i-1}$$

Zeroth Order Estimate $$\Delta t_{0,oth} = \frac{1}{2} \text{ median}\{\Delta t_i + \Delta t_j, i + \epsilon_0 \leq j \leq 1, \ldots n\}$$

Where $\epsilon_0$ is optimally 0, 1, 2 or 3
First Order Estimate $$S_{ij} = \frac{\Delta t_j - \Delta t_i}{j - i} \quad 1 \leq i + \epsilon_1 < j \leq n$$

where $\epsilon_1$ is optimally 0, 1, 2, or 3

$$\Delta t_{0,1st} = \text{median}\{S_{ij}, 1 \leq i \leq \epsilon_1 < j \leq n\}$$

Predicted Interval Length for Current Respiration cycle $$\Delta t_{0,pred} = \Delta t_{0,0th} + \Delta t_{0,1st} \cdot \left(\frac{n+1}{2}\right)$$

Next Predicted Offset $$t_{0,pred} = t_1 + \Delta t_{0,pred}$$

Begin Therapy Delivery at
$t_{therapy} = t_1 + (1-DC)) * \Delta t_{0,pred}$, where DC may be the allowable duty cycle for therapy delivery.

Stimulation may then commence at the calculated $t_{therapy}$.

With reference to FIG. 48, a self adjusting predictive algorithm may be implemented in the following manner.

The Programmer block illustrates means by which PSG-derived data may be uploaded into the device.

The Sensors and Device Memory block includes the sources of real-time data and historical fiducial variables which the current algorithm uses to generate a stimulation trigger signal.

The Patient PSG Titration Data block includes conventional polysomnographic (PSG) data obtained in a sleep study. A self-adjusting predictive algorithm utilizes a reference datum to which the algorithm can be adjusted. Onset may be defined as onset of inspiration as measured by airflow or pressure sensor used in a sleep study, for example. Estimated Onset may be defined as an estimate of Onset calculated solely from information available from the device sensors and memory. To enable the predictive algorithm to be self-adjusting, either Onset or Estimated Onset data is used. During actual use, the implanted device will typically not have access to Onset as that would require output from an airflow sensor. The device then may rely on an estimate of Onset or Estimated Onset. The calibration of Estimated Onset to Onset may be based on PSG data collected during a sleep study. The calibration may be unique to a person and/or sleep stage and/or sleep position and/or respiratory pattern.

The Historical Fiducial Variables block represents the Historical Fiducial Variables (or data) which have been extracted from the bio-Z waveform and stored in the device memory. This block assumes that the raw sensor data has been processed and is either clean or has been flagged for cardiac, movement, apnea or other artifacts. Note that fiducial data includes fiducials, mathematical combinations of fiducials or a function of one or more fiducials such as a fuzzy logic decision matrix.

The Real-Time Data and Historical Fiducial Variables block incorporates all the information content of the Historical Fiducial Variables block and also includes real-time bio-Z data.

The Default Algorithm block represents one or more pre-set trigger algorithms pre-programmed into the INS or physician programmer. The default algorithm used at a specific point in time while delivering therapy may be selected from a library of pre-set algorithms. The selection of the algorithm can be made automatically by the INS based on: patient sleep position (position sensor), heart rate (detectable through the impedance measuring system) or respiration rate. Clinical evidence supports that the algorithm used to predict the onset of inspiration may be dependent on sleep position, sleep state or other detectable conditions of the patient.

The Modify Algorithm block represents the process of modifying the Default Algorithm based on historical data to yield the Current Algorithm. Once the calibration of Estimated Onset to Onset is resident in the device memory it can be used to calculate Estimated Onset for past respiratory cycles from Fiducial Variables. The variable used to represent the Estimated Onset will be TEST or TEST(i) where the "i" indicates the cycle number. Note that Estimated Onset is calculated for past respiratory cycles. This means that sensor fiducial variables which either proceed or follow each Onset event may be used to calculate the Estimated Onset.

The Current Algorithm block represents the process of using the Modified Default Algorithm to predict the next inspiratory onset (Predicted Onset). The Predicted Onset for the next respiratory cycle may be calculated from real-time data and historical fiducial variables. The calculation may be based on the Modified Default Algorithm. Modification of the Modified Default Algorithm to derive the Current Algorithm may be dependent on the calibration of Estimated Onset to Onset which was input from the physician programmer and may be based on comparison of real-time bio-Z data to data collected during a PSG titration study. The Current Algorithm may use historic and/or real-time sensor fiducial variables to predict the next onset of inspiration. This predicted onset of inspiration may be referred to as Predicted Onset. The variable used to represent Predicted Onset may be TPRED or TPRED(i) where the "i" indicates the respiratory cycle.

The Stimulation Trigger Signal block represents the Current Algorithm generating a trigger signal which the device uses to trigger stimulation to the hypoglossal nerve.

FIG. 49 is a table of some (not all) examples of waveform fiducials which can be extracted from each respiratory cycle waveform. For each fiducial there is a magnitude value and a time of occurrence. Each waveform has a set of fiducials associated with it. As a result, fiducials may be stored in the device memory for any reasonable number of past respiratory cycles. The values from past respiratory cycles which are stored in device memory are referred to as Historical Fiducial Variables.

Figure 50:
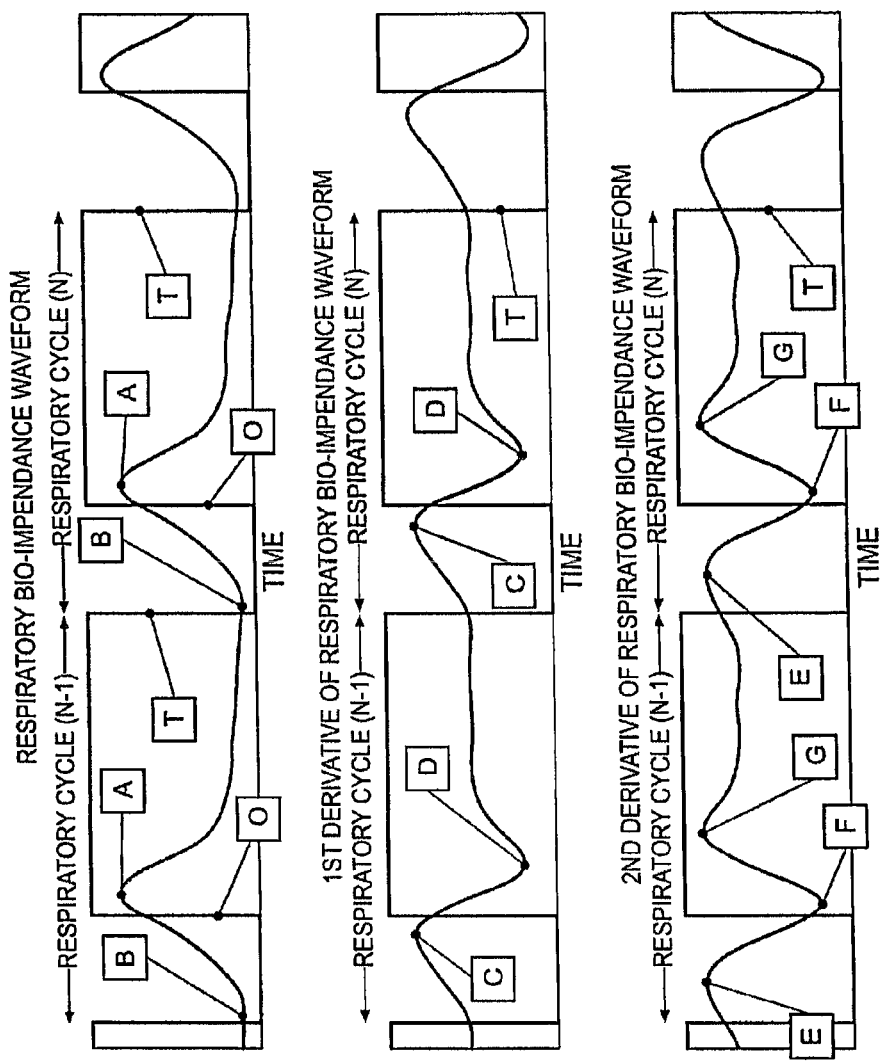

The graphs illustrated in FIG. 50 are examples of fiducials marked on bio-Z waveforms. The first of the three graphs illustrate the bio-impedance signal after it has been filtered and cleared of cardiac and motion artifacts. The first graph will be referred to as the primary signal. The second graph is the first derivative of the primary signal and the third graph is the second derivative of the primary signal. Each graph also displays a square wave signal which is derived from airflow pressure. The square wave is low during inspiration. The falling edge of the square wave is onset of inspiration.

Due to the fact that it may be difficult to identify onset of inspiration in real-time from respiratory bio-impedance, a goal is to construct an algorithm which can reliably predict onset of inspiration "T" for the next respiratory cycle from information available from the current and/or previous cycles. A reliable, distinct and known reference point occurring prior to onset of inspiration, "T", is "A", the peak of the primary signal in the current cycle. As can be seen in FIG. 50, the upper peak of the bio-Z waveform "A" approximately corresponds to the onset of expiration "O." A dependent variable $t_{T-PK}$ is created to represent the period of time between the positive peak of the primary signal for the current cycle, t.Vmax(n), indicated by "$A_n$" on the graph, and onset of inspiration for the next cycle, t.onset(n+1), indicated by "T" on the graph. The variable $t_{T-PK}$ may be defined as:

$$t_{T-PK} = t.\text{onset}(n+1) - t.V\text{max}(n)$$

Note that t.Vmax could be replaced by any other suitable fiducial in defining a dependent variable for predicting onset.

A general model for a predictive algorithm may be of the following form:

$$t_{T-PK} = f(\text{fiducials extracted from current and/or previous cycles})$$

A less general model would be to use a function which is a linear combination of Fiducial Variables and Real-Time Data.

The following fiducials may be both highly statistically significant and practically significant in estimating T:

t.Vmax(n)=the time where positive peak occurs for the current cycle;
t.dV.in(n)=the time of most positive 1st derivative during inspiration for the current cycle; and
t.Vmax(n−1)=the time of positive peak for the previous cycle.

This model can be further simplified by combining the variables as follows:

$$\Delta t.pk(n) = t.V\text{max}(n) - t.V\text{max}(n-1)$$
$$\Delta t.in(n) = t.V\text{max}(n) - t.dV.in(n)$$

Either Δt.pk(n) or Δt.in(n) is a good predictor of Onset.

The following example uses Δt.pk(n). The time from a positive peak until the next inspiration onset can be estimated by:

$$T_{pred} = t.V\text{max}(n) + k0 + k1 * \Delta t.pk(n)$$

The coefficients k0 and k1 would be constantly modified by optimizing the following equation for recent historical respiratory cycles against $T_{est}$:

$$T_{est} = t.V\text{max}(n) + k0 + k1 * \Delta t.pk(n)$$

Thus, the predictive trigger time $T_{pred}$ may be determined by adding $t_{T-PK}$ to the time of the most recent peak (PK) of the bio-Z signal, where:

$$t_{T-PK} = k0 + k1 * \Delta t.pk(n)$$

The predictive equation we are proposing is based on the fact that the very most recent cycle times should be negatively weighted. Regression analysis supports this approach and indicates a negative weighting is appropriate for accurate prediction of onset. Thus, predicting onset is more effective if the most recent historical cycle time is incorporated into an algorithm with a negative coefficient.

As noted above, stimulation may be delivered for only a portion of the respiratory cycle, such as, for example, during inspiration. Additionally, it may be desirable to begin stimulation approximately 300 milliseconds before the onset of inspiration to more closely mimic normal activation of upper airway dilator muscles. However, predicting and/or measuring inspiration, in particular, the onset of inspiration, may be relatively challenging. Thus, since the onset of expiration may be relatively easy to measure and/or predict (as discussed in greater detail below) when an adequate measure of respiration is available, it is contemplated that stimulation may be triggered as a function of expiration onset.

Figure 50A:
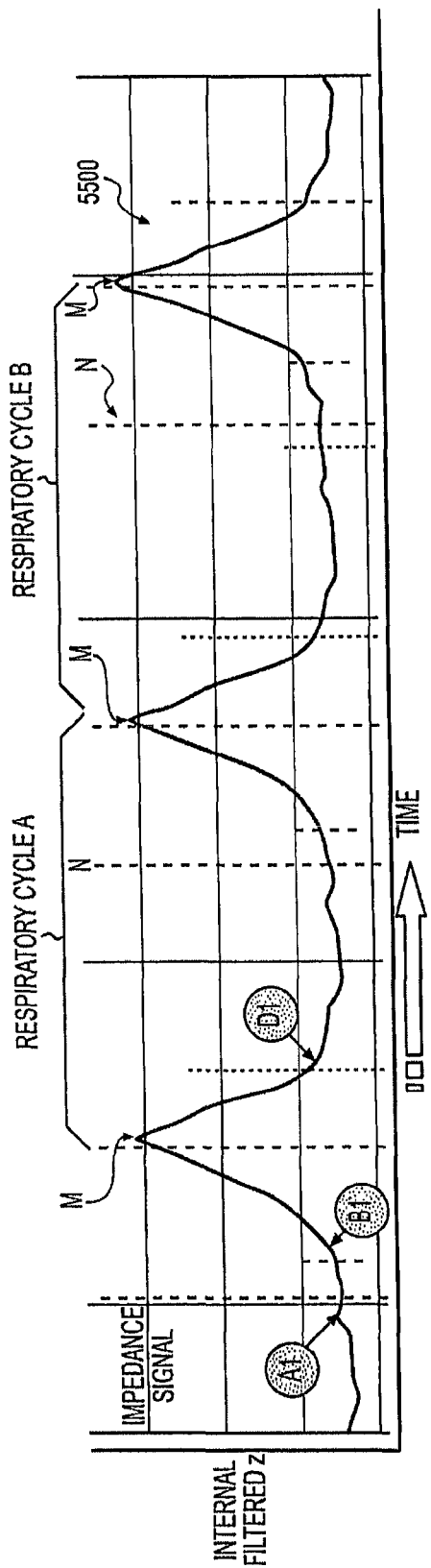
FIG. 50A illustrates an exemplary waveform of a patient's respiratory cycle.

Turning now to FIG. 50A, there is depicted an exemplary respiratory waveform 5500 for two complete respiratory cycles A and B. In analyzing exemplary waveform 5500, it may be determined that peaks M of the waveform 5500 may indicate onset of the expiratory phases of respiration cycles A and B. Furthermore, it may be discovered that peaks M occur at regular intervals of approximately 3-4 seconds. Thus, it may be relatively easy to predict the occurrence of subsequent peaks M, and consequently, the onset of expiration for future respiratory cycles.

Therefore, in order to deliver a stimulus to a patient in accordance with the principles of the present disclosure, the start of stimulation may be calculated by first predicting the time intervals between the start of expiration for subsequently occurring respiratory cycles. Next, in order to capture the entire inspiratory phase, including the brief pre-inspiratory phase of approximately 300 milliseconds, stimulation may be started at the time N that is prior to the next onset of expiration by approximately 30% to 50% of the time between subsequently occurring expiratory phases. Stimulating less than 30% or more than 50% prior to the next expiratory phase may result in an inadequate stimulation period and muscle fatigue, respectively.

In some embodiments, however, it is contemplated that an adequate measure of respiration may not be available, such as, for example, when a relied upon signal has failed. In these embodiments, it is contemplated that the implanted neurostimulator system may be configured to respond in one or more of the following three ways. First, the implanted neurostimulator may completely cease stimulation until an adequate signal is acquired. Second, the neurostimulator may deliver continuous simulation pulses of predetermined durations (e.g., up to 60 seconds) until an adequate signal is acquired; or if an adequate signal is not acquired in this time, the stimulation will be turned off. Third, the neurostimulator may continue to stimulate at the same or a fraction (e.g., one quarter) of the stimulation rate for the most recently measured respiratory cycle. That is to say, the neurostimulator may deliver stimulation pulses of relatively long durations at a frequency that is less than the frequency of stimulation utilized with an adequate measure of respiration. Alternatively, the neurostimulator may deliver stimulation pulses of relatively short durations at a frequency that is greater than the frequency used with an adequate measure of respiration.

Respiratory Waveform Analysis Techniques

Referring to FIG. 50A, features of the respiratory waveform, such as the waveform 5500 characterized with an impedance value, can be identified and analyzed to determine patient status, sleep-related events, and responsiveness to therapy, and can be used to adjust therapy parameters.

In an exemplary embodiment, individual waveforms can be identified within the respiratory waveform 5500 and further analyzed to identify patient status and the occurrence of obstructive sleep apnea events. An individual waveform can be defined to be a portion of the respiratory waveform extending between two sequential impedance peaks or between two other similar waveform features. The amplitude of the impedance peaks, or the peaks of a waveform measured by another means, can be compared to a threshold to determine the level of effort required for a respiration cycle. A high or otherwise significant level of effort in the respiratory effort of an individual respiratory waveform can identify disordered or atypical breathing indicative of an obstructive sleep apnea event. As can be appreciated, the measurement technique used to acquire the respiratory waveform, and the selection of the threshold, would require calibration based on a baseline related to the normal or usual respiratory effort for the patient, and to account for the configuration of the sensors measuring respiratory effort.

In another exemplary embodiment, the inspiratory stage of a restricted breath can be analyzed to determine whether it provides a value that exceeds the value associated with a normal breath. The inspiratory stage can be defined to be a portion of the respiratory waveform, such as respiratory waveform 5500, that relates to the intake or the attempted intake of air into the lungs. One method of measuring the inspiratory stage can be to measure the period between the impedance peak of the inspiration and the preceding impedance negative peak to represent the inspiratory period of breath. By isolating and analyzing the inspiratory stage of the respiratory waveform, and by analyzing the effort required over the period of time correlated to the inspiratory stage, the amount of effort over time can be determined for an entire inspiration and provided as a value that can be compared to a threshold. In an exemplary use of a threshold, a measured inspiratory period of breath can be identified and compared to the entire duration of the respiratory period and, for example, a disordered breath can be identified when it is determined that the inspiratory period of breath is at least 40% of the entire respiratory period. As can be appreciated, the technique can be applied to only a portion of the inspiratory stage, such as an initial portion of the inspiration stage, to provide a value for the effort or energy required to initial the inspiration, and a value can be provided representing initial inspiration effort that can be compared to a threshold.

Description of an Exemplary Stimulation Pulse

Figure 50B:
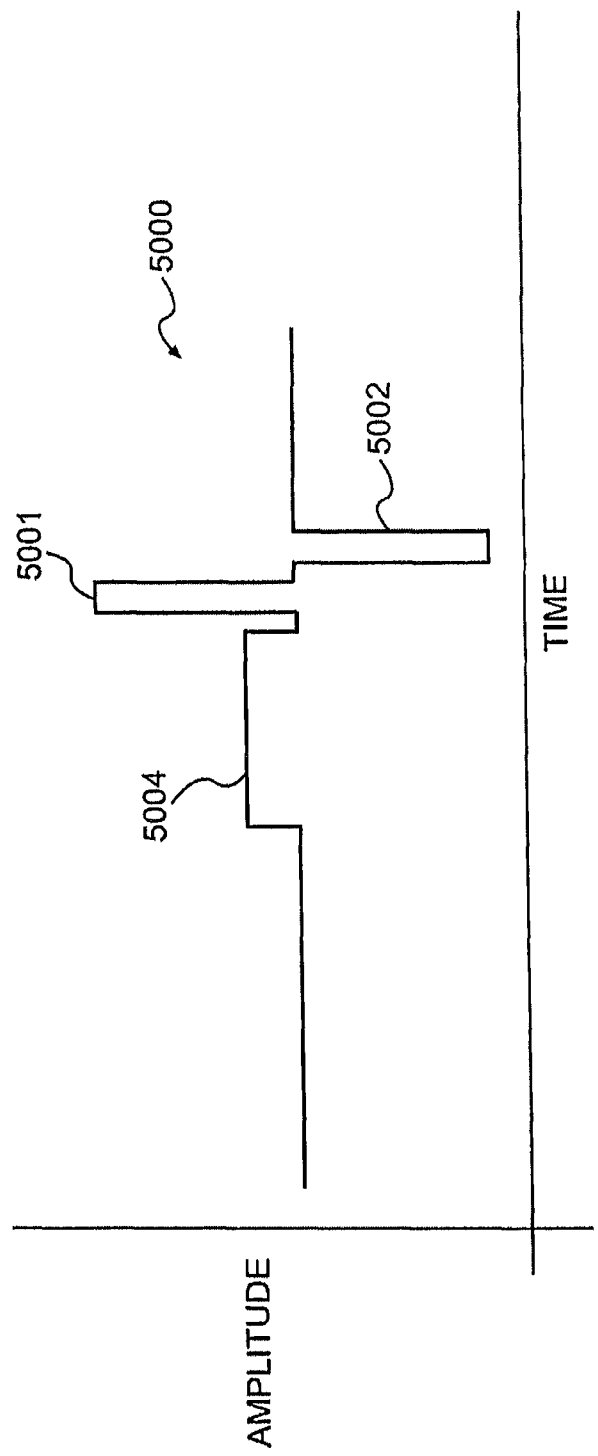
FIG. 50B illustrates an exemplary stimulation waveform.

Turning now to FIG. 50B, there is depicted an exemplary stimulation pulse waveform 5000 that may be emitted from an INS in accordance with the principles of the present disclosure. Typically, exemplary stimulation pulse waveform 5000 may include a square wave pulse train having one or more square wave pulses 5001 of approximately 1 to 3 volts in amplitude, a duration of approximately 100 ms, and a frequency of approximately 30 Hz, assuming a 1000 ohm impedance at the electrodes and a constant current or voltage.

In some embodiments, exemplary stimulation pulse waveform 5000 may include a bi-phasic charge balanced waveform square pulses 5001 and 5002, as depicted in FIG. 50B. Square pulse 5002 may be included in waveform 5000 to, among other things, promote efficient stimulation and/or mitigate electrode corrosion. However, square pulse 5002 may be excluded from waveform 5000 as desired. Furthermore, although the depicted exemplary waveform 5000 includes square pulse 5002 that exactly balances the stimulation wave pulse 5001, in certain circumstances, square pulse 5002 may not exactly balance the stimulation wave pulse 5001, and may not be a square pulse.

In some embodiments, exemplary stimulation pulse waveform 5000 may include the delivery of a low amplitude (e.g., below the stimulation threshold), long duration, pre-stimulation pulse 5004. The pre-stimulation pulse 5004 may include any suitable low amplitude, long duration pulse, and may be provided approximately 0.5 ms before the delivery of a first stimulation pulse 5001.

Pre-stimulation pulse 5004 may facilitate selectively stimulating certain fibers of a nerve, such as, for example, the hypoglossal nerve or the superior laryngeal nerve. In particular, when stimulating the hypoglossal nerve, the presence of a pre-stimulation pulse, such as, for example, pulse 5004, before a stimulation pulse (e.g., the bi-phasic stimulation pulse 5001 depicted in FIG. 50B) may serve to saturate the large diameter fibers of the nerve so as to allow the stimulation pulse 5001 to only affect (e.g., stimulate) the smaller diameter fibers of the nerve. In circumstances where a nerve (e.g., the hypoglossal nerve) may be stimulated for extended periods of time, a pre-stimulation pulse 5004 may be selectively introduced to waveform 5000, so as to permit selective switching between stimulating the large and small diameter fibers of the nerve, in order to reduce muscle fatigue. Similarly, in situations where OSA may be treated by stimulating the superior laryngeal nerve to open the upper airway through a reflex mechanism, the presence of pre-stimulation pulse 5004 may serve to saturate the larger diameter efferent fibers so as to allow the stimulation pulse 5001 to only affect the smaller diameter afferent fibers of the nerve.

Description of External (Partially Implanted) System

Figure 51B:
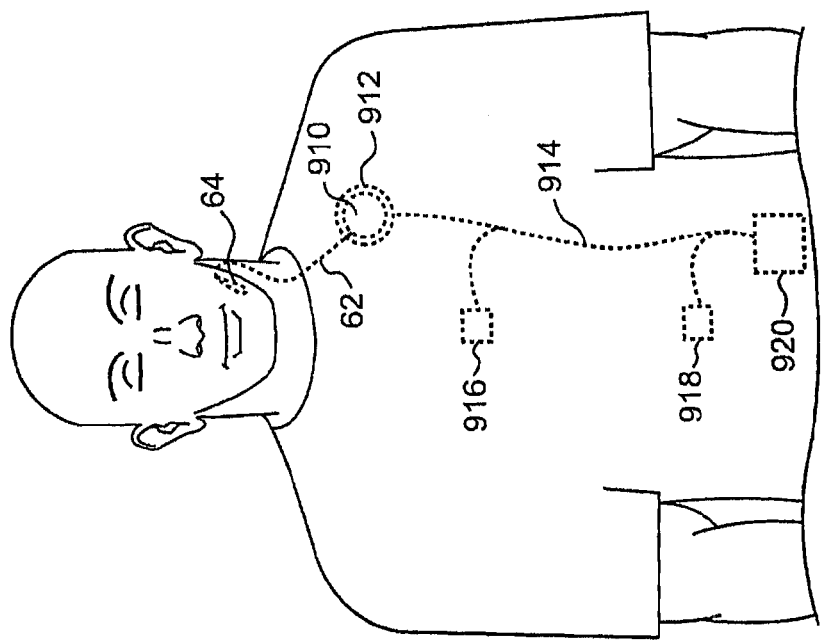
FIGS. 51A-51M are schematic illustrations of various external (partially implanted) neurostimulation systems for treating obstructive sleep apnea.
Figure 51A:
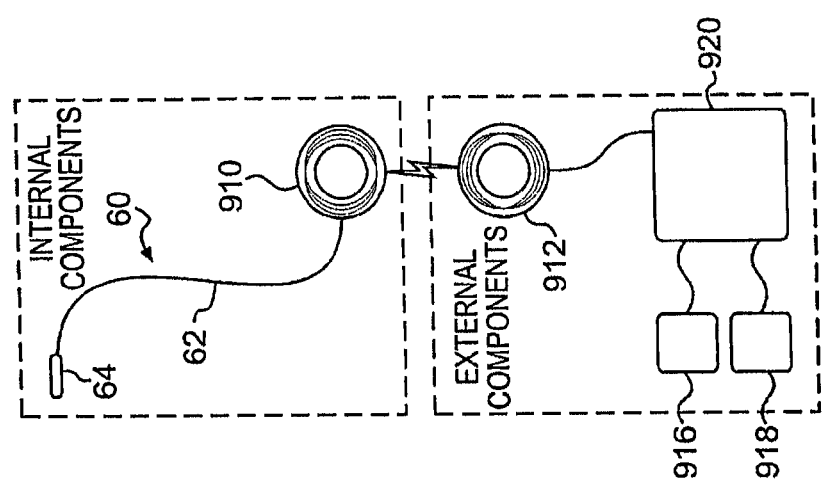

With reference to FIGS. 51A and 51B, an example of an external neurostimulator system inductively coupled to an internal/implanted receiver is shown schematically. The system includes internal/implanted components comprising a receiver coil 910, a stimulator lead 60 (including lead body 62, proximal connector and distal nerve electrode 64). Any of the stimulation lead designs and external sensor designs described in more detail herein may be employed in this generically illustrated system, with modifications to position, orientation, arrangement, integration, etc. made as dictated by the particular embodiment employed. The system also includes external components comprising a transmit coil 912 (inductively linked to receiver coil 910 when in use), an external neurostimulator or external pulse generator 920 (ENS or EPG), and one or more external respiratory sensors 916/918.

As illustrated, the receiver coil 910 is implanted in a subcutaneous pocket in the pectoral region and the stimulation lead body 62 is tunneled subcutaneously along the platysma in the neck region. The nerve electrode 64 is attached to the hypoglossal nerve in the submandibular region.

The transmitter coil 912 may be held in close proximity to the receiver coil 910 by any suitable means such as an adhesive patch, a belt or strap, or an article of clothing (e.g., shirt, vest, brazier, etc.) donned by the patient. For purposes of illustration, the transmitter coil 912 is shown carried by a t-shirt 915, which also serves to carry the ENS 920 and respiratory sensor(s) 916, 918. The ENS 920 may be positioned adjacent the waist or abdomen away from the ribs to avoid discomfort while sleeping. The respiratory sensor(s) 916, 918 may be positioned as a function of the parameter being measured, and in this embodiment, the sensors are positioned to measure abdominal and thoracic/chest expansion which are indicative of respiratory effort, a surrogate measure for respiration. The external components may be interconnected by cables 914 carried by the shirt or by wireless means. The shirt may incorporate recloseable pockets for the external components and the components may be disconnected from the cables such that the reusable components may be removed from the garment which may be disposed or washed.

The transmitting coil antenna 912 and the receiving coil antenna 910 may comprise air core wire coils with matched wind diameters, number of wire turns and wire gauge. The wire coils may be disposed in a disc-shaped hermetic enclosure comprising a material that does not attenuate the inductive link, such as a polymeric or ceramic material. The transmitting coil 912 and the receiving coil 910 may be arranged in a co-axial and parallel fashion for coupling efficiency, but are shown side-by-side for sake of illustration only.

Because power is supplied to the internal components via an inductive link, the internal components may be chronically implanted without the need for replacement of an implanted battery, which would otherwise require re-operation. Examples of inductively powered implantable stimulators are described in U.S. Pat. No. 6,609,031 to Law et al., U.S. Pat. No. 4,612,934 to Borkan, and U.S. Pat. No. 3,893,463 to Williams, the entire disclosures of which are incorporated herein by reference.

With reference to FIGS. 51C-51G, alternative embodiments of an external neurostimulator system inductively coupled to an internal/implanted receiver are schematically shown. These embodiments are similar to the external embodiment described above, with a few exceptions. In these embodiments, the receiver coil 910 is implanted in a positioned proximate the implanted stimulation lead body 62 and nerve electrode 64. The receiver coil 910 may be positioned in a subcutaneous pocket on the platysma muscle under the mandible, with the lead body 62 tunneling a short distance to the nerve electrode 64 attached to the hypoglossal nerve. Also in these embodiments, the respiratory sensor(s) 916/918 may be integrated into the ENS 920 and attached to a conventional respiratory belt 922 to measure respiratory effort about the abdomen and/or chest. An external cable 914 connects the ENS 920 to the transmitter coil 912.

Figure 51D:
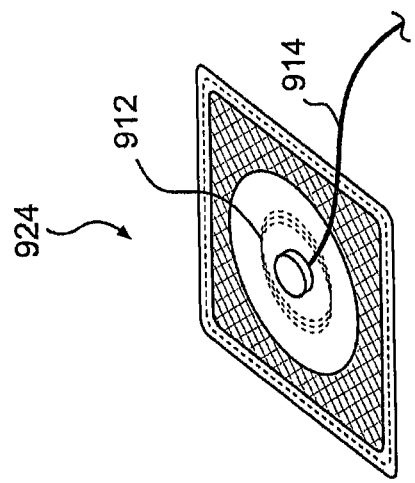
Figure 51C:
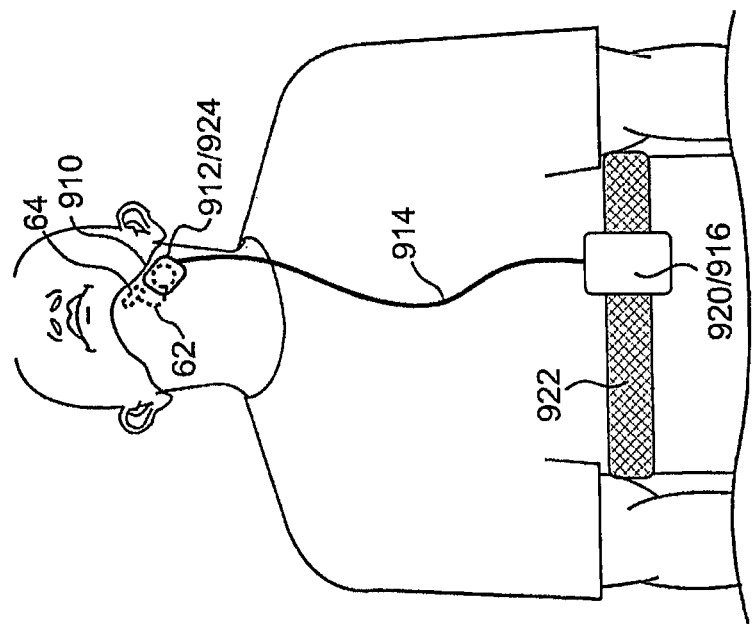
Figure 51F:
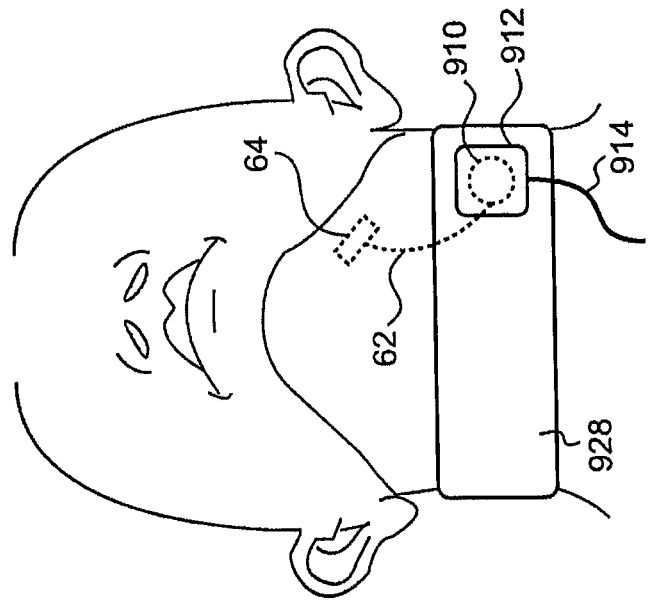
Figure 51E:
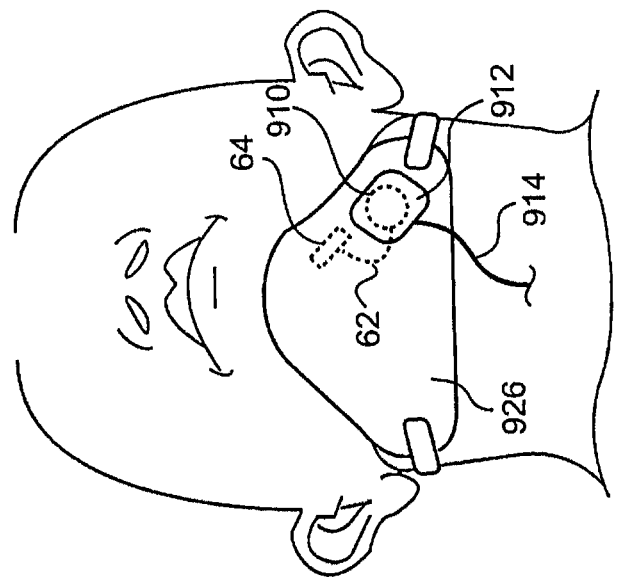
Figure 51G:
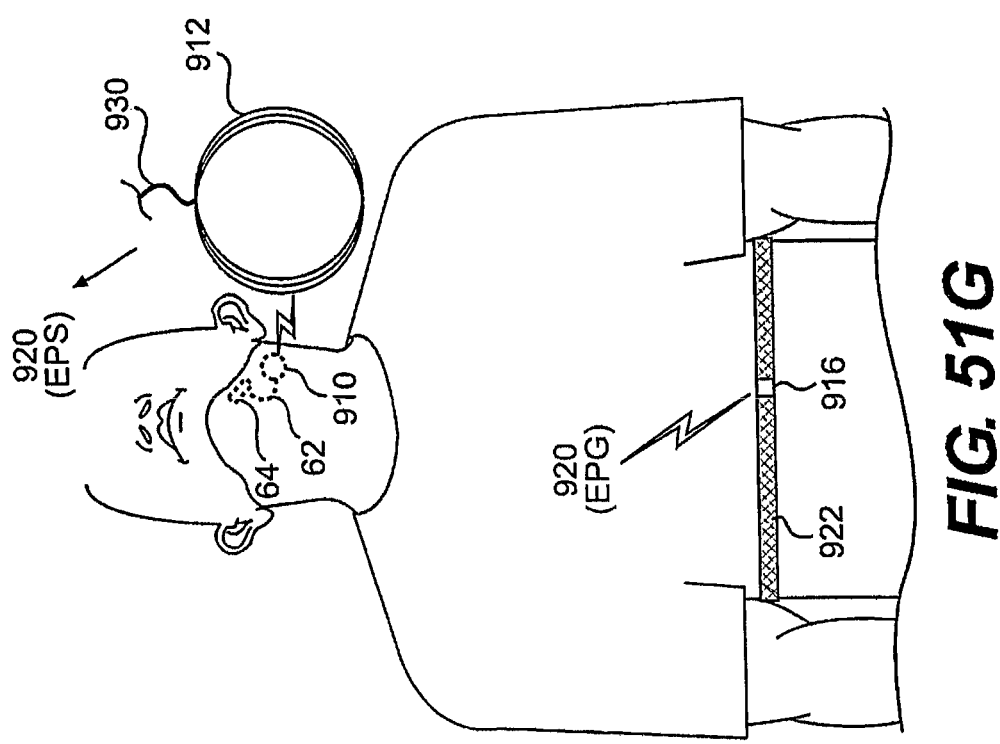

In the embodiment of FIG. 51D, the transmitter coil 912 is carried by an adhesive patch 924 that may be placed on the skin adjacent the receiver coil 910 under the mandible. In the embodiment of FIG. 51E, the transmitter coil 912 is carried by an under-chin strap 926 worn by the patient to maintain the position of the transmitter coil 912 adjacent the receiver coil 910 under the mandible. In the embodiment of FIG. 51F, the receiver coil 910 may be positioned in a subcutaneous pocket on the platysma muscle in the neck, with the lead body 122 tunneling a slightly greater distance. The transmitter coil 912 may be carried by a neck strap 928 worn by the patient to maintain the position of the transmitter coil 912 adjacent the receiver coil 910 in the neck.

With reference to FIGS. 51G-51K, additional alternative embodiments of an external neurostimulator system inductively coupled to an internal/implanted receiver are schematically shown. These embodiments are similar to the external embodiment described above, with a few exceptions. As above, the receiver coil 910 may be positioned in a subcutaneous pocket on the platysma muscle under the mandible, with the lead body 62 tunneling a short distance to the nerve electrode 64 attached to the hypoglossal nerve. However, in these embodiments, the ENS 920 (not shown) may be located remote from the patient such as on the night stand or headboard adjacent the bed. The ENS 920 may be connected via a cable 930 to a large transmitter coil 912 that is inductively coupled to the receiver coil 910. The respiratory sensor 916 may comprise a conventional respiratory belt 922 sensor to measure respiratory effort about the abdomen and/or chest, and sensor signals may be wirelessly transmitted to the remote ENS 920. As compared to other embodiments described above, the transmitter coil 912 is not carried by the patient, but rather resides in a proximate carrier such as a bed pillow, under a mattress, on a headboard, or in a neck pillow, for example. Because the transmitter coil 912 is not as proximate the receiver coil as in the embodiments described above, the transmitter coil may be driven by a high powered oscillator capable of generating large electromagnetic fields.

Figure 51I:
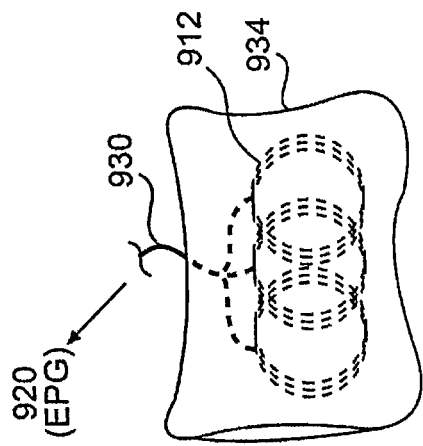
Figure 51J:
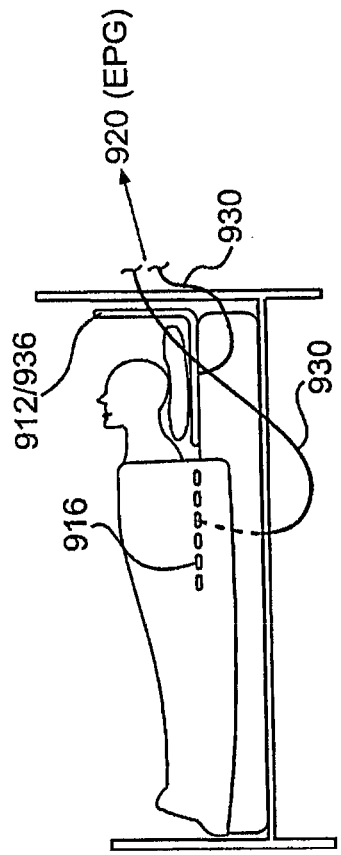
Figure 51H:
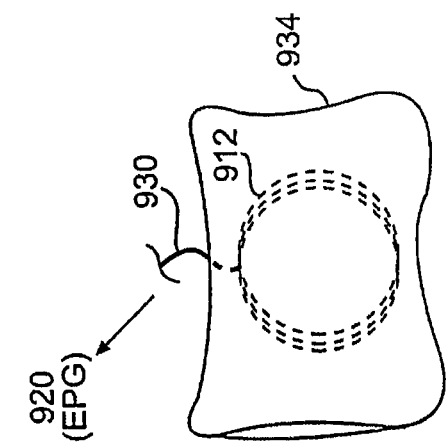
Figure 51K:
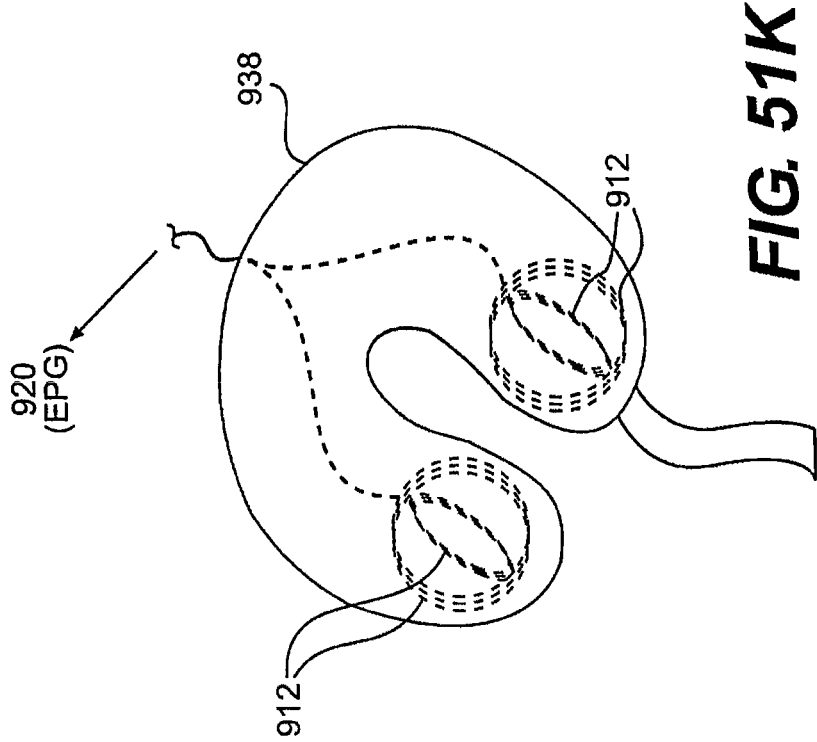
Figure 51M:
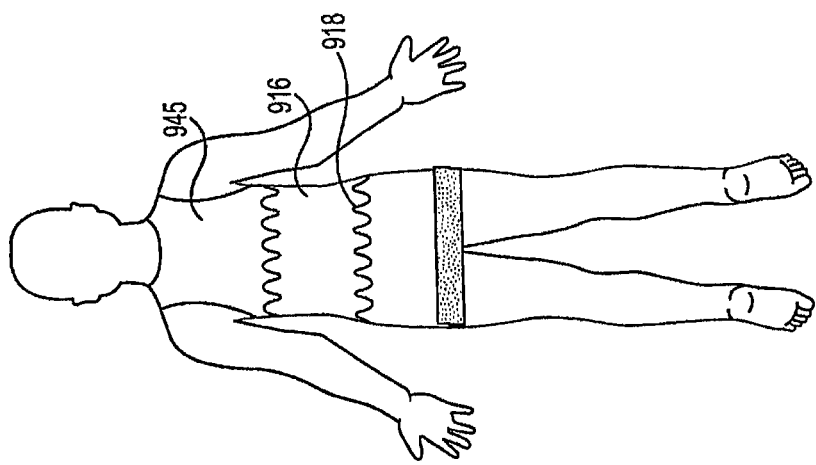

As shown in FIG. 51H, the transmitter coil 912 may be disposed in a bed pillow 934. As shown in FIG. 51I, the transmitter coil 912 may comprise a series of overlapping coils disposed in a bed pillow 934 that are simultaneously driven or selectively driven to maximize energy transfer efficiency as a function of changes in body position of the patient corresponding to changes in position of the receiver coil 910. This overlapping transmitter coil arrangement may also be applied to other embodiments such as those described previously wherein the transmitter coil is carried by an article donned by the patient. In FIG. 51J, two or more transmitter coils 912 are carried by orthogonal plates 936 arranged as shown to create orthogonal electromagnetic fields, thereby increasing energy transfer efficiency to compensate for movement of the patient corresponding to changes in position of the receiver coil 910. FIG. 51J also illustrates a non-contact respiratory sensor 916 arrangement as utilized for detecting sudden infant death syndrome (SIDS). As shown in FIG. 51K, two orthogonal transmitter coils 912 are located on each side of a neck pillow 938, which is particularly beneficial for bilateral stimulation wherein a receiver coil 910 may be located on either side of the neck.

Figure 51L:
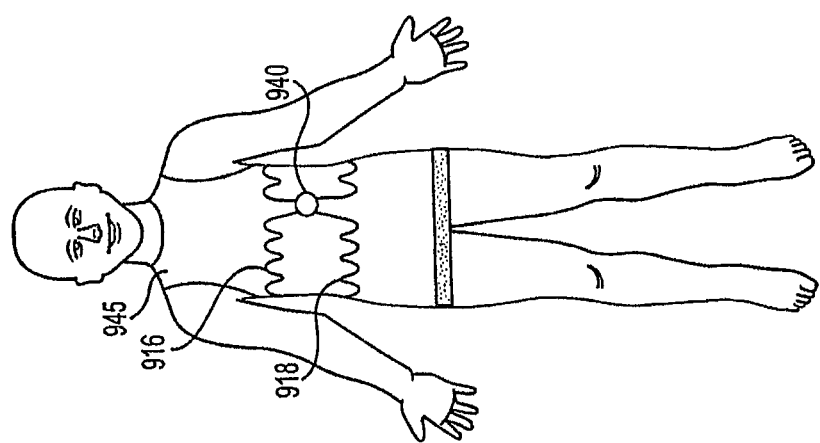

With reference to FIGS. 51L (front view) and 51M (rear view), external respiratory effort sensors 916/918 are schematically shown incorporated into a stretchable garment 945 donned by the patient. The sensors 916/918 generally include one or more inductive transducers and an electronics module 942. The inductive transducers may comprise one or more shaped (e.g., zig-zag or sinusoidal) stranded wires to accommodate stretching and may be carried by (e.g., sewn into) the garment 945 to extend around the patient's abdomen and chest, for example. As the patient breathes, the patient's chest and/or abdomen expands and contracts, thus changing the cross-sectional area of the shape (i.e., hoop) formed by the wire resulting in changes in inductance. The electronics module may include an oscillator (LC) circuit with the inductive transducer (L) comprising a part of the circuit. Changes in frequency of the oscillator correspond to changes in inductance of the shaped wires which correlate to respiratory effort. The electronics module may be integrated with an ENS (not shown) or connected to an ENS via a wired or wireless link for triggering stimulus as described previously.

The garment 945 may include features to minimize movement artifact and accommodate various body shapes. For example, the garment 945 may be form-fitting and may be sleeveless (e.g., vest) to reduce sensor artifacts due to arm movement. Further, the garment 945 may be tailored to fit over the patient's hips with a bottom elastic band which helps pull the garment down and keep the sensors 916/918 in the proper location.

Description of a Specific External (Partially Implanted) Embodiment

With reference to FIGS. 52A-52H a specific embodiment utilizing an external neurostimulator system inductively coupled to an internal/implanted receiver is schematically shown. With initial reference to FIG. 52A, the illustrated hypoglossal nerve stimulator includes several major components, namely: an implantable electronics unit that derives power from an external power source; a stimulation delivery lead that is anchored to the nerve or adjacent to the nerve and provides electrical connection between the electronics unit and the nerve, an external (non-implanted) power transmitting device that is inductively coupled with the implant to convey a powering signal and control signals; a power source for the external device that is either small and integrated into the body-worn coil and transmitter or is wired to the transmitter and transmit induction coil and can be powered by primary or secondary batteries or can be line powered; and a respiratory sensor such as those described previously.

These components may be configured to provide immediate or delayed activation of respiration controlled stimulation. Initiation of the stimulation regimen may be by means of activation of an input switch. Visual confirmation can be by an LED that shows adequate signal coupling and that the system is operating and is or will be applying stimulation. As a means of controlling gentleness of stimulation onset and removal, either pulse width ramping of a constant amplitude stimulation signal can be commanded or amplitude of a constant pulse width stimulation signal or a combination thereof can be performed.

The electrical stimulation signal is delivered by the stimulation lead that is connected to the implanted nerve stimulator and attached to or in proximity of a nerve. The implanted electronics unit receives power through a magnetically coupled inductive link. The operating carrier frequency may be high enough to ensure that several cycles (at least 10) of the carrier comprise the output pulse. The operating frequency may be in a band of frequencies approved by governmental agencies for use with medical instruments operating at high transmitted radio frequency (RF) power (at least 100 milliwatts). For example, the operating frequency may be 1.8 MHz, but 13.56 MHz is also a good candidate since it is in the ISM (Industrial/Scientific/Medical) band. The non-implanted (external) transmitter device integrates respiration interface, waveform generation logic and transmit power driver to drive an induction coil. The power driver generates an oscillating signal that drives the transmitter induction coil and is designed to directly drive a coil of coil reactance that is high enough or can be resonated in combination with a capacitor. Power can come from a high internal voltage that is used to directly drive the transmit induction coil or power can come from a low voltage source applied to a tap point on the induction coil.

With reference to FIGS. 52B-52E and 52H, the waveform generation logic may be used to modulate the carrier in such a way that narrow gaps in the carrier correspond to narrow stimulation pulses. When stimulator pulses are not needed, interruptions to the carrier are stopped but the carrier is maintained to ensure that power is immediately available within the stimulator upon demand. Presence or absence of electrical nerve stimulation is based on respiration or surrogates thereof. The transmitted signal may comprise a carrier of about 1.8 MHz. To control the implanted electronics unit to generate individual nerve stimulation pulses, the carrier signal is interrupted. The duration of the interruption is about equal to the duration of the output stimulation pulse. The stimulation pulses may be about 110 microseconds in duration and are repeated at a rate of approximately 33 per second. In addition, multiple pulses can be transmitted to logic within the implant to control stimulation pulse amplitude, pulse width, polarity, frequency and structure if needed. Further, onset and removal of stimulation can be graded to manage patient discomfort from abruptness. Grading may comprise pulse width control, signal amplitude control or a combination thereof.

An indicator (not shown) may be used to show when the transmitter is properly positioned over the implant. The indicator may be a part of the transmitter or by way of communication with the transmitter, or a part of related patient viewable equipment. Determination of proper position may be accomplished by monitoring the transmitter power output loading relative to the unloaded power level. Alternatively, the implant receive signal level transmitted back by a transmitter within the implant may be monitored to determine proper positioning. Or, the implant receive signal level that is communicated back to the transmitter by momentarily changing the loading properties presented to the transmitter, such a shorting out the receive coil may be monitored to determine proper positioning. Such communication may be by means of modulation such as pulse presence, pulse width, pulse-to-pulse interval, multi-pulse coding.

The transmitter may be powered by an internal primary power source that is used until it is exhausted, a rechargeable power source or a power source wired to a base unit. In the case of the wired base unit, power can be supplied by any combination of battery or line power.

The respiration interface may transduce sensed respiratory activity to an on-off control signal for the transmitter. Onset of stimulation may be approximately correlated slightly in advance of inspiration and lasts through the end of inspiration, or onset may be based on anticipation of the next respiration cycle from the prior respiration cycle or cycles. The respiration sensor may comprise any one or combination of devices capable of detecting inspiration. The following are examples: one or more chest straps; an impedance sensor; an electromyographical measurement of the muscles involved with respiration; a microphone that is worn or is in proximity to the patients' face; a flow sensor; a pressure sensor in combination with a mask to measure flow; and a temperature sensor to detect the difference between cool inspired air versus warmed expired air.

Figure 52A:
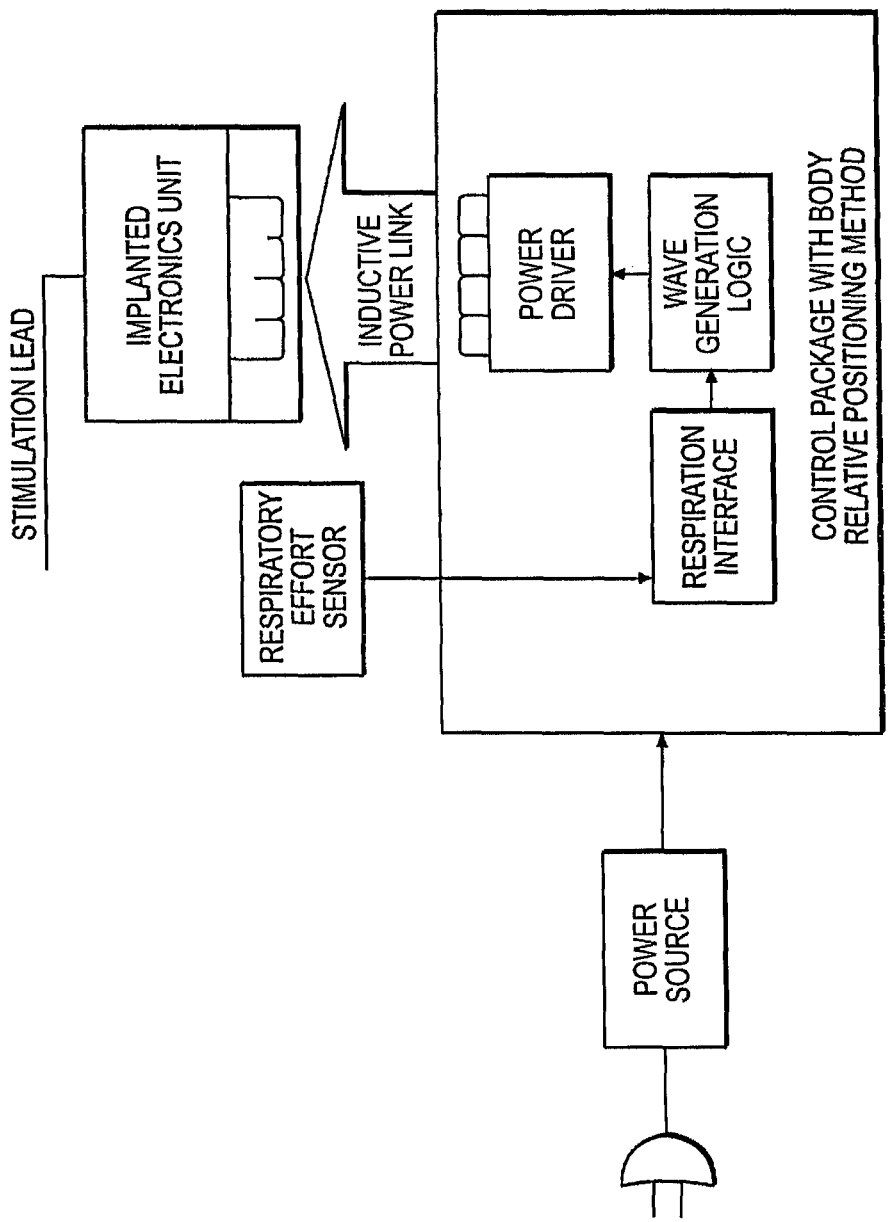
FIGS. 52A-52H are schematic illustrations of a specific embodiment of an external (partially implanted) neurostimulation system.
Figure 52C:
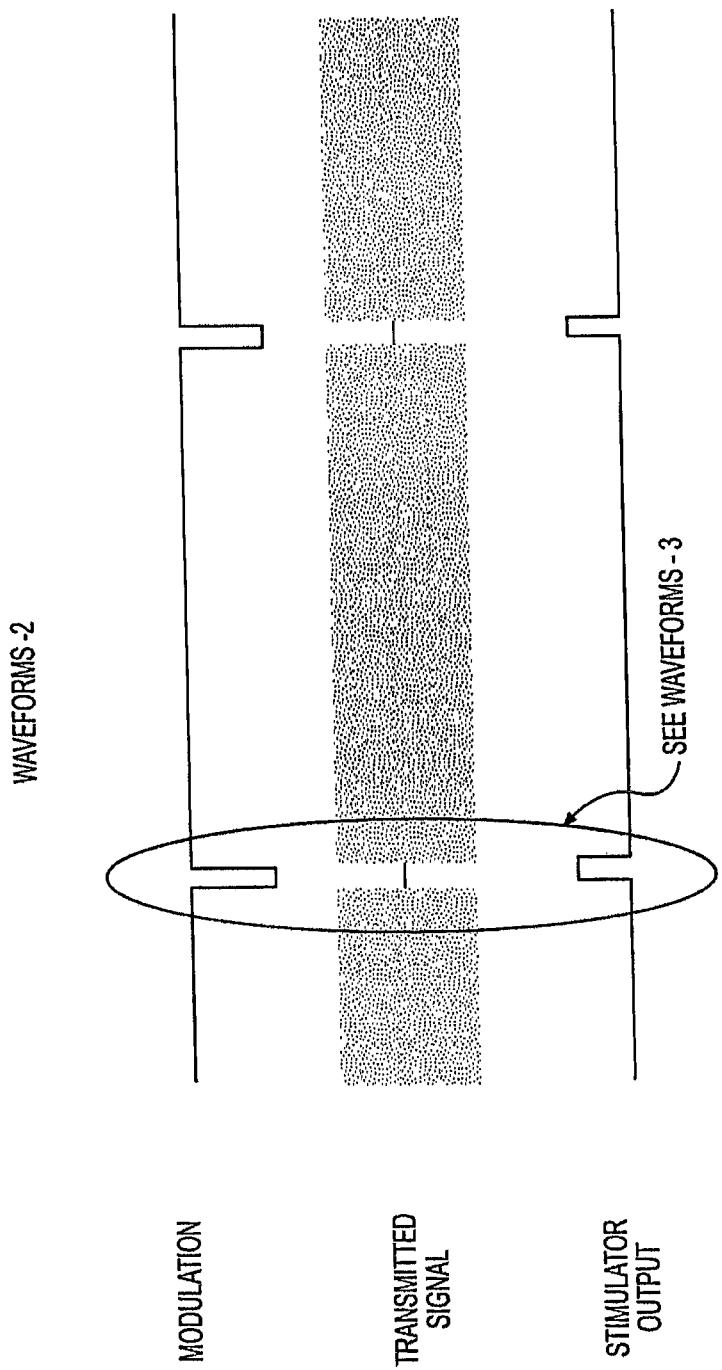
Figure 52E:
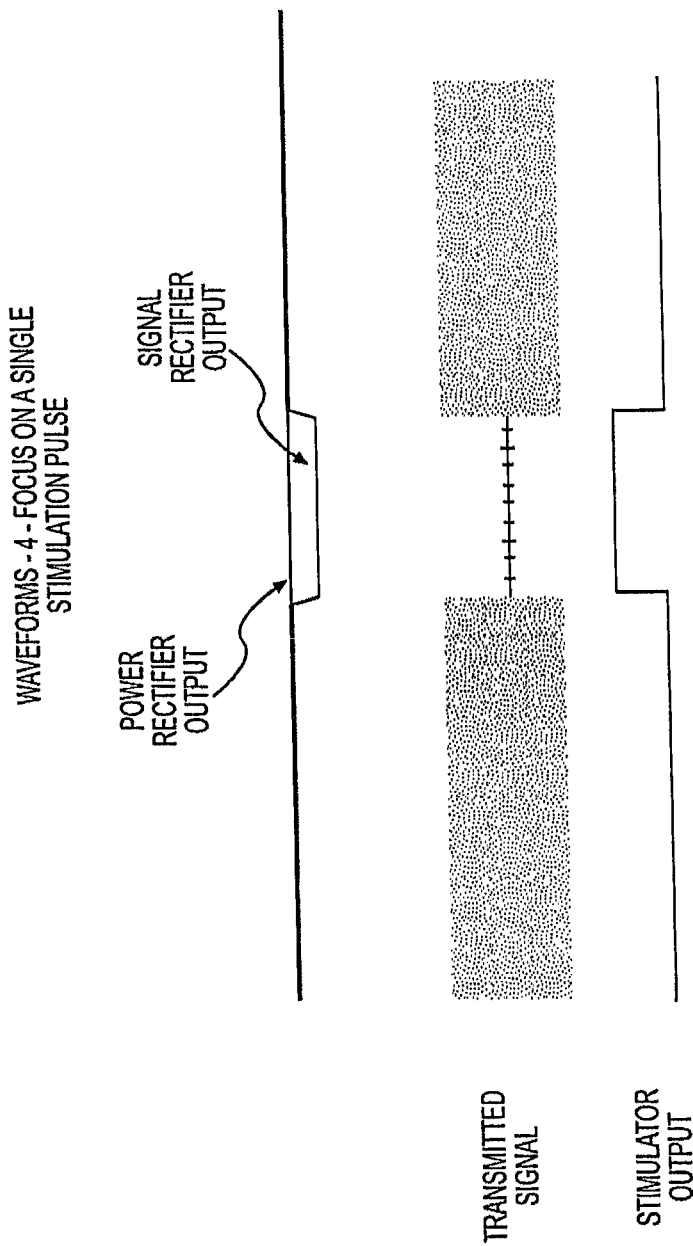
Figure 52F:
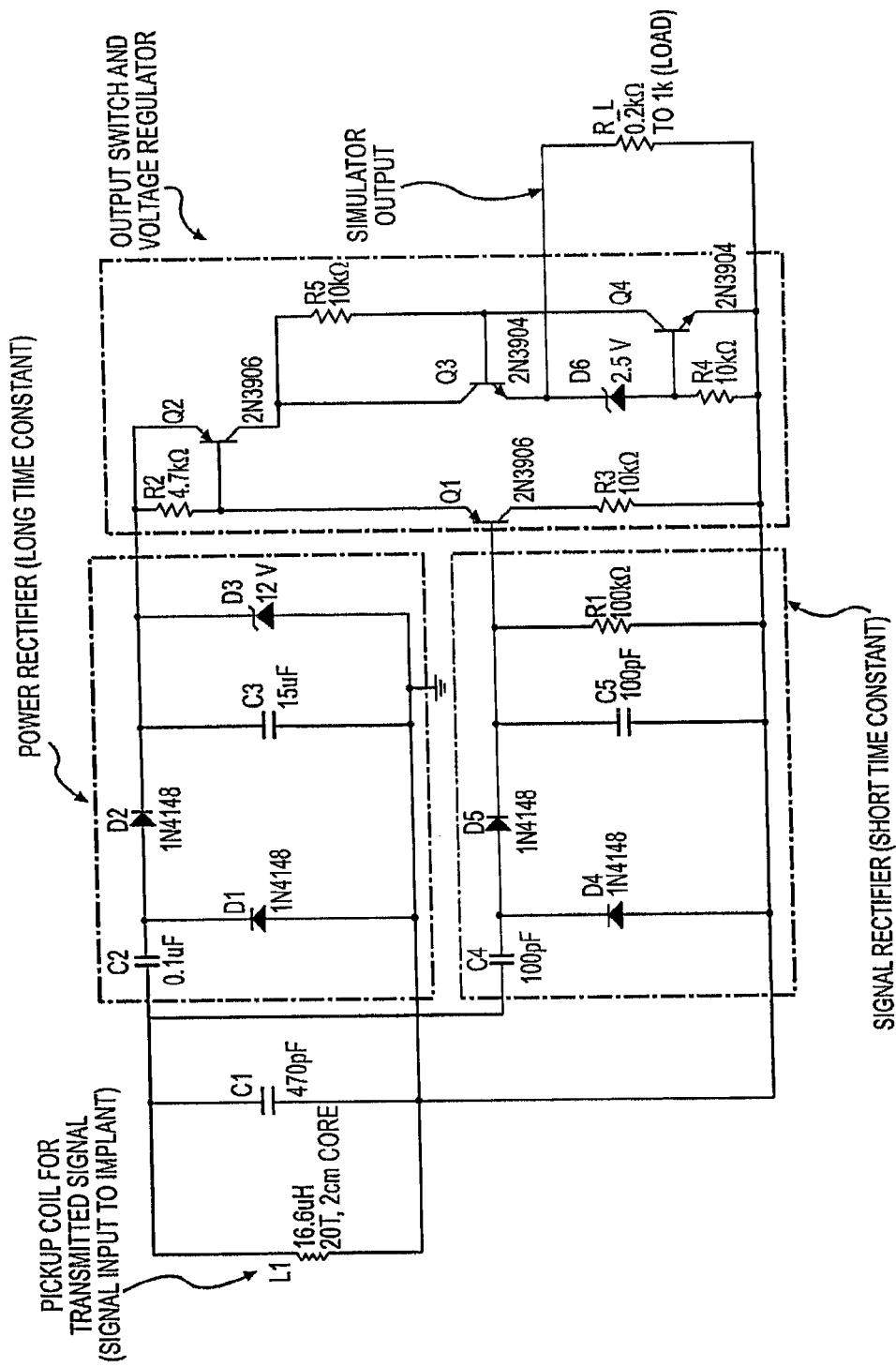

The circuit illustrated in FIG. 52F may be used for the implanted electronics unit. There are five main subsystems within the design: a receive coil, a power rectifier, a signal rectifier, an output switch and an output regulator. The signal from the inductive link is received by L1 which is resonated in combination with C1 and is delivered to both the power and signal rectifiers. Good coupling consistent with low transmitter coil drive occurs when the transmit coil diameter is equal to the receive coil diameter. When coil sizes are matched, coupling degrades quickly when the coil separation is about one coil diameter. A large transmit coil diameter will reduce the criticality of small coil spacing and coil-to-coil coaxial alignment for maximum signal transfer at the cost of requiring more input drive power.

The power rectifier may comprise a voltage doubler design to take maximum advantage of lower signal levels when the transmit to receive coil spacing is large. The voltage doubler operates with an input AC voltage that swing negative (below ground potential) causes D1 to conduct and forces C2 to the maximum negative peak potential (minus a diode drop). As the input AC voltage swings away from maximum negative, the node of C2, D1, D2 moves from a diode drop below ground to a diode drop above ground, forward biasing diode D2. Further upswing of the input AC voltage causes charge accumulated on C2 to be transferred through D2 to C3 and to "pump up" the voltage on C3 on successive AC voltage cycles. To limit the voltage developed across C3 so that an over-voltage condition will not cause damage, and Zener diode, D3 shunts C3. Voltage limiting imposed by D3 also limits the output of the signal rectifier section. The power rectifier has a long time constant, compared to the signal rectifier section, of about 10 milliseconds.

The signal rectifier section may be similar in topology to the power rectifier except that time constants are much shorter—on the order of 10 microseconds—to respond with good fidelity to drop-outs in the transmitted signal. There is an output load of 100K (R1) that imposes a controlled discharge time constant. Output of the signal rectifier is used to switch Q1, in the output switching section, on and off.

The output switching section compares the potential of C3 to that across C5 by means of the Q1, Q2 combination. When there is a gap in the transmitted signal, the voltage across C5 falls very rapidly in comparison with C3. When the voltage difference between C5 and C3 is about 1.4 volts, Q1 and Q2 turn on. Q1 and Q2 in combination form a high gain amplifier stage that provides for rapid output switching time. R3 is intended to limit the drive current supplied to Q2, and R2 aids in discharging the base of Q2 to improve the turn-off time.

In the output regulator section, the available power rectifier voltage is usually limited by Zener diode D3. When the coil separation becomes suboptimal or too large the power rectifier output voltage will be come variable as will the switched voltage available at the collector of Q2. For proper nerve stimulation, it may be necessary to regulate the (either) high or variable available voltage to an appropriate level. An acceptable level is about 3 volts peak. A switched voltage is applied to Zener diode D6 through emitter follower Q3 and bias resistor R5. When the switched voltage rises to a level where D6 conducts and develops about 0.6 volts across R4 and the base-emitter junction of Q4, Q4 conducts. o Increased conduction of Q4 is used to remove bias from Q3 through negative feedback. Since the level of conduction of Q4 is a very sensitive function of base to emitter voltage, Q4 provides substantial amplification of small variations in D6 current flow and therefore bias voltage level. The overall result is to regulate the bias voltage applied to Zener diode D6. Output is taken from the junction of the emitter of Q3 and D6 since that point is well regulated by the combination of Zener diode breakdown voltage combined with the amplification provided by Q4. In addition to good voltage regulation a the junction of the emitter of Q3 and D6, the output is very tolerant of load current demand since the conductivity of Q3 will be changed by shifts in the operating point of Q4. Due to amplification by Q3 and Q4, the circuit can drive a range of load resistances. Tolerable load resistances above 1000 ohms and less than 200 ohms. The regulator has the advantage of delivering only the current needed to operate the load while consuming only moderate bias current. Further, bias current is only drawn during delivery of the stimulation pulse which drops to zero when no stimulation is delivered. As a comparison, a simple series resistance biased Zener diode requires enough excess current to deliver a stimulation pulse and still maintain adequate Zener bias. As a further comparison, conventional integrated circuit regulators, such as three terminal regulators are not designed to well regulate and respond quickly to short input pulses. Experiment shows that three-terminal regulators exhibit significant output overshoot and ramp-up time upon application of an input pulse. This can be addressed by applying a constant bias to a regulator circuit or even moving the regulator before the output switching stage but this will be at the cost of constant current drain and subsequently reduced range.

The implanted electronics unit may be used to manage the loss of control and power signals. With this design, more than enough stimulation power is stored in C3 to supply multiple delivered stimulation pulses. This design is intended to ensure that the voltage drop is minimal on any individual pulse. One of the consequences is that when signal is lost, the circuit treats the condition as a commanded delivery of stimulation and will apply a single, extended duration, energy pulse until the full stored capacity of C3 is empty. An alternative method may be to use an indirect control modulation to command delivery of a nerve stimulation pulse through logic and provide for a time-out that limits pulse duration.

Figure 52G:
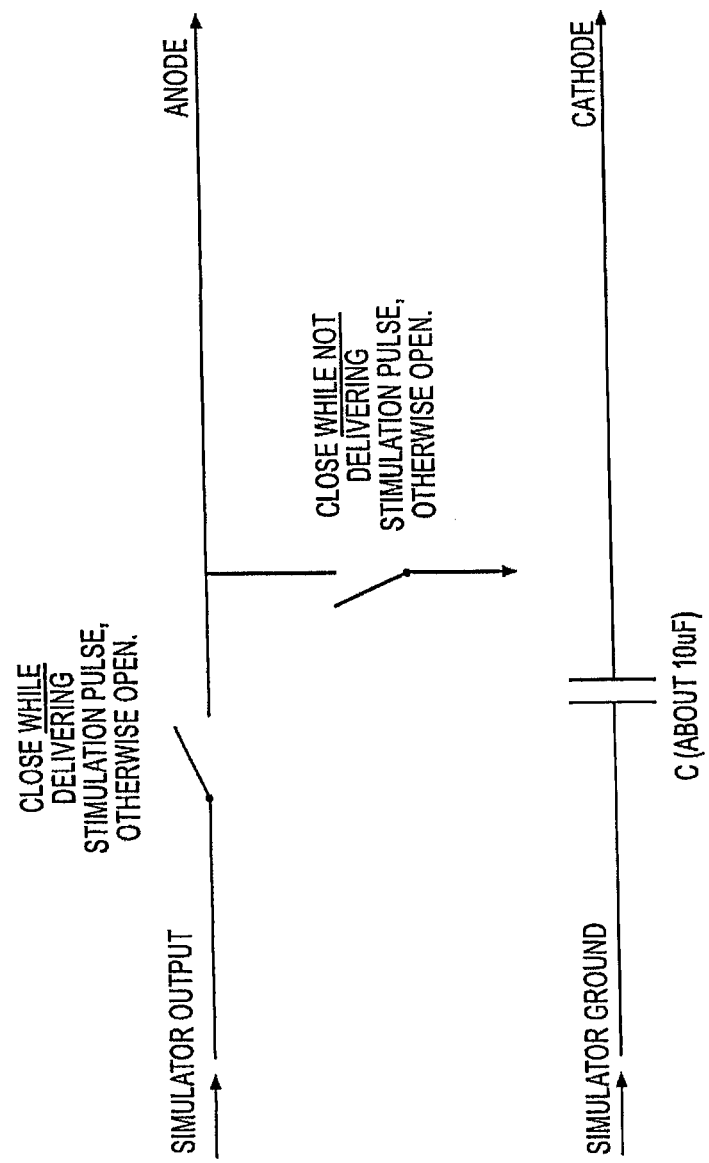
Figure 52:
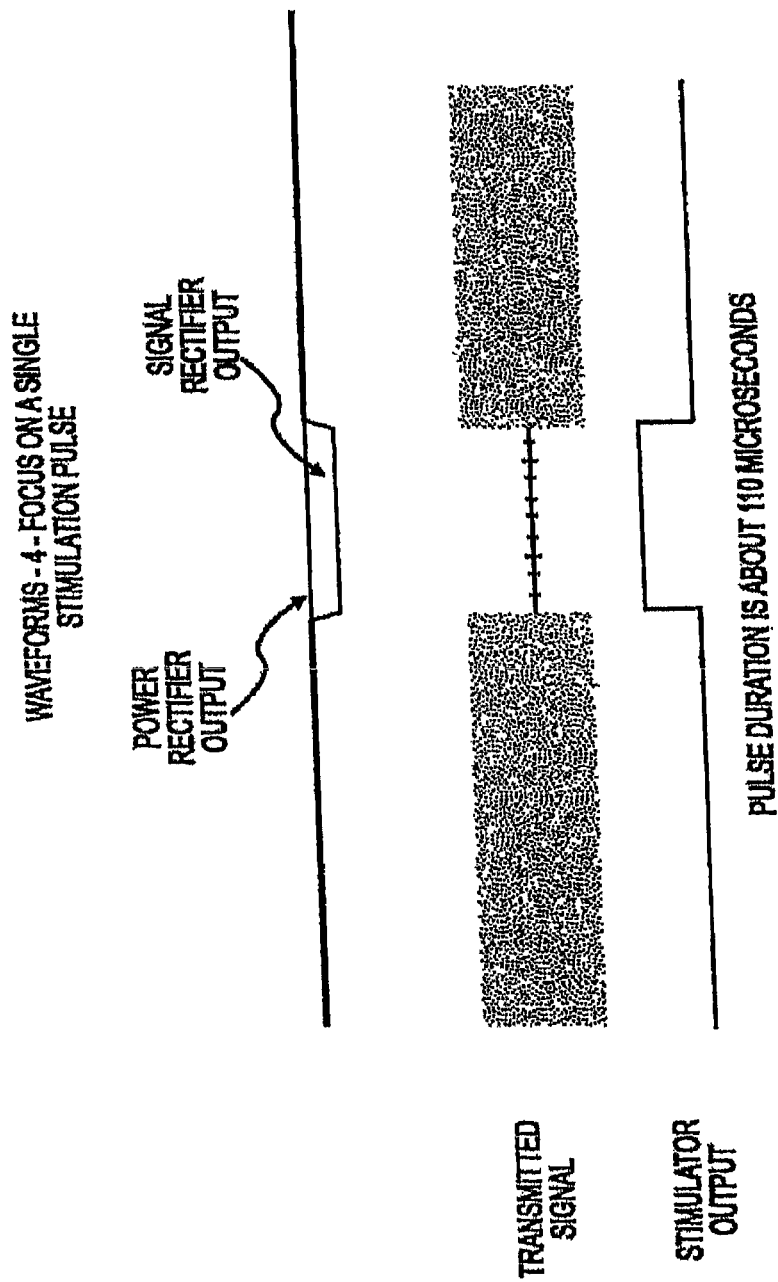

To stimulate tissue, a modified output stage may be used to mitigate electrode corrosion and establish balanced charging. The output stage is illustrated in FIG. 52G and includes a capacitive coupling between the ground side of the stimulator and tissue interface in addition to a shunt from the active electrode to circuit ground for re-zeroing the output coupling capacitor when an output pulse is not being actively delivered.

Description of Alternative Screening Methods

Screening generally refers to selecting patients that will be responsive to the therapy, namely neurostimulation of the upper airway dilator nerves and/or muscles such as the hypoglossal nerve that innervates the genioglossus. Screening may be based on a number of different factors including level of obstruction and critical collapse pressure (Pcrit) of the upper airway, for example. Because stimulation of the hypoglossal nerve affects the genioglossus (base of tongue) as well as other muscles, OSA patients with obstruction at the level of the tongue base and OSA patients with obstruction at the level of the palate and tongue base (collectively patients with tongue base involvement) may be selected. Because stimulation of the hypoglossal nerve affects upper airway collapsibility, OSA patients with airways that have a low critical collapse pressure (e.g., Pcrit of less than about 5 cm water) may be selected. Pcrit may be measured using pressure transducers in the upper airway and measuring the pressure just prior to an apnea event (airway collapse). Alternatively, a surrogate for Pcrit such as CPAP pressure may be used. In this alternative, the lowest CPAP pressure at which apnea events are mitigated may correlate to Pcrit.

The critical collapse pressure (Pcrit) may be defined as the pressure at which the upper airway collapses and limits flow to a maximal level. Thus, Pcrit is a measure of airway collapsibility and depends on the stability of the walls defining the upper airway as well as the surrounding pressure. Pcrit may be more accurately defined as the pressure inside the upper airway at the onset of flow limitation when the upper airway collapses. Pcrit may be expressed as:

$$Pcrit = Pin - Pout$$

where

Pin=pressure inside the upper airway at the moment of airway collapse; and

Pout=pressure outside the upper airway (e.g., atmospheric pressure).

Other screening methods and tools may be employed as well. For example, screening may be accomplished through acute testing of tongue protruder muscle contraction using percutaneous fine wire electrodes inserted into the genioglossus muscle, delivering stimulus and measuring one or more of several variables including the amount of change in critical opening pressure, the amount of change in airway caliber, the displacement of the tongue base, and/or the retraction force of the tongue (as measured with a displacement and/or force gauge). For example, a device similar to a CPAP machine can be used to seal against the face (mask) and control inlet pressure down to where the tongue and upper airway collapse and occlude during inspiration. This measurement can be repeated while the patient is receiving stimulation of the geneoglossus muscle (or other muscles involved with the patency of the upper airway). Patients may be indicated for the stimulation therapy if the difference in critical pressure (stimulated vs. non-stimulated) is above a threshold level.

Similarly, a flexible optical scope may be used to observe the upper airway, having been inserted through the mask and nasal passage. The difference in upper airway caliber between stimulation and non-stimulation may be used as an inclusion criterion for the therapy. The measurement may be taken with the inlet air pressure to the patient established at a pre-determined level below atmospheric pressure to better assess the effectiveness of the stimulation therapy.

Another screening technique involves assessing the protrusion force of the tongue upon anterior displacement or movement of the tongue with and without stimulation while the patient is supine and (possibly) sedated or asleep. A minimum increase in protrusion force while under stimulation may be a basis for patient selection.

Figure 53:
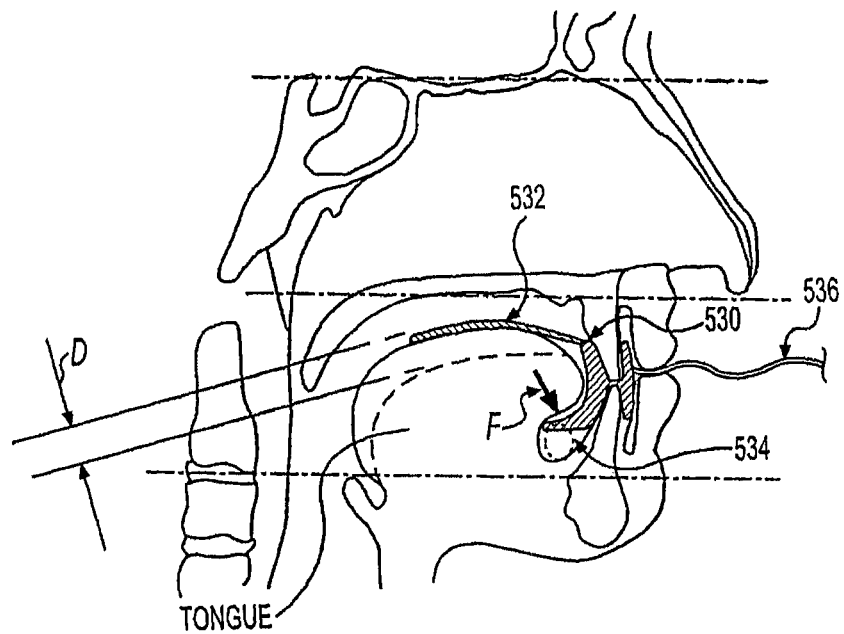
FIGS. 53-56 schematically illustrate alternative screening tools.

For example, with reference to FIG. 53, a non-invasive oral appliance 530 may be worn by the patient during a sleep study that can directly measure the protrusion force of the tongue as a basis for patient selection. The oral appliance 530 may include a displacement probe 532 for measuring tongue movement protrusion force by deflection (D). The oral appliance 530 may also include a force sensor 534 for measuring the force (F) applied by protrusion of the tongue. The sensors in the displacement probe 532 and the force sensor 534 may be connected to measurement apparatus by wires 536.

Figure 54:
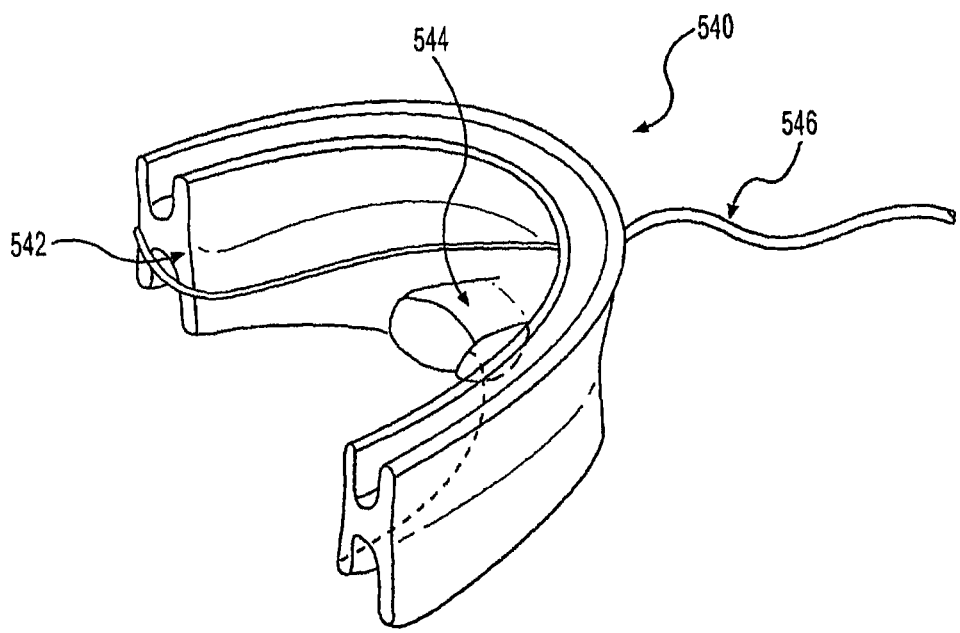

FIG. 54 illustrates another example of a non-invasive oral appliance 540 that may be worn by the patient during a sleep study to directly measure the protrusion force of the tongue as a basis for patient selection. The oral appliance 540 includes a displacement sensor 542 for measuring tongue movement and a force sensor for measuring tongue protrusion force. The displacement sensor and the force sensor may be connected to measurement apparatus by wires 546.

Oral appliances 530 and 540 could be worn during a sleep study and would measure the tongue protrusion force during (and just prior to) an apnea event when the protruder muscle tone is presumed to be inadequate to maintain upper airway patency. The protrusion force measured as the apnea is resolved by the patient will increase as the patient changes sleep state and the airway again becomes patent. The force difference may be used as a basis for patient selection.

Another screening technique involves the use of an oral appliance with sub-lingual surface electrodes contacting the base of the tongue or fine wire electrodes inserted into the genioglossus muscle to stimulate the tongue protruder muscle(s) synchronous with respiration during a sleep study. The oral appliance may be fitted with a drug delivery system (e.g., drug eluting coating, elastomeric pump, electronically controlled pump) for topical anesthesia to relieve the discomfort of the electrodes.

Figure 55:
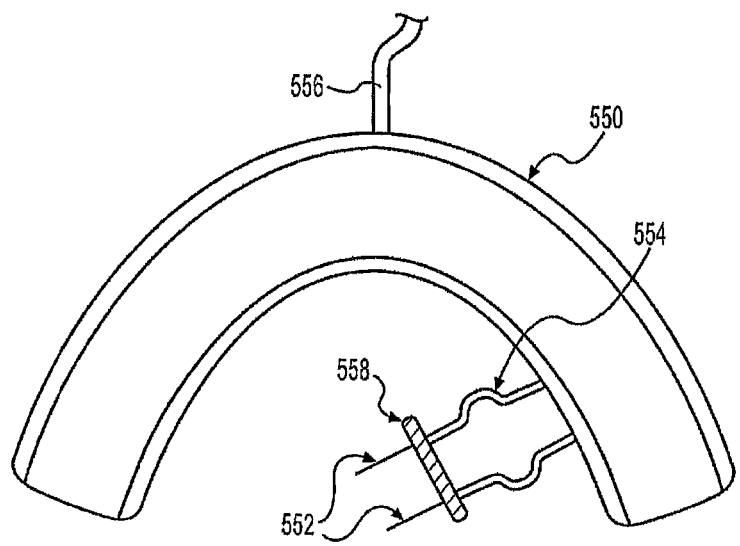

For example, with reference to FIG. 55, an oral appliance 550 includes a pair of small needle intramuscular electrodes 552 that extend into the genioglossus. The electrodes 552 are carried by flexible wires 554 and may be coupled to an external pulse generator (not shown) by wires 556. The electrodes 552 may be supported by a drug (e.g., anesthetic) eluting polymeric member 558.

Figure 56:
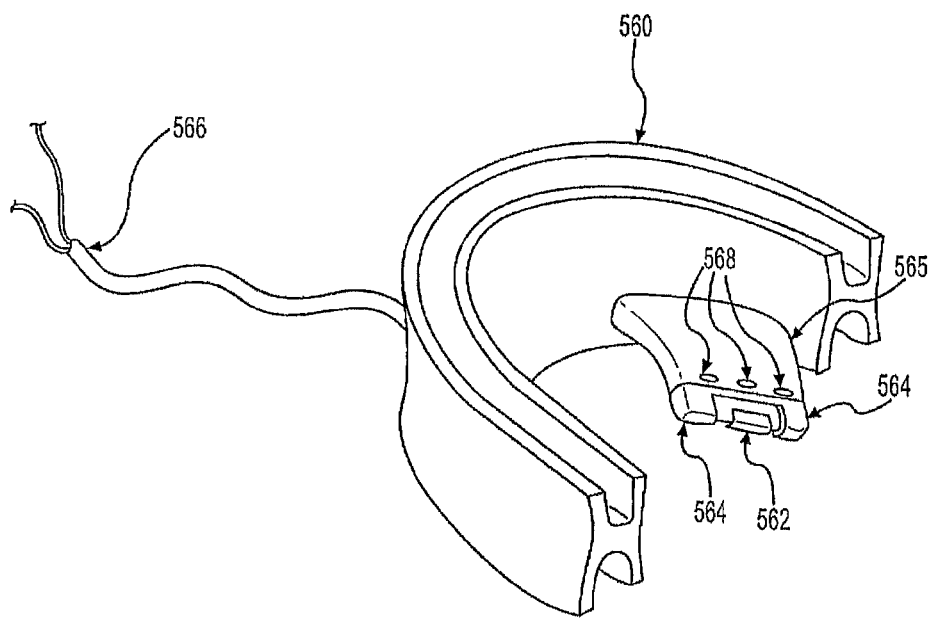

Alternatively, with reference to FIG. 56, an oral appliance 560 includes a cathode electrode 562 guarded by two anode electrodes 564 carried by a soft extension 565 that extends under the tongue. The surface electrodes 562 and 564 contact the floor of the mouth under the tongue to indirectly stimulate the genioglossus. The electrodes 562 and 564 may be coupled to an external pulse generator (not shown) by wires 566. The extension 565 may incorporate holes 568 through which a drug (e.g., anesthetic) may be eluted.

Oral appliances 550 and 560 may be used during a sleep study and stimulation of the target tissue can be performed synchronous with respiration and while inlet airflow pressure can be modulated. The ability to prevent apneas/hypopneas can be directly determined. Also the critical opening pressure with and without stimulation can be determined. Alternatively or in addition, the intramuscular or surface electrodes may be used to measure genioglossus EMG activity, either with or without stimulation. On any of theses bases, patient selection may be made.

Patient selection may also be applied to the respiratory sensors to determine if the respiratory sensors will adequately detect respiration for triggering stimulation. For example, in the embodiment wherein bio-Z is used to detect respiration using an implanted lead 70, skin surface or shallow needle electrodes may be used prior to implantation to determine if the signal will be adequate. This method may also be sued to determine the preferred position of the electrodes (i.e., optimal bio-Z vector). This may be done while the patient is sleeping (i.e., during a sleep study) or while the patient is awake.

Description of Alternative Intra-Operative Tools

Intra-operatively, it may be desirable to determine the correct portion of the nerve to stimulate in order to activate the correct muscle(s) and implant the nerve cuff electrode accordingly. Determining the correct position may involve stimulating at different locations along the length or circumference of the nerve and observing the effect (e.g., tongue protrusion). In addition or in the alternative, and particularly in the case of field steering where multiple combinations of electrode contacts are possible, it may be desirable to determine optimal electrode or filed shape combinations.

An example of an intra-operative stimulating tool 570 is shown in FIGS. 57A and 57B. In this embodiment, the tool 570 includes a first shaft 571 with a distal half-cuff 573. Tool 570 further includes a second shaft 575 with a proximal movable collar 574 and a distal half-cuff 575. Stimulating tool 570 includes multiple electrodes 572 on half-cuff 573 and/or half-cuff 575 that may be arranged in an array or matrix as shown in FIG. 57C, which is a view taken along line A-A in FIG. 57B. The half-cuffs 573 and 575 may be longitudinally separated for placement about a nerve and subsequently closed such that the half-cuffs 573 and 575 gently grasp the nerve. The electrodes 575 may be sequenced through a series of electrode/field shape combinations to optimize (lower) the critical opening pressure, airway caliber, tongue protrusion force or other acute indicia of therapeutic efficacy.

The tool 570 may be part of an intra-operative system including: (1) tool 570 or other tool with one or more stimulating electrodes that are designed to be easily handled by the surgeon during implant surgery; (2) an external pulse generator which triggers off of a respiration signal; (3) a feedback diagnostic device that can measure critical closing pressure intra-operatively; and (4) an algorithm (e.g., firmware or software in the programmer) that is design to automatically or manually sequence through a series of electrode configurations that will identify the best placement of electrode cuffs on the nerves and configuration of electrode polarity and amplitude settings. Information from the intra-operative system may greatly speed the process of identifying where to place the electrode cuff(s) on the hypoglossal nerve and what field steering may be optimal or necessary to provide efficacy.

Figure 58A:
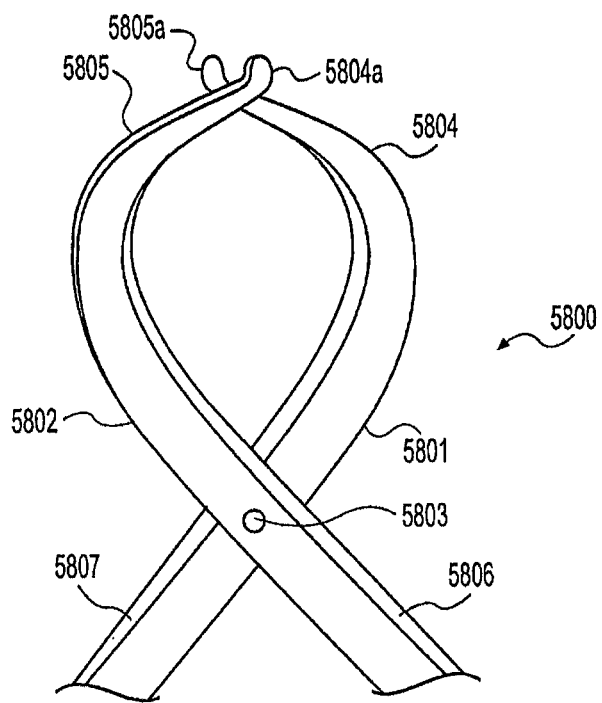
Figure 58B:
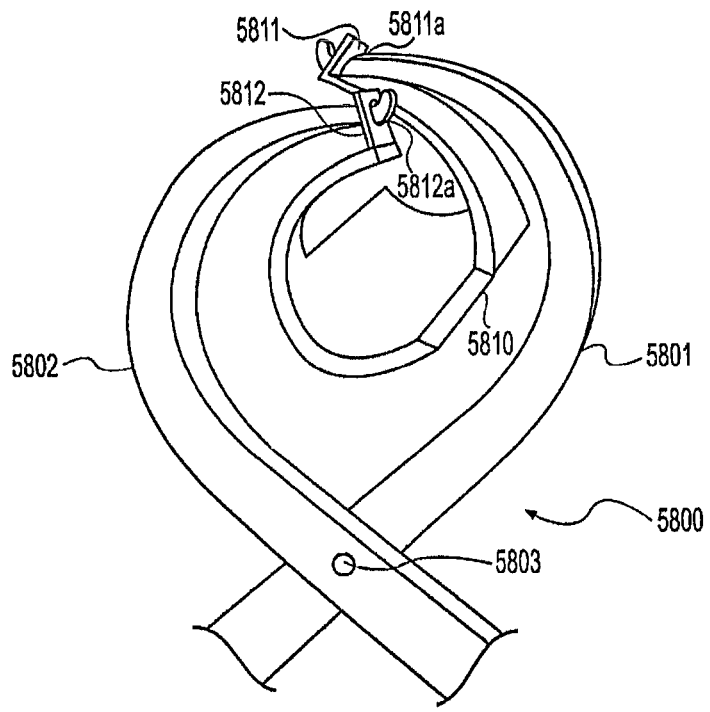

In certain circumstances, such as, when treating a child or a small adult, it may be difficult to implant a nerve cuff electrode of the present disclosure about a nerve in a patient's body. Accordingly, it may be desirable to provide a tool capable of facilitating temporary expansion of a nerve cuff electrode of the present disclosure, so as to slip the nerve cuff electrode around a patient's nerve. Turning now to FIGS. 58A-58B, there is depicted a tool 5800 for temporarily expanding a nerve cuff electrode in accordance with the principles of the present disclosure. Tool 5800 may include a substantially scissor-like configuration having a first element 5801 and a second element 5802 pivotably secured together by a suitable fastener, such as, for example, pivot pin 5803, acting as a fulcrum. Elements 5801 and 5802 may be substantially similar to each other or may differ as necessary. In the depicted embodiment, elements 5801 and 5802 may include levers having distal effecting portions 5804, 5805 and proximal actuating portions 5806, 5807.

Proximal actuating portions 5806, 5807 may be of any suitable length and may be connected to respective handles (not shown), which may be used to operate tool 5800. Alternatively, proximal actuating portions 5806, 5807 themselves may be used to operate tool 5800. Distal effecting portions 5804, 5805 may include any suitable configuration to achieve the desired effect. For example, each portion 5804, 5805 may include a substantially curved configuration. Additionally, a distal end of each portion 5804, 5805 may be provided with a fastening mechanism, such as, for example, hook-like projection 5804a, 5805a, for facilitating connection of tool 5800 to a nerve cuff electrode. As shown in FIGS. 58A-58B, hook-like projections 5804a, 5805a may be configured to be disposed in differing parallel planes, such that projections 5804a, 5805a may be spaced (offset) horizontally from one another. In use, distal effecting portions 5804, 5805 may be opened and closed as proximal actuating portions 5806, 5807 may be rotated about pivot pin 5803.

In embodiments where tool 5800 may be used to temporarily expand a nerve cuff electrode for implantation purposes, the nerve cuff electrode, e.g., nerve cuff electrode 5810, may be provided with one more geometric configurations for facilitation connection with tool 5800. In the depicted embodiment, nerve cuff electrode 5810 may be provided with extensions 5811, 5812 for facilitating connection with tool 5800. Each extension 5811, 5812 may be provided with openings 5811a, 5812a, respectively, for receiving hook-like projections 5804a, 5805a, so as to operably couple nerve cuff electrode 5811 with tool 5800.

Description of Miscellaneous Alternatives

The implanted neurostimulation system may be configured so that stimulation of the nerve is set at a relatively low level (i.e., low voltage amplitude, narrow pulse width, lower frequency) so as to maximize battery life of the INS and to minimize the chances that the electrical stimulation will cause arousal from sleep. If apneas/hypopneas are detected, then the electrical stimulation can be increased progressively until the apneas/hypopneas are no longer detected, up to a maximum pre-set stimulation level. This auto titration may automatically be reset to the low level after the patient is awakened and sits up (position detector) or manually reset using the patient controller. The stimulation level may be automatically reduced after a period of time has elapsed with no (or few) apneas/hypopneas detected.

The stimulation level (i.e., voltage amplitude, pulse width, frequency) may be adjusted based on changes in respiration rate. Respiration rate or patterns of rate change may be indicative of sleep state. A different power level based on sleep state may be used for minimal power consumption, minimal unwanted stimulation (sensory response), etc., while providing adequate efficacy.

The electrical field shape used to stimulate the target nerve can be changed while the system is proving therapy based on feedback indicating the presence (or lack) of apneas/hypopneas. The electrical field shape for an implanted system can be changed by adjusting the polarity, amplitude and other stimulation intensity parameters for each of the electrodes within the nerve stimulating cuff. An algorithm within the INS may change the currently operating electrical field shape if the presence of apneas/hypopneas is detected, and then wait a set period of time to determine if the new configuration was successful in mitigating the apneas/hypopneas before adjusting the field shape again. Additionally, the system may be designed to keep a log of the most successful stimulation patterns and when they were most likely to be effective. This may allow the system to "learn" which settings to be used during what part of the night, for example, or with specific breathing patterns or cardiac signal patterns or combinations thereof.

The proportion of stimulation intensity of two electrode cuffs used to stimulate a nerve can be modulated while the system is providing therapy based on feedback indicating the presence (or lack) of apneas/hypopneas. For example, one nerve stimulating electrode cuff may be place on the more proximal section of the hypoglossal nerve, while a second is placed more distally. The proximal cuff will be more likely to stimulate branches of the hypoglossal nerve going to muscles in the upper airway involved with tongue or hyoid retrusion while the more distal electrode cuff will more likely stimulate only the muscles involved with tongue/hyoid protrusion. Research suggests that to best maintain upper airway patency, stimulating both protrudes and retruders (in the right proportion) may be more effective that stimulating protruders alone. Software within the INS may change the currently operating proportion of electrical stimulation going to the distal electrode cuff in proportion to that going to the proximal cuff based on the presence of apneas/hypopneas detected. The system may then wait a set period of time to determine if the new configuration was successful in mitigating the apneas/hypopneas before adjusting the system again. Additionally, the system software may be designed to keep a log of the most successful stimulation proportion and when they were most likely to be effective. This may allow the system to "learn" which settings to be used during what part of the night, for example, or with specific breathing patterns or cardiac signal patterns or combinations thereof.

The system described above may modulate electrical stimulation intensity proportion based on electromyogram (EMG) feedback from the muscles in the upper airway being stimulated or others in the area. This feedback may be used to determine the correct proportion of stimulation between protruders and retruders. The correct ratio of EMG activity between retruders and protruders may be determined during a sleep study for an individual, may be determined to be a constant for a class of patients or may be "learned" my the implanted system by using the detection of apneas/hypopneas as feedback.

A library of electrical stimulation parameter settings can be programmed into the INS. These settings listed in the library may be selected by the patient manually using the patient programmer based on, for example: (1) direct patient perception of comfort during stimulation; (2) a log of the most successful settings compiled by the software in the INS (assumes apnea/hypopnea detection capability); (3) a sleep physician's or technician's assessment of the most effective stimulation as determined during a sleep study; and/or (4) a list of the most effective parameters produced for a particular class of patient or other.

The electrical stimulation parameters described above may be adjusted based on patient position as detected by a position sensor within the INS. The best setting for a given position may be determined by, for example: (1) a log of the most successful settings compiled or learned by the software in the INS (assumes apnea/hypopnea detection capability); (2) a sleep physician's or technician's assessment of the most effective stimulation as determined during a sleep study; and/or (3) a list of the most effective parameters produced for a particular class of patient or other.

To avoid fatigue using a normal duty cycle or to extend the time that the upper airway is opened through neurostimulation, different parts of the genioglossus muscle and/or different muscles involved with establishing patency of the upper airway can be alternately stimulated. For example, using two or more nerve or muscle electrode cuffs, the left and right side genioglossus muscles can be alternately stimulated, cutting the effective duty cycle on each muscle in half. In addition, different protruder muscles on the ipsilateral side such as the geniohyoid and the genioglossus muscle can be alternately stimulated to the same effect. This may also be accomplished through one electrode cuff using field steering methods that selectively stimulated the fascicles of the hypoglossal nerve going to one group of protruders alternating with stimulating the fascicles leading to a different protruder muscle group. This method may also be used to alternately stimulate one group of muscle fibers within the genioglossus muscle with the compliment of muscle fibers in the same muscle group.

To increase the ability of the upper airway to open during a (sensed) apnea/hypopnea through neurostimulation, different parts of the genioglossus muscle and/or different muscles involved with establishing patency of the upper airway can toe simultaneously stimulated. For example, using two or more nerve or muscle electrode cuffs, the left and right side genioglossus muscles can be simultaneously stimulated, greatly increasing the protrusion forces. In addition, different protruder muscles on the ipsilateral side such as the geneohyoid and the genioglossus muscle can be simultaneously stimulated to the same effect. This may also be accomplished through one electrode cuff using field steering methods that selectively stimulated the fascicles of the hypoglossal nerve going to one group of protruders simultaneously with stimulating the fascicles leading to a different protruder muscle group. This may be achieved with one electrode cuff using field steering on a more proximal location on the hypoglossal nerve or two or more electrode cuffs, one on each branch going to a muscle involved with maintaining muscle patency.

A sensor inside the INS (or elsewhere in system implanted) may detect body position and automatically shut off stimulation when patient sits up or stands up. This will prevent unwanted stimulation when patient is no longer sleeping. The device may automatically restart the stimulation after the sensor indicates the patient is again horizontal, with or without a delay. The system may also be configured so that the stimulation can only be restarted using the patient controller, with, or without a delay.

The respiration signal using impedance and/or EMG/ENG are easily capable of determining heart rate. The stimulation may be interrupted or turned off when the heart rate falls outside out a pre-determined acceptable range. This may be an effective safety measure that will decrease the chance that hypoglossal nerve stimulation will interfere with mitigating physiological processes or interventional emergent medical procedures.

Respiration waveforms indicating apneas/hypopneas or of other clinical interest may be recorded and automatically telemetered to a bed-side receiver unit or patient programmer. Respiration waveforms indicating frequent apneas/hypopneas, abnormal breathing patterns, irregular heart rate/rhythm may be recorded and automatically telemetered to a bed-side deceiver unit or patient programmer causing an alarm to be issued (audible/visible). The INS status such as low battery or system malfunction may also trigger an alarm.

Electrical stimulation intensity could be ramped up for each respiration cycle by increasing amplitude or pulse width from 0 to a set point to prevent sudden tongue protrusion or sudden airway opening causing the patient to wake up. During inspiration, the system may deliver approximately 30 pulses per second for a length of time of one to one and one half seconds, totaling between about 30 and 45 pulses per respiration cycle. Prior to delivery of these 30 to 45 pulses, amplitude of each individual therapy pulse (in an added group of pulses) could be ramped up from 0 to a set point at a rate of <10% of the amplitude intended for the active duty cycle or 200 mS, whichever is less. The pulse width of each individual therapy pulse could be ramped up from 0 to a set point at a rate of <10% of the active duty cycle or 200 mS, whichever is less. Each of these ramp methods would require a predictive algorithm that would stimulate based on the previous inspiration cycle.

Nerves innervating muscles that are involved with inspiration, such as the hypoglossal nerve, have been shown to have greater electrical activity during apnea or hypopnea. This signal cannot be easily measured while simultaneously stimulating the same nerve. One method of stimulating and sensing using the same lead is to interleave a sensing period within the stimulation pulse bursts during the duty cycle. In other words, the sensing period may occur between pulses within the stimulation pulse train. This approach may be used with electrodes/leads that directly stimulate and alternately sense on a nerve involved with inspiration or on a muscle involved with inspiration or a combination of the two. The approach may allow sensing of apnea/hypopnea, as well as therapeutic stimulation.

From the foregoing, it will be apparent to those skilled in the art that the present invention provides, in exemplary non-limiting embodiments, devices and methods for nerve stimulation for OSA therapy. Further, those skilled in the art will recognize that the present invention may be manifested in a variety of forms other than the specific embodiments described and contemplated herein. Accordingly, departures in form and detail may be made without departing from the scope and spirit of the present invention as described in the appended claims.

Overall Hypoglossal Nerve Stimulation System

Figure 59:
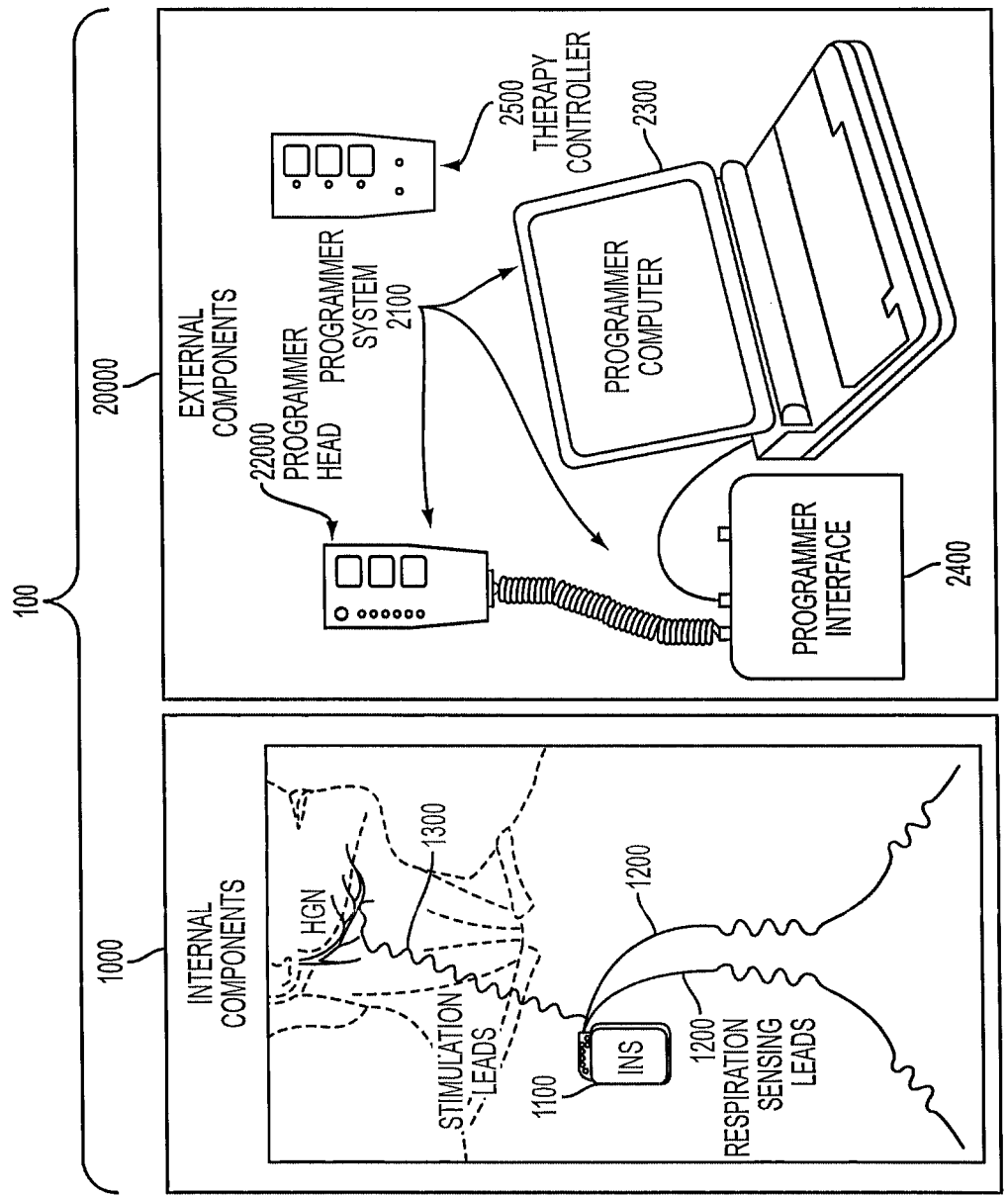
FIG. 59 is a schematic illustration of a system according to an embodiment of the present invention, including internal (chronically implanted) and external components.
Figure 77:
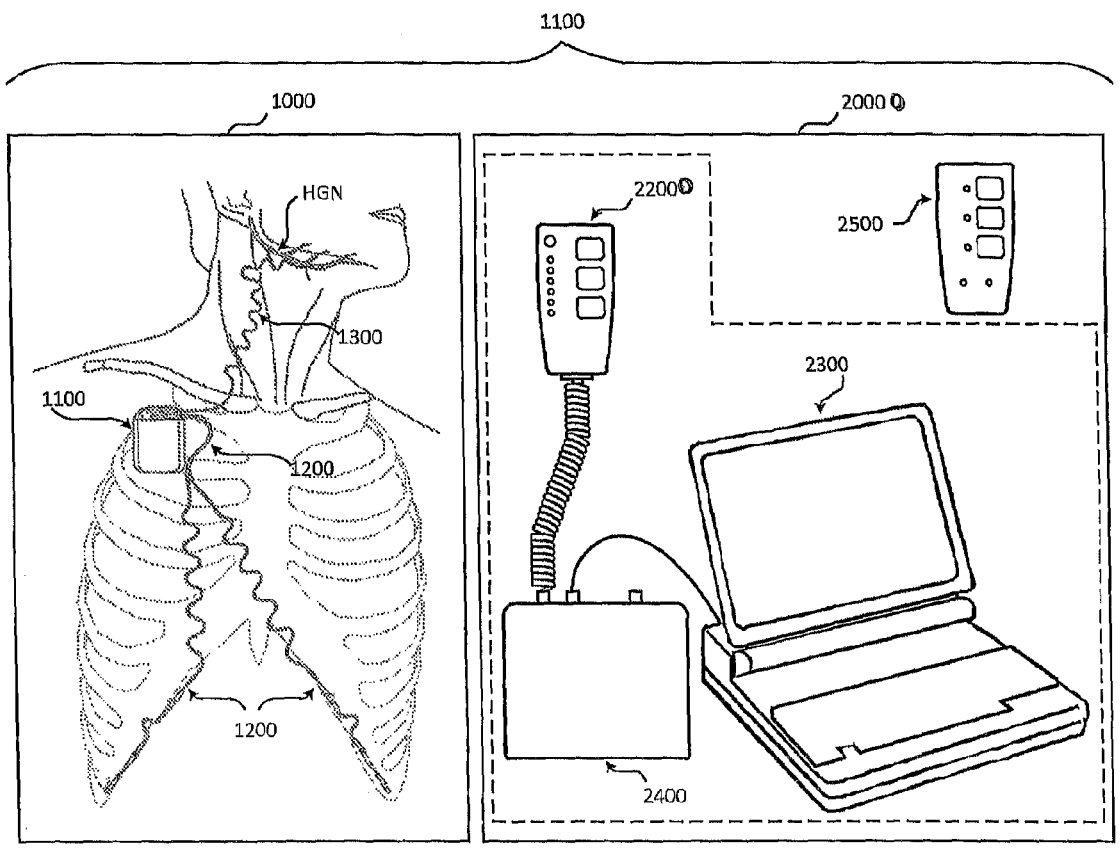
FIG. 77 is a schematic illustration of a system according to an embodiment of the present embodiment, including internal (chronically implanted) and external components.

FIGS. 59 and 77 schematically illustrate a hypoglossal nerve stimulation (HGNS) system 100 comprising internal components 1000 and external components 20000. The HGNS system 100 treats obstructive sleep apnea (OSA) by restoring and/or increasing neuromuscular activity to the genioglossus muscle via stimulation of the hypoglossal nerve (HGN) synchronous with inspiration to mitigate upper airway collapse during sleep. Stimulation is generated by an implantable neurostimulator (INS) 1100, synchronized with inspiration as measured by the respiration sensing lead (RSL) 1200 using bio-impedance, and delivered to the hypoglossal nerve by a stimulation lead (STL) 1300. A programmer system 2100 and a therapy controller 2500 are wirelessly linked to the INS 1100. The programmer system 2100 includes a computer 2300, a programmer interface 2400, and a programmer head 22000. The programmer system 2100 is used by the physician to control and program the INS 1100 during surgery and therapy titration, and the therapy controller 2500 is used by the patient to control limited aspects of therapy delivery.

The implanted components 1000 of the HGNS system 100 include the INS 1100, STL 1300, and RSL 1200. The INS is designed to accommodate one or two STLs 1300 and one or two RSLs 1200. One STL 1300 may be used for unilateral implantation and unilateral hypoglossal nerve stimulation. Two STLs 1300 may be used for bilateral implantation on both the right and left hypoglossal nerves to enhance the effects of stimulation. Alternatively, a second STL 1300 may be used as a back-up in the event of re-operation necessitated by failure or suboptimal placement of the first STL 1300. Similarly, one RSL 1200 may be used for respiration detection, but two RSLs 1200 may be used for enhanced sensing capability or redundancy. Alternatively, a second RSL 1200 may be used as a back-up in the event of re-operation necessitated by failure or suboptimal placement of the first RSL 1200. Port plugs (not shown) may be used to seal the unused ports in the header of the INS 1100. If only one STL 1300 and one RSL 1200 are to be used, the INS 1100 may be simplified to accommodate one of each lead, thus reducing the size and complexity of the INS 1100, as well as increasing battery longevity. For purposes of illustration, not limitation, the INS 1100 is shown with two RSLs 1200 and one STL 1300.

The INS may also be designed to accommodate one STL 1300 and one RSL 1200. One STL 1300 may be used for unilateral implantation and unilateral hypoglossal nerve stimulation. Similarly, one RSL 1200 may be used for respiration detection. Alternative embodiments of the RSL 1200 are described below and may be substituted. Therefore, for purposes of illustration not limitation, the INS 1100 is shown with STL 1300 and a bifurcated RSL 1200.

The implanted components 1000 may be surgically implanted with the patient under general anesthesia. The INS 1100 may be implanted in a subcutaneous pocket inferior to the clavicle over the pectoralis fascia. The distal end of the STL 1300 (cuff 1350) may be implanted on the hypoglossal nerve or a branch of the hypoglossal nerve in the submandibular region, and the proximal end of the STL 1300 may be tunneled under the skin to the INS 1100. The RSL 1200 may be tunneled under the skin from the INS 1100 to the rib cage and placed on the costal margin. The INS 1100 detects respiration via the RSL 1200 using bio-impedance.

Stimulation Lead (STL)

Figure 60:
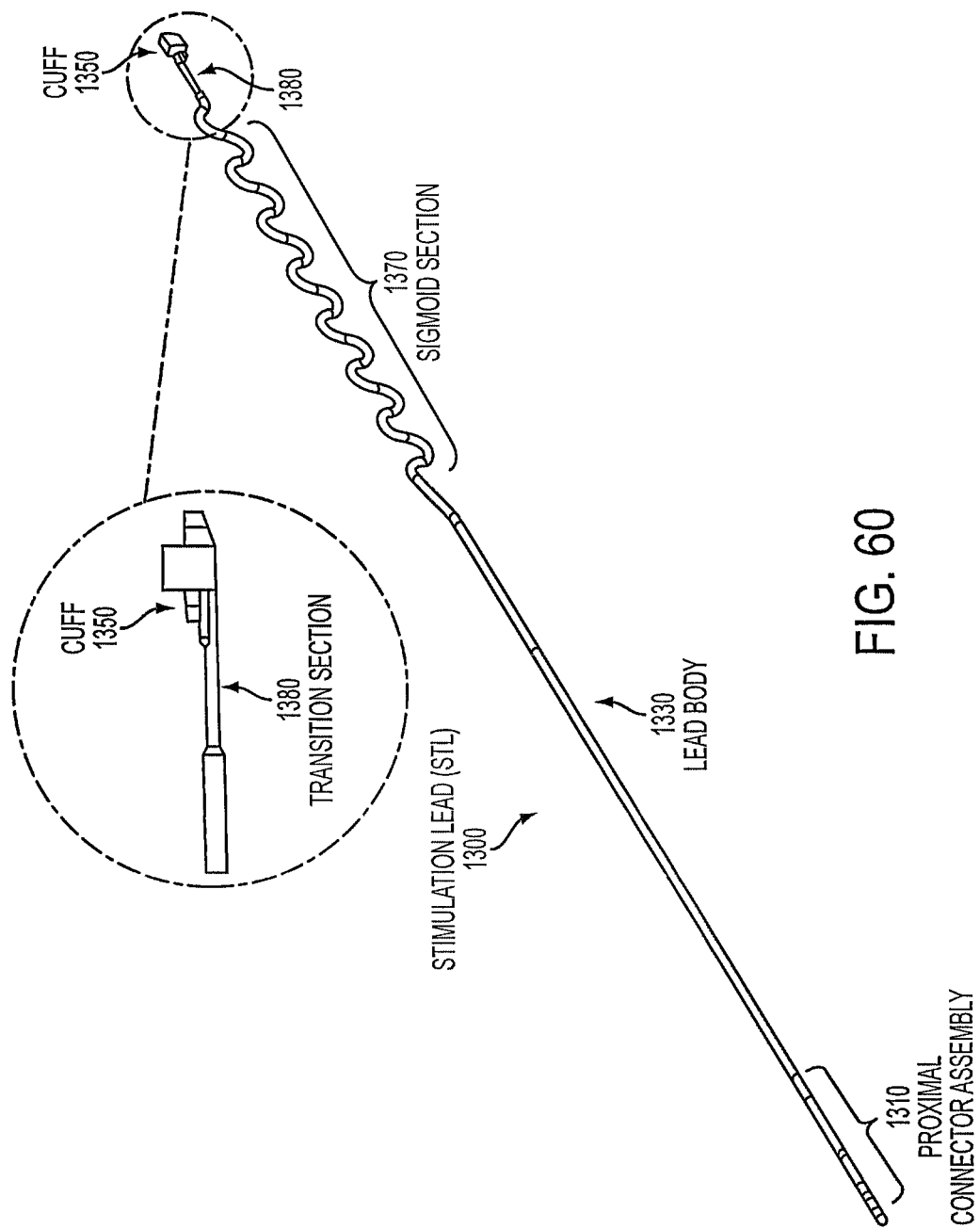
FIG. 60 is a perspective view of a stimulation lead for use in the system shown in FIG. 59, including a detailed view of the distal end of the stimulation lead.

FIG. 60 schematically illustrates the STL 1300 in more detail. The STL 1300 is designed to deliver the stimulation signal from the INS 1100 to the hypoglossal nerve and includes a proximal connector assembly 1310, a main tubular body 1330, and a distal cuff 1350. The main tubular body of the STL includes a sigmoid shaped section 1370 and a distal flexible transition section 1380 proximal of the cuff. The STL may have a nominal outside diameter of 0.062 inches to have minimal cosmetic impact, and a nominal overall length of 17.7 inches (45 cm) (including cuff) to extend from the infraclavicular region (INS) to the submandibular region (hypoglossal nerve) and to accommodate anatomical variation.

The main tubular body 1330 of the STL 1300 is designed to withstand gross neck movement as well as mandibular movement and hypoglossal nerve movement caused by talking, chewing, swallowing, etc. To survive in this high fatigue environment, the main tubular body 1330 incorporates a highly compliant silicone jacket in the form of a sigmoid, and two conductors 1390 (one for cathode electrodes, one for anode electrodes) each comprising ETFE insulated MP35N multifilament cable disposed inside the jacket in the form of a bi-filar coil (not visible). This design provides high fatigue resistance and three-dimensional flexibility (bending and elongation).

The proximal connector assembly 1310 is designed to provide a reliable mechanical and electrical connection of the STL 1300 to the INS 1100. It has a number of strain relief elements that enable it to withstand handling during insertion and removal from the INS 1100, as well as adverse conditions encountered when implanted. The connector assembly 1310 includes two in-line stainless steel ring contacts (one for each conductor 1390) and two silicone ring seals. STL proximal connector contacts 1310 may have a nominal outside diameter of about 0.122 inches. Set screws in the header of the INS 1100 bear down on the contacts, and together with the ring seals, provide a sealed mechanical and electrical connection to the INS 1100. As an alternative, wound coil spring contacts may provide mechanical and electrical connections.

Figure 61A:
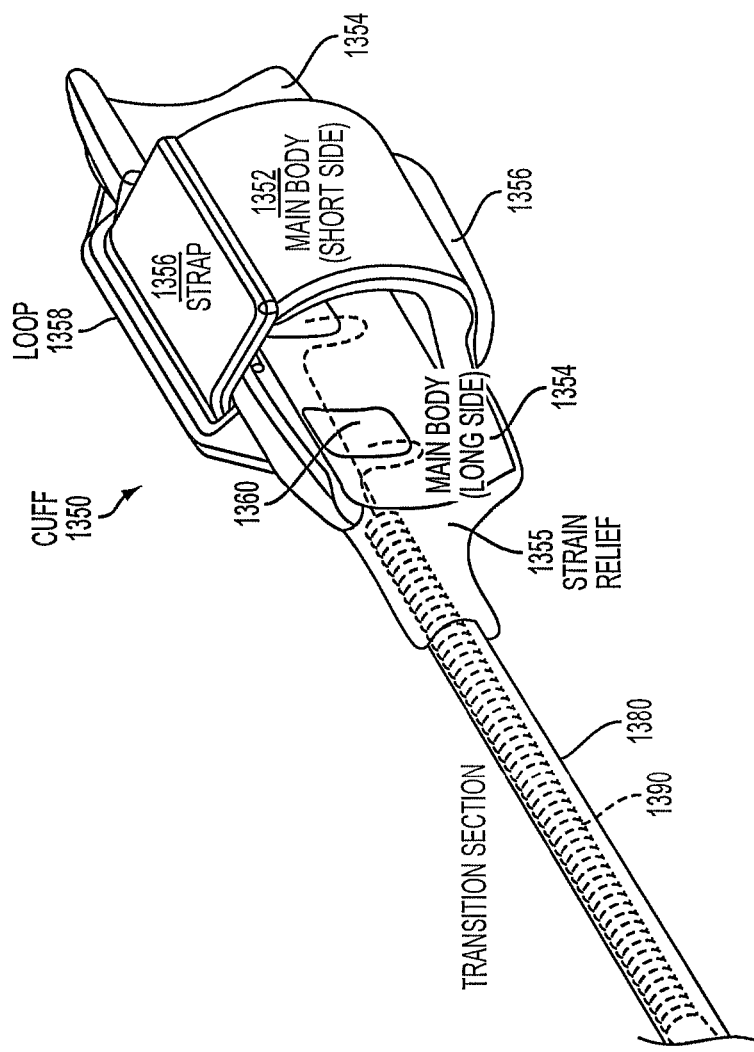
FIG. 61A is a detailed perspective view of the cuff of the stimulation lead shown in FIG. 60.
Figure 61B:
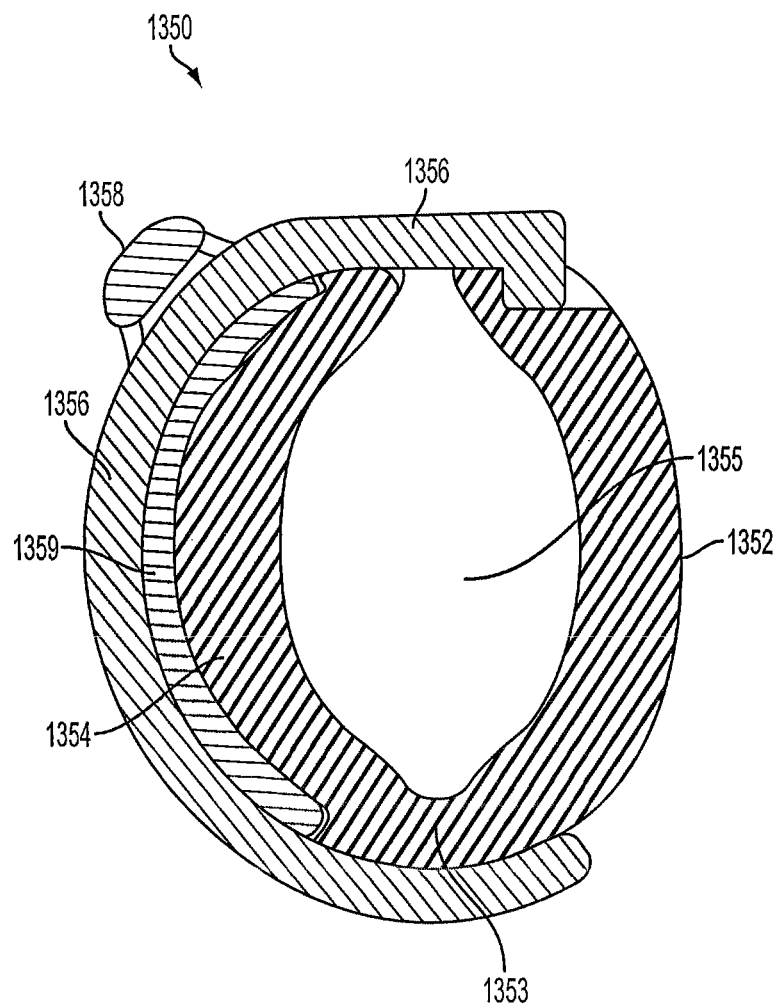
FIG. 61B is a lateral cross-sectional view of the cuff shown in FIGS. 60 and 61A.

More detailed views of the cuff 1350 are shown in FIGS. 61A and 61B, wherein FIG. 61A schematically illustrates the cuff 1350 in isometric view, and FIG. 61B schematically illustrates the cuff 1350 in cross-sectional view. The cuff 1350 has a hinged oval-shaped silicone body (collectively 1352 and 1354) to define an oval lumen 1355 that provides secure and gentle retention around the hypoglossal nerve. The cuff 1350 may be designed to fit the nerve very closely to minimize tissue growth between the electrode and nerve. The cuff is designed to be self-sizing such that different nerve diameters may be accommodated safely. The self-sizing can safely adjust to larger sizes if swelling occurs. This reduces the likelihood of nerved damage caused by unsafe pressures. Thus, the cuff may be available in two sizes to accommodate nerves of different diameter: a small size to accommodate nerves having a diameter of up to about 2.5-3.0 mm, and a large size to accommodate nerves having a diameter of up to 3.2-4.0 mm. At 3.0 mm nerve diameter, either size cuff will fit the nerve with minimal open space for tissue ingrowth. Using a large cuff on a 2.5 mm nerve allows clearance between the nerve and electrode which promotes capsule formation between the cuff and nerve. This may cause an increase in capture threshold but will not affect safety. Conversely, a small cuff placed on a large nerve minimizes electrode coverage around the nerve and may fall off with swelling. The short side 1352 (e.g., 4.0 mm long) of the cuff body fits between nerve branches and connective tissue on the deep side of the nerve, thereby minimization nerve dissection. The long side 1354 (e.g., 10.0 mm long) of the cuff body rests on the superficial side of the nerve (where few branches exist) and is connected to the transition section 1380 of the main lead body 1330.

A silicone strap 1356 is connected to and extends from the short side 1352 of the cuff body. A silicone top plate comprising an integral base portion 1359 and loop 1358 is attached to and covers the exterior surface of the long side 1354 of the cuff body. The strap 1356 freely slides through the loop 1358, and wraps around the long side 1354 of the cuff body. The strap 1356 is removed from the loop 1358 for placement of the cuff 1350 around the nerve and reinserted into the loop 1358 to hold the cuff 1350 on the nerve. A mark may be disposed on the strap 1356 of the small size cuff to indicate that the cuff is too small and that a larger size cuff should be used if the mark does not pass through the loop 1358. The cuff body readily expands along a hinge line 1353 (defined at the junction of the short side 1352 to the long side 1354) as well as other portions of the cuff 1350 structure. Expansion of the cuff body accommodates nerves of different diameters and nerve swelling after implantation, while the strap 1356 remains in the loop 1358 to retain the cuff 1350 on the nerve. In the event of excess nerve swelling (e.g., >50% increase in nerve diameter) or traction from the lead 1300 (e.g., as may accidentally occur during implantation), the strap 1356 pulls out of the loop 1358 and releases the cuff 1350 from the nerve to minimize the potential for nerve damage.

The cuff body carries four platinum-iridium electrodes 1360 (e.g., 2.0 mm$^2$ exposed area each for small cuff, 3.0 mm$^2$ exposed area each for large cuff), with one cathode electrode 1360 on the short side 1352, another cathode electrode 1360 (not visible) diametrically opposed on the long side 1354, and two anode electrodes 1360 guarding the cathode electrode 1360 on the long side 1354. This guarded dual cathode arrangement provides a more uniform electrical field throughout the cross-section of the nerve while minimizing electrical field outside of the cuff. One conductor 1390 may be connected to the cathode electrode 1360 on the long side, to which the other cathode electrode 1360 on the short side is connected by a jumper wire. Similarly, the other conductor 1390 may be connected to the distal anode electrode 1360, to which the proximal anode electrode 1360 is connected by jumper wire. With this arrangement, the cathode electrodes are commonly connected to one conductor 1390 and the anode electrodes are commonly connected to the other conductor 1390.

With the exception of the metal electrode contacts in the cuff, all external surfaces of the STL 1300 exposed to the body when implanted may comprise implantable grade polymers selected from the following: silicone, and fully cured silicone adhesive. The metal electrode contacts in the cuff may comprise implantable grade platinum-iridium and are secured to the silicone cuff body with silicone adhesive, for example.

Respiration Sensing Lead (RSL)

Figure 62A:
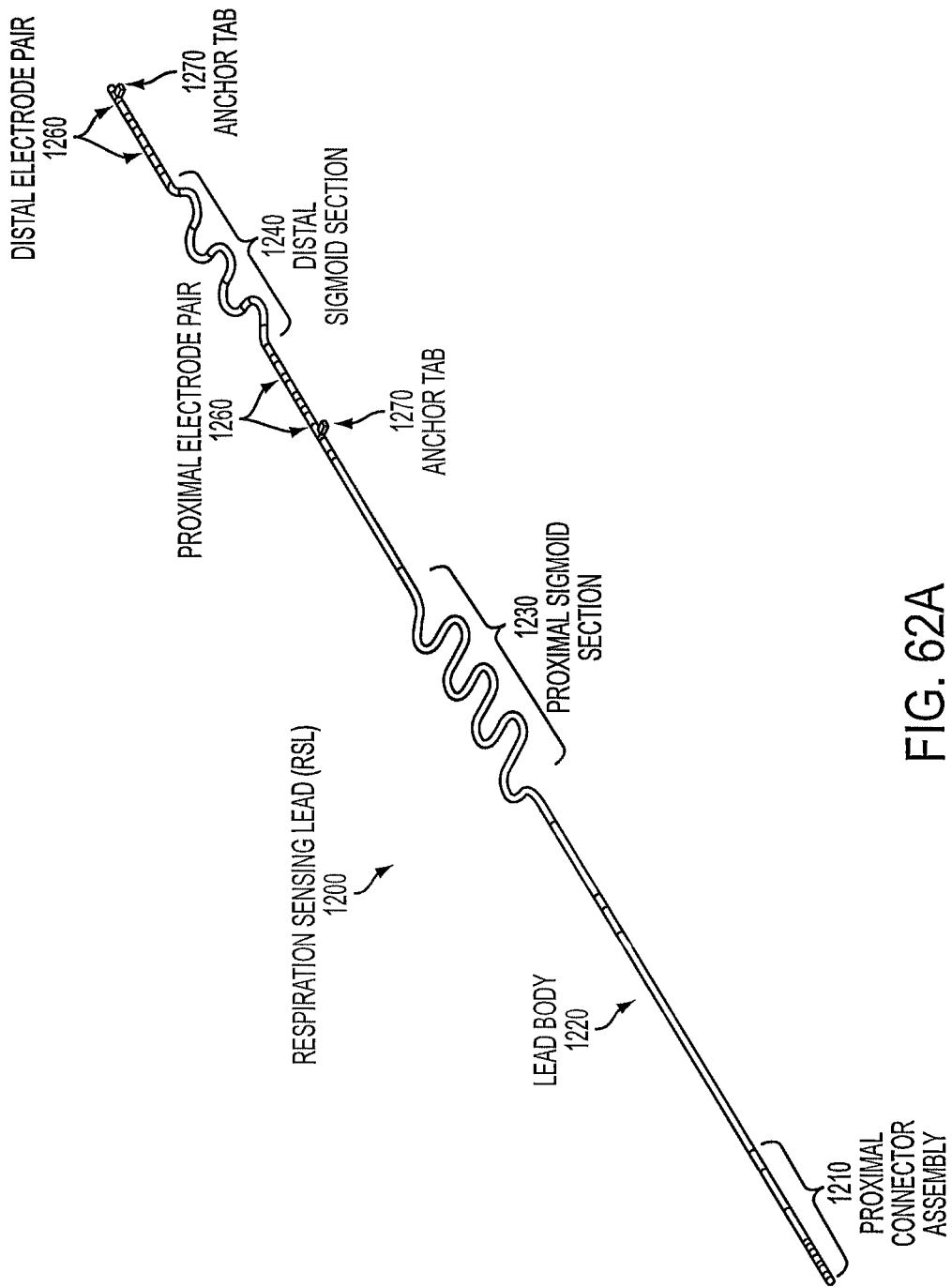
FIG. 62A is a perspective view of a respiration sensing lead for use in the system shown in FIG. 59.
Figure 62B:
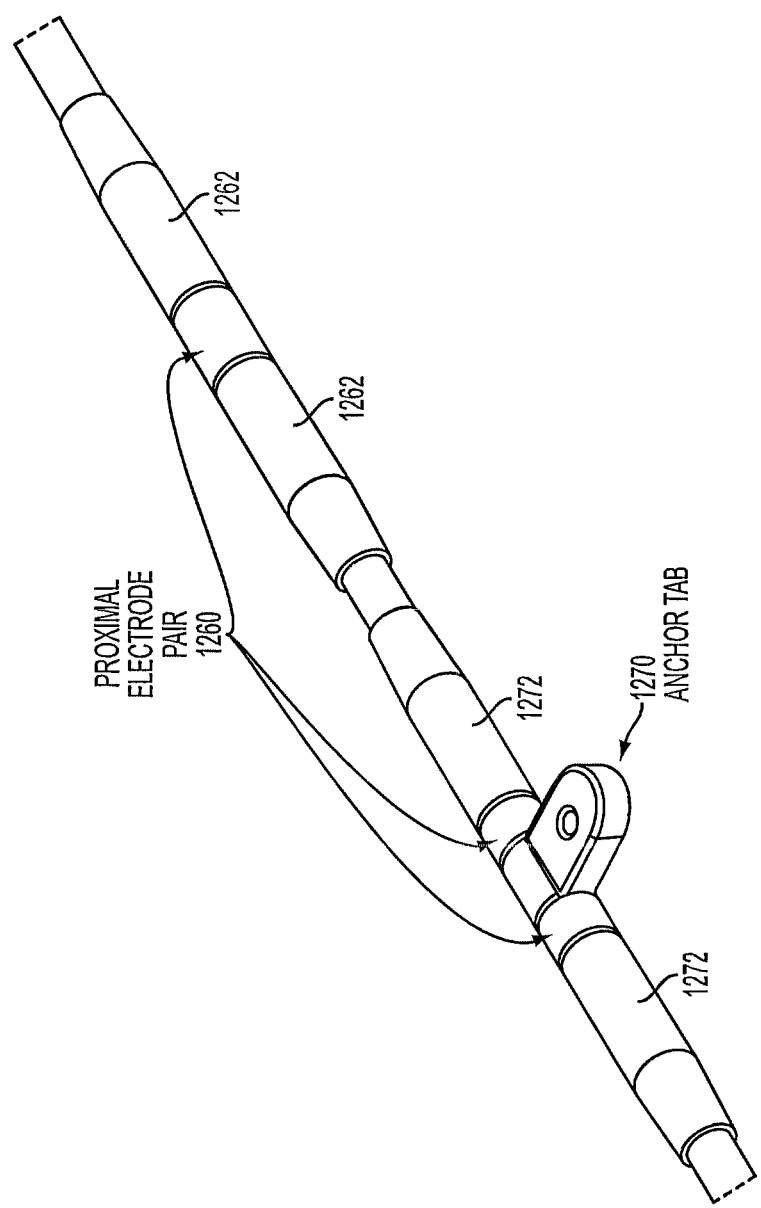
FIG. 62B is a detailed perspective view of the proximal electrode pair of the respiration sensing lead shown in FIG. 62A.

FIGS. 62A and 62B schematically illustrate the respiration sensing lead 1200 in more detail. The respiration sensing lead 1200 is designed to measure bio-impedance and includes a proximal connector assembly 1210, a main tubular body 1220, and two distal ring electrode pairs 1260. The main tubular body 1220 of the RSL 1200 includes a proximal sigmoid section 1230 and a distal sigmoid section 1240 between the electrode pairs 1260. The RSL 1200 may have a nominal outside diameter of 0.072 inches to have minimal cosmetic impact, and an overall length of 24.3 inches (61.6 cm) unstretched, 32.0 inches (81.3 cm) stretched to extend from the infraclavicular region (where the INS 1100 is implanted) to the right or left rib cage (where the RSLs 1200 may be implanted) and to accommodate anatomical variation.

The main tubular lead body 1220 of the RSL 1200 is designed to withstand thoracic movement due to flexion, extension, rotation and breathing. To withstand this environment, the main tubular body 1220 may include a flexible silicone jacket formed into two sigmoid sections 1230, 1240 and four conductors comprising small diameter ETFE insulated MP35NLT wires (not visible) disposed inside the jacket in the form of a quad-filar coil. The proximal sigmoid section 1230 isolates movement of the INS 1100 from the electrode pairs 1260 and accommodates anatomic variations in thoracic length. The distal sigmoid section 1240 allows adjustment in the distance between electrode pairs 1260 and reduces strain applied between the anchor tabs 1270, which may be secured with sutures to the underlying fascia when implanted. The proximal sigmoid 1230 section may have 3 1/2 wavelengths with a peak-to-peak dimension of approximately 0.94 inches (2.4 cm) and an overall length of 5.5 inches (14.0 cm). The distal sigmoid 1240 section may have 2 1/2 wavelengths with a peak-to-peak dimension of approximately 0.94 inches (2.4 cm) and an overall length of 5.5 inches (14.0 cm).

The two distal electrode pairs 1260 may comprise four electrodes total, and each may comprise MP35N rings having an exposed surface area of 28.0 mm$^2$, for example. As shown in FIG. 62B, tubular strain relief segments 1262 and 1272 may be disposed on the lead body on either side of each electrode 1260. Where the strain relief segments 1262 and 1272 are adjacent each other, a gap may be provided there between as shown in FIG. 62B or the segments may abut each other to avoid a stress concentration point. The anchor tab 1270 may be disposed over an electrode as shown in FIG. 62B leaving the proximal and distal extremities of the electrode exposed.

At any given time, the INS 1100 detects impedance along a vector, with each end of the vector defined by one active pair of electrodes 1260. In each active pair of electrodes 1260, one electrode delivers a small excitation current, and the other electrode monitors the corresponding change in voltage. The INS 1100 may also act as a current emitting and/or voltage sensing electrode. Changes in impedance are calculated by dividing the change in voltage by the excitation current, which correspond to movement of the diaphragm and lung to produce a signal indicative of respiratory activity.

The proximal connector assembly 1210 of the RSL 1200 is designed to provide a reliable mechanical and electrical connection of the RSL 1200 to the INS 1100. It has a number of strain relief elements that enable it to withstand handling during insertion and removal from the INS 1100, as well as adverse conditions encountered when implanted. The connector assembly 1210 may include four in-line stainless steel ring contacts (one for each conductor) and four silicone ring seals. Set screws in the header of the INS 1100 bear down on the contacts, and together with ring seals, provide a sealed mechanical and electrical connection to the INS 1100.

With the exception of the distal electrodes, all external surfaces of the RSL 1200 exposed to the body when implanted may comprise implantable grade polymers selected from the following: silicone, and fully cured silicone adhesive. The distal electrodes may comprise implantable grade MP35N and are sealed to the lead body with silicone adhesive, for example.

Figure 62C:
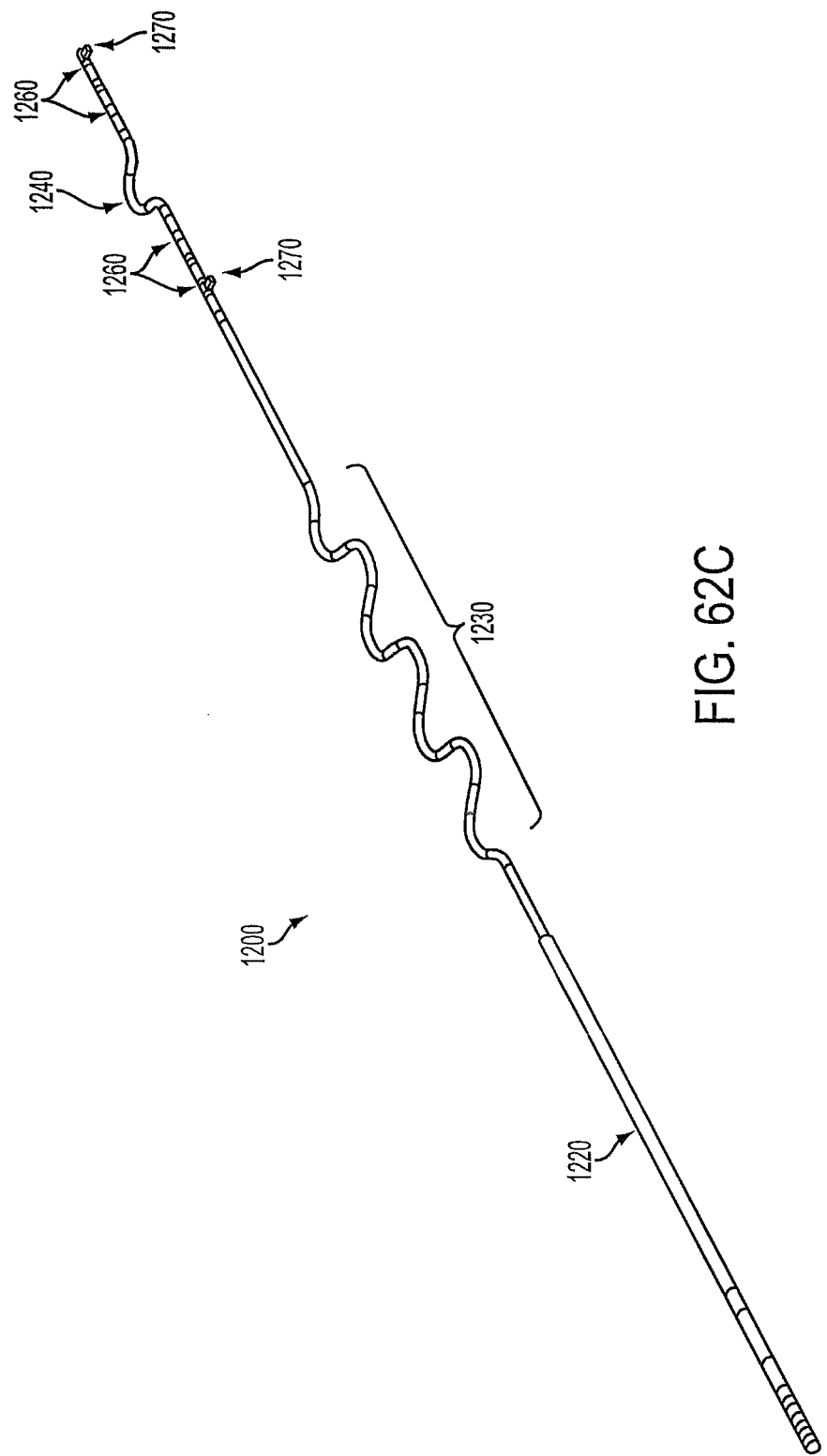
FIG. 62C is a perspective view of an alternative respiration sensing lead for use in the system shown in FIG. 59.

FIG. 62C schematically illustrates an alternative embodiment of the respiration sensing lead 1200. In this embodiment, the RSL 1200 may have a nominal outside diameter of 0.072 inches to have minimal cosmetic impact, and an overall length of 23.5 inches (59.7 cm) unstretched, 26.5 inches (67.2 cm) stretched. The proximal sigmoid 1230 section may have 3 1/2 wavelengths with a peak-to-peak dimension of approximately 0.94 inches (2.4 cm) and an overall length of 5.5 inches (14.0 cm). The distal sigmoid 1240 section may have 1/2 wavelength with an amplitude of approximately 1.7 inches (4.4 cm) and an overall length of about 0.5 inches (1.3 cm).

FIGS. 78A-78G schematically illustrate the respiration sensing lead (RSL) 1200 in more detail. The respiration sensing lead 1200 is designed to measure bio-impedance and includes a proximal portion with a proximal connector assembly 1210, a proximal tubular body 1220 ending in a bifurcation section 1280, and ipsi-lateral and contra-lateral distal portions extending from the bifurcation section. Each distal portion may include a tubular body 1220, a proximal sigmoid section 1230, a distal sigmoid section 1240, one or more current injection ring electrodes 1250, one or more voltage sensing ring electrodes 1260, anchor tabs 1270, and a suture hole 1290 in the most distal ring electrodes. Alternatively, the ring electrodes 1250 and 1260 may be dual-function, such that each electrode may function as either a current emitting electrode or voltage sensing electrode. The ipsi-lateral distal portion may contain three ring electrodes, the most distal being a current emitting electrode 1250 and containing a suture hole 1290, and the other two electrodes being voltage sensing electrodes 1260. The contra-lateral distal portion may contain two ring electrodes, the distal being a current emitting electrode 1250 and containing a suture hole 1290, and the proximal a voltage sensing electrodes. It may be advantageous to have the suture holes in the most distal ring electrodes since no wires pass through this point and because this provides a robust anchor point for the electrode to be sutured on the costal margin muscle fascia. The RSL 1200 may have a nominal outside diameter of about 0.072 inches to have minimal cosmetic impact. The RSL proximal connector contacts 1210 may have a nominal outside diameter of about 0.122 inches (same as the STL proximal connector contacts 1310). The distal ring electrodes (here, current emitting electrodes 1250), may also have a nominal outside diameter of 0.122 inches. This uniformity in diameters may be advantageous, allowing the same lead carrier 3100 to place both STL 1300 and RSL 1200 leads for tunneling.

The distance from the tip of the proximal connector 1210 to the bifurcation section 1280 may have an overall length of 8.9 inches (22.5 cm). The distance from the bifurcation section 1280 to the ipsi-lateral proximal anchor tab 1270 may be 9.6 inches (24.4 cm) unstretched and 12.2 inches (31 cm) stretched. The distance from the bifurcation section 1280 to the contra-lateral proximal anchor tab 1270 may be 13.5 inches (34.3 cm) unstretched and 16.1 inches (41 cm) stretched. The distance from the proximal anchor tab 1270 to the distal suture hole 1290 may be 2.8 inches (7 cm) unstretched and 3.1 inches (8 cm) stretched on both the contra-lateral and ipsi-lateral distal portions. The RSL 1200 may extend from the infraclavicular region (where the INS 1100 is implanted) to the ipsi-lateral and contra-lateral thorax where the RSL 1200 may be implanted to accommodate anatomical variation.

The bifurcated RSL 1200 design enables one RSL 1200 to sense bio-impedance on the contra-lateral and ipsi-lateral sides of the thorax. Two RSLs 1200, one on each side of the patient's chest, may also achieve this. The bifurcated design achieves this result while reducing the number of implanted components and reducing volume of the INS header 1110 since only one RSL port 1112 is required.

The main tubular lead body 1220 of the RSL 1200 is designed to withstand thoracic movement due to flexion, extension, rotation and breathing. To withstand this environment, the main tubular body 1220 may include a flexible silicone jacket formed such that each distal end has two sigmoid sections, 1230 and 1240, and conductors comprising small diameter ETFE insulated MP35NLT cables (not visible) disposed inside the jacket. An injection molded Y-fitting (yoke) connects the proximal portion of the RSL 1200 to the distal portions, creating the bifurcation section 1280. Conductors, here five, are continuously fed from the connector assembly through the proximal tubing body 1220 and proximal portion of the Y-fitting. Three of these conductors continue through the ipsi-lateral distal portion of the Y-fitting to the ipsi-lateral distal tubing body of the RSL. The other two conductors continue through the contra-lateral distal portion of the Y-fitting and to the contra-lateral distal tubing body of the RSL. The tubing bodies may be adhesively bonded or molded to the Y-fitting. The number of conductors may equal the number of contacts in the INS header 1112, here five. Two of the conductors, one on each side, may connect proximally to current emitting header contacts, (e.g., R1 and L1), and terminate distally in current emitting electrodes 1250. Three of the conductors may connect proximally to voltage sensing header contacts (e.g., R2, R3, and L3) and terminate distally in voltage sensing electrodes. As mentioned previously, dual-function electrodes may enable any electrode (ring electrode 1250 or 1260) to emit current or sense voltage. This switching may occur via components on the INS circuit board 1130. Alternatively, a bridge may be formed joining two contacts in the proximal connector assembly such that the corresponding electrode may function as either a current emitting electrode 1250 or voltage sensing electrode 1260. Dual-function electrodes enable more vectors in an implanted region without additional electrodes.

The proximal sigmoid section 1230 isolates movement of the INS 1100 from the electrodes 1250 and 1260, and accommodates anatomic variations in thoracic length. The distal sigmoid section 1240 allows adjustment in the distance between electrodes 1250 and 1260, and reduces strain applied between the anchor tabs 1270, which may be secured with sutures to the underlying fascia when implanted. The proximal sigmoid 1230 section may have 5 wavelengths with an outside peak-to-peak dimension of approximately 0.84 inches (2.1 cm) and an overall length of 7.0 inches (17.8 cm). The distal sigmoid 1240 section may have half a wavelength with a center-to-center peak-to-peak dimension of approximately 0.43 inches (2.1 cm) and an overall length of 0.869 inches (2.2 cm).

The two distal portions' electrodes 1250 and 1260 may comprise five electrodes total, and each may comprise MP35N rings having an exposed surface area. The distal electrode containing a suture hole 1290 may have an exposed surface area of 73.8 $mm^2$ including the suture hole 1290, and 66.4 $mm^2$ not including the suture hole 1290. The proximal electrode containing an anchor tab 1270 may have an exposed surface area of 30.5 $mm^2$ and the electrode without an anchor tab may have an exposed surface area of 32.0 $mm^2$. Tubular strain relief segments may be disposed on the lead body on either side of electrode 1250 or 1260. Where the strain relief segments are adjacent to each other, a gap may be provided there between the strain relief segments or the segments may abut one another to avoid a stress concentration point. Strain reliefs may also be disposed on each end of the electrodes 1250 or 1260 to avoid stress concentration points. The anchor tab 1270 may be disposed over an electrode leaving the proximal and distal extremities of the electrode exposed.

At any given time, the INS 1100 detects impedance along a vector, with each end of the vector defined by a current delivery electrode 1250 and a voltage sensing electrode 1260. In each vector, a small excitation current is delivered between the two current emitting electrodes 1250, and the corresponding change in voltage is measured by the two voltage sensing electrodes 1260. The INS housing 1120 may also act as a current emitting and/or voltage sensing electrode, or contain smaller current emitting and/or voltage sensing electrodes on its surface. Changes in impedance are calculated by dividing the change in voltage by the excitation current, which correspond to movement of the diaphragm, lung, and other tissues to produce a signal indicative of respiratory activity.

The proximal connector assembly 1210 of the RSL 1200 is designed to provide a reliable mechanical and electrical connection of the RSL 1200 to the INS 1100. It has a number of strain relief elements that enable it to withstand handling during insertion and removal from the INS 1100, as well as adverse conditions encountered when implanted. The connector assembly 1210 may include five in-line stainless steel ring contacts (one for each conductor) and five silicone ring seals. Set screws in the header of the INS 1100 bear down on the contacts, and together with ring seals, provide a sealed mechanical and electrical connection to the INS 1100. Ring seals may be part of the RSL 1200 or the INS header 1110. With the exception of the distal electrodes, all external surfaces of the RSL 1200 exposed to the body when implanted may comprise implantable grade polymers selected from the following: silicone, and fully cured silicone adhesive. The distal electrodes may comprise implantable grade MP35N and are sealed to the lead body with silicone adhesive, for example.

A wide variety of respiration sensing lead designs may be employed to provide at least one bio-impedance vector (current injection electrode pair and voltage sensing electrode pair) from a point along the costal margin to a point along the opposite (trans-lateral) costal margin, to a point along the same side (ipsi-lateral) costal margin, or to a point in the infraclavicular region, as seen in FIG. 78C. For example, an alternative embodiment of the RSL 1200 is shown in FIG. 78B, wherein the bifurcation section 1280 and contra-lateral distal portion are eliminated. In this three electrode straight RSL 1200 embodiment, there is one current emitting ring electrode 1250 and two voltage sensing ring electrodes 1260. The lead body may contain three conductors. The connector assembly 1210 may include three in-line stainless steel ring contacts (one for each conductor) and three silicone ring seals. The RSL may have an overall length of 21.2 inches (53.9 cm). The distance from the proximal tip of the proximal connector assembly 1210 to the first sigmoid may be 9.5 inches (24.1 cm). The proximal sigmoid 1230 section may have 5 wavelengths with an outside peak-to-peak dimension of approximately 0.84 inches (2.1 cm) and an overall length of 7.0 inches (17.8 cm). The distal sigmoid 1240 section may have a ½ wavelength with a center-to-center peak-to-peak dimension of approximately 0.43 inches (2.1 cm) and a length of 0.869 inches (2.2 cm). The RSL 1200 may be implanted ipsi-laterally on the ipsi-lateral costal margin, a less invasive surgery, while maintaining vectors from the ipsi-lateral costal margin to the infraclavicular region, see FIG. 78D.

Further alternative embodiments are illustrated in FIGS. 78E, 78F, 78G, and 78H, wherein the RSL 1200 may contain four electrodes, one or more of which can function as either a current emitting electrode 1250 or voltage sensing electrode 1260, as described previously. Here, this is achieved by exposing the conductor of the bi-functional electrode to two contacts (one voltage sensing, one current emitting) in the INS header 1110, and selecting only one contact for sensing. Alternatively, this functionality may be built into the INS circuit board 1130. These embodiments of the RSL 1200 may be implanted ipsi-laterally (e.g. on the right costal margin), which is a less invasive surgery, while maintaining vectors from the ipsi-lateral costal margin to the infraclavicular region.

Figure 78E:
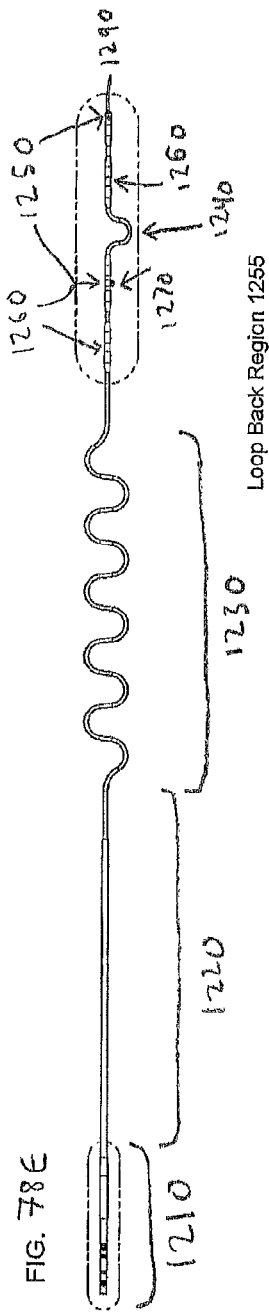
FIG. 78E illustrates an alternative embodiment of the respiration sensing lead which may be used in the system shown in FIG. 77.

FIG. 78E illustrates a straight four electrode RSL 1200. This is similar in design to the RSL 1200 of FIG. 78B, wherein there are a first, second, third, and fourth electrodes, from proximal to distal.

Figure 78F:
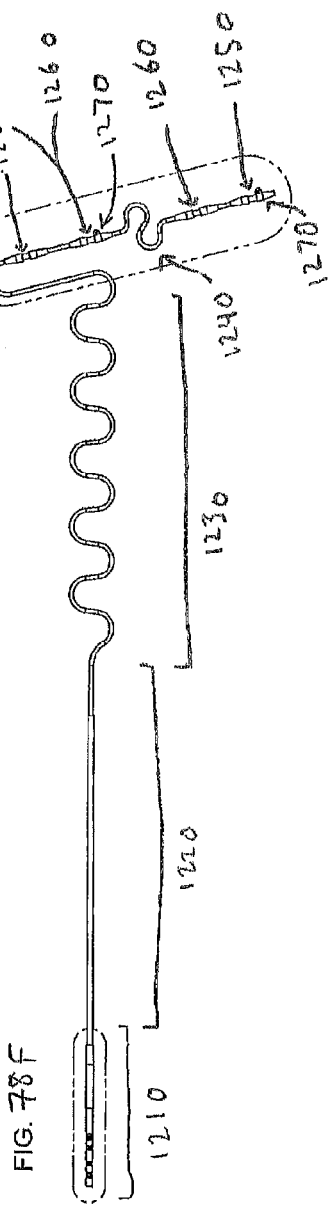
FIG. 78F illustrates an alternative embodiment of the respiration sensing lead containing a loop-back region. This lead may be used in the system shown in FIG. 77

FIG. 78F illustrates a four electrode RSL 1200 with a loop back region 1255. This differs from the above embodiments in that there is an extra half sigmoid in the proximal sigmoid section 1230 after which the lead body enters the loop back region 1255. Here, the lead body runs in the medial direction, then loops back in the lateral direction. The loop back region 1255 may act as a strain relief and allow the medial anchor tab 1270 to be sutured at the intersection of the two tunneling paths (from INS incision to medial incision, and between two RSL incisions). This may allow the RSL 1200 to lie in an unbiased preferred configuration along the costal margin. Here again, the first and third most distal electrodes are current emitting, and the second, third, and fourth most distal electrodes are voltage sensing.

Figure 78G:
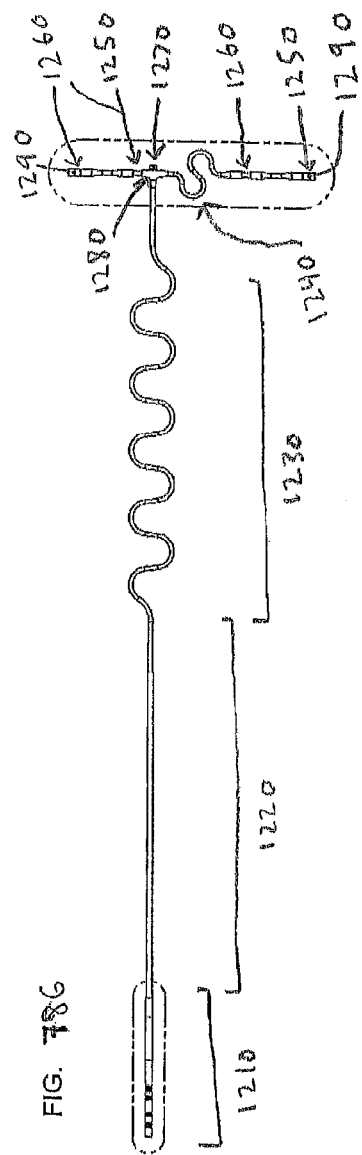
FIG. 78G illustrates an alternative embodiment of the respiration sensing lead which may be used in the system shown in FIG. 77.

FIG. 78G illustrates a four electrode RSL 1200 with a bifurcation section 1280 created by a T-fitting. An injection molded T-fitting connects the proximal portion of the RSL 1200 to the distal portions, creating the bifurcation section 1280. Conductors, here four, are continuously fed from the connector assembly through the proximal tubing body 1220 and proximal portion of T-fitting. Two of these conductors continue through the proximal distal portion of the T-fitting to the proximal distal tubing body of the RSL. The other two conductors continue through the medial distal portion of the T-fitting and to the medial distal tubing body of the RSL. The tubing bodies may be adhesively bonded or molded to the T-fitting. The anchor tab 1270 may be adhesively bonded to the bifurcation section 1280. Again, this may allow the RSL 1200 to lie in an unbiased preferred configuration along the costal margin. In addition, the T-fitting may act as a strain relief. Both medial and lateral distal electrodes may contain suture holes 1290.

Figure 78H:
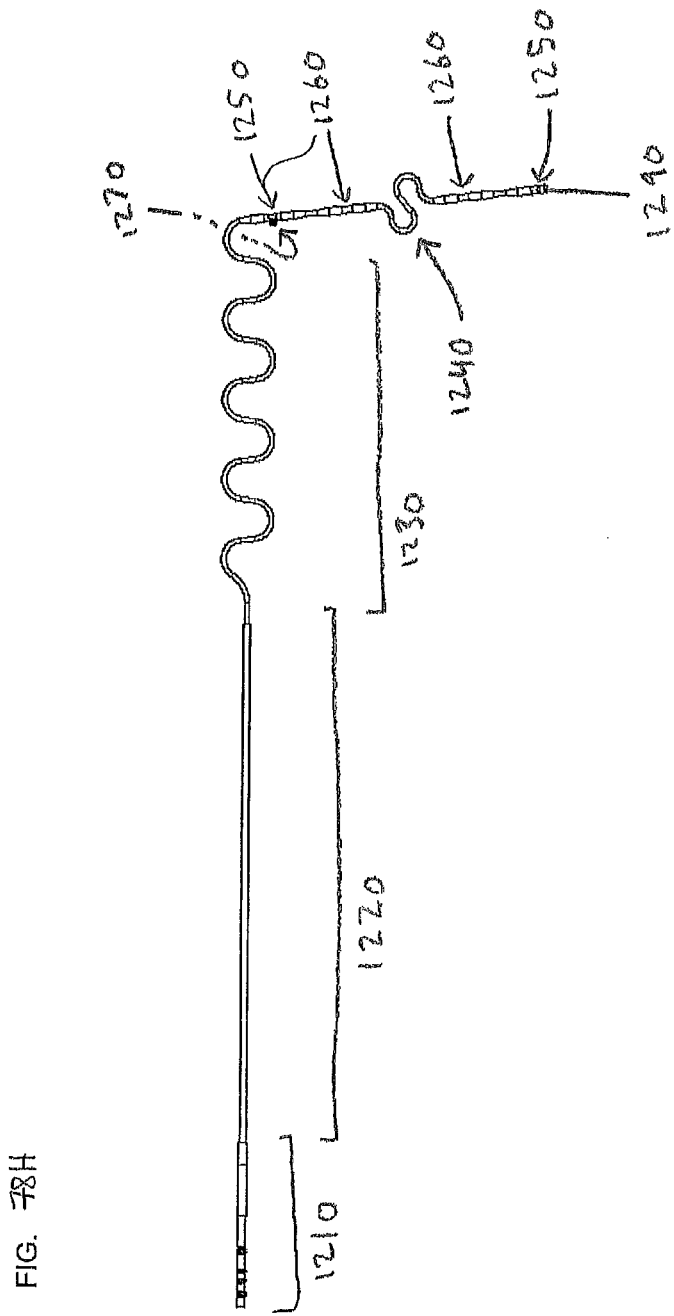
FIG. 78H illustrates an alternative embodiment of the respiration sensing lead which may be used in the system shown in FIG. 77.

FIG. 78H illustrates an alternative embodiment of the RSL 1200, wherein the RSL 1200 has an overall L-shape. In this embodiment, there may be four ring electrodes, numbered one through four from most proximal to furthest distal. The first and fourth electrodes may be current emitting electrodes 1250. The second and third electrodes may be voltage sensing electrodes 1260. The lead body may contain four conductors. The connector assembly 1210 may include four in-line stainless steel ring contacts (one for each conductor) and four silicone ring seals. The proximal portion of the RSL 1200 (including the proximal connector and proximal sigmoid) may have an overall length of 17.0 inches (43.2 cm). The distance from the proximal tip of the proximal connector assembly 1210 to the first sigmoid may be 11.1 inches (28.1 cm). The proximal sigmoid 1230 section may have 4.5 wavelengths, each wavelength 1.25 inches (3.2 cm), and with an outside peak-to-peak dimension of approximately 0.84 inches (2.1 cm). The distal portion of the RSL 1200 (from the distal end of the proximal sigmoid 1230 to the distal suture hole 1290) may have an overall length of 4.9 inches (12.5 cm). The length from the distal end of the proximal sigmoid 1230 to the proximal end of the distal sigmoid 1240 may be 2.2 inches (5.7 cm). The length from the distal end of the distal sigmoid 1240 to the distal suture hole 1290 may be 1.8 inches (4.6 cm). The distal sigmoid 1240 section may have a center-to-center peak-to-peak dimension of approximately 0.92 inches (2.3 cm). The RSL 1200 may be implanted ipsi-laterally on the ipsi-lateral costal margin, a less invasive surgery, while maintaining vectors from the ipsi-lateral costal margin to the infraclavicular region.

Implantable Neurostimulator (INS)

Figure 63A:
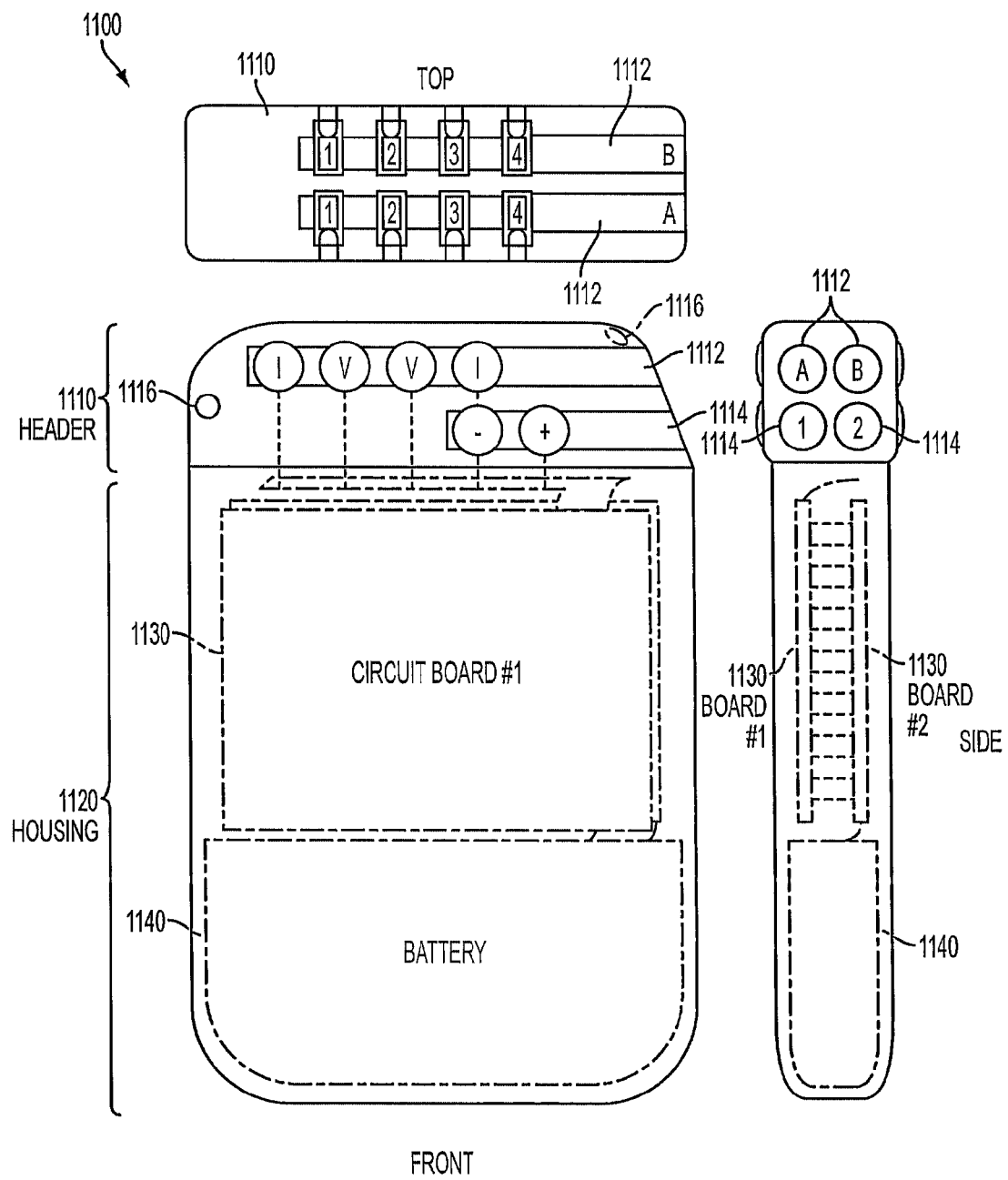
FIG. 63A shows front, side and top views of an implantable neurostimulator for use in the system shown in FIG. 59.

FIG. 63A schematically illustrates the INS 1100 in more detail, including a front view, a top view and a side view. The INS 1100 is similar in certain aspects to commercially available implantable pulse generators and implantable neurostimulators, which may be obtained from suitable manufacturers such as CCC Medical Devices (Montevideo, Uruguay). The INS 1100 generally includes a header 1110 for connection of the STL 1300 and RSLs 1200, and a hermetically sealed housing 1120 for containing the associated electronics 1130 and battery 1140 (e.g., WGL 9086).

The electronic circuitry 1130 contained in the INS 1100 enables telemetry communication with the programmer system 2100 and therapy controller 2500, detection of respiration via the RSLs 1200, determination of the trigger point for stimulation, and delivery of a controlled electrical stimulation signal (pulse train) via the STL 1300. The INS 1100 also records therapy data (device settings, respiration data, stimulation delivery data, etc.).

The header 1110 may comprise epoxy that is hermetically sealed to the housing 1120. The housing 1120 may comprise titanium. As mentioned in the context of respiration sensing, the housing 1120 may be used as an electrode for bio-impedance respiration measurement. For example, the housing 1120 may comprise a combination current emitting and voltage sensing electrode for respiration detection.

The header 1110 includes four ports: two RSL ports 1112 (labeled "sense" A and B) for receiving the proximal connectors of up to two RSLs 1200 and two STL ports 1114 (labeled "stim" 1 and 2) for receiving the proximal connectors of up to two STLs 1300. Each port that is configured to receive a STL 1300 includes two set screws (labeled "−" for cathode and "+" for anode) with associated set screw blocks and seals for mechanical and electrical connection to corresponding contacts on the proximal connector 1310 of the STL 1300. Similarly, each port that is configured to receive a RSL 1200 includes four set screws (two labeled "I" for current emitting electrodes and two labeled "V" for voltage sensing electrodes) with associated set screw blocks and seals for mechanical and electrical connection to corresponding contacts on the proximal connector 1210 of the RSL 1200. The header 1110 farther includes two suture holes 1116 (only one is visible) for securing the INS 1100 to subcutaneous tissue such as muscle fascia using sutures when implanted in a subcutaneous pocket. As shown, approximate dimensions, component values and component configurations are given by way of example, not limitation.

The INS 1100 generates the stimulation output for delivery to the hypoglossal nerve by way of the STL 1300. For this purpose, the INS 1100 has two bipolar stimulation output channels, one channel corresponding to each STL port 1114, with each channel providing a pulse train of constant current with a frequency range of 20 to 50 Hz, a pulse width range of 30 to 215.mu.s, an amplitude range of 0.4 to 5.0 mA, and a stimulation duty cycle range of 41%-69%, by way of example, not limitation.

The INS 110 also generates the excitation signal and measures voltage by way of the RSLs 1200 for bio-impedance respiration detection. For this purpose, the INS 1100 also has two respiration sensing channels, one channel corresponding to each RSL port 1112, with each channel providing a small excitation current ("I") and measuring voltage ("V"). The excitation signal may comprise a 10 Hz biphasic constant current pulse, with the positive and negative phases of each biphasic pulse having an amplitude of 300.mu.A, a duration of 50.mu.s, and a charge of 15 nC. Changes in impedance ("Z") are calculated by dividing the change in measured voltage ("V") by the excitation current ("I"), which corresponds to movement of the diaphragm, lung, and other structures to produce a signal indicative of respiratory activity.

Figure 63B:
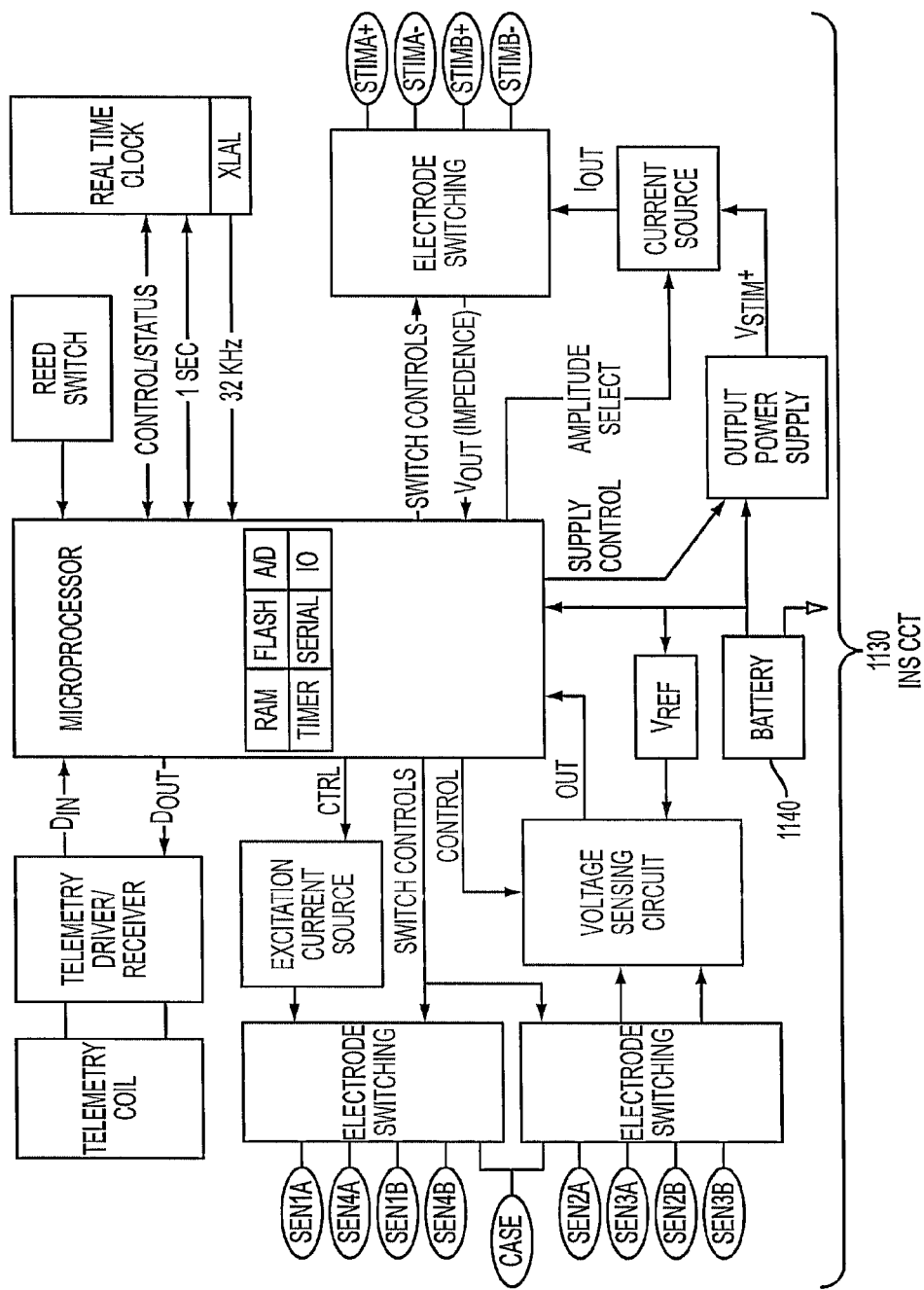
FIG. 63B is a schematic block diagram of electronic circuitry for use in the implantable neurostimulator shown in FIG. 63A.

With reference to FIG. 63B, a block diagram of an example of the INS circuit 1130 is shown schematically. The INS circuit 1130 utilizes a microprocessor to control telemetry communications with the programmer system 2100, operating the sensing circuits to monitor respiration via the RSLs 1200, controlling the delivery of output stimuli via the STLs 1300, monitoring the magnetically sensitive reed switch and the real-time clock. The microprocessor contains built-in support circuits (RAM, Flash Memory, Analog to Digital (A/D) Converter, Timers, Serial Ports and Digital IO) used to interface with the rest of the INS circuit 1130. The microprocessors. Two microprocessors communicating via a serial link may be used instead of one microprocessor, with the first microprocessor for telemetry communications, monitoring the magnetically sensitive reed switch and the real-time clock; and the second microprocessor for operating the sensing circuits and controlling the delivery of output stimuli.

The telemetry interface circuits consist of a tuned telemetry coil circuit and a telemetry driver/receiver circuit to allow pulse encoded communication between the external programmer system 2100 and the microprocessor. As an alternative to telemetry coils and an inductive link, RF antennae with associated circuitry may be used to establish a RF link to provide for arms-length telemetry. The reed switch provides a means for the INS 1100 to be controlled by using a magnet placed in close proximity thereto. The real-time clock provides the basic time base (32 KHz) for the INS circuit 1130 as well as a clock (year, day, hour, minute, second) which can be used to control the scheduled delivery of therapy. The clock is also used to time-stamp information about the operation of the system that is recorded on a nightly basis.

The respiratory sensing circuits comprise two main parts: the excitation current source (output) and the voltage sensing circuit (input). As will be described in more detail hereinafter, respiration is detected via the RSLs 1200 using a 4-wire impedance measurement circuit, where an excitation current is driven through a pair of electrodes, and the resulting voltage is measured on a separate pair of electrodes. Electrode switching circuits (one for each RSL 1200) allows the INS 1100 to monitor one of several different vectors from the two separate 4 electrode RSLs 1200. The INS housing 1120 may also be used as both an excitation and sensing electrode. The excitation current circuit delivers biphasic pulses of low level (300 uA) current to the selected electrode pair every 100 ms during sensing. The voltage sensing amplifier circuit synchronously monitors the voltage produced by the excitation current on the selected electrode pair. The resulting output signal is proportional to the respiratory impedance (0.20 to 10.OMEGA.) and is applied to the A/D circuit in the microprocessor for digitization and analysis.

The stimulation output circuits deliver bursts of biphasic stimulation pulses to either STL 1300. These bursts may be synchronized to the sensed respiratory waveform. The stimulation output circuits include an electrode switching network, a current source circuit, and an output power supply. The electrode switching network allows selection of the stimulation output channel (pair A or B), each corresponding to a STL 1300. The electrode switching network also allows for a charge balancing cycle following each stimulation pulse during which the outputs are connected together with no applied output pulse. The timing and polarity of the pulse delivery is provided by control outputs of the microprocessor. The microprocessor selects the amplitude (e.g., 0.5 mA to 5 mA) of the output current from the current source circuit which is applied through the switching network. The output power supply converts battery voltage to a higher voltage (e.g., 5V to 13V) which is sufficient to provide the selected current into the load impedance of the STL 1300. The microprocessor measures the voltage output from the electrode switching network resulting from the delivered current and the load impedance. The microprocessor divides the output voltage by the output current resulting in a measure of the load impedance (600.OMEGA. to 2500.OMEGA.) which can be an indicator of integrity of the STL 1300.

Figure 64A:
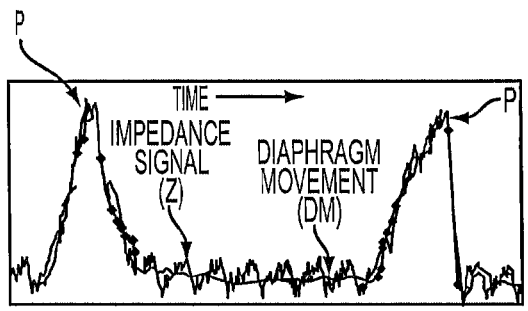
FIGS. 64A, 64B, 64C and 64D illustrate a bio-impedance signal, the corresponding physiological events, and trigger algorithms for use in the system shown in FIG. 59.

With reference to FIG. 64A, the bio-impedance respiration signal ("Z"), which is generated by dividing the change in measured voltage ("V") by the excitation current ("I"), tracks with diaphragm movement (DM) over time and therefore is a good measure of respiratory activity, and may be used to measure respiratory effort, respiratory rate, respiratory (tidal) volume, minute volume, etc. If the excitation current (I) is constant or assumed constant, then the bio-impedance (Z) is proportional to the measured voltage (V), and thus the voltage (V) may be used as a surrogate for bio-impedance (Z), thereby eliminating the division step. As used in this context, diaphragm movement includes movements and shape changes of the diaphragm and adjacent tissue that occur during normal breathing and during obstructed breathing. The (positive or negative) peak (P) of the impedance signal (Z) corresponds to the end of the inspiratory phase and the beginning of the expiratory phase. If the signal is normal (as shown), the positive peak is used; and if the signal is inverted, the negative peak is used. The beginning of the inspiratory phase occurs somewhere between the peaks and may not be readily discernable. Thus, the impedance signal provides a reliable fiducial (P) for end-inspiration and begin-expiration (also called expiratory onset), but may not provide a readily discernable fiducial for begin-inspiration (also called inspiratory onset). Therefore, algorithms described herein do not rely on begin-inspiration (or inspiratory onset) for triggering stimulation as proposed in the prior art, but rather use a more readily discernable fiducial (P) corresponding to begin-expiration (or expiratory onset) in a predictive algorithm as described below. Other non-predictive (e.g., triggered) algorithms are described elsewhere herein.

In people without OSA, the hypoglossal nerve usually activates approximately 300 ms before inspiration and remains active for the entire inspiratory phase. To mimic this natural physiology, it is desirable to deliver stimulation to the hypoglossal nerve during the inspiratory phase plus a brief pre-inspiratory period of about 300 ms. As mentioned previously, a reliable fiducial for the beginning of the inspiratory phase may not be available from the impedance signal, and a reliable fiducial for the pre-inspiratory period may not be available either. However, there are reliable fiducials for the beginning of the expiratory phase (peak P) which may be used to trigger stimulation to cover the inspiratory phase plus a brief pre-inspiratory period.

Accordingly, an algorithm is used to predict respiratory period and determine stimulation trigger time. The predictive algorithm is contained in software and executed by a microprocessor resident in the INS circuitry 1130, thus enabling the INS 1100 to generate stimulation synchronous with inspiration.

Figure 64B:
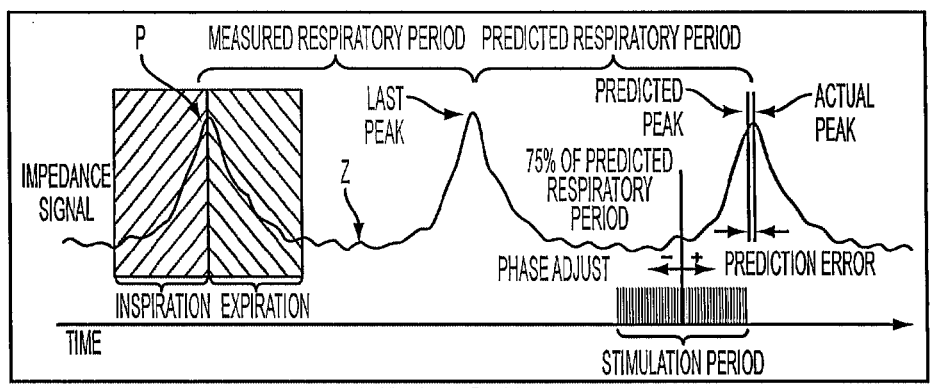

One example of a predictive algorithm is illustrated in FIG. 64B. In this example, the stimulation period is centered about a percentage (e.g., 75%) of the predictive respiratory period. The predictive algorithm uses historical peak data (i.e., begin-expiration data) to predict the time to the next peak, which is equivalent to the predicted respiratory period. The stimulation period is centered at 75%, for example, of the predicted respiratory time period. Thus, the stimulation trigger point is calculated by predicting the time to the next peak, adding 75% of that predicted time to the last peak, and subtracting ½ of the stimulation period (trigger time=time of last peak+75% of predicted time to next peak-½ stimulation period). A phase adjustment parameter (range: −1500 ms to +500 ms, for example) permits the stimulation period to be biased early or late. A default setting (e.g., −500 ms) of the phase adjustment parameter moves the stimulation period early relative to the anticipated start of inspiration.

Figure 64C:
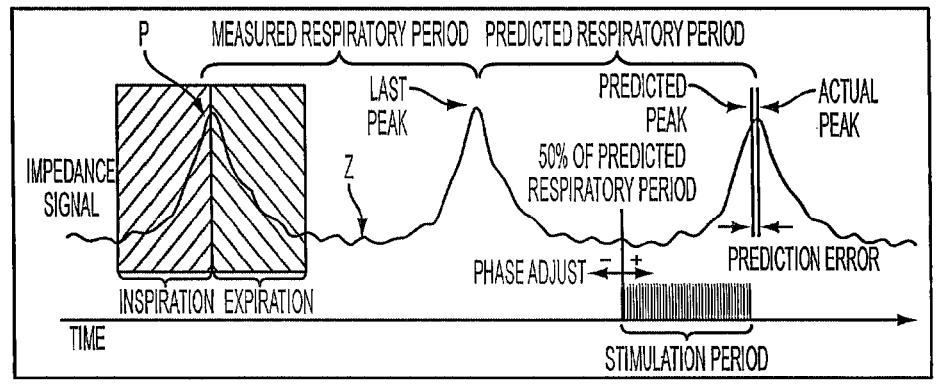

Another example of a predictive algorithm is illustrated in FIG. 64C. This example differs for the example illustrated in FIG. 64B in that the stimulation period is initiated (not centered) at a percentage (e.g., 50%) of the predicted respiratory period. However, the two examples have essentially equivalent results for a duty cycle of 50%. As in the prior example, the predictive algorithm uses historical peak data (i.e., begin-expiration data) to predict the time to the next peak, which is equivalent to the predicted respiratory period. The stimulation period may start at 50%, for example, of the predicted time period. Thus, the stimulation trigger point is calculated by predicting the time to the next peak and adding 50% of that predicted time to the last peak (trigger time=time of last peak+50% of predicted time to next peak). A phase adjustment parameter (range: −1500 ms to +500 ms, for example) permits the stimulation period to be biased early or late. A default setting (e.g., −500 ms) of the phase adjustment parameter moves the stimulation period early relative to the anticipated start of inspiration.

Figure 64D:
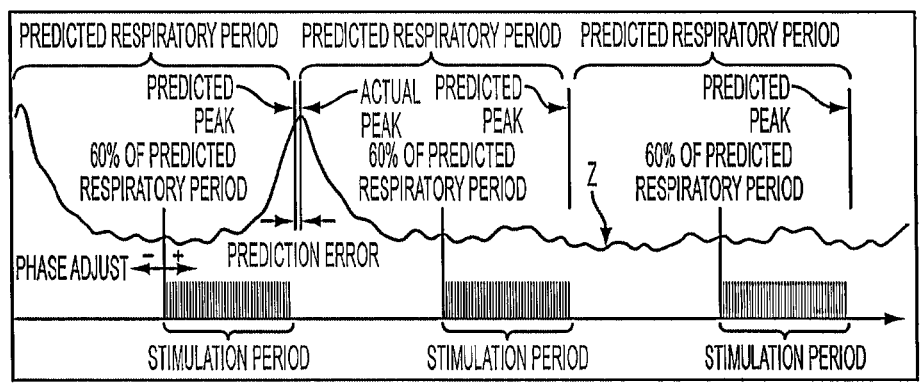

A feature common to the predictive algorithms is illustrated in FIG. 64D. This feature provides a sequence of predicted respiratory periods in case the respiration impedance signal ("Z") is temporarily lost (e.g., due to change in respiratory effort). Until a subsequent respiratory peak is detected, stimulation parameters which are based on the measured respiratory period (e.g., stimulation period) are unchanged. Thus, stimulation timing remains synchronous to the last detected peak.

The stimulation duty cycle may vary to meet efficacy and safety requirements. Generally, the stimulation duty cycle is used to determine the stimulation period as a percentage of the predicted respiratory period (stimulation period=duty cycle.times.predicted respiratory period). After a stimulation period is started, stimulation continues until the end of the stimulation period as set by the stimulation duty cycle, or until the next actual peak is detected, whichever occurs first. Note that the result of the algorithm illustrated in FIG. 64B is the same as the result of the algorithm illustrated in FIG. 64C for a stimulation duty cycle of 50%.

The stimulation duty cycle may be fixed or adaptive. In the fixed mode, the stimulation duty cycle is set using to programmer system 2100 to a fixed value. This fixed value may be increased when the respiratory signal is lost. In adaptive mode, the duty cycle is allowed to vary as a function of a characteristic of respiration. For example, the adaptive duty cycle may increase with an increase in respiratory period variability or with the loss of respiratory signal. Thus, in some instances, the stimulation duty cycle may run above normal (e.g., above 50% to 60%) to achieve a better likelihood of covering the inspiratory phase. Because above normal stimulation duty cycle may result in nerve and/or muscle fatigue if prolonged, it may be desirable to offset above-normal stimulation periods with below-normal stimulation periods to result in a net normal duty cycle. For example, if a X % stimulation duty cycle is defined as normal and the adaptive mode results in a period T1 where the stimulation duty cycle runs Y % more than X %, the above-normal stimulation period may be proportionally offset by a below-normal stimulation period T2 where the stimulation duty cycle runs Z % less than X % to satisfy the equation Y.times.T1=Z.times.T2. This equation is approximate and may vary slightly depending on the averaging technique used. Other offset methods may be used as an alternative.

The following stimulation duty cycle parameters are given by way of example, not limitation. In fixed mode, the maximum stimulation duty cycle may be set from 41% to 69% in 3% increments, and the default setting may be 50%. In adaptive mode, the stimulation duty cycle for a respiratory period may vary from 31% to 69% in 3% increments, and the maximum miming average may be set to 53%. As mentioned above, the adaptive mode allows the duty cycle to increase with respiratory period variability, for example, and the stimulation duty cycle may run in excess of 53% for a limited period of time, but those periods are proportionally offset by periods where the stimulation duty cycle runs less than 53% (e.g., according to an exponentially weighted moving average). For example, an adaptive duty cycle set to 69% would run at that level for no longer than 5 to 7 minutes before being offset by a lower stimulation duty cycle at 47% to result in a miming average of 53%.

Figure 79A:
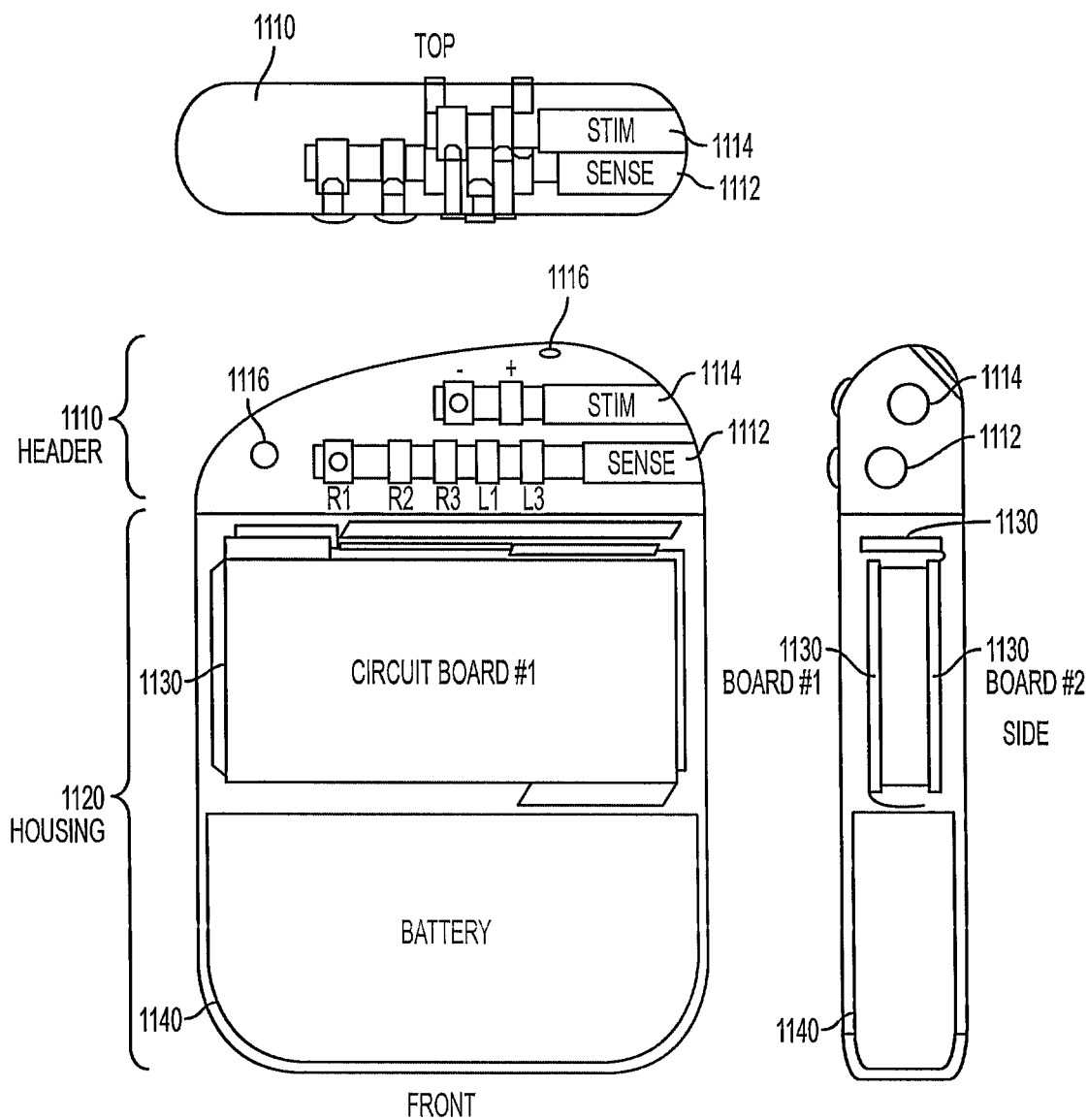
FIG. 79A shows front, side and top views of an implantable neurostimulator for use in the system shown in FIG. 77.

FIG. 79A schematically illustrates the INS 1100 in more detail, including a front view, a top view and a side view. The INS 1100 is similar in certain aspects to commercially available implantable pulse generators and implantable neurostimulators, which may be obtained from suitable manufacturers such as CCC Medical Devices (Montevideo, Uruguay). The INS 1100 generally includes a header 1110 for connection of the STL 1300 and RSLs 1200, and a hermetically sealed housing 1120 for containing the associated electronics 1130, a battery 1140 (e.g., Greatbatch 9086), and an accelerometer 1150. The INS 1100 may contain an oxygen sensor (e.g., SaO$_2$, SpO$_2$, ion, etc.). Alternatively, the oxygen sensor may be incorporated in a lead with connection to the INS 1100.

The electronic circuitry 1130 contained in the INS 1100 enables telemetry communication with the programmer system 2100 and therapy controller 2500, detection of respiration via the RSL 1200, determination of the start time and duration of a stimulation signal, and delivery of a controlled electrical stimulation signal (pulse train) via the STL 1300. The INS 1100 also records therapy history data (device settings, status, measured data, device use, respiration data, stimulation delivery data, statistics based on measured signals, etc.).

The header 1110 may comprise epoxy that is hermetically sealed to the housing 1120. The housing 1120 may comprise titanium. As mentioned in the context of respiration sensing, the housing 1120 may be used as an electrode for bio-impedance respiration measurement. Similarly, electrodes 1360 may be used as an electrode for bio-impedance respiration measurement. For example, the housing 1120 may comprise a combination current emitting and voltage sensing electrode for respiration detection. Alternatively, separate electrodes may be included in the header of the device from which to sense or stimulate.

The header 1110 includes two ports: one RSL port 1112 (labeled "sense") for receiving the proximal connector of the RSL 1200 and one STL port 1114 (labeled "stim") for receiving the proximal connector of the STL 1300. The port configured to receive a STL 1300 includes two set screws (labeled "−" for cathode and "+" for anode) with associated set screw blocks and seals for mechanical and electrical connection to corresponding contacts on the proximal connector 1310 of the STL 1300. Similarly, the port that is configured to receive a RSL 1200 includes five set screws (two labeled R1 and L1 for current emitting electrodes and three labeled R2, R3, and L3, for voltage sensing electrodes) with associated set screw blocks and seals for mechanical and electrical connection to corresponding contacts on the proximal connector 1210 of the RSL 1200. Seals are located between electrical contacts as well as between the distal-most electrical contact and the remainder of the proximal connector assembly 1210. These seals electrically isolate each contact.

Alternatively, wound coil spring contacts may provide electrical connections between the INS header 1110 and the proximal connector assemblies 1210 and 1310. Typically, one electrical connection is still achieved with a set screw which also serves to hold the connector assembly in place. This embodiment provides a sealed mechanical and electrical connection of the RSL 1200 and STL 1300 to the INS 1100. An example of this technology is Bal Seal's Canted Coil™ Spring Technology.

The header 1110 further includes two suture holes 1116 for securing the INS 1100 to subcutaneous tissue such as muscle fascia using sutures when implanted in a subcutaneous pocket. As shown, component values and component configurations are given by way of example, not limitation.

The INS 1100 generates the stimulation output for delivery to the hypoglossal nerve by way of the STL 1300. For this purpose, the INS 1100 has a bipolar stimulation output channel corresponding to the STL port 1114, with the channel providing a pulse train of bi-phasic constant current pulses with a frequency range of 20 to 50 Hz, a pulse width range of 30 to 215.mu.s, an amplitude range of 0.4 to 5.0 mA, and a stimulation duty cycle range of 41%-69%, by way of example, not limitation.

The INS 1100 also generates the excitation signal and measures voltage by way of the RSL 1200 for bio-impedance respiration detection. For this purpose, the INS 1100 also has two respiration sensing channels for simultaneous acquisition of bio-impedance sensing on different vectors. This may be achieved by sequential or alternating sampling of different vectors. The INS 1100 measures bio-impedance via the RSL port 1112, with each channel providing a small excitation current ("I") and measuring voltage ("V"). The excitation signal may comprise a 10 Hz biphasic constant current pulse, with the positive and negative phases of each biphasic pulse having amplitude of 450.mu.A, duration of 80.mu.s, and charge of 36 nC. Current ("I") may be fixed, allowing voltage ("V") to be a relative measure of impedance ("Z"), which corresponds to movement of the diaphragm, lung, and other structures to produce a signal indicative of respiratory activity.

Figure 79B:
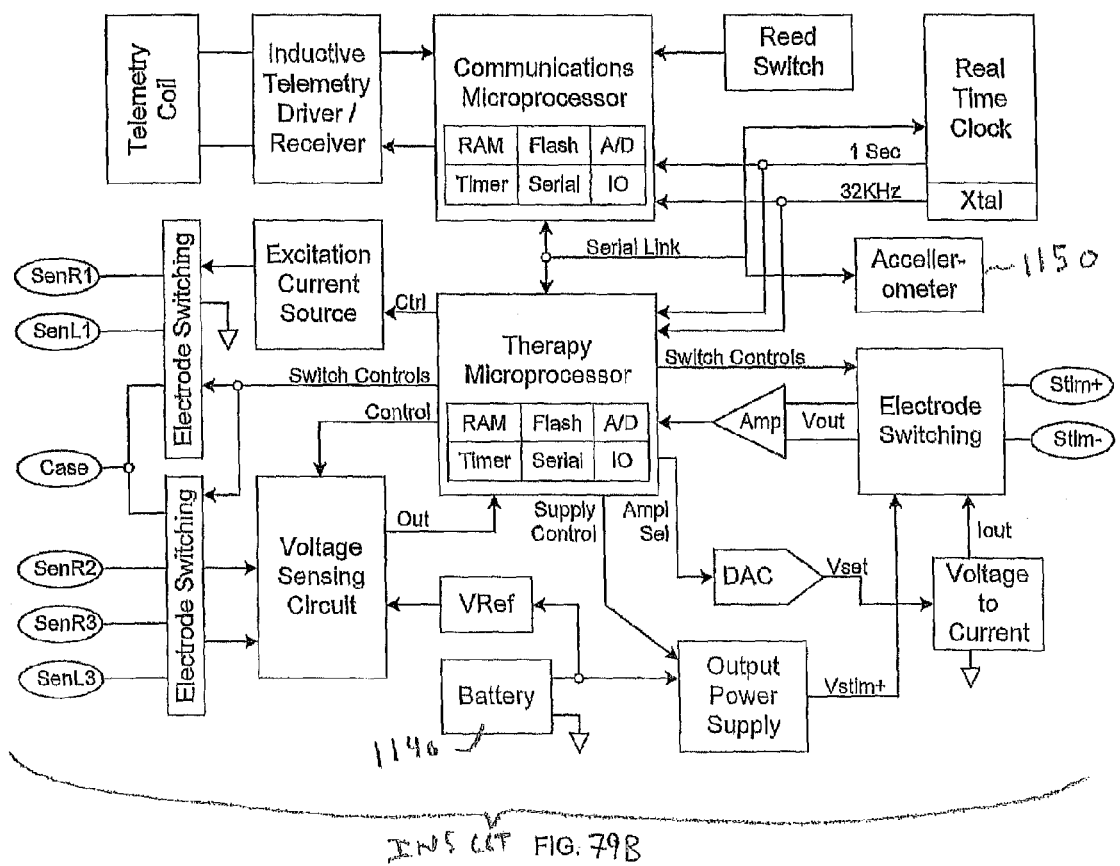
FIG. 79B is a schematic block diagram of electronic circuitry for use in the implantable neurostimulator shown in FIG. 5A.

With reference to FIG. 79B, a block diagram of an example of the INS circuit 1130 is shown schematically. The INS circuit 1130 utilizes a microprocessor to control telemetry communications with the programmer system 2100, operating the sensing circuits to monitor respiration via the RSL 1200, controlling the delivery of output stimuli via the STL 1300, monitoring the accelerometer, magnetically sensitive reed switch and the real-time clock. The microprocessor contains built-in support circuits (RAM, flash memory, analog to digital (A/D) converter, timers, serial ports and digital 10) used to interface with the rest of the INS circuit 1130, including the accelerometer 1150. Two microprocessors communicating via a serial link may be used instead of one microprocessor, with the first microprocessor for telemetry communications, monitoring the accelerometer, magnetically sensitive reed switch and the real-time clock; and the second microprocessor for operating the sensing circuits and controlling the delivery of output stimuli. Alternatively, a single microprocessor could perform these functions.

The telemetry interface circuits consist of a tuned telemetry coil circuit and a telemetry driver/receiver circuit to allow pulse encoded communication between the external programmer system 2100 and the microprocessor. As an alternative to telemetry coils and an inductive link, RF antennae with associated circuitry may be used to establish a RF link to provide for arms-length telemetry. The reed switch provides a means for the INS 1100 to be controlled by using a magnet placed in close proximity thereto. The real-time clock provides the basic time base (768 Hz) for the INS circuit 1130 as well as a clock (year, day, hour, minute, second) which can be used to control the scheduled delivery of therapy. The clock is also used to time-stamp information about the operation of the system that is recorded on a nightly basis.

The respiratory sensing circuit is comprised of two main parts: the excitation current source (output) and the voltage sensing circuit (input). As will be described in more detail hereinafter, respiration is detected via the RSL 1200 using a 3 or 4-wire impedance measurement circuit. In a 4-wire measurement, an excitation current is driven through a pair of electrodes, and the resulting voltage is measured on a separate pair of electrodes. The electrode switching circuits allow the INS 1100 to monitor one of several different vectors from the RSL electrodes 1250 and 1260. As mentioned previously, each physical electrode may function as a current emitting electrode 1250 or a voltage sensing electrode 1260, depending on the programmable vector configuration. In one embodiment of a 3-wire measurement, the INS housing 1120 may be used as both an excitation and sensing electrode. The excitation current circuit delivers biphasic pulses of low level (450 uA) current to the selected electrode pair every 100 ms during sensing. The voltage sensing amplifier circuit synchronously monitors the voltage produced by the excitation current on the selected electrode pair. The resulting output signal is proportional to the respiratory impedance (0.071 to 10.OMEGA.) and is applied to the A/D circuit in the microprocessor for digitization and analysis.

The stimulation output circuits deliver bursts of biphasic stimulation pulses to the STL 1300. These bursts may be synchronized to the sensed respiratory waveform to deliver stimulation and thus airway opening at the appropriate time. The stimulation output circuits include an electrode switching network, a current source circuit, and an output power supply. The electrode switching network also allows for a charge balancing cycle following each stimulation pulse during which the outputs are connected together with no applied output pulse. The timing and polarity of the pulse delivery is provided by control outputs of the microprocessor. The microprocessor selects the amplitude (e.g., 0.4 mA to 5 mA) of the output current from the current source circuit which is applied through the switching network. The output power supply converts battery voltage to a higher voltage (e.g., 5V to 14V) which is sufficient to provide the selected current into the load impedance of the STL 1300. The microprocessor measures the voltage output from the electrode switching network resulting from the delivered current and the load impedance. The microprocessor divides the output voltage by the output current resulting in a measure of the load impedance (400.OMEGA. to 2700.OMEGA.) which can be an indicator of integrity of the STL 1300.

The INS 1100 (or lead connected to the INS 1100) may contain an oxygen sensor to monitor oxygen levels, for example during a therapy session. This may be used to monitor efficacy as well to set stimulation settings during a therapy session. For example, the INS 1100 may be programmed to increase stimulation when oxygen de-saturations are detected at a programmable threshold rate and/or severity. In addition, the INS 1100 may turn stimulation on once de-saturations are detected, wherein thresholds of rate and severity are programmable. Desaturations may act to indicate the sleep state or wakefulness. In a similar manner, electroneurogram (ENG) may be used to monitor nerve activity, which may also be indicative of sleep state and/or wakefulness. The INS 1100 may use the indication of sleep state or wakefulness to change stimulation settings. For example, stimulation may be increased when the patient is in N3 or REM sleep. In addition, stimulation level may be decreased or turned off during stage N1, N2, or wakefulness.

The INS 1100 circuitry may contain a three-axis accelerometer 1150 that can be used to determine the patient's body position (supine, prone, upright, left, or right side) and/or detect motion events (wakefulness). These data may be used to change stimulation settings or inhibit output. The INS 1100 may be programmed to increase stimulation intensity when the patient is in specific body positions (e.g., supine, a more challenging position). The INS 1100 may segregate recorded therapy statistics (e.g., cycling detector events, oxygen desaturations) with respect to body position. For example, a patient's cycling detector may record very few events in the lateral position and many events in the supine position, indicative of the patient being treated in the lateral position.

Figure 80A:
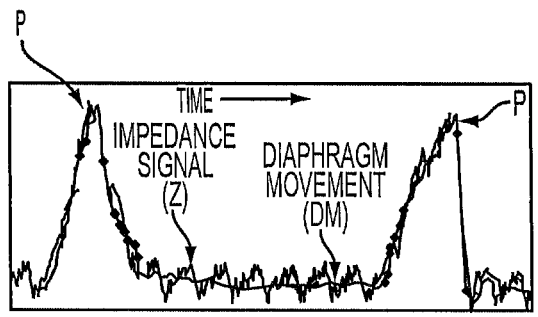
FIGS. 80A, 80B, and 80C illustrate a bio-impedance signal, the corresponding physiological events, and stimulation delivery algorithms for use in the system shown in FIG. 77.

With reference to FIG. 80A, the bio-impedance respiration signal ("Z"), which is generated by dividing the change in measured voltage ("V") by the excitation current ("I"), tracks with diaphragm movement (DM) over time and therefore is a good measure of respiratory activity, and may be used to measure respiratory effort, respiratory rate, respiratory (tidal) volume, minute volume, etc. If the excitation current (I) is constant or assumed constant, then the bio-impedance (Z) is proportional to the measured voltage (V), and thus the voltage (V) may be used as a surrogate for bio-impedance (Z), thereby eliminating the division step. As used in this context, diaphragm movement includes movements and shape changes of the diaphragm and adjacent tissue that occur during normal breathing and during obstructed breathing. The bio-impedance waveform may be filtered to reduce noise and eliminate cardiac artifact, clarifying positive and negative peak occurrence. The signal may be filtered using a first order low pass filter. Alternatively, a higher order curve fit approach could be utilized to filter the signal. The (positive or negative) peak (P) of the impedance signal (Z) corresponds to the end of the inspiratory phase and the beginning of the expiratory phase. If the signal is normal (as shown), the positive peak is used; and if the signal is inverted, the negative peak is used. The beginning of the inspiratory phase occurs somewhere between the peaks and may not be readily discernable. Thus, the impedance signal provides a reliable fiducial (P) for end-inspiration and begin-expiration (also called expiratory onset), but may not provide a readily discernable fiducial for begin-inspiration (also called inspiratory onset). Therefore, algorithms described herein do not rely on begin-inspiration (or inspiratory onset) to determine the start of stimulation bursts as proposed in the prior art, but rather use a more readily discernable fiducial (P) corresponding to begin-expiration (or expiratory onset) in a predictive algorithm as described below. Other non-predictive (e.g., triggered) algorithms are described elsewhere herein.

Gross body motion is often indicative of patient wakefulness and may change the bio-impedance signal (Z). A motion event may be detected, for example, by assessing variability in the bio-impedance peak-to-peak signal strength (P-P). Different thresholds of sensitivity may be utilized such that minor movements are not grouped with motion events. When a motion event is determined, stimulation may be turned off or turned down until motion stops or for a programmable duration of time. The frequency and duration of these motion events may be recorded in device history. The accelerometer 1150 could be utilized in a similar fashion to detect and record motion events.

Waxing and waning of the bio-impedance signal (Z) is often indicative of apneas or hypopneas. Generally referred to as cycling, this pattern may be detected, for example, by assessing trends of increasing and decreasing average P-P amplitude values. Different thresholds of sensitivity may be utilized such that minor changes in P-P values are not declared cycling events. When cycling is detected, stimulation parameters may be initiated or changed (e.g., increased intensity, increased duty cycle, etc.) to improve therapy. The frequency and duration of these cyclic breathing patterns may be recorded in therapy history. These values may be used as an indicator of how well the patient is being treated, providing an estimate of AHI.

The INS 1100 may be programmed to change stimulation level between therapy sessions, days, or other programmable value. The stimulation level may be recorded alongside therapy session data, for example cycling rate (via the cycling detector), oxygen desaturation frequency and severity, stimulation time, variations in respiratory rate, variations in respiratory prediction, etc.

In people without OSA, inspiration is typically 25-50% of the respiratory cycle, with variations in respiration rate being common. Variations may cause actual inspiration to differ from predicted inspiration. The hypoglossal nerve usually activates approximately 300 ms before inspiration and remains active for the entire inspiratory phase. To mimic this natural physiology, it is desirable to deliver stimulation to the hypoglossal nerve during the inspiratory phase plus a brief pre-inspiratory period of about 300 ms. To maximize stimulation coverage of actual inspiration, it may be advantageous to account for this variability by centering stimulation on the predicted inspiration. As mentioned previously, there are reliable fiducials for the beginning of the expiratory phase (peak P) which may be used to deliver stimulation to cover the inspiratory phase plus brief pre and/or post-inspiratory periods.

Accordingly, an algorithm is used to predict respiratory period and determine the start of the stimulation burst. The predictive algorithm is contained in software and executed by a microprocessor resident in the INS circuitry 1130, thus enabling the INS 1100 to generate stimulation synchronous with inspiration. One example of a prediction algorithm uses the respiratory period of previous breaths to predict the respiratory period of each subsequent breath. In this algorithm, a respiratory period is determined by calculating the time between peaks in the bio-impedance signal (Z). If the actual respiratory period is different from the predicted respiratory period, then the subsequent predicted respiratory period is resynchronized and updated to equal the actual period, up to a programmable value (e.g., 300 ms). If the difference in respiratory period exceeds the programmable value, then the predicted respiratory period is incremented or decremented by this value.

Figure 80B:
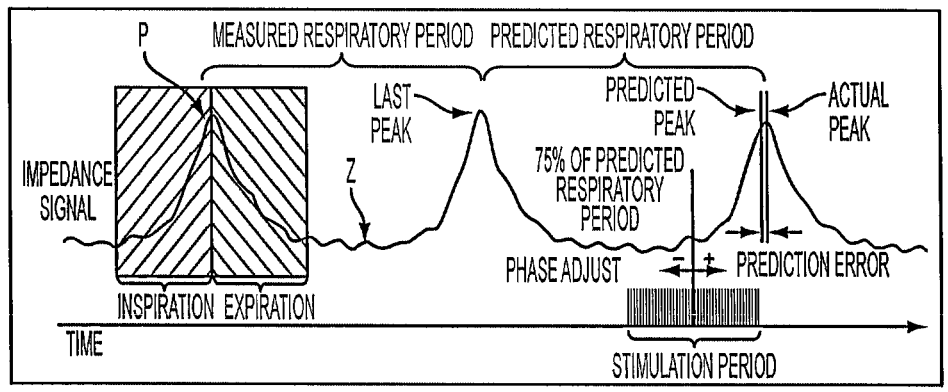

One example of a predictive algorithm is illustrated in FIG. 80B. In this example, the stimulation period is centered about a percentage (e.g., 75%) of the predictive respiratory period. The predictive algorithm uses historical peak data (i.e., begin-expiration data) to predict the time to the next peak, which is equivalent to the predicted respiratory period. The stimulation period is centered at 75%, for example, of the predicted respiratory time period. Thus, the time to start a stimulation burst is calculated by predicting the time to the next peak, adding 75% of that predicted time to the last peak, and subtracting ½ of the stimulation period (stimulation start time=time of last peak+75% of predicted time to next peak-½ stimulation period). A phase adjustment parameter (range: +/−1000 ms, for example) permits the stimulation period to be biased early or late.

Figure 80C:
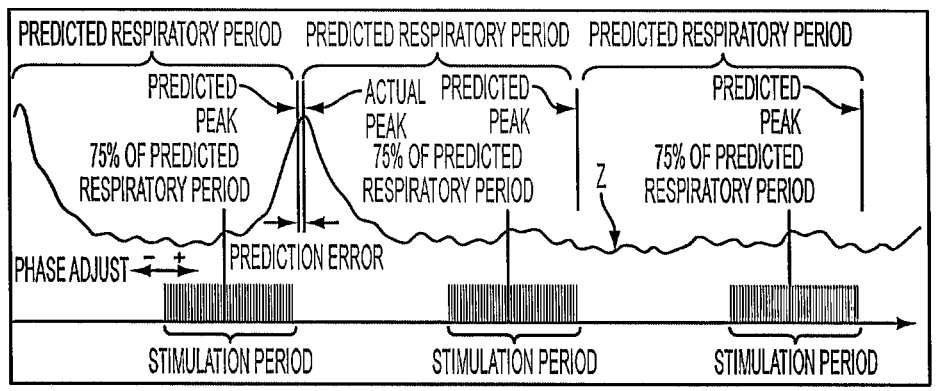

A feature common to the predictive algorithms is illustrated in FIG. 80C. This feature provides a sequence of predicted respiratory periods in case the respiration impedance signal ("Z") is temporarily lost (e.g., due to change in respiratory effort). Until a subsequent respiratory peak is detected, stimulation parameters which are based on the measured respiratory period (e.g., stimulation period) are unchanged. Thus, stimulation timing remains synchronous to the last detected peak.

The stimulation duty cycle may vary to meet efficacy and safety requirements. Generally, the stimulation duty cycle is used to determine the stimulation period as a percentage of the predicted respiratory period (stimulation period=duty cycle.times.predicted respiratory period). After a stimulation burst (pulse train) is started, stimulation continues until the end of the stimulation burst as set by the stimulation duty cycle, or until the next actual peak is detected, whichever occurs first. Alternatively, the feature of terminating a stimulation period when an actual peak is detected may be turned off.

The stimulation duty cycle may be fixed or adaptive. In the fixed mode, the stimulation duty cycle is set using to programmer system 2100 to a fixed percentage value. This fixed value may be increased when the respiratory signal is lost, increasing the likelihood of aligning with actual inspiration. In adaptive mode, the duty cycle is allowed to vary as a function of a characteristic of respiration. For example, the adaptive duty cycle may increase when prediction is less accurate (higher variability in respiration rate) or when the respiratory signal is lost. Thus, in some instances, the stimulation duty cycle may run above normal (e.g., above 50% to 60%) to achieve a better likelihood of covering the inspiratory phase. Because above normal stimulation duty cycle may result in nerve and/or muscle fatigue if prolonged, it may be desirable to offset above-normal stimulation periods with below-normal stimulation periods to result in a net normal duty cycle. Thus, when the prediction is highly accurate (stable respiration rate), the stimulation duty cycle may be reduced.

The following stimulation duty cycle parameters are given by way of example, not limitation. In fixed mode, the maximum stimulation duty cycle may be set from 41% to 69% in 3% increments, and the default setting may be 50%. In adaptive mode, the stimulation duty cycle for a respiratory period may vary from 31% to 69% in 3% increments, and the maximum running average may be set to 53%. As mentioned above, the adaptive mode allows the duty cycle to decrease when respiratory period is stable and increase with respiratory period variability, for example, and the stimulation duty cycle may run in excess of 53% for a limited period of time, but those periods are proportionally offset by periods where the stimulation duty cycle runs less than 53% (e.g., according to an exponentially weighted moving average). For example, an adaptive duty cycle set to 69% would run at that level for no longer than 5 to 7 minutes before being offset by a lower stimulation duty cycle at 47% to result in a running average of 53%. This equation is approximate and may vary slightly depending on the averaging technique used. Other offset methods may be used as an alternative.

The stimulation duty cycle may be nominally 50%. A duty cycle limiter may be enabled such that it prevents the device from exceeding a programmable long term average stimulation duty cycle threshold (e.g., 53%). Long term average duty cycle may be calculated using a first order filter of duty cycle measured over a fixed time period (e.g., 6 seconds), with a programmable filter time constant (e.g., each iterative calculation is given a weighting of 1/32). If the long term average duty cycle reaches the programmable threshold, then stimulation duty cycle is decreased to a programmable value, (e.g., 44%) until the long term average drops below the nominal value (here, 50%), at which time the nominal duty cycle is restored. This safety mechanism may prevent nerve and muscle fatigue.

Figure 80D:
FIGS. 80D, 80E, 80F, 80G, and 80H illustrate various stimulation pulse configurations for the implantable neurostimulator shown in FIG. 77, as may be used for therapy or sleep titration, for example.

The INS 1100 may deliver stimulation as a train of pulses with constant pulse width and amplitude at a set frequency for a duration limited by duty cycle. This train of pulses may be described as a pulse train envelope and is illustrated in FIG. 80D. The envelope describes a series of biphasic pulses delivered consecutively during a stimulation burst. When the stimulation level of the positive phase of each biphasic pulse is uniform, this level is the level of the stimulation burst. The INS 1100 may also deliver stimulation in pulse train envelopes wherein the pulses are non-uniform (e.g., pulses may have different amplitudes).

Figure 80E:
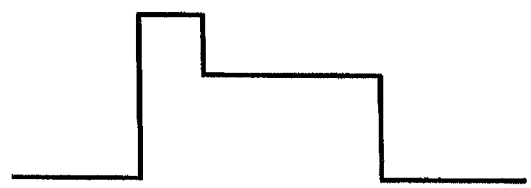

The muscle(s) activated by the stimulation may not require the full stimulation intensity for the duration of the stimulation in order to maintain muscle contraction. Accordingly, the INS 1100 may be programmed to deliver a basic retention intensity pulse configuration, defined as a pulse train envelope wherein each pulse's intensity (e.g., amplitude) is less than or equal to the previous pulse's intensity, (e.g., a two second pulse wherein the first 1000 ms is at 2 mA and the subsequent 1000 ms is at 1.7 mA). This pulse configuration is illustrated in FIG. 80E. This allows the muscle to activate to a level and then remain in that position with a less intense stimulation. This may be more comfortable and allow the patient to fall asleep more easily with the stimulation on, be less likely to cause arousal from sleep, and/or reduce the possibility of muscle/nerve fatigue. Alternatively, the pulse level (amplitude) could be decreased gradually during each burst (rather than abruptly) to reach the same final stimulation level.

Figure 80F:
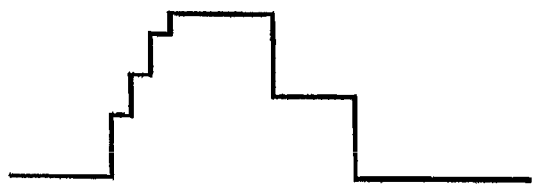
Figure 80G:
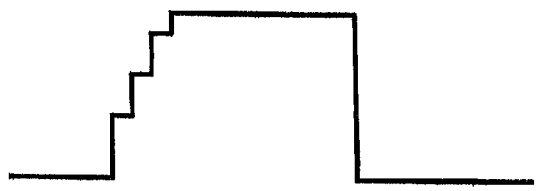

A more gradual transition at the start of each burst may be more comfortable and be less likely to cause arousal from sleep, and/or reduce the possibility of muscle/nerve fatigue. Accordingly, the INS 1100 may be programmed to deliver a soft start pulse configuration, defined as a pulse train envelope wherein at the start of each burst, each pulse's intensity (e.g., amplitude) is greater than or equal to the previous pulse's intensity, (e.g., a two second pulse wherein the first 100 ms is at 1.85 mA, the second 100 ms is at 1.95 mA, the third 100 ms is at 2.05 mA and the remaining 1700 ms is at 2.1 mA). This pulse configuration is illustrated in FIG. 80G. The pulse train envelope would thus have a stair-like appearance as stimulation increases to the full stimulation plateau.

Figure 80H:
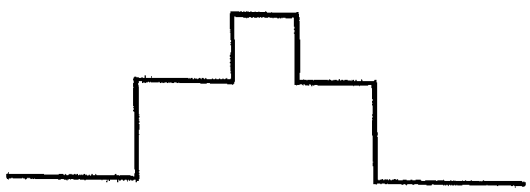

In another embodiment, a pulse train envelope may employ a soft start to reach full stimulation and subsequently decrease intensity (amplitude) to a retention intensity for the remainder of the stimulation, (e.g., a two second pulse wherein the first 100 ms is at 1.85 mA, the second 100 ms is at 1.95 mA, the third 100 ms is at 2.05 mA, and the next 700 ms is at 2.1 mA, and the remaining 1000 ms is at 1.8 mA). This pulse configuration is illustrated in FIG. 80F. This configuration may provide the benefits of both soft start and retention intensity, wherein the stimulation starts gradually to fully activate the muscle(s), then decreases to a level of less intense stimulation, with the muscle remaining in a contracted position. FIG. 80H shows nested mode, a simplified version of the previously mentioned retention intensity, wherein there is one step up to the full amplitude, and then an equal step down to the retention intensity.

Figure 80I:
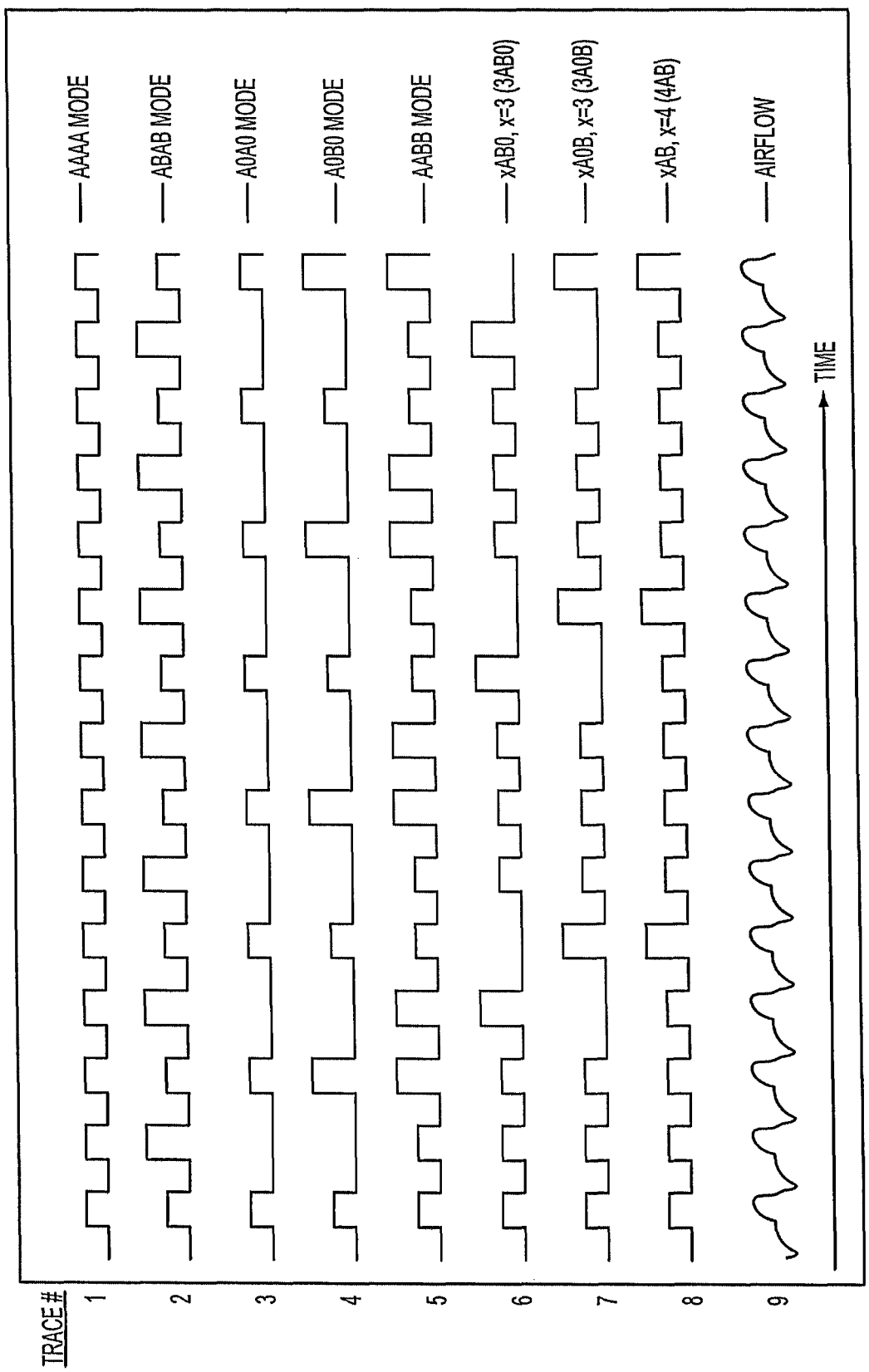
FIG. 80I (traces 1-8) shows various stimulation modes for the implantable neurostimulator shown in FIG. 77, as may be used for therapy or sleep titration, for example.
Figure 98J:
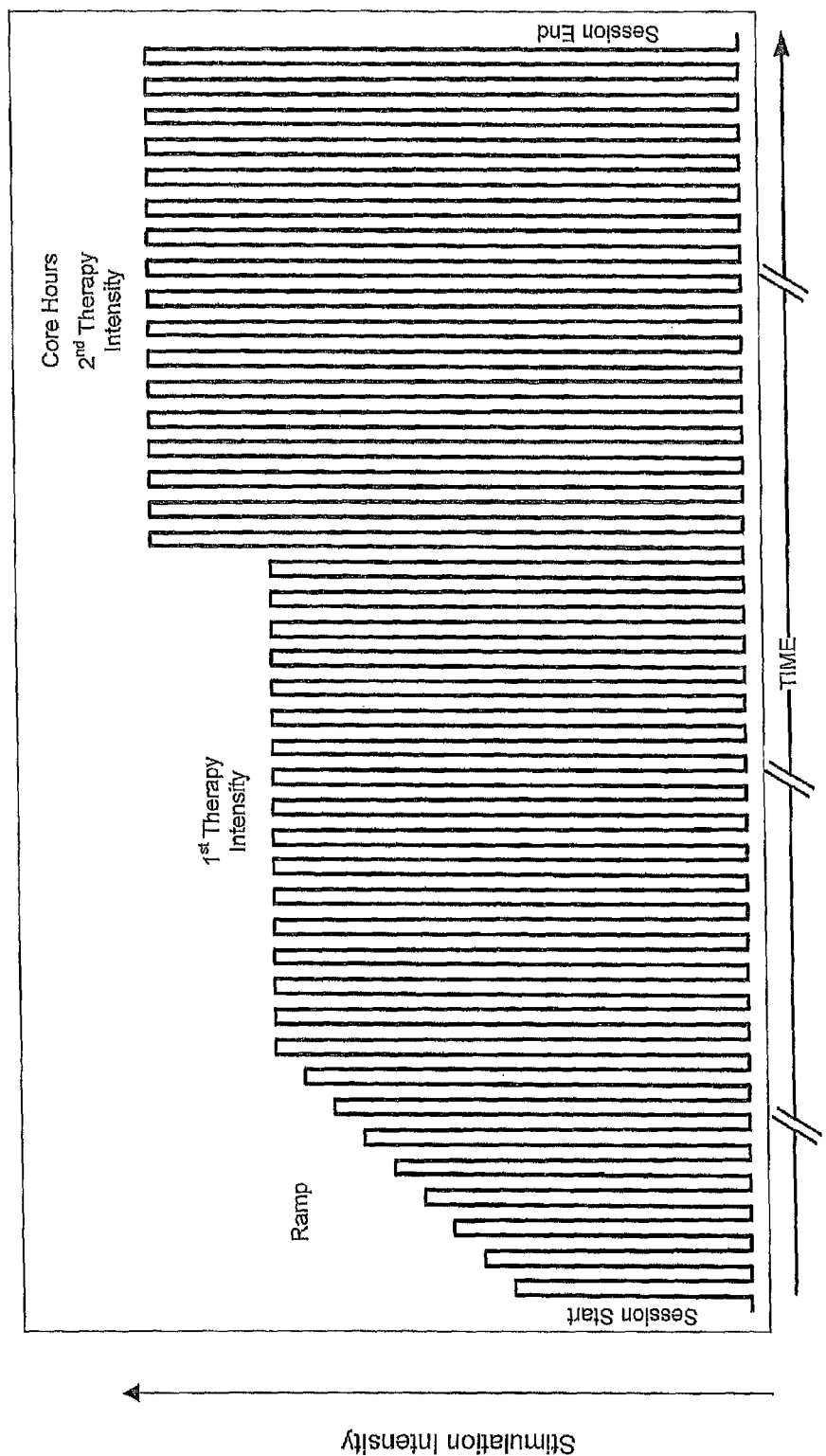
FIGS. 95A-95F, 96A-96B, 97, and 98A-98B are schematic illustrations of methods for shortening pharyngeal tissue.

The INS provides two separate stimulation strengths (A & B) with independent parameters (amplitude, pulse width, frequency, duty cycle and phase adjust). Stimulation may be delivered in different therapy modes, examples of which are shown in FIG. 80I. FIG. 80I (traces 1-8) illustrates some commonly used modes, all of which are inspiratory synchronous, meaning stimulation is automatically delivered according to an algorithm that predicts the inspiratory phase and initiates stimulation delivery at a desired time relative to inspiration, such as centered on the predicted inspiration. These modes may be used as standard therapy as well as to determine device settings during a PSG (e.g. sleep titration PSG). Additionally, these modes may be used to diagnose phenotypes of OSA or other diseases.

FIG. 80I (trace 1) illustrates synchronous mode in which every stimulation has the same pulse configuration and amplitude, known as AAAA mode, the default therapy mode. The term AAAA mode means that four consecutive inspirations are covered by stimulation of level A, where A is 2.0 mA, for example. Inspiration is shown in FIG. 80I (trace 9) in the upward direction.

The inspiratory-synchronous ABAB mode, FIG. 80I (trace 2), also delivers stimulation bursts synchronous with inspiration as determined by the device, therapy delivery algorithm settings, and sensed respiratory signal. This mode is similar to AAAA mode, except that the stimulation is delivered on four consecutive inspirations alternating between stimulation levels A and B on each burst where, for example, A is 2.0 mA and B is 1.8 mA.

FIG. 80I (trace 3) illustrates a subset of ABAB mode known as A0A0 mode, wherein the B breath is not stimulated. A may be 2.0 mA and B may be 0 mA, for example.

FIG. 80I (trace 4) illustrates A0B0 mode, wherein a first breath is stimulated at level "A," followed by an second breath that is unstimulated, followed by a third breath that is stimulated at level "B," followed by a fourth breath that is unstimulated, (e.g., A is 2.0 mA and B is 1.8 mA). This allows for simultaneous assessment of two different levels (A and B) when compared to adjacent non-stimulated breaths.

FIG. 80I (trace 5) illustrates AABB mode wherein two breaths are stimulated at level "A" followed by two breaths stimulated level "B," (e.g. A is 2.0 mA and B is 1.8 mA). In this mode, every stimulated breath is adjacent to a stimulated breath at level "A" and a stimulated breath at level "B." The AABB mode may be used to test if there is a short-term residual cross-over effect when changing from one stimulation level to another stimulation level or from a stimulation level to no stimulation. For example, the airflow measured during the first "A" can be compared to the airflow measured during the second "A" in each sequence over many periods777 to determine if there is a measurable residual effect from the "B" level simulation.

FIG. 80I (trace 6) illustrates xAB0 mode, wherein "x" number of breaths are stimulated at level "A," followed by a breath stimulated at level "B," followed by an unstimulated breath, (e.g. A is 2.0 mA and B is 1.8 mA). The illustration shows x equals 3 (3AB0), although x may be any number of breaths (e.g., 3, 5, 7).

FIG. 80I (trace 8) illustrates xAB mode, wherein "x" number of breaths are stimulated at level "A," followed by an unstimulated breath, followed by a breath stimulated at level "B," (e.g. A is 2.0 mA and B is 1.8 mA). The illustration shows x equals 3 (3A0B), although x may be any number of breaths (e.g., 3, 5, 7

FIG. 80I (trace 8) illustrates xAB mode, wherein "x" number of breaths are stimulated at level "A," followed by a breath stimulated at level "B," (e.g. A is 2.0 mA and B is 1.8 mA). The illustration shows x equals 4 (4AB), although x may be any number of breaths (e.g., 4, 6, 8).

Stimulation may also be delivered in two modes which are not inspiratory synchronous: manual stimulation and asynchronous (fixed) stimulation. Manual mode delivers stimulation at any frequency, pulse width, amplitude, pulse configuration, and/or duration (e.g., up to 12 seconds). In manual mode, stimulation is delivered by manually entering a command via the programmer system to initiate delivery of a stimulation burst or bursts. The stimulation continues until the burst duration expires or stimulation stop is commanded via the programmer system. Manually delivered stimulations may be delivered in any available pulse configuration.

Asynchronous mode (fixed mode) is when stimulation is delivered at regular programmable intervals (e.g., 2.5 seconds of stimulation, followed by 2.5 seconds off). The intervals may be set to a rate similar to a respiratory cycle, (e.g. 5 seconds). Alternatively, longer intervals (e.g. 8 seconds) may decrease the probability of missing two consecutive inspirations, and increase the probability of providing the patient with stimulation during an entire respiratory cycle. This may be used during daytime familiarization, ensuring that the patient receives stimulation in a regular fashion, as breathing patterns during wakefulness may be more irregular and difficult to predict than during sleep. In addition, this mode may be used to test the benefits of asynchronous stimulation compared to inspiratory synchronous stimulation. Asynchronous stimulation may be initiated by programming the device to fixed mode and starting a therapy session. Fixed mode stimulations may be in any available pulse train configuration.

Typically, stimulation is delivered during a therapy session having a start and a stop time. The patient or physician may start a therapy session using the therapy controller 2500 or programmer system 2100. Additionally, a therapy session may begin according to a programmable schedule. During a session, the start of stimulation may be delayed by a programmable delay, subject to patient preference. The patient or physician may stop a therapy session using therapy controller 2500 or programmer system 2100. Additionally, a therapy session may stop according to a programmable schedule or programmable maximum session duration.

A patient or physician may also pause a therapy session for a programmable time using the therapy controller 2500 or programmer system 2100. This pause function may be programmed to turn stimulation off or reduce the stimulation intensity. The pause function may be programmed to smart pause, wherein the stimulation level is automatically reduced after a programmable number of pauses (e.g. after the second pause) in a programmable time period or session. Additionally, the smart pause may increase pause duration after a programmable number of pauses (e.g. the first pause is five minutes, the second pause is ten minutes). These pause functions, including smart pause, may allow a patient to reduce stimulation for brief periods following an arousal from sleep.

At the start of a therapy session or following an interruption in therapy such as a pause, stimulation level may increase incrementally from an initial stimulation level to an initial therapy level during a ramping period. The ramp may occur over a programmable number of stimulations, breaths, or time period. This ramp may also occur after a pause or a motion event. The ramping feature may be more comfortable, allowing the patient to fall asleep more easily with the stimulation on or reduce the likelihood of causing arousal from sleep.

A patient may be able to tolerate more intense stimulation as a therapy session progresses. This higher intensity stimulation may provide enhanced therapy efficacy. The INS 1100 may be programmed to change stimulation level (e.g., amplitude or pulse width) during a therapy session from an initial level to a second, possibly more efficacious level. This therapy stimulation configuration is illustrated in FIG. 80J and is called core hours. This intensity change may occur after a programmable interval, for example after a fixed duration of time, number of breaths or stimulations (e.g., stimulation at 1.8 mA for the first hour of a therapy session, after which stimulation is increased to 2.0 mA). This feature and the related parameters may be programmed by a physician, for example based on patient feedback. This feature may allow a patient to fall asleep at a more tolerable level of stimulation, and then as the therapy session progresses, receive more appropriate therapeutic benefit.

Stimulation may be delivered during a therapy session, which may start and stop according to a programmable schedule or manual use of the therapy controller 2500. The therapy controller 2500 may also allow the patient to pause or adjust therapy settings. Summary history data from each session may be saved in the device memory. Data recorded may include: start, pause, and stop times of the therapy session, scheduled or manual starts/stops, motion detector outputs, cycling detector outputs, prediction algorithm outputs, respiration timing, signal stability outputs, accelerometer outputs, impedance data from STL 1300 and RSL 1200, number of breaths, number of stimulations in a session, average and median P-P sensing impedance ("Z") amplitude values, stimulation settings and changes in stimulation settings such as core hours, pulse configuration, and ramping. These summary data allow a physician or caretaker to understand how the patient is using the device, tolerating the stimulation, troubleshoot errors in programming, and estimate the therapeutic effects of the neurostimulator. This feedback data may aid in determining if adjustments are needed to the patient's therapy (e.g. patient is ready for stimulation up-titration).

Programmer System

Figure 65A:
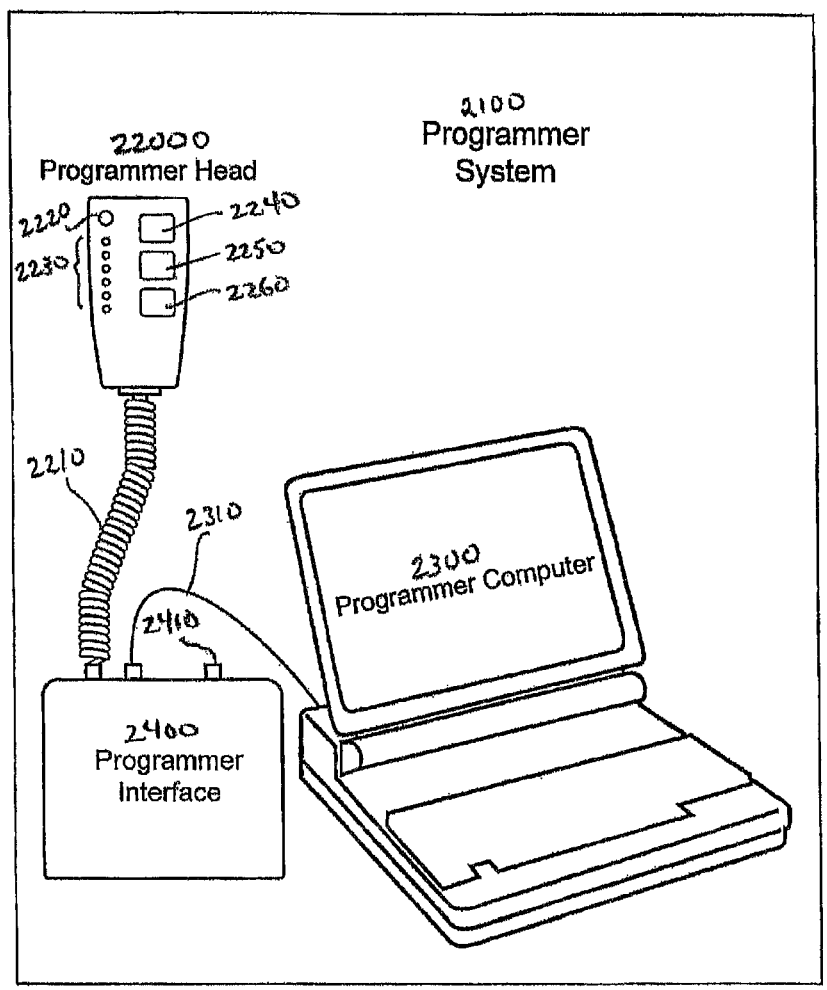
FIG. 65A is a schematic illustration of the programmer system for use in the system shown in FIG. 59.
Figure 85:
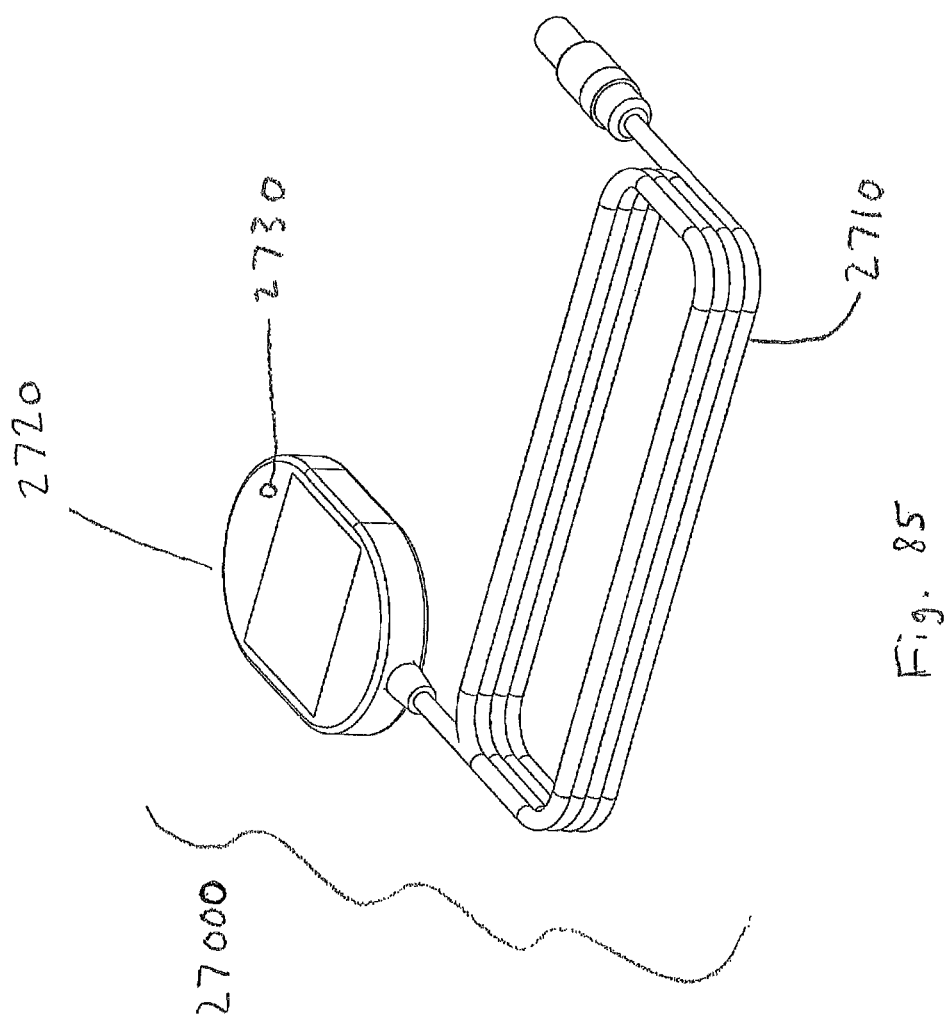
FIG. 85 illustrates a sleep wand, for wireless communication with the neurostimulator during sleep.

As shown schematically in FIG. 65A, the programmer system 2100 includes a computer 2300, a programmer interface 2400, a programmer head 22000, and a sleep wand 27000. The programmer interface 2400 and programmer head 22000 are similar in certain aspects to commercially available programmers, which may be obtained from suitable manufacturers such as CCC Medical Devices (Montevideo, Uruguay). The programmer head 22000 is connected to the programmer interface 2400 via a flexible cable 2210, and the programmer interface 2400 is connected to the computer 2300 via a USB cable 2310. Cable 2210 may be coiled as shown or straight. As shown in FIG. 85, the sleep wand 27000 may comprise a sleep wand head 2720, a flexible cable 2710, and an LED 2730. The sleep wand 27000 may connect to the programmer interface 2400 via a flexible cable 2710. The sleep wand head 2720 may be 3.2 inches in length, 2.1 inches in width, and 0.5 inches deep. The programmer system 2100 wirelessly communicates with the INS 1100 via a wireless telemetry link (e.g., 30 KHz) utilizing an antenna and associated circuitry in the programmer head 22000. The programmer may use long range telemetry such that the programmer head 22000 may rest beside the patient without interfering with sleep. The programmer interface 2400 provides analog to digital conversion and signal processing circuitry allowing the computer 2300 to control and program the INS 1100 via the programmer head 22000. The programmer head includes a power indication LED 2220, a signal strength LED array 2230 (signal strength to/from INS 1100), an interrogate button 2240 (to upload data from INS 1100), a program button 2250 (to download data/commands to the INS 1100) and a therapy-off button 2260 (to stop therapy/stimulation output from the INS 1100). The computer 2300 may comprise a conventional laptop computer with software to facilitate adjustment of a variety of INS 1100 parameters, including, for example: stimulation parameters (stimulation pulse amplitude, stimulation pulse frequency, stimulation pulse width, stimulation duty cycle, etc.); respiration sensing algorithm parameters; stimulation trigger/synchronization algorithm parameters, therapy delivery schedule, and various test functions. The sleep wand 27000 functions like the programmer head 22000, but is reduced in size for patient comfort during sleep. There may be one LED 2730 to indicate signal presence. Frequency of LED light pulses may indicate signal strength. The sleep wand 27000 may exclude functional buttons (i.e. interrogate command, program command, and stop therapy command) found on the programmer head 22000.

Figure 65B:
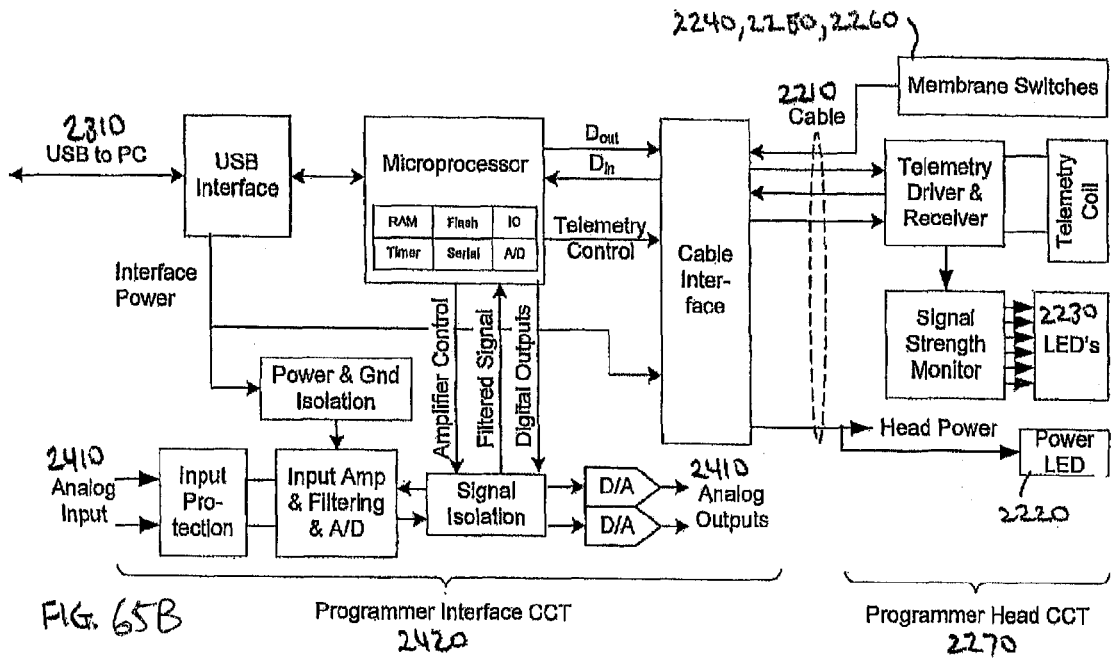
FIGS. 65B and 65C are schematic block diagrams of electronic circuitry for use in the programmer system for shown in FIG. 65A.

With reference to FIG. 65B, a block diagram of example circuits 2420/2270 for the programmer interface 2400 and the programmer head 22000 are shown schematically. The programmer interface circuit 2420 is controlled by a microprocessor having a standard set of peripherals (RAM, flash, digital I/O, timers, serial ports, A/D converter, etc.). The microprocessor communicates with a standard personal computer (PC) 2300 through a Universal Serial Bus (USB) interface. Commands and data are passed from the computer 2300 to/from the microprocessor via the USB interface and cable 2310. The USB interface also provides DC power for the programmer interface circuit 2420 and the programmer head circuit 2270 via cable 2210. The microprocessor controls the cable interface leading to the programmer head circuit 2270 via cable 2210. The programmer head circuit 2270 contains telemetry driver and receiver electronics that interface to the telemetry coil. The telemetry coil is designed to inductively couple signals from the programmer head circuit 2270 to the coil in the INS circuit 1130 when the programmer head 22000 is placed over the INS 1100 with the coils aligned. As an alternative to telemetry coils and an inductive link, RF antennae with associated circuitry may be used to establish a RF link to provide for arms-length telemetry. The programmer head circuit 2270 also contains electronics that monitor the signal strength as received from the INS 1100. The outputs of the signal strength electronics drive display LED's for the user. Another LED indicates that power is available, for example, supplied by the computer 2300. The programmer interface microprocessor controls and receives analog input signals from an isolated sensor interface. The power and ground for the sensor interface are derived from the USB power input, but provide DC isolation for this circuitry to prevent leakage currents from flowing through any patient connections that may be present at the sensor inputs. The sensor inputs may be protected against external high voltages (i.e. defibrillation protection). The sensor input signals are amplified and filtered appropriately for the sensor type. The amplifier gain and filter characteristics may be controlled by microprocessor. The signals to/from the amplifier circuit are DC isolated to prevent leakage currents from flowing through any patient connections that may be present at the sensor inputs. The sensor signals are digitized by the microprocessor and are transmitted through the USB link to the PC along with the telemetered signals from the INS 1100 for recording and display.

Figure 65C:
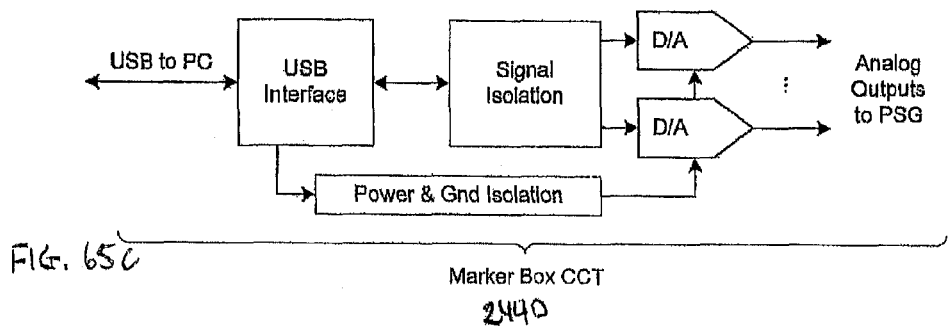

With reference to FIG. 65C, a block diagram of example circuit 2440 for the marker box 2430 is shown schematically. Generally, marker box 2430 and associated circuitry 2440 replace the D/A circuits and analog outputs 2410 of programmer interface circuit 2420 shown in FIG. 65B providing for the alternative arrangement illustrated in FIG. 68B. The marker box circuit 2440 is separately connected to a Universal Serial Bus (USB) port of the programmer computer 2300 via a USB cable. The USB interface also provides DC power for the marker box circuit 2440 via the USB cable. The power and ground for the marker box circuit 2440 are derived from the USB power input, but provide DC isolation for this circuitry to prevent leakage currents from flowing through any equipment that may be connected to the patient. Analog marker output data signals are transmitted from the PC 2300 to control the digital to analog (D/A) converter outputs. These analog output signals may be connected to standard PSG recording equipment 2800. Signals from the INS 1100 (such as sensed respiration impedance and stimulation output amplitude) can be represented by these outputs to allow simultaneous recording with other standard PSG signals (flow, belts, EMG/ECG, etc). The programmer 2300 may be enabled to automatically switch programmable settings at regular time intervals, allowing respiratory sensing vectors, stimulation levels, stimulation modes, or stimulation pulse configurations to be altered at specified intervals during sleep. Sampled values may be selected such that only a limited number of settings are sampled.

As mentioned previously, the INS 1100 records session summary data. The programmer computer 2300 may display these data using text and images to graphically display device settings, session data, and analyses of data. This data may be used to evaluate system performance and guide programming of settings. The patient's name or identifier may be stored in the INS 1100 and/or displayed on the programmer computer 2300. All text and symbols displayed by the programmer 2300 may be in a variety of selectable languages. The programmer 2300 may have the capability to connect to the internet. Through this connection files may be uploaded to a database to enable remote real time monitoring of device operation, recorded data and settings. The connection may also be used to update the programmer application software and or the (indirectly) the INS firmware.

The programmer 2300 may display and tag data to a variety of dates and times. These times may programmed to take into account daylight savings time, local time, Greenwich Mean Time, or a free-running counter in the INS 1100.

The programmer 2300 may display the voltage (or other capacity measurements) of battery 1140. In addition, an elective replacement indicator (ERI) and end of life (EOL) indicator may be displayed on the programmer as the battery nears depletion. There may be several months from ERI to EOL or alternatively, two months from ERI to EOL, with an estimated one month of use after EOL.

Therapy Controller

Figure 66B:
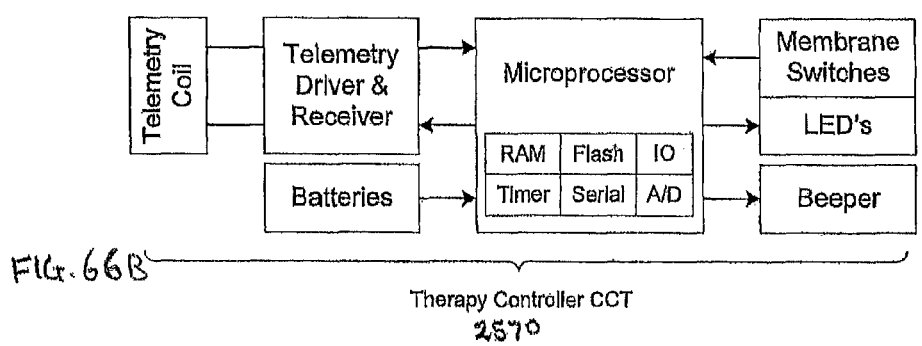
FIG. 66B is a schematic block diagram of electronic circuitry for use in the therapy controller shown in FIG. 66A.
Figure 66A:
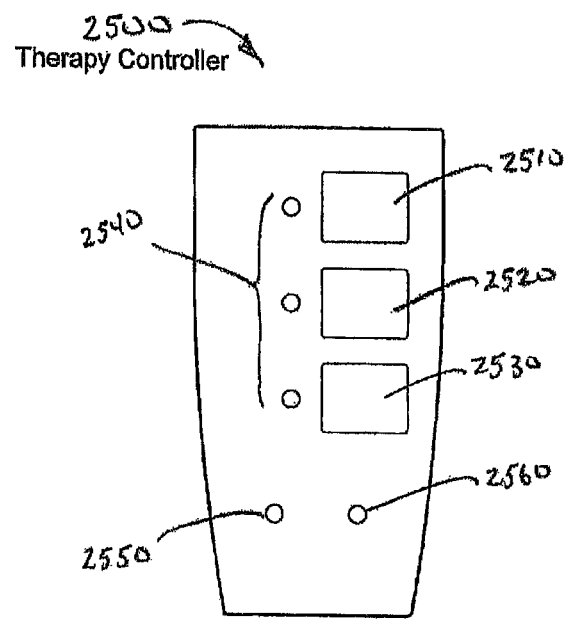
FIG. 66A is a schematic illustration of the therapy controller for use in the system shown in FIG. 59.

As shown schematically in FIG. 66A, the therapy controller 2500 may be used by the patient to control limited aspects of therapy delivery. The therapy controller 2500 is similar in certain aspects to commercially available patient controllers, which may be obtained from suitable manufacturers such as CCC Medical Devices (Montevideo, Uruguay). The therapy controller 2500 houses a battery, an antenna, and associated circuitry (not visible) to control limited aspects of therapy delivery via a wireless telemetry link (e.g., 30 KHz) with the INS 1100. Therapy is normally operated in a manual mode but may also be set for automatic delivery according to a predefined schedule (set by physician using the programmer during titration). The therapy controller has a user interface including start button 2510 (to start therapy delivery), a stop button 2520 (to stop therapy delivery) and a pause button (to pause therapy delivery or reduce stimulation intensity to a programmable value), each with associated LED indicators 2540 which flash when the corresponding button is depressed and illuminate steadily when the command is received by the INS 1100. The buttons may be backlit when pressed for ease of use at night. The user interface also includes a schedule set LED 2550 that illuminates if a therapy delivery schedule has been programmed, and a contact physician LED 2560 that illuminates in the event of a low battery or a malfunction requiring a physician visit. In addition, this light may illuminate at ERI or EOL time points.

The therapy controller may have additional functionality (e.g., more buttons) which can be set to give the patient limited control over select therapy settings. These settings include, but are not limited to, stimulation intensity (e.g., amplitude), stimulation mode, pulse train configuration, core hours stimulation settings, ramp, programmable schedule, clock, and motion inhibit programmable values.

As mentioned previously, the INS 1100 contains data, including metrics from therapy sessions. The therapy controller 2500 may wirelessly communicate with the INS 1100 to download any data to the INS. This data may be stored in internal memory or removable memory such as a USB flash drive or smart card. This data may be uploaded (e.g. from the patient's home computer) for the physician to read. This may allow the physician to monitor device use, home efficacy, or the patient's acclimation.

An alternative embodiment of the user interface may include an LCD display or a touchscreen. This allows for multiple functions to be integrated into the therapy controller while keeping the interface simple. This may also allow for larger text.

With reference to FIG. 66B, a block diagram of an example circuit for the therapy controller 2500 is shown schematically. The therapy controller circuit 2570 includes a battery powered microprocessor having a standard set of peripherals (RAM, flash, digital I/O, timers, serial ports, A/D converter, etc.). The microprocessor operates in a low power mode to conserve battery power. The microprocessor controls the telemetry driver and receiver electronics that interface with the telemetry coil. The telemetry coil is designed to inductively couple signals to the INS telemetry coil when aligned. The microprocessor monitors the membrane switches and reacts to switch closures by activating display LED's and initiating telemetry commands to the INS. As an alternative to telemetry coils and an inductive link, RF antennae with associated circuitry may be used to establish a RF link to provide for arms-length telemetry. After communicating with the INS, status information can be displayed to the user. The microprocessor also controls a beeper which can provide audio feedback to the user when buttons are pressed and to indicate the success or failure of communications with the INS. The beeper may have a mute function or volume control.

Magnet

Figure 67:
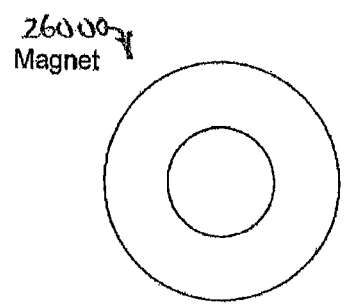
FIG. 67 is a top view of a magnet for use in the system shown in FIG. 59.

As schematically shown in FIG. 67, an annular magnet 26000 may be provided to the patient to deactivate or inhibit the INS 1100 in the event the therapy controller 2500 is not available or functioning. The magnet 26000 may comprise a permanent annular-shaped magnet made of ferrite strontium material coated with epoxy. The magnet 26000 may produce a strong field of 90 Gauss at 1.5 inches from the surface of the magnet along the centerline of the hole. The magnet 26000 may be used (or carried by) the patient in case of emergency. When temporarily (2 seconds or more) placed over the implanted INS 1100 on the skin or clothing, the magnet 26000 disables current and future therapy sessions. Although therapy sessions are disabled by the magnet 26000, all other functions of the INS 1100 may remain enabled including telemetry communication with the programmer system 2100 and therapy controller 2500. Therapy sessions may be re-enabled using the programmer system 2100. The therapy controller 2500 may also re-enable therapy sessions if the therapy controller 2500 has been authorized by the programmer system 2100 to do so. Therapy sessions may be re-enabled using the therapy controller 2500 by initiating a new therapy session. Alternatively, the therapy may be temporarily inhibited during placement of the magnet. If left in place for a specified time period (e.g. one minute), therapy may be deactivated.

Interface with PSG Equipment

Figure 68A:
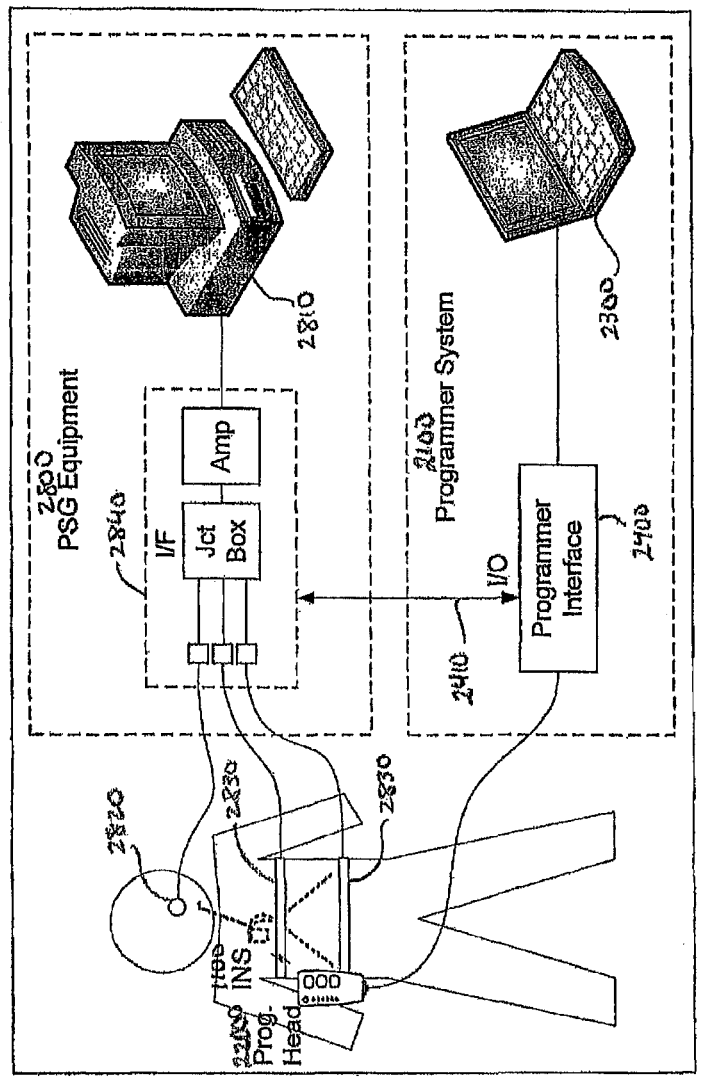
FIG. 68A is a schematic illustration of an interface of the system shown in FIG. 59 and polysomnographic equipment as may be used in a sleep study for therapy titration or therapy assessment, for example.
Figure 68B:
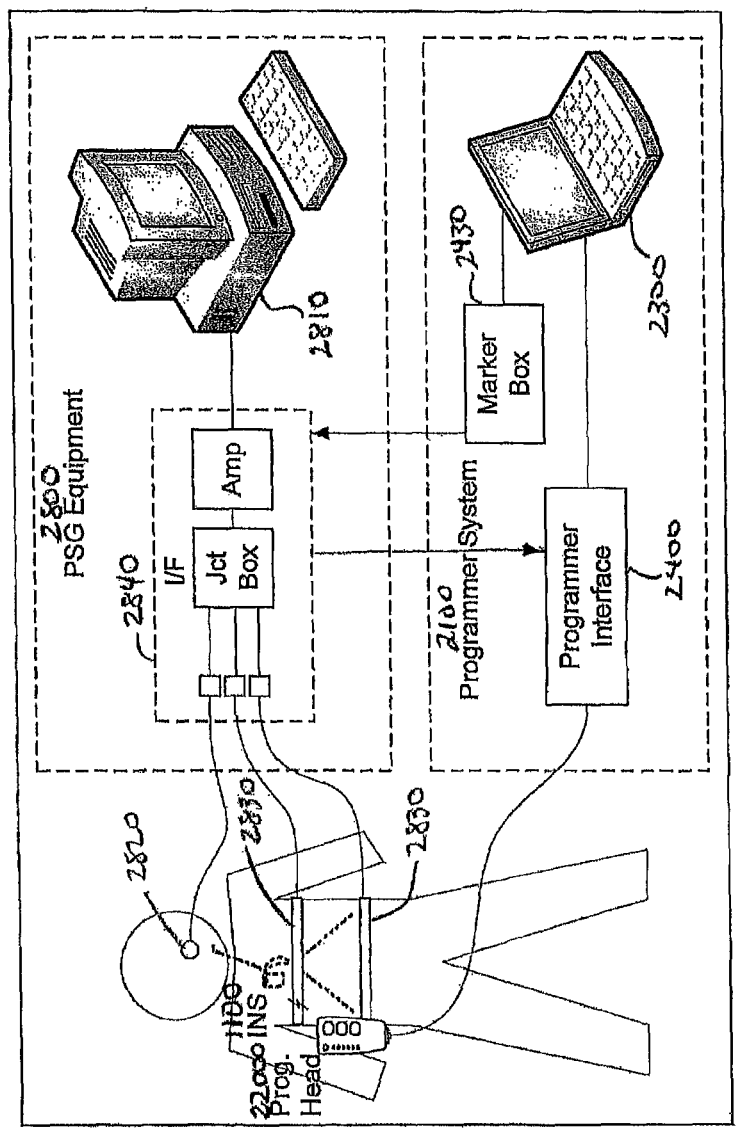
FIG. 68B is a schematic illustration of an alternative interface of the system shown in FIG. 59.

The programmer interface 2400 may include an input/output (I/O) link 2410 to allow connection to polysomnographic (PSG) equipment 2800 as schematically shown in FIG. 68A. Typical PSG equipment 2800 includes a computer 2810 connected to a plurality of sensors (e.g., airflow sensor 2820, respiratory effort belts 2830) via interface hardware 2840. The I/O link 2410 may be used in a number of different ways. For example, analog data signals from the PSG equipment 2800 may be downloaded to the computer 2300 of the programmer system 2100 to record and/or display PSG data (e.g. airflow) together with therapy data. Alternatively or in addition, digital data signals from the INS 1100 and/or the programmer system 2100 may be uploaded to the computer 2810 of the PSG equipment 2800 to record and/or display therapy data (e.g., stimulation amplitude, stimulation pulse width, and/or respiration data such as bio-impedance, vector, filter settings, prediction markers, or accelerometer data) together with PSG data. The circuitry corresponding to I/O link 2410 may be incorporated into the programmer interface 2400 as shown in FIG. 68A, or may be incorporated into a separate marker box 2430 as shown in FIG. 68B.

Synchronizing data from the sensors 2820/2830 of the PSG equipment 2800 with data from the INS 1100 via the programmer system 2100 may be beneficial to facilitate therapy titration and efficacy measurement. Although the programmer system 2100 and the PSG equipment 2800 may be directly connected by I/O link 2410, transmission delay in each system may result in asynchrony. Data synchronization between the systems may be addressed in a number of different ways. For example, if the delays in each system are relatively fixed and below an acceptable threshold (e.g., 0.5 to 1.0 second), no synchronization step need be taken. If the delays in each system are relatively fixed but above an acceptable threshold (e.g., above 0.5 to 1.0 second), data from the system with less delay may be offset (delayed) by a fixed time value to align with data from the system with more delay. As an alternative, a timing signal (e.g., from a clock signal generator separate from or integral with one of the systems) may be input into the PSG equipment 2800 and programmer system 2100 to allow time stamped data independently collected by each system to be merged and synchronized by post processing.

Treatment Overview

Figure 69A:
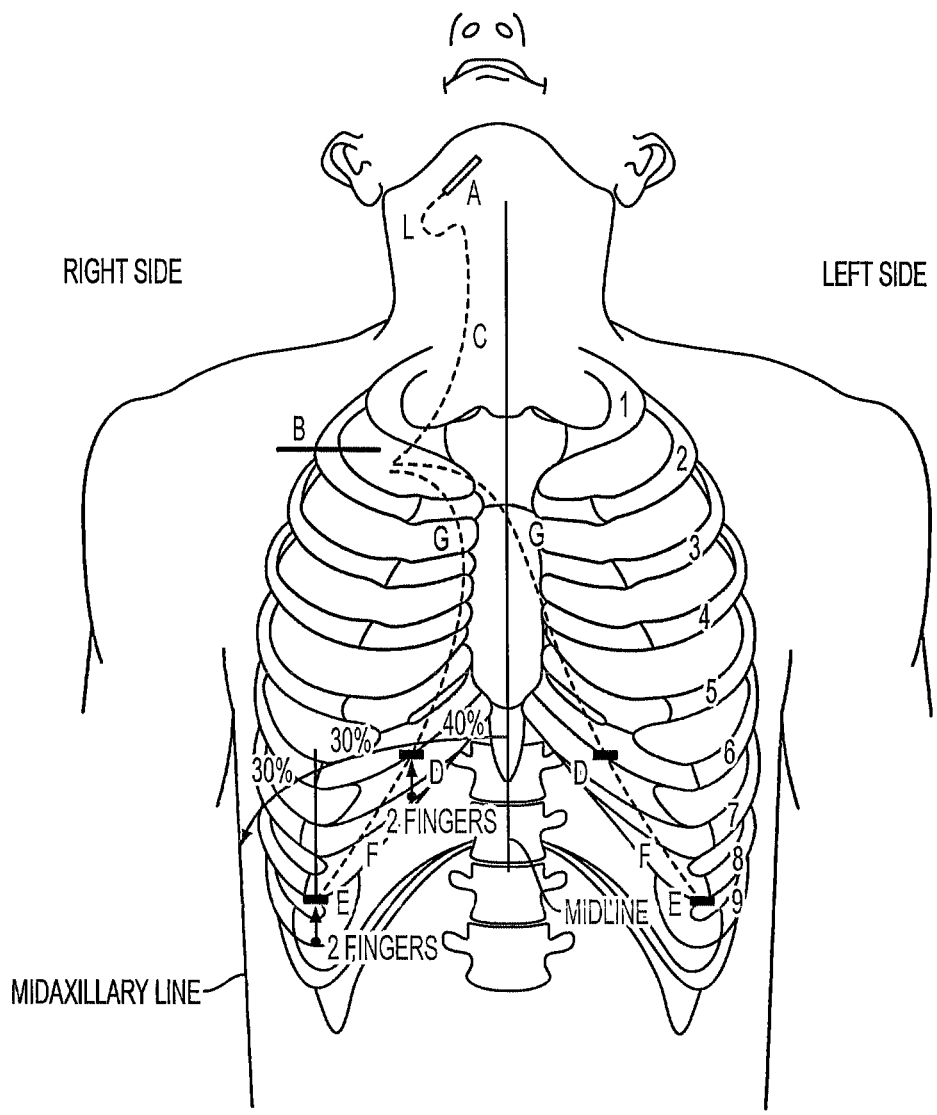
FIG. 69A is an anatomical illustration showing the incision sites and tunneling paths that may be used for implanting the internal components shown in FIG. 59.

FIG. 69A schematically illustrates the incision sites (solid thick lines) and tunneling paths (dotted lines) for implanting the INS 1100, STL 1300 and RSLs 1200. The implant procedure may be performed by a surgeon (e.g., otolaryngologist) in a 1-2 hour surgical procedure with the patient under general anesthesia, for example. In general, the implant procedure involves placing the cuff 1350 of the STL 1300 on the hypoglossal nerve via a submandibular dissection, and tunneling the lead body 1330 and sigmoid section 1370 of the STL 1300 subcutaneously down the neck to the INS 1100 in a subcutaneous pocket in the infraclavicular region. From the infraclavicular pocket, the RSLs 1200 may be tunneled subcutaneously toward midline and then laterally along the costal margins.

After a healing period of a few weeks, the patient returns to the sleep lab where a sleep technician, under the supervision of a certified sleep physician (e.g., pulmonologist), uses the programmer system 2100 to program the INS 1100 (e.g., set the therapy delivery schedule and titrate the stimulus to optimize efficacy during sleep).

Immediately after the titration visit, the patient may return home and begin use. A therapy delivery session may begin according to the pre-defined therapy delivery schedule, which may be set to coincide with when the patient normally goes to sleep. At the beginning of a therapy delivery session, stimulus may be delayed for a period of time to allow the patient to fall asleep. The therapy delivery session may end according to the pre-defined therapy delivery schedule, which may be set to coincide with when the patient normally wakes up. The therapy delivery session may be programmed to not exceed eight hours. The patient can use the therapy controller 2500 to adjust limited aspects of therapy delivery. For example, the patient can use the therapy controller 2500 to stop, pause and restart a scheduled therapy session. In addition, the therapy controller 2500 can be used to manually control therapy delivery rather than operate according to a preset schedule. This may be beneficial when the patient has an irregular sleep schedule, for example. In this mode, the therapy controller 2500 can be used by the patient to manually start, stop, and pause a therapy session.

Surgical Implant Procedure

With continued reference to FIG. 69A, the internal components 1000 may be implanted using the following surgical procedure, which is given by way of example, not limitation. Unless specifically stated, the order of the steps may be altered as deemed appropriate. Although the INS 1100 may be surgically implanted on the right or left side, the right side is preferred to leave the left side available for implantation of cardiac devices that are traditionally implanted on the left side. The right side is also preferred for the RSL 1200 (if one RSL is used) to provide a clean respiratory signal that is less susceptible to cardiac artifact than the left side.

Figure 69B:
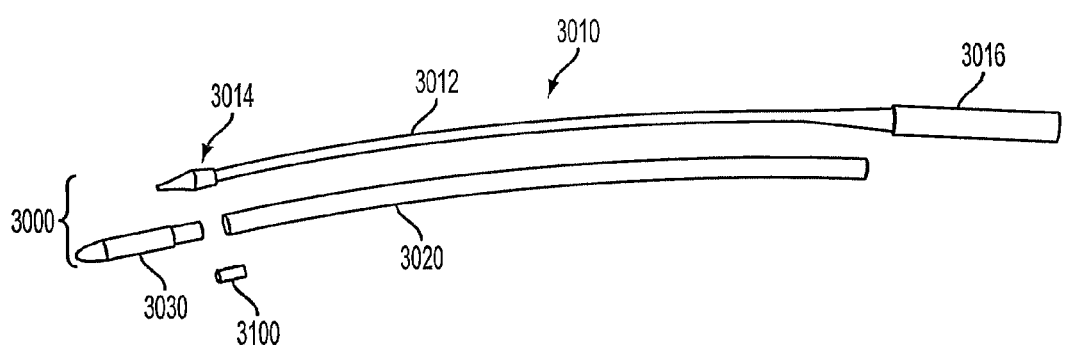
FIG. 69B is a perspective view of a disassembled tunneling tool for use in tunneling the leads of the system shown in FIG. 59.
Figure 69C:
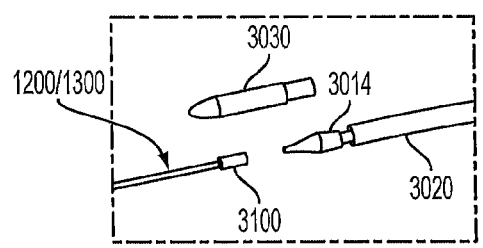
FIG. 69C is a detailed perspective view of the assembled tunneling tool shown in FIG. 69B, but with the cap removed to expose the jaws for grasping the lead carrier disposed on the proximal end of a lead.

Standard surgical instruments may be used for incisions, dissections, and formation of subcutaneous pockets. Commercially available nerve dissection instruments may be preferred for dissecting the hypoglossal nerve and placing the STL cuff 1350 on the nerve. A tunneling tool 3000, as schematically shown in FIGS. 69B and 69C, may be used for tunneling the STL 1300 and RSL 1200 leads. The tunneling tool (also referred to as tunneler) 3000 includes a relatively rigid grasper 3010, a tubular sheath 3020, and a cap 3030. The sheath 3020 and cap 3030 are sized to be slid over the grasper 3010. The cap 3030 may include a radiopaque agent such as barium sulfate loaded at 18% by weight, for example. The grasper 3010 may be formed of stainless steel and includes a shaft 3012, distal jaws (similar to an alligator clip) 3014, and a proximal handle 3016. The jaws 3014 are biased to the closed position and may be used to grasp the proximal end of the RSL 1200 or STL 1300 using the lead carrier 3100 as protection. The lead carrier 3100 may comprise a small polymeric tube with an inside diameter sized to form an interference fit with the proximal end of the RSL 1200 or STL 1330. The sheath 3020 may comprise a polymeric tube with two open ends, and the cap 3030 may comprise a polymeric tube with one open end and one closed end for blunt dissection.

The proximal end of the cap 3030 may include a tapered section to fit into the distal end of the sheath 3020 and form an interference fit therewith. In the embodiment shown in FIGS. 69B and 69C, the sheath 3020 may have an outside diameter of approximately 0.37 inches and a length of about 10.9 inches. The cap may an outside diameter tapering from approximately 0.37 inches and a length of about 1.7 inches. The shaft 3012 may have a diameter of about 0.19 inches and together with the jaws 3014 may have a length sufficient to fill the length of the sheath 3020 and cap 3030. The handle 3016 may have a diameter of about 0.5 inches and a length of about 3.0 inches.

Figure 69D:
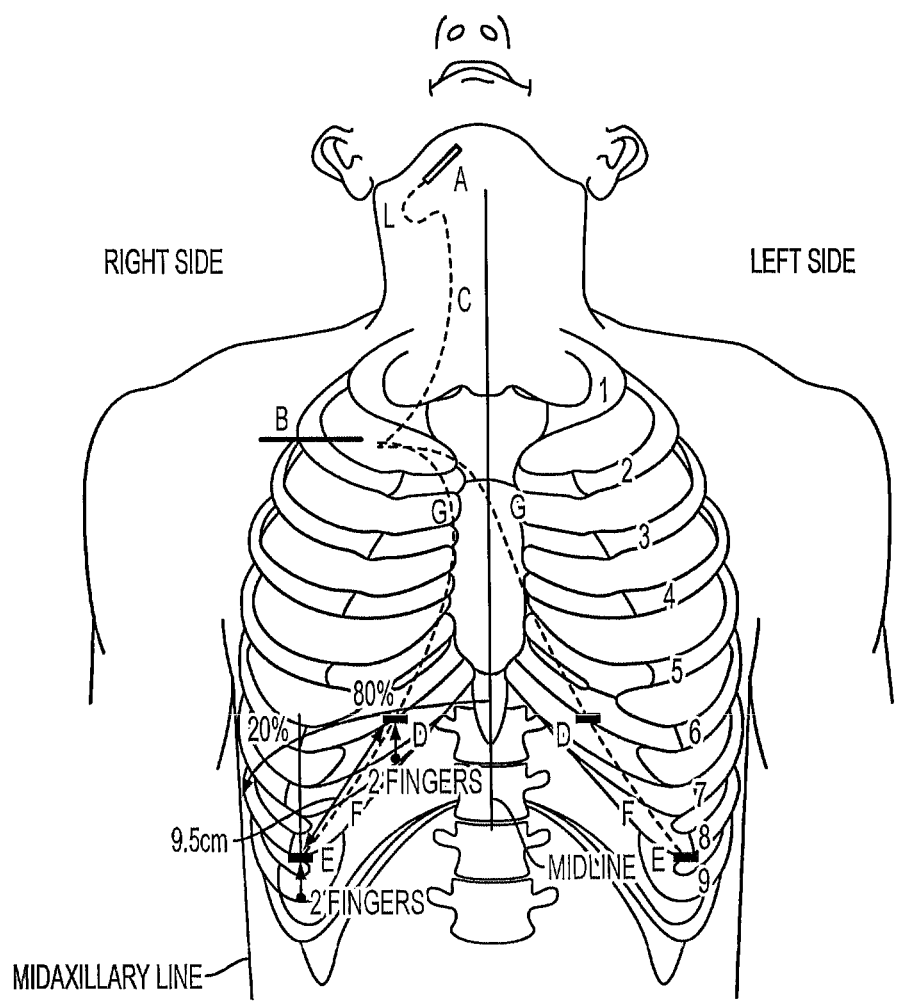
FIG. 69D is an anatomical illustration showing the incision sites and tunneling paths that may be used for implanting the internal components shown in FIG. 59.
Figure 69E:
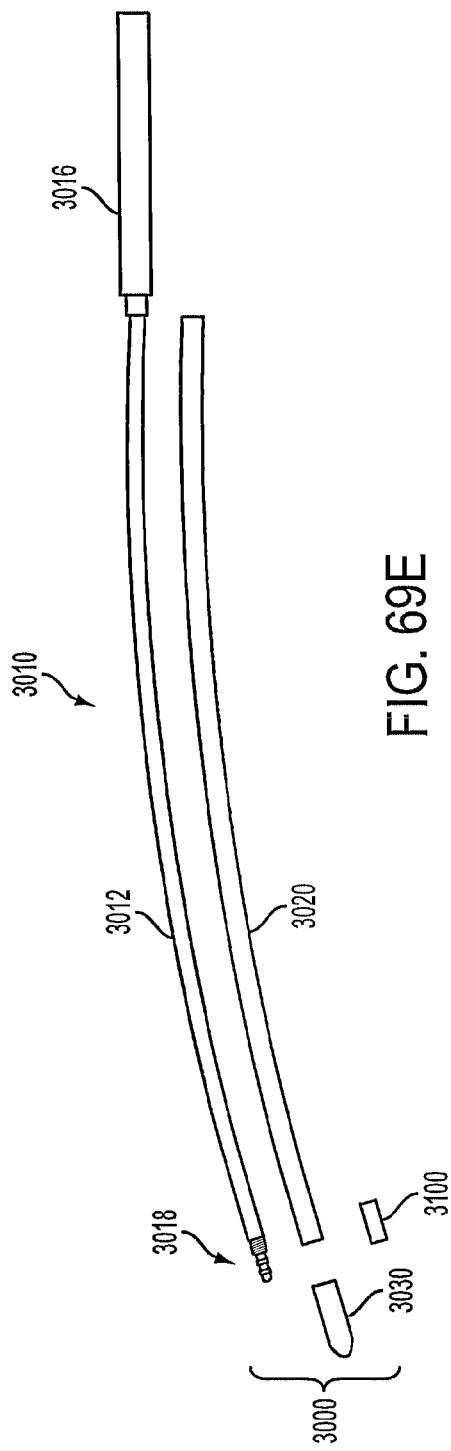
FIGS. 69E and 69F illustrate an alternative tunneling tool for use in tunneling the leads of the system shown in FIG. 59.
Figure 69F:
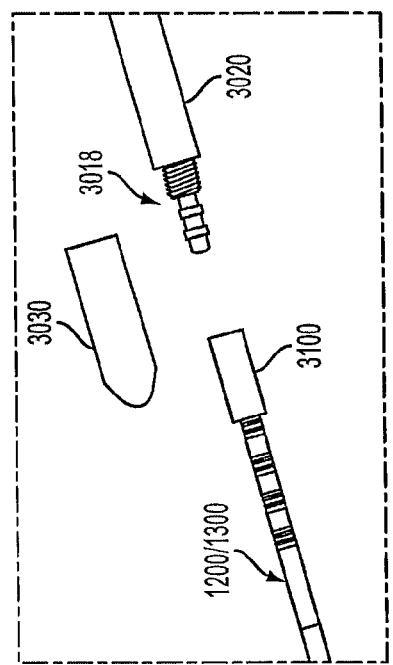

An alternative tunneling tool 3000 is schematically shown in FIGS. 69E and 69F may be used for tunneling the STL 1300 and RSL 1200. In this embodiment, the tunneling tool 3000 includes a relatively rigid grasper 3010, a tubular sheath 3020, and a cap 3030. The sheath 3020 and cap 3030 are sized to be slid over the grasper 3010. The cap 3030 may include a radiopaque agent such as barium sulfate loaded at 18% by weight, for example. The grasper 3010 may be formed of stainless steel and includes a shaft 3012, distal connector 3018, and a proximal handle 3016. The connector 3018 includes threads that mate with corresponding threads in the cap 3030. The connector 3018 may also include ring barbs that form an interference fit with the inside of the lead carrier 3100 for releasable connection thereto. The lead carrier 3100 may comprise a small polymeric tube with an inside diameter sized to form an interference fit with the proximal end of the RSL 1200 or STL 1330. The sheath 3020 may comprise a polymeric tube with two open ends, and the cap 3030 may comprise a polymeric tube with one open end and one closed end for blunt dissection. The proximal end of the cap 3030 includes internal threads to screw onto the connector 3018 and hold the sheath 3020 on the shaft 3012. In the embodiment shown in FIGS. 69E and 69F, the sheath 3020 may have an outside diameter of approximately 0.28 inches and a length of about 12.3 inches. The cap may an outside diameter tapering from approximately 0.13 inches and a length of about 1.0 inches. The shaft 3012 may have a diameter of about 0.22 inches and may have a length sufficient to fill the length of the sheath 3020. The handle 3016 may have a diameter of about 0.5 inches and a length of about 3.74 inches.

The patient is prepared for surgery using conventional practice including standard pre-operative care procedures, administration of antibiotics as appropriate, and administration of steroids as appropriate to reduce swelling around the nerve dissection. Because tongue movement must be observed during test stimulation, it is recommended that no long-acting muscle relaxants be used during surgical preparation no muscle relaxants be used during implant. General anesthesia is administered according to conventional practice and the patient is intubated using an endotracheal tube, taking care to position the endotracheal tube so that the tongue is free to protrude during test stimulation.

The neck is then extended to expose right submandibular region and a sterile field is created around the neck and thorax, taking care to avoid obstructing visualization of the oral cavity (a clear sterile drape over the mouth may be used). By way of a neck incision (A), the hypoglossal nerve is then exposed deep to the submandibular gland. Because the INS 1100 is preferably implanted on the right side to minimize cardiac artifact during respiratory sensing, this dissection is also preferably performed on the right side. The branch of the hypoglossal nerve believed to innervate the genioglossus muscle is then identified and isolated. Confirmation of correct nerve location may be achieved by performing a test stimulation later in the procedure. The identified nerve branch is then circumferentially dissected to accommodate the cuff 1350. The short side 1352 of the cuff 1350 is designed to reside on the deep side of the nerve, and the long side 1354 of the cuff 1350 is designed to reside on the superficial side of the nerve.

The appropriate sized cuff 1350 is then selected based on the nerve diameter at the intended location for cuff placement. Nerve size may be assessed using reference size (e.g., forceps of know width), a caliper, or a flexible gauge that wraps around the nerve, for example. The cuff 1350 is then opened and placed around the nerve. The strap 1356 on the cuff 1350 may be used to facilitate placement of the cuff 1350 around the nerve. A curved forceps may be placed under the nerve to grasp the strap 1356 and gently pull the cuff 1350 onto the nerve. The strap 1356 is then placed through the loop (buckle) 1358 on the cuff 1350. The cuff 1350 may be available in two sizes (small and large), and the small cuff may have an indicator mark (not shown) on the strap 1356 that should be visible after insertion through the loop 1358. If the indicator mark is not visible, the small cuff may be too small and should be replaced with a large cuff. The surgeon then verifies that the cuff 1350 is not pulling or twisting the nerve, and that there is contact between the inside of the cuff 1350 and the nerve.

A test stimulation is then performed to confirm correct positioning of the cuff 1350 on the nerve. To conduct a test stimulation, the proximal end of STL 1300 is plugged into the INS 1100 and the programmer system 2100 is used to initiate a test stimulation signal delivered from the INS 1100 to the nerve via the STL 1300. The test stimulation is performed while observing, for example, tongue movement by direct visual observation, airway caliber by nasal endoscopy, lateral fluoroscopy/cephalogram, etc. Correct placement of the cuff on the nerve may be confirmed by, for example, observing tongue protrusion, an increase in retro-glossal airway caliber, an increase in retro-palatal airway caliber, an increase in stiffness of the anterior and/or lateral walls of the retro-glossal airway with or without an increase in airway caliber, anterior movement with or without inferior movement of the hyoid bone, among others. Incorrect placement of the cuff on the nerve is indicated, for example, when the tongue is observed to retract (posterior movement), a decrease in retro-glossal airway caliber, a decrease in retro-palatal airway caliber, superior movement and particularly unilateral superior movement of the hyoid bone, among others. If necessary, the cuff 1350 may be repositioned at a different location along the length of the nerve to obtain the desired effect. The capture threshold and impedance values are recorded and the STL 1300 is disconnected from the INS 1100. A fascial wrap is then sutured over the cuff on the superficial side of the nerve.

A strain relief loop (L) in the STL 1300 is then created by arranging approximately 6 cm of the STL sigmoid body 1370 in a C-shape inside a small subcutaneous pocket formed via the neck incision (A) by blunt dissection superficially along the lateral surface of the digastric muscle in a posterior direction.

A pocket for the INS 1100 is then created by making an incision (B) down to the pectoralis fascia up to 2 finger breadths below the right clavicle. The INS 1100 is preferably implanted on the right side to minimize cardiac artifact during respiratory sensing. Blunt dissection inferior to the incision is used to create a pocket large enough to hold the INS 1100. The pocket should be inferior to the incision (B) such that the incision (B) does not reside over the INS 1100 when later placed in the pocket.

A tunnel is formed for the STL 1300 using the tunneler 3000 (sheath 3020 and cap 3030 placed over grasper 3010) to tunnel along a path (C) from the infraclavicular INS pocket to the neck incision (A). As shown in FIG. 69C, the lead carrier 3100 is then placed on the most proximal electrical contact of the STL proximal connector 1310. The cap 3030 is removed from the sheath 3020 to expose the jaws 3014 of the grasper 3010 and grab the lead carrier 3100. While holding the sheath 3020 in place, the grasper 3010 is pulled proximally to pull back the STL 1300 through the sheath 3020, taking care not to pull out the C-shaped strain relief or disturb the cuff. If the C-shaped strain relief loop (L) is pulled out, it should be replaced into the small pocket. The grasper 3010 is released from the lead carrier 3100 and the lead carrier 3100 is removed from the STL 1300. The sheath 3020 is then removed from the body leaving the STL 1300 in place. The neck incision (A) need not be closed at this time, but rather may be closed later in the procedure allowing confirmation that the C-shaped strain relief remains in the small pocket.

The right RSL 1200 is placed near the right costal margin by making two small incisions (D and E) as shown. The medial incision (D) may be made approximately 40% (+/− 5%) of the distance from the midline to the midaxillary line, and approximately two finger breadths superior to the costal margin. The lateral incision (E) may be made approximately halfway between the medial incision (D) and the midaxillary line (i.e., extending from the medial incision (D), approximately 30% (+/−5%) of the distance from the midline to the midaxillary line), and approximately up to two finger breadths superior to the costal margin. Using the tunneler 3000 (sheath 3020 and cap 3030 placed over grasper 3010), a tunnel (F) is formed from the medial incision (D) to the posterolateral incision (E). The lead carrier 3100 is then placed on the most proximal electrical contact of the RSL 1200 proximal connector 1210. The cap 3100 is then removed from the sheath 3020 to expose the jaws 3014 of the grasper 3010 and grab the lead carrier 3100. While holding the sheath 3020 in place, the grasper 3010 is pulled proximally to pull back the RSL 1200 through the sheath 3020. The grasper 3010 is released from the lead carrier 3100 and the lead carrier 3100 is removed from the RSL 1200. The sheath 3020 is then removed from the body leaving the RSL 1200 in place. Each suture tab 1270 is secured to the underlying tissue by dissecting down to the muscle fascia adjacent the anchor tabs 1270 on the RSL 1200 and suturing each anchor tab 1270 to the muscle fascia. Permanent sutures are recommended to avoid movement of the RSL 1200 before tissue encapsulation, and braided suture material is recommended for knot retention. The left RSL 1200 is then implanted along the left costal margin in the same manner as described above.

The right RSL 1200 is then tunneled to the pocket (B) for the INS 1100. Using the tunneler 3000 (sheath 3020 and cap 3030 placed over grasper 3010), a tunnel (G) is formed from the infraclavicular pocket to the medial incision (D). The lead carrier 3100 is placed on the most proximal electrical contact of the RSL 1200 proximal connector 1210. The cap 3030 is then removed from the sheath 3020 to expose the jaws 3014 of the grasper 3010 and grab the lead carrier 3100. While holding the sheath 3020 in place, the grasper 3010 is pulled proximally to pull back the RSL 1200 through the sheath 3020. The grasper 3010 is released from the lead carrier 3100 and the lead carrier 3100 is removed from the RSL 1200. The sheath 3020 is then removed from the body leaving the RSL 1200 in place. The left RSL 1200 is then tunneled to the pocket for the INS 1100 in the same manner as described above.

The STL 1300 and RSLs 1200 are then connected to the INS 1100. Since one STL port is not used in this example, a port plug (small silicone cylinder) is inserted into header port STL-2. The RSLs 1200 are plugged into ports RSL-A and RSL-B, the STL 1200 is plugged into port STL-1 and the set screws are tightened to 1 click using a torque wrench.

A closed loop test may be performed to confirm proper operation by observation of tongue protrusion in concert with inspiration. The INS 1100 and proximal portions of the leads 1200/1300 are then placed into the infraclavicular pocket, looping the excess lead length beneath or around the INS 1100. Care should be taken not to pull out the C-shaped strain relief loop (L) in the STL sigmoid lead body 1370 while manipulating the INS 1100 into place. The INS 1100 is then sutured to underlying fascia through both suture holes found in the header 1110 of the INS 1100. Permanent sutures are recommended for to avoid movement of the INS before tissue encapsulation, and braided suture material is recommended for knot retention. Another system test may be performed at this point. After confirming that the C-shaped strain relief loop (L) is present in small pocket at neck incision, the incisions may be irrigated (optionally with an antibiotic solution) and closed using conventional techniques. After a healing period of approximately one month, the patient may undergo a sleep study to confirm proper operation of the system and to titrate therapy.

Figure 70:
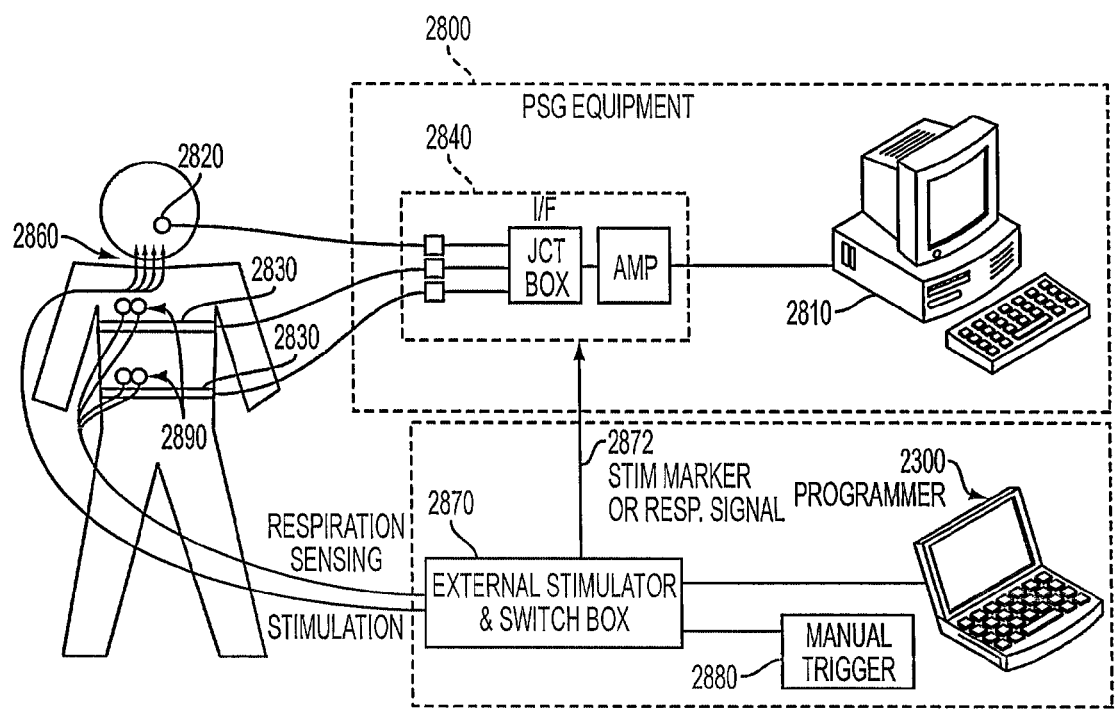
FIG. 70 is a schematic illustration of an external stimulator system and polysomnographic equipment as may be used for direct muscle stimulation using fine wire electrodes as a therapy efficacy screening method, for example.

An alternative lead routing schematic is shown in FIG. 69D. In this alternative embodiment, the left and right lateral incision sites E are located 80% of the distance from the midline to the mid-line, up to two finger breadths above the rib costal margin. The medial incision sites D are then located a straight line distance of 9.5 cm medial, up to two finger breadths above the rib costal margin Screening Methods As schematically shown in FIG. 70, an external system may be used to conduct a stimulation screening session prior to full implantation wherein the genioglossus muscle (innervated by the hypoglossal nerve) is stimulated with fine wire electrodes (FWEs) 2860 inserted submentally with a needle during an otherwise conventional sleep (PSG) study utilizing PSG equipment 2800. The FWEs 2860 may be inserted into the genioglossus under the guidance of ultrasound. Stimulation signals may be delivered to the genioglossus muscle by connecting the FWE's 2860 to an external stimulator and switch box 2870. The external stimulator and switch box 2870 may comprise the INS 1100, programmer head 22000 and programmer interface 2400 in a common housing, with the stimulation output of the INS 1100 connected to the FWEs 2860 and the sensing input of the INS 1100 connected to skin surface electrodes 2890 for bio-impedance respiration measurement. A stimulation marker output signal 2872 from the external stimulator and switch box 2870 to the PSG equipment 2800 allows stimulation and/or respiration data to be synchronized and merged with PSG data in near real time. The external stimulator and switch box 2870 may include a manually operated switch array to select a single FWE or a combination of FWEs 2860 to deliver a stimulation signal to the genioglossus muscle. With this arrangement, stimulation may be delivered via FWEs 2860 automatically triggered by inspiration measured via skin surface electrodes 2890 or manually triggered via activating a manual trigger switch 2880. The efficacy of delivering stimulus to the genioglossus muscle may be observed and measured using conventional PSG parameters. Efficacious results may be indicated by a significant reduction in apnea hypopnea index, an increase in flow, a decrease in critical closing pressure, and/or an increase in airway caliber, for example. Patients that respond adequately to stimulation during the trialing period ("responder") may receive the implanted device. Perhaps more importantly, patients that do not adequately respond to stimulation during the trialing period ("non-responder") would not receive the implanted device.

Figure 71:
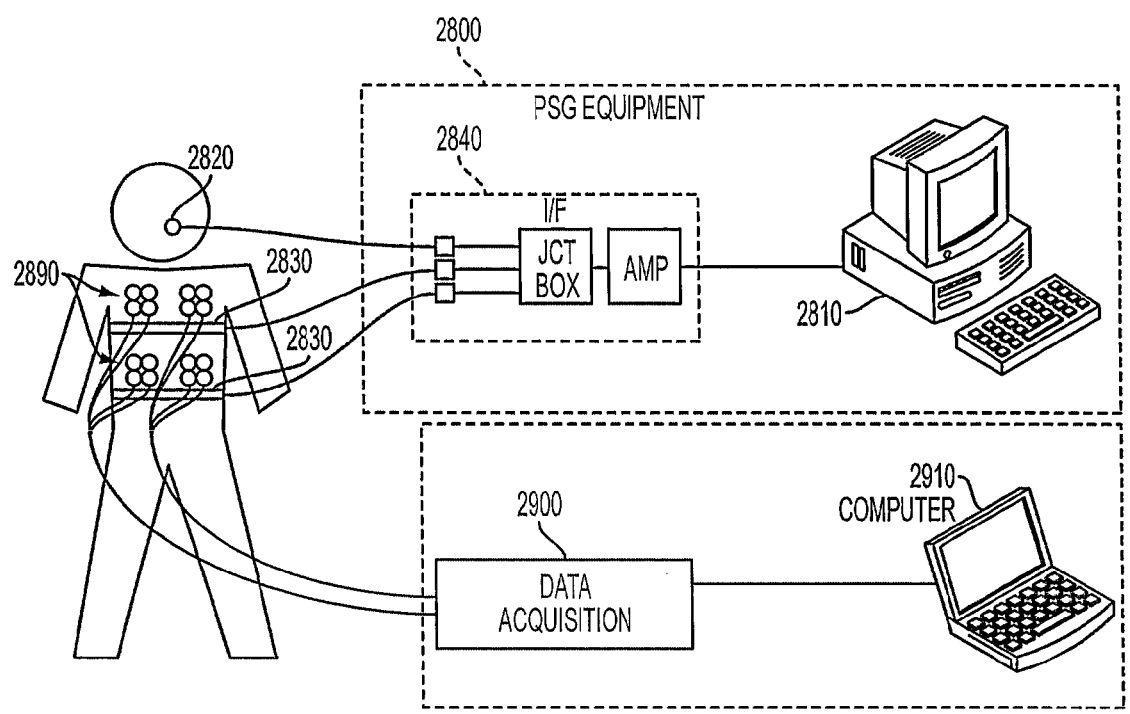
FIG. 71 is a schematic illustration of a bio-impedance monitoring system using surface electrodes and polysomnographic equipment as may be used as a respiratory sensing screening method, for example.

As schematically shown in FIG. 71, an external system may be used to conduct a respiration screening session prior to full implantation wherein skin surface electrodes are placed on the skin at or near the locations that the respiration sensing electrodes and INS would be implanted. Bio-impedance measurements may be taken during a sleep study to determine if an adequate bio-impedance signal may be obtained. In addition, different locations for the skin surface electrodes may be tested to determine the optimal locations for the respiration sensing electrodes during implantation.

The stimulation trialing period and the respiration trialing period may be combined into a single study, wherein skin surface bio-impedance measurements may be used to provide closed-loop feedback for stimulating synchronous with inspiration. Patients would then be categorized as responders or non-responders depending on the outcome of the closed-loop study.

Titrating Methods

As described previously, after implantation and a healing period of approximately one month, the patient may undergo a sleep (PSG) study to confirm proper operation of the system and to titrate therapy. Titration may utilize the set-up illustrated in FIG. 68, wherein the programmer system 2100 interfaces with the PSG equipment 2800. Titration generally involves (1) selecting an optimal respiratory sensing signal and (2) selecting optimal stimulation signal parameters (e.g., stimulation intensity, respiratory phase adjustment). After titration, therapy efficacy may be measured using standard PSG techniques. For example: a respiratory sensing vector may be selected based on signal strength and stability, reliability; the stimulation amplitude may be selected based on maximum airflow; the phase adjustment may be selected based on stimulation alignment with inspiratory airflow; and therapy efficacy may be evaluated based on elimination of indicia of sleep disordered breathing such as AHI.

Selecting an optimal respiratory sensing signal involves selecting the best vector defined by two sets of electrodes on the RSL or one set of electrodes on the RSL and the housing of the INS. Selection may be based on maximum signal strength, consistent correlation to inspiration, and maximum signal stability/reliability across sleep stages, body positions, and disordered breathing events, for example. A stable signal has a minimum probability of signal inversion. A reliable signal has a minimum probability of signal loss, and therefore may preferably have a minimum threshold of 0.2 to 0.5 Ohms peak-to-peak, for example. The optimal vector may be selected by incrementally scrolling through all or a preferred subset of possible vectors while sampling the respiration signal and comparing the signal against themselves or predefined thresholds. This scrolling technique may be performed manually (with inputs via the programmer system) or automatically (i.e., programmed). The sampling technique may also be performed manually (visual observation using programmer system) or automatically (i.e., programmed). For practical purposes, the respiration sensing vector may be evaluated while the patient is awake by having the patient assume different body positions while at resting respiration. Alternatively, the respiration sensing vector may be evaluated while the patient is asleep during different stages of sleep and during different sleep disordered breathing events. The INS is capable of streaming out data from two or more sensing vectors which allows simultaneous comparison. This may be especially useful during titration (body position testing and during sleep study) to minimize chance that evaluation of a given vector is biased by events unrelated to a given vector.

Selecting optimal stimulation signal parameters (e.g., pulse amplitude, pulse frequency, pulse width, duty cycle, phase adjust, etc.) to optimize efficacy (e.g., as measured by apnea index, hypopnea index, respiratory disturbance index, apnea-hypopnea index, and other obstructive sleep apnea efficacy measures) is preferably performed while the patient is sleeping.

The adjustable stimulation parameters include pulse frequency (range of 20 to 50 Hz, nominal 40 Hz), pulse width (range of 30 to 215.mu.s, nominal 90.mu.s), pulse amplitude (range of 0.4 to 5.0 mA, nominal 0.4 mA), duty cycle (range of 41% to 69%, nominal 50%), and phase adjust (range of −1.5 to +0.5 s, nominal −0.5 s). In general, during the stimulation titration process, it is preferable to begin with the lowest settings for pulse width (30.mu.s) and amplitude (0.4 mA) at a nominal frequency (40 Hz). If stimulation produces pulsatile (vibrating) contractions, the frequency may be increased to 50 Hz. The pulse width is incrementally increased to 60.mu.s, then to nominal (90.mu.s), keeping Amplitude at 0.4 mA. With the pulse width set to 90.mu.s, amplitude may be iterated according to the process described hereinafter. If maximum amplitude is reached and additional intensity is required, the pulse width may be increased while reducing amplitude to minimum (0.4 mA). If maximum pulse width (215.mu.s) is reached and additional intensity is required, frequency may be increased while reducing the pulse width to 90.mu.s and the amplitude to minimum (0.4 mA).

An initial step in titrating may involve defining a stimulation operating window, preferably while the patient is awake, defined at its lower limit by a capture threshold and at its upper limit by a comfort threshold. The capture threshold may be defined as the stimulation level at which some indication of a potentially beneficial effect (e.g., gross tongue movement or stiffening) is observed. The comfort threshold may be defined as the stimulation level at which the patient experiences an unacceptable sensation (e.g., pain) while awake or at which the patient partially or completely arouses (e.g., lighter stage of sleep or awake) during sleep. Human subjects have been observed to tolerate (i.e., not arouse) higher stimulation intensities while asleep than they could tolerate while awake. The operating window may be determined at the beginning of the titration sleep study (e.g. during set-up when the patient is awake) to help determine a lower limit or starting point for stimulation (capture threshold) and an upper limit or ending point for stimulation (comfort threshold), between which the stimulation level may be adjusted (e.g., increased) until an efficacious level is found.

Using the programmer system 2100 to set the stimulation parameters, the stimulation level may be initially set at the lower limit or a percentage (e.g., 50%) of the upper limit, followed by a monitoring period where efficacy is measured using standard PSG techniques. After the initial monitoring period, the stimulation level may be incrementally increased, followed by another monitoring period. This may continue in a step-wise fashion up to the upper limit for stimulation or until no significant difference in measured efficacy is discernable between stimulation levels. If no significant difference in measured efficacy is discernable between a lower and higher stimulation level, the lower level may be selected as the desired stimulation dose.

Because efficacy measures (e.g., apnea-hypopnea index) typically take hours to collect, it may be desirable to create a controlled, flow-limited condition and measure a surrogate parameter (e.g., airflow, critical closing pressure, etc.) in order to complete the step-wise titration process in a reasonable amount of time (e.g., a single or half night sleep study). In addition, because a number of sleep conditions (e.g., sleep stage) change over the course of an all night study, it is beneficial to titrate therapy over a shorter period of time during which sleep conditions are less likely to change as significantly. To create a flow-limited state, the patient may be fitted with a CPAP (continuous positive airway pressure) device comprising a blower connected via a hose to a mask (incorporating a airflow meter such as a pneumotachometer) placed over the patient's nose and/or mouth. The CPAP device may have the capability to deliver variable pressure down to approximately 0 cm $H_2O$ or lower, in increments of 0.10 cm $H_2O$ or less, for example. Such a CPAP device is also called a $P_{crit}$ device for its ability to assist in making critical closing pressure measurements of the upper airway using techniques developed by Schwartz et al. The airway in people with obstructive sleep apnea will partially or completely occlude during sleep in the absence of adequate positive airway pressure. Thus, adjusting the CPAP pressure below the therapeutic level for a given patient will create a controlled flow-limited condition. Using these techniques, the stimulation intensity level (e.g., current, mA) or other stimulation parameter (e.g., pulse frequency, pulse duration, phase adjustment, etc.) may be titrated by progressively creating greater flow restriction while determining if a change (e.g., an increase) in a stimulation parameter (e.g., intensity) results in an increase in flow.

Figure 72A:
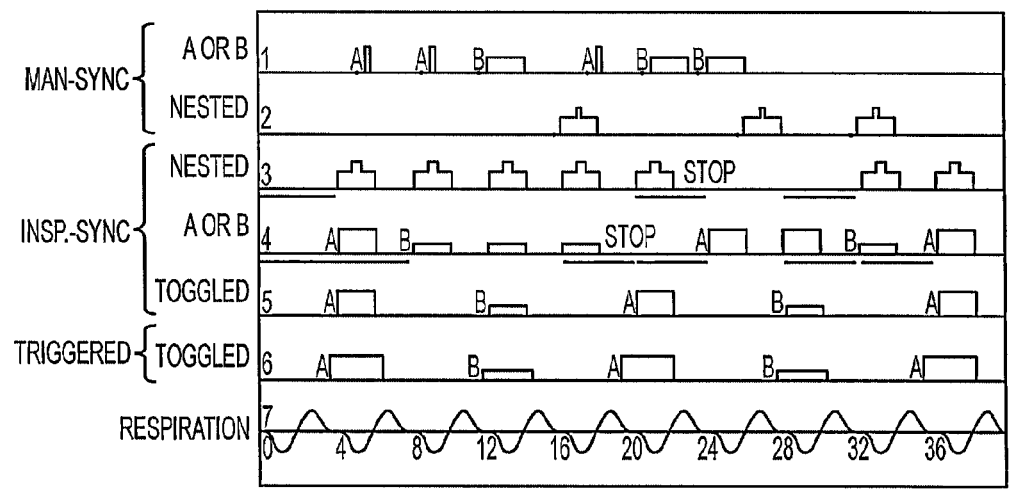
FIGS. 72A and 72B are charts showing various stimulation output modes of the implantable neurostimulator shown in FIG. 59 as may be used for therapy titration, for example.
Figure 72B:
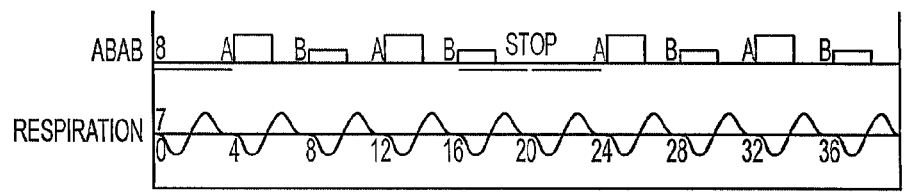

With reference to FIGS. 72A and 72B, stimulation may be delivered at different levels, different sequences, and different modes during titration. These stimulation alternatives may also be used for therapy delivery, if desired. In FIG. 72, each burst of stimulation is shown as a positive square wave and corresponds to a train of pulses as described previously. The bottom trace #7 in FIGS. 72A and 72B correspond to a respiratory flow signal wherein the negative portion of the trace corresponds to inspiration, and the positive portion of the trace corresponds to expiration.

As shown in FIGS. 72A and 72B, stimulation bursts may be delivered at different levels and in different sequences. For example, the stimulation burst may be programmed to be "A or B" (traces #1, #4 and #8), where stimulation is delivered at level "A" until commanded to deliver at level "B", or delivered at level "B" until commanded to deliver at level "A". Stimulation level "A" may correspond to a first selected level and stimulation level "B" may correspond to a second selected level, wherein the first level "A" is different than the second level "B" in terms of amplitude, pulse width and/or duration. Alternatively, the stimulation burst may be programmed to be "nested" (traces #2 and #3), where the stimulation burst comprises a composite of levels "A" and "B". As a further alternative, the stimulation burst may be programmed to "toggle" (traces #5 and #6) between the same or different level in a repeating pattern (e.g., "AB", "ABAB", "0A0B", "AA", etc.).

Also as shown in FIG. 72, stimulation may be delivered in three basic modes: manual synchronized; inspiratory synchronized; and triggered. Traces #1 and #2 illustrate manually synchronized stimulation delivery, wherein stimulation is delivered by manually entering a command via the programmer system to initiate stimulation delivery of each burst (e.g., when the user observes or anticipates inspiration on PSG, the user manually enters a command to initiate stimulation delivery). Traces #3, #4, #5 and #8 illustrate inspiratory synchronized stimulation delivery, wherein stimulation is automatically delivered according to an algorithm that predicts the inspiratory phase and initiates stimulation delivery at a desired time relative to inspiration such as at or just prior to inspiration. Trace #6 illustrates triggered stimulation delivery, wherein each stimulation burst is initiated and terminated by a fiducial of the respiratory signal (e.g., positive peak, negative peak, cross-over point, etc.) which may or may not correspond to a physiological event (e.g., inspiratory onset), and which may or may not incorporate a fixed delay. Thus, in triggered mode, the stimulation burst is initiated by a fiducial and terminated by the next occurrence of the same fiducial in a repeating pattern.

The manually-synchronized A or B mode (trace #1) allows the user to program stimulation parameters for two (A & B) separately deliverable stimulation bursts. On user command, a single burst of stimulation is delivered almost immediately corresponding to A's settings, likewise for B. A and B can be defined with unique amplitudes, pulse widths, and durations; but with a common frequency. The dots on trace #1 indicate the time of manual command followed by the delivery of stimulation immediately thereafter.

The manually-synchronized nested burst (trace #2) allows the user to program stimulation parameters for a nested stimulation burst. On user command, a single burst of stimulation is delivered almost immediately corresponding to the nested burst parameters. The user defines the nested burst parameter by programming stimulation parameters for a primary mode and separately for a secondary mode. The secondary mode is of shorter duration than the primary mode. The secondary mode may be centered on the primary mode as shown, or shifted to the beginning or end of the primary mode. The two modes can be defined with unique amplitudes, pulse widths, and durations; but with a common frequency. The dots on trace #2 indicate the time of command followed by the delivery of stimulation immediately thereafter.

The inspiratory-synchronous nested mode (trace #3) delivers stimulation bursts synchronous with inspiration as determined by device and therapy delivery algorithm settings and sensed respiratory signal. This mode is similar in function to manually-synchronous nested mode (trace #2) with the following three differences: first, after user command the stimulation burst does not begin immediately but instead is delivered during the next inspiration as predicted by the therapy delivery algorithm; second, the duration of the stimulation burst is not programmed but is instead determined by the therapy delivery algorithm; and third, the nested stimulation burst will continue to be delivered on every respiratory cycle until stopped. The lines below trace #3 indicate the times window during which a command will cause therapy to begin on the following inspiration.

The inspiratory-synchronous A or B mode (trace #4) also delivers stimulation bursts synchronous with inspiration as determined by device and therapy delivery algorithm settings and sensed respiratory signal. This mode is similar to the inspiratory-synchronous nested mode (trace #3) except that the stimulation bursts comprise A or B as in the manually-synchronized A or B mode (trace #1). The selected (A or B) stimulation burst will continue to be delivered on every respiratory cycle until the other burst is selected or until stopped. The lines below trace #4 indicate the time window during which a command will cause therapy to begin or change on the following inspiration.

The inspiratory-synchronous ABAB mode (trace #8) also delivers stimulation bursts synchronous with inspiration as determined by device and therapy delivery algorithm settings and sensed respiratory signal. This mode is similar to the inspiratory-synchronous nested mode (trace #4) except that the stimulation bursts alternate between A or B on each burst. The stimulation bursts will continue to be delivered on every respiratory cycle until stopped. The lines below trace #8 indicate the time window during which a command will cause therapy to begin or end on the following inspiration.

The inspiratory-synchronous toggle mode (trace #5) also delivers stimulation bursts synchronous with inspiration as determined by device and therapy delivery algorithm settings and sensed respiratory signal. This mode is similar to the inspiratory-synchronous A or B mode (trace #4) except that the stimulation bursts are toggled. As shown, the toggled stimulation burst sequence comprises 0A0B (i.e., no stimulation, stimulation level A, no stimulation, stimulation level B), which continue to be delivered on each 4-breath series of respiratory cycles until stopped.

The triggered toggle mode (trace #6) is similar in function to the inspiratory-synchronous toggle mode (trace #5) except that the stimulation burst sequence 0A0B is initiated and terminated by a recurring fiducial of the respiratory signal.

Figure 73A:
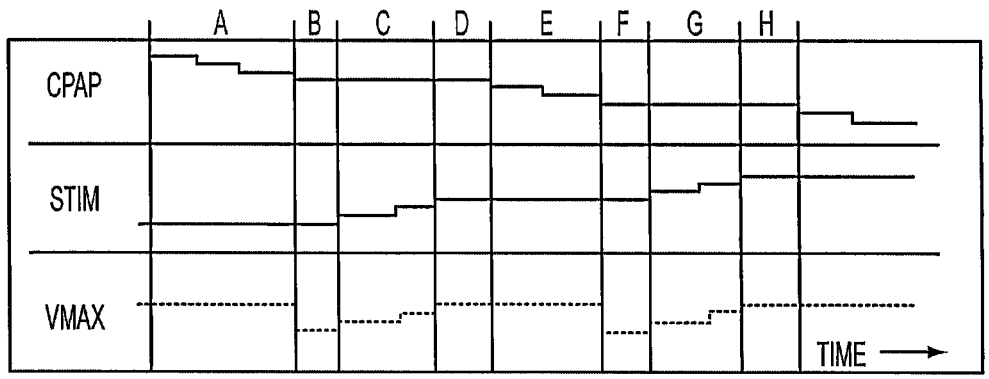

An example of a stimulation amplitude titration method is illustrated in FIG. 73A. In the illustration, three traces are shown: CPAP (pressure in cm $H_2O$); STIM (stimulation amplitude in mA); and $V_{imax}$ (maximum inspiratory nasal airflow in mL/min as measured by pneumotach or other flow sensor). Initially, the stimulation amplitude is set to the capture threshold and the CPAP pressure is set to an efficacious level for a given patient (typically above 5 cm $H_2O$ and determined in a prior sleep study). In period "A", the CPAP pressure is gradually decreased until a flow restricted state is reached in period "B" as detected by a drop in $V_{imax}$. In period "C", the stimulation amplitude is increased while the CPAP pressure remains constant until an unrestricted flow state is reached in period "D" as detected by a rise in $V_{imax}$. In period "E", the CPAP pressure is again gradually decreased until a flow restricted state is again reached in period "F" as detected by a drop in $V_{imax}$. In period "G", the stimulation amplitude is again increased while the CPAP pressure remains constant until an unrestricted flow state is reached in period "H" as detected by a rise in $V_{imax}$. This iterative process is repeated until the CPAP pressure reaches approximately 0 cm $H_2O$ or until no further flow benefit is observed with increasing stimulation amplitude as shown in period "I". The desired stimulation dose may be set to correspond to the lowest stimulation amplitude required to mitigate restricted flow at a CPAP pressure of approximately 0 cm $H_2O$ or the lowest stimulation amplitude for which there is no further benefit in flow, whichever is lower. In addition, therapy can be adjusted to prevent flow restrictions at a nasal pressure slightly below atmospheric to ensure efficacy under varying conditions that may otherwise compromise airflow (e.g., head flexion, nasal congestion, etc.).

Figure 73B:
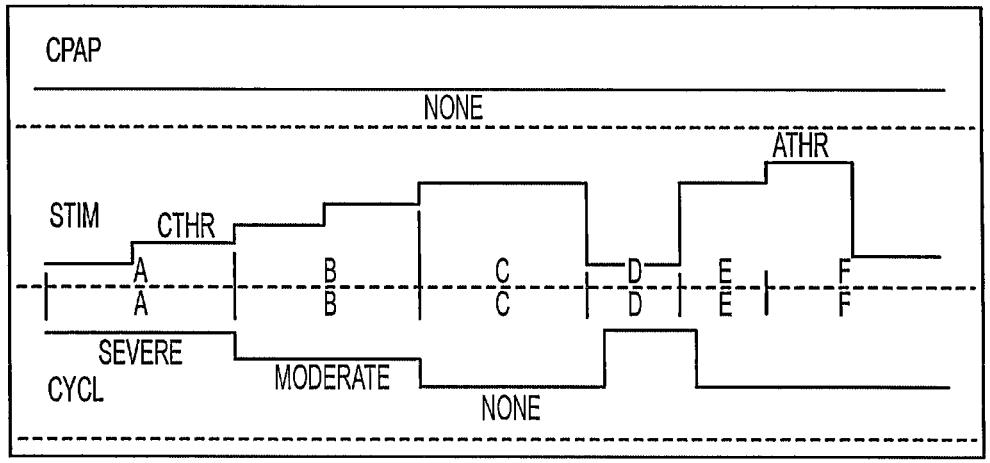

Another example of a stimulation amplitude titration method is illustrated in FIG. 73B. In addition to the stimulation amplitude titration technique described above with reference to FIG. 73A, stimulation amplitude titration can be done through a different approach that has two parts. The two parts are: with patient awake and with patient asleep. These will henceforth be known as awake titration and sleep titration respectively. During awake titration, the stimulation amplitudes that cause the lowest level of muscle contraction, tongue displacement, and muscle contraction at the threshold of comfort are recorded for the different frequency and pulse width settings.

Figure 73C:
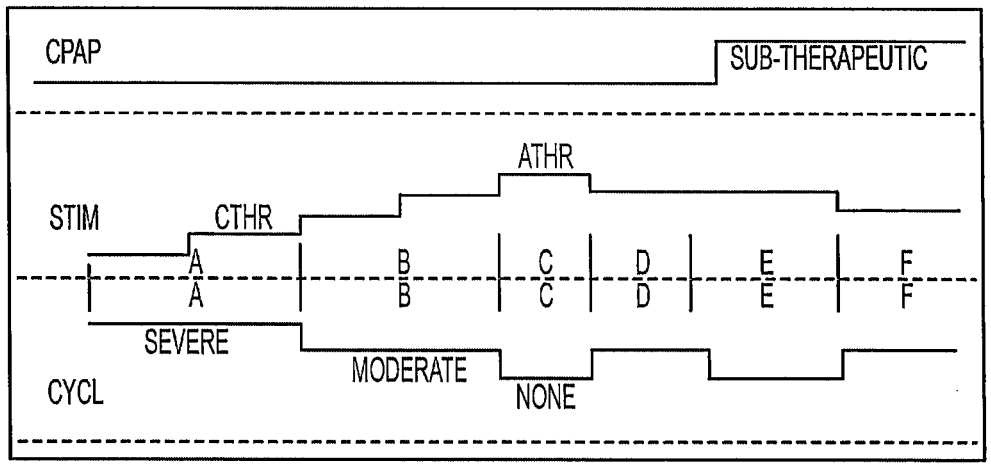

This will be followed by a sleep titration, two examples of which are illustrated in FIGS. 73B and 73C. In FIGS. 73B and 73C, three traces are shown: CPAP (pressure in cm H2O); STIM (stimulation amplitude in mA); and CYCL (cyclic breathing associated with the patient's sleep disordered breathing state). In addition, several points on the STIM trace are indicated: ATHR (the arousal threshold, or the lowest stimulation amplitude that causes arousal); CTHR (the capture threshold, or the lowest stimulation amplitude where muscle contraction is effected). Traces not shown include those of respiratory flow and oxygen saturation level; although these variables are expected to be affected by stimulation. An effect of stimulation on respiratory flow is described with reference to FIG. 73A.

In FIG. 73B, sleep titration is carried out with the patient at atmospheric pressure and preferably in the supine position. However, this stimulation level titration is expected to be repeated throughout the sleep titration period with the patient in different conditions, including different body positions and sleep stages. After onset of sleep, in region A, the patient is experiencing what to them would be considered severe sleep disordered breathing. Stimulation amplitude is also periodically increased in region A. During these periodic increases the lowest stimulation amplitude that causes muscle contraction is also identified. In region B, stimulation amplitude continues to be periodically increased, which reduces the degree of but does not abolish the sleep disordered breathing that the patient experiences. In region C after continued increase of the stimulation amplitude a level that abolishes the sleep disordered breathing of the patient is achieved. If this stimulation amplitude is reached in conditions considered to be most challenging, then this stimulation level could be considered the therapeutic level. In region D stimulation is turned OFF, which causes the patient to go into sleep disordered breathing. In region E, the therapeutic stimulation level is turned back ON and the patient's sleep disordered breathing is abolished once again. In region F, continued periodic increase of stimulation amplitude leads to levels that cause arousal. The arousal threshold is thus identified. In this titration process, the stimulation level that abolishes the patient's sleep disordered breathing without causing arousal and with the patient in the most challenging conditions is identified.

In FIG. 73C, sleep titration is started with the patient at atmospheric pressure. However, if a stimulation level that completely abolishes sleep disordered breathing without causing arousal is not achieved, then some sub-therapeutic CPAP (the patient's therapeutic CPAP will have been identified in a previous sleep study) could be used to complement stimulation for the delivery of therapy. After onset of sleep, in region A, the patient is experiencing what to them would be considered severe sleep disordered breathing. Stimulation amplitude is also periodically increased in region A. During these periodic increases the lowest stimulation amplitude that causes muscle contraction is also identified. In region B, stimulation amplitude continues to be periodically increased, which reduces the degree of but does not abolish the sleep disordered breathing that the patient experiences. In region C, continued periodic increase of stimulation amplitude leads to levels that cause arousal. The arousal threshold is thus identified. Note that, in this example, the stimulation level that causes arousal is reached before the level that completely abolishes sleep disordered breathing could be. In region D, a stimulation level that is just below the arousal threshold is maintained and the patient holds in moderate sleep disordered breathing. In region E, a sub-therapeutic CPAP level that abolishes the patient's disordered breathing is applied. This identifies the level of CPAP that complements stimulation in some patients. In region F, stimulation is either turned down or OFF from the level just below the arousal threshold, leading the patient to go into disordered breathing. In some cases, where the patients' sleep disordered breathing cannot be abolished by stimulation only, some CPAP pressure may be used to complement stimulation. This could help increase the likelihood of CPAP compliance of some patients since the CPAP pressure is reduced. In addition, it could help analyze how far patients are from being completely treated by either stimulation or CPAP.

Figure 74A:
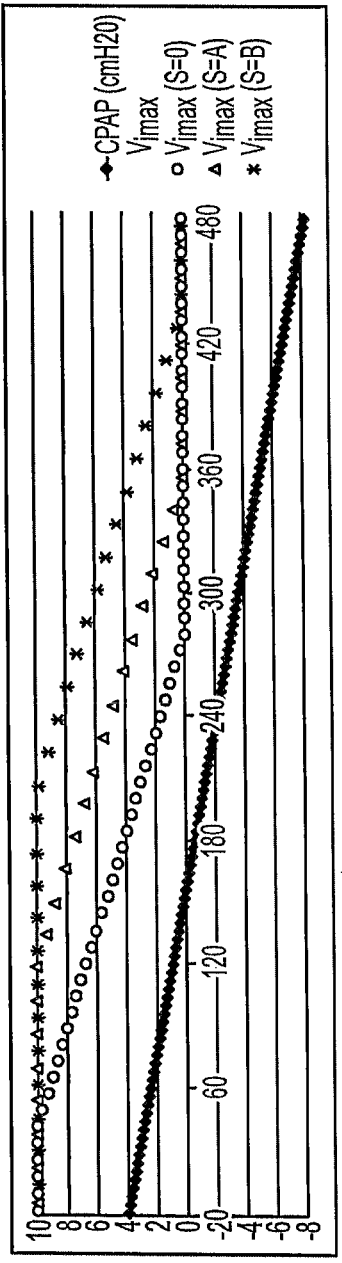
Figure 74B:
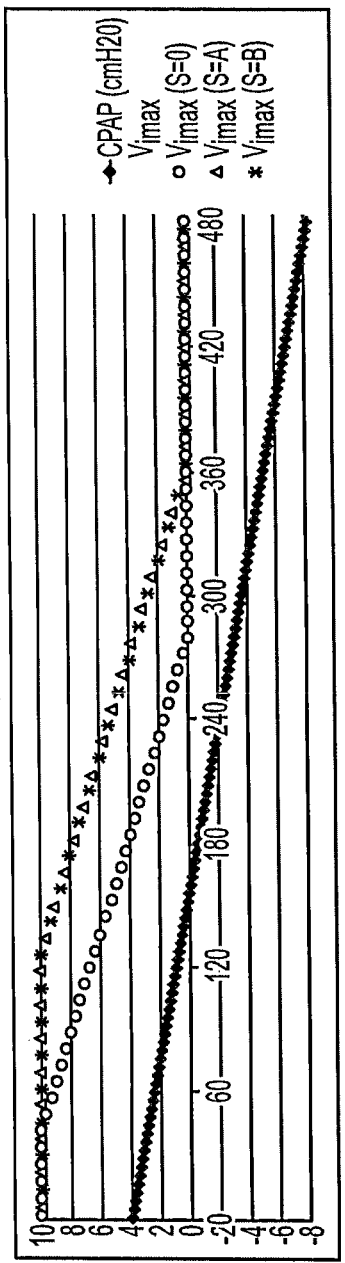

Another example of a stimulation amplitude titration method is illustrated in FIGS. 74A and 74B. This method may be carried out over a period of breaths (e.g., 4-10) or very slowly over several minutes (e.g., dozens of breaths to verify that optimal stimulation intensity has been identified). In the illustration, four traces are shown: one trace for CPAP pressure (designated by a solid diamond, pressure in cm $H_2O$); and three traces for $V_{imax}$ (maximum inspiratory nasal airflow in mL/min as measured by pneumotach or other flow sensor) for stimulation amplitudes "0", "A" and "B". $V_{imax}$ at stimulation amplitude "0" (designated by an open circle) corresponds to flow with stimulation off. $V_{imax}$ at stimulation amplitude "A" (designated by an open triangle) corresponds to flow with stimulation set to a value "A", and $V_{imax}$ at stimulation amplitude "B" (designated by an asterisk) corresponds to flow with stimulation set to a value "B", where "A" is slightly less than "B". Stimulation is delivered alternately at levels "A" and "B" with intermediate "0" levels (e.g., "0A0B"). Alternatively, stimulation may be delivered alternately at levels "A" and "B" without intermediate "0" levels (e.g., "AB"), which may be advantageous because the sequence may be executed faster and because arousal may otherwise occur due to low flow conditions at stimulation level "0".

Initially, the CPAP pressure is set to an efficacious level for a given patient (typically above 5 cm $H_2O$ and determined in a prior sleep study). With the stimulation amplitude set to "0" (i.e., stimulation is turned off), the CPAP pressure is gradually decreased while measuring $V_{imax}$ to obtain a base-line reading when flow is un-restricted (beginning) and subsequently restricted. The stimulation amplitude is then set to alternate between "A" and "B", where "A" is set to the capture threshold and "B" is set slightly higher than "B" (e.g., 0.1=1.0 mA higher). The CPAP pressure is then gradually decreased (or dropped for a short series of breaths and returned to baseline if needed to maintain a passive state) while measuring $V_{imax}$ to determine the flow at each stimulation level as shown in FIG. 74A. The values of "A" and "B" are incrementally increased and the CPAP pressure is again gradually decreased while measuring flow. This iterative process is repeated until the traces converge as shown in FIG. 74B, demonstrating that no further benefit in flow is realized with an increase in stimulation. The therapy setting may then be set to correspond to the lower stimulation amplitude value ("A") where the traces for "A" and "B" converge. Note that FIGS. 74A and 74B display the case where no arousal occurs during the gradual decrease in CPAP pressure. In practice, it is expected that arousals will occur before the process can be taken to complete conclusion as shown in the Figures. In the event of arousals, the iterative process is repeated based upon convergence of the traces prior to the point of arousal.

Figure 75:
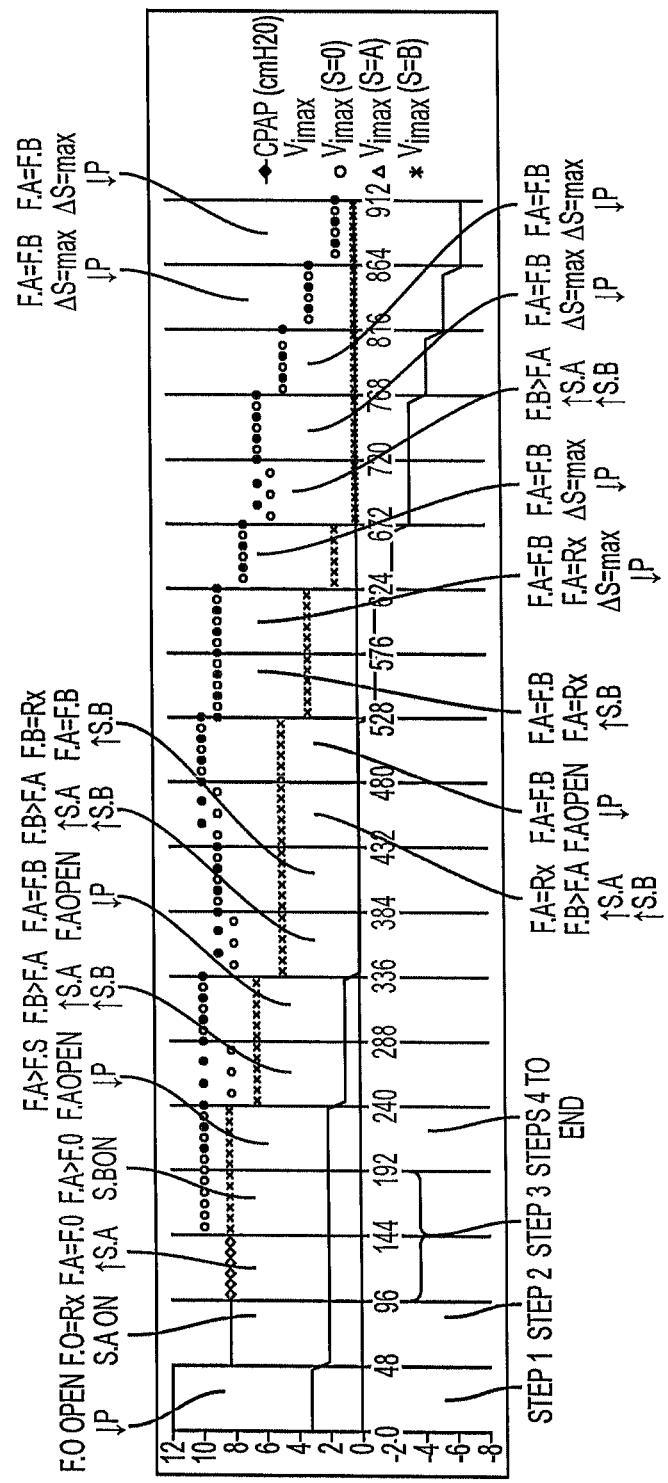

Another example of a stimulation amplitude titration method is illustrated in FIG. 75. FIG. 75 illustrates this method using a stimulation sequence comprising "0A0B", although a stimulation sequence comprising "AB" may be used as an alternative. In FIGS. 75 and 18: "F" refers to peak inspiratory flow; "F.0" refers to flow with no stimulation; "F.A" refers to flow with stimulus intensity "A"; "F.B" refers to flow with stimulus intensity "B"; "OPEN" indicates that the airway is open, with no flow limitation; "Rx" indicates that the airway is restricted (steady state flow limitation); ".uparw.S.A" (or ".uparw.S.B") indicates that the intensity of stimulus "A" (or "B") should be increased; ".dwnarw.P" indicates that CPAP (nasal) pressure should be reduced; ".DELTA.S" is the difference between stimuli A and B; and ".DELTA.S=max" is when stimulus "B" is the maximum difference in intensity from stimulus "A" that will be tested (1.0 mA is recommended for this value).

Step 1 (holding pressure) in this method involves adjusting CPAP (nasal) pressure to the lowest holding pressure where maximum inspiratory flow ($V_{i,max}$) is not limited, and recording various data. Step 2 (attain oscillation/steady state flow limitation) involves reducing CPAP (nasal) pressure until flow oscillation occurs, recording data, increasing CPAP (nasal) pressure until oscillations cease, thereby achieving steady-state flow limitation (SSFL), and recording data. Step 3 (activation threshold, defined as lowest stimulation intensity with a measurable effect on flow) involves selecting triggered toggled stimulation mode OMB with stimulation amplitude level A=stimulation amplitude level B=0.4 mA, and pulse width=30 microseconds (if no effect <90 microseconds, increment to 90 microseconds). Then, with stimulation amplitude level A=B, both amplitude levels A and B are incrementally increased until flow differs between stimulated breaths (level=A=B) and non-stimulated breaths (level=0). If necessary, CPAP (nasal) pressure may be adjusted to ensure SSFL during non-stimulated breaths. Step 4 (optimize stimulation level) involves selecting triggered toggled stimulation mode 0A0B with stimulation amplitude level A=activation threshold (determined in step 3) and stimulation amplitude level B=smallest increment greater than level A, and then executing the following sub-routine:

(a) While there is a significant difference in Vi,max (>10%) between Stim A and B, increase both A and B amplitudes by same amount (0.1 mA-0.5 mA) until no significant difference in Vi,max is observed;

(b) If Stim A breaths not flow limited, reduce CPAP (nasal) pressure until flow limitation is achieved and return to step (a); else, continue to (c);

(c) If Max Delta Stim (difference between Stim A and Stim B=1.0 mA, for example) is reached, decrement CPAP (nasal) pressure; else increase Stim B; continue to (d);

(d) Stop if either the lowest CPAP pressure level to be tested is reached (e.g., atmospheric or sub-atmospheric), or if maximum stimulation intensity of the INS is reached; else return to (a).

The therapy setting may then be set to correspond to the lower stimulation amplitude value ("A" or "B") where there is no increase in flow benefit. Optionally an additional margin may be added to the setting (a fixed value or a percentage of the setting, e.g., 10% to 20%) to accommodate changing physiologic conditions.

Figure 76A:
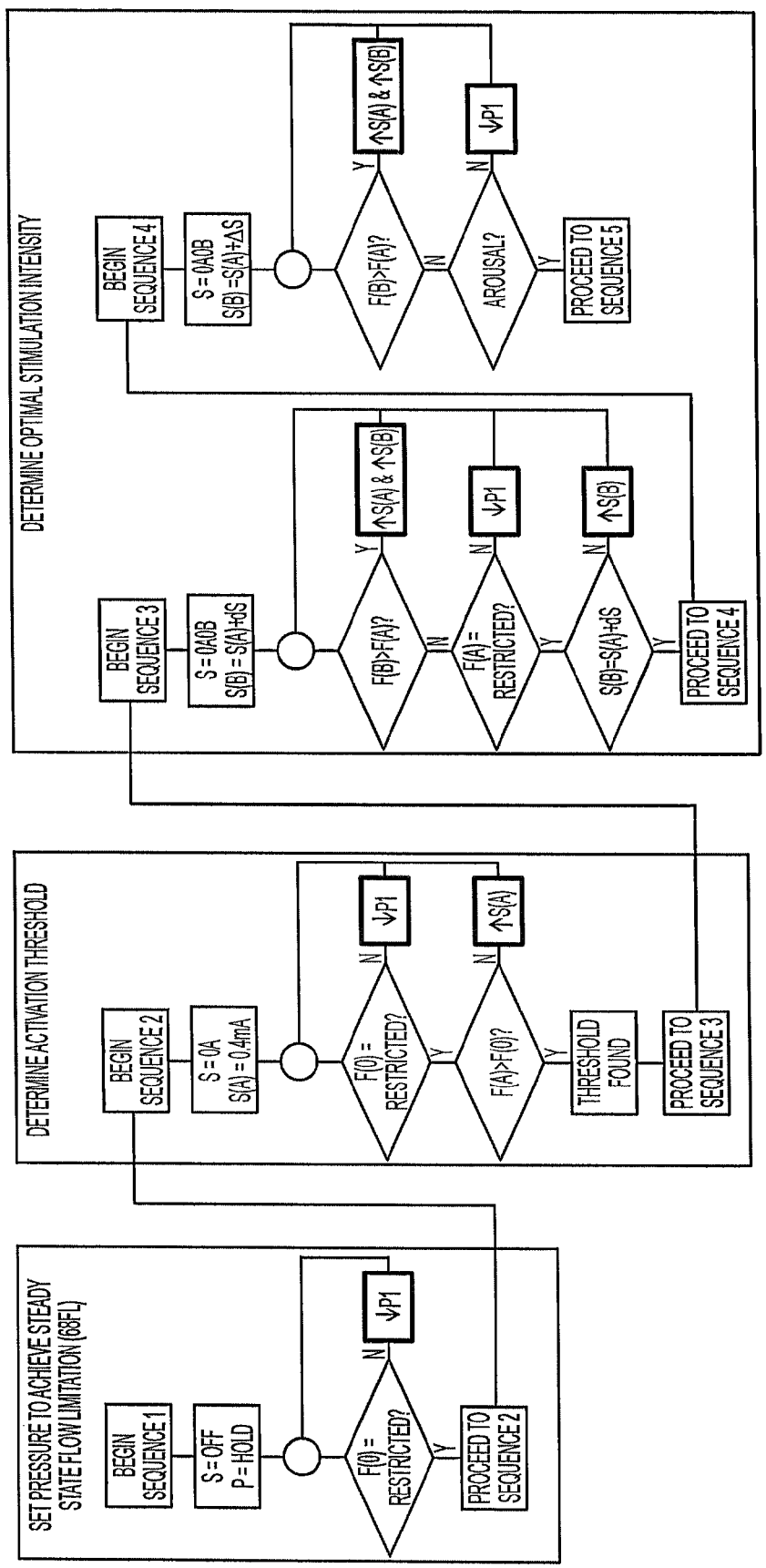

FIG. 76A is a flow chart illustrating the method described with reference to FIG. 75. FIG. 76B provides a legend for the flow chart of FIG. 76A.

From the foregoing, it will be apparent to those skilled in the art that the present invention provides, in exemplary non-limiting embodiments, devices and methods for nerve stimulation for OSA therapy. Further, those skilled in the art will recognize that the present invention may be manifested in a variety of forms other than the specific embodiments described and contemplated herein. Accordingly, departures in form and detail may be made without departing from the scope and spirit of the present invention as described in the appended claims.

Treatment Overview

Figure 82A:
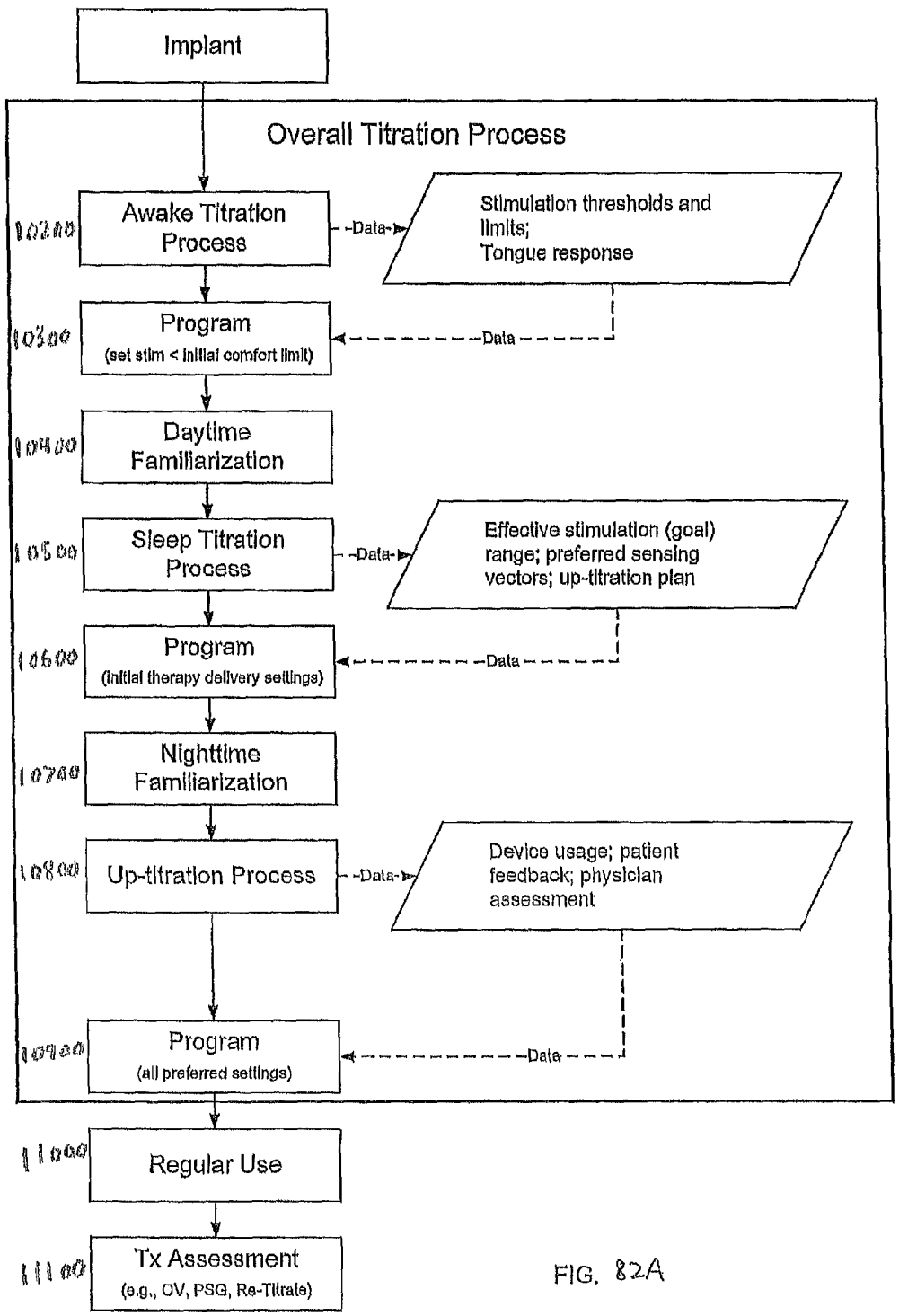
FIG. 82A shows a flowchart of an idealized therapy process and the sub-processes that may be involved.

FIG. 82A illustrates a treatment overview from implant 10100, to awake titration 10200, to daytime familiarization 10400, to sleep titration 10500, to nighttime familiarization 10700, to up-titration 10800, and finally to regular therapeutic use 11000 and therapy assessments 11100.

Figure 81:
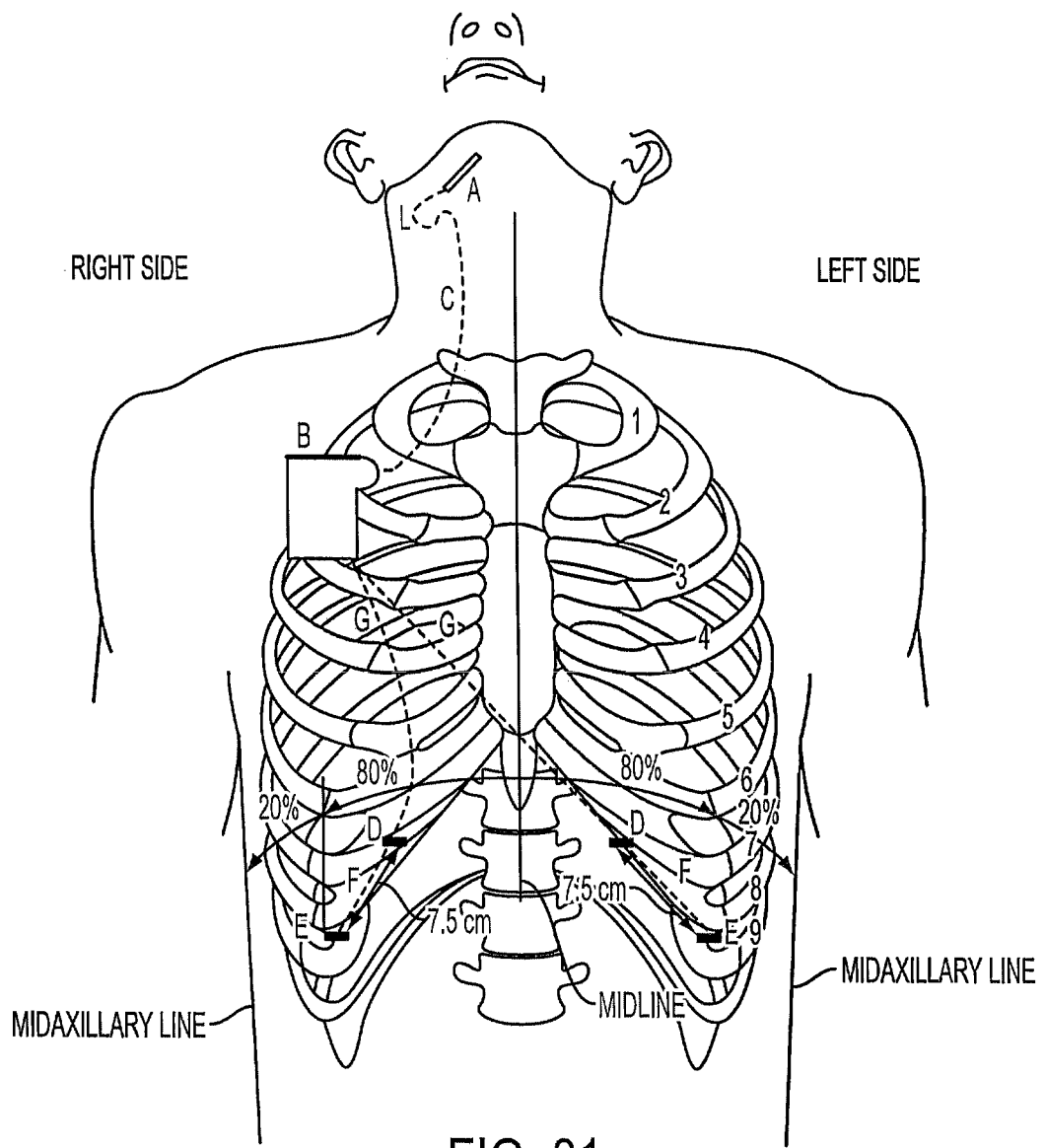
FIG. 81 is an anatomical illustration showing the incision sites and tunneling paths that may be used for implanting the internal components shown in FIG. 77.
Figure 82B:
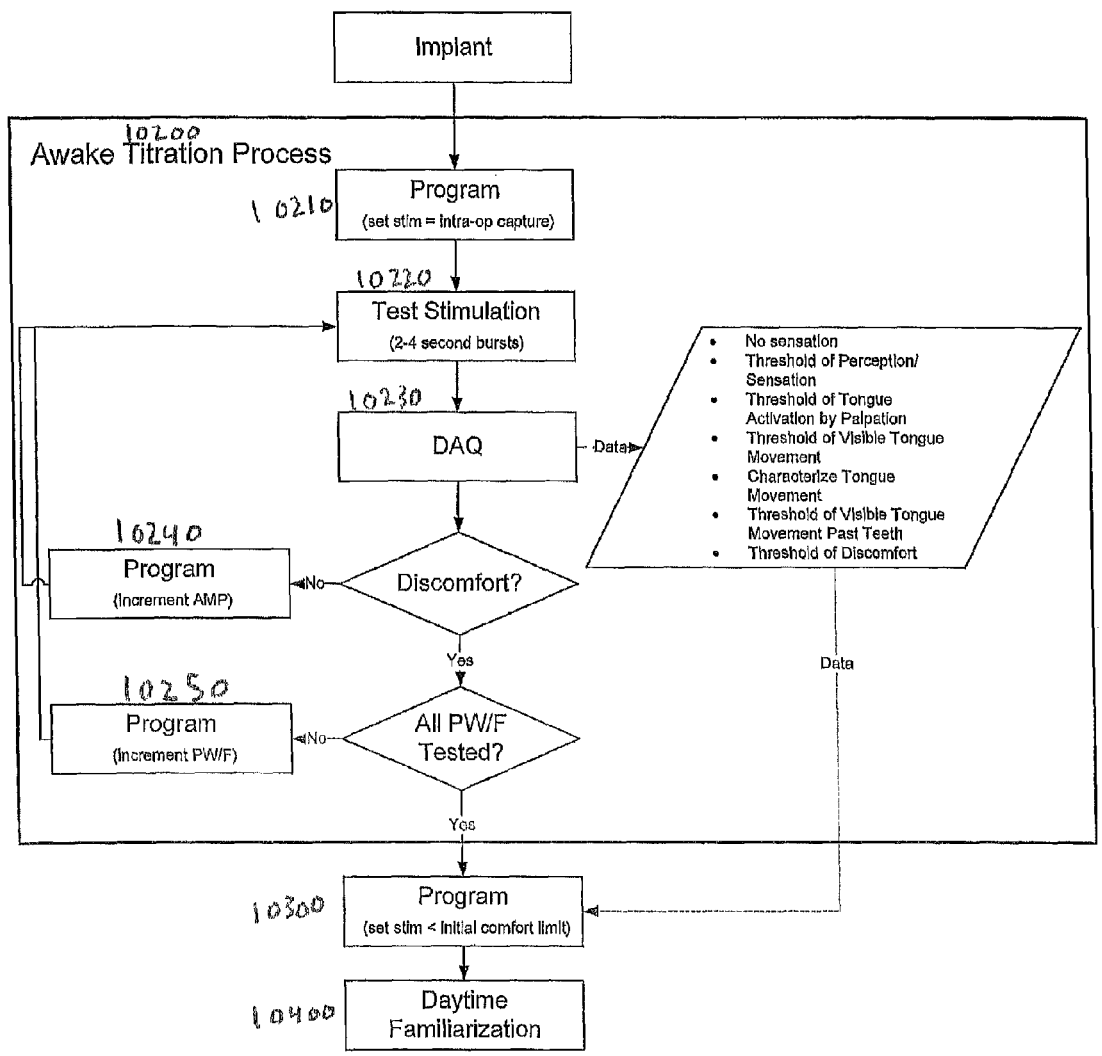
FIGS. 82B, 82C, and 82D show detailed flowcharts of idealized therapy sub-processes shown in FIG. 12A.

Beginning with a surgical implant 10100, FIG. 81 schematically illustrates the incision sites (solid thick lines) and tunneling paths (dotted lines) for implanting the INS 1100, STL 1300 and RSLs 1200. The implant procedure may be performed by a surgeon (e.g., otolaryngologist) in a 1-3 hour surgical procedure with the patient under general or local anesthesia, for example. In general, the implant procedure involves placing the cuff 1350 of the STL 1300 on the hypoglossal nerve via a submandibular dissection, and tunneling the lead body 1330 and sigmoid section 1370 of the STL 1300 subcutaneously down the neck to the INS 1100 in a subcutaneous pocket in the infraclavicular region. From the infraclavicular pocket, the RSL 1200 may be tunneled subcutaneously toward midline and then laterally along the costal margins After a healing period of a few weeks, an awake titration may be performed 10200 wherein the patient's tongue response to stimulation is observed over a range of comfortable stimulations, as illustrated in FIG. 82B. In addition, a global system check may be performed to check the system integrity. The patient is then sent home for a period of daytime familiarization 10400 where the patient may turn on stimulation during wakefulness to introduce the sensation of stimulation. The patient subsequently returns to the sleep lab for a sleep titration 10500 where a sleep technician, under the supervision of a certified sleep physician (e.g., pulmonologist), uses the programmer system 2100 to program the INS 1100 (e.g., set the therapy delivery schedule and titrate the stimulus to determine a range of efficacious settings during sleep). After the sleep titration, the patient may return home and begin the nighttime familiarization (acclimation) and therapy up-titration process, wherein stimulation may be increased over time to an efficacious range. For example, the patient may leave the sleep titration with stimulation programmed to turn on at 1.7 mA and stimulation may be increased by 0.1 mA at two week intervals up to a goal setting of 2.0 mA.

Immediately after the titration visit, the patient may return home and begin using the device at the programmed stimulation level during nighttime familiarization 10700. A therapy delivery session may begin when the therapy controller 2500 is used to manually start, stop, and pause a therapy session. This may be beneficial when the patient has an irregular sleep schedule. At the beginning of a therapy delivery session, stimulus may be delayed for a period of time to allow the patient to fall asleep. The therapy delivery session may be programmed to not exceed a fixed number of hours (e.g., eight hours). In addition, a therapy delivery session may begin according to the pre-defined therapy delivery schedule, which may be set to coincide with when the patient normally goes to sleep. The therapy delivery session may end according to the pre-defined therapy delivery schedule, which may be set to coincide with when the patient normally wakes up, or with a manually stop command from the therapy controller. The patient may use the therapy controller 2500 to adjust limited aspects of therapy delivery as defined previously.

Tunneling System

FIGS. 69E and 69F schematically illustrate the tunneling system 3000 which may be used for tunneling the STL 1300 or RSL 1200. The tunneling system 3000 includes a relatively rigid tool 3010, a tubular sheath 3020, and a tip 3030, and lead carrier 3100.

The tool 3010 may be formed of stainless steel and include a handle 3016, a shaft 3012, and a distal connector 3018. The connector 3018 includes threads that mate with corresponding threads in the tip 3030. The connector 3018 may also include ring barbs that form an interference fit with the inside of the lead carrier 3100 for releasable connection thereto.

The lead carrier 3100 may also form an interference fit with the RSL proximal connector 1210, the STL proximal connector 1310, or a distal ring electrode of the RSL 1250 or 1260.

The sheath 3020 is sized to be slid over the tool 3010 and secured in place via the tip 3030. The tip 3030 may include a radiopaque agent such as barium sulfate loaded at 18% by weight, for example.

The lead carrier 3100 may comprise a small polymeric tube with an inside diameter sized to form an interference fit with the distal connector 3018, the RSL proximal connector assembly 1210, an RSL distal electrode 1250 or 1260, or the STL proximal connector assembly 1310. During tunneling, the proximal end of the lead carrier 3100 may attach to the distal connector 3018 and the distal end of the lead carrier 3100 may attach to the RSL proximal connector assembly 1210, an RSL distal electrode 1250 or 1260, or the STL proximal connector assembly 1310.

The sheath 3020 may comprise a polymeric tube with two open ends, and the tip 3030 may comprise a polymeric tube with one threaded end and one closed end for blunt dissection. The proximal end of the tip 3030 includes internal threads to screw onto the connector 3018 and hold the sheath 3020 on the shaft 3012.

In the embodiment shown in FIGS. 69E and 69F, the tool 3010 may have a pre-bend length of 17.1 inches and a post-bend length of 16.9 inches. The sheath 3020 may have an outside diameter of approximately 0.28 inches, a pre-bend length of 12.4 inches and a post bend length of 12.25 inches. The shaft 3012 may have a diameter of about 0.22 inches, a pre-bend length of 12.375 inches, and a post-bend length of 12.231 inches, sufficient to fill the length of the sheath 3020. The handle 3016 may have a diameter of about 0.5 inches and a length of about 3.50 inches. The tip 3030 may have an outside diameter tapering from approximately 0.13 inches and a length of about 1.0 inches.

Surgical Implant Procedure

With continued reference to FIG. 81, the internal components 1000 may be implanted using the following surgical procedure 10100, which is given by way of example, not limitation. Unless specifically stated, the order of the steps may be altered as deemed appropriate. Although the INS 1100 may be surgically implanted on the right or left side, the right side is preferred to leave the left side available for implantation of cardiac devices that are traditionally implanted on the left side. The right side is also preferred for the RSL 1200 to provide a clean respiratory signal that is less susceptible to cardiac artifact than the left side.

Standard surgical instruments may be used for incisions, dissections, and formation of subcutaneous pockets. Commercially available nerve dissection instruments may be preferred for dissecting the hypoglossal nerve and placing the STL cuff 1350 on the nerve.

The patient is prepared for surgery using conventional practice including standard pre-operative care procedures, administration of antibiotics as appropriate, and administration of steroids as appropriate to reduce swelling around the nerve dissection. Because tongue movement must be observed during test stimulation, it is recommended that no long-acting muscle relaxants be used during surgical preparation or during implants. General anesthesia is administered according to conventional practice and the patient is intubated using an endotracheal tube, taking care to position the endotracheal tube so that the tongue is free to protrude during test stimulation.

The neck is then extended to expose right submandibular region and a sterile field is created around the neck and thorax, taking care to avoid obstructing visualization of the oral cavity (a clear sterile drape over the mouth may be used). By way of a neck incision (A), the hypoglossal nerve is then exposed deep to the submandibular gland. Because the INS 1100 is preferably implanted on the right side to minimize cardiac artifact during respiratory sensing, this dissection is also preferably performed on the right side. A region of the hypoglossal nerve, preferably excluding the branch that innervates retrusive muscles (e.g. styloglossus or hyoglossus), is then identified and isolated. Confirmation of correct nerve location may be achieved by performing a test stimulation later in the procedure. The identified nerve branch is then circumferentially dissected to accommodate the cuff 1350. The short side 1352 of the cuff 1350 is designed to reside on the deep side of the nerve, and the long side 1354 of the cuff 1350 is designed to reside on the superficial side of the nerve.

The appropriate sized cuff 1350 is then selected based on the nerve diameter at the intended location for cuff placement. Nerve size may be assessed using reference size (e.g., forceps of known width), a caliper, or a flexible gauge that wraps around the nerve, for example. The cuff 1350 is then opened and placed around the nerve. The strap 1356 on the cuff 1350 may be used to facilitate placement of the cuff 1350 around the nerve. A curved forceps may be placed under the nerve to grasp the strap 1356 and gently pull the cuff 1350 onto the nerve. The strap 1356 is then placed through the loop (buckle) 1358 on the cuff 1350. The cuff 1350 may be available in two sizes (small and large), and the small cuff may have an indicator mark (not shown) on the strap 1356 that should be visible after insertion through the loop 1358. If a small cuff is selected and the indicator mark does not pass through the loop, the small cuff may be too small and should be replaced with a large cuff.

A strain relief loop (L) in the STL 1300 is then created by arranging approximately 6 cm of the STL sigmoid body 1370 in a C-shape inside a small subcutaneous pocket formed via the neck incision (A) by blunt dissection superficially along the lateral surface of the digastric muscle in a posterior direction.

The surgeon then verifies that the cuff 1350 is not pulling or twisting the nerve, and that there is contact between the inside of the cuff 1350 and the nerve.

A test-stimulation is then performed to confirm correct positioning of the cuff 1350 on the nerve. To conduct a test-stimulation, the proximal end of STL 1300 is plugged into the INS 1100 and the programmer system 2100 is used to initiate a test stimulation signal delivered from the INS 1100 to the nerve via the STL 1300. The test stimulation is performed while observing, for example, tongue movement by direct visual observation, airway caliber by nasal endoscopy, fluoroscopy, cephalogram, etc. Correct placement of the cuff on the nerve may be confirmed by, for example, observing tongue protrusion, an increase in retro-glossal airway caliber, an increase in retro-palatal airway caliber, an increase in stiffness of the anterior and/or lateral walls of the retro-glossal airway with or without an increase in airway caliber, anterior movement without superior movement of the hyoid bone, among others. Incorrect placement of the cuff on the nerve is indicated, for example, when there is insufficient opening of the retro-palatal or retro-lingual space, when the tongue is observed to retract (posterior movement), a decrease in retro-glossal airway caliber, a decrease in retro-palatal airway caliber, superior movement and particularly unilateral superior movement of the hyoid bone, among others. If necessary, the cuff 1350 may be repositioned at a different location along the length of the nerve to obtain the desired effect. The capture threshold and impedance values are recorded and the STL 1300 is disconnected from the INS 1100. The surgeon may create a fascia wrap by suturing fascia around the cuff on the superficial side of the nerve.

A pocket for the INS 1100 is then created by making an incision (B) down to the pectoralis fascia approximately 2 finger breadths below the right clavicle. The INS 1100 is preferably implanted on the right side to minimize cardiac artifact during respiratory sensing. Blunt dissection inferior to the incision is used to create a pocket large enough to hold the INS 1100. The pocket should be inferior to the incision (B) such that the incision (B) does not reside over the INS 1100 when later placed in the pocket.

A tunnel is formed for the STL 1300 using the tunneling system 3000 (sheath 3020 and tip 3030 placed over tool 3010) to tunnel along a path (C) from the infraclavicular INS pocket to the neck incision (A). As shown in FIG. 69F, the lead carrier 3100 is then placed on the most proximal electrical contact of the STL proximal connector 1310. The tip 3030 is removed from the sheath 3020 to expose the connector 3018 of the tool 3010 and attach to the lead carrier 3100. While holding the sheath 3020 in place, the tool 3010 is pulled proximally to pull back the STL 1300 through the sheath 3020, taking care not to pull out the C-shaped strain relief or disturb the cuff. If the C-shaped strain relief loop (L) is pulled out, it should be replaced into the small pocket. The tool 3010 is released from the lead carrier 3100 and the lead carrier 3100 is removed from the STL 1300. The sheath 3020 is then removed from the body leaving the STL 1300 in place. The neck incision (A) need not be closed at this time, but rather may be closed later in the procedure allowing confirmation that the C-shaped strain relief remains in the small pocket.

The following implant instructions refer to an INS 1100 implanted at the patient's right sub-clavicular region. The right and left distal portions of the RSL 1200 are placed near the right and left costal margins, respectively, by making four small incisions (D and E) as shown. The lateral incisions (E) may be made approximately 80% (+/−5%) of the distance from the midline to the mid-axillary line, and on the costal margin. The medial incisions (D) may be made such that the RSL 1200 is relaxed and all electrodes are on the costal margin. Using the tunneling system 3000 (sheath 3020, tip 3030 attached via connector 3018), a tunnel (G) is formed between the pocket (B) and the medial incision (D), such that the right distal portion of the RSL 1200 may be pulled through the tunnel (G) from the pocket (B) to the medial incision (D). A tunnel (F) is then formed between the medial incision (D) and lateral incision (E), such that the right distal portion of the RSL may be pulled through the tunnel (F) from (D) to (E). This is repeated for the left distal portion of the RSL 1200. Alternatively, if the embodiments of RSL 1200 shown in FIG. 78F or 78G are used, a small pocket may be formed medial to (D) in order to accommodate the medial electrodes and/or loop back region 1255.

The previously described tunneling operations (F and G) may be performed as follows: The tunneling tool 3010 including the connector 3018 is inserted into the sheath 3020 and the tip 3030 is connected to the connector 3018, forming the tunneling system 3000. The tunneling system is placed in the origination incision site and pushed beneath the skin towards the destination incision site, forming a tunnel. After tunneling, the tip 3030 is removed from the connector 3018 of the tunneling tool 3010. If needed, the tool 3010 may be removed and reversed such that the connector 3018 is at the other end of the sheath 3020. With the tool 3010 inserted through the sheath 3020, the lead carrier 3100 is attached on its proximal end to the connector 3018 and on its distal end to the distal electrode 1250 or proximal connector 1210 of the RSL 1200. While holding the sheath 3020 in place, the tunneling tool handle 3016 is pulled and the attached lead carrier 3100 and RSL 1200 are pulled into the sheath 3020. This may be visualized through the semi-transparent tunneling tool. The sheath 3020 may then be slid towards the tunneling tool handle 3016, exposing the lead carrier. The lead carrier may then be disconnected from the connector 3018, leaving the RSL 1200 in place. This process may be used to tunnel from (D) to (B) and subsequently from (E) to (D). For tunnel (G), the RSL 1200 may be pulled completely through the sheath 3020 to expose and disconnect the lead carrier.

Each anchor tab 1270 and suture hole 1290 is secured to the underlying tissue by dissecting down to the adjacent muscle fascia and suturing each anchor tab 1270 or suture hole 1290 to the muscle fascia. Permanent sutures are recommended to avoid movement of the RSL 1200 and braided suture material is recommended for knot retention and to prevent corrosion through the silicone anchors.

The STL 1300 and RSL 1200 are then connected to the INS 1100. The RSL 1200 is plugged into the RSL port 1112 and the STL 1200 is plugged into the STL port 1114. The set screws are tightened using a torque wrench.

A closed loop test may be performed to confirm proper operation by observation of tongue protrusion or airway opening in concert with inspiration. The INS 1100 and proximal portions of the leads 1200/1300 are then placed into the infraclavicular pocket, looping the excess lead length beneath or around the INS 1100. Care should be taken not to pull out the C-shaped strain relief loop (L) in the STL sigmoid lead body 1370 while manipulating the INS 1100 into place. The INS 1100 is then sutured to underlying fascia through both suture holes 1116 found in the header 1110 of the INS 1100. Permanent sutures are recommended to avoid movement of the INS both before tissue encapsulation and chronically, and braided suture material is recommended for knot retention. Another system test may be performed at this point. After confirming that the C-shaped strain relief loop (L) is present in small pocket at neck incision, the incisions may be irrigated (optionally with an antibiotic solution) and closed using conventional techniques. After a healing period of approximately one month, the patient may undergo a sleep study to confirm proper operation of the system and to titrate therapy.

Screening Methods

Prior to implant, patients may be screened to estimate the probability of a successful outcome.

The airway can be characterized during sleep by a Pcrit measurement in differing sleep stages and body postures, per the methods of Schwartz et al. A higher Pcrit value is indicative of a more collapsible airway which may be more difficult to treat with this therapy. A surrogate measure for Pcrit may be an auto-PAP device that adjusts airway pressure dynamically to eliminate flow limitation. For example, a patient may require 12 cm $H_2O$ of air pressure to maintain a patent airway in the supine position, yet only require 8 cm $H_2O$ of air pressure in the lateral position. The auto-PAP would automatically adjust for this.

The volume of air expired during a pressure drop may be measured. The pressure drop may occur during natural expiration during wakefulness. Alternatively, the patient may be asleep during the measurement. The timing of the pressure drop during expiration may occur at a certain point during expiration to ensure consistency. The duration of the pressure drop may be fixed. An example of this measure is $V_{NEP\_0.5}$.

The airway may be visualized using an imaging modality such as, but not limited to, cephalogram, MRI, fMRI, CT, ultrasound, OCT, naso-endoscopy, photography, and video imaging. This imaging may be performed during sleep, under sedation, or during wakefulness. The patient may be asked to protrude the tongue, inhale/exhale at specific flow rates, or perform Muller's Maneuver. Tongue protrusion force may also be measured. Tongue size may be observed and/or measured quantitatively or qualitatively (e.g., Modified Mallampati). BMI may also be a good predictor of patient response.

The following metrics (and others) may be measured and used in screening: size of tongue and soft palate, angle of the soft palate, redundancy of tissue, and length of soft palate. Endoscopy is one method for obtaining these metrics. Additional size metrics include craniofacial structures, tonsil size, adenoids, pharyngeal fat pads.

Mechanical linkage or coupling between airway structures may also be assessed. For example, airway opening may be measured at different levels concurrent with other motions, (e.g. measuring opening of the airway at the retro-palatal space during voluntary tongue protrusion or anterior displacement of the tongue).

Nasal airway collapse may be measured using nasal peak inspiratory flow meters in different body positions. Additionally, acoustic rhinometry may provide another way to measure this.

Body Mass Index (BMI) may be a useful tool in screening. Additional metrics include % body fat, % visceral fat, neck circumference, % neck fat, and body fat distribution.

A patient's arousal threshold from sleep may be quantified by measuring intra-pleural arousal pressure. A nasal EPAP device may be used in screening. An EPAP device reduces airflow through the nares. This may increase airway patency during the expiratory phase of respiration. An example of EPAP is the ProVent device (Ventus Medical Inc., Belmont Calif.). Arousals and respiratory events may be assessed with and without the EPAP device. During therapy, the patient's tongue may protrude past the teeth. A dental examination (i.e. identify sharp teeth), patient's use of dentures, and tolerance to oral appliances may be used in screening.

The airway may be characterized using a dual air pump, and valve system, configured for connection to a mask on the patient. In this configuration, the two different pressures (e.g., difference of 1 cm $H_2O$) are maintained by each pump which is connected to the valve. The valve may be attached via a tube to the mask such that the pressure at the mask is from only one of the pumps. The valve may then be automated to alternate between the two pressures at a programmable rate (e.g., 1 Hz). This allows the airway to fluctuate between pressures within breaths. An airway may be characterized by lowering the pressure to a level that brings flow limitation, and then observing what pressures remove this flow limitation.

Awake Titration

As described previously, the patient may undergo an awake titration 10200, an iterative process where the response to stimulation is documented over a range of comfortable stimulation levels (FIG. 82B). These stimulations may be delivered manually (e.g., 2 second commanded stimulation bursts) or synchronous with respiration. A range of amplitudes may be tested across multiple frequencies (range of 20 to 50 Hz, nominal 40 Hz), and pulse widths (range of 30 to 215.mu.s, nominal 90.mu.s) 10220.

The awake titration may involve defining a wake-stimulation operating window, defined at its lower limit by a capture threshold and at its upper limit by a discomfort threshold. The capture threshold may be defined as the lowest stimulation level at which muscle contraction is visible, palpable, or perceptible (e.g., gross tongue movement or stiffening) is observed. The discomfort threshold may be defined as the lowest stimulation level at which the patient experiences an unacceptable sensation (e.g., discomfort, pain) while awake.

While determining this range, the patient may be in the supine position or alternatively, in a posture typical of sleep. In general, during the stimulation titration, it is preferable to begin with the lowest settings for pulse width (30.mu.s) and amplitude (0.4 mA) at a nominal frequency (40 Hz). If stimulation produces pulsatile (vibrating) contractions, the frequency may be increased to 50 Hz. The pulse width is incrementally increased to 60.mu.s, then to nominal (90.mu.s), keeping Amplitude at 0.4 mA. With the pulse width set to 90.mu.s, amplitude may be iterated according to the process described hereinafter. If maximum amplitude is reached and additional intensity is required, the pulse width may be increased while reducing amplitude to minimum (0.4 mA). If maximum pulse width (215.mu.s) is reached and additional intensity is required, frequency may be increased while reducing the pulse width to 90.mu.s and the amplitude to minimum (0.4 mA).

At each stimulation level, observations may be recorded such as: visible tongue motion, palpable genioglossus muscle contraction, perception of muscle movement, tongue protrusion, tongue retrusion, tongue depression, tongue flattening, tongue cupping, and tongue protrusion past the teeth 10230.

After awake titration 10200, the patient may be sent home at a stimulation level in this operating range, beginning the daytime familiarization period 10400. This may occur prior to the sleep titration night, such that the patient may acclimate to the sensation of stimulation. This may allow higher levels of stimulation to be assessed during the sleep titration without patient arousal. Patients have been observed to tolerate (i.e., not arouse) higher stimulation intensities while asleep compared to wakefulness, so the arousal threshold may be higher than the wake discomfort threshold.

Sleep Titration

As described previously, after implantation and a healing period of approximately one month, the patient may undergo a sleep (PSG) study to confirm proper operation of the system and to titrate therapy stimulation levels 10500. Titration may utilize the set-up illustrated in FIG. 10, wherein the programmer system 2100 interfaces with the PSG equipment 2800. Generally, it is preferable to use an oro-nasal mask in order to measure airflow. Alternatively, a nasal cannula may be used. The preferred configuration is a calibrated pneumotach with the oro-nasal mask to measure the patient's airflow 10510. Alternatively, an uncalibrated pneumotach may be used. A thermistor or a thermocouple may also be used to sense airflow. The thermistor or thermocouple may be calibrated or uncalibrated.

Figure 84:
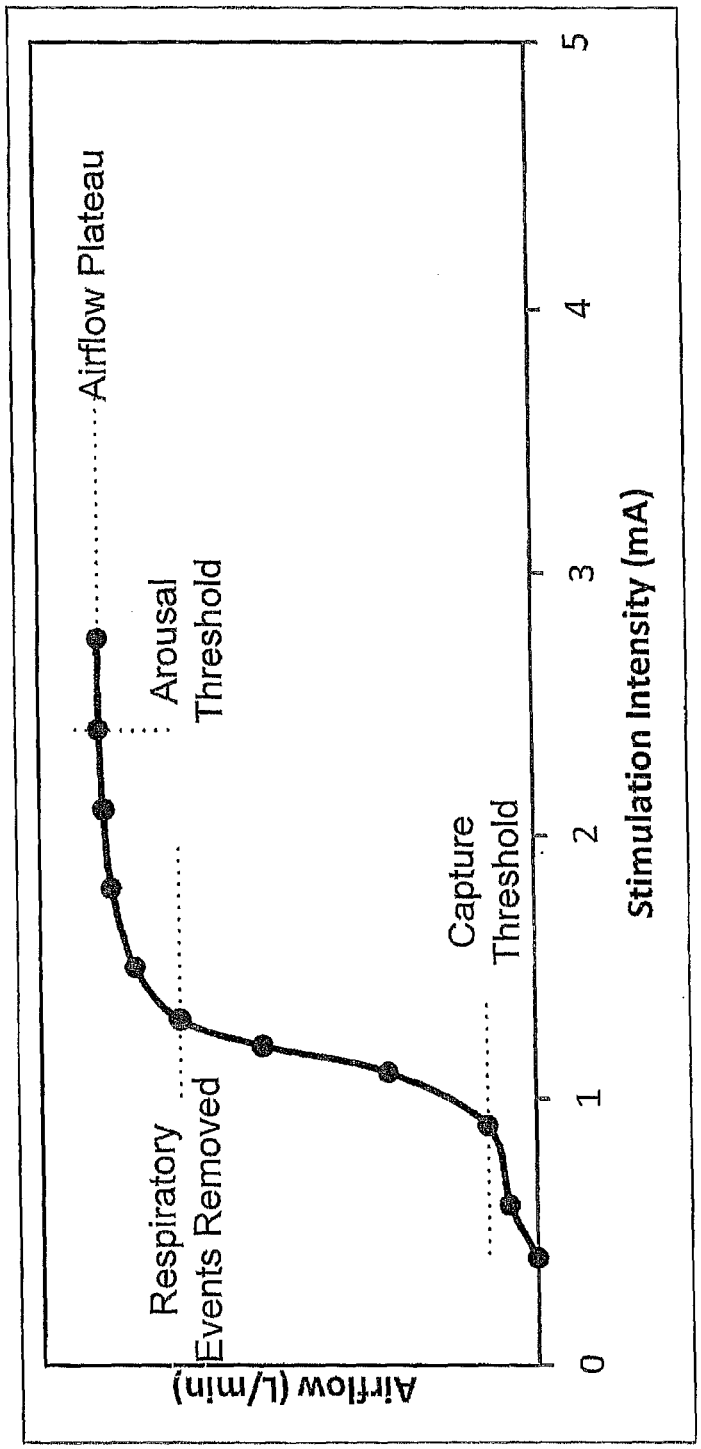
FIG. 84 illustrates an example of the effect of stimulation on airflow.

FIG. 84 illustrates an example of a patient's airflow response to stimulation. As shown in FIG. 84, the inspired airflow increases as stimulation delivered to the nerve increases. The airflow capture threshold is the stimulation level at which an increase in airflow is first observed. As stimulation continues to increase, muscle (i.e. genioglossus) activation and airflow also increase. Prior to full muscle activation, a stimulation level which first removes respiratory events is observed. At full muscle activation, increasing stimulation does not increase airflow, resulting in an airflow plateau. The patient may arouse due to stimulation at a level on the plateau. Data comprising this curve may be acquired during a sleep titration PSG for each patient.

Figure 82C:
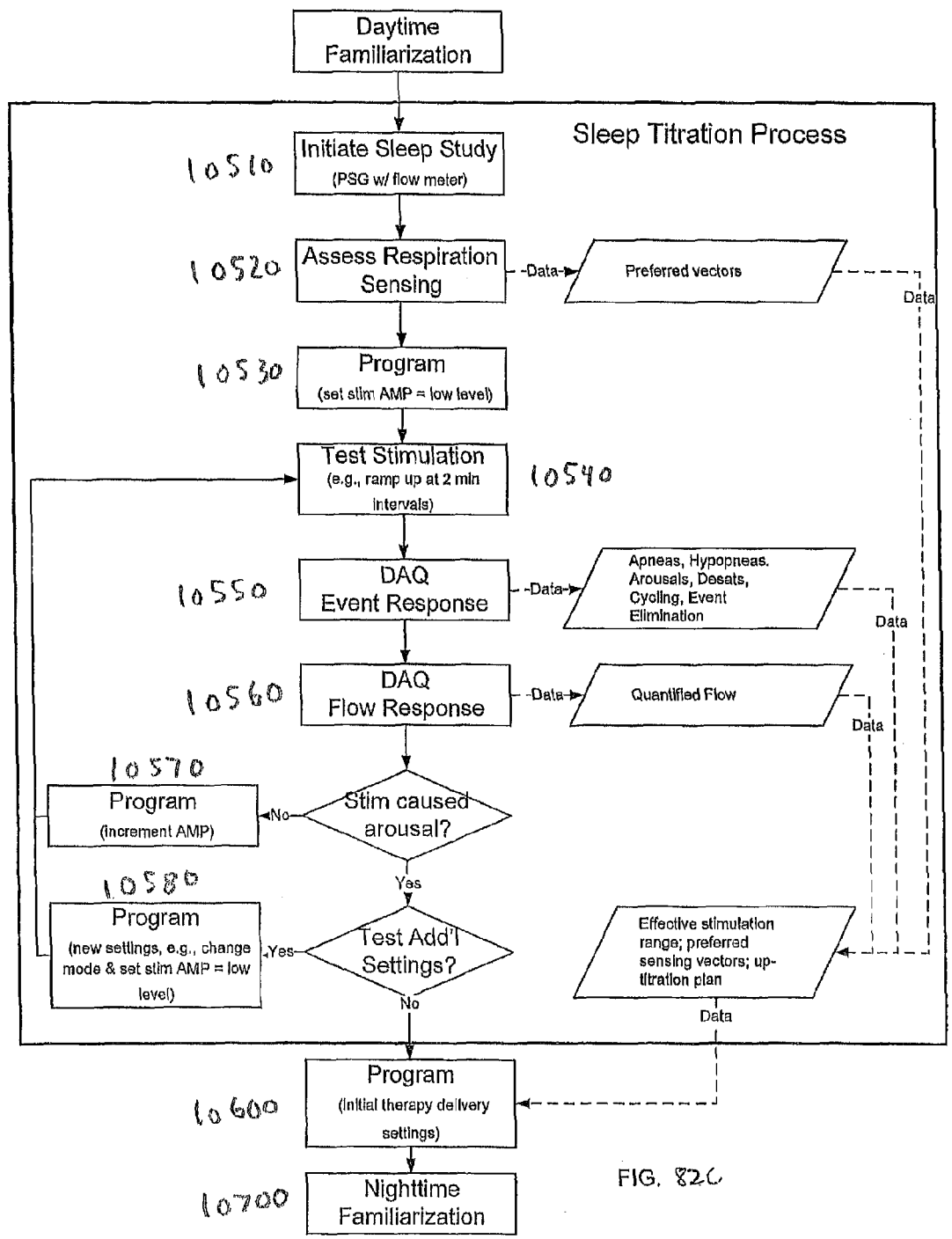

The sleep titration process is illustrated schematically in FIG. 82C. Titration generally involves establishing an effective range of stimulation settings 10540, where the lower end is defined by the lowest stimulation level where respiratory events (e.g., apneas, hypopneas, oxygen desaturations, etc.)

10550 begin to decrease or airflow begins to increase, and the range's upper end is defined by stimulation that arouses the patient. A goal setting at which the patient is effectively treated (i.e. respiratory events removed) may be estimated.

Figure 83:
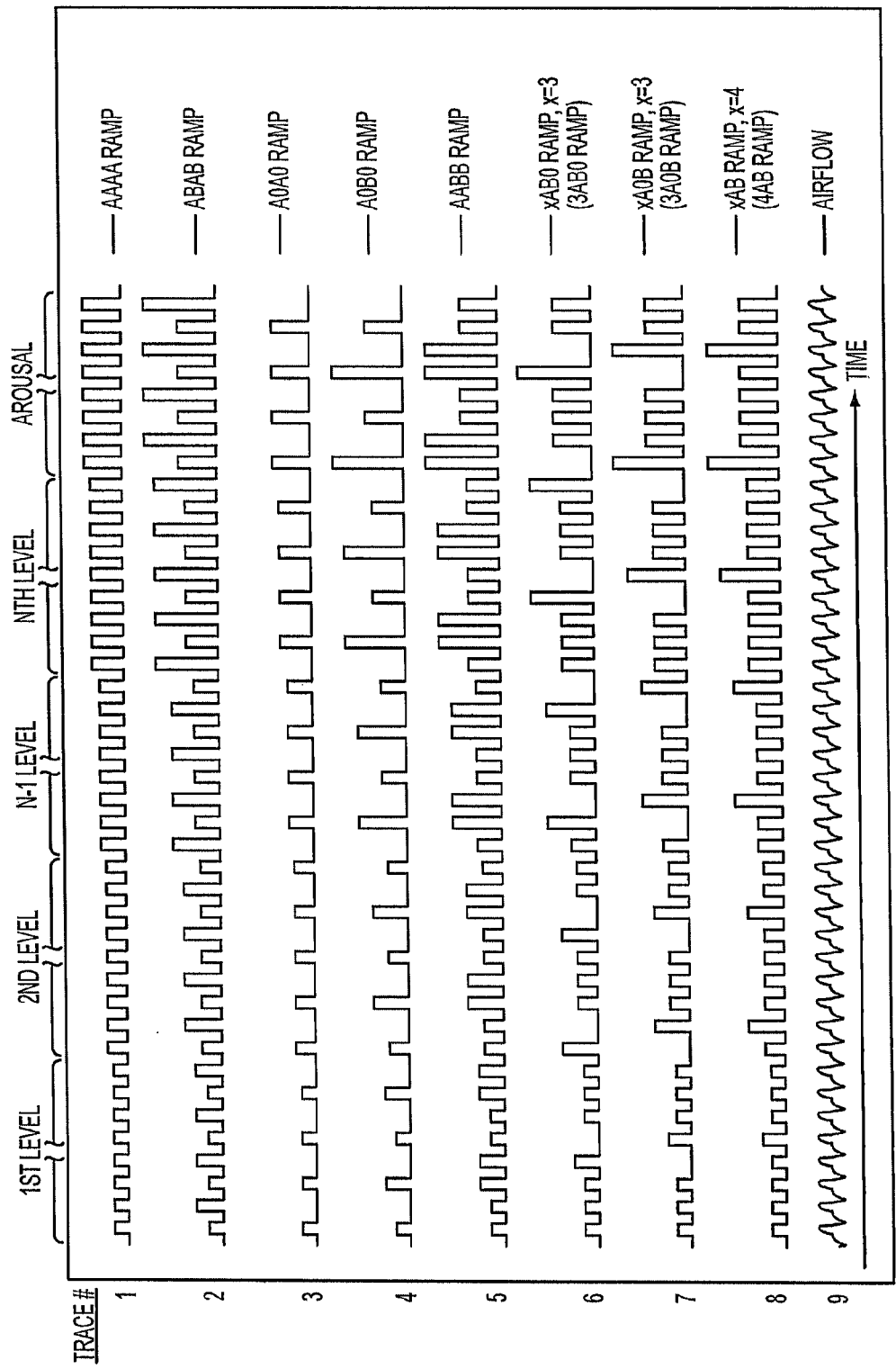
FIG. 83 (traces 1-8) illustrate various stimulation output modes of the implantable neurostimulator shown in FIG. 77.

During a sleep titration, device settings may be programmed using the programmer system 2100. At the start of titration, most stimulation settings will be at their default values (40 Hz frequency, 90 uS pulse width, 50% stimulation duty cycle, 0 ms phase adjust, etc.). Titration typically consists of many series of "ramps" in different body positions and sleep stages, wherein each ramp is a series of intervals where the stimulation intensity is increased from the previous interval in a certain stimulation mode 10540, illustrated in FIG. 83. For example, at 40 Hz, 90 uS, in A0A0 mode, stimulation level of the "A" breaths could be incremented every two minutes, from the nerve capture amplitude to the amplitude that causes arousal, as illustrated in FIG. 83 trace 3. Ramps are typically performed in A0A0, ABAB, AABB, A0B0, or AAAA modes, as illustrated in FIG. 83, traces 1, 2, 3, and 5. In addition, ramps may be performed using any of the previously discussed modes, also shown in FIG. 83. At each interval, observations are made as to whether stimulation causes arousal, reduces respiratory events, or increases airflow (e.g., increased $V_{i,max}$).

Alternative stimulation modes (not illustrated) may be utilized during wakefulness or sleep, (e.g. during a sleep titration PSG). An alternative mode may be x" y0 mode, where stimulation is delivered for "x" breaths wherein "x" is a programmable number of breaths, followed by "y" breaths with no stimulation wherein "y" is a programmable number of breaths. For example, in mode 4A40, stimulation is delivered on four consecutive breaths followed by no stimulation on four consecutive breaths.

A0A0 mode may be useful in determining if a stimulated breath has more flow than an adjacent unstimulated breath. In the same manner, ABAB and AABB modes may be useful in determining if a stimulated "A" breath provides more flow compared to an adjacent breath with less stimulation, "B." Likewise, A0B0 mode may be useful in comparing flows during "A" stimulation, "B" stimulations, and unstimulated breaths. During a ABAB, AABB, and A0B0 ramps, the difference in stimulation between "A" and "B" stimulations may be constant. ABAB, AABB, and AAAA ramps may also be useful in determining absolute flow (e.g., tidal volume, minute volume, etc.) and determining what level of stimulation reduces or eliminates respiratory events, since stimulation is delivered every breath. These observations may be recorded for future reference (e.g. physician use). Each stimulation mode may be combined with any of the pulse configurations, such as nested stimulation, soft start, or retention intensity, as chosen by physician or technician.

When a stimulation level is estimated to be efficacious, it may be tested in AAAA mode for a fixed time (e.g., five minutes) after which stimulation may be turned off for a fixed time (e.g., five minutes). If stimulation noticeably reduced or eliminated respiratory events compared to no stimulation, the settings may be considered the goal setting.

Additional titration PSG studies may be performed, either as a separate sleep study or as a split night study. In order to compare multiple stimulation settings during sleep, a crossover PSG study may be performed wherein the stimulation settings are changed at fixed intervals throughout the night, toggling through a select group of settings. For example, stimulation may alternate between two stimulation settings every five minutes. Afterwards, respiratory events may be determined for each interval such that an index (e.g., AHI, ODI, etc.) can be calculated for each stimulation setting. This may be useful to gauge whether an increase in stimulation would provide addition therapeutic benefits or to gauge whether a decrease in stimulation would not lessen any therapeutic benefits. In addition, the oxygen sensor of the INS 1100 may be used to measure oxygen de-saturations and calculate an ODI.

Another type 4 titration PSG may be a characterization night, per the methods of Schwartz et al, such that a Pcrit may be determined in REM/nREM sleep, both supine and lateral. Another type of sleep study is the home PSG study, which may be utilized to assess efficacy without the burden of an in-lab PSG. Many home PSG systems are available for use.

The patient may also undergo a vector-sweeping sleep study, wherein the programming system 2100 and a respiratory signal (e.g., nasal cannula) are utilized, 10520. During this study, the secondary vector may be changed at regular intervals to cycle through a select group of vectors. These vectors are compared to the primary vector to determine an optimal sensing vector to deliver therapy. Selection may be based on maximum signal strength, consistent correlation to respiratory fiducials (e.g., offset of inspiration), and maximum signal stability/reliability across sleep stages, body positions, and disordered breathing events, for example. A stable signal has a minimum probability of signal inversion. A reliable signal has a minimum probability of signal loss, and may preferably have a minimum threshold of 0.1 to 0.5 Ohms peak-to-peak, for example. The optimal vector may be selected by incrementally scrolling through all or a preferred subset of possible vectors while sampling the respiration signal and comparing the signal against themselves or predefined thresholds. This scrolling technique may be performed manually (with inputs via the programmer system) or automatically (i.e., programmed). The sampling technique may also be performed manually (visual observation using programmer system) or automatically (i.e., programmed).

Post-Sleep-Titration: Nighttime Familiarization and Up-Titration

Figure 82D:
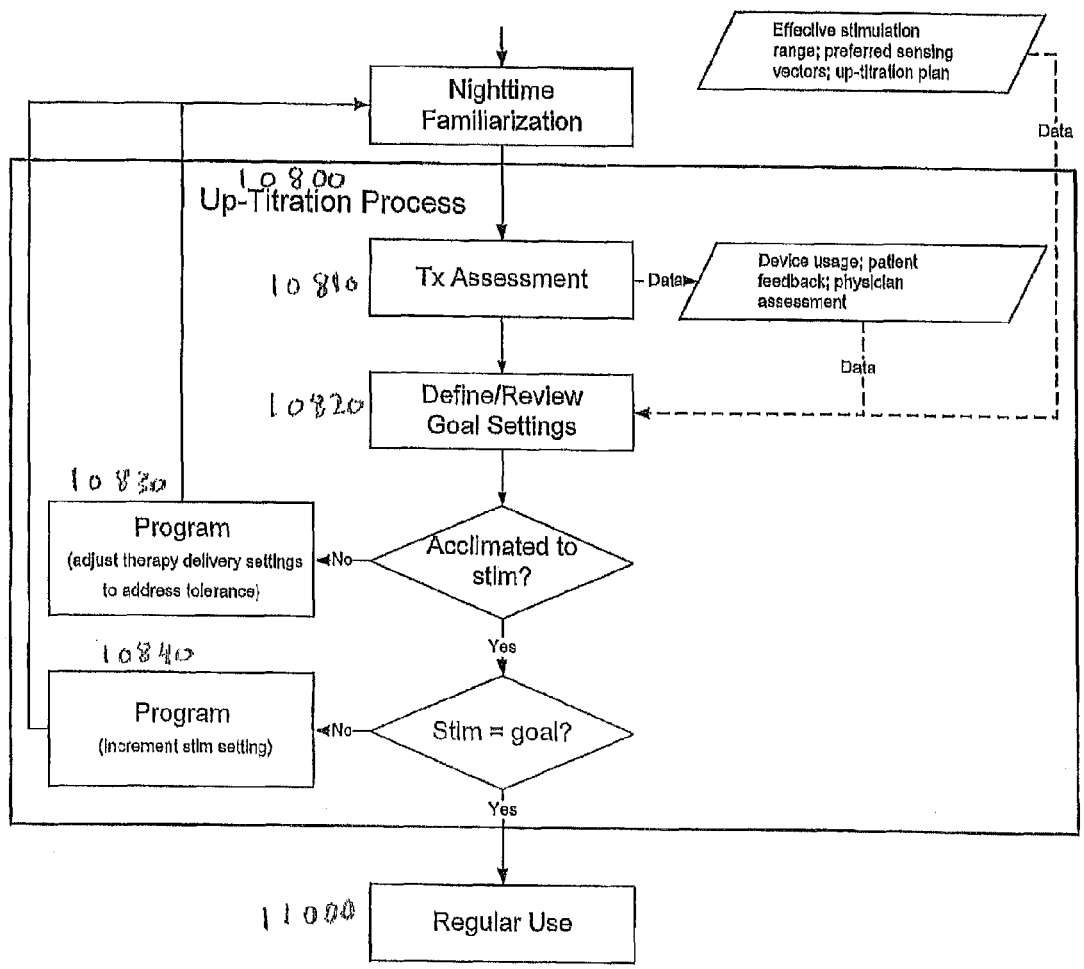

After titration, the patient is typically sent home with the device active and stimulation set to a level at which she can fall asleep. This begins the post-sleep-titration process, as illustrated in FIG. 82D. This process may include nighttime familiarization, up-titration of stimulation, and determining efficacy 10700, 10800, and 11100.

The stimulation settings at which the patient is sent home may initially be below the estimated goal settings. As the patient becomes acclimated to sleeping with the device on 10700, stimulation may be slowly incremented, over the course of days, towards the range where therapeutic effects were observed during the sleep titration and ultimately towards the estimated goal settings. This period is known as up-titration 10800. These increments may be performed by a physician or caretaker, or by the patient, if the physician allows the patient to have limited control of stimulation via the therapy controller 2500.

Several feedback parameters may aid in determining the appropriate time to up-titrate a patient 10810. These include the device's therapy history of frequency and duration of therapy sessions, patient feedback (e.g., more daytime energy, no tongue abrasions, stimulation not causing arousal or pain, etc.), patient's bed-partner feedback (e.g., reduced snoring, perceives patient to be less sleepy, etc.), and most notably, a PSG study. Taken together, these may show whether the patient needs more time to acclimate to stimulation, is ready to have stimulation increased 10840, is receiving therapeutic benefits, or is fully treated. In addition, these feedback may provide data to adjust the patient's estimated goal settings 10820. For example, a patient's upper airway may, over time, undergo muscle remodeling such that less stimulation than originally estimated provides efficacious therapy. Alternatively, a patient may gain weight such that more stimulation than originally estimated may be needed to provide efficacious therapy.

If the stimulation is causing discomfort to the patient such that stimulation disrupts sleep or inhibits falling asleep with stimulation on, many options are available, 10830. Stimulation may be reduced and the patient may be given more time for nighttime familiarization. A different strategy that may increase the therapy provided to the patient is to utilize the device features of core hours, soft start, retention intensity, and nested stimulation. The core hours feature (FIG. 6K) allows the patient to fall asleep at one level of stimulation and after a programmable time interval, have stimulation increased to a more therapeutic level. Patients are often able to tolerate higher stimulations when asleep compared to wakefulness and in addition, tolerate higher stimulations further into a therapy session than at the start of a session.

As mentioned previously, the INS 1100 may be programmed to change stimulation level between therapy sessions, days, or other programmable value, enabling comparisons between stimulation level and therapy session data. For example, the INS 1100 may be programmed to alternate between 1.8 mA and 2.0 mA, where the change occurs between therapy sessions. This may be used as a diagnostic mode to assess the incremental benefit of the higher stimulation level. A patient receiving daily therapy would thus receive therapy at 1.8 mA on one day, 2.0 mA the next, 1.8 mA the next day, 2.0 mA the next day, and so on. This may allow therapy session data to be compared with stimulation level. For example, a physician may compare the cycling rate (via the cycling detector) during therapy sessions at 1.8 mA and 2.0 mA over time to determine if there is an observable difference. If cycling is reduced at 2.0 mA, the physician may increase stimulation and re-test. If there was no observable difference, the physician may decrease stimulation and re-test or simply set stimulation to the lower level. This may reduce the likelihood of delivering stimulation at a level that, compared to a lower level, provides no additional flow or no additional benefit. As mentioned previously, other therapy session data may be compared to stimulation level as well in a similar manner. Examples of other therapy session data are: oxygen desaturation frequency and severity, stimulation time, variations in respiratory rate, and variations in respiratory prediction.

Various pulse configurations may also help a patient acclimate to stimulation. The soft start stimulations (FIG. 80G) may provide a smoother transition from unstimulated breaths to stimulated breaths, reducing the patient's perception of stimulation intensity. Retention intensity (FIGS. 80E and 80F) may also provide therapy with reduced patient perception of stimulation intensity, since the full amplitude is only used for a part of the stimulation. Nested stimulations (FIG. 80H) may be used in a similar manner.

The patient may use positive airway pressure (PAP) therapy (e.g., CPAP, bi-PAP, auto-PAP, etc.) in conjunction with the neurostimulator. This may allow the patient to receive therapeutic benefits in addition to what is provided by the stimulation. The pressure necessary to provide these benefits may decrease as stimulation is up-titrated, 10800. This progress towards lower pressures may be monitored using the auto-PAP technology which automatically adjusts pressure to the level necessary to remove flow limitation. In time, the patient may wish to stop PAP therapy altogether. In a similar manner, other therapies such as but not limited to positional therapy and mandibular advancement may be used in conjunction with the neurostimulator.

If the patient begins noticing tongue abrasions, a tooth guard or other tooth covering (e.g. dental wax) may be used such that the tongue does not scrape against the teeth when stimulation causes tongue protrusion. Tooth guards may be custom-made (e.g., by a dentist).

Additional strategies for acclimation may include another sleep titration night to examine different stimulation frequencies, pulse widths, and modes, as previously described. Different stimulation frequencies and pulse widths may capture different muscle groups in a more therapeutic manner. In additions, respiration vectors may need to be assessed during a vector sweeping titration.

Therapy efficacy may be measured using standard PSG techniques during and after familiarization and up-titration. Therapy efficacy may be evaluated by assessing indicia of sleep disordered breathing such as AHI, apnea index, hypopnea index, respiratory disturbance index, apnea-hypopnea index, ODI, FOSQ, ESS, BDI, PSQI, or other measures.

Alternative Embodiments

The stimulation may be delivered to the nerve by utilizing a variety of stimulation electrode configurations, in addition to the configurations previously mentioned.

Mono-polar stimulation may be delivered to the nerve wherein the cathode (or multiple cathodes) is an electrode (or multiple electrodes) in the STL nerve cuff 1350, and wherein the anode is the INS 1100. Similarly, far-field bi-polar stimulation may be delivered to the nerve wherein the cathode (or multiple cathodes) is an electrode (or multiple electrodes) in the nerve cuff, and wherein the anode is an RSL electrode 1250 or 1260.

Any combination of bi-polar and mono-polar stimulation may be utilized to deliver stimulation to the nerve. For example, mono-polar stimulation may be delivered between a cathode electrode in the STL nerve cuff 1350 and the INS 1100 anode. Simultaneously, far-field bi-polar stimulation may be delivered between a different cathode electrode in the STL nerve cuff 1350 and an RSL electrode 1250 or 1260 anode.

The INS 1100 may be programmed to periodically change stimulation parameters throughout a therapy session to vary which muscle fibers are recruited at any given time. For example, stimulation may be delivered at an initial lower frequency (e.g. 30 Hz) for 5 minutes, followed by stimulation delivered at a higher frequency (e.g. 50 Hz) for 2 minutes. Each frequency may have a unique pulse width, pulse width, and/or amplitude. This sequence could be repeated throughout the night.

This may allow certain muscle fibers to rest during periods when other muscle fibers are active. This may reduce muscle fatigue. Another potential advantage is that stimulation at more than a single frequency and/or pulse width may be a more effective means of building muscle strength and endurance. Another potential advantage is that different stimulation settings (e.g. frequency, pulse width, and/or amplitude) may result in slightly different movement of the tongue. Varying stimulation settings may decrease the possibility of repetition-induced irritation, inflammation or injury.

Alternatively, it may be possible to effectively build muscle strength and endurance by deactivating a portion of the nerve fibers and activating a remaining subset of fibers. This may allow delivery of higher levels of stimulation to the remaining fibers. This may reduce subject discomfort which could have occurred if all the fibers had been activated at that same intensity. Additionally, this may increase airway patency or opening by selecting muscles whose activation results in tongue protrusion and deactivating tongue retrusion muscles.

Certain fibers in the nerve may be selectively deactivated by choosing the cathode of pulse delivery and sequence of pulse delivery such that the fibers are not recruited by subsequent or simultaneous pulses. For example, a nerve fiber that innervates a retrusor muscle may be deactivated by delivering a sub-threshold pulse from a nearby cathode. This may allow a subsequent or simultaneous pulse at a different cathode to activate a nerve protrusor muscle nerve fiber without recruiting the retrusor muscle.

Screening Devices and Methods

Figure 86:
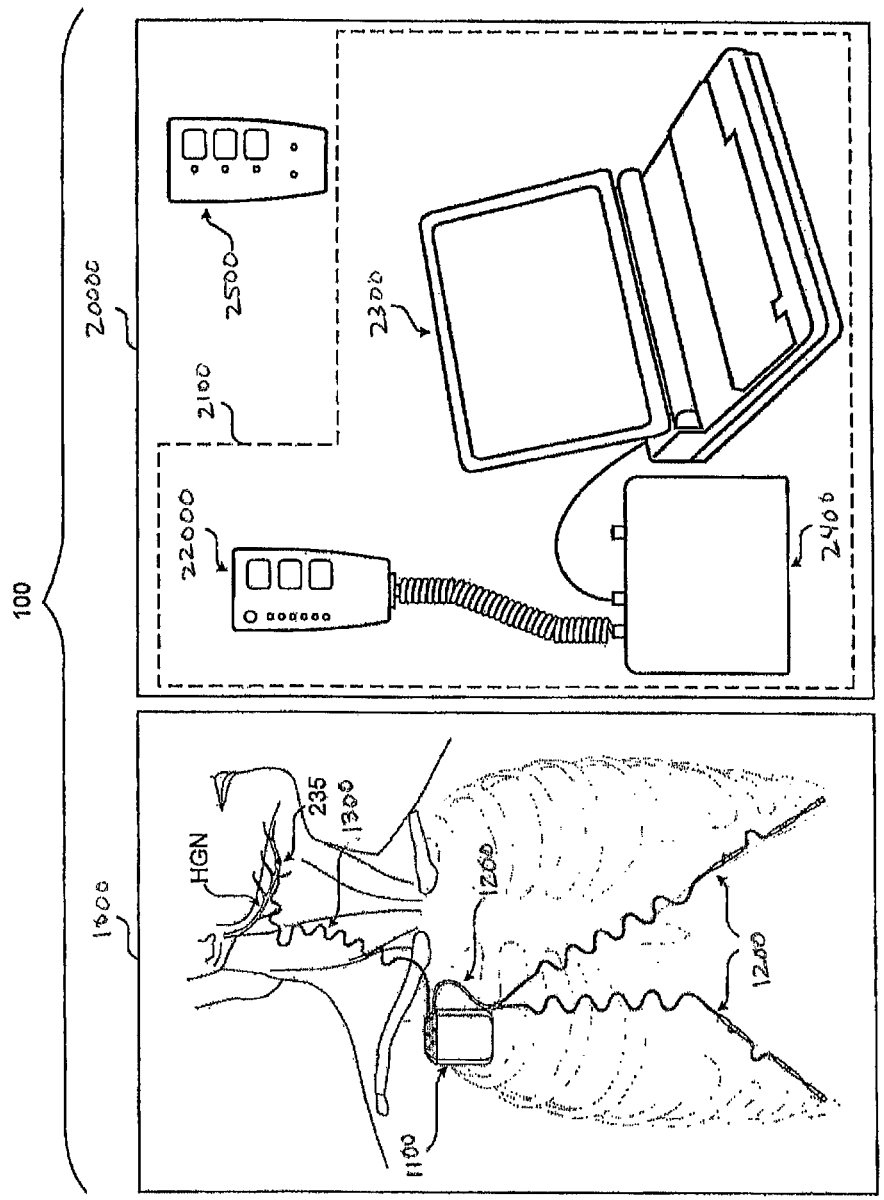
FIG. 86 is a schematic illustration of a hypoglossal nerve stimulation system.

FIG. 86 schematically illustrates an exemplary hypoglossal nerve stimulation (HGNS) system 100 comprising internal components 1000 and external components 20000. The HGNS system 100 is intended to treat obstructive sleep apnea (OSA) by increasing neuromuscular activity of the genioglossus muscle via stimulation of the hypoglossal nerve (HGN) synchronous with inspiration to mitigate upper airway collapse during sleep. Stimulation is generated by an implantable neurostimulator (INS) 1100, synchronized with inspiration as measured by the respiration sensing lead (RSL) 1200 using bio-impedance, and delivered to the hypoglossal nerve by a stimulation lead (STL) 1300. Alternatively, stimulation may be delivered without respect to respiration, negating the need for respiration sensing capability. A programmer system 2100 and a therapy controller 2500 are wirelessly linked to the INS 1100. The programmer system 2100 includes a computer 2300, a programmer interface 2400, and a programmer head 22000. The programmer system 2100 is used by the physician to control and program the INS 1100 during surgery and therapy titration, and the therapy controller 2500 is used by the patient to control limited aspects of therapy delivery (e.g., start, stop, and pause).

The implanted components 1000 of the HGNS system 100 include the INS 1100, STL 1300, and RSL 1200. The INS is designed to accommodate one STL 1300 and one RSL 1200. One STL 1300 may be used for unilateral implantation and unilateral hypoglossal nerve stimulation. Similarly, one RSL 1200 may be used for respiration detection, and may be bifurcated as shown.

The implanted components 1000 may be surgically implanted with the patient under general anesthesia. The INS 1100 may be implanted in a subcutaneous pocket inferior to the clavicle over the pectoralis fascia. The distal end of the STL 1300 (cuff 235) may be implanted on the hypoglossal nerve or a branch of the hypoglossal nerve in the submandibular region, and the proximal end of the STL 1300 may be tunneled under the skin to the INS 1100. The RSL 1200 may be tunneled under the skin from the INS 1100 to the rib cage and placed on both lateral sides of the costal margin. The INS 1100 detects respiration via the RSL 1200 using bio-impedance and stimulates the hypoglossal nerve via the STL 1300 synchronous with inspiration.

Further aspects of the HGNS system 100 may be found in U.S. Provisional Patent Application No. 61/437,573, filed Jan. 28, 2011, entitled OBSTRUCTIVE SLEEP APNEA TREATMENT DEVICES, SYSTEMS AND METHODS, the entire disclosure of which is incorporated herein by reference.

Figure 87B:
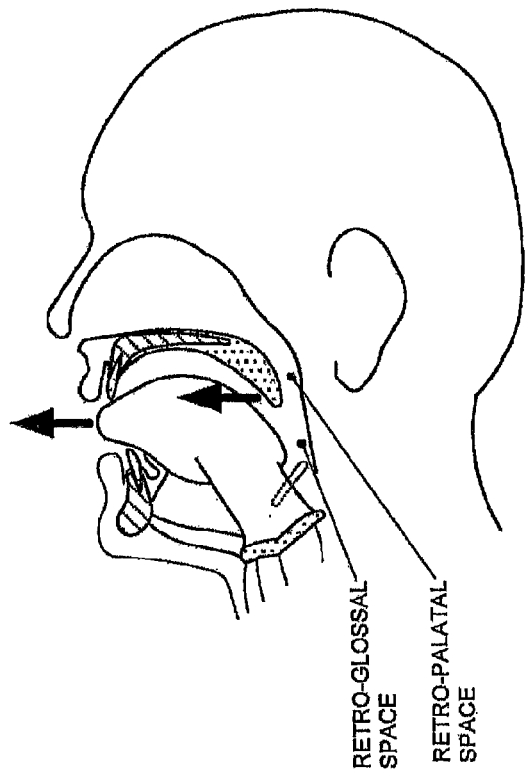
FIGS. 87A and 87B are schematic illustrations showing simplified structures of the upper airway in a lateral dissection with the palate and mandible shown in medial sagittal section.
Figure 87A:
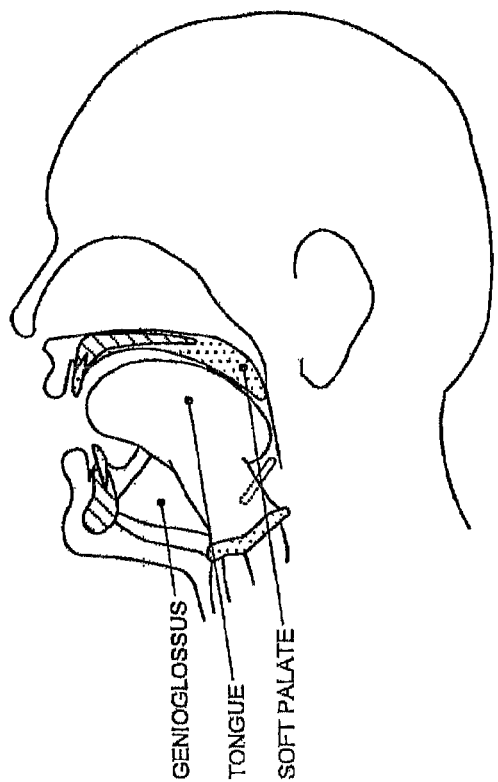

Patients with obstructive sleep apnea have repeated episodes of complete (apnea) or partial (hypopnea) upper airway collapse during sleep. The upper airway is generally defined by four walls: the posterior pharyngeal wall, the right and left lateral pharyngeal walls, and anteriorly, the soft palate and the tongue. The posterior pharyngeal wall is relatively fixed to the spinal column. Thus, collapse of the upper airway generally involves, depending on the level and mode of collapse, the tongue, the soft palate and/or the lateral walls. In rare cases, collapse may involve the nasopharynx and/or hypopharynx. As seen in FIG. 87A, the tongue and the soft palate have been displaced posteriorly, thus occluding the airway at the level of the tongue (retro-glossal collapse) and at the level of the soft palate (retro-palatal collapse). As seen in FIG. 87B, activation of the genioglossus muscle, for example by HGNS, causes anterior displacement of the tongue, thus opening the retro-glossal airway space. Activation of the genioglossus muscle can also cause anterior displacement of the soft palate, thus opening the retro-palatal airway space. Although not visible in this view, activation of the genioglossus muscle can further cause lateral displacement of the lateral pharyngeal walls, thus further opening the upper airway. In this manner, activation of the genioglossus muscle, for example by HGNS, can mitigate upper airway collapse in OSA subjects.

Although the effect of genioglossus activation on the tongue to open the retro-glossal airway is predictable given the mechanism of action, the effect of genioglossus activation on the soft palate and lateral walls has been heretofore poorly understood and variable across subjects. Nevertheless, in the majority of OSA patients, the soft palate and the lateral walls can contribute to upper airway collapse, alone or in combination with the tongue. Thus, observing these effects can be important to predicting the success of HGNS therapy. This is particularly true if the soft palate and/or lateral walls are known to contribute to airway collapse for a given OSA patient.

The present invention offers a method to mimic genioglossus activation to observe and assess the effects thereof on structures of the upper airway. The method generally involves causing the tongue to protrude while observing the response of the upper airway using an imaging technique. In general, the desired response is an increase in airway size. An adequate increase in airway size during the tongue protrusion maneuver is indicative of likely therapeutic success with HGNS. If an adequate increase in airway size is observed during the maneuver, a HGNS device may be implanted in the patient with a higher confidence of a successful outcome.

Figure 88D:
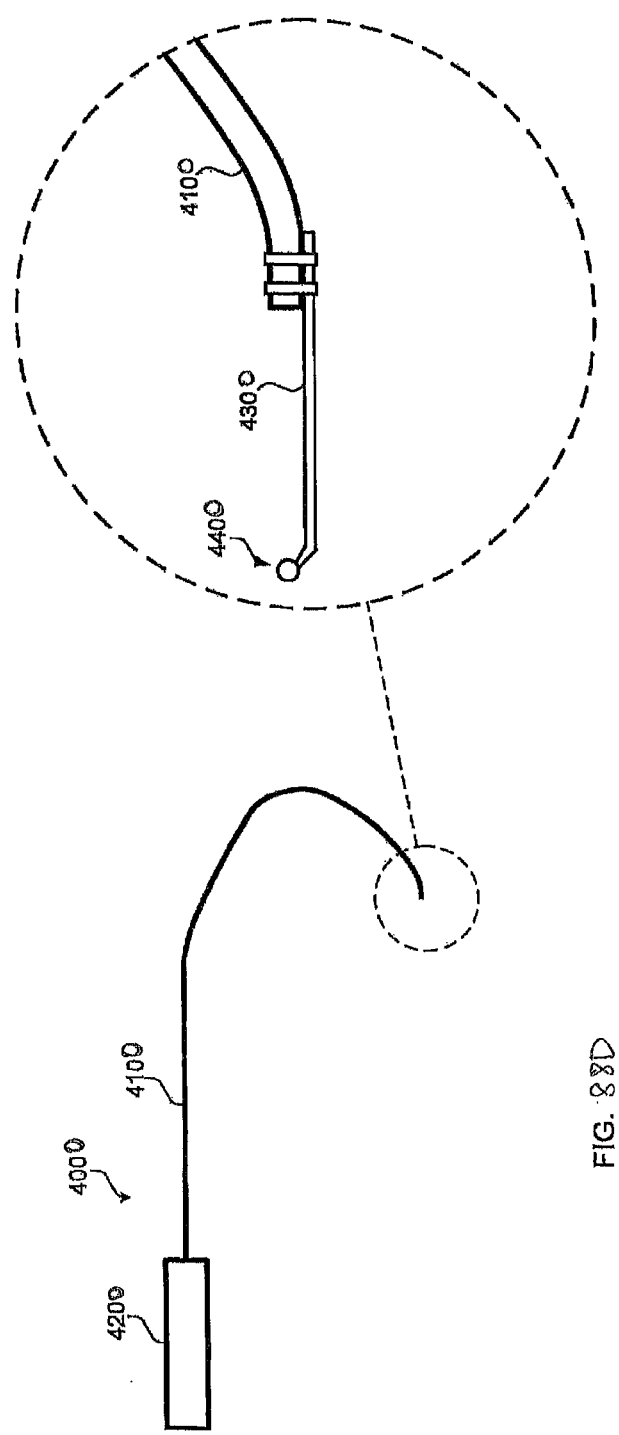
FIG. 88D is a schematic illustration of a modified endoscope.

With reference to FIG. 88A, a naso-endoscope 4000 may be used to visually observe the upper airway while the patient is awake in the supine position. Alternatively, the observation may be made while the patient is in a seated or semi-recumbent position. A conventional naso-endoscope 4000 including a fiber optic shaft 4100 and a hand piece 4200 may be used. Hand piece 4200 may include a light source and a viewing window, and/or facilitate connection to ancillary imaging equipment (e.g., light source, camera, monitor, recorder, etc.). The patient may be asked to volitionally protrude his/her tongue straight and to its maximal extent with the mouth open and the lips loosely touching the tongue. Alternatively, the tongue protrusion may be performed submaximally, which may limit muscle contraction to the genioglossus without recruiting other musculature. Also alternatively, the tongue protrusion may be performed by asking the patient to point the tip of the tongue to one side or the other, which may more closely mimic unilateral hypoglossal nerve stimulation. The distal end of the endoscope may be positioned superior to the soft palate and substantially parallel with the posterior pharyngeal wall to visualize the retro-palatal space. The distal end of the endoscope may be positioned inferior to the soft palate, superior to the tongue base and substantially parallel with the posterior pharyngeal wall to visualize the retro-glossal space. An example of the view of the retro-palatal upper airway space with the tongue in a relaxed (nominal) position is shown in FIG. 88B, and the same view with the tongue protruded is shown in FIG. 88C. As can be seen by comparing the views in FIGS. 88B and 88C, tongue protrusion can result in an increase in airway size, including area, circumference, anterior-posterior dimension, and lateral dimension. The increase in airway size at the level of the tongue and palate may be most discernable by an increase in anterior-posterior (AP) dimension between the posterior pharyngeal wall and the posterior side of the tongue base (retro-glossal) and soft palate (retro-palatal), respectively. Since the posterior pharyngeal wall is fixed relative to the spinal column, the increase in AP dimension involves anterior displacement of the tongue and soft palate, respectively. The increase in airway size may also be discernable by an increase in lateral dimension between the right and left lateral pharyngeal walls.

During the tongue protrusion maneuver, observing an adequate increase in size of the retro-glossal airway is predictive of HGNS efficacy in patients with isolated tongue base collapse. However, as mentioned above, the soft palate contributes to upper airway collapse in the majority of OSA patients, thus also observing an increase in size of the retro-palatal airway during the tongue protrusion maneuver is predictive of HGNS efficacy in patients with isolated soft palate collapse and combined tongue plus soft palate collapse.

By way of example, not limitation, the following procedure may be followed to conduct the assessment and tongue protrusion maneuver. With the patient awake in the supine position, a nasal endoscope is inserted into the pharynx via one of the nares to allow visualization of the upper airway. Video and still images may be captured at both the retro-palatal and retro-glossal levels to document the effect of different maneuvers on anatomic structures of the upper airway (tongue, palate, epiglottis, pharyngeal walls, etc.). When imaging the retro-palatal level, the endoscope may be placed such that all four walls (soft palate, posterior wall, and the two lateral walls) of the pharynx are visible before, during and after maneuvers. Similarly, when imaging the retro-glossal level, the endoscope may be placed such that all four walls (tongue base, posterior wall, and the two lateral walls) of the pharynx are visible before, during and after maneuvers. The endoscope may be placed such that it runs generally parallel to the posterior wall and provides a symmetric field of view. This may be achieved by initially placing the distal end of the endoscope near the level of the epiglottis and subsequently pulling back to the desired level. The patient then performs a series of maneuvers, including a tongue., protrusion maneuver while breathing through their nose. The tongue protrusion maneuvers involves voluntary maximal straight tongue protrusion with lips loosely touching the tongue, with the mouth completely open, and/or with the teeth clenched closed. Other maneuvers such as a Mueller maneuver (inspiratory efforts against a closed airway) may be performed as well. Each maneuver is held for .gtoreq.2 seconds, and performed several times while data (images and measurements) are gathered.

Alternative non-volitional tongue protrusion maneuvers include, for example, manually gripping and pulling the tongue anteriorly (e.g., by the physician), using a tongue retaining device (e.g., as used for the treatment of OSA), both of which are non-invasive. Another alternative is to stretch the palatoglossal arch by pushing the tongue down (depress tongue), by pushing the arch laterally outward, or by pulling the arch anteriorly (all palatoglossal maneuvers) using a tongue depressor or similar device. The palatoglossal maneuver may be used in place of or in combination with the tongue protrusion maneuver, and the entire description herein with respect to the tongue protrusion maneuver is applicable to the palatoglossal maneuver. Other alternative non-volitional tongue protrusion maneuvers include, for example, sub-mental stimulation and intra-muscular stimulation (using fine wire electrodes, for example), both of which are relatively more invasive, but have the benefit of more selectively activating the genioglossus muscle alone to more closely mimic HGNS, as compared to volitional tongue protrusion which may recruit more than the genioglossus muscle.

Although naso-endoscopy is perhaps the most practical imaging technique to employ to assess the response of the upper airway to the tongue protrusion maneuver, other imaging techniques may be used as well. For example, x-ray imaging, fluoroscopy, x-ray computed tomography (CT), and optical coherence tomography (OCT) are suitable alternatives. These alternatives may provide more quantitative measurements by using a reference marker of known dimension in the field of view. Alternatively, improvements may be made to conventional naso-endoscopes to facilitate more quantitative measurements. For example, with reference to FIG. 88D, conventional naso-endoscope 4000 includes a fiber optic shaft 4100 and a hand piece 4200. The distal end of the shaft 4100 may include an attached extension 4300 having a tip 4400. The extension 4300 positions the tip 4400 into the field of view and may be approximated to the upper airway structure being visualized. The tip 4400 may have a known dimension (e.g., diameter of 1 French or 3 mm), such that quantitative measurements of upper airway structures may be made by comparison. Other devices to make quantitative measurements may be employed, such as a laser pointer of know beam diameter projected onto the upper airway structure of interest. As an alternative, a catheter (e.g., nasogastric, nasoesophageal or nasopharyngeal catheter) may be inserted into the nasopharynx such that it resides in the field of view of the endoscope to serve as a quantitative reference of known dimension (e.g., diameter).

As mentioned above, the upper airway assessment during tongue protrusion maneuver may be used as a screening tool wherein the patient is treated with the desired therapy (e.g., HGNS) only if the increase in size of the upper airway meets a predefined criterion. To this end, the response of the upper airway may be measured using a qualitative scale such as a visual analog scale of 0-10, wherein 0 represents a closed airway and 10 represents a completely open or patent airway. The airway size may be scored with the tongue at rest and during the tongue protrusion maneuver. The patient may be treated if the difference between the two scores meets a threshold, if the score during the maneuver meets a threshold, or if both the difference between the scores and the score during the maneuver meet thresholds (e.g., 5 on a scale of 0-10).

Alternatively, the response of the upper airway may be measured using a quantitative scale such as: a pixel count of captured images which may be representative of cross-sectional area; a linear dimension such as anterior-posterior and/or lateral; or a measure of circumference. Here again, the airway size may be measured (e.g., pixel count, AP length, and/or lateral width) with the tongue at rest and during the tongue protrusion maneuver. The patient may be treated if the difference between the two measures meets a threshold, if the measure during the maneuver meets a threshold, or if both the difference in measures and the measure during the maneuver meet thresholds.

In each case, the threshold may be a percentage increase in size (e.g., difference in AP length=50%), an absolute value (e.g., difference of AP length=0.5 cm), or a relative value. The relative value may be with reference to an anatomical landmark such as the width of the superior aspect of the epiglottis (e.g., difference in AP length=50% of epiglottal width).

Other response criteria observed during the tongue protrusion maneuver, in addition to an increase in airway size, may be used as well. For example, movement of the hyoid bone may be observed visually, by palpation or by x-ray. Movement of the hyoid bone in an anterior direction and/or inferior direction during the tongue protrusion maneuver may be predictive of therapeutic success with HGNS.

As mentioned above, although the effect of HGNS and genioglossus activation on the tongue to open the retro-glossal airway is predictable given the mechanism of action, the effect of genioglossus activation on the soft palate and lateral walls has been heretofore poorly understood. The explanation lies in the mechanical linkages between the genioglossus and other pharyngeal structures defining the upper airway. The linkages are primarily muscular, and can be effective without independent activation. Nevertheless, it may be desirable to independently activate any one or a combination of the muscular structures described below by stimulating the muscle directly or by stimulating the corresponding motor nerve innervating the muscle.

Figure 89:
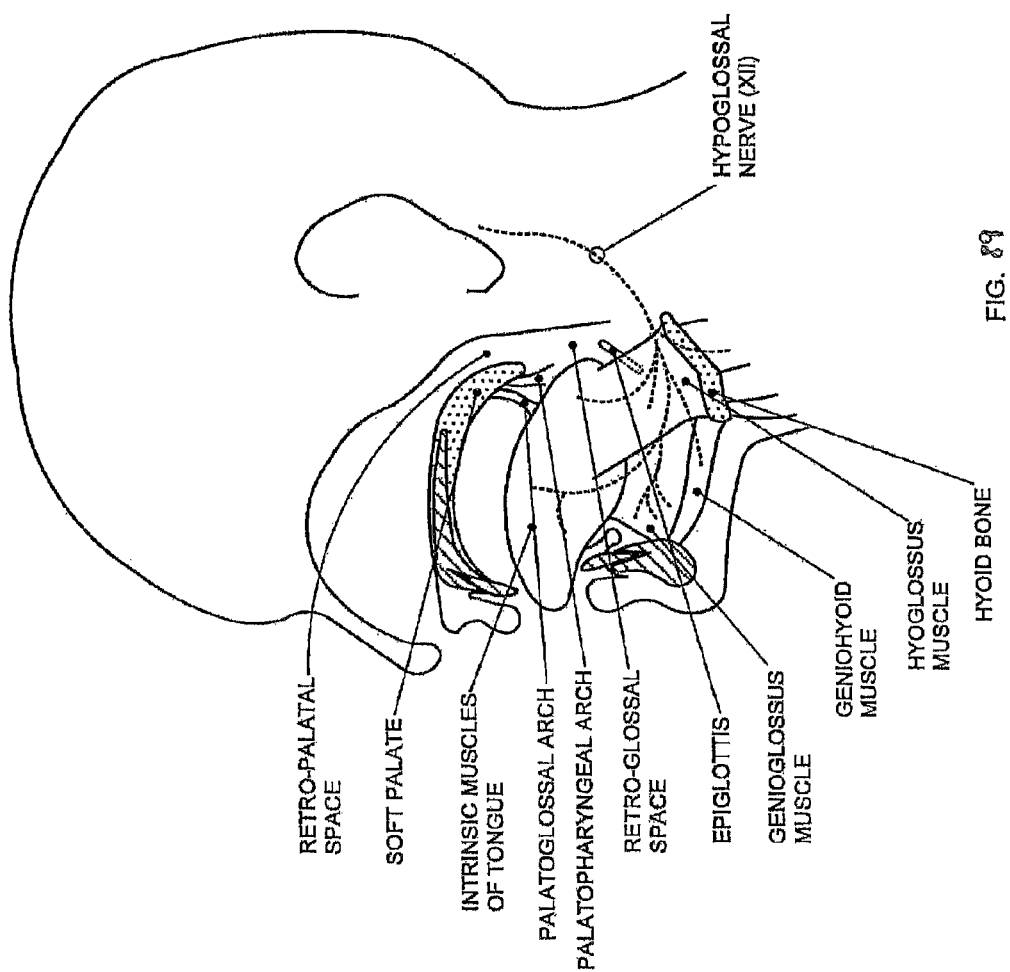
FIG. 89 is a schematic illustration showing the structures of the upper airway in a lateral dissection with the palate and mandible shown in medial sagittal section.

With reference to FIG. 89, the mechanical linkages may be explained in more detail. By way of context, the hypoglossal nerve (cranial nerve XII) innervates the genioglossus muscle, which is the largest upper airway dilator muscle. Activation of the genioglossus muscle causes tongue protrusion and, in some cases, anterior displacement of the soft palate, due to linkage via the palatoglossal arch (muscle). Anterior displacement of the soft palate, in turn, can cause tension to be applied to the lateral pharyngeal walls via the palatopharyngeal arch (muscle), the effect of which is discussed in more detail below. Thus, activation of the genioglossus muscle causes opening of the upper airway at the level of the tongue base (retro-glossal space) and, in some cases, at the level of the soft palate (retro-palatal space). Because the linkage between the genioglossus and the soft palate via the palatoglossal arch varies across subjects, the response to HGNS at the level of the palate will vary as well. This is significant because most people with OSA have some involvement of the palate during obstructive events, and it may be helpful to identify those subjects with inadequate retro-palatal opening due to poor linkage (i.e., poor coupling) between the genioglossus and soft palate, possibly due to tissue redundancy (i.e., slack) in the palatoglossus. Tissue redundancy may also be present in the lateral pharyngeal walls due to the presence of adipose tissue (i.e., fat) at discrete locations (e.g., fat pads) or distributed throughout the pharyngeal walls, particularly in patients with high BMI.

Figure 92:
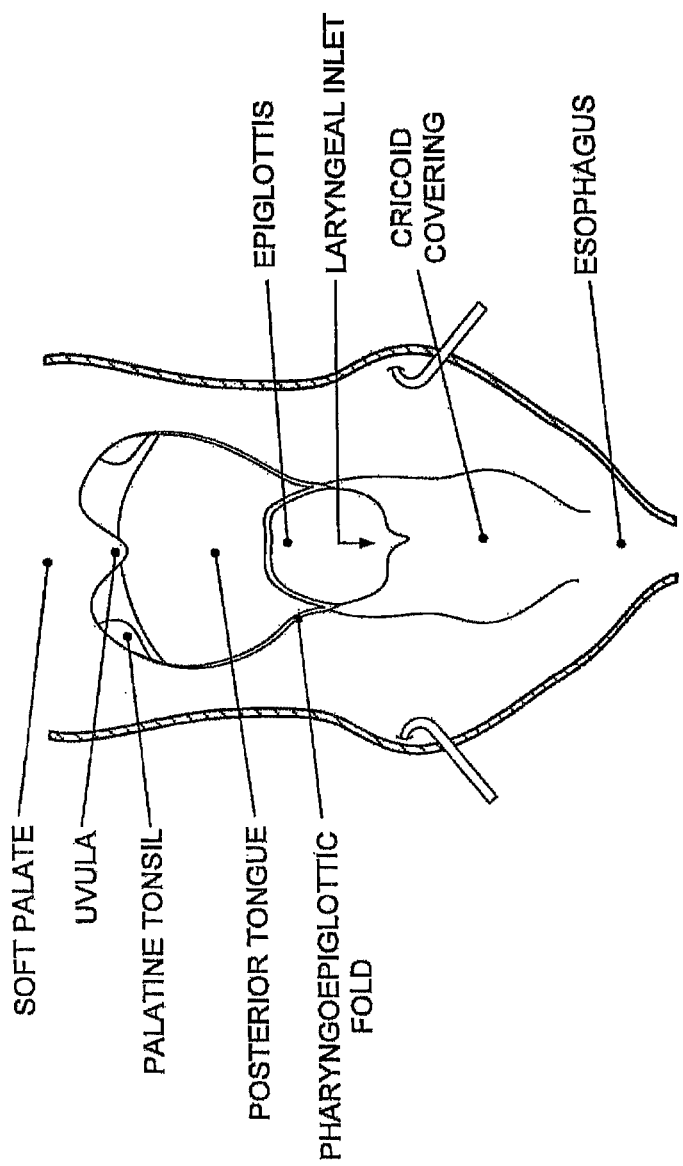
FIG. 92 is a schematic illustration showing structures of the upper airway in a posterior dissection of the interior pharynx.

The anatomical linkage between the tongue base (genioglossus) and the soft palate via the palatoglossal arch may be more clearly seen in FIGS. 90 and 91. The palatoglossus muscle forms the palatoglossal arch and the anterior-inferior aspect of the soft palate on either side of the uvula. The inferior and lateral ends of the palatoglossus muscle insert into the genioglossus muscle. Posterior to the palatoglossal arch are the palatine tonsils, and posterior to the palatine tonsils is the palatopharyngeus muscle forming the palatopharyngeal arch and the posterior-inferior aspect of the soft palate on either side of the uvula. The inferior and lateral ends of the palatopharyngeus muscle insert into the lateral walls of the pharynx. The soft palate is also linked to the lateral pharyngeal walls inferiorly via the pharyngoepiglottic fold as best seen in FIG. 92. Activation of the genioglossus serves to pull the soft palate anteriorly via the palatoglossal linkage. Anterior displacement of the soft palate serves to apply anterior and lateral (outward) tension to the lateral pharyngeal walls via the palatopharyngeal linkage as well as the inferior lateral pharyngeal walls via the pharyngoepiglottic linkage.

Figure 93:
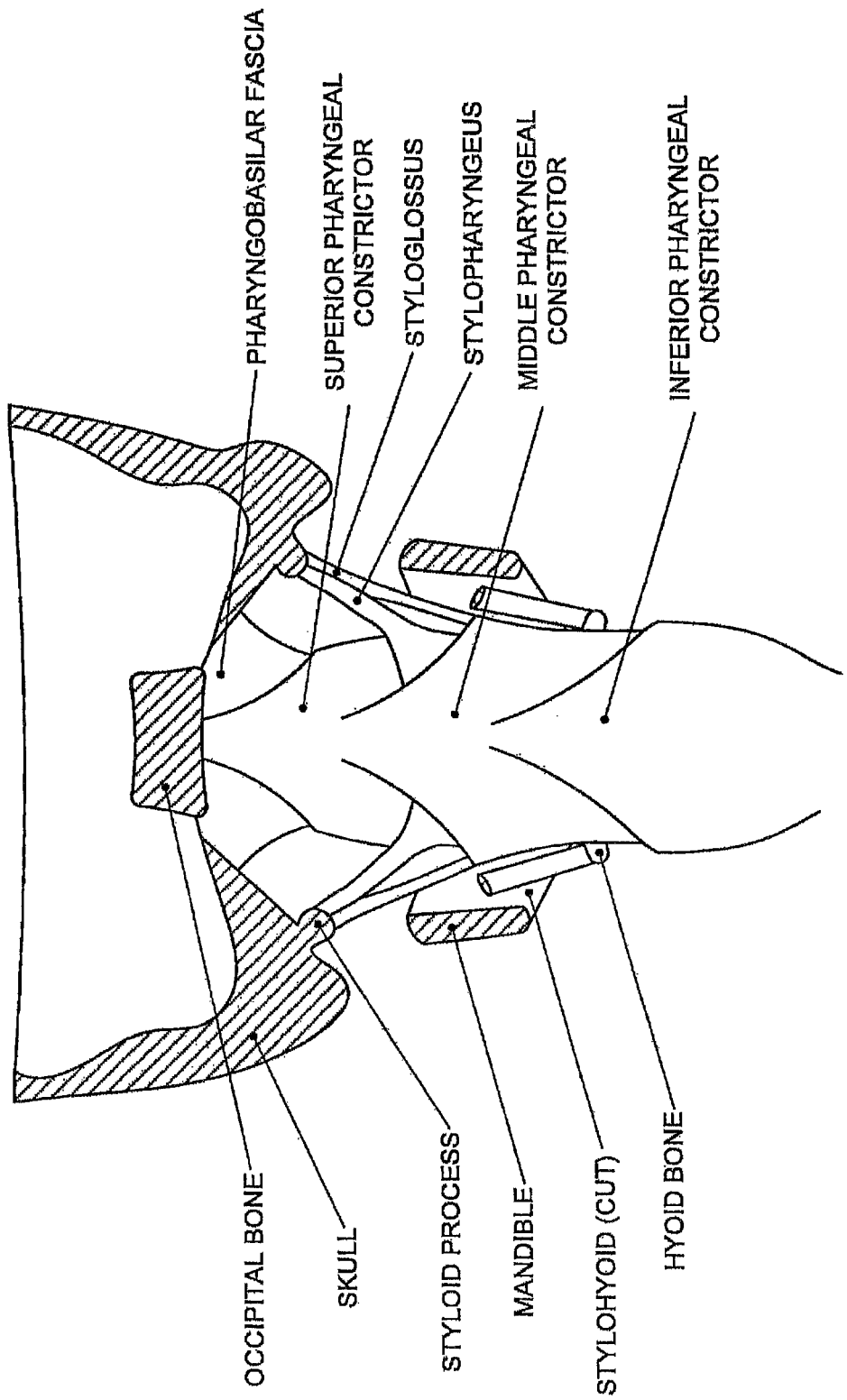
FIG. 93 is a schematic illustration showing structures of the upper airway in a posterior dissection of the exterior pharynx.
Figure 94:
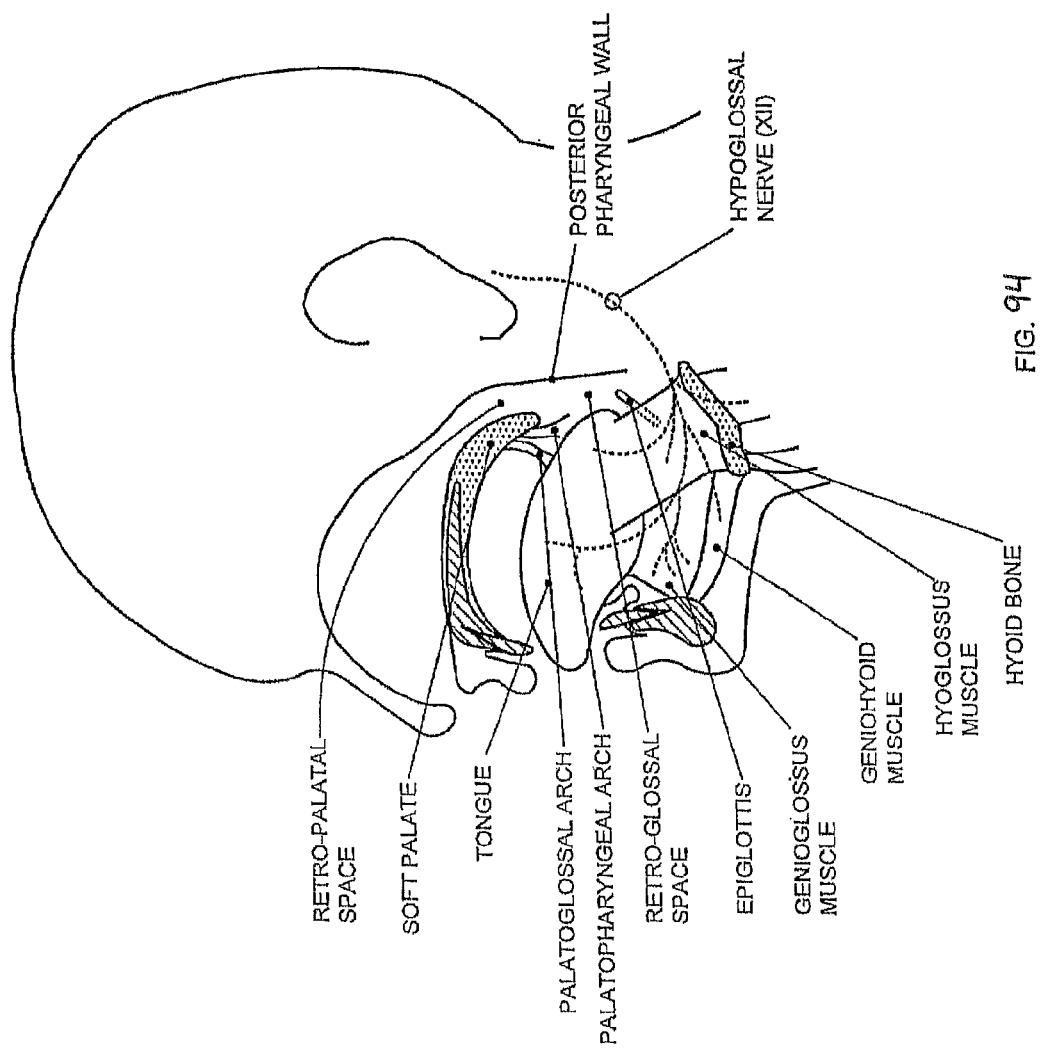
FIG. 94 is a schematic illustration showing the structures of the upper airway in a lateral dissection with the palate and mandible shown in medial sagittal section.

The anatomical linkage between the tongue base (genioglossus) and the lateral pharyngeal walls may be better appreciated with reference to FIG. 93. The anterior-inferior aspect (not visible) of the styloglossus muscles insert into the genioglossus, and the posterior-superior aspect of the styloglossus muscles attach to the styloid process. Similarly, the anterior-inferior aspect (not visible) of the stylopharyngeus muscles insert into the lateral pharyngeal walls, and the posterior-superior aspect of the stylopharyngeus muscles attach to the styloid process. The glossopharyngeal aspects of the superior pharyngeal constrictor muscle also insert into the genioglossus. Thus, activation of the genioglossus serves to apply tension to the styloglossus and the glossopharyngeal aspects of the superior pharyngeal constrictor muscle, which in turn apply lateral outward tension to the lateral pharyngeal walls by virtue of the lateral outward position of the styloid process and the linkage via the stylopharyngeus muscles.

In sum, activation of the genioglossus muscle opens the retro-glossal airway as well as the retro-palatal airway via the linkages described above. In addition, activation of the genioglossus muscle serves to open the lateral pharyngeal walls via the linkages described above. However, the linked effects on the soft palate and the lateral pharyngeal walls is not present in all subjects but may be important for therapeutic success of HGNS depending on the level and mode of collapse in a given patient. By using a tongue protrusion maneuver to mimic the effect on the genioglossus muscle seen with HGNS, the response of the soft palate and lateral walls may be observed using endoscopy, for example. If the palatal and lateral walls respond sufficiently to the tongue protrusion maneuver, the likelihood of successful treatment with HGNS increases. Thus, observing the response of upper airway structures to the tongue protrusion maneuver may be used as a screening tool prior to implantation of a HGNS device.

Optionally, it may be desirable to observe the response of the airway at the level of collapse. The level of collapse may be determined during sleep or simulated sleep (e.g. sedation) using known techniques such as drug induced sleep endoscopy (DISE), or may be determined by examination of the airway structures using known techniques such as naso-endoscopy. The airway may collapse at the level of the tongue base (i.e., retro-glossal), at the level of the palate (i.e. retro-palatal), or both levels. Because most OSA patients have palatal involvement in airway collapse, it may not be necessary to determine the level of collapse. In this case, collapse may be assumed to occur at least at the level of the palate, and therefore an adequate response (e.g., increase in airway size) in the retro-palatal space during the tongue protrusion maneuver would be indicative of likely therapeutic success with HGNS.

The principles of the present invention may be applied to other therapeutic interventions for OSA involving the upper airway. For example, the tongue protrusion maneuver may be used as a screening tool for surgery of the upper airway, such as uvulopalatopharyngoplasty (UPPP), palatal implants, genioglossus advancement, maxillo-mandibular advancement, etc. Also, the tongue protrusion maneuver may be used as a screening tool for oral appliances such as mandibular repositioning devices, tongue retaining devices, etc.

Those skilled in the art will recognize that the present invention may be manifested in a variety of forms other than the specific embodiments described and contemplated herein. Accordingly, departures in form and detail may be made without departing from the scope and spirit of the present invention as described in the appended claims Further aspects of the HGNS system 100 may be found in U.S. patent application Ser. No. 13/106,460, filed May 12, 2011, entitled OBSTRUCTIVE SLEEP APNEA TREATMENT DEVICES, SYSTEMS AND METHODS to Bolea et al., the entire disclosure of which is incorporated herein by reference.

Activation of the genioglossus muscle by HGNS causes anterior displacement of the tongue, thus opening the retro-glossal airway. Activation of the genioglossus muscle can also cause anterior displacement of the soft palate, thus opening the retro-palatal airway space. Activation of the genioglossus muscle can further cause lateral displacement of the lateral pharyngeal walls, thus further opening the upper airway. In this manner, activation of the genioglossus muscle by HGNS can mitigate different levels and modes of upper airway collapse in OSA subjects.

Although the effect of genioglossus activation of the tongue to open the retro-glossal airway is predictable given the mechanism of action, the effect of genioglossus activation on the soft palate and lateral walls has been heretofore poorly understood and variable across subjects. Nevertheless, in the majority of OSA patients, the soft palate and the lateral walls can contribute to upper airway collapse, alone or in combination with the tongue. Thus, to the extent that activation of the genioglossus by HGNS does not fully mitigate upper airway collapse in a given subject, adjunct therapies as described herein may be considered to address other levels and modes of upper airway collapse, thus potentially improving the subject's overall response to therapy.

The present disclosure provides a number of different therapies that may be used adjunctively with another OSA therapy such as therapies targeting the tongue (e.g., hypoglossal nerve stimulation, genioglossus-advancement, mandibular advancement surgery, mandibular advancement oral appliances, etc.). Alternatively, the therapies described herein may be used as a stand-alone therapy for OSA and/or snoring. To better understand the function of the therapies described herein, it is helpful to consider the anatomical structures of the upper airway and the interactions of those structures.

With reference to FIGS. 90-94, the anatomical linkages between the tongue, soft palate and lateral walls may be explained in more detail. With specific reference to FIG. 94, the hypoglossal nerve (cranial nerve XII) innervates the genioglossus muscle, which is the largest upper airway dilator muscle. Activation of the genioglossus muscle via stimulation of the hypoglossal nerve causes tongue protrusion and anterior displacement of the soft palate, due to linkage via the palatoglossal arch (muscle). Anterior displacement of the soft palate, in turn, can cause tension to be applied to the lateral pharyngeal walls via the palatopharyngeal arch (muscle). Thus, activation of the genioglossus muscle causes opening of the upper airway at the level of the tongue base (retro-glossal space), at the level of the soft palate (retro-palatal space) via the palatoglossal arch, and along the lateral walls via the palatopharyngeal arch.

The anatomical linkage between the tongue base (genioglossus) and the soft palate via the palatoglossal arch, and the anatomical linkage between the soft palate and the lateral walls via the palatopharyngeal arch may be more clearly seen in FIGS. 90 and 91. The palatoglossus muscle forms the palatoglossal arch and the anterior-inferior aspect of the soft palate on either side of the uvula. The inferior and lateral ends of the palatoglossus muscle insert into the genioglossus muscle. Posterior to the palatoglossal arch are the palatine tonsils, and posterior to the palatine tonsils is the palatopharyngeus muscle forming the palatopharyngeal arch and the posterior-inferior aspect of the soft palate on either side of the uvula. The inferior and lateral ends of the palatopharyngeus muscle insert into the lateral walls of the pharynx.

The inferior anatomical linkage between the soft palate and the lateral walls via the pharyngoepiglottic fold may be more clearly seen in FIG. 92. Activation of the genioglossus serves to pull the soft palate anteriorly via the palatoglossal linkage. Anterior displacement of the soft palate serves to apply anterior and lateral (outward) tension to the lateral pharyngeal walls via the palatopharyngeal linkage as well as the inferior lateral pharyngeal walls via the pharyngoepiglottic linkage.

The anatomical linkage between the tongue base (genioglossus) and the lateral pharyngeal walls may be better appreciated with reference to FIG. 93. The anterior-inferior aspect (not visible) of the styloglossus muscles insert into the genioglossus, and the posterior-superior aspect of the styloglossus muscles attach to the styloid process. Similarly, the anterior-inferior aspect (not visible) of the stylopharyngeus muscles insert into the lateral pharyngeal walls, and the posterior-superior aspect of the stylopharyngeus muscles attach to the styloid process. The glossopharyngeal aspects of the superior pharyngeal constrictor muscle also insert into the genioglossus. Thus, activation of the genioglossus serves to apply tension to the styloglossus and the glossopharyngeal aspects of the superior pharyngeal constrictor muscle, which in turn apply lateral outward tension to the lateral pharyngeal walls by virtue of the lateral outward position of the styloid process and the linkage via the stylopharyngeus muscles.

The integrity and extent of the aforementioned linkages may vary across subjects, and thus their response to HGNS therapy may vary accordingly. These linkages are significant because most people who snore or have OSA will have some retro-palatal collapse with involvement of the palate and/or lateral walls. In these subjects, retro-palatal collapse may be due to poor linkage (i.e., poor coupling) between the genioglossus and soft palate, the soft palate and lateral walls, and/or the tongue and lateral walls, possibly the result of tissue redundancy (i.e., slack) in the palatoglossus, palatopharyngeus, and/or pharyngoepiglottic fold, respectively. Tissue redundancy may also be present in the lateral pharyngeal walls due to adipose tissue (i.e., fat) at discrete locations (e.g., fat pads) or distributed throughout the pharyngeal walls, particularly in patients with high BMI, which is common in OSA sufferers.

By modifying these connective structures using the devices and methods described herein, the tendency of the tongue, soft palate, and/or lateral walls to collapse may be mitigated as an adjunct to HGNS therapy or as a stand-alone therapy to treat OSA and/or snoring. The connective structures may be modified using the devices and methods described herein by changing their configuration and/or dimension (e.g., shortening their length) and/or changing their mechanical properties (e.g., increasing their stiffness), for example. Although some embodiments are described with reference to a specific pharyngeal structure (e.g., palatoglossal tissue), the same embodiment may be applied to other pharyngeal structures (e.g., palatopharyngeal tissue) in the alternative or in combination.

Figure 95A:
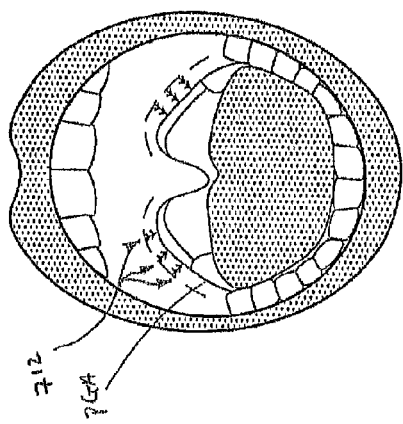
Figure 95B:
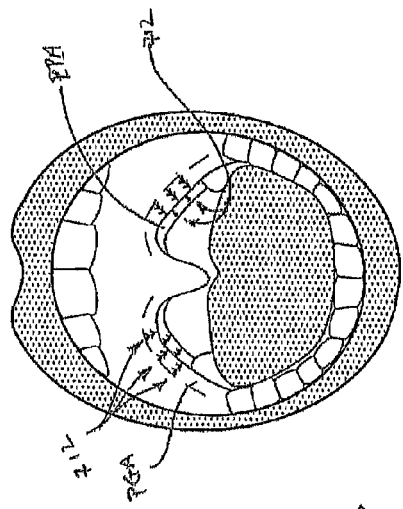

With reference to FIGS. 95A-95B, a method of shortening the palatoglossal arch (PGA) is shown schematically. As seen in FIG. 95A, tissue is removed (cut or ablated) from the PGA to form a void 710 limited to the palatoglossal muscle and surrounding mucosa while leaving the rest of the soft palate unchanged. The amount and shape of the tissue removed may vary, to correspond to the amount of PGA shortening desired. In this example, a triangular notch 710 is formed symmetrically on both sides of the PGA. Subsequently, the notches 710 are surgically closed with sutures 712 or the like to bring the cut edges into approximation and thereby shorten the length of the PGA an amount approximately equal to the sum of the bases of the triangular notches as seen in FIG. 95B. A triangular notch may be beneficial because it removes more tissue from the inferior aspect of the PGA (base of triangle) while minimizing tissue removal from the superior aspect of the PGA (apex of triangle), thus enabling shortening of the PGA while minimizing disruption of the remainder of the soft palate. Thus shortening the length of the PGA applies tension to the soft palate and moves it anteriorly relative to the tongue, thereby mitigating retro-palatal collapse (OSA) and tissue vibration (snoring). Any resultant scarring may serve to stiffen the respective tissue structures thus enhancing the effect.

Figure 95C:
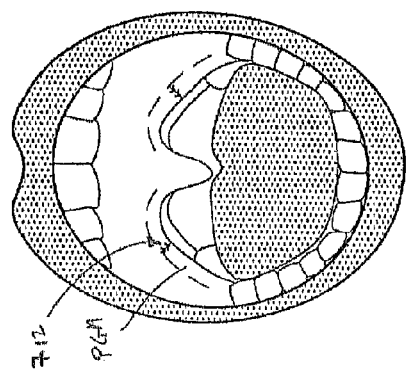
Figure 95E:
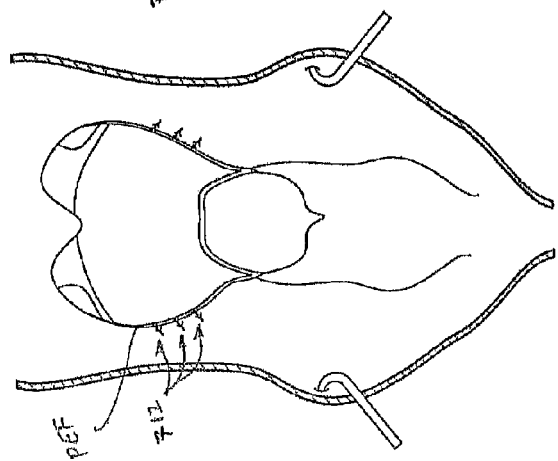
Figure 95D:
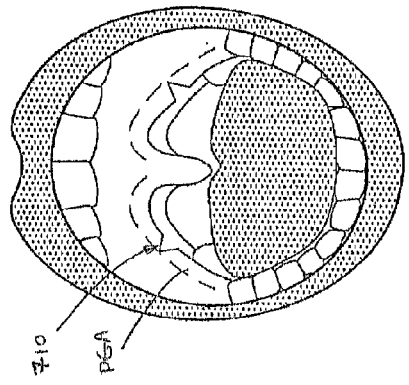
Figure 95F:
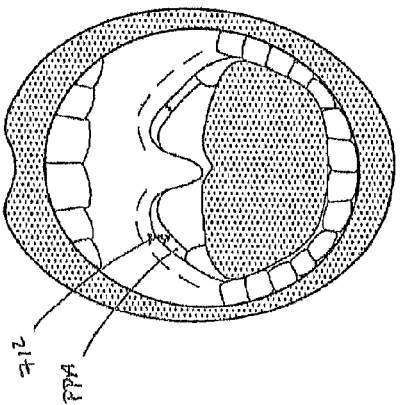

As an alternative, a plurality of tissue sections may be removed and closed from both sides of the PGA as shown in FIG. 95C. In addition, although described with reference to the PGA, the same technique may be applied to other pharyngeal connective structures either alone or in combination. For example, the same technique may be applied to the palatopharyngeal arch (PPA) as shown in FIG. 95D and/or the pharyngoepiglottic fold (PEF) as shown in FIG. 95E. Also by way of example, this technique may be applied to a combination of pharyngeal structures such as the PGA and PPA as shown in FIG. 95F.

Figure 96B:
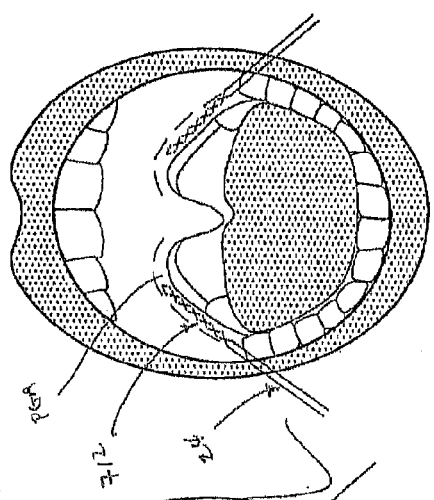
Figure 96A:
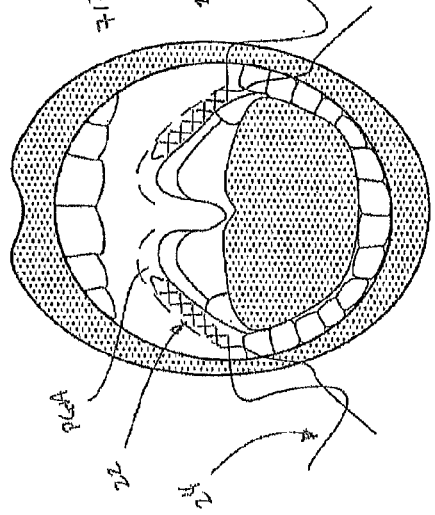

With reference to FIGS. 96A-96B, an alternative method of shortening and/or stiffening the palatoglossal arch (PGA) is shown schematically. As seen in FIG. 96A, sutures 22 are bilaterally placed in the PGA in a crisscross fashion. The sutures 22 may generally follow the arcuate shape of the PGA and its width may be limited to the width of the palatoglossal muscle and surrounding mucosa while leaving the rest of the soft palate unchanged. Once in place, the tags ends 24 of the sutures 22 may be pulled relative to the PGA as shown in FIG. 96B to cinch the adjacent tissue length-wise to thereby shorten the length of the PGA and/or stiffen the PGA. Optionally, tissue may be removed from the PGA prior to placement of the sutures 22 as described with reference to FIG. 95A and elsewhere herein. The method described with reference to FIGS. 96A-96B may be applied to other pharyngeal structures in the alternative or in combination.

Figure 97:
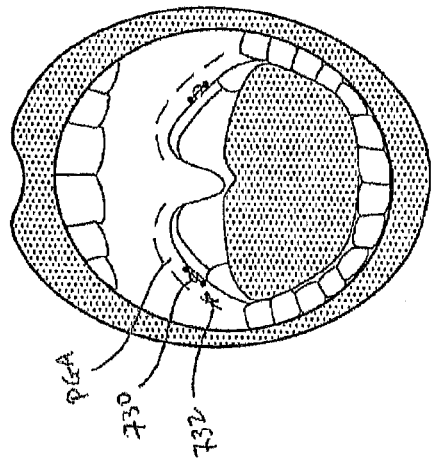

In some instances, it may be desirable to temporarily shorten or stiffen pharyngeal connective structures to determine if there is a positive effect (in terms of mitigating OSA and/or snoring) before performing any of the permanent procedures described herein. To this end, and with reference to FIG. 97, placations 730 may be formed bilaterally in the PGA to shorten its length, and temporary holding devices 732 may be placed across the placations 730 to retain the foreshortened length. Optionally, more than one placation 730 and holding device 732 may be placed on each side of the PGA to adjust the foreshortened length thereof. The holding device 732 may comprise, for example, a stud with a removable end, similar to what is used for body piercing, such as an earring. With the PGA temporarily held in a foreshortened length, the effect thereof may be studied while the patient is awake (e.g., by awake nasoendoscopy) and/or while the patient is asleep (e.g., drug induced sleep endoscopy and/or, polysomnography). If a beneficial result (e.g., enlarged airway, improved coupling, reduced snoring, and/or reduction in apneas and hypopneas) is observed in any of such studies, the temporary holding device 732 may be removed and a permanent procedure as described herein may be performed to have the same foreshortening and/or stiffening effect on the PGA. The method described with reference to FIG. 97 may be applied to other pharyngeal structures in the alternative or in combination.

Figure 98B:
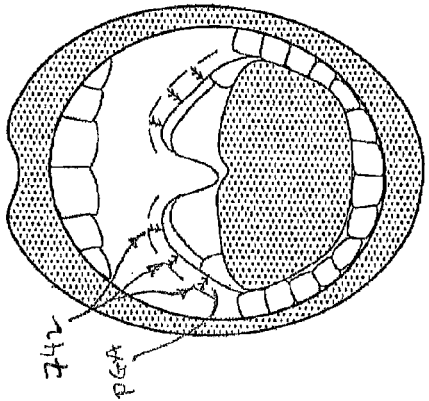
Figure 98A:
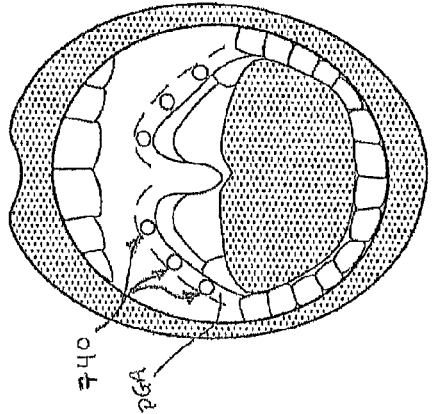

With reference to FIGS. 98A-98B, an alternative method of shortening the palatoglossal arch (PGA) is shown schematically. As seen in FIG. 98A, tissue is removed (cut or ablated) from the PGA to form a circular void 740 between the inferior and superior aspects of the PGA while leaving the rest of the soft palate unchanged. The amount (diameter) removed may vary, to correspond to the amount of PGA shortening desired. In this example, several circular holes are formed symmetrically on both sides of the PGA. Subsequently, the holes 740 are surgically closed with sutures 742 or the like to bring the cut edges into approximation and thereby shorten the length of the PGA an amount approximately equal to the sum of the diameters of the circular holes as seen in FIG. 98B. A circular (or other shape) hole may be beneficial because it is confined to the PGA between the inferior and superior aspects of the PGA. The method described with reference to FIGS. 98A-98B may be applied to other pharyngeal structures in the alternative or in combination.

With reference to FIGS. 99A and 99B, a punch tool 750 is shown which may be used to form the holes 740 shown in FIG. 98A. Punch tool 750 includes a handle 752 with an actuation lever 754 to advance a tubular punch 756 through outer tube 757 to engage die 758. When lever 754 is squeezed relative to handle 752, the punch 756 is advanced in outer tube 757. With die 758 fixed relative to outer tube 757, advancement of the punch 756 as indicated by arrow 751 causes the distal cutting edge of the punch 756 to press against the facing surface of the die 758. The tool 750 may be positioned in the oral cavity with the PGA disposed between the distal cutting edge of the punch 756 and the facing surface of the die 758. When so positioned, the lever 754 may be actuated to advance the die, pinch the PGA tissue between the punch 756 and die 758, and form a hole of any desired shape therein. This step may be repeated for each additional hole to be formed in the PGA or other desired pharyngeal tissue structure.

With reference to FIGS. 100A-100B, an alternative method of shortening and/or stiffening the palatoglossal arch (PGA) is shown schematically. As seen in FIG. 100A, an insertion tool 770 may be used to implant devices 760 bilaterally below the mucosa or in the muscle of the PGA as shown in FIG. 100B. The implant device 760 may comprise an elastic structure having an elongated delivery configuration 760A and a foreshortened deployed configuration 760B as shown in FIGS. 101A and 101B, respectively. The implant device 760 may comprise, for example, braided metal (e.g., stainless steel or super elastic nickel titanium alloy) or braided elastomer (e.g., silicone) formed in a tubular shape, with an elongated state 760A and a relaxed state 760B. Thus, when implant device 760 is implanted submucosally in the PGA, the device 760 expands diametrically to engage the surrounding tissue, and shortens longitudinally to stiffen and/or shorten the length on the PGA. Multiple implant devices 760 may be implanted in the PGA, and this method may be applied to other pharyngeal structures in the alternative or in combination.

An alternative implant device 7160 is shown in FIGS. 101C-101G. In this embodiment, implant device 7160 includes a shaft portion 7162 and two anchors 7164. The implant device 7160 is placed into pharyngeal tissue in a first elongated state 7160A as shown in FIG. 101C, and subsequently assumes a second foreshortened state 7160B as shown in FIG. 101D. To change from the elongated state to the foreshortened state, a length changing core 7166 may be disposed in the shaft portion 7162, with access thereto provided by a plurality of slots 7163 in the shaft portion 7162 as shown in FIG. 101E. The length changing member 7166 may comprise a bio-resorbable material, a heat-shrink polymer that shortens upon application of heat, or a dissolvable material that dissolves upon exposure to a solvent (e.g., saline). The shaft portion 7162 and anchors 7164 may comprise an elastic polymer material such as silicone. Initially, the shaft portion 7162 is stretched lengthwise and the core 7166 is disposed therein to hold the shaft portion 7162 in a stretched or elongated state. Post implantation, the core 7166 shortens (by resorbing, dissolving, or exposure to heat) causing the shaft portion 7162 to shorten as it returns to its relaxed state. As the shaft 7162 shortens, the anchors 7164 engage the surrounding tissue causing the tissue to foreshorten and stiffen. The anchors may comprise tines 7164 as shown in FIG. 101E, a mesh 7164' as shown in FIG. 101F, or a porous material 7164" as shown in FIG. 101G, wherein the mesh 7164' and the porous material 7164" promote tissue ingrowth for anchoring purposes.

To facilitate insertion of the implant device 760 or 7160 under the mucosa or in the muscle of the PGA, an insertion tool 770 may be used as shown in FIGS. 102A and 102B. Insertion tool 770 includes a handle 772 having a lever 774 that may be squeezed as indicated by arrow 773. The lever 774 is mechanically coupled to a flexible outer tube 778, which is retractable relative to an inner member 776 that is fixed relative to handle 772. The outer tube 778 includes a sharpened tip 779 for penetrating into the mucosa and a distal opening for release of the device 760. The distal end of the inner member 776 abuts the proximal end of implant device 760. The outer tube 778 retains the implant device 760 in an elongated, reduced diameter, delivery configuration 760A. When the distal sharpened end of the outer tube 778 is placed under the mucosa or in the muscle of the PGA, the outer tube 778 may be retracted as indicated by arrow 77 by actuation of lever 774 as indicated by arrow 773, thereby releasing the implant device 760 in a shortened, increased diameter, deployed configuration 760B. Thus, the device 760 expands from an elongated delivery configuration 760A to a shortened deployed configuration 760B, thereby stiffening and/or shortening the length of the PGA. The insertion tool 770 may be used to delivery implant device 760 or 7160 to other pharyngeal structures in the alternative or in combination.

Figure 103B:
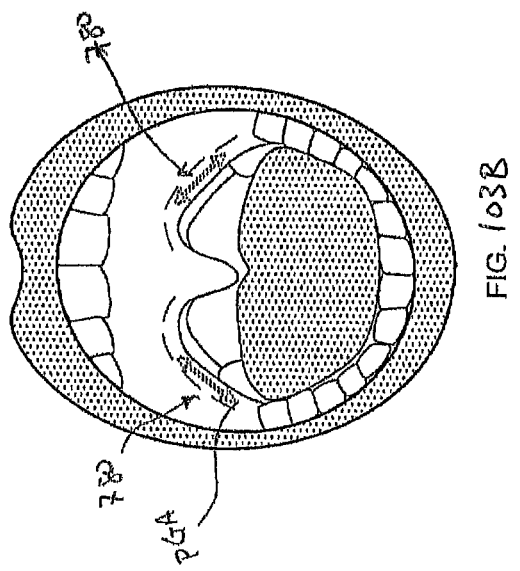
FIGS. 103A-103B are schematic illustrations of an alternative method for shortening pharyngeal tissue using an implant device.
Figure 103A:
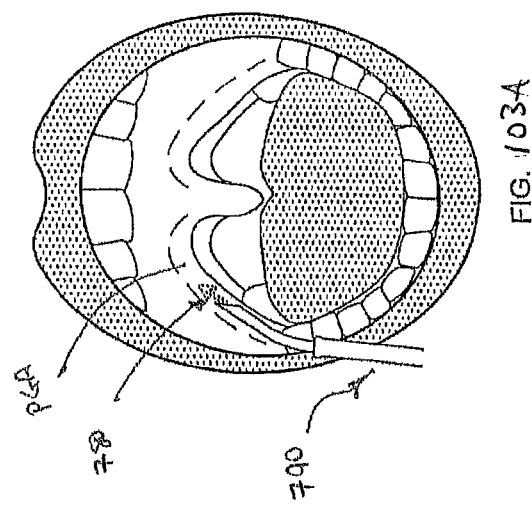

With reference to FIGS. 103A-103B, an alternative method of shortening and/or stiffening the palatoglossal arch (PGA) is shown schematically. As seen in FIG. 103A, an insertion tool 790 may be used to implant devices 780 bilaterally below the mucosa or in the muscle of the PGA as shown in FIG. 103B. Prior to full insertion of the implant devices 780 in the PGA, the PGA tissues are foreshortened using the insertion device 790, for example, such that the implant devices 780 hold the PGA in a foreshortened state. The implant device 780 may comprise a semi-flexible structure that can flex laterally but resists elongation axially. As shown in FIGS. 104A and 104B, the implant device 780 may include a shaft portion 782 with double-barbed anchors 784 at opposite ends of the shaft portion 782. Alternatively, as shown in FIGS. 104C and 104D, the implant device 780 may include a shaft portion 782 with single-barbed anchors 786 at opposite ends of the shaft portion 782. Anchors 784 and 786 may have a low profile delivery configuration 784A and 786A, and an expanded deployed configuration 784B and 786B, as shown. The anchors 784 and 786 are unidirectional such that they can be easily inserted into tissue in one direction but resist withdraw in the other (opposite) direction. For each implant device 780, the unidirectional characteristic of each anchor is opposite, such that the anchor 784/786 on a first end of the shaft 782 is unidirectional in a first direction, and the anchor 784/786 on the second end of the shaft 782 is unidirectional in a second direction opposite from the first direction. This arrangement of the anchors 784/786 allows tissues surrounding the implant device 780 to foreshorten along the shaft portion 782 while holding the tissues in a foreshortened state to shorten the length of the PGA. The implant device 780 may comprise, for example, an implantable grade permanent polymer, a bio-resorbable polymer (e.g., PLLA, PGA), etc. Multiple implant devices 780 may be implanted in the PGA, and this method may be applied to other pharyngeal structures in the alternative or in combination.

To facilitate insertion of the implant device 780 under the mucosa or in the muscle of the PGA, an insertion tool 790 may be used as shown in FIGS. 105A-105D. Insertion tool 790 includes an inner push member 792, an outer push tube 796, and an intermediate tube 794 with a sharpened distal end. Initially, the intermediate tube 794 extends distally beyond the inner push member 792 and the outer push tube 796, with the implant device 780 contained in tube 794 in a delivery configuration with the anchors 784 folded in. In this configuration, all components 792, 794, 796 of the insertion tool 790 are advanced distally in unison as indicated by arrows A, B, C, and the intermediate tube 794 is inserted into the tissue as shown in FIG. 105A. Once the intermediate tube 794 containing the implant device 780 is advanced sufficiently into the target tissue, the inner push member 792 is advanced distally as shown by arrow A, while the intermediate tube 794 and outer tube 796 remain stationary, thus pushing the implant device 780 out of the distal end of the intermediate tube 794 to deploy distal anchor 784 as shown in FIG. 105B. The outer push tube 796 is advanced distally as shown by arrow C, while the inner push member 792 and the intermediate tube 794 remain stationary, thus engaging the distal flared end of the outer tube 796 against the target tissue causing it to foreshorten as shown in FIG. 105C. The intermediate tube 794 is then withdrawn proximally as shown by arrow B, while the inner push member 792 and outer push tube 796 remain stationary, thus deploying the proximal anchor 784 of the implant device 780 to hold the tissue in a foreshortened state as shown in FIG. 105D. The insertion tool 790 may be used to delivery device 780 to other pharyngeal structures in the alternative or in combination.

Figure 106A:
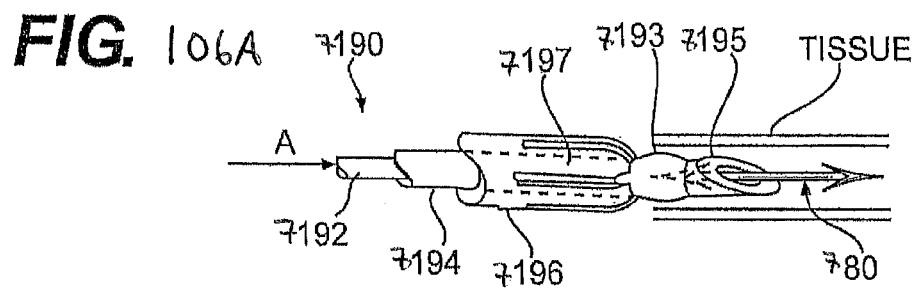
FIGS. 106A-106D are schematic illustrations of an alternative tool for use in the method shown in FIGS. 103A-103B.
Figure 106B:
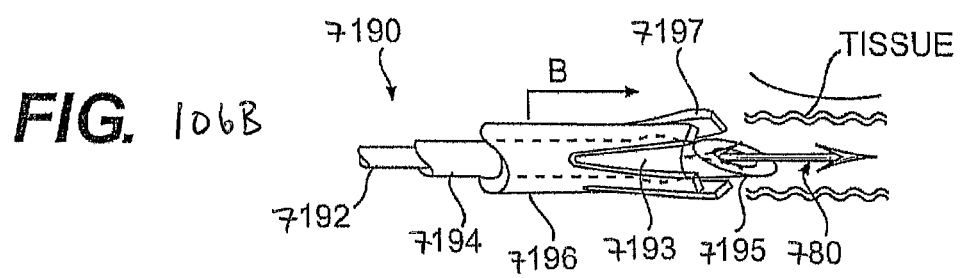
Figure 106C:
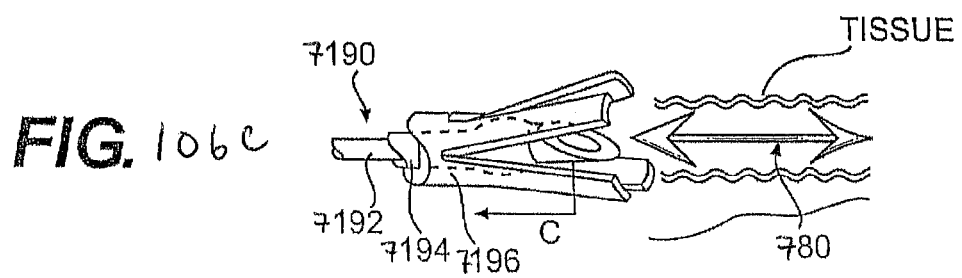
Figure 106D:
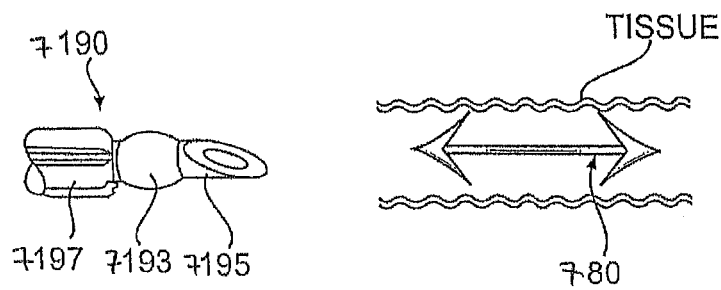

An alternative insertion tool 7190 may be used to facilitate insertion of the implant device 780 under the mucosa or in the muscle of the PGA as shown in FIGS. 106A-106D. Insertion tool 7190 includes an inner push member 7192, an outer push tube 7196, and an intermediate tube 7194. The intermediate tube 7194 includes a sharpened tip 7195 and a bulb portion 7193 having an enlarged diameter. The outer tube 7196 includes a slotted distal end defining a plurality of finger-like projections 7197 that extend outward when advanced over the bulb portion 7193 of the intermediate tube 7194. Initially, the intermediate tube 7194 extends distally beyond the inner push member 7192 and the outer push tube 7196, with the implant device 780 contained in the intermediate tube 7194 in a delivery configuration with the anchors folded in. In this configuration, all components 7192, 7194, 7196 of the insertion tool 7190 are advanced distally in unison, and the intermediate tube 7194 is inserted into the tissue. Once the intermediate tube 7194 containing the implant device 780 is advanced sufficiently into the target tissue, the inner push member 7192 is advanced distally as shown by arrow A, while the intermediate tube 7194 and outer tube 7196 remain stationary, thus pushing the implant device 780 out of the distal end of the intermediate tube 7194 to deploy the distal anchor of the implant device 780 as shown in FIG. 106A. The outer push tube 7196 is advanced distally as shown by arrow B, while the inner push member 7192 and the intermediate tube 7194 remain stationary, thus engaging the finger-like projections 7197 of the outer tube 7196 against the bulb portion 7193 of the intermediate tube 7194 and causing the fingers to flare outward. The flared projections 7197 then push against the target tissue causing it to foreshorten as shown in FIG. 106B. The intermediate tube 7194 is then withdrawn proximally as shown by arrow C, while the inner push member 7192 and outer push tube 7196 remain stationary, thus deploying the proximal anchor of the implant device 780 to hold the tissue in a foreshortened state as shown in FIG. 106C. The insertion tool 7190 may then be removed from the target tissue leaving the implant device in place as shown in FIG. 106D. The insertion tool 7190 may be used to delivery device 780 to other pharyngeal structures in the alternative or in combination.

Figure 107B:
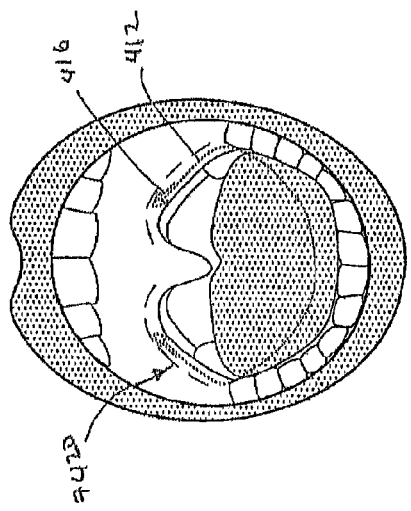
FIGS. 107A-107F are schematic illustrations of alternative methods for shortening pharyngeal tissue using implant devices.
Figure 107C:
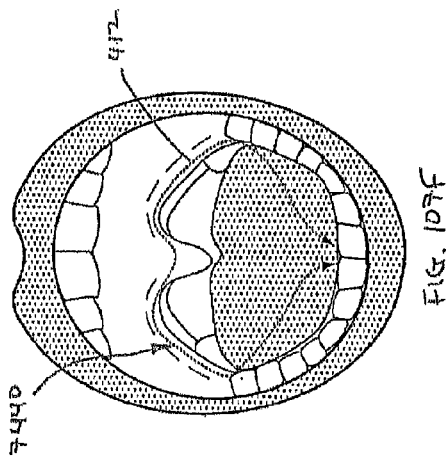
Figure 107E:
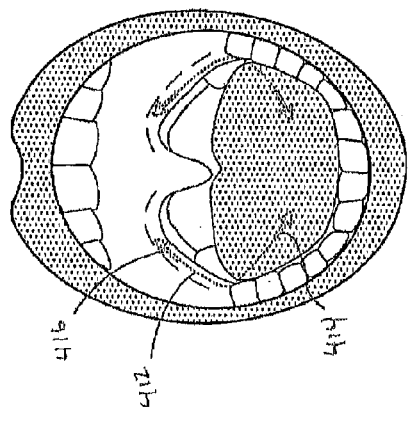
Figure 107F:
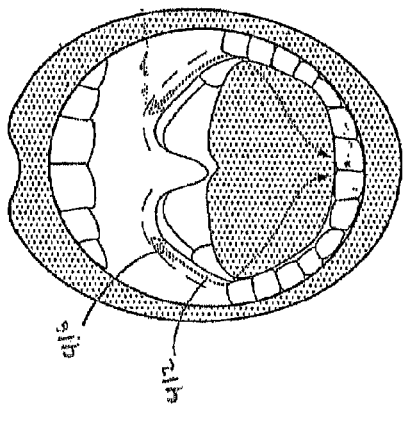
Figure 107A:
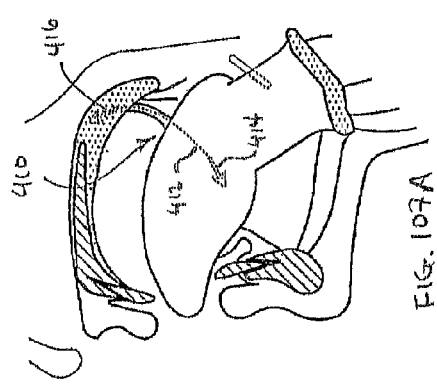

With reference to FIGS. 107A-107F, various implant devices are shown schematically which, in general, improve coupling between the tongue and the soft palate via the palatoglossal arch. In FIGS. 107A and 107B, two implant devices 410 extend from the soft palate, through the palatoglossal arch and into the genioglossus. Each implant device 410 includes a tether member 412 (e.g., multi-filament polymer), and two tissue anchors (e.g., polymer barb) 414 and 416 residing in the genioglossus and soft palate, respectively. The implant devices 410 may be implanted using insertion tool 790 for example, such that it applies tension between the soft palate and tongue via the palatoglossal arch, thereby improving coupling therebetween. In FIG. 107C, a variation of implant device 410 is shown as implant device 7420, which functions in a similar manner but eliminates tissue anchors in the tongue in favor a loop of the tether 412.

Figure 107D:
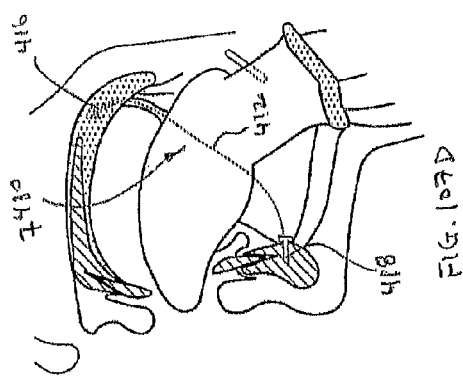

In FIGS. 107D-107E, two implant devices 7430 extend from the soft palate, through the palatoglossal arch and genioglossus, to the mandible. In this embodiment, device 7430 includes a tether member 412, a tissue anchor 416 residing in the soft palate, and a bone anchor 418 residing in the mandible. The implant devices 7430 may be implanted using insertion tool 790 for example, such that it applies tension between the soft palate and tongue via the palatoglossal arch, thereby improving coupling therebetween. In FIG. 107F, a variation of implant device 7430 is shown as implant device 7440, which functions in a similar manner but eliminates tissue anchors in the palate in favor a loop of the tether 412.

Figure 108B:
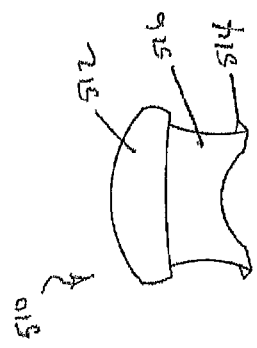
FIGS. 108A-108D are schematic illustrations of a palatal device.
Figure 108D:
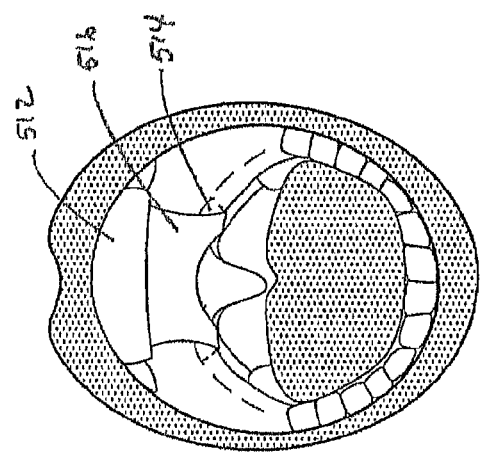
Figure 108A:
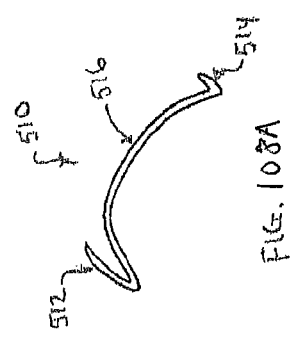
Figure 108C:
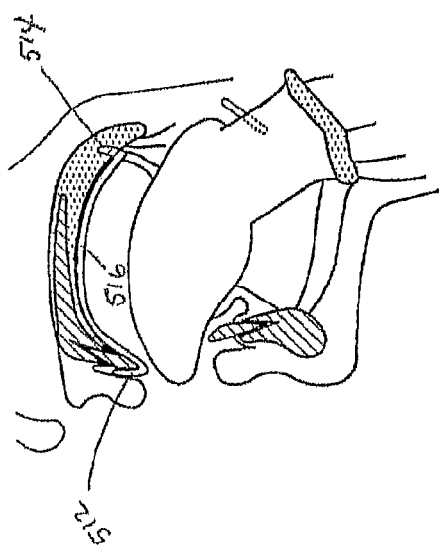

With reference to FIGS. 108A-108D, a palatal appliance 510 is shown schematically. As seen in the side view shown in FIG. 108A and the front view shown in FIG. 108B, the palatal appliance 510 includes a dentition portion 512, a palatal portion 514, and a connecting arch member 516. As shown in FIGS. 108C and 108D, the dentition portion 512 engages the front teeth, the palatal portion 514 includes two tabs that engage the posterior aspect of the soft palate on either side of the uvula, and the arch member 516 extends along the roof of the mouth to connect the dentition portion 512 to the palatal portion 514. The palatal appliance 510 may be formed of conventional materials used for dental appliances, and may be customized for an individual patient using a boil-and-bite technique or a mold-and-thermoform technique. In use, the palatal appliance 510 keeps the soft palate from falling posteriorly, and may be under-sized to displace the soft palate anteriorly from its normal position. Palatal appliance 510 may be used as a stand-alone therapy in the case of isolated retro-palatal collapse, or used as an adjunct to HGNS therapy in the case of poor palatal coupling.

Figure 109:
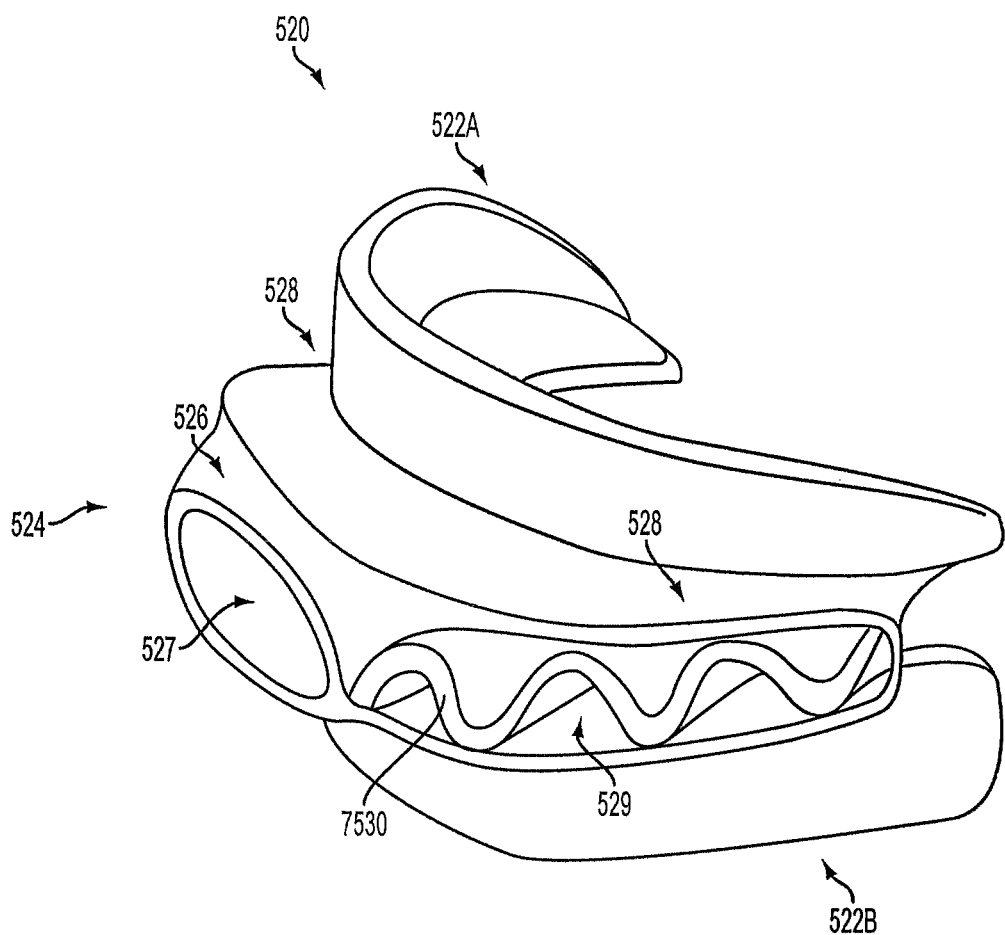
FIG. 109 is a schematic illustration of an oral device.

With reference to FIG. 109, an oral appliance 520 is shown schematically. The oral appliance 520 includes upper and lower dentition portions 522A and 522B, and a spacer portion 524. The dentition portions 522A and 522B engage the teeth, and the spacer 524 resides between the upper and lower teeth as well as the upper and lower lips. An arch member (not shown) may be provided to extend from the spacer along the roof of the mouth. The spacer portion 524 includes a middle portion 526 and two lateral portions 528. The middle portion 526 defines a lumen 527 through which air may flow freely, or into which the tongue may extend (if used in conjunction with HGNS therapy). Similarly, the lateral portions 528 define lumens 529 through which air may flow freely. The lateral portions 528 may include baffles 7530 in a serpentine shape, for example, to provide structural support while permitting airflow therethrough. The arch portion (not shown) may also include a flow path in communication with lumens 527 and 529 through which air may flow freely. The dentition portions 522A and 522B secure the appliance 520 in the mouth during sleep, but permits easy insertion and removal of the appliance 520 to/from the oral cavity at the beginning and ending of the sleep period, respectively. Optionally, one dentition portion 522A or 522B may be used. The spacer 524 keeps the mouth open (teeth and lips) to permit mouth breathing, despite the tendency of the mouth to close during sleep. Similarly, the arch portion maintains a flow path for mouth breathing, despite the tendency of the tongue to fall against the roof of the mouth during sleep. The spacer 524 may have a rectangular housing with a serpentine support baffle 7530 as shown, or the serpentine support structure 7530 without a housing. The oral appliance 520 may be formed of conventional materials used for dental appliances, and may be customized for an individual patient using a boil-and-bite technique or a mold-and-thermoform technique. In use, the oral appliance 520 maintains an open flow path for mouth breathing, despite the tendency of the mouth to close and the tongue to rest against the roof of the mouth during sleep. Oral appliance 520 may be used as a stand-alone therapy in the case of isolated retro-palatal collapse, or used as an adjunct to HGNS therapy in the case of poor palatal coupling.

The adjunct devices and therapies described herein may be used in combination with HGNS therapy, or other therapeutic interventions that directly address retro-glossal collapse. For example, the adjunct therapies described herein may be used in combination with genioglossus advancement surgery, mandibular advancement surgery, mandibular advancement (oral) appliances, etc. Alternatively, the therapies described herein may be used as stand-alone procedures to treat OSA and/or snoring.

Examples of conventional OSA therapies that may be used as an adjunct to HGNS include palate surgeries such as uvulopalatopharyngoplasty (UPPP), palatopharyngoplasty, uvulopalatal flap, and palatal implants (e.g., Pillar® implants sold by Medtronic). Palate surgeries primarily affect upper airway collapse at the level of the palate. As such, these therapies may be considered as adjunct to HGNS in subjects that have residual retro-palatal collapse with HGNS therapy, possibly due to poor anatomical coupling between the tongue and the palate.

From the foregoing, it will be apparent to those skilled in the art that the present disclosure provides, in non-limiting embodiments, devices and methods for treating OSA and snoring by modifying pharyngeal tissue of the upper airway such as, e.g., the palatoglossus, palatopharyngeus, pharyngeoepiglottis, and/or lateral walls. Further, those skilled in the art will recognize that the present disclosure may be manifested in a variety of forms other than the specific embodiments described and contemplated herein. Accordingly, departures in form and detail may be made without departing from the scope and spirit of the present disclosure as described in the appended claims The present disclosure also relates to a method of providing hypoglossal nerve stimulation therapy to a patient for the treatment of obstructive sleep apnea, comprising: performing an assessment of the patient, wherein the assessment comprises protruding the patient's tongue and observing a response of the patient's upper airway; and implanting a hypoglossal nerve stimulation device in the patient only if the response comprises an increase in airway size, wherein implanting the hypoglossal nerve stimulation device comprises implanting a neurostimulator and a stimulation delivery lead in the patient; titrating stimulation settings of the neurostimulator while the patient is awake; and titrating stimulation settings of the neurostimulator while the patient is asleep. In at least one embodiment, the upper airway may be observed while the patient is awake and supine. The tongue protrusion may be volitional. The upper airway may be observed by endoscopy. The increase in airway size may be at least one of retro-glossal and retro-palatal. The increase in airway size may comprise an increase in one of an anterior-posterior dimension and a lateral dimension. The assessment may further comprise determining a level of collapse in the patient's upper airway. In at least one embodiment, the patient is treated with the therapy only if the response of the upper airway is an increase in size, and only if another response is observed during tongue protrusion. In at least one embodiment, the method further comprises delivering an electrical stimulation to the hypoglossal nerve, wherein the electrical stimulation is triggered as a function of aspiration onset. The stimulation delivery lead may include a distal end coupled to a nerve cuff including a plurality of electrodes configured to steer an electrical field.

The present disclosure further relates to a method of treating obstructive sleep apnea, comprising: chronically implanting an electrode on a hypoglossal nerve at a site to stimulate a tongue protrude muscle and a tongue retruder muscle; and periodically delivering a stimulus to the nerve via the electrode to mitigate obstruction of the upper airway, wherein the stimulus is configured to selectively activate the tongue protrude muscle more than or before the tongue retruder muscle, and further wherein the stimulus is delivered if an inspiratory phase of a respiratory cycle is at least 40% of the respiratory cycle. The stimulus may be triggered based on a sensed parameter indicative of respiration. In some embodiments, the sensed parameter may be impedance. Electrical field steering may be used for selective activation.

The foregoing embodiments, which are non-limiting, may be combined in ways beyond those specifically described herein.

I claim:

1. A method of treating a patient, comprising:
    sensing a biological parameter indicative of respiration;
    analyzing the biological parameter to identify a respiratory cycle;
    identifying an inspiratory phase of the respiratory cycle; and
    determining a start time for delivery of a stimulation to a hypoglossal nerve of the patient by identifying a duration of the inspiratory phase of the respiratory cycle that is greater than a predetermined portion of a duration of an entirety of the respiratory cycle.

2. The method of claim 1, wherein sensing the biological parameter includes sensing at least one of impedance, airflow, movement, and pressure, by a sensing device.

3. The method of claim 1, wherein analyzing the biological parameter to identify the respiratory cycle includes identifying biological parameter peaks with a processor, the processor being operatively coupled to the sensing device.

4. The method of claim 3, further comprising:
    comparing amplitudes of the biological parameter peaks to a threshold amplitude.

5. The method of claim 1, wherein determining the start time for delivery of the stimulation includes processing the biological parameter with a processor.

6. The method of claim 5, further comprising:
    delivering the stimulation to the hypoglossal nerve of the patient with a stimulation device operatively coupled to the processor.

7. The method of claim 1, wherein identifying the inspiratory phase of the respiratory cycle includes identifying a biological parameter peak and a preceding biological parameter negative peak, and wherein a portion of the respiratory cycle between the biological parameter peak and the preceding biological parameter negative peak is the inspiratory phase.

8. The method of claim 7, wherein identifying the biological parameter peak and the preceding biological parameter negative peak includes processing the biological parameter with a processor operatively coupled to the sensing device.

9. The method of claim 1, wherein the biological parameter is indicative of a respiratory waveform.

10. The method of claim 9, wherein analyzing the biological parameter to identify the respiratory cycle includes identifying peaks of the respiratory waveform.

11. A method of treating a patient, comprising:
    monitoring a signal relating to a biological parameter indicative of respiration from a sensing device;
    evaluating the signal to identify a respiratory cycle;
    identifying an inspiratory phase of the respiratory cycle; and
    identifying a start time for delivery of a stimulation to a hypoglossal nerve of the patient, wherein identifying the start time includes comparing the inspiratory phase to the respiratory cycle and further includes determining that a duration of the inspiratory phase is greater than a predetermined portion of a duration of an entirety of the respiratory cycle.

12. The method of claim 11, wherein the biological parameter includes at least one of impedance, airflow, movement, and pressure sensed with the sensing device, and wherein identifying the start time for delivery of the stimulation includes processing the sensed biological parameter with a processor operatively coupled to the sensing device.

13. The method of claim 12, further comprising:
    delivering the stimulation to the hypoglossal nerve of the patient with a stimulation device operatively coupled to the processor.

14. The method of claim 11, wherein evaluating the signal includes identifying peaks of a respiratory waveform, wherein the peaks are indicative of the respiratory cycle.

15. The method of claim 14, further comprising:
    comparing amplitudes of the peaks to a threshold amplitude.

16. The method of claim 11, further comprising:
    comparing a duration of a portion of the inspiratory phase to the duration of the entirety of the respiratory cycle.

17. A method of treating a patient, comprising:
    observing a signal indicative of a biological parameter from a sensing device to identify a respiration waveform;
    identifying a respiratory cycle of the respiration waveform;
    identifying an inspiratory phase of the respiratory cycle; and setting a start time for delivery of a stimulation to a hypoglossal nerve of the patient by comparing the inspiratory phase to the respiratory cycle and by determining that a duration of a portion of the inspiratory phase is greater than a predetermined portion of a duration of an entirety of the respiratory cycle.

18. The method of claim 17, wherein comparing the inspiratory phase to the respiratory cycle includes comparing the duration of the portion of the inspiratory phase to the predetermined portion of the duration of the entirety of the respiratory cycle with a processor operatively coupled to the sensing device.

19. The method of claim 18, further comprising:
delivering the stimulation to the hypoglossal nerve of the patient with a stimulation device operatively coupled to the processor.

* * * * *